US011085067B2

(12) United States Patent
Meissner et al.

(10) Patent No.: US 11,085,067 B2
(45) Date of Patent: *Aug. 10, 2021

(54) EARLY DEVELOPMENTAL GENOMIC ASSAY FOR CHARACTERIZING PLURIPOTENT STEM CELL UTILITY AND SAFETY

(71) Applicant: PRESIDENT AND FELLOWS OF HARVARD COLLEGE, Cambridge, MA (US)

(72) Inventors: Alexander Meissner, Cambridge, MA (US); Alexander Tsankov, Cambridge, MA (US); Veronika Akopian, Cambridge, MA (US)

(73) Assignee: PRESIDENT AND FELLOWS OF HARVARD COLLEGE, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/897,410

(22) PCT Filed: Jun. 9, 2014

(86) PCT No.: PCT/US2014/041513
§ 371 (c)(1),
(2) Date: Dec. 10, 2015

(87) PCT Pub. No.: WO2014/200905
PCT Pub. Date: Dec. 18, 2014

(65) Prior Publication Data
US 2016/0122803 A1 May 5, 2016

Related U.S. Application Data

(60) Provisional application No. 61/833,092, filed on Jun. 10, 2013.

(51) Int. Cl.
*C12Q 1/6806* (2018.01)
*C12Q 1/6837* (2018.01)
*C12Q 1/6876* (2018.01)

(52) U.S. Cl.
CPC ........ *C12Q 1/6806* (2013.01); *C12Q 1/6837* (2013.01); *C12Q 1/6876* (2013.01); *C12N 2506/00* (2013.01); *C12N 2506/03* (2013.01); *C12Q 2600/158* (2013.01); *C12Q 2600/16* (2013.01)

(58) Field of Classification Search
CPC .. C12Q 1/6806; C12Q 1/6837; C12Q 1/6876; C12Q 2600/158; C12Q 2600/16
USPC .............. 435/6.1; 536/24.3; 506/9
See application file for complete search history.

(56) References Cited

U.S. PATENT DOCUMENTS

| 8,460,928 B2 | 6/2013 | Bakre et al. |
| 2003/0113910 A1 | 6/2003 | Levanduski |
| 2004/0180347 A1 | 9/2004 | Stanton |
| 2009/0123430 A1* | 5/2009 | De Sousa ............ C12N 5/0662 424/93.7 |
| 2009/0191159 A1 | 7/2009 | Sakurada |
| 2010/0003674 A1 | 1/2010 | Cope et al. |
| 2011/0287974 A1 | 11/2011 | Benvenisty et al. |
| 2012/0329152 A1 | 12/2012 | Pera et al. |
| 2016/0115455 A1 | 4/2016 | Mikkelsen |

FOREIGN PATENT DOCUMENTS

| WO | 02/10347 A2 | 2/2002 |
| WO | 03/093445 A2 | 11/2003 |
| WO | 2004/009758 A2 | 1/2004 |
| WO | 2004/097005 A2 | 11/2004 |
| WO | 2005/120547 A1 | 12/2005 |
| WO | 2009/131568 A1 | 10/2009 |
| WO | 2010/009015 A2 | 1/2010 |
| WO | 2010/111422 A2 | 9/2010 |
| WO | 2011/008541 A2 | 1/2011 |
| WO | 2011/046635 A1 | 4/2011 |
| WO | 2012/037456 A1 | 3/2012 |
| WO | 2011/146607 A2 | 11/2012 |

OTHER PUBLICATIONS

Urbach et al. (PLoS One, 2009, 4(1), 1-9. (Year: 2009).*
Applied Biosystems (Applied Biosystems Pluripotency Array 4385344, 2009, 1-3. (Year: 2009).*
Applied Biosystems Protocol (Applied Biosystems Protocol, 2010, 1-11; of record); (Year: 2010).*
Applied Biosystems User Guide (Applied Biosystems User Guide, 2010, 1-20; of record); and Applied Biosystems Information Card (TaqMan H) (Year: 2010).*
Adewumi et al., "Characterization of human embryonic stem cell lines by the International Stem Cell Initiative", Nature Biotechnology 5(7):803-816 (2007).
Baumann, "Stem cells: Holding on to the memories", Nature Reviews Molecular Cell Biology, 11(9):601 (2010).

(Continued)

*Primary Examiner* — Janet L Epps-Smith
(74) *Attorney, Agent, or Firm* — Nixon Peabody LLP; David S. Resnick; Susanna C. Benn

(57) ABSTRACT

The present invention generally relates to a set of early developmental reference data or "lineage scorecard" for stem cells, and methods, systems and kits to generate a lineage scorecard for predicting the functionality and suitability of stem cell lines. In some aspects, methods for generating a scorecard comprises measuring the gene expression of a plurality of early developmental genes, such as pluripotent, early ectoderm, early mesoderm and early endoderm genes to predict the pluripotency and differentiation potential of the stem cell line and its functionality and/or suitability for a desired use. In some embodiments, a reference scorecard can be compared with the test stem cell line scorecard to accurately predict the utility and/or identify specific characteristics of the stem cell line, e.g., to determine its suitability for downstream applications, e.g., therapeutic use, drug screening, toxicity assays, differentiation into a desired cell lineage, etc.

8 Claims, 14 Drawing Sheets

Specification includes a Sequence Listing.

(56) References Cited

OTHER PUBLICATIONS

Beqqali et al.,"Genome-Wide Transcriptional Profiling of Human Embryonic Stem Cells Differentiating to Cardiomyocytes", Stem Cells, 24:1956-1967 (2006).
Bird, "DNA methylation patterns and epigenetic memory", Genes & Development, 16:6-21 (2002).
Bock et al.,"CpG Island Methylation in Human Lymphocytes is Highly Correlated with DNA Sequence, Repeats, and Predicted DNA Structure", PLoS Genetics 2(3):e26 (2006).
Bock et al., "Computational epigenetics", Bioinformatics 24(1):1-10 (2008).
Bock et al., "EpiGRAPH: user-friendly software for statistical analysis and prediction of (epi)genomic data", Genome Biology, 10:R14 (2009).
Bock et al., "Quantitative comparison of genome-wide DNA methylation mapping technologies", Nature Biotechnology, 28(10):1106-1114 (2010).
Bock et al., "Reference Maps of Human ES and iPS Cell Variation Enable High-Throughput Characterization of Pluripotent Cell Lines", Cell, 144(3):439-52 (2011).
Boland et al., "Adult mice generated from induced pluripotent stem cells", Nature, 461:91-94 (2009).
Borowiak et al., "Small Molecules Efficiently Direct Endodermal Differentiation of Mouse and Human Embryonic Stem Cells", Cell Stem Cell, 4:348-358 (2009).
Boulting et al., "A functionally characterized test set of human induced pluripotent stem cells", Nat Biotechnol., 29 (3): 279-286 (2011).
Chen et al., "Optimal timing of inner cell mass isolation increases the efficiency of human embryonic stem cell derivation and allows generation of sibling cell lines", Cell Stem Cell 4(2):103-106 (2009).
Chin et al., "Induced Pluripotent Stem Cells and Embryonic Stem Cells Are Distinguished by Gene Expression Signatures", Cell Stem Cell, 5(1):111-123 (2009).
Colman el al., "Pluripotent Stem Cells and Disease Modeling", Cell Stem Cell, 5(3):244-247 (2009).
Cowan et al., "Derivation of Embryonic Stem-Cell Lines from Human Blastocysts", N Engl J Med, 350:1353-1356 (2004).
Daley, "Straight talk with . . . George Daley", Interview by Elie Dolgin, Nature Medicine, 16(6):624 (2010).
DiGiorgio et al., "Human Embryonic Stem Cell-Derived Motor Neurons Are Sensitive to the Toxic Effect of Glial Cells carrying an ALS-Causing Mutation", Cell Stem Cell, 3:637-648 (2008).
Dimos et al., "Induced Pluripotent Stem Cells Generated from Patients with ALS Can Be Differentiated into Motor Neurons", Science 321:1218-1221 (2008).
Doi et al., "Differential methylation of tissue- and cancer-specific CpG island shores distinguishes human induced pluripotent stem cells, embryonic stem cells and fibroblasts", Nat Genet., 41(12):1350-1353 (2009).
Ebert et al., "Induced pluripotent stem cells from a spinal muscular atrophy patient", Nature 457(7227):277-280 (2009).
Eiges et al., "Developmental Study of Fragile X Syndrome Using Human Embryonic Stem Cells Derived from Preimplantation Genetically Diagnosed Embryos", Cell Stem Cell, 1:568-577 (2007).
ENCODE Project Consortium, "Identification and analysis of functional elements in 1% of the human genome by the ENCODE pilot project", Nature 447(7146):799-816 (2007).
Flintoft, "Evolution: Gene duplicate holds back its sister", Nature Reviews Genetics, 11(9):593 (2010).
Geiss et al., "Direct multiplexed measurement of gene expression with color-coded probe pairs", Nature Biotechnology, 26(3):317-325 (2008).
Gu et al., "Genome-scale DNA methylation mapping of clinical samples at single-nucleotide resolution", Nat Methods., 7(2):133-136 (2010).

Hanna et al., "Human embryonic stem cells with biological and epigenetic characteristics similar to those of mouse ESCs", PNAS U S A, 107(20):9222-9227 (2010).
Hemberger et al., "Epigenetic dynamics of stem cells and cell lineage commitment: digging Waddington's canal", Nature Reviews Molecular Cell Biology, 10:526-537 (2009).
Hu et al., "Neural differentiation of human induced pluripotent stem cells follows developmental principles but with variable potency", PNAS U S A 107(9):4335-4340 (2010).
Huang et al., "DAVID Bioinformatics Resources: expanded annotation database and novel algorithms to better extract biology from large gene lists", Nucleic Acids Research, 35:W169-W175 (2007).
Huber et al., "Variance stabilization applied to microarray data calibration and to the quantification of differential expression", Bioinformatics, 18(Suppl 1):S96-S104 (2002).
Irizarry et al., "Multiple-laboratory comparison of microarray platforms", Nature Methods, 2(5):345-350 (2005).
Kauffmann et al., "arrayQualityMetrics—a bioconductor package for quality assessment of microarray data", Bioinformatics 25(3):415-416 (2009).
Keshet et al., "Evidence for an instructive mechanism of de novo methylation in cancer cells", Nature Genetics, 38 (2):149-153 (2006).
Laird, "Cancer epigenetics", Human Molecular Genetics, 14(1):R65-676 (2005).
Laird, "Principles and challenges of genome-wide DNA methylation analysis", Nature Reviews Genetics, 11:191-203 (2010).
Laird, "The Power and the Promise of DNA Methylation Markers", Nature Reviews Cancer, 3:253-266 (2003).
Lee et al., "Modelling Pathogenesis and Treatment of Familial Dysautonomia using Patient Specific iPSCs", Nature, 461(7262):402-406 (2009).
Lengner et al., "Derivation of Pre-X Inactivation Human Embryonic Stem Cells under Physiological Oxygen Concentrations", Cell, 141:872-883 (2010).
Li et al., "Mapping short DNA sequencing reads and calling variants using mapping quality scores", Genome Research, 18:1851-1858 (2008).
Lieb et al., "Applying Whole-Genome Studies of Epigenetic Regulation to Study Human Disease", Cytogenet Genome Res., 114(1):1-15 (2006).
Lister et al., "Human DNA methylomes at base resolution show widespread epigenomic differences", Nature, 462: 315-322 (2009).
Liu et al., "Activation of the Imprinted Dlk1-Dio3 Region Correlates with Pluripotency Levels of Mouse Stem Cells", Journal of Biological Chemistry, 285(25):19483-19490 (2010).
Lu et al., "Systems-level dynamic analyses of fate change in murine embryonic stem cells", Nature, 462 (7271):358-362 (2009).
Maherali et al., "Guidelines and Techniques for the Generation of Induced Pluripotent Stem Cells", Cell Stem Cell 3, 595-605 (2008).
Meissner et al., "Genome-scale DNA methylation maps of pluripotent and differentiated cells", Nature, 454:766-770 (2008).
Meneghel-Rozzo et al., "In vivo and in vitro development of mouse pancreatic beta-cells in organotypic slices", Cell Tissue Res., 316(3);295-303 (2004).
Mikkelsen et al., "Dissecting direct reprogramming through integrative genomic analysis", Nature, 454:49-55 (2008).
Mikkelsen et al., "Genome-wide maps of chromatin state in pluripotent and lineage-committed cells", Nature 448 (7153):553-560 (2007).
Mitalipova et al., "Human Embryonic Stem Cell Lines Derived from Discarded Embryos", Stem Cells, 21:521-526 (2003).
Miura et al., "Variation in the safety of induced pluripotent stem cell lines", Nature Biotechnology, 27(8):743-745 (2009).
Muller et al., "Regulatory networks define phenotypic classes of human stem cell lines", Nature, 455(7211):401-405 (2008).
Nam et al., "Gene-set approach for expression pattern analysis", Briefings in Bioinformatics 9(3):189-197 (2008).
Osafune et al., "Marked differences in differentiation propensity among human embryonic stem cell lines", Nature Biotechnology, 26(3):313-315 (2008).
Park et al., "ChIP-Seq: advantages and challenges of a maturing technology", Nat Rev Genet., 10(10):669-680 (2009).
Park et al., "Disease-specific induced pluripotent stem (iPS) cells", Cell, 134(5):877-886 (2008).

(56) References Cited

OTHER PUBLICATIONS

Park et al., "Reprogramming of human somatic cells to pluripotency with defined factors", Nature 451:141-146 (2008).
Polo et al., "Cell type of origin influences the molecular and functional properties of mouse induced pluripotent stem cells", Nat Biotechnol., 28(8):848-855 (2010).
Reik, "Stability and flexibility of epigenetic gene regulation in mammalian development", Nature, 447:425-432 (2007).
Rossant, "Stem Cells and Early Lineage Development", Cell, 132:527-531 (2008).
Segev et al., "Differentiation of Human Embryonic Stem Cells into Insulin-Producing Clusters", Stem Cells, 22:265-274 (2004).
Smith et al., "High-throughput bisulfite sequencing in mammalian genomes", Methods, 48(3):226-232 (2009).
Squazzo et al., "Suz12 binds to silenced regions of the genome in a cell-type-specific manner", Genome Research. 16:890-900 (2006).
Stadtfeld et al., "Aberrant silencing of imprinted genes on chromosome 12qF1 in mouse induced pluripotent stem cells", Nature, 465(7295):175-181 (2010).
Storey et al., "Statistical significance for genomewide studies", PNAS U S A, 100(16):9440-9445 (2003).
Subramanian et al., "Gene set enrichment analysis: A knowledge-based approach for interpreting genome-wide expression profiles", PNAS, 102(43):15545-15550 (2005).
Takahashi et al., "Induction of Pluripotent Stem Cells from Adult Human Fibroblasts by Defined factors", Cell, 131: 861-872 (2007).
Takahashi et al., "Induction of Pluripotent Stem Cells from Mouse Embryonic and Adult Fibroblast Cultures by Defined factors", Cell, 126:663-676 (2006).
Thomson et al., "Embryonic Stem Cell Lines Derived from Human Blastocysts", Science, 282:1145-1147 (1998).
Wichterle et al., "Directed Differentiation of Embryonic Stem Cells into Motor Neurons", Cell, 110:385-397 (2002).
Xu et al., "Endoderm and Pancreatic Islet Lineage Differentiation from Human Embryonic Stem Cells", Cloning and Stem Cells, 8(2):96-107 (2006).

Yoon et al., "Enhanced differentiation of human embryonic stem cells into cardiomyocytes by combining hanging drop culture and 5-azacytidine treatment", Differentiation, 74:149-159 (2006).
Yu et al., "Induced Pluripotent Stem Cell Lines Derived from Human Somatic Cells", Science, 318:1917-1920 (2007).
Zhao et al., "iPS cells produce viable mice through tetraploid complementation", Nature, 461(7260):86-90 (2009).
Applied Biosystems Signature Array, TaqMan Human Stem Cells Pluripotency Array, Applied Biosystems, 2008, 1-2.
Gifford et al., "Transcriptional and epigenetic dynamics during specification of human embryonic stem cells", Cell 153(5) 1149-1163 (2013).
Mandal et al., "Characterization and in vitro differentiation potential of a new human embryonic stem cell line, ReliCellhES1", Differentiation 74(2-3) 81-90 (2006).
Rosenkranz et al., "Characterizing the mouse ES cell transcriptome with Illumina sequencing", Genomics 92(4) 187-194 (2008).
ThermoFisher Scientific, TaqMan Array Human NFAT & Cardiac Hypertrophy 96-Well Plate, 2010, 1. (2010).
Livak et al., "Analysis of relative gene expression data using real-time quantitative PCR and the 2(-Delta Delta C(T)) Method", Methods 25(4) 402-408 (2001).
Agilent, Agilent Gene List 44K Array, Agilent GeneList 44K Array, 2010, 1. (Year: 2007).
Elliot et al., "High Resolution Array-CHG Characterization of Human Stem Cells Using a Stem Cell Focused Microarray", Molecular Biotechnology 46(3):234-242 (2010).
Fogel et al., "RBFOX1 regulates both splicing and transcriptional networks in human neuronal development", Human Molecular Genetics 21(19) 4171-4186 (2012).
Gan et al., "Concise review: Epigenetic mechanisms contribute to pluripotency and cell lineage determination of embryonic stem cells", Stem Cells 25(1) 2-9 (2007).
Kopper et al., "Stepwise differentiation of human embryonic stem cells into early endoderm derivatives and their molecular characterization", Stem Cell Research 8(3) 335-345 (2012).
Riemenschneider et al., "Expression of oligodendrocyte lineage genes in oligodendroglial and astrocytic gliomas", Acta Neuropathol 107 277-282 (2004).

* cited by examiner

DIFFERENTIATION PROPENSITY:
HIGH ↑
MEDIUM ↗→↘
LOW ↓

| CELL LINE | NEURAL LINEAGE | | HEMATOPOIETIC LINEAGE | | ECTODERM GERM LAYER | | MESODERM GERM LAYER | | ENDODERM GERM LAYER | |
|---|---|---|---|---|---|---|---|---|---|---|
| HUES1 | ↓ | -1.84 | → | -0.30 | ↓ | -1.56 | → | 0.06 | ↘ | -0.59 |
| HUES3 | → | -0.29 | → | -0.01 | → | -0.23 | → | -0.07 | → | 0.08 |
| HUES6 | ↘ | -0.78 | → | -0.26 | ↘ | -0.51 | → | -0.05 | → | -0.47 |
| HUES8 | → | -0.15 | ↗ | 0.69 | → | -0.17 | ↗ | 0.68 | ↗ | 1.45 |
| HUES9 | ↘ | -0.89 | → | 0.31 | ↘ | -0.75 | ↗ | 0.51 | → | 0.37 |
| HUES28 | ↘ | -1.33 | → | -0.11 | ↘ | -0.91 | ↗ | 1.03 | → | -0.07 |
| HUES44 | ↗ | 0.70 | → | -0.27 | ↗ | 0.52 | → | -0.48 | → | -0.45 |
| HUES45 | → | -0.46 | → | -0.26 | → | -0.49 | → | -0.02 | ↗ | 0.65 |
| HUES48 | ↗ | 0.83 | → | 0.18 | ↗ | 0.70 | → | 0.24 | ↗ | 0.55 |
| HUES49 | → | 0.19 | → | 0.07 | → | 0.03 | ↘ | -0.66 | → | -0.26 |
| HUES53 | ↘ | -0.95 | ↗ | 0.65 | ↘ | -1.19 | → | -0.22 | → | -0.20 |
| HUES62 | → | 0.25 | → | -0.15 | → | 0.15 | ↘ | -0.60 | → | 0.24 |
| HUES63 | ↗ | 0.62 | → | 0.39 | ↗ | 0.72 | → | 0.34 | ↗ | 0.61 |
| HUES64 | ↗ | 1.45 | → | -0.07 | ↗ | 1.44 | ↘ | -0.56 | ↘ | -0.61 |
| HUES65 | → | 0.19 | → | 0.02 | → | 0.22 | → | 0.19 | → | -0.15 |
| HUES66 | ↗ | 0.59 | ↘ | -0.67 | → | 0.36 | ↘ | -1.22 | → | -0.37 |
| H1 | ↑ | 1.54 | → | -0.29 | ↗ | 1.21 | → | 0.07 | ↘ | -0.56 |
| H9 | ↗ | 1.08 | → | 0.01 | ↗ | 1.10 | ↗ | 0.55 | → | -0.16 |

*FIG. 1B*
*PRIOR ART*

DIFFERENTIATION PROPENSITY:
HIGH ↑
MEDIUM ↗→↘
LOW ↓

| CELL LINE | NEURAL LINEAGE | | HEMATOPOIETIC LINEAGE | | ECTODERM GERM LAYER | | MESODERM GERM LAYER | | ENDODERM GERM LAYER | |
|---|---|---|---|---|---|---|---|---|---|---|
| hiPS 11a | ↘ | -0.69 | → | 0.18 | → | -0.37 | → | -0.23 | ↗ | 0.83 |
| hiPS 11b | ↘ | -1.17 | → | -0.23 | ↘ | -0.96 | ↘ | -1.03 | → | 0.47 |
| hiPS 11c | → | -0.22 | → | 0.40 | → | -0.03 | → | -0.16 | → | 0.37 |
| hiPS 15b | → | -0.48 | ↘ | -0.78 | ↘ | -0.63 | ↘ | -1.11 | ↓ | -2.49 |
| hiPS 17a | → | 0.19 | → | 0.05 | → | 0.33 | → | 0.00 | ↗ | 1.16 |
| hiPS 17b | → | -0.07 | → | -0.48 | → | -0.02 | ↘ | -0.83 | → | 0.20 |
| hiPS 18a | → | 0.28 | ↘ | -0.52 | → | 0.31 | ↘ | -0.67 | → | 0.20 |
| hiPS 18b | ↗ | 0.80 | ↘ | -0.72 | ↗ | 0.84 | ↘ | -0.62 | → | 0.15 |
| hiPS 18c | ↗ | 0.93 | ↘ | -0.65 | ↗ | 1.05 | → | -0.41 | → | 0.10 |
| hiPS 20b | → | -0.37 | → | -0.47 | → | -0.30 | ↘ | -1.16 | ↗ | 0.56 |
| hiPS 27b | ↗ | 0.52 | → | -0.50 | ↗ | 0.68 | ↘ | -0.71 | → | -0.42 |
| hiPS 27e | ↓ | -1.61 | ↘ | -1.04 | ↓ | -2.12 | ↓ | -1.82 | ↓ | -3.27 |
| hiPS 29d | → | -0.25 | → | -0.04 | → | 0.00 | → | -0.11 | ↗ | 0.83 |
| hiPS 29e | ↘ | -0.99 | ↘ | -0.60 | ↘ | -1.15 | ↘ | -1.14 | ↘ | -1.08 |

| | CONTROL | | PLURI | | ENDO | | MESENDO | | MESO | | ECTO | |
|---|---|---|---|---|---|---|---|---|---|---|---|---|
| | mu | sig | mu | sig | mu | sig | mu | sig | mu | sig | mu | sig |
| BJ FIBROBLAST | -0.16 | 4.49 | -7.53 | 4.88 | 1.04 | 3.10 | -2.13 | 4.46 | 2.74 | 4.81 | 0.96 | 3.25 |
| H9 ESC | -0.06 | 0.64 | -0.32 | 1.83 | 0.97 | 1.06 | 0.39 | 0.75 | -0.10 | 0.85 | 0.20 | 1.02 |
| hNSC | -0.70 | 2.43 | -9.46 | 8.03 | -0.53 | 4.81 | -2.42 | 1.73 | -0.29 | 2.46 | 1.26 | 2.75 | t VALUES RELATIVE TO REFERENCE SAMPLE POPULATION

| | CONTROL | | PLURI | | ENDO | | MESENDO | | MESO | | ECTO | |
|---|---|---|---|---|---|---|---|---|---|---|---|---|
| | MIN | MAX | MIN | MAX | MIN | MAX | MIN | MAX | MIN | MAX | MIN | MAX |
| BJ FIBROBLAST | 0.00 | 0.40 | 0.00 | 0.07 | 0.00 | 0.97 | 0.00 | 0.98 | 0.00 | 0.90 | 0.00 | 0.82 |
| H9 ESC | 0.36 | 0.90 | 0.00 | 0.90 | 0.01 | 0.71 | 0.18 | 0.80 | 0.06 | 1.00 | 0.03 | 0.97 |
| hNSC | 0.00 | 0.50 | 0.00 | 0.43 | 0.00 | 0.75 | 0.00 | 0.74 | 0.00 | 0.93 | 0.00 | 0.86 | p VALUES RELATIVE TO REFERENCE SAMPLE POPULATION 0-1: COMPARABLE EXPRESSION TO THE REFERENCE LEVEL
>1: HIGHER EXPRESSION
<0: LOWER EXPRESSION

*FIG. 3*

EXPRESSION RELATIVE TO A REFERENCE STANDARD (E.G., REFERENCE LEVEL FOR THE CLASS OF EARLY DEVELOPMENTAL GENE)

Legend: ↑ HIGHER, ↗ COMPARABLE, → LOWER

| SAMPLES | EXPECTED CATEGORY | CONTROL | MESENDO | PLURI | ENDO | MESO | ECTO |
|---|---|---|---|---|---|---|---|
| H9 ESC-CM/Gtx | PLURI | -0.11 | 0.39 | -1.39 | -0.26 | 0.71 | 0.62 |
| H9 ESC-Day7EB | ENDO, ECTO, MESO | 0.04 | 0.96 | -2.89 | 1.77 | 4.22 | 0.87 |
| H9 ESC-Day14EB | ENDO, ECTO, MESO | -1.43 | -1.17 | -7.27 | 1.98 | 4.78 | 1.03 |
| BS3C iPSC | PLURI | -0.34 | -0.18 | -0.54 | 0.20 | 0.52 | 0.25 |
| BS3C-Day7EB | ENDO, ECTO, MESO | 0.13 | 0.96 | -2.23 | 1.62 | 3.55 | 1.98 |
| BS3C-Day14EB | ENDO, ECTO, MESO | -0.13 | -0.40 | -3.59 | 2.67 | 5.13 | 2.20 |
| H9 ESC Undiff | PLURI | 0.63 | -0.19 | -0.86 | 0.90 | 1.39 | 2.20 |
| H9 ESC-Day7EB | ENDO, ECTO, MESO | 0.24 | 0.56 | -3.48 | 1.75 | 3.16 | 2.79 |
| H9 ESC-Day14EB | ENDO, ECTO, MESO | 0.47 | -0.42 | -4.26 | 3.07 | 4.57 | 3.11 |
| BS3iii iPSC SP/GTX | PLURI | -0.09 | 0.75 | -0.75 | -1.03 | -0.99 | -1.58 |
| BS3iii SP/GTX-Day7EB | ENDO, ECTO, MESO | 0.19 | -0.39 | -1.73 | 0.14 | 1.37 | 1.70 |
| BS3iii SP/GTX-Day14EB | ENDO, ECTO, MESO | 0.26 | 0.22 | -3.26 | 2.03 | 4.34 | 2.68 |
| BS3-iii iPSC E8-VTN | PLURI | -0.68 | -1.43 | -0.03 | -1.40 | -1.43 | -0.61 |
| BS3-iii-E8-VTN-Day7EB | ENDO, ECTO, MESO | -0.32 | 1.03 | -1.86 | 1.16 | 2.67 | 2.24 |
| BS3-iii-E8-VTN-Day14EB | ENDO, ECTO, MESO | 0.11 | 0.11 | -3.31 | 2.79 | 4.22 | 2.47 |
| DFiPSC-4 P6 | PLURI | -0.21 | -1.00 | 0.04 | -0.91 | -0.92 | 0.88 |
| DFiPSC-4 P13 | PLURI | -0.26 | -1.29 | -0.25 | -0.65 | 0.13 | 0.83 |
| DFiPSC-4-Day7EB | ENDO, ECTO, MESO | 0.05 | 1.07 | -2.53 | 1.56 | 3.93 | 2.26 |
| DFiPSC-4-Day14EB | ENDO, ECTO, MESO | -0.09 | -0.28 | -5.63 | 2.46 | 5.24 | 2.14 |

FIG. 4

DAY 0   DAY 2   DAY 4   DAY 7   DAY 9   DAY 11   DAY 14
|SUSPENSION EB|                    |SEEDED AS MONOLAYER|

HIGHER ↑
COMPARABLE ↗
LOWER ↓

| SAMPLES | EXPECTED CATEGORY | CONTROL | | MESENDO | | PLURI | | ENDO | | MESO | | ECTO | |
|---|---|---|---|---|---|---|---|---|---|---|---|---|---|
| H9-Undiff | PLURI | ↑ | 0.09 | ↑ | -0.68 | ↑ | -0.04 | ↑ | -0.27 | ↑ | -0.45 | ↑ | 0.19 |
| H9-ESC-P50 | ENDO, ECTO, MESO | ↗ | -0.18 | ↑ | 0.21 | ↑ | 0.31 | ↑ | 0.43 | ↑ | -0.12 | ↗ | 0.67 |
| EB Day2 | ENDO, ECTO, MESO | ↑ | -0.07 | ↑ | -0.26 | ↓ | -1.20 | ↗ | 0.72 | ↑ | 0.38 | ↓ | 1.48 |
| EB Day4 | ENDO, ECTO, MESO | ↑ | -0.02 | ↑ | -0.35 | ↓ | -2.54 | ↓ | 1.21 | ↓ | 1.67 | ↓ | 3.19 |
| EB Day7 | ENDO, ECTO, MESO | ↗ | -0.54 | ↑ | 0.04 | ↓ | -4.25 | ↓ | 1.33 | ↓ | 2.42 | ↓ | 3.02 |
| EB Day9 | ENDO, ECTO, MESO | ↑ | -0.12 | ↗ | -0.59 | ↓ | -5.32 | ↓ | 2.78 | ↓ | 4.55 | ↓ | 3.07 |
| EB Day11 | ENDO, ECTO, MESO | ↑ | 0.04 | ↑ | -0.23 | ↓ | -4.39 | ↓ | 2.72 | ↓ | 4.30 | ↓ | 3.23 |
| EB Day14 | ENDO, ECTO, MESO | ↑ | 0.04 | ↑ | -0.23 | ↓ | -4.39 | ↓ | 2.72 | ↓ | 4.30 | ↓ | 3.23 |

*FIG. 5*

DAY 0 — SEEDED AS MONOLAYER / SUSPENSION EB  
DAY 4 — SUSPENSION EB / SEEDED AS MONOLAYER  
DAY 7

HIGHER ↑ / COMPARABLE ↗ / LOWER ↓

| SAMPLES | EXPECTED CATEGORY | CONTROL | MESENDO | PLURI | ENDO | MESO | ECTO | |
|---|---|---|---|---|---|---|---|---|
| H9 ESC | PLURI | ↑ -0.06 | ↑ 0.39 | ↑ -0.32 | ↗ 0.97 | ↑ -0.10 | ↑ 0.20 | 100% SSEA4+ |
| H9-D4 EBmonolayer | ENDO, ECTO, MESO | ↗ 0.65 | ↑ 0.34 | ↓ -2.70 | ↓ 1.89 | ↓ 2.05 | ↓ 3.54 | 77% SSEA4+ |
| EB-D7 EBmonolayer | ENDO, ECTO, MESO | ↓ 1.42 | ↗ -0.51 | ↓ -3.74 | ↓ 2.44 | ↓ 3.24 | ↓ 3.95 | 87% SSEA4+ |
| EB-D4 EBsuspension | ENDO, ECTO, MESO | ↗ 0.59 | ↗ 1.16 | ↓ -2.65 | ↓ 3.22 | ↓ 2.85 | ↓ 3.38 | 40% SSEA4+ |
| EB-D7 EBsuspension | ENDO, ECTO, MESO | ↗ 0.70 | ↗ 0.76 | ↓ -3.28 | ↓ 3.29 | ↓ 3.73 | ↓ 3.61 | 12% SSEA4+ |
| EB-D7 EBtraditional (4+3) | ENDO, ECTO, MESO | ↑ 0.26 | ↑ 0.25 | ↓ -4.32 | ↓ 2.32 | ↓ 3.36 | ↓ 2.41 | 14% SSEA4+ |

FIG. 6

PLURIPOTENT CELLS

HIGHER ↑ / COMPARABLE ↗ / LOWER ↓

| SAMPLES | EXPECTED CATEGORY | CONTROL | MESENDO | PLURI | ENDO | MESO | ECTO | |
|---|---|---|---|---|---|---|---|---|
| BS4-iPS3 P8 | PLURI | ↑ -0.18 | ↑ 0.21 | ↑ 0.31 | ↑ 0.43 | ↑ -0.12 | ↗ 0.67 | |
| BS4-iPS5 P8 | PLURI | ↑ -0.12 | ↗ -0.59 | ↓ -5.32 | ↓ 2.78 | ↓ 4.55 | ↓ 3.07 | BAD CLONE OR BAD CULTURE? |
| BS4-iPS7 P8 | PLURI | ↑ 0.09 | ↑ -0.68 | ↑ -0.04 | ↑ -0.27 | ↑ -0.45 | ↑ 0.19 | |
| BS4-iPS8 P8 | PLURI | ↑ -0.38 | ↗ 1.08 | ↑ 0.52 | ↑ 0.27 | ↑ -0.22 | ↑ -0.10 | |
| BS4-iPS1 P8 | PLURI | ↑ -0.13 | ↗ 0.92 | ↑ 0.30 | ↑ 0.49 | ↑ -0.14 | ↑ 0.10 | |

LINEAGE-SKEWED CELLS

HIGHER ↑
COMPARABLE ↗
LOWER ↓

| SAMPLES | EXPECTED CATEGORY | CONTROL | MESENDO | PLURI | ENDO | MESO | ECTO | |
|---|---|---|---|---|---|---|---|---|
| H9 ESC | PLURI | ↑ -0.06 | ↑ 0.39 | ↑ -0.32 | ↗ 0.97 | ↑ -0.10 | ↑ 0.20 | |
| hNSC | ECTO | ↗ -0.70 | ↓ -2.42 | ↓ -9.46 | ↗ -0.53 | ↑ -0.29 | ↑ 1.26 | |
| hNSCDup | ECTO | ↑ -0.18 | ↓ -2.25 | ↓ -6.18 | ↑ -0.01 | ↑ -0.40 | ↑ 2.04 | SKEWED TO ECTODERM |
| hNSC-D5 Diff | ECTO | ↑ -0.35 | ↓ -3.33 | ↓ -4.69 | ↑ 0.07 | ↓ -1.54 | ↑ 1.56 | |

FIG. 7C

NON-PLURIPOTENT CELLS

HIGHER ↑
COMPARABLE ↗
LOWER ↓

| SAMPLES | EXPECTED CATEGORY | CONTROL | MESENDO | PLURI | ENDO | MESO | ECTO | |
|---|---|---|---|---|---|---|---|---|
| BJ FIBROBLAST | NON-PLURI | ↑ -0.16 | ↓ -2.13 | ↓ -7.53 | ↑ 1.04 | ↑ 2.74 | ↗ 0.96 | NOT PLURIPOTENT |
| HDFfetal | NON-PLURI | ↓ -2.79 | ↓ -2.74 | ↓ -12.73 | ↓ -1.91 | ↑ 0.37 | ↑ -0.30 | |
| MEF | NON-PLURI | ↓ -6.75 | ↓ -7.75 | ↓ -8.12 | ↑ -0.24 | ↑ 3.41 | ↑ 4.14 | ~10 PRIMERS CROSS REACT WITH MOUSE |
| MEF + H9ESC (500 TO ~3-5 MILLION CELLS ~10-15% MEF CONTAMINATION) | PLURI WITH NON-PLURI CONTAMINATION | ↑ -0.16 | ↑ 0.01 | ↑ -0.10 | ↗ 0.62 | ↑ 0.05 | ↑ 0.28 | MEF PRESENCE HAS MINIMAL IMPACT ON ESC SIGNATURE |

SEQUENCE LISTING

<160> NUMBER OF SEQ ID NOS: 96

<210> SEQ ID NO 1
<211> LENGTH: 3075
<212> TYPE: DNA
<213> ORGANISM: Homo sapiens

<400> SEQUENCE: 1

| | | | | | | |
|---|---|---|---|---|---|---|
| agatgcatga | agattcagct | gtgaagatac | tataaaaagg | gaagagaagg | accgagacag | 60 |
| aagcaacaac | ggaactgtca | gtgcggagta | gggctaaact | cagttccatt | gttaagcaag | 120 |
| gaaaaacaaa | caatacattg | aatttgacaa | cccactgaag | ttgcagataa | tgaggactta | 180 |
| ccattatata | ccattattca | tctggaccta | tatgttccat | acagttgaca | ccatcctatt | 240 |
| acaagaaaaa | cctaacagtt | atttatcaag | caaaaagata | gcgggtctga | caaaagatga | 300 |
| cggtaaaatg | ctacgtcgca | ccaagcgtgg | ctggatgtgg | aatcagttct | tcttattgga | 360 |
| agagtacaca | ggtactgaca | cacaatatgt | aggcaagctt | cacactgacc | aagataaagg | 420 |
| agatggaaat | ttaaaataca | tactaacagg | agatggggct | ggcagtctat | ttgttataga | 480 |
| tgaaaataca | ggagacattc | atgctgcaaa | gaaactagac | agagaagaaa | aatctctgta | 540 |
| cattcttcgt | gccaaggcta | tagacagaaa | aactgggcgg | caggtggaac | cggaatcgga | 600 |
| atttatcatt | aaaatacatg | atatcaatga | caatgagcca | aaatttacaa | aagacttata | 660 |
| cactgccagt | gttcctgaaa | tgtctggagt | cggtacatct | gttatacaag | taactgcaac | 720 |
| agatgcagat | gacgccaact | atggaaatag | tgccaaagtg | gtctatagca | tattgcaagg | 780 |
| acagccatat | ttttcagtgg | acccagaatc | aggcataata | aaaactgcat | taccagacat | 840 |
| gagcagagaa | aatagagagc | agtaccaggt | tgttatacag | gccaaagaca | tgggtggcca | 900 |
| gatgggaggc | ctttctggaa | ccaccacagt | gaacatcacg | ctgacagatg | tcaacaacaa | 960 |
| ccctcctcga | tttccccaga | gtacgtatca | atttaattct | cctgagtctg | tacctcttgg | 1020 |
| aactcatctt | ggaaggataa | aagccaatga | ccctgacgtg | ggggaaaatg | cagaaatgga | 1080 |
| gtatagcatt | gctgaaggag | atggtgcaga | catgttcgat | gtcatcactg | acaaggatac | 1140 |
| acaggaaggg | attataactg | tcaaacagaa | tttagatttt | gaaaatcaaa | tgctctatac | 1200 |
| tttaagagtg | gatgcaagta | acactcaccc | tgatccacga | ttcttacacc | tgggaccttt | 1260 |
| caaagataca | gctgtggtca | aaatatctgt | ggaagatata | gatgagcctc | ctgtgttcac | 1320 |
| taaagtctct | tacttgatag | aagtagatga | agatgtaaag | gagggcagta | tcattggaca | 1380 |
| ggttacagca | tacgatccag | atgccaggaa | caattttaata | aagtactctg | ttgatcggca | 1440 |
| tactgatatg | gaccgtattt | ttggtattca | ctcagaaaat | ggttctattt | tcactttgaa | 1500 |
| agcccttgac | cgggaatcat | ctccttggca | taacatcact | gttacagcca | cagaaataaa | 1560 |
| taacccaaaa | caaagtagcc | acatccctgt | cttcatcaga | attctagata | taaatgacca | 1620 |
| tgctccggaa | tttgccatgt | attatgaaac | atttgtttgt | gaaaatgcaa | acctgggca | 1680 |
| gttgattcag | actgtcagtg | tcatggataa | ggatgaccct | ccccgaggtc | acaaattctt | 1740 |
| ttttgaacca | gtgccagaat | ttactctcaa | tccgaatttc | accattgtag | ataataaaga | 1800 |
| taatacagca | ggaatcatga | ctcggaaaga | tggctacagt | cgcaacaaaa | tgagcaccta | 1860 |
| cttattgccg | attttaatct | ttgacaacga | ttatccaatt | caaagcagca | ctggtacact | 1920 |
| cactatccgt | gtgtgtgcct | gcgataatca | aggaaacatg | caatcctgca | ccgcagaagc | 1980 |
| cctgatcctt | tcagccggcc | tgagcacggg | agctctcgtt | gcgattctac | tctgtgtcct | 2040 |
| catactgctt | attttagtcg | tgttgtttgc | tgcattgaag | aggcaaagaa | aaaaggaacc | 2100 |

```
tctgataatt tcaaaagacg atgtccggga caacattgtg acctacaacg atgaaggcgg    2160
cggggaagaa gatacccaag cttttgacat tggcacatta aggaatccag aggcaagaga    2220
agacagtaaa cttagacggg atgtaatgcc tgaaactatt tttcagataa ggaggactgt    2280
gcctctgtgg gaaatattg atgtacaaga ttttatccat cgaagattaa aagaaaacga     2340
cgcagaccca agtgcacctc catatgattc gctggcaacg tatgcctatg aagggaatga    2400
ttccatagca gattcgctca gttctttgga atctctcaca gctgattgta accaagatta    2460
tgattacctc agtgactggg ggcctcgttt caaaaaactt gccgatatgt atggggggtga   2520 tgatagtgac cgagactaag aggattgttt gacttaatca atattagtgg aagtactgtc    2580
tatgttatta gattgagtgg cctgcattct cttcctggga ggaaatcttt caaaaattga    2640
agttacaaac aatacgtaga tgttgtcaag tagggatttg cttaatcagt aagtctttgt    2700
gaatgaatac gaatgataca gattttaaa aagtaataa ccagttcacc ctctttgcct      2760
aacaatctcg gaaggaaaat atatcacatc aataatcaat aaaataagt aaaaggcttt     2820 ttgtgccttt tcttaggtat aataatttat aaatgttttc ttaactgact ttcagtcacc    2880
tttacaatta aactaaatat tgtgcaaccg ctttgtaaat taatatgaag aagatatatc    2940
cctaatgaaa taggaatgac tattactgcc atatttattt agttgaagaa tgtctttgtg    3000
ttaattcatt catattttta taaatgtata tttatatttt tgtattttta tgaaataaac    3060
tagtatttat aaaac                                                    3075

<210> SEQ ID NO 2
<211> LENGTH: 5087
<212> TYPE: DNA
<213> ORGANISM: Homo sapiens

<400> SEQUENCE: 2
aacgggcgcc gcggcgggga gaagacgcag agcgctgctg ggctgccggg tctcccgctt      60
ccccctcctg ctccaagggc ctcctgcatg agggcgcggt agagacccgg acccgcgccg     120
tgctcctgcc gtttcgctgc gctccgcccg ggcccggctc agccaggccc gcggtgagc      180 catgattcgc ctcgggctc cccagacgct ggtgctgctg acgctgctcg tcgccgctgt     240
ccttcggtgt cagggccagg atgtccagga ggctggcagc tgtgtgcagg atgggcagag    300
gtataatgat aaggatgtgt ggaagccgga gccctgccgg atctgtgtct gtgacactgg    360
gactgtcctc tgcgacgaca taatctgtga agacgtgaaa gactgcctca gccctgagat    420
ccccttcgga gagtgctgcc ccatctgccc aactgacctc gccactgcca gtgggcaacc    480
aggaccaaag ggacagaaag gagaacctgg agacatcaag gatattgtag acccaaagg    540 acctcctggg cctcagggac ctgcagggga acaaggaccc agaggggatc gtggtgacaa    600
aggtgaaaaa ggtgccccctg gacctcgtgg cagagatgga gaacctggga ccctggaaa    660 tcctggcccc cctggtcctc ccggcccccc tggtccccct ggtcttggtg gaaactttgc    720
tgcccagatg gctggaggat tgatgaaaaa ggctggtggc gcccagttgg gagtaatgca    780
aggaccaatg ggccccatgg gacctcgagg acctccaggc cctgcaggtg ctcctgggcc    840
tcaaggattt caaggcaatc ctggtgaacc tggtgaacct ggtgtctctg gtcccatggg    900
tccccgtggt cctcctggtc cccctggaaa gcctggtgat gatggtgaag ctggaaaacc    960
tggaaaagct ggtgaagggg gtccgccctgg tcctcagggt gctcgtggtt tcccaggaac   1020
cccaggcctt cctggtgtca aggtcacag aggttatcca ggcctggacg gtgctaaggg    1080
```

-continued

```
agaggcgggt gctcctggtg tgaagggtga gagtggttcc ccgggtgaga acggatctcc    1140
gggcccaatg gtcctcgtg gcctgcctgg tgaaagagga cggactggcc ctgctggcgc     1200
tgcgggtgcc cgaggcaacg atggtcagcc aggccccgca gggcctccgg gtcctgtcgg    1260
tcctgctggt ggtcctggct tccctggtgc tcctggagcc aagggtgaag ccggccccac    1320
tggtgcccgt ggtcctgaag gtgctcaagg tcctcgcggt gaacctggta ctcctgggtc    1380
ccctgggcct gctggtgcct ccggtaaccc tggaacagat ggaattcctg agccaaagg    1440 atctgctggt gctcctggca ttgctggtgc tcctggcttc cctgggccac ggggccctcc    1500 tggcccctcaa ggtgcaactg gtcctctggg cccgaaaggt cagacgggtg aacctggtat   1560
tgctggcttc aaaggtgaac aaggccccaa gggagaacct ggccctgctg ccccagggg    1620 agcccctgga cccgctggtg aagaaggcaa gagaggtgcc cgtggagagc ctggtggcgt    1680
tgggcccatc ggtccccctg gagaaagagg tgctcccggc aaccgcggtt tcccaggtca    1740
agatggtctg gcaggtccca agggagcccc tggagagcga gggcccagtg gtcttgctgg    1800
ccccaaggga gccaacggtg accctggccg tcctggagaa cctggccttc ctggagcccg    1860
gggtctcact ggccgccctg gtgatgctgg tcctcaaggc aaagttggcc cttctggagc    1920
ccctggtgaa gatggtcgtc ctggacctcc aggtcctcag ggggctcgtg ggcagcctgg    1980
tgtcatgggt ttccctggcc ccaaaggtgc aacggtgag cctggcaaag ctggtgagaa     2040
gggactgcct ggtgctcctg gtctgagggg tcttcctggc aaagatggtg agacaggtgc    2100
tgcaggaccc cctggcccctg ctggacctgc tggtgaacga ggcgagcagg gtgctcctgg    2160
gccatctggg ttcagggac ttcctggccc tcctggtccc caggtgaag gtggaaaacc     2220 aggtgaccag ggtgttcccg gtgaagctgg agccctggc ctcgtgggtc ccaggggtga    2280
acgaggtttc ccaggtgaac gtggctctcc cggtgcccag ggcctccagg gtccccgtgg    2340
cctccccggc actcctggca ctgatggtcc caaaggtgca tctggcccag caggcccccc    2400
tggggctcag ggccctccag gtcttcaggg aatgcctggc gagaggggag cagctggtat    2460
cgctgggccc aaaggcgaca ggggtgacgt tggtgagaaa ggccctgagg gagccctgg    2520 aaaggatggt ggacgaggcc tgacaggtcc cattggcccc cctggcccag ctggtgctaa    2580
tggcgagaag ggagaagttg gacctcctgg tcctgcagga agtgctggtg ctcgtggcgc    2640
tccgggtgaa cgtggagaga ctgggcccc cggaccagcg ggatttgctg gcctcctgg    2700 tgctgatggc cagcctgggg ccaagggtga gcaaggagag gccggccaga aaggcgatgc    2760 tggtgccct ggtcctcagg gccctctgg agcacctggg cctcagggtc ctactggagt     2820
gactggtcct aaaggagccc gaggtgccca aggcccccg ggagccactg gattccctgg     2880
agctgctggc cgcgttggac ccccaggctc caatggcaac cctggacccc ctggtccccc    2940
tggtccttct ggaaaagatg gtcccaaagg tgctcgagga cacagcggcc ccctggccg    3000 agctggtgaa cccggcctcc aaggtcctgc tggacccct ggcgagaagg gagagcctgg     3060
agatgacggt ccctctggtg ccgaaggtcc accaggtccc cagggtctgg ctggtcagag    3120
aggcatcgtc ggtctgcctg ggcaacgtgg tgagagagga ttccctggct tgcctggccc    3180
gtcgggtgag cccggcaagc aggtgctccc tggagcatct ggagacagag tcctcctgg    3240 ccccgtgggt cctcctggcc tgacgggtcc tgcaggtgaa cctggacgag agggaagccc    3300
cggtgctgat ggccccctg gcagagatgg cgctgctgga gtcaagggtg atcgtggtga    3360
gactggtgct gtgggagctc ctggagcccc tgggcccct ggctcccctg gccccgctgg    3420
tccaactggc aagcaaggag acagaggaga agctggtgca caaggcccca tgggacctc    3480
```

```
aggaccagct ggagcccggg gaatccaggg tcctcaaggc cccagaggtg acaaaggaga     3540
ggctggagag cctggcgaga gaggcctgaa gggacaccgt ggcttcactg gtctgcaggg     3600
tctgcccggc cctcctggtc cttctggaga ccaaggtgct tctggtcctg ctggtccttc     3660
tggccctaga ggtcctcctg gccccgtcgg tccctctggc aaagatggtg ctaatggaat     3720
ccctggcccc attgggcctc ctggtccccg tggacgatca ggcgaaaccg gccctgctgg     3780
tcctcctgga aatcctggac cccctggtcc tccaggtccc cctggccctg gcatcgacat     3840
gtccgccttt gctggcttag gcccgagaga aagggcccc gaccccctgc agtacatgcg     3900
ggccgaccag gcagccggtg gcctgagaca gcatgacgcc gaggtggatg ccacactcaa     3960
gtccctcaac aaccagattg agagcatccg cagccccgag ggctcccgca agaaccctgc     4020
tcgcacctgc agagacctga aactctgcca ccctgagtgg aagagtggag actactggat     4080
tgaccccaac caaggctgca ccttggacgc catgaaggtt ttctgcaaca tggagactgg     4140
cgagacttgc gtctacccca atccagcaaa cgttcccaag aagaactggt ggagcagcaa     4200
gagcaaggag aagaaacaca tctggttttgg agaaaccatc aatggtggct ccatttcag     4260 ctatggagat gacaatctgg ctcccaacac tgccaacgtc cagatgacct tcctacgcct     4320
gctgtccacg gaaggctccc agaacatcac ctaccactgc aagaacagca ttgcctatct     4380
ggacgaagca gctggcaacc tcaagaaggc cctgctcatc cagggctcca atgacgtgga     4440
gatccgggca gagggcaata gcaggttcac gtacactgcc ctgaaggatg gctgcacgaa     4500
acataccggt aagtgggcag agactgttat cgagtaccgg tcacagaaga cctcacgcct     4560
ccccatcatt gacattgcac ccatggacat aggagggccc gagcaggaat cggtgtgga     4620 catagggccg gtctgcttct tgtaaaaacc tgaacccaga acaacacaa tccgttgcaa     4680 acccaaagga cccaagtact ttccaatctc agtcactcta ggactctgca ctgaatggct     4740
gacctgacct gatgtccatt catcccaccc tctcacagtt cggacttttc tccctctct     4800 ttctaagaga cctgaactgg gcagactgca aaataaatc tcggtgttct attatttat     4860 tgtcttcctg taagacctc gggtcaaggc agaggcagga actaactggt gtgagtcaa     4920 atgcccctg agtgactgcc cccagcccag gccagaagac ctcccttcag gtgccgggcg     4980
caggaactgt gtgtgtccta cacaatggtg ctattctgtg tcaaacacct ctgtattttt     5040
taaaacatca attgatatta aaaatgaaaa gattattgga aagtaca               5087
```

<210> SEQ ID NO 3
<211> LENGTH: 2896
<212> TYPE: DNA
<213> ORGANISM: Homo sapiens

<400> SEQUENCE: 3

```
taggcggatg ccgccatgca gcactacggg gtgaacggct actcactgca cgccatgaac      60
tcactcagcg ccatgtacaa cctgcaccag caggcagccc agcaggccca gcatgccccc     120
gactaccggc cttcagtgca tgcgcttaca ttggctgagc gcctggctgg ctgtacattt     180
caagacatca tcttggaggc ccgttatggt tcccagcacc gcaaacaacg tcgcagccgc     240
acagcgttca cggctcagca gctcgaggcc ctggaaaaga ccttccagaa gactcactac     300
ccagatgtgg tgatgcgtga gaggctggcc atgtgcacca acctgcctga ggcccgggtg     360
caggtgtggt tcaagaaccg ccgggccaag ttccggaaga agcagcgtag cctgcagaag     420
gaacagctcc agaagcagaa ggaggctgag ggctcccatg gggaaggcaa ggccgaggcc     480
```

```
cccactccag ataccagct ggacactgag cagcccccac gtctgcctgg cagcgacccc      540
cctgctgagc ttcacctgag tctgtctgag cagtcagcca gtgagtcagc ccccgaggat     600
cagccggacc gtgaggagga ccccagggca ggggctgagg accccaaagc tgagaagagc     660
cctggggctg acagcaaggg gctgggctgc aagaggggca gccccaaggc agattcccca     720
ggcagcctga ccatcactcc tgtggcccca gggggtggcc tcctgggccc ctcccactcc     780
tattcctcgt ccccgctgag cctcttccgt ctgcaggagc aattccgcca gcacatggcg     840
gccaccaaca acctggtgca ctactcgtcc ttcgaagtag ggggtccggc ccctgctgct     900
gcagcggcgg ctgctgctgt gccctacctg ggcgtcaaca tggccccgct gggctcactg     960
cactgccagt cctactacca gtccctgtca gcagccgctg ctgcccacca gggtgtgtgg    1020
gggtctcctc tgctgcctgc accccagca ggcctggctc ctgcatcagc taccctgaac     1080
agtaaaacca caagcatcga gaacctgcgg ctccgggcca agcagcacgc ggcctccctg    1140
ggactcgata cgctgcccaa ctgactgtct ggcttccaac ccagccaggg gtcttaggtg    1200
tcccctccta gccctgtggt tatccctagg tggctctcga ggagttaact ccatgagccc    1260
agggatccta gggcctgggg tcctgttccc tgctccgctt ccccataccc cagcccgagg    1320
tgaagcccac acctacacac cctctgcatg ccctgcctg  acccatgg aggccgaata     1380 gggaggaggt gagaggctgg ggtgccccaa gcttccctcg gagaagtgag aggctctccc    1440
tggctagatc ctcatctcaa tagcacctcc tcccttttct ccctatcctt ctgccccta     1500 gtaagtctac gtgtggaatg tgagatataa atataaatat ataaagctat attttcaggc    1560
tcctgcctgc ccaggcccc ctgccccact cccatctctt cttccctgcc accctccct    1620 gcagcctccg cggctcactc cagccatccc ttctgtttct ccttctctct ccttccttct    1680
tcccttgatc tccctcttcc tgtctctgtc ctggtccctg ccccgtctc ggcccagcct    1740 ctgtattctc caccttgat ctttctcctt gtctctcccg ctgcccctgg tttcttcctt     1800
tggtgttggc tgtgttggta tcatcagttc ttgagctata ttttgtttgg ggttgtggct    1860
ggttttggtt ttagtaattt tgcgacttcc cgttgctctc cttctattcc cttccttctg    1920
ccctgcctgc ctccctgcac ctgcggcctc tctaggaagc tgttcctttc tatgcccaat    1980
agaagcaaca aggccctagc tggagactct ggggatctgg agctgcaggc aggaggtggc    2040
actggctccc actcccaccc ctgcccaggc tggcatctag aaggcgtcat gaattacttt    2100
ctcttctctc ttctcaattt tgaggtcctc attcccaaga ttgaggaggc agtagttaat    2160
ctgggaaggc agtagaatgg ccagcattcc tgcctgtaag tcttcccaag acagaggccc    2220
ggtgacacag ttcagccagg actgaccaca gggctctaga gctctctttg gtgagacttc    2280
cctggatgga gagcagcagc aggggaagag gtgctctcag agacagcagg gctggtgctc    2340
ttctcccaca agctgagcct ccacgttcag cagatactgt ccaaggcagg ggtacggctg    2400
accaggaatg aaggttgaac tctgctcctg agcacggtgc gtgcaaagca tatagcagca    2460
cataggctca ggcttctgta ggcttcctgt cccagagcca attatggaag taagggcttc    2520
cctccagcta gtcactggaa tggaaaagtg tgttcctgtt catagccagg aaacccagct    2580
cagcaaactc cctttcaaag ctgtgtgacc ggctgggcat ggtggctcac acctgtaatc    2640
ccagcacttt gggaggccaa ggcaggcaat cacctgaggt caggagttca agaccagcct    2700
ggctaacatg tgaaactaat aataatacaa aaattagctg ggcgtggtgg cacatgcctg    2760
taatcccagc tacttgggag gctgagttgg gaggattgct gcaatctggg aggtggaagt    2820
tgcagtgagc cgagatcatg ccactgcact ccagcctggg cgacggagtg agactccatc    2880
```
tcaaaaaaaa aaaaaa                                                         2896

<210> SEQ ID NO 4
<211> LENGTH: 1378
<212> TYPE: DNA
<213> ORGANISM: Homo sapiens

<400> SEQUENCE: 4
atggggaacc gcagcaccgc ggacgcggac gggctgctgg ctgggcgcgg gccggccgcg        60
ggggcatctg cggggcatc tgcggggctg gctgggcagg gcgcggcggc gctggtgggg       120
ggcgtgctgc tcatcggcgc ggtgctcgcg gggaactcgc tcgtgtgcgt gagcgtggcc       180
accgagcgcg ccctgcagac gcccaccaac tccttcatcg tgagcctggc ggccgccgac       240
ctcctcctcg ctctcctggt gctgccgctc ttcgtctact ccgaggtcca gggtggcgcg       300
tggctgctga gccccgcct gtgcgacgcc ctcatggcca tggacgtcat gctgtgcacc       360
gcctccatct tcaacctgtg cgccatcagc gtggacaggt tcgtggccgt ggccgtgccg       420
ctgcgctaca accggcaggg tgggagccgc cggcagctgc tgctcatcgg cgccacgtgg       480
ctgctgtccg cggcggtggc ggcgcccgta ctgtgcggcc tcaacgacgt gcgcggccgc       540
gaccccgccg tgtgccgcct ggaggaccgc gactacgtgg tctactcgtc cgtgtgctcc       600
ttcttcctac cctgcccgct catgctgctg ctctactggg ccacgttccg cggcctgcag       660
cgctgggagg tggcacgtcg cgccaagctg cacggccgcg cgccccgccg acccagcggc       720
cctggcccgc cttccccac gccaccgcg ccccgcctcc ccaggaccc ctgcggcccc       780
gactgtgcgc ccccgcgcc cggccttccc cggggtccct gcggccccga ctgtgcgccc       840
gccgcgccca gcctccccca ggaccccgtgc ggccccgact gtgcgccccc gcgcccggc       900
ctcccccgg accctgcgg ctccaactgt gctcccccg acgccgtcag agccgccgcg       960
ctcccaccc agactccacc gcagaccgc aggaggcggc gtgccaagat caccggccgg      1020
gagcgcaagg ccatgagggt cctgccggtg gtggtcgggg ccttcctgct gtgctggacg      1080
cccttcttcg tggtgcacat cacgcaggcg ctgtgtcctg cctgctccgt gccccgcgg       1140
ctggtcagcg ccgtcacctg gctgggctac gtcaacagcg ccctcaaccc cgtcatctac      1200
actgtcttca cgccgagtt ccgcaacgtc ttccgcaagg ccctgcgtgc ctgctgctga      1260
gccgggcacc cccggacgcc ccccggcctg atggccagcc tcagggacc aaggagatgg      1320
ggagggcgct tttgtacgtt aattaaacaa attccttccc aaaaaaaaaa aaaaaaa        1378

<210> SEQ ID NO 5
<211> LENGTH: 2962
<212> TYPE: DNA
<213> ORGANISM: Homo sapiens

<400> SEQUENCE: 5
agctcacaga cccataatcc tgcatttctc taacaagttg tttatggagt tgcttctcca        60
tttgcctaca tcccaaaatt caccccctccc gggtttcttc tgcccctcc tgagtcccgg       120
cctgaaggag ggggagggac gcgggtgcgg gcgcgggtgg gggagggcgg acccgacgca       180
cagggccagc gccgaggcgc cccctctccg ccagcggttg acgccccgg attatttatc       240
cgcaaagtcc cgcgcgcgcc cattgggccg aggcccgagt gtcagcgcga gtcccggctc       300
gccattggct ccgcacacgt gcgggcctga ctcacgtgct tccggtttga aggcaaaaag       360
tgtgcctggg tgattttttt tttaagcgag agagtttgtg caaagatccg agctgtcaga       420

```
gatttgaaaa aaaaaaaaaa aaaaaaaaaa aaaaaaacag cccggcgctg gcggagacgc    480
gctctccctg caaaaaaagc aaaggcgatt aaaggcgctg ccagcctcac gctctgggca    540
cagctgagcg tgacactcgg ggaagtcaaa cccctcacta ctgcctagga agatggctag    600
actttaaata ctatttttt cccttttaaga aaaaaattat tggagctttt tttcttgctt    660 tcttttttcct tttctttttc tttttttcct tcattttttt ggccgtggct tactccccat    720
ttaaatcaaa tcattgaatc tggttgcaga agaaaaaag aaatagccaa gtgtctccat    780
atctggatgt ctacaaatta gagagggaga gacagcgaga tctatctgct agataagaac    840
gagcgatcca ggccagacgc ctgagctttt ttcctgcacc cgccccgtgc cttcgctgag    900
gcttcgcctg cctccttcct ccgcgcaccc ccacgggccg ctggcaaagt ggggtgggga    960
gcgaggcggt gggggcgggg gccggcgcgg cggccggggc ggcggggcgg ccgagcatgg   1020
aagaacagca gccggaacct aaaagtcagc gcgactcggc cctcggcgcg gcggcggcgg   1080
cgactccggg cggcctcagc ctgagcctca gtccgggcgc cagcggcagc agcggcagcg   1140
gcagcgatgg agacagcgtg ccggtgtccc cgcagcctgc gcccccctcg ccgcccgcgg   1200
cgccttgcct ccgcccctg gcccaccacc cgcacctccc cccacacccc cgccccgc     1260 cgcctcagca tctcgcggcg cctgctcacc agccgcagcc agcggcccag ctgcaccgca   1320
ccaccaactt tttcatcgac aacatcctga ggccggactt cggctgcaaa aaggagcagc   1380
cgccaccgca gcttctggtg gctgcggcgg ccagaggagg cgcaggagga ggaggccggg   1440
tcgagcgtga cagaggccag actgccgcag gtagagaccc tgtccacccg ttgggcaccc   1500
gggcgccagg cgctgcctcg ctcctgtgcg ccccggacgc gaactgtggc ccacccgacg   1560
gctcccagcc agccgccgcc ggcgcgggcg cgtctaaagc tgggaacccg gctgcggcgg   1620
cggcggcggc cgcggcggca gtggcggcgg cggcggcggc cgcagcagcc aagccctcgg   1680
acaccggtgg cggcggcagt ggaggcggcg cggggagccc cggagcgcag ggcaccaaat   1740
acccggagca cggcaacccg gctatcctac ttatgggctc agccaacggc gggcccgtgg   1800
tcaaaactga ctcgcagcag cctctcgtat ggcccgcctg ggtgtactgc acacgttatt   1860
cggatcgtcc atcctccggt ccgcgcacca ggaagctgaa gaagaagaag aacgagaagg   1920
aggacaagcg gccgcggacc gcgttcacgg ccgagcagct gcagagactc aaggcggagt   1980
tccaggcaaa ccgctacatc acggagcagc ggcggcagac cctggcccag gaactcagcc   2040
tcaacgagtc ccagatcaag atctggttcc agaacaagcg cgccaagatc aagaaagcca   2100
caggcatcaa gaacggcctg gcgctgcacc tcatggccca gggactgtac aaccactcca   2160
ccaccacggt ccaggacaaa gacgagagcg agtagccgcc acaggccggg gccgcgcccg   2220 cgcccctcc cggcaccgcc gccgtcgtct cccggcccct cgctggggga gaaagcatct   2280
gctccaagga gggagggagc gcagggaaaa gagcgagaga gacagaaaga gagcctcaga   2340
atggacaatg acgttgaaac gcagcatttt tgaaaaggga gaaagactcg gacaggtgct   2400
atcgaaaaat aagatccatt ctctattccc agtataaggg acgaaactgc gaactcctta   2460
aagctctatc tagccaaacc gcttacgacc ttgtatatat ttaatttcag gtaaggaaaa   2520
cacatacgtg tagcgatctc tatttgctgg acattttat taatctcctt tattattatt   2580
gttataatta ttataattat tataattatt ttatcccctc cccaccgcc tcgctgcccc   2640 cgcccagttt cgtttcgtt gccttttca tttgaatgtc attgcttctc cggtgcctcc   2700
cgacccgcat cgccggccct ggtttctctg ggacttttct ttgtgtgcga gagtgtgttt   2760
cctttcgtgt ctgcccacct cttctccccc acctcccggg tcccttctgt cggtctgtct   2820
```

-continued

| | |
|---|---|
| gttctgcccc cctttcgttt tccggagact tgttgagaaa tacgacccca cagactgcga | 2880 |
| gactgaaccg ccgctacaag ccaaagattt tattatgttc agaaacctgt agtctgaaat | 2940 |
| aaagtgtaca ctgtgctcac ga | 2962 |

<210> SEQ ID NO 6
<211> LENGTH: 2657
<212> TYPE: DNA
<213> ORGANISM: Homo sapiens

<400> SEQUENCE: 6

| | |
|---|---|
| tggcttttc cacttggtgt ggtggtttgg ggattcattc attcctattt cagcattcca | 60 |
| ctgtatagtc cagaggtgag caaggcaagg ctggtgggtg gctctgttat ccatctcctg | 120 |
| tgtccaagcg actgctccag ttgtcaccat gtttccagtc accaggtgag agagactctg | 180 |
| gctgcagaga cagggctgag tgtccgtgtc gtccaggtgt ggttccaaaa ccagagagcg | 240 |
| aagatgaaga agctggccag cgacagcag cagcagcagc aagatcagca gaacacccag | 300 |
| aggctgagct ctgctcagac aaacggtggt gggagtgctg ggatggaagg aatcatgaac | 360 |
| ccctacacgg ctctgcccac cccacagcag ctcctggcca tcgagcagag tgtctacagc | 420 |
| tcagatccct tccgacaggg tctcacccca ccccagatgc ctggagacca catgcaccct | 480 |
| tatggtgccg agccctttt ccatgacctg gatagcgacg acacctccct cagtaacctg | 540 |
| ggtgactgtt tcctagcaac ctcagaagct gggcctctgc agtccagagt gggaaacccc | 600 |
| attgaccatc tgtactccat gcagaattct tacttcacat cttgagtctt cccctagagt | 660 |
| tctgtgacta ggctcccata tggaacaacc atattctttg aggggtcact ggctttagga | 720 |
| cagggaggcc agggaagagg tgggttgggg agggagtttt gttggggatg ctgttgtata | 780 |
| atgatatggt gtagctcagc atttccaaag actgaataca ttatggattg catagtttaa | 840 |
| tgtttctaat aagagtctta gcattagata tgaagacgtg tttatcatta aggacagaga | 900 |
| cttttaatat agacattctc atgcaaacta gatacttagg gactcctaac aacttcccac | 960 |
| catgtcgggg aagctcttgt caagaggtgc atatgtctat ccatctacac accaatagac | 1020 |
| agaaggacag atagatagat gtgtgtgtgt gagtgtgtaa cctttcgtat tttaccctca | 1080 |
| aagtttattc ctaattataa cagacaccaa ctgtacagca aaagtaactt tattttcagt | 1140 |
| gtgaactata tttaaggaaa tgcttgatgc acttaagtta taaaatgaga taatttactt | 1200 |
| ttataaactt tattttagc ttgacaagac ttgtcagcag gcagagagg ctgctccac | 1260 |
| ctagccccat agctttgagt gctggggttc attctgtttt cagagtgtct ttcagatctg | 1320 |
| gaaagaaatt ctgtgtggct gatggtgttc tcttgcat tcttgctctc tttggggttg | 1380 |
| aatcactggg caggggtggg acagaataat ctctgatcat gttctgagaa aatgtaaagc | 1440 |
| ccagactcct gggctttctt ttaaattctg acaagtggtt gttgggcagt gctaggatga | 1500 |
| ttggttcagc tcttgagctt cagcatctgc aaatgtggat gaggctaata gtatgtacct | 1560 |
| acctcactgg gaaacaccaa ggcttaattc attcccagga cacatgagca gggctgagac | 1620 |
| taatatctga tatttgttta agatacaacc aggccactca cttggcaaag gagggtacat | 1680 |
| agggttgcag agcaggaggg ctcctgaact ccagagggca gttctgcctg ctgaagtccc | 1740 |
| tctgcaaagc ctgtgctgaa ggagacacca gctcagagca gttcagaggg atcccagagt | 1800 |
| cccagagtgg ggaggaggtg aaggctgagg ggatagagga gggcctggtg gtgttctaga | 1860 |
| gcagggttgg gcaaactcct gcttgcgggc ctgctttcta tggcttgcca gcaaagaatg | 1920 |

-continued

| | |
|---|---|
| gttttacttt tttttttgag gtcattaaaa aaaaggagaa gaagaatata taacaggctg | 1980 |
| tctgtggcct ggaaagcctg aaatatttgc tatctgtatt gtctggccct tacagaaaaa | 2040 |
| gtttggggcc ccttgtttta gagggtctgt ttctaaagaa cctcatggcg ctcatagagg | 2100 |
| cagaaggttc cagtggaaac ccttggctct tccttccaac tcactcctct gatcctcggc | 2160 |
| acagaagacc cagcagccat tgtacatggg gacagttcca caccctggtc tccagttgcg | 2220 |
| gtgctaggat ggtattgttc tgtgctagga agtctcctgg gaacccagaa tgagttggtg | 2280 |
| gggaagacag cgggtcactg tggacccatc caggaggggc caggataggc ttggcctcat | 2340 |
| ttctggggac atcattggag acttgaacac agagacacgt ccctatcact ctggcaaggc | 2400 |
| cagagggaac atgtcccctt atggtagagt ctatgttgtg tgattttgt gctcttgttt | 2460 |
| ataatttatg caaccacca agaaacccaa accagtctga tgagtgaaaa ttatgcagat | 2520 |
| gctgtatggc cccacaggtt tctgtggtaa agaccagttg gagaatgtag gagatactat | 2580 |
| gtgagtgaaa atgaatagag atccttattc cactccttaa tggcatacca agatgaaatt | 2640 |
| aaaatctctt acaaatg | 2657 |

<210> SEQ ID NO 7
<211> LENGTH: 9538
<212> TYPE: DNA
<213> ORGANISM: Homo sapiens

<400> SEQUENCE: 7

| | |
|---|---|
| gggataatgc tcccggagaa ggattctgca gcagttctca aaggctagac ttgagtggta | 60 |
| ttgctgcata tgcgctgatt cttcagcttg tctctaaccg aggaagcatt gattgggagc | 120 |
| tactcattca gaaaattaaa agaaagaagc cagaaaatat tatcaaccct ttgagaacac | 180 |
| gacacaacga actttatatt ttaccacttc cttgaatagt tgcaggagaa ataacaaggc | 240 |
| attgaagaat ggcagatgaa cggaaagatg aagcaaaggc acctcactgg acctcagcac | 300 |
| cgctaacaga ggcatctgca cactcacatc cacctgagat taaggatcaa gcggagcag | 360 |
| gggaaggact tgtccgaagc gccaatggat tcccatacag ggaggatgaa gagggtgcct | 420 |
| ttggagagca tgggtcacag ggcacctatt caaataccaa agagaatggg atcaacggag | 480 |
| agctgacctc agctgacaga gaaacagcag aggaggtgtc tgcaaggata gttcaagtag | 540 |
| tcactgctga ggctgtagca gtcctgaaag gtgaacaaga gaaagaagct caacataaag | 600 |
| accagactgc agctctgcct ttagcagctg aagaaacagc taatctgcct ccttctccac | 660 |
| ccccatcacc tgcctcagaa cagactgtca cagtggagga agatttactt acagcctcga | 720 |
| agatggagtt ccacgatcaa caggaattga ctccctctac agctgagcct tcagaccaga | 780 |
| aggaaaagga gtcagagaag caaagtaagc ctggtgaaga ccttaaacat gctgccttag | 840 |
| tttctcagcc agagacaact aaaacttacc ctgataaaaa ggacatgcaa ggcacggaag | 900 |
| aagaaaaagc acccctagct tgtttgggc acactcttgt tgccagcctg gaagacatga | 960 |
| aacagaagac agaaccaagc cttgtagtac ctggcattga cctccctaaa gagcctccaa | 1020 |
| ctccaaaaga acaaaaggac tggttcatcg aaatgccaac ggaagcaaaa aaggatgagt | 1080 |
| ggggtttagt tgcccccata tctcctggcc tctgactcc catgagggaa aaagatgtat | 1140 |
| ttgatgatat cccaaaatgg gaagggaaac agtttgattc tcccatgcca gtccctttc | 1200 |
| aaggggaag cttcactctt cctttagatg tcatgaagaa tgaaatagtt acagaaacat | 1260 |
| cgcccttgc ccctgccttt ttacagccag atgacaaaaa atctctgcaa caaaccagtg | 1320 |
| gcccagctac tgccaaagat agttttaaaa ttgaagagcc ccatgaggct aaacctgaca | 1380 |

```
aaatggcaga agcaccaccc tcagaggcaa tgaccttacc caaagatgct cacattccag    1440
ttgtagaaga acatgttatg gggaaagttt tagaggaaga aaaggaggcc ataaatcaag    1500
agactgtgca gcaaagggat actttcaccc ccagtggaca ggaacctata cttactgaaa    1560
aggaaactga gctgaagctt gaagaaaaaa ccaccatttc tgacaaagaa gctgtgccaa    1620
aagagagtaa acccccaaaa cctgcagatg aagaaatagg cataattcag acctccacag    1680
agcacacttt ctcagaacag aaagaccaag agcctaccac agatatgttg aaacaggact    1740
cgttccctgt aagtttggag caagcagtta cagattcagc catgacctct aaaacactgg    1800
agaaagccat gaccgaacca tctgcattaa ttgaaaagag ctcaattcag gaacttttg     1860 aaatgagagt tgatgacaaa gataagattg aaggagttgg agctgcaaca tcagctgagc    1920
ttgatatgcc attttatgaa gataaatcag gaatgtccaa gtactttgaa acatctgcct    1980
tgaaagaaga agcaacaaaa agcattgagc caggcagtga ttactatgaa ctgagtgaca    2040
ctagagaaag tgtccatgag tctattgata ccatgtctcc catgcataaa aatggtgaca    2100
aggagtttca aacaggaaaa gaatcccagc ccagtcctcc agcacaagaa gcagggtaca    2160
gcactctcgc acagagttat ccatcagatt tacctgaaga acccagttct cctcaagaaa    2220
gaatgttcac tattgatcca aaagtgtatg gagagaaaag ggacctccac agtaagaata    2280
aggatgattt gacccttagc aggagtttag gacttggtgg taggtctgca atagaacaaa    2340
gaagcatgtc aatcaatttg ccgatgtctt gcctagattc catagccctt ggatttaact    2400
ttggtcgggg acatgatctt tctcctctgg cttccgatat tctaaccaac actagtggaa    2460
gtatggatga aggggatgat taccttccag ccaccacacc tgcactggag aaagccccctt   2520 gcttccctgt agaaagcaaa gaggaagaac agatagagaa agtaaaagct actggagaag    2580
aaagtactca agcggagata tcatgtgagt ctccttttcct agccaaagat ttttacaaaa   2640
atggtactgt catggcacct gaccttcctg aaatgctaga tctggcaggc acaaggtcaa    2700
gattggcttc tgtgagtgca gatgctgagg ttgccaggag gaaatcagtc ccatcagaga    2760
ctgtggttga ggatagtcgt actggcttgc ccccggtaac tgatgaaaac catgtcattg    2820
taaaaacgga cagtcagctc gaagacctgg gctactgtgt gttcaataag tacacagtcc    2880
cattgccatc acctgttcaa gacagtgaga atttatcagg ggagagtggt accttttacg    2940
aaggcactga tgataaagtt cgaagagatt tggccacaga cctttcactg attgaagtga    3000
aactggcagc agccggaaga gtcaaagatg agttcagtgt tgacaaagaa gcatccgcgc    3060
atatctctgg tgacaaatca ggactgagta aggagtttga ccaagagaag aaagctaatg    3120
ataggttgga tactgtacta gaaaagagtg aagaacatgc tgattcaaaa gaacatgcca    3180
agaaaactga gaggctggt gatgaaatag aaacattcgg attaggagta acctatgagc     3240
aagctttggc caaagatttg tcaataccaa cagatgcatc ctctgagaaa gcagagaagg    3300
gtcttagttc agtgccagag atagctgagg tagaaccatc caaaaaggtg aacaaggtc     3360 tggattttgc tgtccagggt caactagatg ttaaaattag tgactttgga cagatggctt    3420
cagggctaaa catagatgat agaagggcaa cagagctaaa acttgaggct acacaggaca    3480
tgaccccctc atccaaagca ccgcaggagg cagatgcatt tatgggtgtt gagtctggcc    3540
acatgaaaga aggcactaaa gttagtgaga cagaagtcaa agagaaggtg gccaagcctg    3600
acttggtgca ccaggaggct gtagacaagg aggagtccta tgaatctagt ggtgagcatg    3660
aaagtctcac catggagtcc ttgaaagctg atgagggcaa gaaggaaaca tctccagaat    3720
```

```
catctctaat tcaagatgag attgccgtca aattgtcagt ggaaatacct tgcccacctg    3780
ctgtttcaga ggctgattta gccacagatg agagagctga tgtccagatg gaatttattc    3840
aggggccaaa agaagaaagc aaagagaccc cagatatatc catcacgcct tctgatgttg    3900
cagagccatt gcatgaaacg atcgtatctg aaccagcaga gattcagagt gaggaagaag    3960
agatagaagc ccagggagaa tatgataaac tgctcttccg ctcagacacc cttcagataa    4020
ctgacctggg tgtctcaggt gccagggagg aatttgtgga gacctgccca agtgaacaca    4080
aaggagtgat tgagtctgtt gtgaccatcg aggatgattt catcactgta gtgcaaacca    4140
caactgatga aggggagtca gggtcccaca gcgtgcgttt tgcagcccta gagcagcctg    4200
aggtggaaag gagaccatct cctcatgatg aagaagagtt tgaagtagaa gaggcagctg    4260
aagcccaggc agaacccaaa gatggttccc cagaggctcc agcttcccct gagagagaag    4320
aggttgcact ttctgaatat aagacagaaa cctatgacga ttacaaagat gagaccacca    4380
ttgacgactc catcatggac gctgacagcc tctgggtgga cactcaagat gatgatagga    4440
gcatcatgac agaacagtta gaaactattc ctaaagagga gaaagctgaa aaggaagctc    4500
ggagatcatc tcttgagaaa catagaaaag aaaagccttt taaaaccggg agaggcagaa    4560
tttccactcc tgaaagaaaa gtagctaaaa aggaacctag cacagtctcc agagatgaag    4620
tgagaaggaa aaaagcagtt tataagaagg ctgaacttgc taaaaaaaca gaagttcagg    4680
cccactctcc ctccaggaaa ttcatttttaa aacctgctat caaatatact agaccaactc    4740
atctctcctg tgttaagcgg aaaaccacag cagcaggtgg ggaatcagct ctggctccca    4800
gtgtatttaa acaggcaaag gacaaagtct ctgacggagt aaccaagagc ccagaaaagc    4860
gctcttctct cccaagacct tcctccattc tccctcctcg gcgaggtgtg tcaggagaca    4920
gagatgagaa ttccttctct ctcaacagtt ctatctcttc ttcagcacgg cggaccacca    4980
ggtcagagcc aattcgcaga gcagggaaga gtggtacctc aacacccact accctgggt    5040
ctactgccat cactcctggc accccaccaa gttattcttc acgcacacca ggcactcctg    5100
gaaccctag ctatcccagg accctcaca caccaggaac ccccaagtct gccatcttgg    5160
tgccgagtga aagaaggtc gccatcatac gtactcctcc aaaatctcct gcgactccca    5220
agcagcttcg gcttattaac caaccactgc cagacctgaa gaatgtcaaa tccaaaatcg    5280
gatcaacaga caacatcaaa taccagccta aggggggca ggttaggatt ttaaacaaga    5340
agatcgattt tagcaaagtt cagtccagat gtggttccaa ggataacatc aaacattcgg    5400
ctggggggcgg aaatgtacaa attgttacca agaaaataga cctaagccat gtgacatcca    5460
aatgtggctc tctgaagaac atccgccaca ggccaggtgg cggacgtgtg aaaattgaga    5520
gtgtaaaact agatttcaaa gaaaaggccc aagctaaagt tggttctctt gataatgctc    5580
atcatgtacc tggaggtggt aatgtcaaga ttgacagcca aaagttgaac ttcagagagc    5640
atgctaaagc ccgtgtggac catggggctg agatcattac acagtcccca ggcagatcca    5700
gcgtggcatc accccgacga ctcagcaatg tctcctcgtc tggaagcatc aacctgctcg    5760
aatctcctca gcttgccact ttggctgagg atgtcactgc tgcactcgct aagcagggct    5820
tgtgaatatt tctcatttag cattgaaata ataatattta ggcatgagct cttggcagga    5880
gtgggctctg agcagttgtt atattcattc tttataaacc ataaaataaa taatctcatc    5940
cccaaactgt agtaattgtt acaatttttct attttaaaaaa tgaatagtac atgcagaaat    6000
tgacctgatt tccatttgca acaggaagac actggcttta catgggttca attggacaat    6060
tattttttgct ctgctctgtt ttgcatggag tattattatt ttaaaaattg catttttacc    6120
```

```
tttcatgtgc ctgaaggcta tccactacat tctgaaggcc ttgttaaaat ccaagctgct   6180
catttcacta ttctgtttct gagtgagaag ataaaaactg cccattgtaa cttatttcag   6240
gttaaattaa accaaggagt ctgattgcag gaagggaaga gcatgtaaga aataagtttt   6300
tttaaagtgt tattttgtat aaatgggaag aaagattcaa ttaagttatt aacatttggg   6360
acctggataa ttatatcaga gtatgtcagt ccaataaatt atttaactaa ttaaaaaata   6420
gttgcaaagc atttgagctg tggttgagga agtggtgtaa aagtgcatcc attaggaatg   6480
atgcactttc attaggatgg actcgtgtct gattagaatg tcagttgatc agctagattt   6540
gtgtccacac taccagtttc acccccctt tccatctgtt tgatacagta ttatagatat    6600
aaatatatat atatttctct gtggccattt gtgatacttc ctcatatact tgaatattat   6660
acttctttat tcacagtatc tgtgtctcct gcacccttg gtgttgcaat tttagatatg    6720
tgaaagtaga tgttagcagg gttctctccc tatttaaaaa aaatacatta aaaaagacaa   6780
aaaattttag catgaagttg ctttctgtaa caactcaaag ccgtaaccct gttttagtgc   6840
cagatacaag tctctcccgt gatgctagac aaaaaattat ttttctttgc tttcaccaac   6900
atggagtttg tgggggtggg tccagttata catgaaaggg tttacagatt gttggtttaa   6960
gattatggat ttatctcatt tttaatcaca ggatagtttg gggtttattc ctattattat   7020
tcatgaaacc gacttaagat tttttcttta ttttttcttt tttttccatt tgctaaagtt   7080
gaaagttgaa actaactata atagtttgaa acatgttttc tcattttcc aaatagtatc    7140 tgtttattaa attctctaat agaagatgtt tgtctttctt acccaaagta aagatcccct   7200
gatcagaaag aaaaaataca atactttggg aagctatagc tataaaacac ttgagacaca   7260
gatatctaaa tcagttttttt tccaagactc caacattgca ctctgtaaag taacacactg   7320
tgatctagta ttatttatca gtagataata ctgttctgac tgtatataca gtctagaact   7380
cacaaatcaa ttagttcctc tcacaaatca ttcatcttag acttacaaat aaggaatgaa   7440
atagtcaatg gcctgattaa ggcaaagagc taccaggcta gatggacact ttttaaaaat   7500
tttatctgtt cttttttcttg ctcagggctg gtaggttgga tctgaaccat taaaatcaaa   7560
tggtccacta ggcgtatgat ctctttgagc caaatcagtt cctgaatata aaggaggaaa   7620
tgatgaggat gtactgaggc aacggggaag tatagaaaca tccaagacaa aagccaaggg   7680
atgcaaaggc agagacacag gtgctttttg gtgacccagt ggatatggca accagtgtaa   7740
ctgccataca agaaacccta ggagcaaacc cacaccactc attctcagct aagagatttt   7800
acacaggcaa acgtgtctta aaccatctat aaatcagtta ttttatatga cagtcaaaac   7860
cttagaaacc ttaggatcat tatatctatt ttctgcctat taattgctgt gaggtttgat   7920
ttgaccaatc tgggcaattt attcatcagc ttcccttgaa gtgcaccaga aaatagaaga   7980
aaggtgtgtg gagacttagg gtattttatt acatgttttc atagtcttaa atagtgatta   8040
aatttctcta gaaagaagtt aacagctcat tagaaaagtt ttaacctgtg aaataagtat   8100
ttttctcaac attctttaaa gttttatat aagttaacac taggtaaaca ttctgcatac    8160
tagaagtcag tttattacaa atacatgtca aaaataaaga ttatacaagg caccaaaacta  8220 ctagatttgg cattaaaaca aatgtttatt tctaatcaca acaaaattat aatgaataaa   8280
tgttcttgct ttgtatggaa atacaattct ttattaaagt taacagaaag gaactgatcg   8340
tttgtaccag taaaagagag aaacacacag gttaaatatc ttcttgtggg gttaaggggt   8400
agaacctatc ttgccttcac tctcaagata acgactcaaa ttaagctttt tgagcaccac   8460
```

```
tcttgtgggg acacacatac gctgatctag gaatgaaatc ttcgtggtct caattctaga    8520
tctactatgc cagtttctct ctggctttag cctttgagaa cctgtataag aatacgtaag    8580
taatccagag ctgtgaagag tttaaaggcc aacttctcca gtgaactcaa cctctgggtc    8640
acttgcaacc agaaattgga tacctcataa tgatgcagga agacccgag ttcatgatga     8700 gtttcaaagg ccacgttcat ttaggaacca actctctctg gatttacctg ctgagttcca    8760
gcagcgtgat gggctgacat cccacctaca agtatgacac ctgtgtaaca ccagctaggt    8820
acggctggag aaggctgaag agagaatgcc attaaatgga agaatgtact gattgtagtg    8880
accttctcca cacacacaca cacacacaca cacacacaca cctacagtaa tacagcaagc    8940
gtggaataat cagccaatat ataacattcc atcagtattt tattaaggaa ataacctgaa    9000
tgtggttgat tttgacatag ctgcaattac agttttcttc tattttttcaa gccacaataa   9060 ggaaaataaa ctactcatgg tctaaatact agagataaag tagattcatg gcttggtaag    9120 gaaatttttaa gcattccttc aaagattgac gtgctaaaat aagcattgat gttttgagtt   9180
tttttacacc taggattttt agcttgggtg tgtaggtgaa ggccaagact ctctgcagga    9240
aaaagcttat tttcaaactc agaaaataaa atgtcaatca taaaaatcta cttcaacttt    9300
agcaaaaaga aaaaaaaatc aacaaaaagt atactctgta tgctgggatt ccgaggttcc    9360
aacacactgt tacaaatctg tggggggttt ctttcttctg ataattctag agcctgttac    9420
catagaaagg catttcttca atggctggtt gtagttagtt catgttttc aatcaaattt     9480 gcaaatgtat ttgttgctgt atagtgattg ttttgcaaaa taaaattgct tgtcacct     9538

<210> SEQ ID NO 8
<211> LENGTH: 6230
<212> TYPE: DNA
<213> ORGANISM: Homo sapiens

<400> SEQUENCE: 8
ctagatcgaa agtcctttgg taatgatgtg tcatacattc tagtcatcaa agacaccatt      60
ttctgggcct gaagtgttct gctggttttt ggaggaatga gaatccaatc tctcataagc     120
cggattcaga aaataggtca tcgatgaaac atctgtatgg attatttcac tataatccta     180
tgatgcttgg acttgaatca cttccagatc ccacagacac ctgggaaatt atagagacca     240
ttggtaaagg cacctatggc aaagtctaca aggtaactaa caagagagat gggagcctgg     300
ctgcagtgaa aattctggat ccagtcagtg atatggatga agaaattgag gcagaataca     360 acatttttgca gttccttcct aatcatccca atgttgtaaa gttttatggg atgttttaca    420
aagcggatca ctgtgtaggg ggacagctgt ggctggtcct ggagctgtgt aatgggggct    480
cagtcactga gcttgtcaaa ggtctactca gatgtggcca gcggttggat gaagcaatga    540
tctcatacat cttgtacggg gccctcttgg gccttcagca tttgcacaac aaccgaatca    600
tccaccgtga tgtgaagggg aataacattc ttctgacaac agaaggagga gttaagctcg    660
ttgactttgg tgtttcagct caactcacca gtacacgtct gcggagaaac acatctgttg    720
gcaccccgtt ctggatggcc cctgaggtca ttgcctgtga gcagcagtat gactcttcct    780
atgacgctcg ctgtgacgtc tggtccttgg ggatcacagc tattgaactg ggggatggag    840 acccctcccct cttttgacatg catcctgtga aaacactctt taagattcca agaaatcctc    900
cacctacttt acttcatcca gaaaaatggt gtgaagaatt caaccacttt atttcacagt     960
gtcttattaa ggatttttgaa aggcgacctt ccgtcacaca tctccttgac cacccattta   1020
ttaaaggagt acatggaaaa gttctgtttc tgcaaaaaca gctggccaag gttctccaag    1080
```

```
accagaagca tcaaaatcct gttgctaaaa ccaggcatga gaggatgcat accagaagac    1140
cttatcatgt ggaagatgct gaaaaatact gccttgagga tgatttggtc aacctagagg    1200
ttctggatga ggatacaatt atccatcagt tgcagaaacg ttatgcagac ttgctaattt    1260
acacatatgt tggagacatc ttaattgcct taaaccccett ccagaatcta agcatatact    1320
ctccacagtt ttccagactt tatcatgggg tgaaacgcgc ctccaatccc ccccacatat    1380
ttgcatcagc agatgctgct taccagtgca tggttactct cagcaaagac cagtgcattg    1440
tcatcagcgg agagagtggc tctgggaaga cagaaagcgc ccacctgatt gttcagcatt    1500
tgactttctt gggaaaggcc aataatcaga ccttgagaga gaaaattcta caagtcaact    1560
ccctggtgga agcctttggg aactcatgca ctgccatcaa tgacaactcg agccgttttg    1620
gaaaatatct ggaaatgatg tttacaccaa ctggagttgt gatggggca agaatctctg    1680 aatatctcct ggaaaaatcc agagttataa acaggcagc gagagagaaa aattttcata    1740
tattttacta tatttatgct ggtcttcatc accaaaagaa gctttctgat ttcagacttc    1800
ctgaggaaaa acctcctagg tacatagctg atgaaactgg aagggtgatg cacgacataa    1860
cttccaagga gtcttacaga agacaattcg aagcaattca gcattgcttc aggattatag    1920
ggttcacgga caaagaggtg cactcagtgt acagaatttt ggctgggatt ttgaatattg    1980
ggaacattga gttcgcagct atttcctctc aacatcagac tgataaagt gaggtgccca    2040 atgctgaagc tttgcaaaat gctgcctctg ttctgtgcat tagccctgaa gagctccagg    2100
aggccctcac ctcccactgt gtggtcaccc ggggcgagac catcatccgt gccaacactg    2160
tagacagggc tgcggacgtt cgagacgcca tgtccaaagc cctgtatggg aggctcttca    2220
gctggattgt gaatcgcatt aatacactcc tgcagccaga cgaaaacata tgtagtgcag    2280
gaggtggaat gaatgtgggg atcttggata tctttggatt cgagaatttt cagagaaatt    2340
catttgagca gctctgcata aacatcgcca atgagcaaat ccagtactat ttcaatcagc    2400
atgtttttgc tcttgagcag atggaatatc agaatgaagg cattgatgct gtacccgtgg    2460
aatatgagga caaccgcccg ctcttggaca tgttcctcca gaaacccctg ggactgcttg    2520
cacttttgga tgaggaaagt cggtttcccc aagcaactga ccagaccctg gttgataaat    2580
ttgaagataa tctacgatgc aaatacttct ggaggcccaa aggagtggaa ctgtgctttg    2640
gcattcagca ttatgctgga aaggtattat atgatgcttc tggggttctt gagaaaaata    2700
gagacactct ccctgccgat gtggttgtgg tcctgagaac gtcagaaaac aagcttcttc    2760
agcagctctt ctcaatccct ctgaccaaaa caggtaattt ggcccagaca agagctagga    2820
taacagtggc ctcaagttct ttgcctccac atttcagtgc tgggaaagcc aaggtggaca    2880
ctctggaggt gatacggcat ccggaagaaa ccaccaacat gaagaggcaa actgtggctt    2940
cttacttccg gtattctctg atggacctgc tctccaaaat ggtggttgga cagccccact    3000
ttgtgcgctg cattaaaccc aatgatgacc gagaggccct gcagttctct cgagagaggg    3060
tgctggccca gctccgctcc acagggattc tggagacagt cagcatccgc cgccagggct    3120
attcccaccg catcctttt gaagaatttg tgaaaggta ttattacttg gcattcacag    3180
cacatcaaac acctcttgct agcaaagaga gctgtgtggc tatcttggaa aagtccagat    3240
tagatcactg ggtactggga aaaacaaagg ttttctcaa atattaccat gttgagcaat    3300
taaatttgct gcttcgagaa gtcataggca gagtggttgt gctgcaggca tataccaagg    3360
ggtggcttgg agccaggaga tacaaagggg tcagagagaa gagagagaag ggagccattg    3420
```

```
ccatccagtc agcctggaga ggatatgatg ctcggaggaa atttaagaaa ataagcaaca    3480
gaaggaatga gtctgctgct cataatcaag caggggacac ttcaaaccaa agcagtgggc    3540
cacattcccc cgtcgcagca ggtacgaggg gaagtgccga ggttcaagac tgcagcgagc    3600
ctggtgacca taaagttctc aggggctctg tacatcgtag gagccattca caagcagaat    3660
ccaacaatgg ccgtacacag acttcaagca actctcctgc tgtcacagag aaaaatgggc    3720
attcacaagc ccagagttct ccaaaagggt gcgatatctt cgcaggacat gcaaacaagc    3780
actcggtttc tgggactgat ttgctgtctt ctcggatatg ccatcctgct ccagatcagc    3840
aaggattgag tctctgggga gcccctcaaa agcctggttc agaaaatggt cttgcacaga    3900
agcatcgaac acctcgccga cgatgtcagc agcccaaaat gctgagtagc cctgaggaca    3960
ccatgtacta taaccagtta aatggaactc tagaatatca agggagcaag aggaagccaa    4020
gaaaacttgg ccaaatcaaa gtacttgatg gggaagatga atattacaaa tctctgtcac    4080
cagtggactg tatccctgag gagaacaact cagcccaccc ttcctttttt tcttcatcct    4140
caaaaggaga ctcttttgct caacattaaa ttgtgcttcc taaccctaaa tctgtccaga    4200
gtaggaacat tcatggtaat cgactgtctg tcattgcgta agaaagcact gatatggggt    4260
cagcttcttt ggacatatgg tccatgcctg aaccttactg aaccacttgc agattccaaa    4320
acatcttatc ctatcctcta ccactctccc acatgtgttg tgcagcctga gctgggcgct    4380
gccttccttt ctcatcccat ggggccctgt gggacactga acaccttt acaatagttt     4440
aaacagtcat tcatgccccc agtgtctagg aagataacag ccagtctcac cccagtctaa    4500
tcatggaccc tgataatatt gcttgatttt tcctatcaag ttacttttca atccattcag    4560
aatctgcccc agtggagacc caggagttcc tttcctgcac tcttctccat cctcccacct    4620
ttgctgggct tttctatcac tcccacctcc cccagagtca gggctccatt gctgagtgcc    4680
ccatcctgga ggattggccc caagatctcc tagaacagga taattgcctg tgtttaggca    4740
gataggccta aatcttttcag attctttcta caaggcaaat aacccctctc ttgttaatta    4800
tgatgctgag aaagcctctg tctctttatt tcaccttgcc aagacaccca cactactttg    4860
gtgatgaaaa gaaaggaatg agagggaaag tttggacctg tcactttggt gacagggaaa    4920
gtccaggtca ctttattctg taactctcca ttcactggtc aaataactcc atgaggctat    4980
cagtggctac agtggaagga cctgatcttg tccatctttg tgtgcacaga gcctagcaca    5040
gggcttggta gagggtatat ctagtgaatg gagaatacat ggagaaactt aactaagtta    5100
cacaagcata tctgacagga atgttacctt caattgtatg ttacatatga ttagtcactt    5160
ttcatacact ataacctctg atttttcact caagtttggg ctgattatat tgtaatgatg    5220
ttagataata ctcaacatga ttcagtatga caaactttt tgagcaccta ctttatataa     5280
aacatgacaa attgcagtgt gatgtaatca aaaacaaaga agcccctaaa gaccatttct    5340
ctagaacaga tgttcttaat atttttctta ctctaaaata tgtggtagat agtatgcaag    5400
aaaagccggg tgcggtggct caggcctgta atcccagcac tttgggaggc caagatgggc    5460
ggatcatgaa gtcaggagtt cgagaccagc ctgaccaaca tggtgaaacc ccgtctctac    5520
taaaaaaat aatgataata caaaaattag cccagcatgg tggtgcatac ctgtaatccc      5580
agctactcag gaggctgacg caggagaatc acttgaaccc gggaagcaaa ggttgcagtc    5640
agctgagagc gcaccactgc actccagcct gggcgacagg gcaagactct gtctcaaaaa    5700
aaaaaaaaaa aaaaaaaaaa agagatagta tgcaagaaga cacctaaatt ttgagagaaa    5760
taaccttgaa gaaaatcttg ttatcagagt tttgaaaggg agcacattaa taggccttt     5820
```

-continued

| | |
|---|---|
| atgaagataa ataatgaaat gaggtattta aagatctcag aaattgtaat tttacaagta | 5880 |
| aaataaatat agccaatttt tcaatagctg aacttcaccc aaaaggtaat gtttataagt | 5940 |
| agagcagaaa aaatgcagat aaattttatt ttattgttta aaaaataatg tgtagaatat | 6000 |
| ataaatttt tatgttactg ttaatatacg agtgcttttg gaagtttcac ttttgtcact | 6060 |
| gattgtctac ttttggtttg ataatatgag ctgcttttca aattgttgaa tggaaatgtt | 6120 |
| cataactccc tgcttgtccg tgcacaatgt aattctaaac ctggcttgtt tctcatttaa | 6180 |
| atatatctat aaataaactt aaaagaaaa caaaaaaaaa aaaaaaaaa | 6230 |

<210> SEQ ID NO 9
<211> LENGTH: 4104
<212> TYPE: DNA
<213> ORGANISM: Homo sapiens

<400> SEQUENCE: 9

| | |
|---|---|
| ataactttgt agcgagtcga aaactgaggc tccggccgca gagaactcag cctcattcct | 60 |
| gctttaaaat ctctcggcca cctttgatga ggggactggg cagttctaga cagtcccgaa | 120 |
| gttctcaagg cacaggtctc ttcctggttt gactgtcctt accccgggga ggcagtgcag | 180 |
| ccagctgcaa gccccacagt gaagaacatc tgagctcaaa tccagataag tgacataagt | 240 |
| gacctgcttt gtaaagccat agagatggcc tgtccttgga aatttctgtt caagaccaaa | 300 |
| ttccaccagt atgcaatgaa tggggaaaaa gacatcaaca acaatgtgga gaaagccccc | 360 |
| tgtgccacct ccagtccagt gacacaggat gaccttcagt atcacaacct cagcaagcag | 420 |
| cagaatgagt ccccgcagcc cctcgtggag acgggaaaga agtctccaga atctctggtc | 480 |
| aagctggatg caaccccatt gtcctcccca cggcatgtga ggatcaaaaa ctggggcagc | 540 |
| gggatgactt tccaagacac acttcaccat aaggccaaag ggattttaac ttgcaggtcc | 600 |
| aaatcttgcc tggggtccat tatgactccc aaaagtttga ccagaggacc cagggacaag | 660 |
| cctaccctc cagatgagct tctacctcaa gctatcgaat ttgtcaacca atattacggc | 720 |
| tccttcaaag aggcaaaaat agaggaacat ctggccaggg tggaagcggt aacaaaggag | 780 |
| atagaaacaa caggaaccta ccaactgacg ggagatgagc tcatcttcgc caccaagcag | 840 |
| gcctggcgca atgccccacg ctgcattggg aggatccagt ggtccaacct gcaggtcttc | 900 |
| gatgcccgca gctgttccac tgcccgggaa atgtttgaac acatctgcag acacgtgcgt | 960 |
| tactccacca caatggcaa catcaggtcg gccatcaccg tgttcccca gcggagtgat | 1020 |
| ggcaagcacg acttccgggt gtggaatgct cagctgtgca tcgacctggg ctggaagccc | 1080 |
| aatggccgtg accctgagct cttcgaaatc ccacctgacc ttgtgcttga ggtggccatg | 1140 |
| gaacatccca atacgagtg gtttcgggaa ctggagctaa agtggtacgc cctgcctgca | 1200 |
| gtggccaaca tgctgcttga ggtgggcggc ctggagttcc agggtgccc cttcaatggc | 1260 |
| tggtacatgg gcacagagat cggagtccgg gacttctgtg acgtccagcg ctacaacatc | 1320 |
| ctggaggaag tgggcaggag aatgggcctg gaaacgcaca agctggcctc gctctggaaa | 1380 |
| gaccaggctg tcgttgagat caacattgct gtgctccata gtttccagaa gcagaatgtg | 1440 |
| accatcatgg accaccactc ggctgcagaa tccttcatga gtacatgca gaatgaatac | 1500 |
| cggtcccgtg ggggctgccc ggcagactgg atttggctgg tccctcccat gtctgggagc | 1560 |
| atcaccccg tgtttcacca ggagatgctg aactacgtcc tgtcccettt ctactactat | 1620 |
| caggtagagg cctggaaaac ccatgtctgg caggacgaga agcggagacc caagagaaga | 1680 |

```
gagattccat tgaaagtctt ggtcaaagct gtgctctttg cctgtatgct gatgcgcaag      1740
acaatggcgt cccgagtcag agtcaccatc ctctttgcga cagagacagg aaaatcagag      1800
gcgctggcct gggacctggg ggccttattc agctgtgcct tcaaccccaa ggttgtctgc      1860
atggataagt acaggctgag ctgcctggag gaggaacggc tgctgttggt ggtgaccagt      1920
acgtttggca atggagactg ccctggcaat ggagagaaac tgaagaaatc gctcttcatg      1980
ctgaaagagc tcaacaacaa attcaggtac gctgtgtttg ccctcggctc cagcatgtac      2040
cctcggttct gcgcctttgc tcatgacatt gatcagaagc tgtcccacct ggggcctct       2100 cagctcaccc cgatgggaga aggggatgag ctcagtgggc aggaggacgc cttccgcagc      2160
tgggccgtgc aaaccttcaa ggcagcctgt gagacgtttg atgtccgagg caaacagcac      2220
attcagatcc ccaagctcta cacctccaat gtgacctggg acccgcacca ctacaggctc      2280
gtgcaggact cacagccttt ggacctcagc aaagccctca gcagcatgca tgccaagaac      2340
gtgttcacca tgaggctcaa atctcggcag aatctacaaa gtccgacatc cagccgtgcc      2400
accatcctgg tggaactctc ctgtgaggat ggccaaggcc tgaactacct gccggggag       2460 caccttgggg tttgcccagg caaccagccg gccctggtcc aaggtatcct ggagcgagtg      2520
gtggatggcc ccacacccca ccagacagtg cgcctggagg ccctggatga gagtggcagc      2580
tactgggtca gtgacaagag gctgcccccc tgctcactca gccaggccct cacctacttc      2640
ctggacatca ccacaccccc aacccagctg ctgctccaaa agctggccca ggtggccaca      2700
gaagagcctg agagacagag gctggaggcc ctgtgccagc cctcagagta cagcaagtgg      2760
aagttcacca acagccccac attcctggag gtgctagagg agttcccgtc cctgcgggtg      2820
tctgctggct tcctgctttc ccagctcccc attctgaagc ccaggttcta ctccatcagc      2880
tcctcccggg atcacacgcc cacagagatc cacctgactg tggccgtggt cacctaccac      2940
acccgagatg ccagggtccc cctgcaccac ggcgtctgca gcacatggct caacagcctg      3000 aagcccaag acccagtgcc ctgctttgtg cggaatgcca gcggcttcca cctccccgag      3060
gatccctccc atccttgcat cctcatcggg cctggcacag gcatcgcgcc cttccgcagt      3120
ttctggcagc aacggctcca tgactcccag cacaagggag tgcggggagg ccgcatgacc      3180
ttggtgtttg ggtgccgccg cccagatgag gaccacatct accaggagga gatgctggag      3240
atggcccaga agggggtgct gcatgcggtg cacacagcct attcccgcct gcctggcaag      3300
cccaaggtct atgttcagga catcctgcgg cagcagctgg ccagcgaggt gctccgtgtg      3360
ctccacaagg agccaggcca cctctatgtt gcggggatg tgcgcatggc ccgggacgtg      3420
gcccacaccc tgaagcagct ggtggctgcc aagctgaaat tgaatgagga gcaggtcgag      3480
gactatttct ttcagctcaa gagccagaag cgctatcacg aagatatctt ggtgctgtga      3540
tttccttacg aggcgaagaa ggacagggtg gcggtgcagc ccagcagcct ggagatgtca      3600
gcgctctgag ggcctacagg aggggttaaa gctgccggca cagaacttaa ggatggagcc      3660
agctctgcat tatctgaggt cacagggcct ggggagatga aggaaagtga tatcccccag      3720
cctcaagtct tatttcctca acgttgctcc ccatcaagcc ctttacttga cctcctaaca      3780
agtagcaccc tggattgatc ggagcctcct ctctcaaact ggggcctccc tggtcccttg      3840
gagacaaaat cttaaatgcc aggcctggca agtgggtgaa agatggaact tgctgctgag      3900
tgcaccactt caagtgacca ccaggaggtg ctatcgcacc actgtgtatt taactgcctt      3960
gtgtacagtt atttatgcct ctgtatttaa aaaactaaca cccagtctgt tccccatggc      4020
cacttgggtc ttccctgtat gattccttga tggagatatt tacatgaatt gcattttact      4080
```
ttaatcacaa aaaaaaaaaa aaaa                                          4104

<210> SEQ ID NO 10
<211> LENGTH: 3734
<212> TYPE: DNA
<213> ORGANISM: Homo sapiens

<400> SEQUENCE: 10

| | | | | | |
|---|---|---|---|---|---|
| cctctttctc | cccctctct | ccctcctctc | ctctctctct | cctctcttct | ctgaacctct | 60 |
| cttctctttc | tcttttctta | catattctac | tagttgtttt | ccccttcttc | ttctcctttc | 120 |
| tctcctttt | ctccctcctc | cttgtctctt | ttactccatt | cctgcagaag | agagagggct | 180 |
| aaacttaaag | aaaaaaaaaa | ggaggaggag | gaggaggagg | caccccttc | gtattcttct | 240 |
| tatcgttatt | ttatacatat | atgatttttt | ttggagggag | ggtgttggtt | gccggctgaa | 300 |
| gagcacttat | ttaaaatact | aaaaaagaa | cattttgg | cgatctccag | ggttttttta | 360 |
| actagctctg | tgtgttatag | cagaagaagc | agaagaagga | gcaagaaga | ggaaaagaag | 420 |
| aggattattt | attcgaccta | ctttggatgt | ctctctcgct | tttccttttt | cctttttttg | 480 |
| gcaattattt | tcttctgatt | tttattttt | ctatttcgct | gtgatttcgt | cgccggcgtg | 540 |
| aattatcccg | tattttctc | ccccttccgt | cacctcccga | agaagaagg | cagcgagagc | 600 |
| ccggcgccac | cggcacaaca | aaagagcaa | agtgtgtgat | cttcctcgcc | ggctgcctcc | 660 |
| cgctctccag | cgctgccttc | ctgaatggct | ggctgcgtcc | ggccctggac | ctggcccccc | 720 |
| gacaccccgcg | cgcccctgatc | gccggcggca | gcctcgccca | gcgccctgct | cggctcaccg | 780 |
| cgctccccgc | actcccgagc | ccggcgaggg | ctcccgccgg | gacagcggcg | gcgccgcggg | 840 |
| cggccccggc | ctccgctcgc | gctccggctg | cggcccgac | tcctgctcgg | actccggccc | 900 |
| gggtcccggc | tcctccagcg | gcgctcgccg | cagcagctcc | ggcggcagct | ccagcggcgc | 960 |
| ctgcagccgc | gacctcctcc | tcctccgccg | ccgccgccgc | ctccgccctc | gccggcttcc | 1020 |
| tctatgtcgg | ctcagcccgc | gcgctgcgcg | tagcccgagc | ggccggcggg | cgggcgcccg | 1080 |
| gcgcgggtga | gcgactgtgt | gtgcgagtgt | gtgtgtgcgc | ggggtgcgg | gcgaggcgga | 1140 |
| gggcgagtgt | gtgcgcgcgc | cgtggcccat | gcccgccgcc | cccggcgctg | cgcccgcgc | 1200 |
| cgctcccggc | tgccgcctgt | gccatttctg | attttgcaac | ttggggaaga | agaaaaaagc | 1260 |
| gagagaaggg | agcttgctcg | ccgggggggtg | gggagggggg | aaggagagcg | cggccccccc | 1320 |
| aggaacggag | cgcgggggga | gcgggcgagg | ggagcagggg | tgttgggggg | ggagcctgag | 1380 |
| agcctggggg | ggctgcaaaa | agagagaaag | aaaacagcag | gaaccacaac | aaaacgccag | 1440 |
| cagggcgggc | gggcgcgcag | cagcagcggg | gcggccgagg | cagtagcggc | ggcagcggcg | 1500 |
| gcggcggcg | aggcagcggc | cggtgtccgg | ctcgggctcg | gctcctgcga | ccccggggcg | 1560 |
| cccggcgggc | ccccgcccc | ctccccctcc | cccttcccc | ttcccttcc | cctcccagcg | 1620 |
| cgcccgcgcg | ccccgcggcc | ctcggcgagc | agctcggctc | ccccagcgc | tccccggcc | 1680 |
| caaagatatg | gcaatggtag | ttagcagctg | gcagatccg | caggacgacg | tggccggggg | 1740 |
| caaccccggc | ggccccaacc | ccgcagcgca | ggcggcccgc | ggcggcggcg | gcggcgccgg | 1800 |
| cgagcagcag | cagcaggcgg | gctcgggcgc | gccgcacacg | ccgcagaccc | cgggccagcc | 1860 |
| cggagcgccc | gccaccccg | gcacggcggg | ggacaagggc | cagggcccgc | ccggttcggg | 1920 |
| ccagagccag | cagcacatcg | agtgcgtggt | gtgcggggac | aagtcgagcg | gcaagcacta | 1980 |
| cggccaattc | acctgcgagg | gctgcaaaag | tttcttcaag | aggagcgtcc | gcaggaactt | 2040 |

| | | | | |
|---|---|---|---|---|
| aacttacaca | tgccgtgcca | acaggaactg | tcccatcgac | cagcaccacc gcaaccagtg | 2100 |
| ccaatactgc | cgcctcaaga | agtgcctcaa | agtgggcatg | aggcgggaag cggttcagcg | 2160 |
| aggaagaatg | cctccaaccc | agcccaatcc | aggccagtac | gcactcacca acggggaccc | 2220 |
| cctcaacggc | cactgctacc | tgtccggcta | catctcgctg | ctgctgcgcg ccgagcccta | 2280 |
| ccccacgtcg | cgctacggca | gccagtgcat | gcagcccaac | aacattatgg gcatcgagaa | 2340 |
| catctgcgag | ctggccgcgc | gcctgctctt | cagcgccgtc | gagtgggccc gcaacatccc | 2400 |
| cttcttcccg | gatctgcaga | tcaccgacca | ggtgtccctg | ctacgcctca cctggagcga | 2460 |
| gctgttcgtg | ctcaacgcgg | cccagtgctc | tatgccgctg | cacgtggcgc cgttgctggc | 2520 |
| cgccgccggc | ctgcatgcct | cgcccatgtc | tgccgaccgc | gtcgtggcct tcatggacca | 2580 |
| catccgcatc | ttccaggagc | aggtggagaa | gctcaaggcg | ctacacgtcg actcagccga | 2640 |
| gtacagctgc | ctcaaagcca | tcgtgctgtt | cacgtcagac | gcctgtggcc tgtcggatgc | 2700 |
| ggcccacatc | gagagcctgc | aggagaagtc | gcagtgcgca | ctggaggagt acgtgaggag | 2760 |
| ccagtacccc | aaccagccca | gccgttttgg | caaactgctg | ctgcgactgc cctcgctgcg | 2820 |
| caccgtgtcc | tcctccgtca | tcgagcagct | cttcttcgtc | cgtttggtag gtaaaacccc | 2880 |
| catcgaaact | ctcatccgcg | atatgttact | gtctgggagc | agcttcaact ggccttacat | 2940 |
| gtccatccag | tgctcctaga | ccttgggcgc | ttcccacctg | ccccgtcccc ctagagactc | 3000 |
| agaggaccca | cctgggccaa | ggactccaaa | gccgcgggga | caccgggaag tgcagcgggc | 3060 |
| caggcaggct | gggtgggagg | gaggagggcc | gagacaggag | cagcccaccc agcagaaata | 3120 |
| caatccgagc | tacaaagcat | gggaaaaaga | gactctttta | ggatcagatc tgtgagcacg | 3180 |
| ttggcgagga | aaacaaaac | aaacaaaaaa | aagaaccttg | tgtctgtctg gtgaaaaaaa | 3240 |
| gaaaaacaaa | ttggaagaga | ggaccatgag | aattttaata | aaacagaagg aaactaatgg | 3300 |
| accttccagg | atttattgtg | gacggatgtg | gatatattct | gtacaggaac aacacatatg | 3360 |
| gaagtggact | gaagcctatg | tagaaacaca | cacacactga | acattgttat tcattttgta | 3420 |
| aaatactagt | ctttatttc | attttttgta | aaatttaaac | atcgtatgcg cataaagaaa | 3480 |
| aaggaaacaa | gaattagggg | aaaataacat | tttccaaata | attataaaaa attgtcctgt | 3540 |
| gtctatgtat | ctatatctgt | tttgtatttt | tttctggttc | caaaccagat ttcctgtgat | 3600 |
| tctatactaa | taattttga | tataaccctt | tgcttcttat | aatgagtgcg atatatgttg | 3660 |
| tcgaggctgt | tcttcaagaa | ttaaaattga | agtgaaaatt | taaacaaaaa taaaagaatt | 3720 |
| tagcaaaaaa | aaaa | | | | 3734 |

<210> SEQ ID NO 11
<211> LENGTH: 5110
<212> TYPE: DNA
<213> ORGANISM: Homo sapiens

<400> SEQUENCE: 11

| | | | | |
|---|---|---|---|---|
| gccgtactgc | cttttttccc | ctctttcatt | ctttctctcc | gtcttttcct cccccctctg | 60 |
| cgcacgaagg | atgtgcttct | aggtggtgat | ctgccctcct | ctctctcttt tatcatttct | 120 |
| cccccgccgc | cggcgagttg | actctttccc | tatgtgtgtg | aggcggcggc ggcagcagca | 180 |
| gcagcagcgg | ctccggcggc | ggcagcagcg | gcagcagcga | cttcagcggc ggcggcggcg | 240 |
| ctagacgcag | cggctccggg | cccgacccgg | cggcttcggc | ggcggctccg gcggcagcgg | 300 |
| cggcccgggc | ggcccgcagg | gaacggcgag | cggcctccac | ccagcgactg cgggcggcgg | 360 |
| cggccggaga | gagcgaggcg | cgcgccggac | gcccggggca | ggcggcggcg gcggcggccc | 420 |

```
agcgccagga cgacgccgcg cagcgcccga cgcggaccac tttcatgctg attccccgg    480
acccgggcag cgctccggcc actccgcggg ccgccggcct ccgccccggc ctgcctggct    540
ccctgggcgc gcccgcaccc ggcgcctccg atctcctagt cctcctgatt tcgatggctt    600
tcctgaatgg ctgactgtgg gctgccctgg acttggcccc cggacagtcg cctctcctcc    660
tcctctacct cctccttcac caccacctcc tcttcctcct cctcctcctc ctcctcctcc    720
gccaactcct cggctgcaca ccagctctaa gagcgagagt gaacgagaga gggagggaga    780
gagtgagagc gagcgagatc tttggagaga ttttttttt tgcctcctac ttctgtcttg     840
aagccagaca atcgacttca gctctccctc ccctccctct ttctccacgt tctgctccca    900
ctcgctctcc tgtccccttc ccctcccctc ccggcggaaa gccccccgaa accaacaaag    960
ctgagccgag agaaacaaac aaaacaaaca caccgggcca gacaagccat cgacaaaact   1020
ttgcaaaagc aaaacaaaa aaggaaaaac taaccaacct caaccaacca gccccgagc    1080
cacccggggc gccctcccgc gccctcttgc accctcgcac acacaaaagg cggcgcgccg   1140
gagcccgaga cccggggagc cgccgccgcc ccgccgccgc ccgcagccag gggagcagga   1200
agtccggacg cagcccccat agatatggca atggtagtca gcacgtggcg cgaccccag    1260
gacgaggtgc ccggctcaca gggcagccag gcctcgcagg cgccgcccgt gcccggcccg   1320
ccgcccggcg ccccgcacac gccacagacg cccggccaag ggggcccagc cagcacgcca   1380
gcccagacgg cggccggtgg ccaggcggc cctggcggcc cgggtagcga caagcagcag    1440
cagcagcaac acatcgagtg cgtggtgtgc ggagacaagt cgagcggcaa gcactacggc   1500
cagttcacgt gcgagggctg caagagcttc ttcaagcgca gcgtgcggag gaacctgagc   1560
tacacgtgcc gcgccaaccg gaactgtccc atcgaccagc accatcgcaa ccagtgccag   1620
tactgccgcc tcaaaaagtg cctcaaagtg ggcatgagac gggaagcggt gcagagggc    1680
aggatgccgc cgacccagcc gacccacggg cagttcgcgc tgaccaacgg ggatcccctc   1740
aactgccact cgtacctgtc cggatatatt tccctgctgt tgcgcgcgga gccctatccc   1800
acgtcgcgct tcggcagcca atgcatgcag cccaacaaca tcatgggtat cgagaacatt   1860
tgcgaactgg ccgcgaggat gctcttcagc gccgtcgagt gggcccggaa catccccttc   1920
ttccccgacc tgcagatcac ggaccaggtg gccctgcttc gcctcacctg gagcgagctg   1980
tttgtgttga atgcggcgca gtgctccatg ccccctccacg tcgccccgct cctggccgcc   2040
gccggcctgc atgcttcgcc catgtccgcc gaccgggtgg tcgcctttat ggaccacata   2100
cggatcttcc aagagcaagt ggagaagctc aaggcgctgc acgttgactc agccgagtac   2160
agctgcctca aggccatagt cctgttcacc tcagatgcct gtggtctctc tgatgtagcc   2220
catgtggaaa gcttgcagga aaagtctcag tgtgctttgg aagaatacgt taggagccag   2280
taccccaacc agccgacgag attcggaaag cttttgcttc gcctcccttc cctccgcacc   2340
gtctcctcct cagtcataga gcaattgttt ttcgtccgtt tggtaggtaa acccccatc    2400
gaaaccctca tccgggatat gttactgtcc ggcagcagtt ttaactggcc gtatatggca   2460
attcaataaa taaataaaat aagaaggggg agtgaaacag agaaagaaaa ggcaaaagac   2520
tggtttgttt gcttaatttc cttctgttaa gaaaggatat aaaaggatgt tacaagtttg   2580
ctaaaagaag agaggggaag aatttaatgg actgtgaatt tcaaaaaaaa aaaaaaagac   2640
tgtcaaatga acttttacag aatgcattaa aaaaaaaaaa aaactcctgt gtcggtcaga   2700
acaacttgct acttatcatt tttgtataaa aaggaaatta gtcttttttct tttttggta    2760
```

```
aattttttgaa aaatattgct aaaagtgcat ttaaggagat tgggagacaa ttagcagaat    2820
ggagaaagta agtctttttt ttttccaaat tattaattgt cctgtgtcta tgtacctcta    2880
gctgttcttt tttgtacttt tctggttcca aaccagttta ttctgtggtt ctataataag    2940
ttttgatata atcttggctt cttaaaaact gtgtatcatt aaaatatatg ttctgcaaga    3000
attaaaactg agtccatgaa aataccatag gaagacataa aactttaaaa ggcaactcaa    3060
agatgatgga aacgcactta caagtggtga ccaaaatttt taggtgaagt cgagcactct    3120
aattagagaa ctggaggaac cacatataac acttaacttc ccctaccctg ccctccccca    3180
aaagaaacca tgacaaacct agcttttaaa aaatatttta agaaagagaa tgaactgtgg    3240
aatttattgg cagccaagga atgtgtccaa gacacatgct gaggttttga ataaaaagtg    3300
aacttttgta atttgaattg ggtcccgctt agttcttgaa ttgttatgaa aatcctatat    3360
ctgtttgtat atttgcaaac cctttgtatt ataattgttg atattttccc ttttttaaaaa    3420 ataccattga aatcagcatg acaaaaataa cactgttggc acttataggt aacgtgattg    3480
attcagtatc ttagagttta cagtttgtgt tttaaaaaaa ctgaaggttt tttttttaag    3540
tgcaacattt ctgtatactg taaaagttat aataactgaa ctgtttggtc gagtctttgt    3600
gtgttatatt ccaaggaaaa ttgaaagtat tcagaaatta aaatattatt tgatatctga    3660
aacctggctg tccccactca ctgtctttac atctagaaga gccctgtga gctctcgctt    3720 agctggccgg gcggggggtg gtggggggg gcatttgttt actcccctca gtcagtttgt    3780
tcaaaggtgg actactgtat ttgcctgttt aatttgggtg tgtgtgtgtt gggggggag    3840 ctgaagttaa tggtttatct atggtttagg aagtgccata ctgatatagt aaaccacccc    3900
cattcaccta atcctccttt taattaaaaa tggattttcc aggaaaaaaa aaaaggccct    3960
tatatttgtc acacttaagt gcctgcttag ggaaggtatt gtgaaaaagt attagaaatc    4020
ttgagatcag tatctatttt atgatcagaa aaaaatactc ttttgtacat ttctgacagt    4080
tactcagaag atcgttcaag caagctaatc acagcattgt aactagagga cagttgtttg    4140
cagtgagttt ttccttaagt aggtacgatt ttttaaaata ttctgtgatt ctactctagc    4200
gtggttgttg agagagtttc aaattcagtg atacaggttc taagactgaa aggtctactt    4260
ttaatgtata tatgataact tgcagttggt ttccctctcc cctccccccc tttaccttca    4320
gtctgtgaga gcatgaccac agggtcaagg gaatcttttc cattggagtt atgtacataa    4380
aaacacatcg acattttgac atttcagatt gtgtggctac aatctgtact gctcttggga    4440
tcctttgtcc ttagaagcca aattaaggaa gagaaagcag gacagagaaa aagaaagaag    4500
gaaggaggga aactttacag ggtgtgctga tttggaagta gtaactattt cttttggagt    4560 cttttttttca tttttcctct ttctcttttc ctggtttgga ggaagctcgg tgctgggagc    4620
ttgcaatttt gttcttattc aaggtttcca accccccccc ccaccgccag tacttcatca    4680
tgttgtggtt taattctaat tggtgggggg ggggaggac tagtgaggga ggtgaaagaa    4740
cagggataat tttgtaaagt gtattaaacg ttaatattca gatccagtca atacatgcag    4800
accagtaaaa tctgatttgt gcagagttct ccatctgact ctcacttatt tctgtagata    4860
tatacatata taaatacaag tatgttctta cggcacagta ttgctgacct ttagttcgag    4920
gttttgtcgg ttgttgttga ttttcttcct cttgcaagtg ctatccatgt gagtgtgtga    4980
agtttctcta ataagtaaaa cacaggccct tttccttgtt tgttttgtgt tagtttattg    5040
taaacagcca tttgttgtaa attattattg gcattaaatt ataatttatg attttcaaag    5100
caaaagacaa                                                           5110
```

<210> SEQ ID NO 12
<211> LENGTH: 3477
<212> TYPE: DNA
<213> ORGANISM: Homo sapiens

<400> SEQUENCE: 12

```
gtagtgatgt catatccgtt gtccaggtct ccacacctct ctcagcagtt aatcccttta      60
tctattcctt gggtcaaaac ttttgaggtg ggctagctat atagcagcgg gggagagggt     120
aaactggggc gcgcggggttg gaggcgcttc agcaccgcgg ccagcgccca ctgcagccca    180
acccactctc tagagctccc ggactcctag ctctgagaat gcctgcggaa tgatcgcccc    240
ccagggcggc tgccgccgct gccgctgctg ctgttattgc tactgctgct gccgccgcct    300
ctgcttccac tcggctctga ctggcaggca gaaagtgcaa ctgacgaggg aaaggtctct    360
gcagtgagtg gagagcctac ataaaagaga gtaaagaggg gcaaaaaccc agatcagaat    420
gcaggcgacg tccaaccttc tcaacctcct gctgctgtct ttgtttgccg gattagatcc    480
ttccaagact cagattagtc ctaaagaagg gtggcaggtg tacagctcag ctcaggatcc    540
tgatgggcgg tgcatttgca cagttgttgc tccagaacaa aacctgtgtt cccgggatgc    600
caaaagcagg caacttcgcc aactactgga aaaggttcag aacatgtccc agtctattga    660
agtcttaaac ttgagaactc agagagattt ccaatatgtt ttaaaaatgg aaacccaaat    720
gaaagggctg aaggcaaaat tcggcagat tgaagatgat cgaaagacac ttatgaccaa    780
gcattttcag gagttgaaag agaaaatgga cgagctcctg cctttgatcc ccgtgctgga    840
acagtacaaa acagatgcta agttaatcac ccagttcaag gaggaaataa ggaatctgtc    900
tgctgtcctc actggtattc aggaggaaat tggtgcctat gactacgagg aactacacca    960
aagagtgctg agcttggaaa caagacttcg tgactgcatg aaaaagctaa catgtggcaa   1020
actgatgaaa atcacaggcc cagttacagt caagacatct ggaacccgat ttggtgcttg   1080
gatgacagac cctttagcat ctgagaaaaa caacagagtc tggtacatgg acagttatac   1140
taacaataaa attgttcgtg aatacaaatc aattgcagac tttgtcagtg gggctgaatc   1200
aaggacatac aaccttcctt tcaagtgggc aggaactaac catgttgtct acaatggctc   1260
actctatttt aacaagtatc agagtaatat catcatcaaa tacagctttg atatggggag   1320
agtgcttgcc caacgaagcc tggagtatgc tggttttcat aatgtttacc cctacacatg   1380
gggtggattc tctgacatcg acctaatggc tgatgaaatc gggctgtggg ctgtgtatgc   1440
aactaaccag aatgcaggca atattgtcat cagccaactt aaccaagata ccttggaggt   1500
gatgaagagc tggagcactg gctaccccaa gagaagtgca ggggaatctt tcatgatctg   1560
tgggacactg tatgtcacca actcccactt aactggagcc aaggtgtatt attcctattc   1620
caccaaaacc tccacatatg agtacacaga cattcccttc cataaccaat actttcacat   1680
atccatgctt gactacaatg caagagatcg agctctctat gcctggaaca atggccacca   1740
ggtgctgttc aatgtcaccc ttttccatat catcaagaca gaggatgaca cataggcaaa   1800
tgtgacatgt tttcattgat ttaaacagtg tgatttgtga taaactctat aagacccctt   1860
ccgttttttt cttcactatt attttttcatc atttctccaa agcaaagcat ttttattgta   1920
aagttggtgt ttcaaaaaca tagctgagct tgtctaactt accatgttgg aaacacatct   1980
taacttctaa atttacaagg cctatcatgt ccttgtcatg aaaagcacta aaaaaaaaa    2040
gagtttaagt ggctaaagtc atagttttgc aagagattaa tgatctgcct tatattagag   2100
```

| | | | | |
|---|---|---|---|---|
| tcagagacta | atggtggctt | aaatgcacga | atgtcttttt | ttttaaaact | gtcattttt | 2160 |
| actgtctttt | gctccatatc | aggaaatatt | ttggtaggaa | ttaggagaac | aaaaagcact | 2220 |
| tttatcccat | ttatttcttt | aaaaaatgta | aggatttcat | ttatattgaa | aaataatatt | 2280 |
| aatcattttg | ctgttaacac | aattctctga | tgcggtgctg | tacagtcatt | tttaaatctc | 2340 |
| ttgctaacat | tttattggca | gtatgtattt | ctaccattgt | aaccaccatt | gtgctattgt | 2400 |
| atctcttcac | ttctgtgaaa | gtaatatttt | ttataaaata | cactgaaatt | taacctcagt | 2460 |
| aattgagtcc | attttcaagt | gtggtcaaga | ataatcttct | tggcttaccc | ctttacataa | 2520 |
| gcattataaa | ctaaaatgaa | aaccaaacca | gacacctgac | atagagtctt | tattttaccc | 2580 |
| caagttttt | gggccactga | cattgaatgc | aacaactgat | ttcatacaac | tgagttactc | 2640 |
| tgttcactcc | actgaatgca | acccatatag | tttcttgcac | aaggtgcatc | tggattccaa | 2700 |
| atattggatt | tgagttgact | ctactcattt | attatacact | aaagaaattt | tgttcttcat | 2760 |
| agttaaatgt | actagcattt | aatttatatt | ttacatacaa | cttgcaataa | tgaaattcct | 2820 |
| tatgtcagga | ccctgaaaat | aagcacattt | gaaaactctt | agaaaaaaaa | aattctgtaa | 2880 |
| tgtcctctag | atttagatta | tgagccctga | ggagttattg | gcaagatttg | tgcaaaataa | 2940 |
| aatatgggga | gacttgggag | ttgtctttgt | ggtttcaaaa | gtgtaaataa | ccaattcaga | 3000 |
| aaacaaaatg | gaaaacgac | cccttgttac | cttgattcac | tgtatgtgga | aaaataatgt | 3060 |
| aaccaaaagg | gaagagcttt | aataatactt | atgttaataa | ctctatgaaa | catataagct | 3120 |
| aactatatat | caaacatttc | attgagtttg | gatgtatttt | ccacatatta | aaaaaatagt | 3180 |
| tccctaaggc | agctttatgg | aaactaatat | aggttggttt | tacaatttaa | aaagtatatt | 3240 |
| ctataataaa | taataaaaca | aattgtttta | aatgtttagt | ttcacacata | catagtacca | 3300 |
| tgattttctt | tgaaagataa | ggatgtaatg | atttagataa | agcatcatgt | aaagaaatcc | 3360 |
| taacatttaa | gtgtaattca | tttcaaatgt | cacaagtaaa | gcatcatcct | caaatatctc | 3420 |
| actgtcaaaa | ttgtagaatt | aaataaccca | atcttgaaac | tgtcaaaaaa | aaaaaaa | 3477 |

<210> SEQ ID NO 13
<211> LENGTH: 5849
<212> TYPE: DNA
<213> ORGANISM: Homo sapiens

<400> SEQUENCE: 13

| | | | | | |
|---|---|---|---|---|---|
| gcgttccttg | cggcccggcc | gacctcgcgg | gcttgggcct | gggcgggcac | cgacggagcg | 60 |
| gccctggctg | cagcctcccg | gcgccagcga | agacaggctg | agatgcggct | gctcctgctc | 120 |
| gtgccgctgc | tgctggctcc | agcgcccggg | tcctcggctc | ccaaggtgag | gcggcagagt | 180 |
| gacacctggg | gaccctggag | ccagtggagc | ccctgcagcc | ggacctgtgg | aggggtgtc | 240 |
| agcttccggg | agcgcccctg | ctactcccag | aggagagatg | gaggctccag | ctgcgtgggc | 300 |
| cccgccggga | gccaccgctc | ttgtcgcacg | gagagctgcc | ccgacggcgc | ccggacttc | 360 |
| cgggccgagc | agtgcgcgga | gttcgacgga | gcggagttcc | aggggcggcg | gtatcggtgg | 420 |
| ctgcccctact | acagcgcccc | aaacaagtgt | gaactgaact | gcattcccaa | gggggagaac | 480 |
| ttctactaca | gcacaggga | ggctgtggtt | gatgggacgc | cctgcgagcc | tggcaagagg | 540 |
| gatgtctgtg | tggatggcag | ctgccgggtt | gtcggctgtg | atcacgagct | ggactcgtcc | 600 |
| aagcaggagg | acaagtgtct | gcggtgtggg | ggtgacggca | cgacctgcta | ccccgtcgca | 660 |
| ggcacctttg | acgctaatga | cctcagccga | gctgtgaaga | atgttcgtgg | ggaatactac | 720 |
| ctcaatgggc | actggaccat | cgaggcggcc | cgggccctgc | cagcagccag | caccatcctg | 780 |

```
cattacgagc gggtgctga gggggacctg gccctgagc gactccatgc cgggccccc      840
acctcggagc ccctggtcat cgagctcatc agccaggagc ccaaccccgg tgtgcactat    900
gagtaccacc tgccctgcg ccgccagc cccggcttca gctggagcca cggctcatgg      960
agtgactgca gcgcggagtg tggcggaggt caccagtccc gcctggtgtt ctgcaccatc   1020
gaccatgagg cctaccccga ccacatgtgc cagcgccagc cacggccagc tgaccggcgt   1080
tcctgcaatc ttcacccttg cccggagacc aagcgctgga aggcagggcc atgggcaccc   1140
tgctcagcct cctgtggagg aggctcccag tcccgctccg tgtactgcat ctcgtctgac   1200
ggggccggca tccaggaggc cgtggaggag gctgagtgtg ccgggctgcc tgggaagccc   1260
cctgccattc aggcctgtaa cctgcagcgc tgtgcagcct ggagcccgga gccctgggga   1320
gagtgttctg tcagttgtgg cgttggcgtc cggaagcgga gcgttacttg ccggggtgaa   1380
agggggttctt tgctccatac cgcagcgtgc tccttggaag accggccacc tctgactgag   1440
ccctgtgtgc atgaggactg cccctcctc agtgaccagg cctggcatgt ggcacctgg    1500
ggtctatgct ccaagagctg cagctcgggc actcggaggc gacaggtcat ctgtgccatt   1560
gggccgccca gccactgcgg gagcctgcag cactccaagc ctgtggatgt ggagccttgt   1620
aacacgcagc cctgtcatct cccccaggag gtccccagca tgcaggatgt gcacacccct   1680
gccagcaacc cctggatgcc gttgggccct caggagtccc ctgcctcaga ctccagaggc   1740
cagtggtggg cagcccagga acacccctca gccagggtg accacagggg agaacgaggt   1800
gaccccaggg gcgaccaagg cacccacctg tcagccctgg gccccgctcc ctctctgcag   1860
cagcccccat accagcaacc cctgcggtcg ggctcagggc ccacgactg cagacacagt    1920
cctcacgggt gctgccccga tggccacacg gcatctctcg ggcctcagtg caaggctgc    1980
cctggggccc cctgtcagca gagcaggtac gggtgctgcc ctgacagggt atctgtcgct   2040
gagggggcccc atcacgctgg ctgcacaaag tcgtatggtg gtgacagcac cggggcatg    2100
cccaggtcaa gggcagtggc ttctacagtc cacaacaccc accagcccca ggcccagcag   2160
aatgagccca gtgagtgccg gggctcccag tttggctgtt gctatgacaa cgtggccact   2220
gcagccggtc tcttggggga aggctgtgtg gccagccca gccatgccta ccccgtgcgg    2280
tgcctgctgc ccagtgccca tggctcttgc gcagactggg ctgcccgctg gtacttcgtt   2340
gcctctgtgg gccaatgtaa ccgcttctgg tatggcggct gccatggcaa tgccaataac   2400
tttgcctcgg agcaagagtg catgagcagc tgccagggat ctctccatgg gccccgtcgt   2460
ccccagcctg ggcttctgg aaggagcacc cacacgatg tggcggcag cagtcctgca    2520
ggcgagcagg aacccagcca gcacaggaca ggggccgcgg tgcagagaaa gccctggcct   2580
tctggtggtc tctggcggca agaccaacag cctgggccag gggaggcccc ccacacccag   2640
gcctttggag aatggccatg ggggcaggag cttgggtcca gggcccctgg actgggtgga   2700
gatgccggat caccagcgcc accttccac agctcctcct acaggattag cttggcaggt   2760
gtggagccct cgttggtgca ggcagccctg ggcagttgg tgcggctctc ctgctcagac   2820
gacactgccc cggaatccca ggctgcctgg cagaaagatg ccagcccat ctcctctgac    2880
aggcacaggc tgcagttcga cggatccctg atcatccacc cctgcaggc agaggacgcg   2940
ggcacctaca gctgtggcag caccggccca ggccgcgact cccagaagat ccaacttcgc   3000
atcataggg gtgacatggc cgtgctgtct gaggctgagc tgagccgctt ccctcagccc   3060
agggacccag ctcaggactt tggccaagcg ggggctgctg ggcccctggg ggccatcccc   3120
```

```
tcttcacacc cacagcctgc aaacaggctg cgtttggacc agaaccagcc ccgggtggtg    3180
gatgccagtc caggccagcg gatccggatg acctgccgtg ccgaaggctt cccgccccca    3240
gccatcgagt ggcagagaga tgggcagcct gtctcttctc ccagacacca gctgcagcct    3300
gatggctccc tggtcattag ccgagtggct gtagaagatg gcggcttcta cacctgtgtc    3360
gctttcaatg gcaggaccg agaccagcga tgggtccagc tcagagttct ggggagctg    3420 acaatctcag gactgccccc tactgtgaca gtgccagagg gtgatacggc caggctattg    3480
tgtgtggtag caggagaaag tgtgaacatc aggtggtcca ggaacgggct acctgtgcag    3540
gctgatggcc accgtgtcca ccagtcccca gatggcacgc tgctcattta aacttgcgg    3600 gccagggatg agggctccta cacgtgcagt gcctaccagg ggagccaggc agtcagccgc    3660
agcaccgagt tgaaggtggt ctcaccagca cccaccgccc agcccaggga ccctggcagg    3720
gactgcgtcg accagccaga gctggccaac tgtgatttga tcctgcaggc ccagctttgt    3780
ggcaatgagt attactccag cttctgctgt gccagctgtt cacgtttcca gcctcacgct    3840
cagcccatct ggcagtaggg atgaaggcta gttccagccc cagtccaaaa tagttcatag    3900
ggctagggag aaaggaagat ggactcttgg cttcctctct ctggctggca aagggagtta    3960
tcttctggaa tacattagct cttcaaaaa cccacccagt gtttagcctc aacggcagcc    4020
agttaccagc ttctctctgt agccttcagc agtgtttgca tctctgacat aaccacaggc    4080
tgctgttttc aagaagagca atctgtttgg ataagaaaaa cctttacttt acagcttccc    4140
tttataattt gttacacagg aatagttaaa tgcatttgtt tgtttgtttt ttgagacaga    4200
gtttcactct tgttgcccag gctggagggc aatggcgcga tctcagctca ctgcaacctc    4260
cgtctcctgg gttcttgatt ctcctgtgtc agccttctga gtagctagga ttacagatgc    4320
ctatcaccat gcctgggtaa ttttgtatt tttagttgag atggggtttc accatgttgg    4380
ccaggctggt ctcgaacttc tgacctcaga tgatctgccc gcctcagcct cccaaagtgc    4440
tgggattaca ggcatgagcc accacgccca gccatcaatg cattttttt attttttttt    4500 tgagacagag tttcgcactt cttgcccagg ctggagtaca atggtgcgat cttggctcac    4560
tgcaacctcc acctcctggg ttcaagcgct tctccagcct cagcctcctg agtagctggg    4620
attacaggta tgtgccacca tgcctggcta attttgtatt tttagtagag acggggtttc    4680
tccatgttgg tcagactggt cttgaactcc cgacctcagg taatccgccc gcctcggcct    4740
cccaaaatgc tgggattaga ggtgtgagcc actgtgccca gcccatcaat gtgttttaaa    4800
gctagctgtc agggttccac ttaatttaaa gctgggcagg gagatgtgta atgatttcaa    4860
agttaacacc tgtttgtttt ctaaagggca tgccaagtcc tgctgtatca gggaagtatt    4920
ctgtgctaaa atcagcgatg gttcattgct ctagtctctc tcaccttct aggcagtgca    4980 tcagtcagct ctaaatctgg tgcagagggt taacagcata accctgttg gcaaaatgga    5040 atagatgtta agacctcaaa tagggatttg ggatgaaaca gctgcagtta gcactgttat    5100
ctgagcatga aagaactgga aacgctcctt acgtcgagat gttggacctt gaagccctcc    5160
tgaggccaac atgcaaatct ggctgtgacg gttcatctga cacctgtgta aagctgacca    5220
gcctgctctg tacagtgaca atgaggagcc cctctcttcc ttaagtagga atctgtgaag    5280
caaaatgttt gctgccaaag acaaatcaga ctgtcagtca ttaaaaacag cattagcagg    5340
atgaggatag caatgggaa gggttgtggg caatgcagta acaggaaat ggcttcagaa    5400 atggtttgag ttggaagaca acattcttca tctctcagga cttctaattc cttgatgcta    5460
aaagaagagg catggattct atgagcttcc aagtcccttt ccactttaac cttctacaaa    5520
```

| | |
|---|---|
| tctttcagag gactgcctag tagcaaaggt tattcctgga cacaggaaag acgggcatta | 5580 |
| cagggaccaa agctctgaaa ggtgactttt attaccaaca cactggctgg aaaagggaca | 5640 |
| aaccacatca cgggtgagtg atacttctca gtcttctcta ctcattcaac aaaggaaatg | 5700 |
| tgggctgggg cagaggtctt ttttcattta atactgaaaa atattgaag agcatccatg | 5760 |
| ttcacttatg gctggttttg ctatagaaat tggaaaataa aggccacttt tttgaaatcc | 5820 |
| ccagtttaat taaaaaaaaa aaaaaaaa | 5849 |

<210> SEQ ID NO 14
<211> LENGTH: 2032
<212> TYPE: DNA
<213> ORGANISM: Homo sapiens

<400> SEQUENCE: 14

| | |
|---|---|
| actcggtgtc accacaggag gagactcagg caggccgcgc tccagcctca ccaggctccc | 60 |
| cggctcgccg tggctctctg agccccctt tcagggaccc cagtcgctgg aacatttgcc | 120 |
| cagactcgta ccaaactttt ccgccctggg ctcgggatcc tggactccgg ggcctccccg | 180 |
| tcctccctt tcccgggttc cagctccggc ctctggacta ggaaccgaca gcccccctcc | 240 |
| ccgcgtccct ccctctctct ccagccgttt tggggagggg ctctccacgc tccggatagt | 300 |
| tcccgagggt catccgcgcc gcactcgcct ttccgtttcg ccttcacctg gatataattt | 360 |
| ccgagcgaag ctgcccccag gatgaccacg ctggccggcg ctgtgcccag gatgatgcgg | 420 |
| ccgggccccgg ggcagaacta cccgcgtagc gggttcccgc tggaagtgtc cactcccctc | 480 |
| ggccagggcc gcgtcaacca gctcggcggt gttttatca acggcaggcc gctgcccaac | 540 |
| cacatccgcc acaagatcgt ggagatggcc caccacggca tccggccctg cgtcatctcg | 600 |
| cgccagctgc gcgtgtccca cggctgcgtc tccaagatcc tgtgcaggta ccaggagact | 660 |
| ggctccatac gtcctggtgc catcggcggc agcaagccca agcaggtgac aacgcctgac | 720 |
| gtggagaaga aaattgagga atacaaaaga gagaacccgg gcatgttcag ctgggaaatc | 780 |
| cgagacaaat tactcaagga cgcggtctgt gatcgaaaca ccgtgccgtc agtgagttcc | 840 |
| atcagccgca tcctgagaag taaattcggg aaaggtgaag aggaggaggc cgacttggag | 900 |
| aggaaggagg cagaggaaag cgagaagaag gccaaacaca gcatcgacgg catcctgagc | 960 |
| gagcgagcct cagcacccca atcagatgaa ggctctgata ttgactctga accagattta | 1020 |
| ccactaaaga ggaaacagcg cagaagccga accaccttca cagcagaaca gctggaggaa | 1080 |
| ctggagcgtg cttttgagag aactcattac cctgacattt atactaggga ggaactggcc | 1140 |
| cagagggcga agctcaccga ggcccgagta caggtctggt ttagcaaccg ccgtgcaaga | 1200 |
| tggaggaagc aagctgggc caatcaactg atggctttca accatctcat tcccgggggg | 1260 |
| ttccctccca ctgccatgcc gaccttgcca acgtaccagc tgtcggagac ctcttaccag | 1320 |
| cccacatcta ttcacaagc tgtgtcagat cccagcagca ccgttcacag acctcaaccg | 1380 |
| cttcctccaa gcactgtaca ccaaagcacg attccttcca acccagacag cagctctgcc | 1440 |
| tactgcctcc ccagcaccag gcatggattt tccagctata cagacagctt tgtgcctccg | 1500 |
| tcggggccct ccaaccccat gaaccccacc attggcaatg cctctcacc tcaggtaatg | 1560 |
| ggactcctga ccaaccacgg tggggtacct catcagcccc agactgatta cgcgctctcc | 1620 |
| cctctcaccg ggggtctgga acctaccacc acggtgtcgg ccagctgcag tcagagacta | 1680 |
| gaccatatga agagcttgga cagtctgcca acatctcagt cctactgtcc acccacctat | 1740 |

| | |
|---|---:|
| agcaccacag gctacagtat ggaccctgtc acaggctacc aatatgggca gtatggacaa | 1800 |
| agtaagcctt ggacttttta gggggcaatt tctcctggaa gggagataaa ctcaactctt | 1860 |
| ccttaagaaa ggtgaattag aggcaagatt aagccacaca tgccggtatc aattttcttt | 1920 |
| ttttttttgca aagccagctg actgttccag caggggcttc cttgtgtaat tattttctta | 1980 |
| actgatgtca acaacatctt gcggttatta attgttgaga cgtgaaacct ga | 2032 |

<210> SEQ ID NO 15
<211> LENGTH: 6969
<212> TYPE: DNA
<213> ORGANISM: Homo sapiens

<400> SEQUENCE: 15

| | |
|---|---:|
| aatattttgt gtgagagcga gcggtgcatt tgcatgttgc ggagtgatta gtgggtttga | 60 |
| aaagggaacc gtggctcggc ctcatttccc gctctggttc aggcgcagga ggaagtgttt | 120 |
| tgctggagga tgatgacaga ggtcaggctt cgctaatggg ccagtgagga gcggtggagg | 180 |
| cgaggccggg cgccggcaca cacacattaa cacacttgag ccatcaccaa tcagcatagg | 240 |
| aatctgagaa ttgctctcac acaccaaccc agcaacatcc gtggagaaaa ctctcaccag | 300 |
| caactccttt aaaacaccgt catttcaaac cattgtggtc ttcaagcaac aacagcagca | 360 |
| caaaaaccc caaccaaaca aaactcttga cagaagctgt gacaaccaga aaggatgcct | 420 |
| cataaagggg gaagacttta actagggggcg cgcagatgtg tgaggccttt tattgtgaga | 480 |
| gtggacagac atccgagatt tcagagcccc atattcgagc cccgtggaat cccgcggccc | 540 |
| ccagccagag ccagcatgca gaacagtcac agcggagtga atcagctcgg tggtgtcttt | 600 |
| gtcaacgggc ggccactgcc ggactccacc cggcagaaga ttgtagagct agctcacagc | 660 |
| ggggcccggc cgtgcgacat tcccgaattc tgcaggtgt ccaacggatg tgtgagtaaa | 720 |
| attctgggca ggtattacga gactggctcc atcagaccca gggcaatcgg tggtagtaaa | 780 |
| ccgagagtag cgactccaga agttgtaagc aaaatagccc agtataagcg ggagtgcccg | 840 |
| tccatctttg cttgggaaat ccgagacaga ttactgtccg agggggtctg taccaacgat | 900 |
| aacataccaa gcgtgtcatc aataaacaga gttcttcgca acctggctag cgaaaagcaa | 960 |
| cagatgggcg cagacggcat gtatgataaa ctaaggatgt tgaacgggca gaccggaagc | 1020 |
| tggggcaccc gccctggttg gtatccgggg acttcggtgc cagggcaacc tacgcaagat | 1080 |
| ggctgccagc aacaggaagg aggggagag aataccaact ccatcagttc caacggagaa | 1140 |
| gattcagatg aggctcaaat gcgacttcag ctgaagcgga agctgcaaag aaatagaaca | 1200 |
| tcctttaccc aagagcaaat tgaggccctg gagaaagagt ttgagagaac ccattatcca | 1260 |
| gatgtgtttg cccgagaaag actagcagcc aaaatagatc tacctgaagc aagaatacag | 1320 |
| gtatggtttt ctaatcgaag ggccaaatgg agaagagaag aaaaactgag gaatcagaga | 1380 |
| agacaggcca gcaacacacc tagtcatatt cctatcagca gtagtttcag caccagtgtc | 1440 |
| taccaaccaa ttccacaacc caccacaccg gtttcctcct tcacatctgg ctccatgttg | 1500 |
| ggccgaacag acacagccct cacaaacacc tacagcgctc tgccgcctat gccagcttc | 1560 |
| accatggcaa ataacctgcc tatgcaaccc ccagtcccca gccagacctc ctcatactcc | 1620 |
| tgcatgctgc ccaccagccc ttcggtgaat gggcggagtt atgataccta cacccccca | 1680 |
| catatgcaga cacacatgaa cagtcagcca atgggcacct cgggcaccac ttcaacagga | 1740 |
| ctcatttccc ctggtgtgtc agttccagtt caagttcccg gaagtgaacc tgatatgtct | 1800 |
| caatactggc caagattaca gtaaaaaaaa aaaaaaaaa aaaaggaaa ggaatattg | 1860 |

```
tgttaattca gtcagtgact atggggacac aacagttgag ctttcaggaa agaaagaaaa    1920
atggctgtta gagccgcttc agttctacaa ttgtgtcctg tattgtacca ctggggaagg    1980
aatggacttg aaacaaggac ctttgtatac agaaggcacg atatcagttg aacaaatct     2040
tcattttggt atccaaactt ttattcattt tggtgtatta tttgtaaatg ggcatttgta    2100
tgttataatg aaaaaaagaa caatgtagac tggatggatg tttgatctgt gttggtcatg    2160
aagttgtttt ttttttttt aaaaagaaaa ccatgatcaa caagctttgc cacgaattta    2220
agagttttat caagatatat cgaatacttc tacccatctg ttcatagttt atggactgat    2280
gttccaagtt tgtatcattc ctttgcatat aattaaacct ggaacaacat gcactagatt    2340
tatgtcagaa atatctgttg gttttccaaa ggttgttaac agatgaagtt tatgtgcaaa    2400
aaagggtaag atataaattc aaggaagaaa aaaagttgat agctaaaagg tagagtgtgt    2460
cttcgatata atccaatttg ttttatgtca aaatgtaagt atttgtcttc cctagaaatc    2520
ctcagaatga tttctataat aaagttaatt tcatttatat ttgacaagaa tatagatgtt    2580
ttatacacat tttcatgcaa tcatacgttt cttttttggc cagcaaaagt taattgttct    2640
tagatatagt tgtattactg ttcacggtcc aatcattttg tgcatctaga gttcattcct    2700
aatcaattaa aagtgcttgc aagagtttta aacttaagtg ttttgaagtt gttcacaact    2760
acatatcaaa attaaccatt gttgattgta aaaaaccatg ccaaagcctt tgtatttcct    2820
ttattataca gttttctttt taaccttata gtgtggtgtt acaaatttta tttccatgtt    2880
agatcaacat tctaaaccaa tggttacttt cacacacact ctgttttaca tcctgatgat    2940
ccttaaaaaa taatccttat agataccata aatcaaaaac gtgttagaaa aaaattccac    3000
ttacagcagg gtgtagatct gtgcccattt atacccacaa catatataca aaatggtaac    3060
atttcccagt tagccattta attctaaagc tcaaagtcta gaaataattt aaaaatgcaa    3120
caagcgatta gctaggaatt gttttttgaa ttaggactgg cattttcaat ctgggcagat    3180
ttccattgtc agcctatttc aacaatgatt tcactgaagt atattcaaaa gtagatttct    3240
taaaggagac tttctgaaag ctgttgcctt tttcaaatag gccctctccc ttttctgtct    3300
ccctccccct tgcacaagag gcatcatttc ccattgaacc actacagctg ttcccatttg    3360
aatcttgctt tctgtgcggt tgtggatggt tggagggtgg aggggggatg ttgcatgtca    3420
aggaataatg agcacagaca catcaacaga caacaacaaa gcagactgtg actggccggt    3480
gggaattaaa ggccttcagt cattggcagc ttaagccaaa cattcccaaa tctatgaagc    3540
agggcccatt gttggtcagt tgttatttgc aatgaagcac agttctgatc atgtttaaag    3600
tggaggcacg cagggcagga gtgcttgagc ccaagcaaag gatggaaaaa aataagcctt    3660
tgttgggtaa aaaaggactg tctgagactt tcatttgttc tgtgcaacat ataagtcaat    3720
acagataagt cttcctctgc aaacttcact aaaaagcctg ggggttctgg cagtctagat    3780
taaaatgctt gcacatgcag aaacctctgg ggacaaagac acacttccac tgaattatac    3840
tctgctttaa aaaaatcccc aaaagcaaat gatcagaaat gtagaaatta atggaaggat    3900
ttaaacatga ccttctcgtt caatatctac tgtttttag ttaaggaatt acttgtgaac     3960
agataattga gattcattgc tccggcatga aatatactaa taattttatt ccaccagagt    4020
tgctgcacat ttggagacac cttcctaagt tgcagttttt gtatgtgtgc atgtagtttt    4080
gttcagtgtc agcctgcact gcacagcagc acatttctgc aggggagtga gcacacatac    4140
gcactgttgg tacaattgcc ggtgcagaca tttctacctc ctgacatttt gcagcctaca    4200
```

```
ttccctgagg gctgtgtgct gagggaactg tcagagaagg gctatgtggg agtgcatgcc    4260
acagctgctg gctggcttac ttcttccttc tcgctggctg taatttccac cacggtcagg    4320
cagccagttc cggcccacgg ttctgttgtg tagacagcag agactttgga gacccggatg    4380
tcgcacgcca ggtgcaagag gtgggaatgg agaaaaagga gtgacgtggg agcggagggt    4440
ctgtatgtgt gcacttgggc acgtatatgt gtgctctgaa ggtcaggatt gccagggcaa    4500
agtagcacag tctggtatag tctgaagaag cggctgctca gctgcagaag ccctctggtc    4560
cggcaggatg ggaacggctg ccttgccttc tgcccacacc ctagggacat gagctgtcct    4620
tccaaacaga gctccaggca ctctcttggg gacagcatgg caggctctgt gtggtagcag    4680
tgcctgggag ttggcctttt actcattgtt gaaataattt ttgtttatta tttatttaac    4740
gatacatata tttatatatt tatcaatggg gtatctgcag ggatgttttg acaccatctt    4800
ccaggatgga gattatttgt gaagacttca gtagaatccc aggactaaac gtctaaattt    4860
tttctccaaa cttgactgac ttgggaaaac caggtgaata gaataagagc tgaatgtttt    4920
aagtaataaa cgttcaaact gctctaagta aaaaaatgca ttttactgca atgaatttct    4980
agaatatttt tcccccaaag ctatgcctcc taaacccttaa atggtgaaca actggtttct    5040
tgctacagct cactgccatt tcttcttact atcatcacta ggtttcctaa gattcactca    5100
tacagtatta tttgaagatt cagctttgtt ctgtgaatgt catcttagga ttgtgtctat    5160
attcttttgc ttatttcttt ttactctggg cctctcatac tagtaagatt ttaaaaagcc    5220
ttttcttctc tgtatgtttg gctcaccaag gcgaaatata tattcttctc ttttttcattt   5280 ctcaagaata aacctcatct gctttttgt ttttctgtgt tttggcttgg tactgaatga    5340
ctcaactgct cggttttaaa gttcaaagtg taagtactta gggttagtac tgcttatttc    5400
aataatgttg acggtgacta tctttggaaa gcagtaacat gctgtcttag aaatgacatt    5460
aataatgggc ttaaacaaat gaatagggg gtccccccac tctcctttg tatgcctatg    5520 tgtgtctgat ttgttaaaag atggacaggg aattgattgc agagtgtcgc ttccttctaa    5580
agtagtttta ttttgtctac tgttagtatt taaagatcct ggaggtggac ataaggaata    5640
aatggaagag aaaagtagat attgtatggt ggctactaaa aggaaattca aaagtctta    5700 gaacccgagc acctgagcaa actgcagtag tcaaaatatt tatctcatgt taaagaaagg    5760
caaatctagt gtaagaaatg agtaccatat aggttttga agttcatata ctagaaacac    5820
ttaaaagata tcatttcaga tattacgttt ggcattgttc ttaagtattt atatctttga    5880
gtcaagctga taattaaaaa aaatctgtta atggagtgta tatttcataa tgtatcaaaa    5940
tggtgtctat acctaaggta gcattattga agagagatat gtttatgtag taagttatta    6000
acataatgag taacaaataa tgtttccaga agaaaggaaa acacattttc agagtgcgtt    6060
tttatcagag gaagacaaaa atacacaccc ctctccagta gcttattttt acaaagccgg    6120
cccagtgaat tagaaaaaca aagcacttgg atatgatttt tggaaagccc aggtacactt    6180
attattcaaa atgcactttt actgagtttg aaaagtttct tttatattta aataagggt    6240 tcaaatatgc atattcaatt tttatagtag ttatctattt gcaaagcata tattaactag    6300
taattggctg ttaattttat agacatggta gccaggaag tatatcaatg acctattaag    6360
tattttgaca agcaatttac atatctgatg acctcgtatc tcttttcag caagtcaaat    6420 gctatgtaat tgttccattg tgtgttgtat aaaatgaatc aacacggtaa gaaaaaggtt    6480
agagttatta aaataataaa ctgactaaaa tactcatttg aatttattca gaatgttcat    6540
aatgctttca aaggacatag cagagctttt gtggagtatc cgcacaacat tatttattat    6600
```

```
ctatggacta aatcaatttt ttgaagttgc tttaaaattt aaaagcacct ttgcttaata    6660
taaagccctt taattttaac tgacagatca attctgaaac tttattttga aaagaaaatg    6720
gggaagaatc tgtgtcttta gaattaaaag aaatgaaaaa aataaaccc g acattctaaa   6780 aaaatagaat aagaaacctg attttagta ctaatgaaat agcgggtgac aaaatagttg     6840 tcttttgat tttgatcaca aaaaataaac tggtagtgac aggatatgat ggagagattt     6900
gacatcctgg caaatcactg tcattgattc aattattcta attctgaata aaagctgtat    6960
acagtaaaa                                                            6969

<210> SEQ ID NO 16
<211> LENGTH: 3817
<212> TYPE: DNA
<213> ORGANISM: Homo sapiens

<400> SEQUENCE: 16
gcggggctag agctgtcgga gaagcgggac cgcgaggccg cgcgcggcg ctctgcgcgg       60 tcagagggag cgcctggcag cagcaggagc agcagcagca gcccgcggcg gggccgccgc    120
cagccgccgc gaccgccgcg gctgcagcct ccgaagggag gccgggtgag ccggcgtacg    180
cactttcccg cggactttcg gagtgtttgt ggatatacat gccaagccgc cacgatgatg    240
tccatgaaca gcaagcagcc tcactttgcc atgcatccca ccctccctga gcacaagtac    300
ccgtcgctgc actccagctc cgaggccatc cggcgggcct gctgcccac gccgccgctg     360 cagagcaacc tcttcgccag cctggacgag acgctgctgg cgcgggccga ggcgctggcg   420
gccgtggaca tcgccgtgtc ccagggcaag agccatcctt tcaagccgga cgccacgtac   480
cacacgatga acagcgtgcc gtgcacgtcc acttccacgg tgcctctggc gcaccaccac   540
caccaccacc accaccacca ggcgctcgaa cccggcgatc tgctggacca catctcctcg   600
ccgtcgctcg cgctcatggc cggcgcgggc ggcgcgggcg cggcggccgg cggcggcggc   660
gcccacgacg gccggggggg cggtggcggc ccggcggcg gcggcggccc ggcggcggc    720 cccgggggag gcggcggtgg cggcccgggg ggcggcggcg gcggcccggg cggcgggctc   780
ctgggcggct ccgcgcaccc tcacccgcat atgcacagcc tgggccacct gtcgcaccc    840 gcggcggcgg ccgccatgaa catgccgtcc gggctgccgc accccgggct ggtggcggcg   900
gcggcgcacc acgcgcgggc agcggcagcg cggcggcgg cggccgggca ggtggcagcg    960
gcatcggcgg cggcggccgt ggtgggcgca gcgggcctgg cgtccatctg cgactcggac  1020 acggaccccgc gcgagctcga ggcgttcgcg gagcgcttca gcagcggcg catcaagctg   1080 ggcgtgacgc aggccgacgt gggctcggcg ctggccaacc tcaagatccc gggcgtgggc  1140
tcactcagcc agagcaccat ctgcaggttc gagtcgctca cgctctcgca caacaacatg  1200
atcgcgctca gcccatcct gcaggcgtgg ctcgaggagg ccgagggcgc ccagcgcgag  1260
aaaatgaaca agcctgagct cttcaacggc ggcgagaaga agcgcaagcg gacttccatc   1320
gccgcgcccg agaagcgctc cctcgaggcc tacttcgccg tgcagcccg gccctcgtcc    1380 gagaagatcg ccgccatcgc cgagaaactg gacctcaaaa agaacgtggt gcgggtgtgg  1440
ttttgcaacc agagacagaa gcagaagcgg atgaaattct ctgccactta ctgagggggc  1500
tgggaggtgt cggcgggac agaatgggga gctgaggagg cattttggg gggctttcct    1560 ctgcttgcct cccctcggat ttggagtgtc cgttatcctg cctgcatttg gggagtccct  1620
tctcgctctc tttcctccac ccattctctg attttcctgc ctttgctgtc ccctagcctt  1680
```

| | | |
|---|---|---|
| gaggactggg gtgctgggtg tggggattgg agtatagggt aggggagaag gggggagca | 1740 |
| ttcgggggag tggggagtgg ggggaaggaa agcggagacc cgagcagggg ttttaaggag | 1800 |
| caggatggtt ctggggtttg ggtgggggga gacgcgggaa gggtaggaaa atggactgtt | 1860 |
| tctgaccaga gacacttacc taaatatcct ggggaccaag gaactatgta caaaaacaaa | 1920 |
| cctaccaacc accaaaaact agacaaataa agacaaacta aaacaaaaca gaacaaaagc | 1980 |
| aaaggaaaat gctttagaaa ttttaactcc ggggagccat aatctgcaac ttcatttcc | 2040 |
| cccatagaag agaaaaaga gcaccaccat tattaccacc tccccaaccc tacacgcacg | 2100 |
| aactgagtcg aaaaacgaaa accaaacgag cgagaagttg aagttctggg tatcaaagct | 2160 |
| agttgttctg tctgcgtgtt taattttcc ctctctcacc tccaccccat ccatatcctc | 2220 |
| tttatttcct ccgttccaat gagaggccta tggctgctct ccaatcccgg gaagtgagtg | 2280 |
| ggagcacagc tgaaaagaga gggtcagggg gaggctggct gcttgcttag gtggaatcca | 2340 |
| agttttcccg tggccctgcc tatactctgg tggcctggtc ctgttggggt ggggtctt | 2400 |
| ggagagaagg gcatagtctt tgagctacta aaaagcagaa ttccggagct tcgagatatc | 2460 |
| ttattctagg aaaatgaaac aattttaaca acagtttttt ttcctcttat gtcgaagatc | 2520 |
| tagttttaga caatttcaaa ataagctttt cccactcata gaactttaac ttgcccttc | 2580 |
| agttttatct tttttttaga gagaggttta aactactgat ttttcctgtt gattcaaata | 2640 |
| gactaatggg gtgaaagtta ttaggagaga tactctctcc tgttttctcc actgaacgag | 2700 |
| actcatcttg ctcttctagg tcccgttct tcctctcttg gaggacatga aattatagaa | 2760 |
| atgttgagaa gttcctgctt tcttttgcgg taggacttgg ctgtgagaaa atcacctaaa | 2820 |
| tcccagaaaa gaggaagaca gatttaaagt gcccccaccc ccatttgttt caagaggtc | 2880 |
| tgcatgttgg gcgaaaacag aacaactgtg tttccttta cttgttctta ttattcaaga | 2940 |
| gtcatttatt acagggata aatgttgggt agcaagaact ttaatttgca ctaccagtct | 3000 |
| cccaaataga aaatcatgta tagtatttca tagtaataat caggtacctt acaagctgct | 3060 |
| ggtggatttt aaaaaattaa gatagttgaa ggtggttagg taaaatgcct gctttgtgta | 3120 |
| caagatactc tttggatctc tcgtagagat ggtttgttac catcctttaa tcataactaa | 3180 |
| aacattgaaa acagaacaaa tgagaaaaga aaaaaaacct gccgattaac aagactgaaa | 3240 |
| tcatgcatga tctgaaaggt gtggaaagaa acacaattag gtctcactct ggttaggcat | 3300 |
| tattttattta attatgttgt atatcattgt ttgcagggca acattctat gcatttgaaa | 3360 |
| ctgagcacta aactgggcta gctttctggt agaccgtttt gtggctagtg cgatttcaca | 3420 |
| gtctactgcc tgtttccact gaaaacattt ttgtcatatt cttgtattca agaaaaagg | 3480 |
| aaaaagatt attgtaaata tttattaa tgcacacatt cacacagtgg taacagactg | 3540 |
| ccagtgttca tcctgaaatg tctcacggat tgatctacct gtccatgtat gtctgctgag | 3600 |
| ctttctcctt ggttatgttt tttctctttt accttctcc tcccttactt ctatcagaac | 3660 |
| caattctatg cgccaaaata caacagggg atgtgtccca gtacacttac aaataaaca | 3720 |
| taactgaaag aagagcagtt ttatgatttg ggtgcgtttt tgtgtttata ctgggccagg | 3780 |
| tcctggtaga accttcaac aaacaaccaa acaaaaa | 3817 |

<210> SEQ ID NO 17
<211> LENGTH: 8787
<212> TYPE: DNA
<213> ORGANISM: Homo sapiens

<400> SEQUENCE: 17

-continued

```
ggccgcagct ccccggcgga ggcaagaggt ggttgggggg gaccatggct gacgttttcc    60
cgggcaacga ctccacggcg tctcaggacg tggccaaccg cttcgcccgc aaaggggcgc   120
tgaggcagaa gaacgtgcac gaggtgaagg accacaaatt catcgcgcgc ttcttcaagc   180
agcccacctt ctgcagccac tgcaccgact tcatctgggg gtttgggaaa caaggcttcc   240
agtgccaagt ttgctgtttt gtggtccaca agaggtgcca tgaatttgtt acttttcctt   300
gtccgggtgc ggataaggga cccgacactg atgaccccag gagcaagcac aagttcaaaa   360
tccacactta cggaagcccc accttctgcg atcactgtgg gtcactgctc tatggactta   420
tccatcaagg gatgaaatgt gacacctgcg atatgaacgt tcacaagcaa tgcgtcatca   480
atgtccccag cctctgcgga atggatcaca ctgagaagag ggggcggatt tacctaaagg   540
ctgaggttgc tgatgaaaag ctccatgtca cagtacgaga tgcaaaaaat ctaatcccta   600
tggatccaaa cgggctttca gatccttatg tgaagctgaa acttattcct gatcccaaga   660
atgaaagcaa gcaaaaaacc aaaccatcc gctccacact aaatccgcag tggaatgagt   720
cctttacatt caaattgaaa ccttcagaca agaccgacg actgtctgta gaaatctggg   780
actgggatcg aacaacaagg aatgacttca tgggatccct ttccttgga gtttcggagc   840
tgatgaagat gccggccagt ggatggtaca agttgcttaa ccaagaagaa ggtgagtact   900
acaacgtacc cattccggaa ggggacgagg aaggaaacat ggaactcagg cagaaattcg   960
agaaagccaa acttggccct gctggcaaca aagtcatcag tccctctgaa gacaggaaac  1020
aaccttccaa caaccttgac cgagtgaaac tcacggactt caatttcctc atggtgttgg  1080
gaaaggggag ttttggaaag gtgatgcttg ccgacaggaa gggcacagaa gaactgtatg  1140
caatcaaaat cctgaagaag gatgtggtga ttcaggatga tgacgtggag tgcaccatgg  1200
tagaaaagcg agtcttggcc ctgcttgaca accccccgtt cttgacgcag ctgcactcct  1260
gcttccagac agtggatcgg ctgtacttcg tcatggaata tgtcaacggt ggggacctca  1320
tgtaccacat tcagcaagta ggaaaattta aggaaccaca agcagtattc tatgcggcag  1380
agatttccat cggattgttc tttcttcata aaagaggaat catttatagg gatctgaagt  1440
tagataacgt catgttggat tcagaaggac atatcaaaat tgctgacttt gggatgtgca  1500
aggaacacat gatggatgga gtcacgacca ggaccttctg tgggactcca gattatatcg  1560
ccccagagat aatcgcttat cagccgtatg gaaaatctgt ggactggtgg gcctatggcg  1620
tcctgttgta tgaaatgctt gccgggcagc ctccatttga tggtgaagat gaagacgagc  1680
tatttcagtc tatcatggag cacaacgttt cctatccaaa atccttgtcc aaggaggctg  1740
tttctatctg caaaggactg atgaccaaac acccagccaa gcggctgggc tgtgggcctg  1800
aggggagag ggacgtgaga gagcatgcct tcttccggag gatcgactgg gaaaaactgg  1860
agaacaggga gatccagcca ccattcaagc ccaaagtgtg tggcaaagga gcagagaact  1920
ttgacaagtt cttcacacga ggacagcccg tcttaacacc acctgatcag ctggttattg  1980
ctaacataga ccagtctgat tttgaagggt tctcgtatgt caaccccag tttgtgcacc   2040
ccatcttaca gagtgcagta tgaaactcac cagcgagaac aaacacctcc ccagccccca   2100
gccctccccg cagtgggaag tgaatcctta accctaaaat tttaaggcca cggccttgtg   2160
tctgattcca tatggaggcc tgaaaattgt agggttatta gtccaaatgt gatcaactgt   2220
tcagggtctc tcttacaa ccaagaacat tatcttagtg aagatggta cgtcatgctc    2280
agtgtccagt ttaattctgt agaagttacg tctggctcta ggttaaccct tcctagaaag   2340
```

```
caagcagact gttgccccat tttgggtaca atttgatata ctttccatac cctccatctg    2400 tggattttc  agcattggaa tcccccaacc agagatgtta aagtgagcct gtcccaggaa    2460
acatctccac ccaagacgtc tttggaatcc aagaacagga agccaagaga gtgagcaggg    2520
agggattggg ggtgggggag gcctcaaaat accgactgcg tccattctct gcctccatgg    2580
aaacagcccc tagaatctga aaggccggga taaacctaat cactgttccc aaacattgac    2640
aaatcctaac ccaaccatgg tccagcagtt accagtttaa acaaaaaaac ctcagatgag    2700
tgttgggtga atctgtcatc tggtaccctc cttggttgat aactgtcttg atacttttca    2760
ttctttgtaa gaggccaaat cgtctaagga cgttgctgaa caagcgtgtg aaatcatttc    2820
agatcaagga taagccagtg tgtacatatg ttcattttaa tctctgggag attatttttc    2880
catccagggt gccatcagta atcatgccac tactcaccag tgttgttcgc caacacccac    2940
ccccacacac accaacattt tgctgcctac cttgttatcc ttctcaagaa gctgaagtgt    3000
acgccctctc ccctttttgtg cttatttatt taataggctg cagtgtcgct tatgaaagta    3060
cgatgtacag taacttaatg gaagtgctga ctctagcatc agcctctacc gattgatttt    3120
cctcccttct ctagccctgg atgtccactt agggataaaa agaatatggt tttggttccc    3180
atttctagtt cacgttgaat gacaggcctg gagctgtaga atcaggaaac ccggatgcct    3240
aacagctcaa agatgttttg ttaatagaag gattttaata cgttttgcaa atgcatcatg    3300
caatgaattt tgcatgtttta taaaacct taataacaag tgaatctata ttattgatat    3360
aatcgtatca agtataaaga gagtattata ataattttat aagacacaat tgtgctctat    3420
ttgtgcaggt tcttgtttct aatcctcttt tctaattaag ttttagctga atcccttgct    3480
tctgtgcttt ccctccctgc acatgggcac tgtatcagat agattacttt ttaaatgtag    3540
ataaaatttc aaaaatgaat ggctagttta cgtgatagat taggctctta ctacatatgt    3600
gtgtgtatat atatgtattt gattctacct gcaaacaaat ttttattggt gaggactatt    3660
tttgagctga cactccctct tagtttcttc atgtcacctt tcgtcctggt tcctccgcca    3720
ctcttcctct tggggacaac aggaagtgtc tgattccagt ctgcctagta cgttggtaca    3780
cacgtggcat tgccgcagca cctgggctga ccttttgtgtg tgcgtgtgtg tgtgtttcct    3840
tcttcccttc agcctgtgac tgttgctgac tccagggtg ggagggatgg ggagactccc    3900
ctcttgctgt gtgtactgga cacgcaggaa gcatgctgtc ttgctgcctc tgcaacgacc    3960
tgtcgtttgc tccagcatgc acaaacttcg tgagaccaac acagccgtgc cctgcaggca    4020
ccagcacgtg ctttcagag gctgcggact ttcttccagc cattgtggca ttggcctttc    4080
cagtcttggg aggagcgcgc tgctttggtg agacaccccc atgcaaggtc ctcagagtag    4140
ccgggttcta ccacaaacag aaacagaatg aaagtagctg tcagtccttg tagagagccg    4200
ctctgtttcc tcccagaagc atctcccagc taagctcgca ttattttct cctctggctg    4260 tttgcctgaa gttcacagaa cacacaacca tgaaaggctt tttgaggtga gaggcccagg    4320
tggtcctggc aaccctgagt agaaggagag acggggtagg gaacgggccc ggccagaaaa    4380
gaaccatttc ttctgccatc ttttatgcac catagacatc gagactccag ggggtcctgg    4440
ctcccctgtc cctgcagccc tgcaggtcag tgcatgatct gggttcgtgt cctgaccagg    4500
tgctcctcct ttgatccgag gggaaaggga ctggtttata gaaagagcct aggagacaaa    4560
agggccagtc cccctgccca gaatggagca gcagcaggac agaccccac  gaggcccccc    4620 agagaggagg aagatcccac ggaggaacac atgaggttag ggacccttgt tcagcacccc    4680
aaacagcctg cctgtttaaa gcaggcagca ggcttaggcc ttccctgcaa ccccaacacc    4740
```

```
cacaagtttg tttctctagg aaacacattc actgtctcag ctggctgtta ctctctcaga   4800
ccatatggca aagttttcca agaaaatgcc ccgacagggg tgcccagcac actgcctgag   4860
ggacaacaga catcagaaca aaccccccaga gagaaacagt caaaatcagg gcccggtgca   4920
gtgttgtcat gtggaacctg ctttatccat tgctgagtgt tgaatgtggg taatggttag   4980
ggctttccag atctcagcag ccaaagacag ttattgttgg aagactgtca tgtagataac   5040
catgagcaat ggctcgcctc agaatcagtt cataaaattc tatggtactg gcccttcgt    5100 gggtattgtg tgaaatgaga tggtggcgag gggtgcgctg tggaactgcc gcagccacgc   5160
aggaggtccc tggggatgc tttgggaagt ccttgcccct gagcactgcc tgattgccag     5220
ggcctgtgga ggtctaggcc gcctggcaga atctagcacc gtccgaatcc ccgcaggacc   5280
catggagcta tgaccacacc aggccattca aatggctctg cattatcttc ccttggaagg   5340
tggccactcc tcggtggcag ggcctttccc tgaggctgca ggccgtgggc tggcagcccg   5400
tctcttggca tttcaattga aggtcaccag gtgctgggtt tgaaaggaag tcactggagt   5460
gctgccaggg gccgccctcc aaggttaatg agaggcccac atccaggcaa gaactaattc   5520
aaaaggcaga tcagaaacca caggagtcaa aattattgct ccggcagtgc ttcccttcct   5580
ttcatccact ggcctcgtgt ggtccatgca gggccactgt ctgcccttc tgatgccacg     5640 tattaggctt tcttactcag aattttgata gaaaaccatg gggccaagag ctctggaagc   5700
ctggccggaa agaccaaggt tcatgcagcc caacaaatga ttgttgagca cctctcggag   5760
ccaaagtcct taggcgagtg tggtgacttc ctggaaggag gatgcagact tccagagagc   5820 cccccccaacg gacgtgctga agggagag ggaggcgggg gctgtagtca ggaaggagcc      5880
agagaagaac agggtttggg tgcatccaga aatatgcctg cagtaggagg gagaggaagg   5940
ggtgccaccg tcaacggctt cccatcggag gtggttggtg cagatggaag tttctgtctg   6000
ctggccctca agagagtgtt ttgccaggga cacagtctgt tcctcctcag aaaacacccc   6060
ccaaatgcta acaacatccc caccagctgc tagaagcccc tttcccctcc ccaccttgaa   6120
gtagctcata gttctctggg cagagccaga ccatccagtg tacccagag gccagtaggt     6180 tcctgcccat tttcctctct ggcttcctgc caagaattat ggcagctgag gatgaatgga   6240
gaagtaaaaa caactaacac cgcacaacta acaactaaca ccgcagttcc cacctgggtt   6300
ccacttagca ggagacattt cggagggttt ttttttgtttt tgttcctgtt tttttttttt   6360
ttgctggaat ttgttttctc agtactgaaa agagaaaaag tgacaatctt gtattttaa    6420 aagcctcgga aaggtgatac catctgacag tcatttttctc acgttggtct tctaaagtca   6480
cctatttctt gtgtgtgcac atcacaccat ttcctgtttc tttataaccc gacaagggta   6540
ggagtgcctg tttcccctgc tgggcacacc agacaatcgt aatcacaaaa cagacactga   6600 gccagggcc caaagggtgt gatcatgaga gttaccggga cagcagtagg catgacagtc    6660
accaggaagg acaagggtgc tctgttgtta gtggccacac accaatttga caaggagtgt   6720
tgcgaaattt ttattatttt atttatttat tttgagatgg agtttcactc ttgttgccca   6780
ggctggagtg cggtggtaca atctcggctc actgcaacct ccacctccca ggttcaagcg   6840
attctcctgc ctcagcctcc caagtacctg ggactacagg tgcgtgccac cacacccagc   6900
taaattttgt gttttagta gagatggggt ttcaccatgt tggccaggat ggtcttgaac    6960
ccctgacctc atgatctgcc tgcctcggcc tcccaaagtg ctgggattac aggcatgagc   7020
caccacgccc agccaaaata tttttttaaa gtcattttcc ttaagctgct tgggctacat   7080
```

```
gtgaaataca ctggacggtc aacattcctg tctcctccca tttgggctga tgcagcagat    7140
ccagggaatg ttacctgttt ctgctgctag aagatccagg aaattgggaa ggttacctga    7200
cgcacacatg gatgaaggcc atcatctaga aatggggtca accacaattg tgttaattcc    7260
gtagtgtcag ggattcttcg ggaaggtcaa cagtatgaag gattctgacc cctgtgcctc    7320
ccatttatgt gatcaggtga cagttaataa ccgtggaggt cacactcagc catccaacag    7380
ccttacagtg accctacaca aaagccccca aattccaaag acttttctt aacctaaagg     7440 aagaaattat tgttaattc cagtagagca actgaatata ctgggctatt tgtactttt     7500 tatagagaac tttaataata attctttaaa aatgagtttt tagaacaaag caactgacga    7560
tttcctaaga ttccaatgcc ctggagcttg taggaggact tagcctgggt cagctggagc    7620 accccgacc tgatctccca ctgccagatt tcccatgct cctagggtat ggagtccacg      7680
tgggaatgac tgcaagttca ggtggaactt ggccgactga tgctctgcga gttttaata    7740 gacactgggg acaactgctt aaggtttaga aacttccaaa ccacaggaaa acatttta     7800 gtgtcccca tccagaggca gccctggaat aggattccca ggggtttctg gaccccttt      7860 ccttgctccg tgaggctctg tggccatctt ttggcaggag gaggatgctt ccttggctct    7920
gtgcccagac ccgcctggtc cccaggtctc tcaccttggg tgaagattca gagatgccct    7980
gtaaggattt tgcccactgg gcaactcaga aatacttcga tctcccaaga tataagaggc    8040
agcagcaaac gtgcctattg acgtctgttt catagttacc acttacgcga gtagacagaa    8100
ctcggctttt cagaaaatag gtgtcaagtc cactttataa gaaccttttt ttctaaaata    8160
agataaaagg tggctttgca ttttctgatt aaacgactgt gtctttgtca cctctgctta    8220
actttaggag tatccattcc tgtgattgta gacttttgtt gatattcttc ctggaagaat    8280 atcattctt tcttgaaggg ttggtttact agaatattca aaatcaatca tgaaggcagt    8340
tactattttg agtctaaagg ttttctaaaa attaacctca catcccttct gttagggtct    8400
ttcagaatat cttttataaa cagaagcatt tgaagtcatt gcttttgcta catgatttgt    8460
gtgtgtgaag gacataccac gtttaaatca ttaattgaaa aacatcatat aagccccaac    8520
tttgtttgga ggaagagacg gaggttgagg tttttccttc tgtataagca cctactgaca    8580
aaatgtagag gccattcaac cgtcaaacac catttggtta tatcgcagag gagacggatg    8640
tgtaaattac tgcattgctt ttttttttcag tttgtataac ctctaatctc cgtttgcatg    8700
atacgctttg ttagaaacat taattgtagt ttggaagcaa gtgtgtatga ataaagataa    8760
tgatcattcc aaaaaaaaaa aaaaaaa                                        8787
```

<210> SEQ ID NO 18
<211> LENGTH: 3485
<212> TYPE: DNA
<213> ORGANISM: Homo sapiens

<400> SEQUENCE: 18

```
agtcgcccag gggagcccgg agaagcaggc tcaggaggga gggagccaga ggaaaagaag     60
aggaggagaa ggaggaggac ccggggaggg aggcgcggcg cgggaggagg aggggcgcag    120
ccgcggagcc agtggccccg cttggacgcg ctgctctcca gatacccccg gagctccagc    180
cgcgcggatc gcgcgctccc gccgctctgc ccctaaactt ctgccgtagc tccctttcaa    240
gccagcgaat ttattcctta aaaccagaaa ctgaacctcg gcagggaaa ggagtccgcg     300 gaggagcaaa accacagcag agcaagaaga gcttcagaga gcagccttcc cggagcacca    360
actccgtgtc gggagtgcag aaaccaacaa gtgagagggc gccgcgttcc cggggcgcag    420
```

```
ctgcgggcgg cgggagcagg cgcaggagga ggaagcgagc gccccgagc cccgagcccg      480 agtccccgag cctgagccgc aatcgctgcg gtactctgct ccggattcgt gtgcgcgggc      540
tgcgccgagc gctgggcagg aggcttcgtt ttgccctggt tgcaagcagc ggctgggagc      600
agccggtccc tggggaatat gcggcgcgcg tggatcctgc tcaccttggg cttggtggcc      660
tgcgtgtcgg cggagtcgag agcagagctg acatctgata agacatgta ccttgacaac       720 agctccattg aagaagcttc aggagtgtat cctattgatg acgatgacta cgcttctgcg      780
tctggctcgg gagctgatga ggatgtagag agtccagagc tgacaacatc tcgaccactt      840
ccaaagatac tgttgactag tgctgctcca aaagtggaaa ccacgacgct gaatatacag      900
aacaagatac ctgctcagac aaagtcacct gaagaaactg ataagagaa agttcacctc      960 tctgactcag aaaggaaaat ggacccagcc gaagaggata caaatgtgta tactgagaaa     1020
cactcagaca gtctgtttaa acggacagaa gtcctagcag ctgtcattgc tggtggagtt     1080
attggctttc tctttgcaat ttttcttatc ctgctgttgg tgtatcgcat gagaaagaag     1140
gatgaaggaa gctatgacct tggagaacgc aaaccatcca gtgctgctta tcagaaggca     1200
cctactaagg agttttatgc gtaaaactcc aacttagtgt ctctatttat gagatcactg     1260
aacttttcaa ataaagctt  ttgcatagaa taatgaagat cttt gttttt tgttttcatt     1320 aaagagccat tctggcactt taatgataaa atcccattgt atttaaaaca tttcatgtat     1380
ttctttagaa caacataaaa ttaaaattta acatctgcag tgttctgtga atagcagtgg     1440
caaaatatta tgttatgaaa accctcgatg ttcatggaat tggtttaaac ttttatgcgc     1500
aaatacaaaa tgattgtctt tttcctatga ctcaaagatg aaagctgttt catttgtgtc     1560
agcatgtctc agattgacct taccaagttg gtcttacttt gttaatttat ctgttgtccc     1620
cttcctctcc tctgccctcc cttcttgtgc ccttaaaacc aaaccctatg cctttt gtag    1680 ctgtcatggt gcaatttgtc tttggaaaat tcagataatg gtaatttagt gtatatgtga     1740
ttttcaaata tgtaaacttt aacttccact ttgtataaat ttt aagtgt cagactatcc     1800 attttacact tgcttt atttt tcatt acct gtagctttgg gcagatttgc aacagcaaat    1860
taatgtgtaa aattggatta ttactacaaa accgttagt catatctatc taatcagatc      1920
ttcttttggg aggatttgat gtaagttact gacaagcctc agcaaaccca aagatgttaa     1980
cagtatttta agaagttgct gcagattcct ttggccactg tatttgttaa ttt cttgcaa    2040 tttgaaggta cgagtagagg tttaaagaaa aatcagtttt tgttcttaaa aatgcattta     2100
agttgtaaac gtctttttaa gcctttgaag tgcctctgat tctatgtaac ttgttgcaga     2160
ctggtgttaa tgagtatatg taacagttta aaaaaaagt tggtatttta taagcacaga     2220
caattctaat ggtaactttt gtagtcttat gaatagacat aaattgtaat ttgggaacat     2280
aaaaactact gaataaatca tgtggcctaa tattgaaaat gtcactgtta taaattttgt     2340 acattttga  tcaaatgtac atctcccctt tgctaacggc cgtctgctct caaggatgac     2400
gtgggtttga tttctaagtg tttcacagtg tctgtaaatc aagaccaaag agcctgtcga     2460
tgagactgtt tattaccaga ttcacttctg aattggccag aggaaatctg aatgtattat     2520
cctgtgtgtg tctaggtaga gatattggaa ggctgccagg ggatttcgaa gtttgcaacc     2580
tttataggat aactgatggc aatattaaga cagacgcctg cttttgcaaa taacttacaa     2640
gactgtaaat tccaaagatc tgaatggggc tttcctgatg ttggtatcta aggcttaggc     2700
ctatagattg atttaccttt ggaattgtgc tccaaatgtc tactgaagct taaccgaaga     2760
```

```
actaataaat ggactacagt agctcacgtt acagggaagg agggtaggca gggaggctct    2820
gtgtgttaaa atgagggtct cactgcttta ggattgaagt ggctggaaag agtgatgcct    2880
ggggaaggag atggagttat gagggtactg tggctggtac tttctgtact aaacatttcc    2940
tttttctatt ttaccactaa ttttgtttta aactgtgagc cgtccaagtc agaagaagac    3000
agcaaaaaaa gcaacttttc caacatacaa tttactttta ataaagtatg aatatttcat    3060
tttgagaaca ttccctggaa ttgccacata attcattaaa acatttttt taagcaacac    3120
ttggaacagt gtttacttta aatccttaat ggccttaatt aattctcaga ttcctgcccc    3180
atcacttaca gaaccaattc actttagagt gactaaaagg aaacgatagc ctagcttttct    3240
aaagccacgc tgtgtccctc aattacagag ggtaggaatg ggtatacctc taactgtgca    3300
aagcagagtg aaattcaatt catagaataa caactgctgg gaatatccgt gccaggaaaa    3360
gaaaaatttc tggcaaatat tttgtcactg ctgtaaagca aatatttgt gaaagtgcca    3420
aaataaagtc tgtcatgcca aaagtaaatc attgtataga ctgacatcca gttttcttca    3480
actgt                                                                 3485

<210> SEQ ID NO 19
<211> LENGTH: 4108
<212> TYPE: DNA
<213> ORGANISM: Homo sapiens

<400> SEQUENCE: 19
ccggccgtct atgctccagg ccctctcctc gcggtgccgg tgaacccgcc agccgccccg      60
atgtacagca tgatgatgga gaccgacctg cactcgcccg gcggcgccca ggcccccacg     120
aacctctcgg gccccgccgg ggcgggcggc ggcggggggcg gaggcggggg cggcggcggc    180
ggcggggggcg ccaaggccaa ccaggaccgg gtcaaacggc ccatgaacgc cttcatggtg    240
tggtcccgcg ggcagcggcg caagatggcc caggagaacc ccaagatgca caactcggag    300
atcagcaagc gcctgggggc cgagtggaag gtcatgtccg aggccgagaa gcggccgttc    360
atcgacgagg ccaagcggct gcgcgcgctg cacatgaagg agcacccgga ttacaagtac    420
cggccgcgcc gcaagaccaa gacgctgctc aagaaggaca gtactcgct ggccggcggg    480
ctcctggcgg ccggcgcggg tggcggcggc gcggctgtgg ccatgggcgt gggcgtgggc    540
gtgggcgcgg cggccgtggg ccagcgcctg gagagcccag gcggcgcggc gggcggcggc    600
tacgcgcacg tcaacggctg gccaacggc gcctaccccg gctcggtggc ggcggcggcg    660
gcggccgcgg ccatgatgca ggaggcgcag ctggcctacg ggcagcaccc gggcgcgggc    720
ggcgcgcacc cgcacgcgca ccccgcgcac ccgcacccgc accaccccgca cgcgcacccg    780
cacaacccgc agcccatgca ccgctacgac atgggcgcgc tgcagtacag ccccatctcc    840
aactcgcagg gctacatgag cgcgtcgccc tcgggctacg gcggcctccc ctacggcgcc    900
gcggccgccg ccgccgccgc tgcgggcggc gcgcaccaga actcggccgt ggcggcggcg    960
gcggcggcgg cggccgcgtc gtcgggcgcc ctggcgcgc tgggctctct ggtgaagtcg   1020
gagcccagcg gcagcccgcc cgccccagcg cactcgcggg cgccgtgccc cggggacctg   1080
cgcgagatga tcagcatgta cttgcccgcc ggcgaggggg cgacccggc ggcggcagca   1140
gcggccgcgg cgcagagccg gctgcactcg ctgccgcagc actaccaggg cgcgggcgcg   1200
ggcgtgaacg gcacggtgcc cctgacgcac atctagcgcc ttcggacgc cggggactct   1260
gcggcggcga cccacgagct cgcggcccgc gcccggctcc cgccccgccc cggcgcggcg   1320
tggcttttgt acagacgttc ccacattctt gtcaaaagga aaatactgga gacgaacgcc   1380
```

```
gggtgacgcg tgtcccccac tcaccttccc cggagaccct ggcgaccgcc gggcgctgac    1440
accagacttg ggttttagac tgaacttcgg tgttttcttg agacttttg tacagtattt    1500 atcacctacg gaggaagcgg aaagcgtttt ctttgctcga ggggacaaaa aagtcaaaac    1560
gaggcgagag gcgaagccca cttttgtata ccggccggcg cgctcacttt cctccgcgtt    1620
gcttccggac ggcgccgacc gccggagccc aagtgacgcg gagctcgtcg catttgttat    1680
aaatgtagta aggcaggtcc aagcacttac aagttttttg tagttgttac cgctcttttg    1740
ggttggtttg ttaatttata caaagagatt accaccacca cccctcctt cagacggcgg    1800 agttatattc tgggttttgt aaaactttat gtatctgagc atttccattt ttttttttgg    1860
gttttgtatt atttcttgta aatgcattgt gaaaatttt attttcggcg ttgcaatgcg    1920
gggaggagaa gtcagattat gtacatagtt ttctaaaaag cctttcttct aaaaacgaaa    1980
aaagaccccc cacccaaaat gtttcgagtc aacaaattta agagacagag cccattttct    2040
ccataaattt gtaacatgct atttttatgt gcatgtttta tgagttcaaa atgcaatgag    2100
gaaatctgac agggaaatta tctgtatgaa ctaaagtaa gggaaccccg gggaatggga    2160
ggacaggatt tttcaaggaa cctttttcaa tgaaagagaa ggaagttaaa acctataggt    2220
tattttgtag agctgagtgt taatacgggc cgagaaataa aagtatcttc tgctccggct    2280
gtttcactgc ggacggctgg ggctgctgcg cgttaccttg ctgcaagcgg ggcgccttcc    2340
acctggctgg gggtctgcgc cacagtttgg tccagaggag ggaggaggaa gggaagaccc    2400
cagtggtggg accctggacc aggccatgga tgaaggacaa agaccagggc aggtcacggg    2460
tttcccaatt ccccagcaat taagatttcg agcagaattt atctaaatgt gtttcaagga    2520
aacacaatcg ctgaaccaaa acgtactgca gccgagcccc ctccgtccat cctctgcccc    2580
tccccctggc ttctttctct tgggaaaacg ggcaaaataa ttgtgctgga ttctcacaca    2640
cacagaaata tcgaccatca ccctccccg cgtgaactgg gatgcaagtt gctaaccgat    2700
gtgaacgcaa aatgccttgt tcattattcc tgacgagatc ttgaggttgt ttgatgcttt    2760
aaatttttta attatattat tttctaggtg tttattggta cattgcagtt tttttttga    2820 aatttaaaaa tttctgtaaa actttgtctt caagtaatct gacagcatta aatattgcat    2880
ttaaaaatta tactgtagca aatacattta aaaattaatc acaacgttaa gatgaaatta    2940 tattttgga aaaaaaaac acttgaagcc cagatgaaa tacgtttatt tcagcagcct    3000
taggtttccc ctcgctttct caacacccctt ccttgtcctg gagtatggac tgtccgtcca    3060
aaagtgagcc tatgctataa gtttaatgag aaccgaattc agcctgcatt cgagaatagc    3120
tttaagtata atgctgatct gacaattgac gtgtaatttg ggaagtcatt ttgataattt    3180
tgcttaaacc actcattcgt taaagtgatt acaaaaaagt tcaagaatga tgtccactgc    3240
tttctaacaa gataataaac cccccccctc ttttctttt ctttatttt atttctttta    3300 gctatttgat cctttctgaa gcagttgttt ctggaagagt ctgtgcgccc atggatggct    3360
gagcaccact acgacttagt ccgggataag ggcctcccca gtcctctccg ggagatgatt    3420
tgggaaattt tataatgctt gttctgttaa ctcaccggga ccttgagggt ccaatgggac    3480
cttgagggtt ttctctgaaa tatacaaact taaaggactc tctctgaggt tctttgactg    3540
acgtccactc tcagtctggc ccctgtgctc ccctgtgtgt accctggagt ttctgtgtcc    3600
aattgttggc atctaggtct tggctcaaga ttaggatgtg ggcccacttt tagaggcaca    3660
gactatgaaa agctgagtta gtgcgcccgg gacgccaggc aagcagcttt tacagtttgg    3720
```

| | |
|---|---:|
| catcttattg caggtgcttc gtgcacagtc agctgaaata gccaatgcca ggtgctccaa | 3780 |
| ccaccttatt tccttgtttt gttgattaga acaacacaga aaaaagcaaa tataaatttt | 3840 |
| taatgactcc atttaaaaat atcacagggt gggggcaagg aaattagctg agattcatct | 3900 |
| caggattgag attctatccc cccttccccg cccccagcag tgtcgctcca attcaaatta | 3960 |
| gtggagaaaa gattacagta ggccctgagc cgactgtgaa ttcggtgctt ggccaaggta | 4020 |
| acactcatcg tattcacgga gtgaaatact atatgatgat agttattata ttatatgacg | 4080 |
| acttcattca cttcccaaat cacagggt | 4108 |

<210> SEQ ID NO 20
<211> LENGTH: 5621
<212> TYPE: DNA
<213> ORGANISM: Homo sapiens

<400> SEQUENCE: 20

| | |
|---|---:|
| aagaaaatcc tgcttgacaa aaaccgtcac ttaggaaaag atgtcctttc gggcagccag | 60 |
| gctcagcatg aggaacagaa ggaatgacac tctggacagc acccggaccc tgtactccag | 120 |
| cgcgtctcgg agcacagact tgtcttacag tgaaagcgac ttggtgaatt ttattcaagc | 180 |
| aaattttaag aaacgagaat gtgtcttctt taccaaagat tccaaggcca cggagaatgt | 240 |
| gtgcaagtgt ggctatgccc agagccagca catggaaggc acccagatca accaaagtga | 300 |
| gaaatggaac tacaagaaac acaccaagga atttcctacc gacgcctttg gggatattca | 360 |
| gtttgagaca ctggggaaga agggaagta tatacgtctg tcctgcgaca cggacgcgga | 420 |
| aatcctttac gagctgctga cccagcactg gcacctgaaa acacccaacc tggtcatttc | 480 |
| tgtgaccggg ggcgccaaga acttcgccct gaagccgcgc atgcgcaaga tcttcagccg | 540 |
| gctcatctac atcgcgcagt ccaaaggtgc ttggattctc acgggaggca cccattatgg | 600 |
| cctgatgaag tacatcgggg aggtggtgag agataacacc atcagcagga gttcagagga | 660 |
| gaatattgtg gccattggca tagcagcttg ggcatggtc tccaaccggg acaccctcat | 720 |
| caggaattgc gatgctgagg gtattttttt agcccagtac cttatggatg acttcacaag | 780 |
| agatccactg tatatcctgg acaacaacca cacacatttg ctgctcgtgg acaatggctg | 840 |
| tcatggacat cccactgtcg aagcaaagct ccggaatcag ctagagaagt atatctctga | 900 |
| gcgcactatt caagattcca actatggtgg caagatcccc attgtgtgtt ttgcccaagg | 960 |
| aggtggaaaa gagactttga agccatcaa tacctccatc aaaaataaaa ttccttgtgt | 1020 |
| ggtggtggaa ggctcgggcc agatcgctga tgtgatcgct agcctggtgg aggtggagga | 1080 |
| tgccctgaca tcttctgccg tcaaggagaa gctggtgcgc ttttttacccc gcacggtgtc | 1140 |
| ccggctgcct gaggaggaga ctgagagttg atcaaatgg ctcaaagaaa ttctcgaatg | 1200 |
| ttctcaccta ttaacagtta ttaaaatgga agaagctggg gatgaaattg tgagcaatgc | 1260 |
| catctcctac gctctataca aagccttcag caccagtgag caagacaagg ataactggaa | 1320 |
| tgggcagctg aagcttctgc tggagtggaa ccagctggac ttagccaatg atgagatttt | 1380 |
| caccaatgac cgccgatggg agtctgctga ccttcaagaa gtcatgttta cggctctcat | 1440 |
| aaaggacaga cccaagtttg tccgcctctt tctggagaat ggcttgaacc tacgaagtt | 1500 |
| tctcacccat gatgtcctca ctgaactctt ctccaaccac ttcagcacgc ttgtgtaccg | 1560 |
| gaatctgcag atcgccaaga attcctataa tgatgccctc tcacgtttg tctggaaact | 1620 |
| ggttgcgaac ttccgaagag gcttccggaa ggaagacaga aatggccggg acgagatgga | 1680 |
| catagaactc cacgacgtgt ctcctattac tcggcacccc ctgcaagctc tcttcatctg | 1740 |

```
ggccattctt cagaataaga aggaactctc caaagtcatt tgggagcaga ccagggctg    1800 cactctggca gccctgggag ccagcaagct tctgaagact ctggccaaag tgaagaacga   1860
catcaatgct gctggggagt ccgaggagct ggctaatgag tacgagaccc gggctgttga   1920
gctgttcact gagtgttaca gcagcgatga agacttggca gaacagctgc tggtctattc   1980
ctgtgaagct tggggtggaa gcaactgtct ggagctggcg gtggaggcca cagaccagca   2040
tttcatcgcc cagcctgggg tccagaattt tcttctaag caatggtatg gagagatttc    2100
ccgagacacc aagaactgga agattatcct gtgtctgttt attataccct tggtgggctg   2160
tggctttgta tcatttagga agaaacctgt cgacaagcac aagaagctgc tttggtacta   2220
tgtggcgttc ttcacctccc ccttcgtggt cttctcctgg aatgtggtct tctacatcgc   2280
cttcctcctg ctgtttgcct acgtgctgct catggatttc cattcggtgc acaccccccc   2340
cgagctggtc ctgtactcgc tggtctttgt cctcttctgt gatgaagtga cagtggta    2400 cgtaaatggg gtgaattatt ttactgacct gtggaatgtg atggacacgc tggggctttt   2460
ttacttcata gcaggaattg tatttcggct ccactcttct aataaaagct ctttgtattc   2520
tggacgagtc atttttctgtc tggactacat tattttcact ctaagattga tccacatttt   2580
tactgtaagc agaaacttag gacccaagat tataatgctg cagaggatgc tgatcgatgt   2640
gttcttcttc ctgttcctct tgcggtgtg gatggtggcc tttggcgtgg ccaggcaagg   2700
gatccttagg cagaatgagc agcgctggag gtggatattc cgttcggtca tctacgagcc   2760
ctacctggcc atgttcggcc aggtgcccag tgacgtggat ggtaccacgt atgactttgc   2820
ccactgcacc ttcactggga atgagtccaa gccactgtgt gtggagctgg atgagcacaa   2880
cctgccccgg ttccccgagt ggatcaccat cccctggtg tgcatctaca tgttatccac    2940
caacatcctg ctggtcaacc tgctggtcgc catgtttggc tacacggtgg caccgtcca    3000 ggagaacaat gaccaggtct ggaagttcca gaggtacttc ctggtgcagg agtactgcag   3060
ccgcctcaat atcccccttcc ccttcatcgt cttcgcttac ttctacatgg tggtgaagaa   3120
gtgcttcaag tgttgctgca aggagaaaaa catggagtct tctgtctgct gtttcaaaaa   3180
tgaagacaat gagactctgg catgggaggg tgtcatgaag gaaaactacc ttgtcaagat   3240
caacacaaaa gccaacgaca cctcagagga aatgaggcat cgattagac aactggatac     3300 aaagcttaat gatctcaagg gtcttctgaa agagattgct aataaaatca ataaaactg     3360 tatgaactct aatggagaaa aatctaatta tagcaagatc atattaagga atgctgatga   3420
acaattttgc tatcgactac taaatgagag attttcagac ccctgggtac atggtggatg   3480 atttttaaatc acccctagtgt gctgagacct tgagaataaa gtgtgtgatt ggttcatac    3540 ttgaagacgg atataaagga agaatatttc ctttatgtgt ttctccagaa tggtgcctgt   3600
ttctctctgt gtctcaatgc ctgggactgg aggttgatag tttaagtgtg ttcttaccgc   3660
ctcctttttc ctttaatctt attttttgatg aacacatata taggagaaca tctatcctat    3720
gaataagaac ctggtcatgc tttactcctg tattgttatt ttgttcattt ccaattgatt    3780
ctctactttt ccctttttg tattatgtga ctaattagtt ggcatattgt taaaagtctc    3840
tcaaattagg ccagattcta aaacatgctg cagcaagagg acccccgctct cttcaggaaa   3900 agtgttttca tttctcagga tgcttcttac ctgtcagagg aggtgacaag gcagtctctt   3960
gctctcttgg actcaccagg ctcctattga aggaaccacc cccattccta aatatgtgaa   4020
aagtcgccca aaatgcaacc ttgaaaggca ctactgactt tgttcttatt ggatactcct    4080
```

| | |
|---|---|
| cttattattt ttccattaaa aataatagct ggctattata gaaaatttag accatacaga | 4140 |
| gatgtagaaa gaacataaat tgtccccatt accttaaggt aatcactgct aacaatttct | 4200 |
| ggatggtttt tcaagtctat ttttttttcta tgtatgtctc aattctcttt caaaatttta | 4260 |
| cagaatgtta tcatactaca tatatacttt ttatgtaagc ttttcactt agtattttat | 4320 |
| caaatatgtt tttattatat tcatagcctt cttaaacatt atatcaataa ttgcataata | 4380 |
| ggcaacctct agcgattacc ataattttgc tcattgaagg ctatctccag ttgatcattg | 4440 |
| ggatgagcat ctttgtgcat gaatcctatt gctgtatttg ggaaaatttt ccaaggttag | 4500 |
| attccaataa atatctattt attattaaat attaaaatat ctatttatta ttaaaaccat | 4560 |
| ttataaggct ttttcataaa tgtatagcaa ataggaatta ttaacttgag cataagatat | 4620 |
| gagatacatg aacctgaact attaaaataa aatattatat ttaacccttta gtttaagaag | 4680 |
| aagtcaatat gcttatttaa atattatgga tggtgggcag atcacttgag gtcaggagtt | 4740 |
| cgagaccagc ctggccaaca tggcaaaacc acatctctac taaaaataaa aaaattagct | 4800 |
| gggtgtggtg gtgcactcct gtaatcccag ctactcagaa ggctgaggta caagaattgc | 4860 |
| tggaacctgg gaggcggagg ttgcagtgaa ccaagattgc accactgcac tccagccggg | 4920 |
| gtgacagagt gagactccga ctgaaaataa ataaataaat aaataaataa ataaataaat | 4980 |
| attatggatg gtgaagggaa tggtatagaa ttggagagat tatcttactg aacacctgta | 5040 |
| gtcccagctt tctctggaag tggtcgtatt tgagcaggat gtgcacaagg caattgaaat | 5100 |
| gcccataatt agtttctcag ctttgaatac actataaact cactggctga aggaggaaat | 5160 |
| tttagaagga agctactaaa agatctaatt tgaaaaacta caaagcatt aactaaaaaa | 5220 |
| gtttatttc cttttgtctg ggcagtagtg aaaataacta ctcacaacat tcactatgtt | 5280 |
| tgcaaggaat taacacaaat aaaagatgcc ttttttactta aacaccaaga cagaaaactt | 5340 |
| gcccaatact gagaagcaac ttgcattaga gagggaactg ttaaatgttt tcaacccagt | 5400 |
| tcatctggtg gatgttttg caggttactc tgagaatttt gcttatgaaa aatcattatt | 5460 |
| tttagtgtag ttcacaataa tgtattgaac atacttctaa tcaaaggtgc tatgtccttg | 5520 |
| tgtatggtac taaatgtgtc ctgtgtactt ttgcacaact gagaatcctg cagcttggtt | 5580 |
| taatgagtgt gttcatgaaa taaataatgg aggaattgtc a | 5621 |

<210> SEQ ID NO 21
<211> LENGTH: 2284
<212> TYPE: DNA
<213> ORGANISM: Homo sapiens

<400> SEQUENCE: 21

| | |
|---|---|
| gcggtgccgc cgccgtggc cgcctcagcc caccagccgg gaccgcgagc catgctgtcc | 60 |
| gccgcccgcc cccagggttg ttaaagccag actgcgaact ctcgccactg ccgccaccgc | 120 |
| cgcgtcccgt cccaccgtcg cgggcaacaa ccaaagtcgc cgcaactgca gcacagagcg | 180 |
| ggcaaagcca ggcaggccat ggggctctgg gcgctgttgc ctggctgggt ttctgctacg | 240 |
| ctgctgctgg cgctggccgc tctgcccgca gccctggctg ccaacagcag tggccgatgg | 300 |
| tggggtattg tgaacgtagc ctcctccacg aacctgctta cagactccaa gagtctgcaa | 360 |
| ctggtactcg agcccagtct gcagctgttg agccgcaaac agcggcgtct gatacgccaa | 420 |
| aatccgggga tcctgcacag cgtgagtggg gggctgcaga gtgccgtgcg cgagtgcaag | 480 |
| tggcagttcc ggaatcgccg ctggaactgt cccactgctc cagggcccca cctcttcggc | 540 |
| aagatcgtca accgaggctg tcgagaaacg gcgtttatct tcgctatcac ctccgccggg | 600 |

```
gtcacccatt cggtggcgcg ctcctgctca gaaggttcca tcgaatcctg cacgtgtgac    660
taccggcggc gcggccccgg gggccccgac tggcactggg ggggctgcag cgacaacatt    720
gacttcggcc gcctcttcgg ccgggagttc gtggactccg gggagaaggg gcgggacctg    780
cgcttcctca tgaaccttca caacaacgag gcaggccgta cgaccgtatt ctccgagatg    840
cgccaggagt gcaagtgcca cgggatgtcc ggctcatgca cggtgcgcac gtgctggatg    900
cggctgccca cgctgcgcgc cgtgggcgat gtgctgcgcg accgcttcga cggcgcctcg    960
cgcgtcctgt acggcaaccg cggcagcaac cgcgcttcgc gggcggagct gctgcgcctg   1020
gagccggaag acccggccca caaaccgccc tcccccacg acctcgtcta cttcgagaaa    1080
tcgcccaact tctgcacgta cagcggacgc ctgggcacag caggcacggc agggcgcgcc   1140
tgtaacagct cgtcgcccgc gctggacggc tgcgagctgc tctgctgcgg caggggccac   1200
cgcacgcgca cgcagcgcgt caccgagcgc tgcaactgca ccttccactg gtgctgccac   1260
gtcagctgcc gcaactgcac gcacacgcgc gtactgcacg agtgtctgtg aggcgctgcg   1320
cggactcgcc cccaggaacg ctctcctcga gccctccccc aaacagactc gctagcactc   1380
aagacccggt tattcgccca cccgagtacc tccagtcaca ctcccgcgg ttcatacgca    1440 tcccatctct cccacttcct cctacctggg gactcctcaa accacttgcc tggggcggca   1500
tgaaccctct gccatcctg atggacctgc cccggaccta cctccctccc tctccgcggg    1560
agaccccttg ttgcactgcc ccctgcttgg ccaggaggtg agagaaggat gggtcccctc   1620
cgccatgggg tcggctcctg atggtgtcat tctgcctgct ccatcgcgcc agcgacctct   1680
ctgcctctct tcttcccctt tgtcctgcgt tttctccggg tcctcctaag tcccttccta   1740
ttctcctgcc atgggtgcag accctgaacc cacacctggg catcagggcc tttctcctcc   1800
ccacctgtag ctgaagcagg aggttacagg gcaaaagggc agctgtgatg atgtggaaat   1860
gaggttgggg gaaccagcag aaatgccccc attctcccag tctctgtcgt ggagccattg   1920
aacagctgtg agccatgcct ccctgggcca cctcctaccc cttcctgtcc tgcctcctca   1980
tcagtgtgta ataatttgc actgaaacgt ggatacagag ccacgagttt ggatgttgta    2040
aataaaacta tttattgtgc tgggtcccag cctggtttgc aaagaccacc tccaacccaa   2100
cccaatccct ctccactctt ctctcctttc tccctgcagc cttttctggt ccctcttctc   2160
tcctcagttt ctcaaagatg cgtttgcctc ctggaatcag tatttccttc cactgtagct   2220
attagcggct cctcgccccc accagtgtag catcttcctc tgcagaataa aatctctatt   2280
ttta                                                                 2284

<210> SEQ ID NO 22
<211> LENGTH: 2417
<212> TYPE: DNA
<213> ORGANISM: Homo sapiens

<400> SEQUENCE: 22
gcagcagaga ggagttgagg gcgatgagag cgggtactgc gaactgccgg gcgatgctgt     60
cgctgccgcc gtgatacgga gagcaacagt tccccagcaa caccctccc cgacacaggc    120 acacacccc cgacaggcac gcacacccac cccacagtgc ccggctcggc tgcgcctcct    180
ctattggccc aggaagccca cccagccccg ccacgcagag cccagaagga agaaagcct    240 catgcctgag ccgaggggag caccatggat ctgacaaaaa tggcatgat ccagctgcag     300 aaccctagcc accccacggg gctactgtgc aaggccaacc agatgcggct ggccgggact    360
```

```
ttgtgcgatg tggtcatcat ggtggacagc caggagttcc acgcccaccg gacggtgctg    420
gcctgcacca gcaagatgtt tgagatcctc ttccaccgca atagtcaaca ctatactttg    480
gacttcctct cgccaaagac cttccagcag attctggagt atgcatatac agccacgctg    540
caagccaagg cggaggacct ggatgacctg ctgtatgcgg ccgagatcct ggagatcgag    600
tacctggagg aacagtgcct gaagatgctg agaccatcc aggcctcaga cgacaatgac     660
acggaggcca ccatggccga tggcggggcc gaggaagaag aggaccgcaa ggctcggtac    720
ctcaagaaca tcttcatctc gaagcattcc agcgaggaga gtgggtatgc cagtgtggct    780
ggacagagcc tccctgggcc catggtggac cagagccctt cagtctccac ttcatttggt    840
cttccagcca tgagtcccac caaggctgca gtggacagtt tgatgaccat aggacagtct    900
ctcctgcagg gaactcttca gccacctgca gggcccgagg agccaactct ggctgggggt    960
gggcggcacc ctggggtggc tgaggtgaag acggagatga tgcaggtgga tgaggtgccc    1020
agccaggaca gccctgggc agccgagtcc agcatctcag gagggatggg ggacaaggtt    1080
gaggaaagag gcaaagaggg gcctgggacc ccgactcgaa gcagcgtcat caccagtgct    1140
agggagctac actatgggcg agaggagagt gccgagcagg tgccaccccc agctgaggct    1200
ggccaggccc ccactggccg acctgagcac ccagcacccc cgcctgagaa gcatctgggc    1260
atctactccg tgttgcccaa ccacaaggct gacgctgtat tgagcatgcc gtcttccgtg    1320
acctctggcc tccacgtgca gcctgccctg gctgtctcca tggacttcag cacctatggg    1380
gggctgctgc cccagggctt catccagagg gagctgttca gcaagctggg ggagctggct    1440
gtgggcatga agtcagagag ccggaccatc ggagagcagt gcagcgtgtg tggggtcgag    1500
cttcctgata cgaggctgt ggagcagcac aggaagctgc acagtgggat gaagacgtac    1560
gggtgcgagc tctgcgggaa gcggttcctg gatagtttgc ggctgagaat gcacttactg    1620
gctcattcag cgggtgccaa agcctttgtc tgtgatcagt gcggtgcaca gttttcgaag    1680
gaggatgccc tggagacaca caggcagacc catactggca ctgacatggc cgtcttctgt    1740
ctgctgtgtg ggaagcgctt ccaggcgcag agcgcactgc agcagcacat ggaggtccac    1800
gcgggcgtgc gcagctacat ctgcagtgag tgcaaccgca ccttccccag ccacacggct    1860
ctcaaacgcc acctgcgctc acatacaggc gaccacccct acgagtgtga gttctgtggc    1920
agctgcttcc gggatgagag cacactcaag agccacaaac gcatccacac gggtgagaaa    1980
ccctacgagt gcaatggctg tgcaagaag ttcagcctca gcatcagct ggagacgcac     2040 tatagggtgc acacaggtga gagcccttt gagtgtaagc tctgccacca gcgctcccgg    2100
gactactcgg ccatgatcaa gcacctgaga acgcacaacg gcgcctcgcc ctaccagtgc    2160
accatctgca gagagtactg ccccagcctc tcctccatgc agaagcacat gaagggccac    2220
aagcccgagg agatcccgcc cgactggagg atagagaaga cgtacctcta cctgtgctat    2280
gtgtgaaggg aggcccgcgg cggtggagcc gagcggggag ccaggaaaga gagttggag    2340 tgagatgaag gaaggactat gacaaataaa aaggaaaag aaaaaaaaaa acagaaggaa    2400
aaggaaaaaa aaaaaaa                                                  2417
```

<210> SEQ ID NO 23
<211> LENGTH: 2057
<212> TYPE: DNA
<213> ORGANISM: Homo sapiens

<400> SEQUENCE: 23

```
atattgtgct tccaccactg ccaataacaa ataactagc aaccatgaag tgggtggaat      60
```

```
caattttttt aatttttccta ctaaattttta ctgaatccag aacactgcat agaaatgaat    120
atggaatagc ttccatattg gattcttacc aatgtactgc agagataagt ttagctgacc    180
tggctaccat attttttgcc cagtttgttc aagaagccac ttacaaggaa gtaagcaaaa    240
tggtgaaaga tgcattgact gcaattgaga acccactgg agatgaacag tcttcagggt    300
gtttagaaaa ccagctacct gcctttctgg aagaactttg ccatgagaaa gaattttgg    360 agaagtacgg acattcagac tgctgcagcc aaagtgaaga gggaagacat aactgttttc    420
ttgcacacaa aaagcccact ccagcatcga tcccactttt ccaagttcca gaacctgtca    480
caagctgtga agcatatgaa gaagacaggg agacattcat gaacaaattc atttatgaga    540
tagcaagaag gcatcccttc ctgtatgcac ctacaattct tctttgggct gctcgctatg    600
acaaaataat tccatcttgc tgcaaagctg aaaatgcagt tgaatgcttc caaacaaagg    660
cagcaacagt tacaaaagaa ttaagagaaa gcagcttgtt aaatcaacat gcatgtgcag    720
taatgaaaaa ttttgggacc cgaactttcc aagccataac tgttactaaa ctgagtcaga    780
agtttaccaa agttaatttt actgaaatcc agaaactagt cctggatgtg gcccatgtac    840
atgagcactg ttgcagagga gatgtgctgg attgtctgca ggatggggaa aaaatcatgt    900
cctacatatg ttctcaacaa gacactctgt caaacaaaat aacagaatgc tgcaaactga    960
ccacgctgga acgtggtcaa tgtataattc atgcagaaaa tgatgaaaaa cctgaaggtc   1020
tatctccaaa tctaaacagg ttttttaggag atagagattt taaccaattt tcttcagggg   1080
aaaaaaatat cttcttggca agttttgttc atgaatattc aagaagacat cctcagcttg   1140
ctgtctcagt aattctaaga gttgctaaag gataccagga gttattggag aagtgtttcc   1200
agactgaaaa ccctcttgaa tgccaagata aggagaaga gaattacag aaatacatcc   1260 aggagagcca agcattggca aagcgaagct gcggcctctt ccagaaacta ggagaatatt   1320
acttacaaaa tgcgtttctc gttgcttaca caaagaaagc cccccagctg acctcgtcgg   1380
agctgatggc catcaccaga aaaatggcag ccacagcagc cacttgttgc caactcagtg   1440 aggacaaaact attggcctgt ggcgaggag cggctgacat tattatcgga cacttatgta   1500
tcagacatga aatgactcca gtaaaccctg gtgttggcca gtgctgcact tcttcatatg   1560
ccaacaggag gccatgcttc agcagcttgg tggtggatga acatatgtc cctcctgcat   1620 tctctgatga caagttcatt ttccataagg atctgtgcca agctcagggt gtagcgctgc   1680
aaacgatgaa gcaagagttt ctcattaacc ttgtgaagca aaagccacaa ataacagagg   1740
aacaacttga ggctgtcatt gcagatttct caggcctgtt ggagaaatgc tgccaaggcc   1800
aggaacagga agtctgcttt gctgaagagg acaaaaact gatttcaaaa actcgtgctg   1860
ctttgggagt ttaaaattact tcaggggaag agaagacaaa acgagtcttt cattcggtgt   1920
gaacttttct ctttaatttt aactgattta acacttttg tgaattaatg aaatgataaa   1980
gacttttatg tgagatttcc ttatcacaga aataaaatat ctccaaatgt ttcctttca   2040 aaaaaaaaaa aaaaaaa                                                  2057
```

<210> SEQ ID NO 24
<211> LENGTH: 3001
<212> TYPE: DNA
<213> ORGANISM: Homo sapiens

<400> SEQUENCE: 24

```
ggggccgcca ccggcccatg agccccggcc tcaaagtttg cggcgggcgg gcgggcgcgg     60
```

-continued

```
agcctccaag atgccgttcc acccggtgac ggcggcgttg atgtaccggg gcatctacac      120
cgtgcccaac ctgctgtcgg agcagcgccc ggtggacatc ccggaggacg agctggagga      180
gatccgagag gccttcaagg tgtttgaccg tgacggcaat ggcttcatct ccaagcagga      240
gctgggcaca gccatgcgct cactgggtta catgcccaac gaggtggagc tggaggtcat      300
catccagcgg ctggacatgg atggtgatgg tcaagtggac tttgaggagt tgtgacccct      360
tctgggaccc aaactctcca cctcagggat cccagagaag ttccatggca ccgactttga      420
tactgtcttc tggaagtgcg acatgcagaa gctgacggtg gatgagctga agcggctgct      480
ctacgacacc ttctgcgagc acctgtccat gaaggacata gagaacatca tcatgacgga      540
ggaggagagc cacctgggca gccgagga gtgtcccgtg gatgtggaga cctgctccaa       600
ccagcagatc cgccagactt gcgtgcgcaa gagtctcatc tgcgccttcg ccatcgcctt      660
catcatcagt gtcatgctca ttgcggccaa ccaggtgctg cgcagtggca tgaagtagac      720
gccacctgga tgccccatcc accgcatgcg gtgcccgtgg cccgcccac accaccgccg       780 cctgcagacc tctcccttgg ccggctccct gggccgccat ctgcgtgtac ttcagggcct      840
gggtatccag cgagccctcc ccacccaccc acggtcctca cctggagctg tggcctggct      900
gtggagggcc ggtggtggc tctgaggatg gtccccagcc ccaccctgtc cccaccctgg       960
cctgtaagga gcactcactc ttcctaccat ccaggggctc ctgggaaatt aaggagggat     1020
ttgcacagga acccccagga cccagtcgct gctgtggtcc cttgggcagg agcgggcacc     1080
ctgtgccttg agacagcagc ctatctgggg ccacacagcc aacccagccc tggtccctga     1140
ggtctgccca gggcacaggg cacaggcagg gacagaaagc cttctcctgg gggagggtgg     1200
gaagccaggg tgtcctgggc cttgctgcct ggcatagcct gaggaggccc ctggtcttct     1260
ccttgggccc cttcctctga ccctcgttgg accccaaccc agacccctt ttctccatgt      1320 acctgctggg ccagcccatt tcacaggtga ggaacccgag gctcagggcc ccgagacttg     1380
gcctcagttc ttccttccac agggattttc aggaaaggca gaagctcgtg gaggatgggc     1440
atctgaggtg gccctgcagc cccccacctt ctggccctcc caccagaggc ccagctacca     1500
aggccacatt gtccaccacc ccagcctaga gcctagaact gtagtccagc tgaggaagga     1560
ggcagagctg gggcctgaag gctctgagca gcctccagcc aggggctcc tccagggctg      1620 aactttggga gggcccctgt actacctcct gggccaagaa actggcacag ccccacactg     1680
tcagtgccaa gaggctgcgc caggccactc tctcagccca gggcctgccc tcctgtcctc     1740
ccacttctct acgccctcaa ggttggagac cccgctccca tgccccagct gtgccatccc     1800
aaatacttgg gcagcagctc agcatgggca gacatggggg ctgtggattc ttccagggcg     1860
gggatggcag atggagccct tgggctcctt gggcctagag ccacttctta ccaggcaacg     1920
ggcacagcca ccctggcaca ccctctgcct ggccgtgctg aacctctgct ggtcccaagg     1980
gagaagggag tgagcgtggg tcacctgggg aaaatctcat ctgattccct ccttgcccga     2040
cctctgctag gggctggaga acagagctca gagcacccag tgtagggaaa cacagccaga     2100
ccactgtggt gacagacttt ctttataaac atttggaagt tttctccccc atcttcttaa     2160
gaagcagggg ggcaggtgga ggagagtgag gggagagctg cccggtgcag acccaggacg     2220
agggctgcac ttggtgtggc cgtgtcctga gcctcagtga ggctgggcag atggtctcgg     2280
agcctccatg gggcgtagca ggaaccgggc ttggcttcct attgtgactg atgagaaaag     2340
tgaccacgtg ggggtcagtc gggggcaagg ggctcagccc cactggactc tgggctgcag     2400
aggccacccc ccaggtgggg gtgcccgcag ggatggaggc agctcctgaa ctggtggcca     2460
```

```
gcccacgggg tactggaaga cagtggttct gatgggttca gccctagaga gagagagaga    2520
agcggggaga ataagagtgc actacagccc aggcttatgc cacccccagc ccacctgcct    2580
caccaccctg gctgtgggga gggtcagctg cctgcatgac ttttctggaa ggcagagcct    2640
cgaaaatagg cagaccgttt gagccagcga cctcacctct aggaactgag cccaaggaaa    2700
tagcggggtt gcaggcagac attgagctgc gagacaatgg gaataacctt cgtgtccacc    2760
tgtgggggac tgattcaata catatgcacg tccacagcag agaatgccat gcggcctgtg    2820
taagaattaa ggcagattta tatgcactga tgaggaaaga catactgtgt gatagggaga    2880
aaaagcagct tataaaataa tgtatatagc atgatactat ttttgtttaa aaatatataa    2940
aatatataaa tgcataaaaa aatcctggaa gacacagcaa aaaaaaaaa aaaaaaaaa     3000 a                                                                    3001

<210> SEQ ID NO 25
<211> LENGTH: 2855
<212> TYPE: DNA
<213> ORGANISM: Homo sapiens

<400> SEQUENCE: 25
cctggcaatc ccatgtggac ttctggtaga atgagcaatg caaagaactg gcttggactt      60
ggcatgtcct tgtacttctg ggggctgatg gaccttacga ccaccgttct ctcggacacc     120
ccaacaccac aaggtgaatt agaagcactc ctgtcagaca agccacagtc acatcagcgg     180
accaagagga gctgggtttg gaaccagttt ttcgttctgg aagagtacac tgggaccgac     240
cctttgtatg tcggcaagct tcattcagat atggacaggg gagacggatc catcaaatac     300
atcctctcgg gagaaggtgc tggcatcgtg tttaccatcg acgacaccac tggagacatc     360
cacgccattc agaggctcga ccgagaggaa agagcccagt atactctaag ggctcaagcc     420
ctagacaggc ggacgggcag gccaatggag cccgagtcag agttcatcat caaaattcaa     480
gacatcaatg acaatgagcc caagttcctg gacggaccct atgtggccac tgtgccagaa     540
atgtcccctg tgggtacctc cgtcatccaa gtgacagcca cagatgcaga tgacccgacc     600
tacggcaaca gtgccagggt ggtgtacagc attcttcagg ccagccata ttttctgtg      660 gactctaaaa caggtgtaat taggacagcg ctcatgaaca tggacagaga agccaaagaa     720
tactacgaag tgattatcca agccaaggac atgggagggc agcttggagg attagctggg     780
accacaacag tcaacatcac cctctcagat gtcaatgata cccacccccg ctttccccag     840
aaacattacc agatgagtgt gttggaatca gctccaatta gctccactgt cgggagagtg     900
tttgccaagg acttggatga aggcatcaat gcagagatga atatactat tgtggatgga      960 gatggtgcag atgccttcga cattagcaca gatcccaatt tccaagttgg tatcataact    1020
gtgaagaagc ccctgagttt tgaaagcaag aaaagctaca ccttaaaggt ggagggagcc    1080
aatcctcacc tagagatgcg ttttctgaac ttggcccat tcaggacac aacaacagtg      1140 cacatcagtg tggaagacgt ggacgagccc cctgtgtttg aacctggctt ttactttgtg    1200
gaggtgcctg aggatgtggc gattggaaca accatacaga tcatttctgc caaggaccca    1260
gatgtgacca acaactcaat cagatactcc attgatagaa gcagtgaccc tggaagattt    1320
ttctatgttg acattacaac aggtgcccta atgacagcaa gacccctaga ccgggaagaa    1380 tttttcttggc ataatatcac tgtccttgct atggaaatga acaatccctc ccaggttgga    1440
agtgttcctg tcacaatcaa agtcttagat gtgaatgaca atgctccaga gttccccaga    1500
```

| | |
|---|---|
| ttctatgaag cttttgtctg tgagaacgcc aaggcaggac agctgatcca gacagtgagt | 1560 |
| gcggtggacc aagatgaccc acgcaatggt cagcatttct actacagctt ggctcctgag | 1620 |
| gctgctaaca accccaactt taccataagg gacaaccaag ataacacagc acggattcta | 1680 |
| accaggaggt ctggtttccg gcagcaggag cagagtgtct ttcacctgcc tatcctgata | 1740 |
| gcagatagcg ggcagcccgt gctgagcagc acaggcacac tgaccatcca agtgtgcagc | 1800 |
| tgtgatgacg acggccacgt catgtcctgc agcccagagg cctacatgct cccagtcagt | 1860 |
| ttgagccggg gcgccctcat tgccatcctc gcctgcatct ttgtcctctt agtgctggtg | 1920 |
| ttgctcattt tgtccatgag gcggcaccgg aaacaaccat acatcatcga cgacgaggaa | 1980 |
| aacatccacg agaacatcgt ccgctacgac gacgagggcg gcggcgagga ggacaccgag | 2040 |
| gccttcgaca tcgcggccat gtggaacccc cgggaggcgc aggcggggc cgcccccaag | 2100 |
| acgcggcagg acatgctgcc cgagatcgag agcctctccc gctacgtgcc tcagacgtgc | 2160 |
| gcagtgaaca gcactgtcca cagctacgtg ctggccaagc tctacagggc cgacatggac | 2220 |
| ctgtgggcac cgcccttcga ctccctccag acgtatatgt tcgaggggga cggctctgtg | 2280 |
| gcggggtcgc tgagctccct gcagtcggcc acgtcggact cggaacagag cttcgacttc | 2340 |
| ctgacggact gggggcccg cttccggaag ctggccgagc tctacggggc gtcggaggga | 2400 |
| cccgcgccgc tgtggtgacg gaagccagga ggcaggcgcg cgtccaaatc cagacgttct | 2460 |
| ccgcgggtgc ttcgcggaca aggtgcagcc aaccacacga gcaatactgt gctggagagt | 2520 |
| gagaatgggg gtgagcaggc gaacagagct ctctctggat cagctttact tgggtagatt | 2580 |
| aagttaaata agcaaaagga aacccagaag gaagagggca gaatctttaa ttaccttttt | 2640 |
| ttcttttctt tttgattttt ctgacactgt gtgcgaaggc ttggagtcca aggtgttctg | 2700 |
| acaagggtgg cttttctctg ccattcgcta aggcctttgt cacttttcca ccacagaaag | 2760 |
| gctctggcct tggatacaga gatgccaatt gaaagcagaa agttctactc tcgtatctgt | 2820 |
| tttttatctt atcttattct ccatttaaga gtttt | 2855 |

<210> SEQ ID NO 26
<211> LENGTH: 3452
<212> TYPE: DNA
<213> ORGANISM: Homo sapiens

<400> SEQUENCE: 26

| | |
|---|---|
| gtctcagttc ccgagcctgg gagcaaccgc agcttctagt atccagactc cagcgccgcc | 60 |
| ccgggcgcgg accccaaccc cgacccgag cttctccagc ggcggcgcag cgagcagggc | 120 |
| tccccgcctt aacttcctcc gcggggccca gccaccttcg ggagtccggg ttgcccacct | 180 |
| gcaaactctc cgccttctgc acctgccacc cctgagccag cgcggcgcc cgagcgagtc | 240 |
| atggccaacg cggggctgca gctgttgggc ttcattctcg ccttcctggg atggatcggc | 300 |
| gccatcgtca gcactgccct gccccagtgg aggatttact cctatgccgg cgacaacatc | 360 |
| gtgaccgccc aggccatgta cgagggggctg tggatgtcct cgtgtcgca gagcaccggg | 420 |
| cagatccagt gcaaagtctt tgactccttg ctgaatctga gcagcacatt gcaagcaacc | 480 |
| cgtgccttga tggtgttgg catcctcctg ggagtgatag caatctttgt ggccaccgtt | 540 |
| ggcatgaagt gtatgaagtg cttggaagac gatgaggtgc agaagatgag gatggctgtc | 600 |
| attgggggtg cgatatttct tcttgcaggt ctggctattt tagttgccac agcatggtat | 660 |
| ggcaatagaa tcgttcaaga attctatgac cctatgaccc cagtcaatgc caggtacgaa | 720 |
| tttggtcagg ctctcttcac tggctgggct gctgcttctc tctgccttct gggaggtgcc | 780 |

-continued

| | |
|---|---|
| ctactttgct gttcctgtcc ccgaaaaaca acctcttacc caacaccaag gccctatcca | 840 |
| aaacctgcac cttccagcgg gaaagactac gtgtgacaca gaggcaaaag gagaaaatca | 900 |
| tgttgaaaca aaccgaaaat ggacattgag atactatcat taacattagg accttagaat | 960 |
| tttgggtatt gtaatctgaa gtatggtatt acaaaacaaa caaacaaaca aaaaacccat | 1020 |
| gtgttaaaat actcagtgct aaacatggct taatcttatt ttatcttctt tcctcaatat | 1080 |
| aggagggaag attttttccat ttgtattact gcttcccatt gagtaatcat actcaactgg | 1140 |
| gggaaggggt gctccttaaa tatatataga tatgtatata tacatgtttt tctattaaaa | 1200 |
| atagacagta aaatactatt ctcattatgt tgatactagc atacttaaaa tatctctaaa | 1260 |
| ataggtaaat gtatttaatt ccatattgat gaagatgttt attggtatat tttctttttc | 1320 |
| gtctatatat acatatgtaa cagtcaaata tcatttactc ttcttcatta gctttgggtg | 1380 |
| cctttgccac aagacctagc ctaatttacc aaggatgaat tctttcaatt cttcatgcgt | 1440 |
| gcccttttca tatacttatt ttatttttta ccataatctt atagcacttg catcgttatt | 1500 |
| aagcccttat ttgttttgtg tttcattggt ctctatctcc tgaatctaac acatttcata | 1560 |
| gcctacattt tagtttctaa agccaagaag aatttattac aaatcagaac tttggaggca | 1620 |
| aatctttctg catgaccaaa gtgataaatt cctgttgacc ttcccacaca atccctgtac | 1680 |
| tctgacccat agcactcttg tttgctttga aaatatttgt ccaattgagt agctgcatgc | 1740 |
| tgttcccca ggtgttgtaa cacaacttta ttgattgaat ttttaagcta cttattcata | 1800 |
| gttttatatc cccctaaact acctttttgt tccccattcc ttaattgtat tgttttccca | 1860 |
| agtgtaatta tcatgcgttt tatatcttcc taataaggtg tggtctgttt gtctgaacaa | 1920 |
| agtgctagac tttctggagt gataatctgg tgacaaatat tctctctgta gctgtaagca | 1980 |
| agtcacttaa tctttctacc tctttttttct atctgccaaa ttgagataat gatacttaac | 2040 |
| cagttagaag aggtagtgtg aatattaatt agtttatatt actctcattc tttgaacatg | 2100 |
| aactatgcct atgtagtgtc tttatttgct cagctggctg agacactgaa gaagtcactg | 2160 |
| aacaaaacct acacacgtac cttcatgtga ttcactgcct tcctctctct accagtctat | 2220 |
| ttccactgaa caaaacctac acacatacct tcatgtggtt cagtgccttc ctctctctac | 2280 |
| cagtctattt ccactgaaca aaacctacgc acataccttc atgtggctca gtgccttcct | 2340 |
| ctctctacca gtctatttcc attctttcag ctgtgtctga catgtttgtg ctctgttcca | 2400 |
| ttttaacaac tgctcttact tttccagtct gtacagaatg ctatttcact tgagcaagat | 2460 |
| gatgtaatgg aaagggtgtt ggcattggtg tctggagacc tggatttgag tcttggtgct | 2520 |
| atcaatcacc gtctgtgttt gagcaaggca tttggctgct gtaagcttat tgcttcatct | 2580 |
| gtaagcggtg gtttgtaatt cctgatcttc ccacctcaca gtgatgttgt ggggatccag | 2640 |
| tgagatagaa tacatgtaag tgtggttttg taatttaaaa agtgctatac taagggaaag | 2700 |
| aattgaggaa ttaactgcat acgttttggt gttgcttttc aaatgtttga aaacaaaaaa | 2760 |
| aatgttaaga aatgggtttc ttgccttaac cagtctctca agtgatgaga cagtgaagta | 2820 |
| aaattgagtg cactaaacaa ataagattct gaggaagtct tatcttctgc agtgagtatg | 2880 |
| gcccgatgct ttctgtggct aaacagatgt aatgggaaga aataaaagcc tacgtgttgg | 2940 |
| taaatccaac agcaagggag attttgaat cataataact cataaggtgc tatctgttca | 3000 |
| gtgatgccct cagagctctt gctgttagct ggcagctgac gctgctagga tagttagttt | 3060 |
| ggaaatggta cttcataata aactcacaca ggaaagtcag ccactgtgtc ttatgaggaa | 3120 |

```
ttggacctaa taaattttag tgtgccttcc aaacctgaga atatatgctt ttggaagtta      3180
aaatttaaat ggcttttgcc acatacatag atcttcatga tgtgtgagtg taattccatg      3240
tggatatcag ttaccaaaca ttacaaaaaa attttatggc ccaaaatgac caacgaaatt      3300
gttacaatag aatttatcca attttgatct ttttatattc ttctaccaca cctggaaaca      3360
gaccaataga cattttgggg ttttataata ggaatttgta taaagcatta ctctttttca      3420
ataaattgtt ttttaattta aaaaaaggat ta                                    3452
```

<210> SEQ ID NO 27
<211> LENGTH: 4676
<212> TYPE: DNA
<213> ORGANISM: Homo sapiens

<400> SEQUENCE: 27

```
catctggaag gggagcggta gaacgtcagg gcccggctga ggggcgtgat tggagggcgc        60
cttcggcagc cgcccgcggc agaagccgcg gctccagctc gcctggcgga attgcacgcg       120
gcggcgggag ctggaatagc agaaggaacc acctcgtgga gtcgggccgg agccctgcag       180
tggctcagac ggttgcaggg accgccaggt tgtcacatct tcccaagcca ggccagccag       240
gagcgctgca tgcaaattct gccgtgggct aaggcacgct aaccagagcc ggcggcatgg       300
acttcgtcat gaagcaggcc cttggagggg ccacaaagga catggggaag atgctggggg       360
gagaggagga gaaggacccc gacgcgcaga aaaaggagga ggagcggcag gaggcgctgc       420
ggcagcagga ggaggagcgt aaggccaagc acgcgcgcat ggaggcggag cgggagaagg       480
tccggcagca gatccgagat aagtatgggc tgaagaagaa ggaggagaag gaagcagagg       540
agaaagcagc cctggagcag ccctgcgagg ggagcctgac ccggcccaag aaggccatcc       600
ctgcgggctg cggggacgag gaggaggagg aagaggagag catcctggac acggtgctca       660
aatacctgcc cgggccgctg caggacatgt tcaagaagta accaggcctc ctgccccagc       720
ctactccacc tgttactact tctttttggt tctttctttt cttttttatta ggttaagtct       780 caattctgaa ggggaaaacc tcagttggcc tctgcccctc ttccctggcc aggggcttct       840 cccccctcagc tctccctcac acctcccttc atcccagggt atccacctgc accccactcc       900
caagtagctt gaaaaaggga ggacagtctt tcccagcag gggtcagggg ggcccctcag       960
gaagcctaag gtcgtgctag tgtggtgacc cccatacatt cctccctgct ccccactgcc      1020
aggaggacca ctgtccccag ccagccaaag taatgacaca ttccagccct gcccagcatg      1080
ctgacctttg gcctctaacc ctcagtgggc cccaggtca gggcaggggc actgagtggc      1140
ctggctctga ggaagggagt caggggaagc ctgtcccggg aaggcccagg ctgagaggcc      1200
ctggctctgg ccaggctggg atctggtgg gaggctgggg ctcttcttct tccatctcct      1260
tggtgacacc cagcccaggg gcacccccct cccagcccc cacctggaga gacatggccc      1320
ctgccaagct ggtcccttca aatggatcct ttgtggactt tagctcattt gtggaggaac      1380
cccaggtagg gacgcccctt gttcctcacc cccaccccac ttaggtcctg ggccccact      1440 gccaggctgg gccagcttg ctcagtcaag gggctgccag gccccagaa acacttgga      1500 gccatcgggt agcgatggtc tatgccatgg ggaacacctc cattggtgtg gccaagctgc      1560
ccccattcct atccacccct ctccccaccc cgtcctgtcc atgcgcttcc agggccccac      1620
ggtccccagg aggacgcttc ctggccaaag cccaagcct ttggtgagaa gccaattccc      1680
acttgacaga aggcgtccat ccattcatct cattggccaa ggacaaactc tcctctggga      1740
cgtctgggac tggcatttgt cccccactca aattatcaaa gctttctgct cagtcagttg      1800
```

```
tgtggggatg gtgagggaag aggggtcaca tgagggagga aactgtatcc atgcatgcat    1860
gataatgcgt ggcagagact gcaacaggga ttgtgtgttc agagatcata tgcatatgtg    1920
tagggctgga gcgtgtgtgt gtcttgagat tgtgtgtgtt gcagtcatca tatctatgtg    1980
ttacagattg tgtatgttag ccttgtgtat gtgtgcttga ttgaggtggt gtatttgggt    2040
tgaaattgtg tcatatgtgt gtgctatcca tctcgtgttt agaggctgta tatgttagct    2100
tgtgtaagaa tgtgttttca aaacagtgtg tgtattggga gtgatgggta tgtgttaggt    2160
atgtgatggg ttgtagaagc gtgtgtttga gagaattcag agacatttga aggctgctgt    2220
gtgcatgttt gggggtctga aaagacagtt gtgtgcatgg atgtgtgcgt ggggagaaag    2280
aacgtgggta agatgtccct tcccagccct gagaccactg gtcacagttg gccacctcca    2340
acgggagacc ttgtccttgg cctagagtcc tcccacccct gggggggctcc tgcctgaggt    2400 cctcagaatc ccactgcaat ggacccaggc agcgccccag gaagccatgc tgggcccccg    2460
ccagggccta tcccaaaagc aggggccagg gaggggggcga cttgcctgcc cctgaagccc    2520
ttgttcccat tggccccagt ttgcattctg caggttttcc attttagtgg gttctgcttt    2580
tatttcagag acagacatgt gtcttctctg tccgttttcca ataggtaaag ccatatcagt    2640
tagactgcaa tactttaaac acgagacaaa acaatccata tgtttaggga accagaaaag    2700 tccctggtc tgtcccttct ttgggggagca gggcctcgac agctccagct cccttgacct    2760
accttcctcc ccgcacccccg ccccaccttt gtgccctgt gtccagcccc caggggggcc    2820
tgtgtctgtg tctgtgcctg tgtctgtgat ggggagccgc ctcgcacccc tgttgtctgc    2880 ttgtctctttt gtgtctgtta tcctgggcag gatggtcatt ctcaaaaacc ctgggggtcct    2940 gggccagaga caggcagggc ccagtccagg ggccccaggc ctccccagtc ccagtgtgcg    3000
agccccactt ggacacaagt gttcagagag gtccccctct gccacttgac agggaccttc    3060
aaacctcgac agtgatgcaa ggacacagag agtaccagat aggtagcaga gaccaaggcg    3120
cagggtgctt cagatgagca agagaaccca gtcgaaccag ataccccagg tgggccggag    3180
ggaccccaga ccttcagagg gctgccctgg tgttctccac agtgcagtcc ctctgtattc    3240
ccagagtggg atcggggctt tcagccccac cctgatgcct gccctccagg atggctggtt    3300
tagtctgggt ccatgtccca gacccctcta ttctgctcca ggacagcagg acttcaggtc    3360
ttcctggggg tggatatagg agaaaatttc tgcctggcac acacctggct ccaaccactg    3420
ccaagtgatc actcttaggc ccaggggaac acaatgacta tcattactga tgcagacctg    3480
gctgtggaga gcagctaatg tgtgcccag agagcctgtc tgtgtggagc acgtagtgca    3540
cagaatacgt gagagttgct ctggcagggg cagaatcctc acaggatcgc ctgggaggtg    3600
aggtgtgtgt gacccactgg atgggagggc aatgagtgtg cacatacaaa tggggcagtg    3660
tgcatgcaac acacttaggg gaggagtggc cccagaattc agcacgcaca caacacacaa    3720
gggagagaac cccagatgaa gaaaatagga aggagcaatc atttgtagat gggtgaaaaa    3780
agaatgaggt tcaagggagc gtgcaccagg tgaggtgagc gtgtgtgctc tcagggaagg    3840
gcccaggatc ccatgcctgg gaggagctgc cagagagaag caaaaaggcg gctgtggatc    3900
gccctgggct gggcaccagt gacaggtcag gatctccaaa catggacgtc ctccccctcca    3960 aatccagaag ctcccagaag gtgtccttaa ctgcaaagct gtgcagggta ctcctccaga    4020
tggaatcagg aagtcgagac accatcccag gtgtgtgtaa gagagagaga gagaacaggg    4080
aggatacaga agtattgcag cccagatccc ctatcagggg gacagctggt gggcaaagca    4140
```

| | |
|---|---|
| gccaccccac agccttgtgg ctagagtaca gtggggtaga ccctccagcc ccaatagccc | 4200 |
| tagtacccag ctggcagggt tgcccacccc tgctgtccac ctgctccatc ctctagggtt | 4260 |
| ccacaggccc ctgaccgcac agggaggctg gggccagcct ggtctcccag gcctgaggac | 4320 |
| atgcctccca ccaaatgtcc cctgctccag tcccactcct gtcacccac gctctgcact | 4380 |
| ggggagaaaa cggaggtgc tcgtgctggc cctgggtggg agcggggagt cctggtgaga | 4440 |
| ccccggtgag atggaccatc ctgccccgt ggggatccc ctttcccaca tccgtgctgt | 4500 |
| gtcattgttg ctctgcttcc tttcaatgtg tcagtgcctg gggggagggg aggagcaccc | 4560 |
| cctcagcccc cctgaacctg accaaaagcc atggctgttg ctccccctt tgtatgatgc | 4620 |
| aaatgctgaa atgtacaaaa tcaaccatga caacaaagaa aaagaccttg tacagc | 4676 |

<210> SEQ ID NO 28
<211> LENGTH: 4661
<212> TYPE: DNA
<213> ORGANISM: Homo sapiens

<400> SEQUENCE: 28

| | |
|---|---|
| ggacttgaac acacgggacc ggacaggacc gaccgagggg cggcggcgaa aggcagagcg | 60 |
| ccgcgatctc tgtcgggaag cgcaacctcc ccgggccccg cggggccgcg caggggggcgt | 120 |
| cctcaacccc gcgcccgctc cctctttcca tcccctgccg cccgcaggcc accccggggc | 180 |
| ccggccatcc gcgcgcgcat ccccgggttc ggccccgtcc ctggccctcg agggagccgc | 240 |
| cgccttcatc gccacatctg cagcggccgc accagaggcc gccgggcgg daccccagcg | 300 |
| tgagcatcgg gcgcccccct aggagtgcac caccccgga gcccccctca cacggaccg | 360 |
| cgcccgccgg gcacacaaga atggtcactc agatactggg ggccatggag tctcaggtgg | 420 |
| gggggggccc ggccggcccg gccctgccca acgggccact ccttggtaca aatggagcca | 480 |
| ctgacgacag caagaccaac ctcatcgtca actacctgcc ccagaacatg acccaggatg | 540 |
| agttcaagag tctcttcggc agcattggcg acatcgagtc ctgcaagttg gttcgggaca | 600 |
| agatcacagg gcagagcctt ggctacgggt ttgtgaacta ttctgacccc aatgatgcag | 660 |
| acaaagccat caacaccctc aacggcctca aattacagac gaagaccatc aaggtgtcct | 720 |
| atgccagacc cagttcagca tccatccggg atgctaacct gtacgtcagc gggctcccca | 780 |
| agaccatgag ccagaaagag atggagcagc tcttctccca gtacggccgc atcatcacgt | 840 |
| cccgcatcct ggtggaccag gtcacaggtg tctctcgggg tgtgggattc atccgctttg | 900 |
| acaagaggat tgaggccgaa gaggctatca aaggactgaa tggcagaag ccgctgggcg | 960 |
| cagctgagcc catcacagtc aagttcgcga acaacccaag tcagaagacg gggcaggcgc | 1020 |
| tgctcaccca cctctaccag tcatccgccc ggcgctacgc aggcccccta caccatcaga | 1080 |
| cccagcgttt ccggctggac aatttgctca acatggccta cggcgtcaag aggttctcgc | 1140 |
| cgatcgccat cgatggtatg agcggcctgg cgggcgtggg cctgtcgggg ggcgcggcgg | 1200 |
| gcgccggctg gtgcatcttc gtgtacaacc tgtcaccgga ggcagacgag agcgtgctgt | 1260 |
| ggcagctgtt cgggcctttt ggggcagtca ccaacgtcaa ggtcatccgt gatttcacca | 1320 |
| ccaacaagtg caaggttttc ggcttcgtga ccatgaccaa ctatgacgag gcggccatgg | 1380 |
| ccatcgccag cctgaacggc tatcgcctgg gcagcgcgt gctgcaggtc ccttcaaga | 1440 |
| ccagcaaaca gcacaaggcg tgagcccacc ccgcctgccc tcccaccccc tcccgggca | 1500 |
| gcagagagag agagagagaa agagagagag agagagaaa ggggcccaag agagacagca | 1560 |
| caggcagccc cacggacgac gcgagggccc cacgtccctg cggaagccac agggtgagca | 1620 |

```
ctctggggtg ggagggtctg cagggaattg ggggggtgcc cggggatccc ccgccccatc    1680
ctcctgcccc caccccaggc tgggctgttc actctctcgt cttggtttgg ttcatggtga    1740 aggttttgt  ttcttttttc ggctaaaaag aatgcagaga tgtgccccca cccccaccct    1800
cgaccacccc cgatgggatg gcttgggggg ctccagggg  tgccctccca gaccccttg     1860 cccaggcctc cccagcacct aggtgggcc  tgggtagga ggaacaggtt taaaaatccc     1920 caaaaagcg  aaccgtgagg aggggtgtgg gcacccccgg cccagtgccc ctggtggaa     1980 tgcgggggag caggcagtgg ggctggaagc agaaacaaaa tgaaaaaaaa ggggggtgg     2040 gaggggaaga aaaactctat ttttgtaaaa agggaaaaag acctcgtgga gaattttac     2100 tggggattct tgaacttgaa aaaaaaaac  acaaaaaaag acaaaaaaaa aaaagaaaa     2160 tattttggca ggttatgttt accaactggg gcggggtgg  gggggccca  gggagcaggg    2220 cttaggggct agcagcccac ggggccacac agagaaacaa ccacgcagac agtcacacca    2280
cggggacaca cggacagacg cagacggaca cagcgcatg  cccagacac  gttaagggac    2340 tggttggcca aactcagaca cgtggacagg gatagacaga aagagacaga agctggggct    2400
acgtccatgt ggacacagac cacagatgtg gcacacgaa  tccatccacc tgtccacgtg    2460
cacacgtgaa tgtagcgata gatatttgga catcaaattt ggacaccagg tcacggagaa    2520
acacaaacac cacccaggaa cacgcagaca tatgcccata gcatcccaca ggcccaggca    2580
ggaggtccca ccccagaccc tgccccagac gctccctcac cctctcggcc cctcgccct    2640 ggcccccagg ttctctgcag agatctctcc tggaccccca gcggtctcct tggcgcccac    2700
gaacacaggc gtgcacacgc agcgcacatg cattgagaca cacgatacct cgttccacct    2760
tggcgtcacg gtgggctgga ggcagccccc cccccacaa  cacttgaggc caaaggacac    2820
ccctgtcccc ggggctcagc ctcccccctgg gccgaggcct tgcccacac  agctgaggga    2880 gaggcccagc cctgagcctc ccccaccagg actgggcctc cccggcagca agaccccggc    2940
actccccgcc aggcccaggg tggggtggat gggcccaaag gcccagcccc cacactccttt    3000 cccgtccact tgtcacctac ctatcccctt tcggtttgtt gggttttttcg tctttccaga    3060 ttgcagtgga cacagccccc gatctcgagc cccgcccccc ggcttctgtc tggacattgc    3120
atcgccctag ttttctttct ttaaaaaaaa aaaattccaa cagaagccac aggccggagc    3180
ccctgggagc cctcgcaccg ctccccaccc cactcagcgg ccccatcgga actgagaatt    3240
gcaaaacccc cgactttagc tatagttaag ttgccttccc ccggtgtccc cacgtttggt    3300
gtctggctat ggcgccccca tctgactgtc cagctctctc tcccccaccc ctcccggtgt    3360
tgttattaaa cgtctgtgga gcttctgctg caaggaacaa aaaagaaaaa aatcaaaaaa    3420
gcgacaaaaa aacacaaaca gaagaggaaa aaaagcaac  aaaaaagaa  acacacaga     3480 agagatttaa aaaaaaaaaa ggaaaaaaaa aaaagacata aactggcacc agttaactt     3540 cttgtacttt tttgctgaat ttagcttctt gtagttttaa cttattgcta tgttaactat    3600
ttattctcct cgttgccctg taaggacatc cgtgtatatt tctgttactt catccggttt    3660
gcaagttaaa ggaacgacaa tgttctcttt gtttctttaa gttttgccga gacatggtta    3720
tgcctaattt atttataaaa ggggaagtgg aatcattaaa gtaataataa ttattaataa    3780
cagtaatggt agccgagtgg cacgcggggg cgtgtgctct gcgggacagt ccccacggcc    3840
agcgacgtcc aggtcaccaa tgggattctt tttgctcttg tcttgagaat ttttttcagtc    3900 ctatttagct ggtgaaatcc ctagcttgtt cttgatacac gaacctattt attctcgtgg    3960
```

| | |
|---|---|
| ttttaagtcc tccctgccct ctctcctctc ccctgcagca gggcagggac ccctctcccc | 4020 |
| tgctgtctct tggggctctc tccctccgc cctctgcatt cgggaacacg cacgtccgcg | 4080 |
| tgggaagctt gcagcagggc gtccgagcaa taagggctgg gtttgtcccc caccctgggg | 4140 |
| ggggccaggc tccagagagg gggcacctcc ccacacaccc ccccccacc gaggcctagg | 4200 |
| ccctgccac ccccaagact gggaggggac ttcttttct aaaacacaaa actcagccca | 4260 |
| gccaggcccc ctccctggag gccagcccct cccgcaggg ggccaggccg ggctcccag | 4320 |
| gcgagggga cttgggcttt ccacgtccct gggggcagg ggccaggcca gggggaggg | 4380 |
| ggctcagccc ctccacccct cccttcatcc tgttattat tcggaaggtt tcaaatcacg | 4440 |
| acagagtcca tgttggaggt gataaaaaac tgtaaaaaaa aaaaaaaa aaaagacaaa | 4500 |
| acaaaagaca aaaaaaaaa aaaacccaa caagaacact tcgcgttgcg tttagactat | 4560 |
| ttattaccgg gatcacaggc ctggccgcgg taacagactt ttacatggaa ttgtttaatt | 4620 |
| atttgtactt ttcatgccag aaaataaaag ttcagaatct t | 4661 |

<210> SEQ ID NO 29
<211> LENGTH: 3396
<212> TYPE: DNA
<213> ORGANISM: Homo sapiens

<400> SEQUENCE: 29

| | |
|---|---|
| gggcttcctc ttcgcccggg tggcgttggg cccgcgcggg cgctcgggtg actgcagctg | 60 |
| ctcagctccc ctcccccgcc ccgcgccgcg cggccgcccg tcgcttcgca cagggctgga | 120 |
| tggttgtatt gggcagggtg gctccaggat gttaggaact gtgaagatgg aagggcatga | 180 |
| aaccagcgac tggaacagct actacgcaga cacgcaggag gcctactcct ccgtcccggt | 240 |
| cagcaacatg aactcaggcc tgggctccat gaactccatg aacacctaca tgaccatgaa | 300 |
| caccatgact acgagcggca acatgacccc ggcgtccttc aacatgtcct atgccaaccc | 360 |
| gggcctaggg gccggcctga gtccggcgc agtagccggc atgccggggg gctcggcggg | 420 |
| cgccatgaac agcatgactg cggccggcgt gacggccatg ggtacggcgc tgagcccgag | 480 |
| cggcatgggc gccatgggtg cgcagcaggc ggcctccatg aatggctggg cccctacgc | 540 |
| ggccgccatg aacccgtgca tgagccccat ggcgtacgcg ccgtccaacc tgggccgcag | 600 |
| ccgcgcgggc ggcggcggcg acgccaagac gttcaagcgc agctacccgc acgccaagcc | 660 |
| gccctactcg tacatctcgc tcatcaccat ggccatccag caggcgccca gcaagatgct | 720 |
| cacgctgagc gagatctacc agtggatcat ggacctcttc ccctattacc ggcagaacca | 780 |
| gcagcgctgg cagaactcca tccgccactc gctgtccttc aatgactgct tcgtcaaggt | 840 |
| ggcacgctcc ccggacaagc cgggcaaggg ctcctactgg acgctgcacc cggactccgg | 900 |
| caacatgttc gagaacggct gctacttgcg ccgccagaag cgcttcaagt gcgagaagca | 960 |
| gccggggcc ggcggcgggg gcgggagcgg aagcgggggc agcggcgcca agggcggccc | 1020 |
| tgagagccgc aaggacccct ctggcgcctc taaccccagc gccgactcgc ccctccatcg | 1080 |
| gggtgtgcac gggaagaccg gccagctaga gggcgcgccg gcccccgggc ccgccgccag | 1140 |
| ccccccagact ctggaccaca gtggggcgac ggcgacaggg ggcgcctcgg agttgaagac | 1200 |
| tccagcctcc tcaactgcgc ccccataag ctccgggccc ggggcgctgg cctctgtgcc | 1260 |
| cgcctctcac ccggcacacg gcttggcacc ccacgagtcc cagctgcacc tgaaagggga | 1320 |
| ccccccactac tccttcaacc cccgttctc catcaacaac ctcatgtcct cctcggagca | 1380 |
| gcagcataag ctggacttca aggcatacga acaggcactg caatactcgc cttacggctc | 1440 |

```
tacgttgccc gccagcctgc ctctaggcag cgcctcggtg accaccagga gccccatcga    1500
gccctcagcc ctggagccgg cgtactacca aggtgtgtat tccagacccg tcctaaacac    1560
ttcctagctc ccgggactgg ggggtttgtc tggcatagcc atgctggtag caagagagaa    1620
aaaatcaaca gcaaacaaaa ccacacaaac caaaccgtca acagcataat aaaatcccaa    1680
caactatttt tatttcattt ttcatgcaca acctttcccc cagtgcaaaa gactgttact    1740
ttattattgt attcaaaatt cattgtgtat attactacaa agacaacccc aaaccaattt    1800
ttttcctgcg aagtttaatg atccacaagt gtatatatga aattctcctc cttccttgcc    1860
cccctctctt tcttccctct ttcccctcca gacattctag tttgtggagg gttatttaaa    1920
aaaacaaaaa aggaagatgg tcaagtttgt aaaatatttg tttgtgcttt ttccccctcc    1980
ttacctgacc ccctacgagt ttacaggtct gtggcaatac tcttaaccat aagaattgaa    2040
atggtgaaga aacaagtata cactagaggc tcttaaaagt attgaaagac aatactgctg    2100
ttatatagca agacataaac agattataaa catcagagcc atttgcttct cagtttacat    2160
ttctgataca tgcagatagc agatgtcttt aaatgaaata catgtatatt gtgtatggac    2220
ttaattatgc acatgctcag atgtgtagac atcctccgta tatttacata acatatagag    2280
gtaatagata ggtgatatac atgatacatt ctcaagagtt gcttgaccga aagttacaag    2340
gaccccaacc cctttgtcct ctctacccac agatggccct gggaatcaat tcctcaggaa    2400
ttgccctcaa gaactctgct tcttgctttg cagagtgcca tggtcatgtc attctgaggt    2460
cacataacac ataaaattag tttctatgag tgtataccat ttaaagaatt tttttttcag    2520
taaaagggaa tattacaatg ttggaggaga gataagttat agggagctgg atttcaaaac    2580
gtggtccaag attcaaaaat cctattgata gtggccattt taatcattgc catcgtgtgc    2640
ttgtttcatc cagtgttatg cactttccac agttggacat ggtgttagta tagccagacg    2700
ggtttcatta ttatttctct ttgctttctc aatgttaatt tattgcatgg tttattcttt    2760
ttctttacag ctgaaattgc tttaaatgat ggttaaaatt acaaattaaa ttgttaattt    2820
ttatcaatgt gattgtaatt aaaaatattt tgatttaaat aacaaaaata ataccagatt    2880
ttaagccgtg gaaaatgttc ttgatcattt gcagttaagg actttaaata aatcaaatgt    2940
taacaaaaga gcatttctgt tattttttttt cacttaacta aatccgaagt gaatatttct    3000
gaatacgata tttttcaaat tctagaactg aatataaatg acaaaaatga aaataaaatt    3060
gttttgtctg ttgttataat gaatgtgtag ctagtaaaaa ggagtgaaag aaattcaagt    3120
aaagtgtata agttgattta atattccaag agttgagatt tttaagattc tttattccca    3180
gtgatgttta cttcatttt tttttttttt ttgacaccgg cttaagcctt ctgtgtttcc    3240
tttgagcctt tcactacaa aatcaaatat taatttaact accttcctc cttccccaat    3300 gtatcacttt tctttatctg agaattcttc caatgaaaat aaaatatcag ctgtggctga    3360
tagaattaag ttgtgtccaa aaaaaaaaaa aaaaaa                              3396
```

<210> SEQ ID NO 30
<211> LENGTH: 2415
<212> TYPE: DNA
<213> ORGANISM: Homo sapiens

<400> SEQUENCE: 30

```
cggccgctgc tagaggggct gcttgcgcca ggcgccggcc gccccactgc gggtccctgg      60
cggccggtgt ctgaggagtc ggagagccga ggcggccaga ccgtgcgccc cgcgcttctc     120
```

```
ccgaggccgt tccgggtctg aactgtaaca gggaggggcc tcgcaggagc agcagcgggc    180
gagttaaagt atgctgggag cggtgaagat ggaaggcac gagccgtccg actggagcag     240
ctactatgca gagcccgagg gctactcctc cgtgagcaac atgaacgccg gcctggggat    300
gaacggcatg aacacgtaca tgagcatgtc ggcggccgcc atgggcagcg gctcgggcaa    360
catgagcgcg ggctccatga acatgtcgtc gtacgtgggc gctggcatga gcccgtccct    420
ggcggggatg tccccggcg cgggcgccat ggcgggcatg gcggctcgg ccggggcggc      480
cggcgtggcg ggcatggggc cgcacttgag tcccagcctg agcccgctcg ggggcaggc     540
ggccggggcc atgggcggcc tggcccccta cgccaacatg aactccatga gccccatgta    600
cgggcaggcg ggcctgagcc gcgccgcga ccccaagacc tacaggcgca gctacacgca     660
cgcaaagccg ccctactcgt acatctcgct catcaccatg gccatccagc agagccccaa    720
caagatgctg acgctgagcg agatctacca gtggatcatg gacctcttcc ccttctaccg    780
gcagaaccag cagcgctggc agaactccat ccgccactcg ctctccttca cgactgttt     840
cctgaaggtg ccccgctcgc cgacaagcc cggcaagggc tccttctgga ccctgcaccc    900
tgactcgggc aacatgttcg agaacggctg ctacctgcgc cgccagaagc gcttcaagtg    960
cgagaagcag ctggcgctga aggaggccgc aggcgccgcc ggcagcggca agaaggcggc   1020
cgccggagcc caggcctcac aggctcaact cggggaggcc gccgggccgg cctccgagac   1080
tccggcgggc accgagtcgc tcactcgag cgcctcccg tgccaggagc acaagcgagg    1140
gggcctggga gagctgaagg ggacgccggc tgcggcgctg agccccccag agccggcgcc   1200
ctctcccggg cagcagcagc aggccgcggc ccacctgctg ggcccgcccc accccggg    1260
cctgccgcct gaggcccacc tgaagccgga acaccactac gccttcaacc acccgttctc   1320
catcaacaac ctcatgtcct cggagcagca gcaccaccac agccaccacc accaccaacc   1380
ccacaaaatg gacctcaagg cctacgaaca ggtgatgcac taccccggct acggttcccc   1440
catgcctggc agcttggcca tgggcccggt cacgaacaaa acgggcctgg acgcctcgcc   1500
cctggccgca gataccctcct actaccaggg ggtgtactcc cggcccatta tgaactcctc   1560
ttaagaagac gacggcttca ggcccggcta actctggcac cccggatcga ggacaagtga   1620
gagagcaagt gggggtcgag actttgggga gacggtgttg cagagacgca agggagaaga   1680
aatccataac cccccacccc caacacccccc aagacagcag tcttcttcac ccgctgcagc   1740
cgttccgtcc caaacagagg gccacacaga taccccacgt tctatataag gaggaaaacg   1800
ggaaagaata taaagttaaa aaaaagcctc cggtttccac tactgtgtag actcctgctt   1860
cttcaagcac ctgcagattc tgatttttt gttgttgttg ttctcctcca ttgctgttgt    1920
tgcagggaag tcttacttaa aaaaaaaaa aatttgtg agtgactcgg tgtaaaacca      1980
tgtagtttta acagaaccag agggttgtac tattgtttaa aaacaggaaa aaaataatg    2040
taagggtctg ttgtaaatga ccaagaaaaa gaaaaaaaaa gcattcccaa tcttgacacg   2100
gtgaaatcca ggtctcgggt ccgattaatt tatggtttct gcgtgcttta tttatggctt   2160
ataaatgtgt attctggctg caagggccag agttccacaa atctatatta aagtgttata   2220
cccggtttta tcccttgaat cttttcttcc agatttttct tttctttact ggcttacaa    2280
aatatacagg cttggaaatt atttcaagaa ggagggaggg ataccctgtc tggttgcagg   2340
ttgtatttta ttttggccca gggagtgttg ctgttttccc aacatttat taataaaatt    2400
ttcagacata aaaaa                                                    2415
```

<210> SEQ ID NO 31
<211> LENGTH: 6373
<212> TYPE: DNA
<213> ORGANISM: Homo sapiens

<400> SEQUENCE: 31

| | | | | | |
|---|---|---|---|---|---|
| cttgaacctt | tgtcacccct | cacgttgcac | accaaagaca | taccctagtg | attaaatgct | 60 |
| gattttgtgt | acgattgtcc | acggacgcca | aaacaatcac | agagctgctt | gatttgtttt | 120 |
| aattaccagc | acaaaatgcc | atcagtctgg | gacgtgatcg | ggcagaggtg | tactcacagt | 180 |
| agtgtaaata | ctgctgtaaa | tagttgtctg | atggtggctt | tgacagtgag | ctagcttctg | 240 |
| agttttccct | tcttttata | ctgttttctg | tgctggcttt | tttgaatctt | cctaattttt | 300 |
| catctcttta | acaaactcct | atgaagttga | aaccgggaag | tttgctctaa | catttccaga | 360 |
| gaaggtatta | agtcatgatg | caggaatctg | cgacagagac | aataagcaac | agttcaatga | 420 |
| atcaaaatgg | aatgagcact | ctaagcagcc | aattagatgc | tggcagcaga | gatggaagat | 480 |
| caagtggtga | caccagctct | gaagtaagca | cagtagaact | gctgcatctg | caacaacagc | 540 |
| aggctctcca | ggcagcaaga | caacttcttt | tacagcagca | aacaagtgga | ttgaaatctc | 600 |
| ctaagagcag | tgataaacag | agaccactgc | aggtgcctgt | gtcagtggcc | atgatgactc | 660 |
| cccaggtgat | caccctcag | caaatgcagc | agatccttca | gcaacaagtc | ctgtctcctc | 720 |
| agcagctaca | agcccttctc | caacaacagc | aggctgtcat | gctgcagcag | caacaactac | 780 |
| aagagtttta | caagaaacag | caagagcagt | tacatcttca | gcttttgcag | cagcagcagc | 840 |
| aacagcagca | gcagcaacaa | cagcagcaac | aacagcagca | gcaacaacaa | caacaacagc | 900 |
| agcaacaaca | gcagcagcag | cagcaacagc | agcagcagca | gcaacagcat | cctggaaagc | 960 |
| aagcgaaaga | gcagcagcag | cagcagcagc | agcaacagca | attggcagcc | cagcagcttg | 1020 |
| tcttccagca | gcagcttctc | cagatgcaac | aactccagca | gcagcagcat | ctgctcagcc | 1080 |
| ttcagcgtca | gggactcatc | tccattccac | ctggccaggc | agcacttcct | gtccaatcgc | 1140 |
| tgcctcaagc | tggcttaagt | cctgctgaga | ttcagcagtt | atggaaagaa | gtgactggag | 1200 |
| ttcacagtat | ggaagacaat | ggcattaaac | atggagggct | agacctcact | actaacaatt | 1260 |
| cctcctcgac | tacctcctcc | aacacttcca | agcatcacc | accataact | catcattcca | 1320 |
| tagtgaatgg | acagtcttca | gttctaagtg | caagacgaga | cagctcgtca | catgaggaga | 1380 |
| ctggggcctc | tcacactctc | tatggccatg | gagtttgcaa | atggcaggc | tgtgaaagca | 1440 |
| tttgtgaaga | ttttggacag | tttttaaagc | accttaacaa | tgaacacgca | ttggatgacc | 1500 |
| gaagcactgc | tcagtgtcga | gtgcaaatgc | aggtggtgca | acagttagaa | atacagcttt | 1560 |
| ctaaagaacg | cgaacgtctt | caagcaatga | tgacccactt | gcacatgcga | ccctcagagc | 1620 |
| ccaaccatc | tcccaaacct | ctaaatctgg | tgtctagtgt | caccatgtcg | aagaatatgt | 1680 |
| tggagacatc | cccacagagc | ttacctcaaa | ccctaccac | accaacggcc | ccagtcaccc | 1740 |
| cgattaccca | gggaccctca | gtaatcaccc | cagccagtgt | gcccaatgtg | ggagccatac | 1800 |
| gaaggcgaca | ttcagacaaa | tacaacattc | ccatgtcatc | agaaattgcc | ccaaactatg | 1860 |
| aattttataa | aaatgcagat | gtcagacctc | catttactta | tgcaactctc | ataaggcagg | 1920 |
| ctatcatgga | gtcatctgac | aggcagttaa | cacttaatga | aatttacagc | tggtttacac | 1980 |
| ggacatttgc | ttacttcagg | cgtaatgcag | caacttggaa | gaatgcagta | cgtcataatc | 2040 |
| ttagcctgca | caagtgtttt | gttcgagtag | aaaatgttaa | aggagcagta | tggactgtgg | 2100 |
| atgaagtaga | ataccagaag | cgaaggtcac | aaaagataac | aggaagtcca | accttagtaa | 2160 |

```
aaaatatacc taccagttta ggctatggag cagctcttaa tgccagtttg caggctgcct    2220
tggcagagag cagtttacct ttgctaagta atcctggact gataaataat gcatccagtg    2280
gcctactgca ggccgtccac gaagacctca atggttctct ggatcacatt gacagcaatg    2340
gaaacagtag tccgggctgc tcacctcagc cgcacataca ttcaatccac gtcaaggaag    2400
agccagtgat tgcagaggat gaagactgcc caatgtcctt agtgacaaca gctaatcaca    2460
gtccagaatt agaagacgac agagagattg aagaagagcc tttatctgaa gatctggaat    2520
gagaactgac ttgtgaaacc tcagcgtgaa gggacatatc actgaccttc ataaccactc    2580
cacaaccatg aatatttgac aaattttttac tgtgactatt tattaagcat ggataaagga    2640
gacagcccta aaggaactta ctaagccagc cctttgggat tcagtaccaa caggcaaatt    2700
gcttgttttc ttcttcttct tcttcttttt tttttttttt ttagaaaaaa agacaaaaac    2760
tgattttctt gaaaaaaaaa aatgaactgt tctttctata atggctttgc ccatttaaaa    2820
aatgtggctc ttaagggttc atgaaatgac tgaatatgag gatacatgtc ctgtagaaag    2880
caaatgcgcc tcatatactg ccaaaaatag tgttagtttc attaatgtga attttccagc    2940
attcagtagt tgtaatgtta gaaacaattg ctggtcaagt tcaacttgtt gctattgttt    3000
ttaatttgca caggagtagt atcagaaatt agtgtcactg cttgtatcta gctgaatttt    3060
aaacaacaga acattagttt tttatgttgg tgccaccaac tgtaaatgac ataagttagt    3120
tattacaaaa cacagtaatt agactgttgc aaccatctaa aaccttaggc ttccagtctg    3180
tgctgttagt gttaagatgt aaagtgcaat cctaagctaa cattatctgt gcaagcacca    3240
tagaaacatt tgcatatctg catagatctt acaactgtac tctttacctc cttgtgataa    3300
agctttgtct acctgcaaac acagtcaaag gctacagctg caaaccaaag ccaactctaa    3360
ccatggccaa gagctcaagg acagaagcag ccacatgctt tggtcagcct tctgtaactt    3420
caattagtac aaaggaacct tttccatgaa ctacctgctg ttttctgatg acctctggga    3480
tcttttcatt tagccctaaa caaagaaaca aatatgacaa aaaccacaac taaaaaatgt    3540
taattcagtc acagagtaat cttctgaggc caaaagtcca tctaaatgca atgaagattt    3600
gctttcatta aagacagagg tgaggacaaa atccgcagtg gaagttatga tatgctagaa    3660
agcaacaaat gtggatcact gaccaaaacg attatgtact tgatgcaaat gcagattgca    3720
tattgttata tatatagtac tttgtgtttt tgttttccct cattcagtca gttattttca    3780
gtggtgaata catgttgtta gaagatgtct tgtatggtct taatctttgt tgtgtactat    3840
ttttttatag tcttaagtta taatgaaaaa acaaaaagta ggaaccaaac ataaaaggtc    3900
tagtaaagcc aaaaattaat ttcatattga ttttaaagtg atctagctga gttttttacac    3960
tgaaagcaaa gattatagca attgtagtcc atggtattta ttttcagtca aaccaaagtt    4020
acatataatt ctgcctctgc ttatacggga tattaacact aacaatacac tcccttcaaa    4080
gacttgcaca ggccaaattg ttggaatgct ggttttcttg acaattccaa accccaaaac    4140
tatgataatg agttatgatg tagttgaaaa tagcatagtc agatgtttgc ttaaaaccta    4200
gaaacttaac atgttgcttt tcatgtgctg tgccaagtct tgataatact ttttccccca    4260
accaagggac ctcataacct gattatggtt attgctttac aaacagtttt gacagaaggt    4320
ggctgctaga gcttaacata cgttcccgtt ccatgtgatg gaaccggttc ttgcaaacta    4380
agctcatcat tgattctttg ctgaagtcag caaatagagt tagagagata cccagtcatc    4440
tatcacacca aataaaagga cataacggct ttcaaagggg ttttcccact tacccaaaag    4500
gctttctgaa agcttctacc tctgcaaaaa aaaaaaaga aaaaaaaaa aagaaaaaca    4560
```

```
ttagaacaat tatggcagat tgcatgaaac gtgagaacgt cacagtaact gctacttttc    4620
attatgtttg tctttgggtc atgatcaacg aaccggaagt ttacaatatg gtattaaaag    4680
aaagatgggt atggtgaaag atggttttca gtcatctagg atcctactgt aaggattatc    4740
tgaaaggaaa aatgggtctt tcaggtgcat gttcaaaagg ctttgaggga ctggaagtaa    4800
ctgcgagagt tgtaccatca gaagggtggc ctaagactac aatgctaaag tatgcatacc    4860
tcagttagaa aacttttgaa aggaagtctc agccacagaa tgcatatacc tgtagagttt    4920
tgcatgggtt ttatatgaat acaattttaa aaaatagctg cttgcacatt ataccagaaa    4980
aacctccaaa actgcaattg ctttgaaaat agatttttagg ttttttggag tttcctgaaa    5040
tgcttggtct gtattttgat aattgtgcat attatgtaaa aatgttggtg gacccataaa    5100
tgaccagact ttttctaaga aaaatgttgc tttaatgcat ttcatgaatt tttactctta    5160
tatcattgct tgctagtaat agcaaatctg cttttctgca tctgctttgc gtagctattg    5220
taaggctttg aactaatgta tgtatttatt gcttgaactt ctgtgcatac cttataaagc    5280
ataatgtctg acaatttaaa tggctcatgt attcttgctt ctatcataag ctgattatgg    5340
ggactatgat cttttgtata cagcaaattt taaactgtag cacaaacatc tgtttatgta    5400
ttggtggaat atacctgttt tatttatctt ttttgaggta aactaatttt tgatacttttt   5460 cattactgtg tactatgttc atactttgaa ttctctgacg ttagaagtca tggttgagaa    5520
ttgtaacagc tgttattcgt tctgtattca tggctttcac tgctgaataa aataaaggac    5580
caaacctagg atttgaaaga aaactgtcta cctctaacac cagggagtta tcagatttta    5640
ttttacatag ttttagtcta caaagacaca attgcttaaa cctagtgggc ttaaggctta    5700
tattctatgt ggttggattc gtggcacagt tgtactattt gaaaatcaat taaaatttta    5760
tgtgaatgtt acaagtattt ggtagaatta ccactaactg ggttttcttt agataactca    5820
gatatggaga aaatgtcatc agcattctgt gtctacagct gcttaacttc ataagaatgc    5880
atttctttgt gattagggaa tcgaagaata gtcagctagg aatagagcta cagaagtaca    5940
cttacataaa ccatcctgga ctttaatgtc cctgggcaga ttcagtcgca aaatccaata    6000 tgatatttg taaagttttc aagttggaca tttacatttt tgagaatttt gagacttcat     6060
cttacacatg ccagtattaa cacacatttg acaatagct ttattaagtc tataaagcta     6120
ttgaaaggaa catggcttac ccttgttatt tcactagttc aggttgcaac gaaaggtttt    6180
tttgtccatg aacacttggc atatcttact tagcaaaaaa gaaggatgta cattttacta    6240
tagaattaat gtatgaacag tgtgtcactg ctgttggatg taaaaatgta tatgaaacca    6300
tttcattcac ttgattacat ttctgaagta taaataaaaa aatctaattc tttttgaccc    6360
atttataaaa aaa                                                       6373

<210> SEQ ID NO 32
<211> LENGTH: 3419
<212> TYPE: DNA
<213> ORGANISM: Homo sapiens

<400> SEQUENCE: 32
ttggaggcgg ccggcgcagg ggccgcgaga ggcttcgtcg ccgctgcagc tccgggggct      60
cccaggggag cgtgcgcgga acctccaggc ccagcaggac cccggctgcg gcgaggagga     120
aggagccagc ctagcagctt ctgcgcctgt ggccgcgggt gtcctggagg cctctcggtg     180
tgacgagtgg gggacccgaa ggctcgtgcg ccacctccag gcctggacgc tgccctccgt     240
```

-continued

```
cttctgcccc caataggtgc gccggacctt caggccctgg ggtgaattca gctgctccta    300
catcagcttc cggaaccacc aaaaattcaa attgggattt tccggagtaa acaagagcct    360
agagcccttt gctcaatgct ggatttaata cgtatatatt tttaagcgag ttggttttt     420
ccccttttgat ttttgatctt cgcgacagtt cctcccacgc atattatcgt tgttgccgtc   480
gttttctctc cccgcgtggc tccttgacct gcgagggaga gagaggacac cgaagccggg   540
agctcgcagg gaccatgtat cagagcttgg ccatggccgc caaccacggg ccgccccccg    600
gtgcctacga ggcgggcggc cccggcgcct tcatgcacgg cgcgggcgcc gcgtcctcgc    660
cagtctacgt gcccacaccg cgggtgcccc cctccgtgct gggcctgtcc tacctccagg    720
gcggaggcgc gggctctgcg tccggaggcg cctcgggcgg cagctccggt ggggccgcgt    780
ctggtgcggg gccgggacc cagcagggca gcccgggatg gagccaggcg ggagccgacg     840
gagccgctta caccccgccg ccggtgtcgc cgcgcttctc cttcccgggg accaccgggt    900
ccctggcggc cgccgccgcc gctgccgcgg cccgggaagc tgcggcctac agcagtggcg    960
gcggagcggc gggtgcgggc ctggcgggcc gcgagcagta cggggcgcgcc ggcttcgcgg   1020
gctcctactc cagcccctac ccggcttaca tggccgacgt gggcgcgtcc tgggccgcag   1080
ccgccgccgc ctccgccggc cccttcgaca gcccggtcct gcacagcctg cccggccggg   1140
ccaacccggc cgcccgacac cccaatctcg atatgtttga cgacttctca gaaggcagag   1200
agtgtgtcaa ctgtggggct atgtccaccc gctctggag gcgagatggg acgggtcact    1260
atctgtgcaa cgcctgcggc ctctaccaca agatgaacgg catcaaccgg ccgctcatca   1320
agcctcagcg ccggctgtcc gcctcccgcc gagtgggcct ctcctgtgcc aactgccaga   1380
ccaccaccac cacgctgtgg cgccgcaatg cggagggcga gcctgtgtgc aatgcctgcg   1440
gcctctacat gaagctccac ggggtcccca ggcctcttgc aatgcggaaa gaggggatcc   1500
aaaccagaaa acggaagccc aagaacctga ataaatctaa gacaccagca gctccttcag   1560
gcagtgagag ccttcctccc gccagcggtg cttccagcaa ctccagcaac gccaccacca   1620
gcagcagcga ggagatgcgt cccatcaaga cggagcctgg cctgtcatct cactacgggc   1680
acagcagctc cgtgtcccag acgttctcag tcagtgcgat gtctggccat gggccctcca   1740
tccaccctgt cctctcggcc ctgaagctct ccccacaagg ctatgcgtct cccgtcagcc   1800
agtctccaca gaccagctcc aagcaggact cttggaacag cctggtcttg gccgacagtc   1860
acggggacat aatcactgcg taatcttccc tcttccctcc tcaaattcct gcacggacct   1920
gggacttgga ggatagcaaa gaaggaggcc ctgggctccc aggggccggc ctcctctgcc   1980
tggtaatgac tccagaacaa caactgggaa gaaacttgaa gtcgacaatc tggttagggg   2040
aagcgggtgt tggatttct cagatgcctt tacacgctga tgggactgga gggagcccac   2100
ccttcagcac gagcacactg catctctcct gtgagttgga gacttctttc caagatgtc    2160
cttgtcccct gcgttcccca ctgtggccta gaccgtgggt tttgcattgt gtttctagca   2220
ccgaggatct gagaacaagc ggagggccgg gccctgggac ccctgctcca gcccgaatga   2280
cggcatctgt ttgccatgta cctggatgcg acgggcccct ggggacaggc ccttgcccca   2340
tccatccgct tgaggcatgg caccgccctg catccctaat accaaatctg actccaaaat   2400
tgtggggtgt gacatacaag tgactgaaca cttcctgggg agctacaggg gcacttaacc   2460
caccacagca cagcctcatc aaaatgcagc tggcaacttc tccccaggt gccttccccc    2520
tgctgccggc ctttgctcct tcacttccaa catctctcaa aataaaaatc cctcttcccg   2580
ctctgagcga ttcagctctg cccgcagctt gtacatgtct ctcccctggc aaaacaagag   2640
```

| | |
|---|---|
| ctgggtagtt tagccaaacg gcaccccctc gagttcactg cagacccttc gttcaccgtg | 2700 |
| tcacacatag aggggttctg agtaagaaca aaacgttctg ctgctcaagc cagtctggca | 2760 |
| agcactcagc ccagcctcga ggtccttctg gggagagtgt aagtggacag agtcctggtc | 2820 |
| aggggggcagg agtgtcccaa gggctggccc acctgctgtc tgtctgctcc tcctagccct | 2880 |
| tggtcagatg gcagccagag tccctcagga cctgcagcct cgccccggca gaagtctttt | 2940 |
| gtccaggagg caaaaagcca gagattctgc aacacgaatt cgaagcaaac aaacacaaca | 3000 |
| caacagaatt cctggaaaga gacgactgc taagacacgg cagggggggcc tggagggagc | 3060 |
| ctccgactct gagctgctcc gggatctgcc gcgttctcct ctgcacattg ctgtttctgc | 3120 |
| ccctgatgct ggagctcaag gagactcctt cctctttctc agcagagctg tagctgactg | 3180 |
| tggcattact acgcctcccc acacgcccag acccctcact ccaaaatcct actggctgta | 3240 |
| gcagagaata cctttgaacc aagattctgt tttaatcatc atttacattg ttttcttcca | 3300 |
| aaggccccct cgtataccct ccctaaccca caaacctgtt aacattgtct taaggtgaaa | 3360 |
| tggctggaaa atcagtattt aactaataaa tttatctgta ttcctcttaa aaaaaaaaa | 3419 |

<210> SEQ ID NO 33
<211> LENGTH: 3785
<212> TYPE: DNA
<213> ORGANISM: Homo sapiens

<400> SEQUENCE: 33

| | |
|---|---|
| agttccgacc cacagcctgg caccttcgg cgagcgctgt tgtttaggg ctcggtgagt | 60 |
| ccaatcagga gcccaggctg cagttttccg gcagagcagt aagaggcgcc tcctctctcc | 120 |
| tttttattca ccagcagcgc ggcgcagacc ccggactcgc gctcgcccgc tggcgccctc | 180 |
| ggcttctctc cgcgcctggg agcaccctcc gccgcggccg ttctccatgc gcagcgcccg | 240 |
| cccgaggagc tagacgtcag cttggagcgg cgccggaccg tggatggcct tgactgacgg | 300 |
| cggctggtgc ttgccgaagc gcttcggggc gcgggtgcg gacgccagcg actccagagc | 360 |
| ctttccagcg cgggagccct ccacgccgcc ttcccccatc tcttcctcgt cctcctcctg | 420 |
| ctcccggggc ggagagcggg gccccggcgg cgccagcaac tgcggacgc ctcagctcga | 480 |
| cacggaggcg gcggccggac ccccggcccg ctcgctgctg ctcagttcct acgcttcgca | 540 |
| tcccttcggg gctccccacg gaccttcggc gcctggggtc gcgggccccg ggggcaacct | 600 |
| gtcgagctgg gaggacttgc tgctgttcac tgacctcgac caagccgcga ccgccagcaa | 660 |
| gctgctgtgg tccagccgcg cgccaagct gagccccttc gcacccgagc agccggagga | 720 |
| gatgtaccag accctcgccg ctctctccag ccagggtccg gccgcctacg acggcgcgcc | 780 |
| cggcggcttc gtgcactctg cggccgcggc ggcagcagcc gcggcggcgg ccagctcccc | 840 |
| ggtctacgtg cccaccaccc gcgtgggttc catgctgccc ggcctaccgt accacctgca | 900 |
| ggggtcgggc agtgggccag ccaaccacgc gggcggcgcg ggcgcgcacc ccggctggcc | 960 |
| tcaggcctcg gccgacagcc ctccatacgg cagcggaggc ggcgcggctg gcggcggggc | 1020 |
| cgcgggggcct ggcggcgctg gctcagccgc ggcgcacgtc tcggcgcgct tcccctactc | 1080 |
| tcccagcccg cccatggcca acggcgccgc gcgggagccg ggaggctacg cggcggcggg | 1140 |
| cagtgggggc gcgggaggcg tgagcggcgg cggcagtagc ctggcggcca tgggcggccg | 1200 |
| cgagccccag tacagctcgc tgtcggccgc gcggccgctg aacgggacgt accaccacca | 1260 |
| ccaccaccac caccaccacc atccgagccc ctactcgccc tacgtggggg cgccactgac | 1320 |

```
gcctgcctgg cccgccggac ccttcgagac cccggtgctg cacagcctgc agagccgcgc    1380 cggagcccg ctcccggtgc cccggggtcc cagtgcagac ctgctggagg acctgtccga    1440
gagccgcgag tgcgtgaact gcggctccat ccagacgccg ctgtggcggc gggacggcac    1500
cggccactac ctgtgcaacg cctgcgggct ctacagcaag atgaacgcc tcagccggcc    1560 cctcatcaag ccgcagaagc gcgtgccttc atcacggcgg cttggattgt cctgtgccaa    1620
ctgtcacacc acaactacca ccttatggcg cagaaacgcc gagggtgaac ccgtgtgcaa    1680
tgcttgtgga ctctacatga aactccatgg ggtgcccaga ccacttgcta tgaaaaaaga    1740
gggaattcaa accaggaaac gaaaacctaa gaacataaat aaatcaaaga cttgctctgg    1800
taatagcaat aattccattc ccatgactcc aacttccacc tcttctaact cagatgattg    1860
cagcaaaaat acttccccca caacacaacc tacagcctca ggggcgggtg ccccggtgat    1920
gactggtgcg ggagagagca ccaatcccga gaacagcgag ctcaagtatt cgggtcaaga    1980
tgggctctac ataggcgtca gtctcgcctc gccggccgaa gtcacgtcct ccgtgcgacc    2040
ggattcctgg tgcgccctgg ccctggcctg agcccacgcc gccaggaggc agggagggct    2100
ccgccgcggg cctcactcca ctcgtgtctg cttttgtgca gcggtccaga cagtggcgac    2160
tgcgctgaca gaacgtgatt ctcgtgcctt tattttgaaa gagatgtttt cccaagagg    2220 cttgctgaaa gagtgagaga agatggaagg gaagggccag tgcaactggg cgcttgggcc    2280
actccagcca gcccgcctcc ggggcggacc ctgctccact tccagaagcc aggactagga    2340
cctgggcctt gcctgctatg gaatattgag agagattttt taaaaaagat tttgcatttt    2400
gtccaaaatc atgtgcttct tctgatcaat tttggttgtt ccagaatttc ttcatacctt    2460
ttccacatcc agatttcatg tgcgttcatg gagaagatca cttgaggcca tttggtacac    2520
atctctggag gctgagtcgg ttcatgaggt ctcttatcaa aaatattact cagtttgcaa    2580
gactgcattg taactttaac atacactgtg actgacgttt ctcaaagttc atattgtgtg    2640
gctgatctga gtcagtcgg aatttgtaaa cagggtagca aacaagatat ttttcttcca    2700
tgtatacaat aattttttta aaagtgcaa tttgcgttgc agcaatcagt gttaaatcat    2760
ttgcataaga tttaacagca tttttttataa tgaatgtaaa cattttaact taatggtact    2820
taaaataatt taaaagaaaa atgttaactt agacattctt atgcttcttt tacaactaca    2880 tcccattta tatttccaat tgttaaagaa aaatatttca agaacaaatc ttctctcagg    2940
aaaattgcct ttctctattt gttaagaatt tttatacaag aacaccaata tacccccttt    3000
attttactgt ggaatatgtg ctggaaaaat tgcaacaaca ctttactacc taacggatag    3060
catttgtaaa tactctaggt atctgtaaac actctgatga agtctgtata gtgtgactaa    3120
cccacaggca ggttggttta cattaatttt ttttttgaa tgggatgtcc tatgaaaacc    3180
tatttcacca gagttttaaa aataaaaagg gtattgtttt gtcttctgta cagtgagttc    3240
cttccctttt caaagctttc ttttatgct gtatgtgact atagatattc atataaaaca    3300
agtgcacgtg aagtttgcaa aatgctttaa ggccttcctt tcaaagcata gtcctttgg    3360 agccgttttg tacctttat accttggctt atttgaagtt gacacatggg gttagttact    3420
actctccatg tgcattgggg acagttttta taagtgggaa ggactcagta ttattatatt    3480
tgagatgata agcattttgt ttgggaacaa tgcttaaaaa tattccagaa agttcagatt    3540
tttttttctt gtgaatgaaa tatattctgg cccacgaaca gggcgatttc ctttcagttt    3600
tttccttttg caacgtgcct tgaagtctca agctcacct gaggttgcag acgttacccc    3660
caacagaaga taggtagaaa tgattccagt ggcctctttg tattttcttc attgttgagt    3720
```
agatttcagg aaatcaggag gtgtttcaca atacagaatg atggccttta actgtgaaaa    3780
aaaaa    3785

<210> SEQ ID NO 34
<211> LENGTH: 1772
<212> TYPE: DNA
<213> ORGANISM: Homo sapiens

<400> SEQUENCE: 34
ggataaatgt agcgccgcgg cgcgggccag cagctctgcg aggggccgga gcgcggcgga     60
gccatgcagt acccgcaccc cgggccggcg gcgggcgccg tgggggtgcc gctgtacgcg    120
cccacgccgc tgctgcaacc cgcacacccg acgcccttt acatcgagga catcctgggc    180
cgcgggcccg ccgcgccccac gcccgccccc acgctgccgt cccccaactc ctccttcacc    240
agcctcgtgt cccctaccg accccggtg tacgagccca cgccgatcca tccagccttc    300
tcgcaccact ccgccgccgc gctggccgct gcctacggac ccggcggctt cggggggcct    360
ctgtacccct tcccgcggac ggtgaacgac tacacgcacg ccctgctccg ccacgacccc    420
ctgggcaaac ctctactctg gagcccttc ttgcagaggc ctctgcataa aaggaaaggc    480
ggccaggtga gattctccaa cgaccagacc atcgagctgg agaagaaatt cgagacgcag    540
aaatatctct ctccgcccga gaggaagcgt ctggccaaga tgctgcagct cagcgagaga    600
caggtcaaaa cctggtttca gaatcgacgc gctaaatgga ggagactaaa acaggagaac    660
cctcaaagca ataaaaaaga agaactggaa agtttggaca gttcctgtga tcagaggcaa    720
gatttgccca gtgaacagaa taaaggtgct tctttggata gctctcaatg ttcgccctcc    780
cctgcctccc aggaagacct tgaatcagag atttcagagg attctgatca ggaagtggac    840
attgagggcg ataaaagcta ttttaatgct ggatgatgac cactggcatt ggcatgttca    900
gaaaactgga tttaggaata atgttttgct acagaaaatc ttcatagaag aactggaagg    960
ctatataaga aagggaatca attctctggt attctggaaa cctaaaaata tttggtgcac   1020
tgctcaatta acaaacctac atggagacct taatttgac ttaacaaata gtttatgtac   1080
tgctcttagg ttgttttgat aaagtgacat tatagtgatt aaattcttcc ccctttaaaa   1140
aaacagttag tggttttcac tatttataaa aaattaattt tgaactttt gttaaatttt   1200 taagttatag ctttaaaggt tttaatagga ccttcttgaa cgacttttct gtaatctgtt   1260
tatctcccac ttaatggaaa ggcaagggg taccccaaat ccagaggtgc ctacatttca   1320
ggcagccttg gagtattta aaggaaaac attctttact tttatatgac attcttatac   1380
tgctgtctca aatccaaaaa catttcagag ctcttgtctc agagatgtgt gttcttttg   1440 tcagagatat ggttgatgag aatcttaaat gcttgttttg cactatcact tagtacctgt   1500
ttgaccaagg tgttaagggg atagtacctc ccaattcaag cagagaaact gacctgacta   1560
aagttaatcg cagatgaact agaagtcaca ggttaattaa atgtaagtag attgtagata   1620 ctgtttata tcaaacaatg tttataatgt gtatatagaa ttgttcactg taaaaaaaat   1680
ggccaaaatg tgttttttt ttaataagta acttgactat aaaataaagc cgtccgtggg   1740
acgactgacc tcgttgcaaa aaaaaaaaaa aa   1772

<210> SEQ ID NO 35
<211> LENGTH: 2473
<212> TYPE: DNA
<213> ORGANISM: Homo sapiens

<400> SEQUENCE: 35

```
acagatggtg tgggagcgcg ttccccggta ggaggggcg cgagcgagca agcaggcagg      60
cagctgccag gagctcttcc ctgctcgctc acgcctgctc tcagaagctc cgatccagac    120
acacgcgagg cgctgtcctt tcagcaccac aagctcgggc tgaggaggga ggactcctgg    180
ccgtcctcct cctcttcaaa ttggcttgaa tctgctctga ccccccacga gtgcagcaca    240
gtctgggaag aaaggcgtaa ggatggtgaa gctgaacagt aaccccagcg agaagggaac    300
caagccgcct tcagttgagg atggcttcca gaccgtccct ctcatcactc ccttggaggt    360
taatcactta cagctgcctg ctccagaaaa ggtgattgtg aagacaagaa cggaatatca    420
gccggaacag aagaacaaag ggaagttccg ggtgccgaaa atcgctgaat ttacggtcac    480
catccttgtc agcctggccc tagctttcct tgcgtgcatc gtgttcctgg tggtttacaa    540
agccttcacc tatgatcaca gctgcccaga gggattcgtc tataagcaca acgctgtat    600
cccagcctcc ctggatgctt actactcctc ccaggacccc aattccgaaa gccgcttcta    660
cacagtcatc agccactaca gcgtggccaa gcagagcact gcccgggcca tcgggccgtg    720
gctgtcagca gccgctgtca tccatgagcc caagccgccc aagacccagg gccactagag    780
gcctgcccca gccagaatgg ggggcggggt ggagaggagg accccccattg gctaagccaa    840
gctccagtta caagacaaca ctgtactcct gggatatggg ggcggggcg gggcagggca    900
gggtgggggg aagaacgcac caaaaacgtg gtgtgtgctg gagttgtctg aaccgatatt    960
tcttttgtt ccttggtatt gttgattcgt cgccgagtca ggctcatgta caaaggcatg   1020
tttcgtgttg attgttccca tgtaagatat ttttaaagcc actgcttatt ctttgttagg   1080
aaaatgtaac agcagaaaag gaaagaaaca agaacatga acaaaaagca ttaaactggc   1140
tccatcagaa gacgttgaag ggcagtgaag agcacagact ctgtgggctt cttagataag   1200
aaaacgtagc ttcagtgggg gctccagggt tgcagagtat gagtgacaca gaccgggact   1260
attccattag cctgtggtct gcagggtagg cccgcaggaa atgaggaatg gccgagctgg   1320
agagaagagc tgattttggc attactaagc ccagaacgca cataacccat agtgaaatgt   1380
gctggcctct ggtgcatttt gcaagatgag cacaaacttt ctgggcctcc atcctaggac   1440
ctgggcagac ccacatggcc tgggctctga atgcccaccc tgcgacggtg ggttctgcat   1500
cagcaaacgc tgaggagtgg gcagattttc tttgtctttt gcttgcattt tctagatcca   1560
cacctggata ctgcccatgt tgacgagaca gcagcagggg gagagggagg gaaggaaggt   1620
gcggctgcaa gaaggaaggc acgggacagg catgtgacac taggccacaa gcgataagca   1680
caggcacctg acttttaagt ttttgtttgt ttgttgtttc ccaaagtgct gataacaata   1740
acaacaacaa taggattcca accaggagcc tcaagtgaca gccaggaaga gacctgaagg   1800
ttggggccac cacaatgcca aatcgtttct aaaggaagct gaaaaatggg actgtctttt   1860
gcccacttcg ttgtgttaaa aggggacatt tgtccaaact ccccaaccga gttctagaag   1920
ctcctgacaa ggaggcagca tccagccttg accaggcctc ccagttccct ggaaccgtat   1980
caggcattcg cctgcctctc acaaatgttt cagggaggcc agttctgcag ggtgtcagct   2040
ccaggaccca cagggccaga accagctggg agaattggtt atttgagatg tggtactgct   2100
tcctcacaag tctcccacag gccatgtaaa gggtatttt ttgtggcttg ctgtgttgct   2160
gagatcatcg tatgcaacag ctgggtaata agactagcat agctcaaact atcctgccaa   2220
acgctctcat ctgattttc ctcccttctc ccccaacctc caatcaccct gagtcacctg   2280
taaattcatt tgtcattcaa agcggaataa caagttgtcc ctagcaaaac cgctgagcgc   2340
```

```
tttataattt tgtggtgtat ttttgtcagt aggtagcaga ggcggaagta ttttttggtg    2400
taattcttga aattttctga caggaaacaa ataaagatag atgtgtctga gaaaaaaaaa    2460
aaaaaaaaaa aaa                                                       2473

<210> SEQ ID NO 36
<211> LENGTH: 2842
<212> TYPE: DNA
<213> ORGANISM: Homo sapiens

<400> SEQUENCE: 36
aatttgcata tcttatatgg cctaatggtg gcgatcatgg caagttagaa gtttttctgac     60 tcctttcgga ggagcctccg ggaccccggg gagtaacagg tgtctggagg ctgaagggtg    120
gaggggttcc tggatttggg gtttgcttgt gaaactcccc tccaccctcc tctctcgcac    180
ccacccaccc cctcaccccc ttcttttttcc gtccttggaa aatggtgtcc aagctcacgt    240
cgctccagca agaactcctg agcgccctgc tgagctccgg ggtcaccaag gaggtgctgg    300
ttcaggcctt ggaggagttg ctgccatccc cgaacttcgg ggtgaagctg gagacgctgc    360
ccctgtcccc tggcagcggg gccgagcccg acaccaagcc ggtcttccat actctcacca    420
acggccacgc caagggccgc ttgtccggcg acgagggctc cgaggacggc gacgactatg    480
acacacctcc catcctcaag gagctgcagg cgctcaacac cgaggaggcg gcggagcagc    540
gggcggaggt ggaccggatg ctcagtgagg acccttggag ggctgctaaa atgatcaagg    600
gttacatgca gcaacacaac atcccccaga gggaggtggt cgatgtcacc ggcctgaacc    660
agtcgcacct ctcccagcat ctcaacaagg gcacccctat gaagacccag aagcgtgccg    720
ctctgtacac ctggtacgtc agaaagcaac gagagatcct ccgacaattc aaccagacag    780
tccagagttc tggaaatatg acagacaaaa gcagtcagga tcagctgctg tttctctttc    840
cagagttcag tcaacagagc catgggcctg gcagtccga tgatgcctgc tctgagccca    900
ccaacaagaa gatgcgccgc aaccggttca atgggggcc cgcgtcccag caaatcttgt    960
accaggccta cgatcggcaa aagaacccca gcaaggaaga gagagaggcc ttagtggagg    1020
aatgcaacag ggcagaatgt ttgcagcgag gggtgtcccc ctccaaagcc cacggcctgg    1080
gctccaactt ggtcactgag gtccgtgtct caactggtt tgcaaaccgc aggaaggagg    1140
aggcattccg gcaaaagctg gccatggacg cctatagctc caaccagact cacagcctga    1200
accctctgct ctcccacggc tccccccacc accagcccag ctcctctcct ccaaacaagc    1260
tgtcaggagt gcgctacagc cagcagggaa acaatgagat cacttcctcc tcaacaatca    1320
gtcaccatgg caacagcgcc atggtgacca gccagtcggt tttacagcaa gtctccccag    1380
ccagcctgga cccaggccac aatctcctct cacctgatgg taaaatgatc tcagtctcag    1440 gaggagggttt gccccagtc agcaccttga cgaatatcca cagcctctcc caccataatc    1500
cccagcaatc tcaaaacctc atcatgacac ccctctctgg agtcatggca attgcacaaa    1560
gcctcaacac ctcccaagca cagagtgtcc ctgtcatcaa cagtgtggcc ggcagcctgg    1620
cagccctgca gccgtccag ttctcccagc agctgcacag ccctcaccag cagcccctca    1680
tgcagcagag cccaggcagc cacatggccc agcagccctt catggcagct gtgactcagc    1740
tgcagaactc acacatgtac gcacacaagc aggaaccccc ccagtattcc cacacctccc    1800
ggtttccatc tgcaatggtg gtcacagata ccagcagcat cagtacactc accaacatgt    1860
cttcaagtaa acagtgtcct ctacaagcct ggtgatgccc acacaccact tacttcgtgc    1920
```

| | |
|---|---|
| gcaacaacaa ggaccctgtt ttccacacca tcaccctctg ggcagctgtc atggaaaagc | 1980 |
| ccagtgacct gaccggcacc tgcgagaggt ccctgcttac ctgacggacg tcctgctggc | 2040 |
| acctcagaca atccactctc aggaggcgca gcccgaagcc cagtttccct tctatgcagt | 2100 |
| attgccacaa tgcctctccc acgatgtcaa ggactcctgt ctgtcctgga ggtgggagac | 2160 |
| aaggaaccac cgaagaggaa gcaagaaagc cgtactgtct atgttgtgat ccttcatcga | 2220 |
| acaaactgat gcgaaaactt gaatctgtta ctgaaatgag gagagaagga catgtgctat | 2280 |
| tgaactgagc aaacacact gtaaatatcc acagactccc tccctgccc ccatcccaca | 2340 |
| tgatcttgag atttctttta aagaagtaaa tttgtccaat ggctgtaaac tataaactac | 2400 |
| tgtaattaag tgcaatttcc cctctgtgtc ctctcccctc tgccctgtat ataatactaa | 2460 |
| agtgtctatt agttttcttt gtaaaggtca gagtcaaaat ttcaaaagtg atctgtcccc | 2520 |
| tctcccctca tggagaaaca tcctaagtgg gaagtgaagc cccttgtcct ctcccgcggg | 2580 |
| cctggacact tatggggaca gcataccttg gactgactac cagctaactc cagtctcctg | 2640 |
| acattaagac acacctctgg atccctggag gggctgaatg tagtgtgtca gagtaacatg | 2700 |
| ccagcttcct gtgggccagg agctcagccg tgcactccct aagaaacccc agggcaggga | 2760 |
| aactggctgt tgatagcag aagaaaaagt tgcagtctca gaaagccttc cattaaaaca | 2820 |
| atttattta tcactaaaaa aa | 2842 |

<210> SEQ ID NO 37
<211> LENGTH: 4707
<212> TYPE: DNA
<213> ORGANISM: Homo sapiens

<400> SEQUENCE: 37

| | |
|---|---|
| ggtttgaaag gaaggcagag agggcactgg gaggaggcag tgggagggcg gagggcgggg | 60 |
| gccttcgggg tgggcgccca gggtagggca ggtggccgcg gcgtggaggc agggagaatg | 120 |
| cgactctcca aaaccctcgt cgacatggac atggccgact acagtgctgc actggaccca | 180 |
| gcctacacca ccctggaatt tgagaatgtg caggtgttga cgatgggcaa tgacacgtcc | 240 |
| ccatcagaag gcaccaacct caacgcgccc aacagcctgg tgtcagcgc cctgtgtgcc | 300 |
| atctgcgggg accgggccac gggcaaacac tacggtgcct cgagctgtga cggctgcaag | 360 |
| ggcttcttcc ggaggagcgt gcggaagaac cacatgtact cctgcagatt tagccggcag | 420 |
| tgcgtggtgg acaaagacaa gaggaaccag tgccgctact gcaggctcaa gaaatgcttc | 480 |
| cgggctggca tgaagaagga agccgtccag aatgagcggg accggatcag cactcgaagg | 540 |
| tcaagctatg aggacagcag cctgccctcc atcaatgcgc tcctgcaggc ggaggtcctg | 600 |
| tcccgacaga tcacctcccc cgtctccggg atcaacggcg acattcgggc gaagaagatt | 660 |
| gccagcatcg cagatgtgtg tgagtccatg aaggagcagc tgctggttct cgttgagtgg | 720 |
| gccaagtaca tccagctttt ctgcgagctc cccctggacg accaggtggc cctgctcaga | 780 |
| gcccatgctg gcgagcacct gctgctcgga gccaccaaga gatccatggt gttcaaggac | 840 |
| gtgctgctcc taggcaatga ctacattgtc cctcggcact gcccggagct ggcggagatg | 900 |
| agccgggtgt ccatacgcat ccttgacgag ctggtgctgc ccttccagga gctgcagatc | 960 |
| gatgacaatg agtatgccta cctcaaagcc atcatcttct ttgacccaga tgccaagggg | 1020 |
| ctgagcgatc cagggaagat caagcggctg cgttcccagg tgcaggtgag cttggaggac | 1080 |
| tacatcaacg accgccagta tgactcgcgt ggccgctttg agagctgct gctgctgctg | 1140 |
| cccaccttgc agagcatcac ctggcagatg atcgagcaga tccagttcat caagctcttc | 1200 |

```
ggcatggcca agattgacaa cctgttgcag gagatgctgc tgggagggtc ccccagcgat   1260
gcaccccatg cccaccaccc cctgcaccct cacctgatgc aggaacatat gggaaccaac   1320
gtcatcgttg ccaacacaat gcccactcac ctcagcaacg acagatgtc caccectgag    1380 accccacagc cctcaccgcc aggtggctca gggtctgagc cctataagct cctgccggga   1440
gccgtcgcca caatcgtcaa gcccctctct gccatccccc agccgaccat caccaagcag   1500
gaagttatct agcaagccgc tggggcttgg gggctccact ggctccccc agccccctaa    1560 gagagcacct ggtgatcacg tggtcacggc aaaggaagac gtgatgccag gaccagtccc   1620
agagcaggaa tgggaaggat gaagggcccg agaacatggc ctaagggcca catcccactg   1680
ccacccttga cgccctgctc tggataacaa gactttgact tggggagacc tctactgcct   1740
tggacaactt ttctcatgtt gaagccactg ccttcacctt caccttcatc catgtccaac   1800
ccccgacttc atcccaaagg acagccgcct ggagatgact tgaggcctta cttaaaccca   1860
gctcccttct ccctagcct ggtgcttctc ctctcctagc ccctgtcatg gtgtccagac    1920
agagccctgt gaggctgggt ccaattgtgg cacttgggc accttgctcc tccttctgct    1980
gctgccccca cctctgctgc ctccctctgc tgtcaccttg ctcagccatc ccgtcttctc   2040
caacaccacc tctccagagg ccaaggaggc cttggaaacg attcccccag tcattctggg   2100
aacatgttgt aagcactgac tgggaccagg caccaggcag ggtctagaag ctgtggtga    2160 gggaagacgc ctttctcctc caacccaacc tcatcctcct tcttcaggga cttgggtggg   2220
tacttgggtg aggatccctg aaggccttca acccgagaaa acaaacccag gttggcgact   2280
gcaacaggaa cttggagtgg agaggaaaag catcagaaag aggcagacca tccaccaggc   2340
ctttgagaaa gggtagaatt ctggctggta gagcaggtga gatgggacat tccaaagaac   2400
agcctgagcc aaggcctagt ggtagtaaga atctagcaag aattgaggaa gaatggtgtg   2460
ggagagggat gatgaagaga gagagggcct gctggagagc atagggtctg gaacaccagg   2520
ctgaggtcct gatcagcttc aaggagtatg cagggagctg ggcttccaga aaatgaacac   2580
agcagttctg cagaggacgg gaggctgaa gctgggaggt caggtggggt ggatgatata    2640
atgcgggtga gagtaatgag gcttgggggct ggagaggaca agatgggtaa accctcacat  2700
cagagtgaca tccaggagga ataagctccc agggcctgtc tcaagctctt ccttactccc   2760
aggcactgtc ttaaggcatc tgacatgcat catctcattt aatcctccct tcctccctat   2820
taacctagag attgtttttg ttttttattc tcctcctccc tccccgccct cacccgcccc   2880
actccctcct aacctagaga ttgttacaga agctgaaatt gcgttctaag aggtgaagtg   2940
attttttttc tgaaactcac acaactagga agtggctgag tcaggacttg aacccaggtc   3000
tccctggatc agaacaggag ctcttaacta cagtggctga atagcttctc caaaggctcc   3060
ctgtgttctc accgtgatca agttgagggg cttccggctc ccttctacag cctcagaaac   3120
cagactcgtt cttctgggaa ccctgcccac tccaggacc aagattggcc tgaggctgca    3180
ctaaaattca cttagggtcg agcatcctgt ttgctgataa atattaagga gaattcatga   3240
ctcttgacag ctttttctctc ttcactcccc aagtcaaggg gaggggtggc aggggtctgt  3300
ttcctggaag tcaggctcat ctggcctgtt ggcatggggg tgggacagtg tgcacagtgt   3360
gggggcaggg gagggctaag caggcctggg tttgagggct gctccggaga ccgtcactcc   3420
aggtgcattc tggaagcatt agaccccagg atggagcgac cagcatgtca tccatgtgga   3480
atcttggtgg cttttgaggac attctggaaa atgccactga ccagtgtgaa caaaagggat   3540
```

-continued

| | |
|---|---|
| gtgttatggg gctggaggtg tgattaggta ggagggaaac tgttggaccg actcctgccc | 3600 |
| cctgctcaac actgacccct ctgagtggtt ggaggcagtg ccccagtgcc cagaaatccc | 3660 |
| accattagtg attgttttt atgagaaaga ggcgtggaga agtattgggg caatgtgtca | 3720 |
| gggaggaatc accacatccc tacggcagtc ccagccaagc ccccaatccc agcggagact | 3780 |
| gtgccctgct cagagctccc aagccttccc ccaccacctc actcaagtgc ccctgaaatc | 3840 |
| cctgccagac ggctcagcct ggtctgcggt aaggcaggga ggctggaacc atttctgggc | 3900 |
| attgtggtca ttcccactgt gttcctccac ctcctccctc cagcgttgct cagacctctg | 3960 |
| tcttgggaga aaggttgaga taagaatgtc ccatggagtg ccgtgggcaa cagtggccct | 4020 |
| tcatgggaac aatctgttgg agcagggggt cagttctctg ctgggaatct accccttcct | 4080 |
| ggaggagaaa cccattccac cttaataact ttattgtaat gtgagaaaca caaacaaag | 4140 |
| tttacttttt tgactctaag ctgacatgat attagaaaat ctctcgctct cttttttt | 4200 |
| ttttttttt tttttggcta cttgagttgt ggtcctaaaa cataaaatct gatggacaaa | 4260 |
| cagagggttg ctggggggac aagcgtgggc acaatttccc caccaagaca ccctgatctt | 4320 |
| caggcgggtc tcaggagctt ctaaaaatcc gcatggctct cctgagagtg gacagaggag | 4380 |
| aggagagggt cagaaatgaa cgctcttcta tttcttgtca ttaccaagcc aattacttt | 4440 |
| gccaaattt tctgtgatct gccctgatta agatgaattg tgaaatttac atcaagcaat | 4500 |
| tatcaaagcg ggctgggtcc catcagaacg acccacatct ttctgtgggt gtgaatgtca | 4560 |
| ttaggtcttg cgctgacccc tgagccccca tcactgccgc ctgatggggc aaagaaacaa | 4620 |
| aaaacatttc ttactcttct gtgttttaac aaaagtttat aaaacaaaat aaatggcgca | 4680 |
| tatgttttct aaaaaaaaaa aaaaaa | 4707 |

<210> SEQ ID NO 38
<211> LENGTH: 3583
<212> TYPE: DNA
<213> ORGANISM: Homo sapiens

<400> SEQUENCE: 38

| | |
|---|---|
| gcggccgccc tgcgcgcgaa gctcgtggcc cgagagggt gcggtcgggc cgacggaggc | 60 |
| ggggcccctgg ctgcctctct ccctgctcat aggctggccg ctcaggcctg gccggcctcg | 120 |
| gggcctcggg attcgcggcg cgctgccaa tcaggcgatc gggccccgcc ccccggagt | 180 |
| tgggtgaaat agaggcgggc gtcaagtgtc agtagtcgcg gggcaggtac gtgcgctcgc | 240 |
| ggttctctcg cggaggtcgg cggtggcggg agcgggctcc ggagagcctg agagcacggt | 300 |
| ggggcggggc gggagaaagt ggccgcccgg aggacgttgg cgtttacgtg tggaagagcg | 360 |
| gaagagtttt gcttttcgtg cgcgccttcg aaaactgcct gccgctgtct gaggagtcca | 420 |
| cccgaaacct cccctcctcc gccggcagcc ccgcgctgag ctcgccgacc caagccagcg | 480 |
| tgggcgaggt gggaagtgcg cccgacccgc gcctggagct gcgcccccga gtgcccatgg | 540 |
| ctacaagggt gctgagcatg agccgcccgcc tgggacccgt gccccagccg ccggcgccgc | 600 |
| aggacgagcc ggtgttcgcg cagctcaagc cggtgctggg cgccgcgaat ccggcccgcg | 660 |
| acgcggcgct cttccccggc gaggagctga agcacgcgca ccaccgcccg caggcgcagc | 720 |
| ccgcgcccgc gcaggccccg cagccggccc agccgcccgc caccggcccg cggctgcctc | 780 |
| cagaggacct ggtccagaca agatgtgaaa tggagaagta tctgacacct cagcttcctc | 840 |
| cagttcctat aattccagag cataaaaagt atagacgaga cagtgcctca gtcgtagacc | 900 |
| agttcttcac tgacactgaa gggttacctt acagtatcaa catgaacgtc ttcctccctg | 960 |

```
acatcactca cctgagaact ggcctctaca aatcccagag accgtgcgta acacacatca  1020
agacagaacc tgttgccatt ttcagccacc agagtgaaac gactgcccct cctccggccc  1080
cgacccaggc cctccctgag ttcaccagta tattcagctc acaccagacc gcagctccag  1140
aggtgaacaa tattttcatc aaacaagaac ttcctacacc agatcttcat ctttctgtcc  1200
ctacccagca gggccacctg taccagctac tgaatacacc ggatctagat atgcccagtt  1260
ctacaaatca gacagcagca atggacactc ttaatgtttc tatgtcagct gccatggcag  1320
gccttaacac acacacctct gctgttccgc agactgcagt gaaacaattc cagggcatgc  1380 cccttgcac atacacaatg ccaagtcagt ttcttccaca acaggccact tactttcccc  1440
cgtcaccacc aagctcagag cctggaagtc cagatagaca agcagagatg ctccagaatt  1500
taaccccacc tccatcctat gctgctacaa ttgcttctaa actggcaatt cacaatccaa  1560
atttacccac caccctgcca gttaactcac aaaacatcca acctgtcaga tacaatagaa  1620
ggagtaaccc cgatttggag aaacgacgca tccactactg cgattaccct ggttgcacaa  1680
aagtttatac caagtcttct catttaaaag ctcacctgag gactcacact ggtgaaaagc  1740
catacaagtg tacctgggaa ggctgcgact ggaggttcgc gcgatcggat gagctgaccc  1800
gccactaccg gaagcacaca ggcgccaagc ccttccagtg cggggtgtgc aaccgcagct  1860
tctcgcgctc tgaccacctg gccctgcata tgaagaggca ccagaactga gcactgcccg  1920
tgtgacccgt tccaggtccc ctgggctccc tcaaatgaca gacctaacta ttcctgtgta  1980
aaaacaacaa aaacaaacaa aagcaagaaa accacaacta aaactggaaa tgtatatttt  2040
gtatatttga gaaaacaggg aatacattgt attaatacca aagtgtttgg tcattttaag  2100
aatctggaat gcttgctgta atgtatatgg ctttactcaa gcagatctca tctcatgaca  2160
ggcagccacg tctcaacatg ggtaaggggt gggggtggag gggagtgtgt gcagcgtttt  2220
tacctaggca ccatcattta atgtgacagt gttcagtaaa caaatcagtt ggcaggcacc  2280
agaagaagaa tggattgtat gtcaagattt tacttggcat tgagtagttt ttttcaatag  2340
taggtaattc cttagagata cagtatacct ggcaattcac aaatagccat tgaacaaatg  2400
tgtgggtttt taaaaattat atacatatat gagttgccta tatttgctat tcaaaatttt  2460
gtaaatatgc aaatcagctt tataggttta ttacaagttt tttaggattc ttttggggaa  2520
gagtcataat tcttttgaaa ataaccatga atacacttac agttaggatt tgtggtaagg  2580
tacctctcaa cattaccaaa atcatttctt tagagggaag gaataatcat tcaaatgaac  2640
tttaaaaaag caaatttcat gcactgatta aaataggatt atttttaaata caaaggcat  2700 tttatatgaa ttataaactg aagagcttaa agatagttac aaaatacaaa agttcaacct  2760
cttacaataa gctaaacgca atgtcatttt taaaagaag gacttagggt gtcgttttca  2820
catatgacaa tgttgcattt atgatgcagt ttcaagtacc aaaacgttga attgatgatg  2880
cagttttcat atatcgagat gttcgctcgt gcagtactgt tggttaaatg acaatttatg  2940
tggattttgc atgtaataca cagtgagaca cagtaatttt atctaaatta cagtgcagtt  3000
tagttaatct attaatactg actcagtgtc tgcctttaaa tataaatgat atgttgaaaa  3060
cttaaggaag caaatgctac atatatgcaa tataaaatag taatgtgatg ctgatgctgt  3120
taaccaaagg gcagaataaa taagcaaaat gccaaagggg tcttaattg aaatgaaaat  3180 ttaattttgt ttttaaaata ttgtttatct ttatttattt tgtggtaata tagtaagttt  3240
ttttagaaga caatttttcat aacttgataa attatagttt tgtttgttag aaaagttgct  3300
```

```
cttaaaagat gtaaatagat gacaaacgat gtaaataatt ttgtaagagg cttcaaaatg   3360
tttatacgtg gaaacacacc tacatgaaaa gcagaaatcg gttgctgttt tgcttctttt   3420
tccctcttat ttttgtattg tggtcatttc ctatgcaaat aatggagcaa acagctgtat   3480
agttgtagaa ttttttgaga gaatgagatg tttatatatt aacgacaatt ttttttttgg   3540
aaaataaaaa gtgcctaaaa gatgtaaaaa aaaaaaaaaa aaa                     3583
```

<210> SEQ ID NO 39
<211> LENGTH: 2187
<212> TYPE: DNA
<213> ORGANISM: Homo sapiens

<400> SEQUENCE: 39

```
gtcctttcta gacagccccc tcctccaggc tcagggacct gtctggctgt gagctcccag     60
gaggtcccag gggtgtgacc tccctccctc cctccctccc tcttcccttc accccaggcc    120
agcccagggc cagctataaa gctggcccag cctggctctc agcacaccca gctgcctgag    180
accctccttc aacctcccta gaggacagcc ccactctgcc tcctgctccc cagggcagc    240 accatgtggc cctgtggct ctgctgggca ctctgggtgc tgccctggc tggccccggg     300 gcggccctga ccgaggagca gctcctgggc agcctgctgc ggcagctgca gctcagcgag    360
gtgcccgtac tggacagggc cgacatggag aagctggtca tccccgccca cgtgagggcc    420
cagtatgtag tcctgctgcg gcgcagccac ggggaccgct cccgcggaaa gaggttcagc    480
cagagcttcc gagaggtggc cggcaggttc ctggcgtcgg aggccagcac acacctgctg    540
gtgttcggca tggagcagcg gctgccgccc aacagcgagc tggtgcaggc cgtgctgcgg    600
ctcttccagg agccggtccc caaggccgcg ctgcacaggc acgggcggct gtccccgcgc    660
agcgcccagg cccgggtgac cgtcgagtgg ctgcgcgtcc gcgacgacgg ctccaaccgc    720
acctccctca tcgactccag gctggtgtcc gtccacgaga gcggctggaa ggccttcgac    780
gtgaccgagg ccgtgaactt ctggcagcag ctgagccggc cccggcagcc gctgctgcta    840
caggtgtcgg tgcagaggga gcatctgggc ccgctggcgt ccggcgccca aagctggtc    900 cgctttgcct cgcaggggc gccagccggg cttggggagc cccagctgga gctgcacacc    960
ctggacctca gggactatgg agctcagggc gactgtgacc ctgaagcacc aatgaccgag   1020
ggcacccgct gctgccgcca ggagatgtac attgacctgc aggggatgaa gtgggccaag   1080
aactgggtgc tggagccccc gggcttcctg gcttacagt gtgtgggcac ctgccagcag   1140
cccccggagg ccctggcctt caattggcca tttctgggc cgcgacagtg tatcgcctcg   1200
gagactgcct cgctgcccat gatcgtcagc atcaaggagg aggcaggac caggcccag   1260 gtggtcagcc tgcccaacat gagggtgcag aagtgcagct gtgcctcgga tgggcgctc   1320 gtgccaagga ggctccagcc ataggcgcct ggtgtatcca ttgagccctc taactgaacg   1380
tgtgcataga ggtggtctta atgtaggtct taactttata cttagcaagt tactccatcc   1440
caatttagtg ctcctgtgtg accttcgccc tgtgtccttc catttcctgt ctttcccgtc   1500
catcacccat cctaagcact tacgtgagta aataatgcag ctcagatgct gagctctagt   1560
aggaaatgct ggcatgctga ttacaagata cagctgagca atgcacacat tttcagctgg   1620
gagtttctgt tctctggcaa attcttcact gagtctggaa caataatacc ctatgattag   1680
aactggggaa acagaactga attgctgtgt tatatgagga attaaaacct tcaaatctct   1740
atttccccca aatactgacc cattctggac ttttgtaaac ataccttaggc ccctgttccc   1800 ctgagagggt gctaagagga aggatgaagg gcttcaggct gggggcagtg gacagggaat   1860
```

| | |
|---|---|
| tgggatacct ggattctggt tctgacaggg ccacaagcta ggatctctaa caaacgcaga | 1920 |
| aggctttggc tcgtcatttc ctcttaaaaa ggaggagctg ggcttcagct ctaagaactt | 1980 |
| cattgccctg gggatcagac agcccctacc taccoctgcc cactcctctg gagactgagc | 2040 |
| cttgcccgtg catatttagg tcatttccca cactgtctta gagaacttgt caccagaaac | 2100 |
| cacatgtatt tgcatgtttt ttgttaattt agctaaagca attgaatgta gatactcaga | 2160 |
| agaaataaaa aatgatgttt cactctg | 2187 |

<210> SEQ ID NO 40
<211> LENGTH: 3033
<212> TYPE: DNA
<213> ORGANISM: Homo sapiens

<400> SEQUENCE: 40

| | |
|---|---|
| ttaaattcta attagagatg caggaatcaa tgatagggag gttggacagc tcagttcccc | 60 |
| agtgccagcc caatagacgg atgagttatt gtcatgtaaa aagcgccagc aataagacca | 120 |
| accgctttgc tattgtccaa gtggaaagag ccaagtttat tatgaggact atatgctcta | 180 |
| gagacctcag acaaggcatc tcataggagg cttttttcata aaactaggct ctgctggtag | 240 |
| taaggaggcc agtttggagg caggcgttga gctgtgcaca tctccccact ccagccacct | 300 |
| tctccatatc catctttttat ttcattttc cacttggctg agccatccag aaccttttca | 360 |
| atgtataaaa tggaatattc ttacctcaat tcctctgcct acgagtcctg tatggctggg | 420 |
| atggacacct cgagcctggc ttcagcctat gctgacttca gttcctgcag ccaggccagt | 480 |
| ggcttccagt ataaccgat aaggaccact tttggggcca cgtccggctg cccttccctc | 540 |
| acgccgggat cctgcagcct gggcaccctc agggaccacc agagcagtcc gtacgccgca | 600 |
| gttccttaca aactcttcac ggaccacggc ggcctcaacg agaagcgcaa gcagcggcgc | 660 |
| atccgcacca ctttcaccag tgcccagctc aaagagctgg aaagggtctt cgcggagact | 720 |
| cactaccccg acatctacac tcgggaggag ctggccctga agatcgacct cacagaggcg | 780 |
| cgagtccagg tgtggttcca gaaccgccgc gccaagtttc gcaagcagga gcgcgcagcg | 840 |
| gcagccgcag cggccgcggc caagaacggc tcctcgggca aaaagtctga ctcttccagg | 900 |
| gacgacgaga gcaaagaggc caagagcact gaccggga gcactggggg cccaggtccc | 960 |
| aatcccaacc ccaccccag ctgcggggcg aatggaggcg gcggcggcgg gcccagcccg | 1020 |
| gctggagctc cggggggcggc ggggcccggg ggcccgggag gcgaacccgg caagggcggc | 1080 |
| gcagcagcag cggcggcggc cgcggcagcg gcggcggcgg cagcggcagc ggcggcagct | 1140 |
| ggaggcctgg ctgcggctgg gggccctgga caaggctggg ctcccggcc cggccccatc | 1200 |
| acctccatcc cggattcgct tgggggtccc ttcgccagcg tcctatcttc gctccaaaga | 1260 |
| cccaacggtg ccaaagccgc cttagtgaag agcagtatgt tctgatctgg aatcctgcgg | 1320 |
| cggcggcggc ggcggcgaca gcgggcgagc cagggcccgg gcgggcgagt gggcgagcgg | 1380 |
| gtaggcccaa ggctattgtc gtcgctgctg ccatggcttt tcattgagg gcctaaagta | 1440 |
| atcgcgctaa gaataaaggg aaaacggcgt cgccctcatt tcaacccac tcctaccccc | 1500 |
| ttcctcaacc cccaaacaaa acaaacaaac ttccctggct tcgcacctgc ctggggcctc | 1560 |
| gcagcgggc cagggctccg cctgctgatc ggggggttgtg agcagcgcgg cctggacgcg | 1620 |
| gggcactctc agggggctgt gtctgcgtgt cagtttgtgt ctgtctcggg gaatgtgtgt | 1680 |
| ctgtggccca agcaggtgac aggaagagat gggggggcctc aaccaactta gtgacttgtt | 1740 |

-continued

| | | | | |
|---|---|---|---|---|
| tagaaaaaaa | agacaaaaaa | gtaaaaataa | aaacaaaaaa | gttggaaggc agaaaccatt | 1800 |
| aaaaaacaaa | aagccaacaa | cccagaaagg | tttaaaaaac | ataaggaaaa aaaagacaaa | 1860 |
| ttaaaggagg | ggctagggga | gaagctgcag | ctggagctga | aggctcgatc ttgtgaaccc | 1920 |
| ctaaatccgc | tccctcctaa | cagcacggat | tctcttgggg | ctcttcttca gggaagagta | 1980 |
| gggacgccgt | tccagccccc | cttcctatcg | tgtccttggg | ttcgggtcac tgcggcgacg | 2040 |
| acttgctcag | actgtcccgg | cggccggagt | gactttctcg | cacccccttg cctgtcccac | 2100 |
| ctcgctgaac | accatcccgc | cattagcgca | tcggaacccc | acacagttgc aactcccaac | 2160 |
| cccgaatctt | tgcagccgtt | cggccctgaa | agatgccta  | tccatgagat gccttttcat | 2220 |
| ctgcaaactc | tgcaaaatgt | gtctcatgtt | tcgcaactct | ttttttcccc ctcgctcccg | 2280 |
| cctaccccgt | cggcattttc | ttcttccacc | agctttact  | gaactttttg gcactgcttt | 2340 |
| ggattggggt | caattgcagt | ccacgtaact | ggctgcagag | aaatctaccg agcaaggaaa | 2400 |
| aggcacacac | acacgtttgc | aggggtgtct | cggtttgcat | ttctgttgga atgatccgaa | 2460 |
| ctggactcac | atcctgtatg | gtggatggac | tgtatattga | gggttccatt cttcgcgcag | 2520 |
| tttagacatc | tctgtttga  | ttctttgttg | ttgtttttat | tttaaaaggc acaaactcta | 2580 |
| gatattagtt | gaatgttgag | gctttaactt | tttcggtgtc | tttctacaac tgtgttctgt | 2640 |
| gactcaattg | tatcgtgtta | atatcagtgc | agactgtctc | ctctacgtga ccgtataatg | 2700 |
| tttttctctt | cttgtagtct | ctatggcgtg | tctttatggt | gtaataaggt tctcacgggt | 2760 |
| tcaatctttt | gtgtttagag | aggccacggt | tcagacaatg | gtatatattt ttgttatcag | 2820 |
| gtgcatgtct | gtctgatttc | ttttttttc  | ctgttggact | atgtttgtga acataattgt | 2880 |
| cataagttat | gtttcagatt | tttgaattta | tttatatgtg | ttataatgaa tgcttctatt | 2940 |
| taaaagggaa | atatttctac | atgtgcatat | agttttccaa | gagtgtacca ttaacttgat | 3000 |
| tgttgataat | aaaaacaaaa | agcaagtcta | aaa | | 3033 |

<210> SEQ ID NO 41
<211> LENGTH: 1503
<212> TYPE: DNA
<213> ORGANISM: Homo sapiens

<400> SEQUENCE: 41

| | | | | |
|---|---|---|---|---|
| atggccacgg | cggcttctaa | ccctacctg  | ccggggaaca | gcctgctcgc ggccggctct | 60 |
| attgtgcact | cggacgcggc | aggggctggc | ggcggcgggg | gtggcggcgg cggcggcggc | 120 |
| ggggcggcg  | caggggcgg  | gggcggcggc | atgcagccgg | gcagcgccgc cgtgacctcg | 180 |
| ggcgcctacc | gggggaccc  | gtcctctgtc | aagatggtcc | agagcgactt catgcagggg | 240 |
| gccatggccg | ccagcaacgg | cggccatatg | ctgagccacg | cgcaccagtg ggtcacagcc | 300 |
| ctgccccacg | ccgccgccgc | cgccgccgct | gccgccgccg | ccgccgtgga ggcgagctcg | 360 |
| ccgtggtcgg | gcagcgccgt | gggcatggct | ggcagccccc | agcagccacc gcagccgccg | 420 |
| ccgccaccgc | cgcagggccc | cgacgtgaag | ggcggcgccg | ggcgcgacga cctgcacgcg | 480 |
| ggcacagcgc | tgcaccaccg | cgggccgccg | cacctcggac | cccgccgcc  gccccacac  | 540 |
| cagggccacc | ctggggctg  | ggggcggcc  | ccgctgccg  | cagccgcagc cgccgccgcc | 600 |
| gccgccgccg | cgcacctccc | gtccatggcc | ggggccagc  | agccgccgcc gcagagtctg | 660 |
| ctctactcgc | agcccggagg | cttcacggtg | aacggcatgc | tgagcgcgcc accggggccc | 720 |
| ggcggcggcg | gcggcggcgc | gggcggtgga | gcccagagct | ggtgcaccc  ggggctggtg | 780 |
| cgcggggaca | cgccagagct | ggccgagcac | caccaccacc | accaccacca cgcgcatcct | 840 |

```
cacccgccgc acccgcacca cgcgcaggga ccccgcacc acggcggcgg cggcggcggc    900
gcggggcctg gactcaacag ccacgacccg cactcggacg aggacacgcc gacgtcggac    960
gacctggagc agttcgccaa gcagttcaag cagcggcgca tcaagctggg cttcacgcag   1020
gccgacgtgg ggttggcgct gggcacactc tacggcaact gttctcgca gaccaccatc    1080 tgccgcttcg aggccctgca gctgagcttc aagaacatgt gcaagctcaa gccgctgctg    1140
aacaagtggc tggaggaggc ggactcaagc ccggcagcc cacaagcat cgacaagatc     1200 gcggcgcagg gccgcaagcg caagaagcgg acctctatcg aggtgagcgt caagggcgcg    1260
ctggagagcc acttcctcaa gtgccccaag ccctccgcgc aggagatcac caacctggcc    1320
gacagcctgc agctcgagaa ggaggtggtg cgggtctggt tctgcaatcg gcgccaaaag    1380
gagaagcgca tgacgccgcc cgggatccaa cagcagacgc ccgacgacgt ctactcgcag    1440
gtgggcaccg tgagcgccga cacgccgccg cctcaccacg ggctgcagac gagcgttcag    1500
tga                                                                  1503

<210> SEQ ID NO 42
<211> LENGTH: 4753
<212> TYPE: DNA
<213> ORGANISM: Homo sapiens

<400> SEQUENCE: 42
agtttgacgt cgtcagccgg cttggtcttc tacccagtga ctcaaagcac taaaagtcag     60
cataatcgga actgaagtca gtagcatcgc ccatttgcca ttcactgcag tagcaaaagt    120
agtactctgt ggtgggttaa tcggtttgag gcagctcctt aaatgaacat tgtgtttca    180 tttttctgtt attttcccga acatgaaaag acgataaaac tgaaatggaa aagatctatt    240
ccagagggga gcttcaccac ttcattgacg gctttaatga agagaaaagc aactggatgc    300
gctatgtgaa tccagcacac tctcccccggg agcaaaacct ggctgcgtgt cagaacggga    360
tgaacatcta cttctacacc attaagccca tccctgccaa ccaggaactt cttgtgtggt    420
attgtcggga ctttgcagaa aggcttcact acccttatcc cggagagctg acaatgatga    480
atctcacaca aacacagagc agtctaaagc aaccgagcac tgagaaaaat gaactctgcc    540
caaagaatgt cccaaagaga gagtacagcg tgaaagaaat cctaaaattg gactccaacc    600
cctccaaagg aaaggacctc taccgttcta acatttcacc cctcacatca gaaaggacc    660 tcgatgactt tagaagacgt gggagccccg aaatgcctt ctaccctcgg gtcgtttacc     720
ccatccgggc ccctctgcca gaagactttt tgaaagcttc cctggcctac gggatcgaga    780
gacccacgta catcactcgc tcccccattc catcctccac cactccaagc cctctgcaa    840 gaagcagccc cgaccaaagc ctcaagagct ccagccctca cagcagccct gggaatacgg    900
tgtcccctgt gggccccggc tctcaagagc accgggactc ctacgcttac ttgaacgcgt    960 cctacgcac ggaaggtttg gctcctacc ctggctacgc accctgccc cacctccgc        1020 cagctttcat ccctcgtac aacgctcact acccaagtt cctcttgccc cctacggca      1080 tgaattgtaa tggcctgagc gctgtgagca gcatgaatgg catcaacaac tttggcctct    1140
tcccgaggct gtgccctgtc tacagcaatc tcctcggtgg gggcagcctg ccccacccca    1200
tgctcaaccc cacttctctc ccgagctcgc tgccctcaga tggagccgg aggttgctcc     1260 agccggagca tccagggag gtgcttgtcc cggcgcccca cagtgccttc tccttttaccg    1320 gggccgccgc cagcatgaag gacaaggcct gtagccccac aagcgggtct cccacggcgg    1380
```

```
gaacagccgc cacggcagaa catgtggtgc agcccaaagc tacctcagca gcgatggcag    1440 ccccagcag cgacgaagcc atgaatctca ttaaaaacaa agaaacatg accggctaca      1500 agacccttcc ctaccgctg aagaagcaga acggcaagat caagtacgaa tgcaacgttt     1560
gcgccaagac tttcggccag ctctccaatc tgaaggtcca cctgagagtg cacagtggag    1620
aacggccttt caaatgtcag acttgcaaca agggctttac tcagctcgcc cacctgcaga   1680
aacactacct ggtacacacg ggagaaaagc cacatgaatg ccaggtctgc acaagagat    1740 ttagcagcac cagcaatctc aagacccacc tgcgactcca ttctggagag aaaccatacc   1800
aatgcaaggt gtgccctgcc aagttcaccc agtttgtgca cctgaaactg cacaagcgtc   1860
tgcacacccg ggagcggccc cacaagtgct cccagtgcca caagaactac atccatctct   1920
gtagcctcaa ggttcacctg aagggaact gcgctgcggc cccggcgcct gggctgccct    1980
tggaagatct gacccgaatc aatgaagaaa tcgagaagtt tgacatcagt gacaatgctg   2040
accggctcga ggacgtggag gatgacatca gtgtgatctc tgtagtggag aaggaaattc   2100
tggccgtggt cagaaaagag aaagaagaaa ctggcctgaa agtgtctttg caaagaaaca   2160
tggggaatgg actcctctcc tcagggtgca gcctttatga gtcatcagat ctaccctca    2220 tgaagttgcc tcccagcaac ccactacctc tggtacctgt aaaggtcaaa caagaaacag   2280
ttgaaccaat ggatccttaa gattttcaga aaacacttat tttgtttctt aagttatgac   2340
ttggtgagtc agggtgcctg taggaagtgg cttgtacata atcccagctc tgcaaagctc   2400
tctcgacagc aaatggttc ccctcacctc tggaattaaa aaggaactc caaagttact    2460 gaaatctcag ggcatgaaca aggcaaaggc catatatata tatatatata tatctgtata   2520
catattatat atacttattt acacctgtgt ctatatattt gccctgtgt attttgaata    2580 tttgtgtgga catgtttgca tagccttccc attactaaga ctattaccta gtcataatta   2640
ttttttcaat gataatcctt cataatttat tatacaattt atcattcaga aagcaataat   2700
taaaaaagtt tacaatgact ggaaagattc cttgtaattt gagtataaat gtattttgt    2760 cttgtggcca ttctttgtag ataatttctg cacatctgta taagtaccta agatttagtt   2820
aaacaaatat atgacttcag tcaacctctc tctctaataa tggtttgaaa atgaggtttg   2880
ggtaattgcc aatgttggac agttgatgtg ttcattcctg ggatcctatc atttgaacag   2940
cattgtacat aacttggggg tatgtgtgca ggattaccca agaataactt aagtagaaga   3000
aacaagaaag ggaatcttgt atattttgt tgatagttca tgttttccc ccagccacaa    3060 ttttaccgga agggtgacag gaaggcttta ccaacctgtc tctccctcca aaagagcaga   3120
atcctcccac cgccctgccc tccccaccga gtcctgtggc cattcagagc ggccacatga   3180
cttttgcatc cattgtatta tcagaaaatg tgaagaagaa aaaatgcca tgttttaaaa    3240 ccactgcgaa aatttcccca agcataggt ggctttgtgt gtgtgcgatt tggggcttg     3300 agtctgggtg gtgtttttgtt gttggttttt gttgctttt tttttttttt tttttttaatg 3360 tcaaaattgc acaaacatgg tgctctacca ggaaggattc gaggtagata ggctcaggcc   3420
acactttaaa aacaaacaca caaacaacaa aaaacgggta ttctagtcat cttggggtaa   3480
aagcgggtaa tgaacattcc tatccccaac acatcaattg tatttttct gtaaaactca   3540 gattttcctc agtatttgtg ttttacatt ttatggttaa tttaatggaa gatgaaaggg   3600
cattgcaaag ttgttcaaca acagttacct cattgagtgt gtccagtagt gcaggaaatg   3660
atgtcttatc taatgatttg cttctctaga ggagaaaccg agtaaatgtg ctccagcaag   3720
atagactttg tgttattcta tcttttattc tgctaagccc aaagattaca tgttggtgtt   3780
```

| | | | | |
|---|---|---|---|---|
| caaagtgtag | caaaaaatga | tgtatattta | taaatctatt | tataccacta tatcatatgt | 3840 |
| atatatattt | ataaccactt | aaattgtgag | ccaagccatg | taaaagatct acttttttcta | 3900 |
| agggcaaaaa | aaaaaaaaaa | aaaaaagaa | cactcctttc | tgagactttg cttaatactt | 3960 |
| ggtgacctca | caatcacgtc | ggtatgattg | ggcacccttg | cctactgtaa gagaccctaa | 4020 |
| aaccttggtg | cagtggtggg | gaccacaaaa | caaccaggga | ggaagagata catcattttt | 4080 |
| tagtattaag | gaccatctaa | gacagctcta | tttttttttt | gccactttat gattatgtgg | 4140 |
| tcacacccaa | gtcacagaaa | taaaaaactg | actttaccgc | tgcaattttt ctgttttcct | 4200 |
| ccttactaaa | tactgataca | ttactccaat | ctattttata | attatatttg acattttgtt | 4260 |
| cacatcaact | aatgttcacc | tgtagaagag | aacaaatttc | gaataatcca gggaaaccca | 4320 |
| agagccttac | tggtcttctg | taacttccaa | gactgacagc | ttttttatgta tcagtgtttg | 4380 |
| ataaacacag | tccttaactg | aaggtaaacc | aaagcatcac | gttgacatta gaccaaatac | 4440 |
| ttttgattcc | caactactcg | tttgttcttt | ttctccttttt | gtgctttccc atagtgagaa | 4500 |
| tttttataaa | gacttcttgc | ttctctcacc | atccatcctt | ctcttttctg cctcttacat | 4560 |
| gtgaatgttg | agcccacaat | caacagtggt | tttattttttt | cctctactca aagttaaaac | 4620 |
| tgaccaaagt | tactggcttt | ttactttgct | agaacaacaa | actatcttat gtttacatac | 4680 |
| tggtttacaa | tgttatttat | gtgcaaattg | tcaaaatgta | aattaaatat aaatgttcat | 4740 |
| gctttaccaa | aat | | | | 4753 |

<210> SEQ ID NO 43
<211> LENGTH: 2205
<212> TYPE: DNA
<213> ORGANISM: Homo sapiens

<400> SEQUENCE: 43

| | | | | |
|---|---|---|---|---|
| acctacaccg | ggcggtcata | catcgattgg | cttcctagat | aatagatcgt gccacccggt | 60 |
| agggacctct | ggggacgcgc | cgggagctgg | aagagtcgca | cgcagcagcc caaccctgag | 120 |
| ttaatcaaac | tagcaacagg | atctcaagca | gcagcgacgg | cggtggcaag agtagcggtg | 180 |
| acggcggcgg | cggcggcggc | ggcagcatta | tgcgtgatta | ctgacaggca ccagctgctg | 240 |
| ccgccacagc | cgtctcaaac | gcactatgtg | gactctccga | tctagaggca gattcctgac | 300 |
| taatcccaga | gggctggccc | agcctgtgct | ccccgggctg | ctaggaagcg atgaccactc | 360 |
| ttgttagccc | aagttgaaga | aagccggggct | gtgcctggga | gccgagagag gcggtaatat | 420 |
| ttagaagctg | cacaggagag | gaacatgaac | tgacgagtaa | acatgtatgg aaattattct | 480 |
| cacttcatga | agtttcccgc | aggctatgga | ggctcccctg | gccacactgg ctctacatcc | 540 |
| atgagcccat | cagcagcctt | gtccacaggg | aagccaatgg | acagccaccc cagctacaca | 600 |
| gatacccccag | tgagtgcccc | acggactctg | agtgcagtgg | ggacccccct caatgccctg | 660 |
| ggctctccat | atcgagtcat | cacctctgcc | atgggcccac | cctcaggagc acttgcagcg | 720 |
| cctccaggaa | tcaacttggt | tgccccaccc | agctctcagc | taaatgtggt caacagtgtc | 780 |
| agcagttcag | aggacatcaa | gcccttacca | gggcttcccg | ggattggaaa catgaactac | 840 |
| ccatccacca | gccccggatc | tctggttaaa | cacatctgtg | ccatctgtgg agacagatcc | 900 |
| tcaggaaagc | actacggggt | atacagttgt | gaaggctgca | aagggttctt caagaggacg | 960 |
| ataaggaagg | acctcatcta | cacgtgtcgg | gataataaag | actgcctcat tgacaagcgt | 1020 |
| cagcgcaacc | gctgccagta | ctgtcgctat | cagaagtgcc | ttgtcatggg catgaagagg | 1080 |

| | |
|---|---|
| gaagctgtgc aagaagaaag acagaggagc cgagagcgag ctgagagtga ggcagaatgt | 1140 |
| gctaccagtg gtcatgaaga catgcctgtg gagaggattc tagaagctga acttgctgtt | 1200 |
| gaaccaaaga cagaatccta tggtgacatg aatatggaga actcgacaaa tgaccctgtt | 1260 |
| accaacatat gtcatgctgc tgacaagcag cttttcaccc tcgttgaatg ggccaagcgt | 1320 |
| attccccact tctctgacct caccttggag gaccaggtca ttttgcttcg ggcagggtgg | 1380 |
| aatgaattgc tgattgcctc tttctcccac cgctcagttt ccgtgcagga tggcatcctt | 1440 |
| ctggccacgg gtttacatgt ccaccggagc agtgcccaca gtgctggggt cggctccatc | 1500 |
| tttgacagag tcctaactga gctggttttcc aaaatgaaag acatgcagat ggacaagtcg | 1560 |
| gaactgggat gcctgcgagc cattgtactc tttaacccag atgccaaggg cctgtccaac | 1620 |
| ccctctgagg tggagactct gcgagagaag gtttatgcca cccttgaggc ctacaccaag | 1680 |
| cagaagtatc cggaacagcc aggcaggttt gccaagctgc tgctgcgcct cccagctctg | 1740 |
| cgttccattg gcttgaaatg cctggagcac ctcttcttct tcaagctcat cggggacacc | 1800 |
| cccattgaca ccttcctcat ggagatgttg agacccccgc tgcagatcac ctgagcccca | 1860 |
| ccagccacag cctcccccacc caggatgacc cctgggcagg tgtgtgtgga cccccaccct | 1920 |
| gcactttcct ccacctccca ccctgacccc cttcctgtcc ccaaaatgtg atgcttataa | 1980 |
| taaagaaaac cttctacac atgagacttt tataggtgga cttttgtata gatgttaaag | 2040 |
| gtaatacgct ttgctgtcta cagggctggg agactttctg gaagttcttg ggaaaactaa | 2100 |
| tcaagcctct gtacatacaa ttggtttaaa ttatttttc acttgccctg gaaagcaaac | 2160 |
| aaatgagtaa taaaataata tgtgtgaaat tggcaaaaaa aaaaa | 2205 |

<210> SEQ ID NO 44
<211> LENGTH: 2350
<212> TYPE: DNA
<213> ORGANISM: Homo sapiens

<400> SEQUENCE: 44

| | |
|---|---|
| gcagtgtcac taggccggct gggggccctg ggtacgctgt agaccagacc gcgacaggcc | 60 |
| agaacacggg cggcggcttc gggccgggag acccgcgcag ccctcggggc atctcagtgc | 120 |
| ctcactcccc acccctccc ccgggtcggg ggaggcggcg cgtccggcgg agggttgagg | 180 |
| ggagcggggc aggcctggag cgccatgagc agcccggatg cgggatacgc cagtgacgac | 240 |
| cagagccaga cccagagcgc gctgccgcg gtgatggccg ggctgggccc ctgcccctgg | 300 |
| gccgagtcgc tgagcccat cggggacatg aaggtgaagg gcgaggcgcc ggcgaacagc | 360 |
| ggagcaccgg ccggggccgc gggccgagcc aagggcgagt cccgtatccg gcggccgatg | 420 |
| aacgctttca tggtgtgggc taaggacgag cgcaagcggc tggcgcagca gaatccagac | 480 |
| ctgcacaacg ccgagttgag caagatgctg ggcaagtcgt ggaaggcgct gacgctggcg | 540 |
| gagaagcggc ccttcgtgga ggaggcagag cggctgcgcg tgcagcacat gcaggaccac | 600 |
| cccaactaca agtaccggcc gcggcggcgc aagcaggtga agcggctgaa gcgggtggag | 660 |
| ggcggcttcc tgcacggcct ggctgagccg caggcggccg cgctgggccc cgagggcggc | 720 |
| cgcgtggcca tggacggcct gggctccag ttccccgagc agggcttccc cgccggcccg | 780 |
| ccgctgctgc ctccgcacat gggcggccac taccgcgact gccagagtct gggcgcgcct | 840 |
| ccgctcgacg gctaccgtt gcccacgcc gacgtcccc gctggacgg cgtggacccc | 900 |
| gaccggctt tcttcgccgc ccgatgccc ggggactgcc cggcggccgg cacctacagc | 960 |
| tacgcgcagg tctcggacta cgctggcccc ccggagcctc ccgccggtcc catgcacccc | 1020 |

```
cgactcggcc cagagcccgc gggtccctcg attccgggcc tcctggcgcc acccagcgcc    1080
cttcacgtgt actacggcgc gatgggctcg cccggggcgg gcggcgggcg cggcttccag    1140
atgcagccgc aacaccagca ccagcaccag caccagcacc acccccgggg ccccggacag    1200
ccgtcgcccc ctccggaggc actgcccgc cgggacggca cggaccccag tcagcccgcc    1260
gagctcctcg gggaggtgga ccgcacggaa tttgaacagt atctgcactt cgtgtgcaag    1320
cctgagatgg gcctccccta ccaggggcat gactccggtg tgaatctccc cgacagccac    1380
ggggccattt cctcggtggt gtccgacgcc agctccgcgg tatattactg caactatcct    1440
gacgtgtgac aggtccctga tccgccccag cctgcaggcc agaagcagtg ttacacactt    1500
cctggaggag ctaaggaaat cctcagactc ctgggttttt gttgttgctg ttgttgtttt    1560
ttaaaaggtg tgttggcata taatttatgg taatttattt tgtctgccac ttgaacagtt    1620 tggggggtg aggtttcatt taaaatttgt tcagagattt gtttcccata gttggattgt    1680
caaaacccta tttccaagtt caagttaact agctttgaat gtgtcccaaa acagcttcct    1740
ccatttcctg aaagtttatt gatcaaagaa atgttgtcct gggtgtgttt tttcaatctt    1800
ctaaaaaata aaatctggaa tcctgctttt ttgctctact agtacctctg tcacactagt    1860
cttatcaaaa accagttctt aagatcaatg ttaagtttat tagttaatgt aaatttctca    1920
tcctcgaaaa gggtgaacat aaatgccttt aaggagtata tctaaaaata aacattagga    1980
tatctaagtt tgatgtaatt gtttcaggaa ggaaaaaga aaagcattct ggaatgagcc    2040
tacttcaagt aatcttagtt tctaaaacta acagttaata ttttcaattc cagtatatca    2100
ctttaagtag aaggggatgt ccaagtaatt ttggttttct aactgttgaa tcataagctt    2160
gacctgcccc cagaggcttt ttggatgttt ttatctgtgt tttgccatct ctttacactc    2220
ctcgacattc agtttacctt aatcttcaca tttttacacc ttgggaagtg gcaagcatcg    2280
ctgggtttaa gataaaggag tcacaaaaac taatcaaaat aaaatttgca ttatgacaac    2340
ttttaataca                                                          2350

<210> SEQ ID NO 45
<211> LENGTH: 3617
<212> TYPE: DNA
<213> ORGANISM: Homo sapiens

<400> SEQUENCE: 45
aagtttccaa gtggtcaact tgaccgatgc tttggcaatt gaaaagggc agaaaggcgc      60 gggctagtgg gtggatgggg acaaagatct aagtcacctt cttccagcgt gtgagcctgg    120
gaggagggtg gggtcctga ggagcaagag gtacgaggaa ggaaaaggag agggcttctg     180
ggttagtttc cacctcctgc tttcaactc acggcgcttt ccttccggaa aggacgctgg    240
attcagggcg cgccagtacg cgcagtagcg gcccgcgagt cggcaggtgg gtagccccgg   300
cgcgggagga aggggaagtt accttcccct cggaagaggg cgctggctcc cccatcctgc    360
ctttataata aggccaccgg aggagaggaa gcagccagct gccgtctgcg ctttgcaaag    420
catgcagtta ggggagcagc tcttggtgag ctcagtgaac ctgcctggcg cgcacttcta    480
cccgctggag agtgcgcgag gcggcagcgg cgggagcgct ggccacctcc ccagcgcggc   540 ccctctcct cagaagttgg acttagacaa agcgtccaag aagttttccg gcagtctctc     600
ctgcgaggcg gtgagcgggg agcccgcagc cgccagcgca ggggccccg cggccatgct     660 tagtgacacc gacgccgggg acgcatttgc cagcgctgcg gcagtggcca agccggggcc    720
```

```
cccggacggc cgcaagggct cccctgcgg ggaggaggag ctgccctccg ccgctgcagc      780
cgccgccgcc gccgccgccg cggctgcggc cactgcgcgc tactccatgg acagcctgag      840
ctccgagcgg tactacctcc agtccccgg tcctcagggg tcggagctgg ctgcgccctg      900
ctcactcttc ccgtaccagg cggcggctgg ggcgccccac ggacctgtgt acccggctcc      960
taacggggcg cgctacccct acggctccat gctgccccc ggcggcttcc ccgcggctgt     1020
gtgcccaccc gggagggcgc agttcggccc aggagccggt gcgggcagtg gcgcgggcgg     1080
tagcagcggc gggggcggcg gcccgggcac ctatcagtac agccaggggg ctccgctcta     1140
cgggccgtac cctggagccg cagcggcggg atcttgcgga ggactggggg gcctgggggt     1200
tccaggttct ggcttccgtg cccacgtcta cctgtgcaac cggcctctgt ggctcaaatt     1260
ccaccgccac caaactgaga tgatcattac gaaacagggc aggcgcatgt ttcctttctt     1320
gagcttcaac ataaacggac tcaatcccac tgcccactac aatgtgttcg tagaggtggt     1380
gctggcggac cccaaccact ggcgcttcca ggggggcaaa tgggtgacct gtggcaaagc     1440
cgacaataac atgcagggca acaaaatgta tgttcaccca gagtctccta atactggttc     1500
ccactggatg agacaggaga tttcattcgg gaaattaaaa ctcaccaata acaaaggcgc     1560
aaataacaac aacaccccaga tgatagtctt acaatcctta cacaaatacc aaccccgact     1620
gcatattgtt gaagttacag aggatggcgt ggaggacttg aatgagccct caaagaccca     1680
gacttttacc ttctcagaaa cgcaattcat tgcagtgact gcctaccaaa acaccgtata     1740
tactcaacta aagattgatc ataacccctt tgcaaaaggc ttcagagaca actatgattc     1800
atcccatcag attgtccctg gaggtcggta cggcgttcaa tccttcttcc cggagcccct     1860
tgtcaacact ttacctcaag cccgctatta taatggcgag agaaccgtgc cacagaccaa     1920
cggcctcctt tcaccccaac agagcgaaga ggtggccaac cctccccagc ggtggccttgt     1980
cacgcctgtc cagcaacctg ggaccaacaa actagacatc agttcctatg aatctgaata     2040
tacttctagc acattgctcc catatggcat taaatccttg ccccttcaga catcccatgc     2100
cctggggtat tacccagacc caaccttccc tgcaatggca gggtggggag gtcgaggttc     2160
ttaccagagg aagatggcag ctggactacc atggacctcc agaacaagcc ccactgtgtt     2220
ctctgaagat cagctctcca aggagaaagt gaaagaggaa attggctctt cttggataga     2280
gacacccct tccatcaaat ctctagattc caatgattca ggagtataca ccagtgcttg     2340
taagcgaagg cggctgtctc ctagcaactc cagtaatgaa aattcaccct ccataaagtg     2400
tgaggacatt aatgctgaag agtatagtaa agacacctca aaaggcatgg gagggtatta     2460
tgcttttac acaactccct aaagagttat tttaacctca aaaattagct aacttttgc     2520
agatggactt ggtggtgttt tttgttgtct tctttgccta ggttgccaaa agatgtttg     2580
ccttccacct tgatgcatcc tgttttgtgc aattctctaa agaaggtgc caaagcttt     2640
tgattgctgc aggtaactga aacaaaccta gcattttaa aaataagat taatggaaga     2700
ctttaaggta tttaaaatt cgaagggtat ccaaggttct gtatttattt attggggaga     2760
cactaaccct tcaaagaagc aggctgtgaa cattgggtgc ccagtgctat cagatgagtt     2820
aaaacctttg attctcattt ctatttgtaa attcttaagc aaatagaagc cgagtgttaa     2880
ggtgttttgc ttctgaaaga gggctgtgcc ttccgtttca gaggagaca ttttgctgtt     2940
acattctgcc aggggcaaaa gatactaggc ccaggagtca agaaaagctt ttgtgaaagt     3000
gatagtttca cctgactttg attccttaac ccccggcttt tggaacaagc catgtttgcc     3060
ctagtccagg attgcctcac ttgagacttg ctaggcctct gctgtgtgct ggggtggcca     3120
```

```
gtgggactca ggagagagca agctaaggag tcaccaaaaa aaaaaaaaaa aaaaagggag    3180
aatttaaaag tgtacagttg tgtgtttaga tacactatag aataatgtgg tatatattgt    3240
acaaatagtc tacataggtg tctgggataa tgtaaaactg gtgctttggc tttgtaaaga    3300
atttgcaaat cacttaacag ctgcagggc aaggggagag tttcatcatc ccatgatat      3360 ttgggaatat tctgtttact tcttagatag ttaagaatgt attcagctac tatgtactaa    3420
cttgaaccgt gtttaaggaa aactcctatt tcatcctctt cttgcgccat cccctctccc    3480
taacttggta atgtgaagaa actaaaacct gataccacag ctcctatagg cattttagag    3540
atcttggatt tttatgtaca gtcttagtca tttttaataa atgtggttca gtaagggaac    3600
ggaaaaaaaa aaaaaaa                                                    3617

<210> SEQ ID NO 46
<211> LENGTH: 1220
<212> TYPE: DNA
<213> ORGANISM: Homo sapiens

<400> SEQUENCE: 46
gggagcgggc gagtaggagg gggcgccggg ctatatatat agcggctcgg cctcgggcgg      60
gcctggcgct cagggaggcg cgcactgctc ctcagagtcc cagctccagc cgcgcgcttt     120
ccgcccggct cgccgctcca tgcagccggg gtagagcccg cgcccggggg ccccgtcgc     180 ttgcctcccg cacctcctcg gttgcgcact cctgcccgag gtcggccgtg cgctcccgcg    240
ggacgccaca ggcgcagctc tgccccccag cttcccgggc gcactgaccg cctgaccgac    300
gcacggccct cgggccggga tgtcggggcc cgggacggcc gcggtagcgc tgctcccggc    360
ggtcctgctg gccttgctgg cgccctgggc gggccgaggg ggcgccgccg cacccactgc    420
acccaacggc acgctggagg ccgagctgga gcgccgctgg gagagcctgg tggcgctctc    480
gttggcgcgc ctgccggtgg cagcgcagcc caaggaggcg gccgtccaga gcggcgccgg    540
cgactacctg ctgggcatca gcggctgcg gcggctctac tgcaacgtgg gcatcggctt    600
ccacctccag gcgctccccg acggccgcat cggcggcgcg cacgcggaca cccgcgacag    660
cctgctggag ctctcgcccg tggagcgggg cgtggtgagc atcttcggcg tggccagccg    720
gttcttcgtg gccatgagca gcaagggcaa gctctatggc tcgcccttct tcaccgatga    780
gtgcacgttc aaggagattc tccttcccaa caactacaac gcctacgagt cctacaagta    840
ccccggcatg ttcatcgccc tgagcaagaa tgggaagacc aagaagggga accgagtgtc    900
gcccaccatg aaggtcaccc acttcctccc caggctgtga ccctcagag gacccttgcc    960 tcagcctcgg gaagccctg ggagggcagt gccgagggtc accttggtgc actttcttcg    1020
gatgaagagt ttaatgcaag agtaggtgta agatatttaa attaattatt taaatgtgta    1080
tatattgcca ccaaattatt tatagttctg cgggtgtgtt ttttaatttt ctgggggaa    1140 aaaaagacaa acaaaaaac caactctgac ttttctggtg caacagtgga gaatcttacc    1200
attggatttc tttaacttgt                                                1220

<210> SEQ ID NO 47
<211> LENGTH: 1224
<212> TYPE: DNA
<213> ORGANISM: Homo sapiens

<400> SEQUENCE: 47
ggagctctcc ccggtctgac agccactcca gaggccatgc ttcgtttctt gccagatttg      60
```

```
gctttcagct tcctgttaat tctggctttg ggccaggcag tccaatttca agaatatgtc    120
tttctccaat ttctgggctt agataaggcg ccttcacccc agaagttcca acctgtgcct    180
tatatcttga agaaaatttt ccaggatcgc gaggcagcag cgaccactgg ggtctcccga    240
gacttatgct acgtaaagga gctgggcgtc cgcgggaatg tacttcgctt tctcccagac    300
caaggtttct ttctttaccc aaagaaaatt tcccaagctt cctcctgcct gcagaagctc    360
ctctacttta acctgtctgc catcaaagaa agggaacagt tgacattggc ccagctgggc    420
ctggacttgg ggcccaattc ttactataac ctgggaccag agctggaact ggctctgttc    480
ctggttcagg agcctcatgt gtggggccag accaccccta agccaggtaa aatgtttgtg    540
ttgcggtcag tcccatggcc acaaggtgct gttcacttca acctgctgga tgtagctaag    600
gattggaatg acaaccccg gaaaaatttc gggttattcc tggagatact ggtcaaagaa    660
gatagagact caggggtgaa ttttcagcct gaagacacct gtgccagact aagatgctcc    720
cttcatgctt ccctgctggt ggtgactctc aaccctgatc agtgccaccc ttctcggaaa    780
aggagagcag ccatccctgt ccccaagctt tcttgtaaga acctctgcca ccgtcaccag    840
ctattcatta acttccggga cctggggttgg cacaagtgga tcattgcccc caaggggttc    900
atggcaaatt actgccatgg agagtgtccc ttctcactga ccatctctct caacagctcc    960
aattatgctt tcatgcaagc cctgatgcat gccgttgacc cagagatccc ccaggctgtg   1020
tgtatcccca ccaagctgtc tcccatttcc atgctctacc aggacaataa tgacaatgtc   1080
attctacgac attatgaaga catggtagtc gatgaatgtg ggtgtgggta ggatgtcaga   1140
aatgggaata gaaggagtgt tcttagggta aatcttttaa taaaactacc tatctggttt   1200
atgaccactt agatcgaaat gtca                                            1224

<210> SEQ ID NO 48
<211> LENGTH: 1644
<212> TYPE: DNA
<213> ORGANISM: Homo sapiens

<400> SEQUENCE: 48
acatccagct gcctgagacc ctcctgcagc cttctcaagg gacagcccca ctctgcctct     60
tgctcctcca gggcagcacc atgcagcccc tgtggctctg ctgggcactc tgggtgttgc    120
ccctggccag ccccgggggcc gcccctgaccg gggagcagct cctgggcagc tgctgcggc    180 agctgcagct caaagaggtg cccaccctgg acagggccga catggaggag ctggtcatcc    240
ccacccacgt gagggcccag tacgtggccc tgctgcagcg cagccacggg gaccgctccc    300
gcggaaagag gttcagccag agcttccgag aggtggccgg caggttcctg gcgttggagg    360
ccagcacaca cctgctggtg ttcggcatgg agcagcggct gcgcccaac agcgagctgg    420 tgcaggccgt gctgcggctc ttccaggagc cggtccccaa ggccgcgctg cacaggcacg    480
ggcggctgtc cccgcgcagc gcccgggccc gggtgaccgt cgagtggctg cgcgtccgcg    540
acgacggctc caaccgcacc tccctcatcg actccaggct ggtgtccgtc cacgagagcg    600
gctggaaggc cttcgacgtg accgaggccg tgaacttctg gcagcagctg agccggcccc    660
ggcagccgct gctgctacag gtgtcggtgc agagggagca tctgggcccg ctggcgtccg    720
gcgcccacaa gctggtccgc tttgcctcgc aggggcgcc agccgggctt ggggagcccc    780
agctggagct gcacaccctg gaccttgggg actatggagc tcaggcgac tgtgaccctg    840 aagcaccaat gaccgagggc acccgctgct gccgccagga gatgtacatt gacctgcagg    900
ggatgaagtg ggccgagaac tgggtgctgg agcccccggg cttcctggct tatgagtgtg    960
```

| | |
|---|---|
| tgggcacctg ccggcagccc ccggaggccc tggccttcaa gtggccgttt ctggggcctc | 1020 |
| gacagtgcat cgcctcggag actgactcgc tgcccatgat cgtcagcatc aaggagggag | 1080 |
| gcaggaccag gccccaggtg gtcagcctgc ccaacatgag ggtgcagaag tgcagctgtg | 1140 |
| cctcggatgg tgcgctcgtg ccaaggaggc tccagccata ggcgcctagt gtagccatcg | 1200 |
| agggacttga cttgtgtgtg tttctgaagt gttcgagggt accaggagag ctggcgatga | 1260 |
| ctgaactgct gatggacaaa tgctctgtgc tctctagtga gccctgaatt tgcttcctct | 1320 |
| gacaagttac ctcacctaat ttttgcttct caggaatgag aatctttggc cactggagag | 1380 |
| cccttgctca gttttctcta ttcttattat tcactgcact atattctaag cacttacatg | 1440 |
| tggagatact gtaacctgag ggcagaaagc ccaatgtgtc attgtttact tgtcctgtca | 1500 |
| ctggatctgg gctaaagtcc tccaccacca ctctggacct aagacctggg gttaagtgtg | 1560 |
| ggttgtgcat ccccaatcca gataataaag actttgtaaa acatgaataa aacacatttt | 1620 |
| attctaaaaa aaaaaaaaaa aaaa | 1644 |

<210> SEQ ID NO 49
<211> LENGTH: 2086
<212> TYPE: DNA
<213> ORGANISM: Homo sapiens

<400> SEQUENCE: 49

| | |
|---|---|
| ataagggctg gaggtgctgc tttcaggcct ggccagccca ccatgcacgc ccactgcctg | 60 |
| cccttccttc tgcacgcctg gtgggcccta ctccaggcgg gtgctgcgac ggtggccact | 120 |
| gcgctcctgc gtacgcgggg gcagccctcg tcgccatccc ctctggcgta catgctgagc | 180 |
| ctctaccgcg acccgctgcc gagggcagac atcatccgca gcctacaggc agaagatgtg | 240 |
| gcagtggatg ggcagaactg gacgtttgct tttgacttct ccttcctgag ccaacaagag | 300 |
| gatctggcat gggctgagct ccggctgcag ctgtccagcc ctgtggacct ccccactgag | 360 |
| ggctcacttg ccattgagat tttccaccag ccaaagcccg acacagagca ggcttcagac | 420 |
| agctgcttag agcggtttca gatggaccta ttcactgtca ctttgtccca ggtcaccttt | 480 |
| tccttgggca gcatggtttt ggaggtgacc aggcctctct ccaagtggct gaagcaccct | 540 |
| ggggccctgg agaagcagat gtccagggta gctggagagt gctggccgcg gccccccaca | 600 |
| ccgcctgcca ccaatgtgct ccttatgctc tactccaacc tctcgcagga gcagaggcag | 660 |
| ctgggtgggt ccaccttgct gtgggaagcc gagagctcct ggcgggccca ggagggacag | 720 |
| ctgtcctggg agtggggcaa gaggcaccgt cgacatcact tgccagacag aagtcaactg | 780 |
| tgtcggaagg tcaagttcca ggtggacttc aacctgatcg gatgggggctc ctggatcatc | 840 |
| taccccaagc agtacaacgc ctatcgctgt gagggcgagt gtcctaatcc tgttggggag | 900 |
| gagtttcatc cgaccaacca tgcatacatc cagagtctgc tgaaacgtta ccagccccac | 960 |
| cgagtccctt ccacttgttg tgccccagtg aagaccaagc cgctgagcat gctgtatgtg | 1020 |
| gataatggca gagtgctcct agatcaccat aaagacatga tcgtggaaga atgtgggtgc | 1080 |
| ctctgatgac atcctggagg gagactggat ttgcctgcac tctggaaggc tgggaaactc | 1140 |
| ctggaagaca tgataaccat ctaatccagt aaggagaaac agagagggc aaagttgctc | 1200 |
| tgcccaccag aactgaagag gaggggctgc ccactctgta aatgaagggc tcagtggagt | 1260 |
| ctggccaagc acagaggctg ctgtcaggaa gaggggaggaa gaagcctgtg caggggggctg | 1320 |
| gctggatgtt ctctttactg aaaagacagt ggcaaggaaa agcacaagtg catgagttct | 1380 |

```
ttactggatt ttttaaaaac ctgtgaaccc cccgaaactg tatgtgaaag ttgagacata    1440
tgtgcatgta ttttggaggt gggatgaagt cacctatagc tttcatgtat tctccaaagt    1500
agtctgtgtg tgacctgtcc ccctccccaa agattaagga tcactgtata gattaaaaag    1560
agtccgtcaa tctcattgcc tcaggctggg ttggggagc cccacagctt tctggctggc    1620
cagtggcaat ctactggcct tgtccagagg ctcactggag tggttctctg ctaatgagct    1680
gtacaacaat aaagccattg tctagttctc ctgggccagc tggtgcctgt gaaggcagag    1740
gcaggaactc atccaagagg accggccatg ttgggttaca gaagacatcc ctgcgtcagt    1800
ctgcttcggc agacacagcc tgagtttgtt aaagttggtg acaatccacc tcagtctctc    1860
aatgtgtgct attaatgagg cctctgagct tcctatccag cagtggtgaa ggccttgccc    1920
tgggtggcaa gatacttgct ctatggtcac agctcagcca ctggaagctg tgcgacctca    1980
ggtgagcaat tcactgtcca gtctccactt gtaaaaggaa cgctggtgaa tcctaatgca    2040
ttcatattaa atgtctgttg tcaggctcag aagagccatg agcttt              2086

<210> SEQ ID NO 50
<211> LENGTH: 708
<212> TYPE: DNA
<213> ORGANISM: Homo sapiens

<400> SEQUENCE: 50
ccccgcaggc tgagggcagg tgggaagcaa acccggacgc atcgcagcag cagcagcagc      60
agcagaagca gcagcagcag cctccgcagt ccctccagag acatggatcc ccagacagca     120
ccttcccggg cgctcctgct cctgctcttc ttgcatctgg cttcctggg aggtcgttcc      180 cacccgctgg gcagccccgg ttcagcctcg gacttggaaa cgtccgggtt acaggagcag     240
cgcaaccatt tgcagggcaa actgtcggag ctgcaggtgg agcagacatc cctggagccc     300
ctccaggaga gccccgtcc cacaggtgtc tggaagtccc gggaggtagc caccgagggc      360
atccgtgggc accgcaaaat ggtcctctac accctgcggg caccacgaag ccccaagatg     420
gtgcaagggt ctggctgctt tgggaggaag atggaccgga tcagctcctc cagtggcctg     480
ggctgcaaag tgctgaggcg gcattaagag gaagtcctgg ctgcagacac ctgcttctga     540
ttccacaagg ggcttttttcc tcaaccctgt ggccgccttt gaagtgactc attttttttaa    600 tgtatttatg tatttatttg attgtttttat ataagatggt ttcttaccctt tgagcacaaa    660 atttccacgg tgaaataaag tcaacattat aagctttaaa aaaaaaa                   708

<210> SEQ ID NO 51
<211> LENGTH: 5094
<212> TYPE: DNA
<213> ORGANISM: Homo sapiens

<400> SEQUENCE: 51
gaaactggat acatggttta cagcaggtca ctaatgttgg aaaaagtaca gagtccaggg      60
aaagacttgc ttgtaacttt atgaattctg gatttttttt tttccttttgc ttttctttaa    120 cttttcactaa gggttactgt agtctgatgt gtccttccca aggccacgaa atttgacaag     180
ctgcactttt cttttgctca atgatttctg ctttaagcca aagaactgcc tataatttca     240
ctaagaatgt cttctaattc agatactggg gatttacaag agtctttaaa gcacggactt     300
acacctattg gtgctgggct tccggaccga cacggatccc ccatcccgc ccgcggtcgc      360 cttgtcatgc tgcccaaagt gggagacgaa gccctgggac tggctcgatc gcatgggaa     420 cagggccaga tgccggaaaa catgcaagtg tctcaattta aaatggtgaa ttactcctat     480
```

```
gatgaagatc tggaagagct ttgtcccgtg tgtggagata aagtgtctgg gtaccattat    540
gggctcctca cctgtgaaag ctgcaaggga tttttaagc gaacagtcca aaataataaa    600
aggtacacat gtatagaaaa ccagaactgc caaattgaca aaacacagag aaagcgttgt    660
ccttactgtc gttttcaaaa atgtctaagt gttggaatga agctagaagc tgtaagggcc    720
gaccgaatgc gtggaggaag gaataagttt gggccaatgt acaagagaga cagggccctg    780
aagcaacaga aaaagccct catccgagcc aatggactta agctagaagc catgtctcag    840
gtgatccaag ctatgccctc tgacctgacc atttcctctg caattcaaaa catccactct    900
gcctccaaag gcctacctct gaaccatgct gccttgcctc ctacagacta tgacagaagt    960 cccttgtaa catcccccat tagcatgaca atgccccctc acggcagcct gcaaggttac   1020
caaacatatg gccactttcc tagccgggcc atcaagtctg agtacccaga ccctatacc   1080 agctcacccg agtccataat gggctattca tatatggata gttaccagac gagctctcca   1140
gcaagcatcc cacatctgat actggaactt ttgaagtgtg agccagatga gcctcaagtc   1200
caggctaaaa tcatggccta tttgcagcaa gagcaggcta accgaagcaa gcacgaaaag   1260
ctgagcacct ttgggcttat gtgcaaaatg gcagatcaaa ctctcttctc cattgtcgag   1320
tgggccagga gtagtatctt cttcagagaa cttaaggttg atgaccaaat gaagctgctt   1380
cagaactgct ggagtgagct cttaatcctc gaccacattt accgacaagt ggtacatgga   1440
aaggaaggat ccatcttcct ggttactggg caacaagtgg actattccat aatagcatca   1500
caagccggag ccaccctcaa caacctcatg agtcatgcac aggagttagt ggcaaaactt   1560
cgttctctcc agtttgatca acgagagttc gtatgtctga aattcttggt gctctttagt   1620
ttagatgtca aaaaccttga aaacttccag ctggtagaag gtgtccagga acaagtcaat   1680
gccgccctgc tggactacac aatgtgtaac tacccgcagc agacagagaa atttggacag   1740
ctacttcttc gactacccga atccgggcc atcagtatgc aggctgaaga atacctctac   1800
tacaagcacc tgaacgggga tgtgccctat aataaccttc tcattgaaat gttgcatgcc   1860
aaaagagcat aagttacaac ccctaggagc tctgctttca aaacaaaaag agattggggg   1920 agtgggagg gggaagaaga acaggaagaa aaaaagtact ctgaactgct ccaagtaacg   1980
ctaattaaaa acttgcttta aagatattga atttaaaaag gcataataat caaatactta   2040
atagcaaata aatgatgtat cagggtattt gtattgcaaa ctgtgaatca aaggcttcac   2100
agccccagag gattccatat aaaagacatt gtaatggagt ggattgaact cacagatgga   2160
taccaacacg gtcagaagaa aaacggacag aacggttctt gtatatttaa actgatctcc   2220
actatgaaga aatttaggaa ctaatcttat taattaggct tatacagcgg gggatttgag   2280
cttacaggat tcctccatgg taaagctgaa ctgaaacaat tctcaagaat gcatcagctg   2340
tacctacaat agcccctccc tcttcctttg aaggcccag cacctctgcc ctgtggtcac   2400
cgaatctgta ctaaggacct gtgttcagcc acacccagtg gtagctccac caaatcatga   2460
acagcctaat tttgagtgtc tgtgtcttag acctgcaaac agctaatagg aaattctatt   2520
aatatgttag cttgccattt taaatatgtt ctgagggttg ttttgtctcg tgttcatgat   2580
gttaagaaaa tgcaggcagt atccctcatc ttatgtaagt gttaattaat attaagggaa   2640
atgactacaa actttcaaag caaatgctcc atagctaaag caacttagac cttatttctg   2700
ctactgttgc tgaaatgtgg ctttggcatt gttggatttc ataaaaaatt tctggcagga   2760
agtcttgtta gtatacatca gtcttttca tcatccaagt ttgtagttca tttaaaaata   2820
```

```
caacattaaa cacattttgc taggatgtca aatagtcaca gttctaagta gttggaaaca    2880
aaattgacgc atgttaatct atgcaaagag aaaggaaagg atgaggtgat gtattgactc    2940
aaggttcatt cttgctgcaa ttgaacatcc tcaagagttg ggatggaaat ggtgattttt    3000
acatgtgtcc tggaaagata ttaaagtaat tcaaatcttc cccaaagggg aaaggaagag    3060
agtgatactg accttttaa gtcatagacc aaagtctgct gtagaacaaa tatgggagga     3120
caaagaatcg caaattcttc aaatgactat tatcagtatt attaacatgc gatgccacag    3180
gtatgaaagt cttgccttat ttcacaattt taaaaggtag ctgtgcagat gtggatcaac    3240
atttgtttaa aataaagtat taatacttta aagtcaaata agatatagtg tttacattct    3300
ttaggtcctg aggggcaggg ggatctgtga tataacaaaa tagcaaaagc ggtaatttcc    3360
ttaatgttat ttttctgatt ggtaattatt tttaacagta cttaattatt ctatgtcgtg    3420
agacactaaa atcaaaaacg ggaatctcat ttagactttta attttttga gattatcggc    3480
ggcacaatca ctttgtagaa actgtaaaaa ataaaagtat ctcctagtcc cttaatttt     3540
tcataaatat ttctggcttt tgagtagtgt atttatattg tatatcatac tttcaactgt    3600
agacaattat gatgctaatt tattgtttct tggtttcacc tttgtataag atatagccaa    3660
gactgaagaa accaaatata tgtgtttact gtagcatgtc ttcaaattag tggaacttag    3720
ttcagggaca tagaagagtc ttaatgaatt aaaatcattc acttgattaa atgtctgtaa    3780
atcttcatca ttcctactgt agtttattta atatctattg taaattatgt gacttgtagc    3840
ttcctctggt tttcaagtaa actcaacaag gtggagtctt acctggtttt cctttccaag    3900
cattgtaaat tgtataccaa agatattagt tattacttct gtgtgtacaa agaggattat    3960
tttattatgt ttattaatca cctctaatac tcatccacat gaagggtaca cattaggtaa    4020
gctgggcgtt gactcatgcg cagtctcagt cacccgtgtt atcttcgtgg ctcaaaggac    4080
aatgcaaaat cgccgatcag agctcatacc caaagcatta cagagaacag cagcatcatt    4140
gccctcccca gctgaaaaac aagttggcta gaagatacat ggagaggaat ggtgtggtca    4200
acagttaatg aaacggttct atcatgcatg tgtaatgtgg atggagacaa ttataagatt    4260
tgactataac tatttggagg gtctttaaca ttgccaaaaa aacaaatatg ttgattttta    4320
ttttatttta ttttttattt taagaggcgg gatcttgatc tcacatgttg cccaggctgg    4380
ccttgaactc ctgggctcaa gcattcctcc tgcctcagcc tccccatag ctgggactag     4440
gggtgcatgc cagcatacct ggctacgttg actcttaaaa tctatgttct cttattttaa    4500
agatacagtg ctccccactg aaaattaaac ctaaaaaatg tcacatattg gtatgttgtt    4560
aacctggtag attaaatcat gagaatgatt agaaagacgg gcaacacagc gggttacatc    4620
cacactgctg atcacaccaa cgacaggagc tgataagcaa gaaagcgtca cagccagcgt    4680
ctgttcaccc aaggttgaca agtgaagttt ctctaatgtt gattgttagc cgatttgtaa    4740
cctggcattt acttagcaac tgccttatca attacaggat ttgccggtaa aagcagactc    4800
aaatataaag gttttggct taacttggtt tattatagtt gctctatgtt tgtaaacaga     4860
caatctctaa tgtctgatta tttgtatcac agatctgcag ctgccttgga cttgaatcca    4920
tgcaatgttt agagtgtgaa gtcagttact tgttgatgtt tcttactgt atcaatgaaa     4980
tacatattgt catgtcagtt cttgccagga acttctcaac aaaatggaat ttttttttc     5040
agtatttcaa taaatattga tatgcccagc ctgataattt ttaaaaaaaa aaaa          5094
```

<210> SEQ ID NO 52
<211> LENGTH: 1862

<212> TYPE: DNA
<213> ORGANISM: Homo sapiens

<400> SEQUENCE: 52

```
ctggttcgca aagaagctga cttcagaggg ggaaactttc ttcttttagg aggcggttag        60
ccctgttcca cgaacccagg agaactgctg gccagattaa ttagacattg ctatgggaga       120
cgtgtaaaca cactacttat cattgatgca tatataaaac cattttattt tcgctattat       180
ttcagaggaa gcgcctctga tttgtttctt ttttcccttt ttgctctttc tggctgtgtg       240
gtttggagaa agcacagttg gagtagccgg ttgctaaata agtcccgagc gcgagcggag       300
acgatgcagc ggagactggt tcagcagtgg agcgtcgcgg tgttcctgct gagctacgcg       360
gtgccctcct gcgggcgctc ggtggagggt ctcagccgcc gcctcaaaag agctgtgtct       420
gaacatcagc tcctccatga caaggggaag tccatccaag atttacggcg acgattcttc       480
cttcaccatc tgatcgcaga aatccacaca gctgaaatca gagctacctc ggaggtgtcc       540
cctaactcca agccctctcc caacacaaag aaccaccccg tccgatttgg gtctgatgat       600
gagggcagat acctaactca ggaaactaac aaggtggaga cgtacaaaga gcagccgctc       660
aagacacctg ggaagaaaaa gaaaggcaag cccgggaaac gcaaggagca ggaaaagaaa       720
aaacggcgaa ctcgctctgc ctggttagac tctggagtga ctgggagtgg gctagaaggg       780
gaccacctgt ctgacacctc cacaacgtcg ctggagctcg attcacggta acaggcttct       840
ctggcccgta gcctcagcgg ggtgctctca gctgggtttt ggagcctccc ttctgccttg       900
gcttggacaa acctagaatt ttctcccttt atgtatctct atcgattgtg tagcaattga       960
cagagaataa ctcagaatat tgtctgcctt aaagcagtac cccctacca cacacacccc      1020
tgtcctccag caccatagag aggcgctaga gcccattcct ctttctccac cgtcacccaa      1080
catcaatcct ttaccactct accaaataat ttcatattca agcttcagaa gctagtgacc      1140
atcttcataa tttgctggag aagtgtgttt cttcccctta ctctcacacc tgggcaaact      1200
ttcttcagtg tttttcattt cttacgttct ttcacttcaa gggagaatat agaagcattt      1260
gatattatct acaaacactg cagaacagca tcatgtcata aacgattctg agccattcac      1320
actttttatt taattaaatg tatttaatta aatctcaaat ttattttaat gtaaagaact      1380
taaattatgt tttaaacaca tgccttaaat ttgtttaatt aaatttaact ctggtttcta      1440
ccagctcata caaaataaat ggtttctgaa aatgtttaag tattaactta caaggatata      1500
ggttttctc atgtatcttt ttgttcattg gcaagatgaa ataattttc tagggtaatg      1560
ccgtaggaaa aataaaactt cacatttatg tggcttgttt atccttagct cacagattga      1620
ggtaataatg acactcctag actttgggat caaataactt agggccaagt cttgggtctg      1680
aatttattta agttcacaac ctagggcaag ttactctgcc tttctaagac tcacttacat      1740
cttctgtgaa atataattgt accaacctca tagagtttgg tgtcaactaa atgagattat      1800
atgtggacta aatatctgtc atatagtaaa cactcaataa attgcaacat attaaaaaaa      1860
aa                                                                   1862
```

<210> SEQ ID NO 53
<211> LENGTH: 2500
<212> TYPE: DNA
<213> ORGANISM: Homo sapiens

<400> SEQUENCE: 53

```
ggaggacact tctcagaagg ggttgttttg cttttgctta tttccgtcca tttccctctc        60
```

```
tgcgcgcgga ccttccttt  ccagatggtg agagccgcgg ggacacccga cgccggggca    120
ggctgatcca cgatcctggg tgtgcgtaac gccgcctggg gctccgtggg cgagggacgt    180
gtggggacag gtgcaccgga aactgccaga ctggagagtt gaggcatcgg aggcgcgaga    240
acagcactac tactgcggcg agacgagcgc ggcgcatccc aaagcccggc caaatgcgct    300
cgtccctggg aggggaggga ggcgcgcctg gagcggggac agtcttggtc cgcgccctcc    360
tcccgggtct gtgccgggac ccgggacccg ggagccgtcg caggtctcgg tccaaggggc    420
cccttttctc ggaagggcgg cggccaagag cagggaaggt ggatctcagg tagcgagtct    480
gggcttcggg gacggcgggg aggggagccg gacgggagga tgagctcccc tggcaccgag    540
agcgcgggaa agagcctgca gtaccgagtg gaccacctgc tgagcgccgt ggagaatgag    600
ctgcaggcgg gcagcgagaa gggcgacccc acagagcgcg aactgcgcgt gggcctggag    660
gagagcgagc tgtggctgcg cttcaaggag ctcaccaatg agatgatcgt gaccaagaac    720
ggcaggagga tgtttccggt gctgaaggtg aacgtgtctg gcctggaccc caacgccatg    780
tactccttcc tgctggactt cgtggcggcg acaaccacc gctggaagta cgtgaacggg    840
gaatgggtgc cggggggcaa gccggagccg caggcgccca gctgcgtcta catccacccc    900
gactcgccca cttcggggc ccactggatg aaggctcccg tctccttcag caaagtcaag    960
ctcaccaaca gctcaacgg agggggccag atcatgctga actccttgca taagtatgag   1020
cctcgaatcc acatagtgag agttgggggt ccacagcgca tgatcaccag ccactgcttc   1080
cctgagaccc agttcatagc ggtgactgct tatcagaacg aggagatcac agctcttaaa   1140
attaagtaca atccatttgc aaaagctttc cttgatgcaa aggaaagaag tgatcacaaa   1200
gagatgatgg aggaacccgg agacagccag caacctgggt actcccaatg ggggtggctt   1260
cttcctggaa ccagcaccct gtgtccacct gcaaatcctc atcctcagtt tggaggtgcc   1320
ctctcccctcc cctccacgca cagctgtgac aggtacccaa ccctgaggag ccaccggtcc   1380
tcaccctacc ccagccccta tgctcatcgg aacaattctc caacctattc tgacaactca   1440
cctgcatgtt tatccatgct gcaatcccat gacaattggt ccagccttgg aatgcctgcc   1500
catcccagca tgctccccgt gagccacaat gccagcccac ctaccagctc cagtcagtac   1560
cccagcctgt ggtctgtgag caacggcgcc gtcaccccgg gctcccaggc agcagccgtg   1620
tccaacgggg tgggggccca gttcttccgg ggctcccccg cgcactacac accccctcacc   1680
catccggtct cggcgccctc ttcctcggga tccccactgt acgaaggggc ggccgcggcc   1740
acagacatcg tggacagcca gtacgacgcc gcagcccaag gccgcctcat agcctcatgg   1800
acacctgtgt cgccaccttc catgtgaagc agcaaggccc aggtcccgaa agatgcagtg   1860
acttttttgtc gtggcagcca gtggtgactg gattgaccta ctaggtaccc agtggcagtc   1920
tcaggttaag aaggaaatgc agcctcagta acttcctttt caaagcagtg gaggagcaca   1980
cggcaccttt ccccagagcc ccagcatccc ttgctcacac ctgcagtagc ggtgctgtcc   2040
caggtggctt acagatgaac ccaactgtgg agatgatgca gttggcccaa cctcactgac   2100
ggtgaaaaaa tgtttgccag ggtccagaaa cttttttttgg tttatttctc atacagtgta   2160
ttggcaactt tggcacacca gaatttgtaa actccaccag tcctacttta gtgagataaa   2220
aagcacactc ttaatcttct tccttgttgc tttcaagtag ttagagttga gctgttaagg   2280
acagaataaa atcatagttg aggacagcag gttttagttg aattgaaaat ttgactgctc   2340
tgcccccctag aatgtgtgta ttttaagcat atgtagctaa tctcttgtgt tgttaaacta   2400
taactgtttc atatttttct tttgacaaag tagccaaaga caatcagcag aaagcatttt   2460
```

```
ctgcaaaata aacgcaatat gcaaaaaaaa aaaaaaaaa                            2500
```

<210> SEQ ID NO 54
<211> LENGTH: 7326
<212> TYPE: DNA
<213> ORGANISM: Homo sapiens

<400> SEQUENCE: 54

```
aggacacagc gtccggagcc agaggcgctc ttaacggcgt ttatgtcctt tgctgtctga      60
ggggcctcag ctctgaccaa tctggtcttc gtgtggtcat tagcatgggc ttcgtgagac     120
agatacagct tttgctctgg aagaactgga ccctgcggaa aaggcaaaag attcgctttg     180
tggtggaact cgtgtggcct ttatctttat ttctggtctt gatctggtta aggaatgcca     240
acccgctcta cagccatcat gaatgccatt tccccaacaa ggcgatgccc tcagcaggaa     300
tgctgccgtg gctccagggg atcttctgca atgtgaacaa tccctgtttt caaagcccca     360
ccccaggaga atctcctgga attgtgtcaa actataacaa ctccatcttg caagggtat      420
atcgagattt tcaagaactc ctcatgaatg caccagagag ccagcacctt ggccgtattt     480
ggacagagct acacatcttg tcccaattca tggacaccct ccggactcac ccggagagaa     540
ttgcaggaag aggaatacga ataagggata tcttgaaaga tgaagaaaca ctgacactat     600
ttctcattaa aaacatcggc ctgtctgact cagtggtcta ccttctgatc aactctcaag     660
tccgtccaga gcagttcgct catggagtcc cggacctggc gctgaaggac atcgcctgca     720
gcgaggccct cctggagcgc ttcatcatct tcagccagag acgcgggggca aagacggtgc     780
gctatgccct gtgctccctc tcccagggca ccctacagtg gatagaagac actctgtatg     840
ccaacgtgga cttcttcaag ctcttccgtg tgcttcccac actcctagac agccgttctc     900
aaggtatcaa tctgagatct tggggaggaa atattatctga tatgtcacca agaattcaag     960
agtttatcca tcggccgagt atgcaggact tgctgtgggt gaccaggccc ctcatgcaga    1020
atggtggtcc agagaccttt acaaagctga tgggcatcct gtctgacctc ctgtgtggct    1080
accccgaggg aggtggctct cgggtgctct ccttcaactg gtatgaagac aataactata    1140
aggcctttct ggggattgac tccacaagga aggatcctat ctattcttat gacagaagaa    1200
caacatcctt ttgtaatgca ttgatccaga gcctggagtc aaatccttta accaaaatcg    1260
cttggagggc ggcaaagcct ttgctgatgg gaaaaatcct gtacactcct gattcacctg    1320
cagcacgaag gatactgaag aatgccaact caacttttga agaactggaa cacgttagga    1380
agttggtcaa agcctgggaa gaagtagggc cccagatctg gtacttcttt gacaacagca    1440
cacagatgaa catgatcaga gatacctgg ggaacccaac agtaaaagac ttttgaata      1500
ggcagcttgg tgaagaaggt attactgctg aagccatcct aaacttcctc tacaagggcc    1560
ctcgggaaag ccaggctgac gacatggcca acttcgactg gagggacata tttaacatca    1620
ctgatcgcac cctccgcctg gtcaatcaat acctggagtg cttggtcctg ataagtttg     1680
aaagctacaa tgatgaaact cagctcaccc aacgtgccct ctctctactg gaggaaaaca    1740
tgttctgggc cggagtggta ttccctgaca tgtatccctg gaccagctct ctaccacccc    1800
acgtgaagta taagatccga atggacatag acgtggtgga gaaaaccaat aagattaaag    1860
acaggtattg ggattctggt cccagagctg atcccgtgga gatttccgg tacatctggg    1920
gcggtttgc ctatctgcag gacatggttg aacaggggat cacaaggagc caggtgcagg    1980
cggaggctcc agttggaatc tacctccagc agatgcccta cccctgcttc gtggacgatt    2040
```

```
ctttcatgat catcctgaac cgctgtttcc ctatcttcat ggtgctggca tggatctact   2100
ctgtctccat gactgtgaag agcatcgtct tggagaagga gttgcgactg aaggagacct   2160
tgaaaaatca gggtgtctcc aatgcagtga tttggtgtac ctggttcctg gacagcttct   2220
ccatcatgtc gatgagcatc ttcctcctga cgatattcat catgcatgga agaatcctac   2280
attacagcga cccattcatc ctcttcctgt tcttgttggc tttctccact gccaccatca   2340
tgctgtgctt tctgctcagc accttcttct ccaaggccag tctggcagca gcctgtagtg   2400
gtgtcatcta tttcacccct cacctgccac acatcctgtg cttcgcctgg caggaccgca   2460
tgaccgctga gctgaagaag gctgtgagct tactgtctcc ggtggcattt ggatttggca   2520
ctgagtacct ggttcgcttt gaagagcaag gcctggggct gcagtggagc aacatcggga   2580
acagtcccac ggaaggggac gaattcagct tcctgctgtc catgcagatg atgctccttg   2640
atgctgctgt ctatggctta ctcgcttggt accttgatca ggtgtttcca ggagactatg   2700
gaaccccact tccttggtac tttcttctac aagagtcgta ttggcttggc ggtgaagggt   2760
gttcaaccag agaagaaaga gccctggaaa agaccgagcc cctaacagag aaacggagg    2820
atccagagca cccagaagga atacacgact ccttctttga acgtgagcat ccagggtggg   2880
ttcctggggt atgcgtgaag aatctggtaa agattttga gccctgtggc cggccagctg    2940
tggaccgtct gaacatcacc ttctacgaga accagatcac cgcattcctg gccacaatg    3000
gagctgggaa aaccaccacc ttgtccatcc tgacgggtct gttgccacca acctctggga   3060
ctgtgctcgt tggggaagg gacattgaaa ccagcctgga tgcagtccgg cagagccttg    3120
gcatgtgtcc acagcacaac atcctgttcc accctcac ggtggctgag cacatgctgt     3180
tctatgccca gctgaaagga aagtcccagg aggagcccca gctggagatg aagccatgt    3240
tggaggacac aggcctccac cacaagcgga atgaagaggc tcaggaccta tcaggtggca   3300
tgcagagaaa gctgtcggtt gccattgcct ttgtgggaga tgccaaggtg gtgattctgg   3360
acgaaccccac ctctggggtg gacccttact cgagacgctc aatctgggat ctgctcctga   3420
agtatcgctc aggcagaacc atcatcatgt ccactcacca catggacgag gccgacctcc   3480
ttggggaccg cattgccatc attgcccagg gaaggctcta ctgctcaggc accccactct   3540
tcctgaagaa ctgctttggc acaggcttgt acttaaccct ggtgcgcaag atgaaaaaca   3600
tccagagcca aaggaaaggc agtgagggga cctgcagctg ctcgtctaag gtttctccca   3660
ccacgtgtcc agcccacgtc gatgacctaa ctccagaaca agtcctggat ggggatgtaa   3720
atgagctgat ggatgtagtt ctccaccatg ttccagaggc aaagctggtg gagtgcattg   3780
gtcaagaact tatcttcctt cttccaaata agaacttcaa gcacagagca tatgccagcc   3840
ttttcagaga gctggaggag acgctggctg accttggtct cagcagtttt ggaatttctg   3900
acactcccct ggaagagatt tttctgaagg tcacggagga ttctgattca ggacctctgt   3960
ttgcgggtgg cgctcagcag aaaagagaaa acgtcaaccc ccgacacccc tgcttgggtc   4020
ccagagagaa ggctggacag acaccccagg actccaatgt ctgctcccca ggggcgccgg   4080
ctgctcaccc agagggccag cctccccag agccagagtg cccaggcccg cagctcaaca   4140
cggggacaca gctggtcctc cagcatgtgc aggcgctgct ggtcaagaga ttccaacaca   4200
ccatccgcag ccacaaggac ttcctggcgc agatcgtgct cccggctacc tttgtgtttt   4260
tggctctgat gctttctatt gttatccctc cttttggcga ataccccgct ttgacccttc   4320
accccctggat atatgggcag cagtacacct tcttcagcat ggatgaacca ggcagtgagc   4380
agttcacggt acttgcagac gtcctcctga ataagccagg cttttggcaac cgctgcctga   4440
```

-continued

```
aggaagggtg gcttccggag tacccctgtg gcaactcaac accctggaag actccttctg    4500
tgtccccaaa catcacccag ctgttccaga agcagaaatg gacacaggtc aacccttcac    4560
catcctgcag gtgcagcacc agggagaagc tcaccatgct gccagagtgc cccgagggtg    4620
ccggggggcct cccgccccccc cagagaacac agcgcagcac ggaaattcta caagacctga    4680
cggacaggaa catctccgac ttcttggtaa aaacgtatcc tgctcttata agaagcagct    4740
taaagagcaa attctgggtc aatgaacaga ggtatgagg aatttccatt ggaggaaagc    4800
tcccagtcgt ccccatcacg ggggaagcac ttgttgggtt tttaagcgac cttggccgga    4860
tcatgaatgt gagcggggggc cctatcacta gagaggcctc taaagaaata cctgatttcc    4920
ttaaacatct agaaactgaa gacaacatta aggtgtggtt taataacaaa ggctggcatg    4980
ccctggtcag ctttctcaat gtggcccaca acgccatctt acgggccagc ctgcctaagg    5040
acaggagccc cgaggagtat ggaatcaccg tcattagcca acccctgaac ctgaccaagg    5100
agcagctctc agagattaca gtgctgacca cttcagtgga tgctgtggtt gccatctgcg    5160
tgatttctc catgtccttc gtcccagcca gctttgtcct ttatttgatc caggagcggg    5220
tgaacaaatc caagcacctc cagtttatca gtggagtgag ccccaccacc tactgggtga    5280
ccaacttcct ctgggacatc atgaattatt ccgtgagtgc tgggctggtg gtgggcatct    5340
tcatcgggtt tcagaagaaa gcctacactt ctccagaaaa ccttcctgcc cttgtggcac    5400
tgctcctgct gtatggatgg gcggtcattc ccatgatgta cccagcatcc ttcctgtttg    5460
atgtccccag cacagcctat gtggctttat cttgtgctaa tctgttcatc ggcatcaaca    5520
gcagtgctat taccttcatc ttggaattat ttgagaataa ccggacgctg ctcaggttca    5580
acgccgtgct gaggaagctg ctcattgtct tcccccactt ctgcctgggc cggggcctca    5640
ttgaccttgc actgagccag gctgtgacag atgtctatgc ccggtttggt gaggagcact    5700
ctgcaaatcc gttccactgg gacctgattg ggaagaacct gtttgccatg gtggtggaag    5760
gggtggtgta cttcctcctg accctgctgg tccagcgcca cttcttcctc tcccaatgga    5820
ttgccgagcc cactaaggag cccattgttg atgaagatga tgatgtggct gaagaaagac    5880
aaagaattat tactggtgga aataaaactg acatcttaag gctacatgaa ctaaccaaga    5940
tttatccagg cacctccagc ccagcagtgg acaggctgtg tgtcggagtt cgccctggag    6000
agtgctttgg cctcctggga gtgaatggtg ccggcaaaac aaccacattc aagatgctca    6060
ctggggacac cacagtgacc tcaggggatg ccaccgtagc aggcaagagt attttaacca    6120
atatttctga agtccatcaa aatatgggct actgtcctca gtttgatgca attgatgagc    6180
tgctcacagg acgagaacat ctttaccttt atgcccggct tcgaggtgta ccagcagaag    6240
aaatcgaaaa ggttgcaaac tggagtatta agagcctggg cctgactgtc tacgccgact    6300
gcctggctgg cacgtacagt gggggcaaca agcggaaact ctccacagcc atcgcactca    6360
ttggctgccc accgctggtg ctgctggatg agccccaccac agggatggac ccccaggcac    6420
gccgcatgct gtggaacgtc atcgtgagca tcatcagaga agggagggct gtggtcctca    6480
catcccacag catggaagaa tgtgaggcac tgtgtacccg gctggccatc atggtaaagg    6540
gcgcctttcg atgtatgggc accattcagc atctcaagtc caaatttgga gatggctata    6600
tcgtcacaat gaagatcaaa tcccgaagg acgacctgct tcctgacctg aaccctgtgg    6660
agcagttctt ccaggggaac ttcccaggca gtgtgcagag ggagaggcac tacaacatgc    6720
tccagttcca ggtctcctcc tcctcccctgg cgaggatctt ccagctcctc ctctcccaca    6780
```

| | |
|---|---:|
| aggacagcct gctcatcgag gagtactcag tcacacagac cacactggac caggtgtttg | 6840 |
| taaattttgc taaacagcag actgaaagtc atgacctccc tctgcaccct cgagctgctg | 6900 |
| gagccagtcg acaagcccag gactgatctt tcacaccgct cgttcctgca gccagaaagg | 6960 |
| aactctgggc agctggaggc gcaggagcct gtgcccatat ggtcatccaa atggactggc | 7020 |
| cagcgtaaat gaccccactg cagcagaaaa caaacacacg aggagcatgc agcgaattca | 7080 |
| gaaagaggtc tttcagaagg aaaccgaaac tgacttgctc acctggaaca cctgatggtg | 7140 |
| aaaccaaaca aatacaaaat ccttctccag accccagaac tagaaacccc gggccatccc | 7200 |
| actagcagct ttggcctcca tattgctctc atttcaagca gatctgcttt tctgcatgtt | 7260 |
| tgtctgtgtg tctgcgttgt gtgtgatttt catggaaaaa taaaatgcaa atgcactcat | 7320 |
| cacaaa | 7326 |

<210> SEQ ID NO 55
<211> LENGTH: 2707
<212> TYPE: DNA
<213> ORGANISM: Homo sapiens

<400> SEQUENCE: 55

| | |
|---|---:|
| catctttgag caagatgggt ctctaccgca tccgcgtgtc cactggggcc tcgctctatg | 60 |
| ccggttccaa caaccaggtg cagctgtggc tggtcggcca gcacggggag gcggcgctcg | 120 |
| ggaagcgact gtggcccgca cggggcaagg agacagaact caaggtggaa gtaccggagt | 180 |
| atctggggcc gctgctgttt gtgaaactgc gcaaacggca cctccttaag gacgacgcct | 240 |
| ggttctgcaa ctgatctct gtgcaggcc ccggagccgg ggacgaggtc aggttccctt | 300 |
| gttaccgctg ggtggagggc aacggcgtcc tgagcctgcc tgaaggcacc ggccgcactg | 360 |
| tgggcgagga ccctcaggc ctgttccaga acaccgggga agaagagctg gaagagagaa | 420 |
| ggaagttgta ccggtgggga aactggaagg acgggttaat tctgaatatg ctggggcca | 480 |
| aactatatga cctccctgtg gatgagcgat ttctggaaga caagagagtt gactttgagg | 540 |
| tttcgctggc caaggggctg gccgacctcg ctatcaaaga ctctctaaat gttctgactt | 600 |
| gctggaagga tctagatgac ttcaaccgga ttttctggtg tggtcagagc aagctggctg | 660 |
| agcgcgtgcg ggactcctgg aaggaagatg ccttatttgg gtaccagttt cttaatggcg | 720 |
| ccaaccccgt ggtgctgagg cgctctgctc accttcctgc tcgcctagtg ttccctccag | 780 |
| gcatggagga actgcaggcc cagctggaga aggagctgga gggaggcaca ctgttcgaag | 840 |
| ctgacttctc cctgctggat gggatcaagg ccaacgtcat tctctgtagc cagcagcacc | 900 |
| tggctgcccc tctagtcatg ctgaaattgc agcctgatgg gaaactcttg cccatggtca | 960 |
| tccagctcca gctgccccgc acaggatccc caccacctcc cctttttcttg cctacgcggatc | 1020 |
| cccccaatggc ctgcttctg gccaaatgct gggtgcgcag ctctgacttc cagctccatg | 1080 |
| agctgcagtc tcatcttctg aggggacact gatggctga ggtcattgtt gtggccacca | 1140 |
| tgaggtgcct gccgtcgata catcctatct tcaagcttat aattccccac ctgcgataca | 1200 |
| ccctggaaat taacgtccgg gccaggactg ggctggtctc tgacatggga attttcgacc | 1260 |
| agataatgag cactggtggg ggaggccacg tgcagctgct caagcaagct ggagccttcc | 1320 |
| taacctacag ctccttctgt cccctgatg acttggccga ccggggggctc ctgggagtga | 1380 |
| agtcttcctt ctatgcccaa gatgcgctgc ggctctggga aatcatctat cggtatgtgg | 1440 |
| aaggaatcgt gagtctccac tataagacag acgtggctgt gaaagacgac ccagagctgc | 1500 |
| agacctggtg tcgagagatc actgaaatcg ggctgcaagg ggcccaggac cgagggtttc | 1560 |

```
ctgtctcttt acaggctcgg gaccaggttt gccactttgt caccatgtgt atcttcacct   1620
gcaccggcca acacgcctct gtgcacctgg gccagctgga ctggtactct tgggtgccta   1680
atgcaccctg cacgatgcgg ctgccccgc caaccaccaa ggatgcaacg ctggagacag    1740
tgatggcgac actgcccaac ttccaccagg cttctctcca gatgtccatc acttggcagc   1800
tgggcagacg ccagcccgtt atggtggctg tgggccagca tgaggaggag tattttcgg    1860 gccctgagcc taaggctgtg ctgaagaagt tcagggagga gctggctgcc ctggataagg   1920
aaattgagat ccggaatgca aagctggaca tgccctacga gtacctgcgg cccagcgtgg   1980
tggaaaacag tgtggccatc taagcgtcgc caccctttgg ttatttcagc ccccatcacc   2040
caagccacaa gctgacccct tcgtggttat agccctgccc tcccaagtcc accctcttc    2100 ccatgtccca ccctccctag aggggcacct tttcatggtc tctgcaccca gtgaacacat   2160
tttactctag aggcatcacc tgggacctta ctcctctttc cttccttcct cctttcctat   2220
cttccttcct ctctctcttc ctcttcttc attcagatct atatggcaaa tagccacaat    2280
tatataaatc atttcaagac tagaataggg ggatataata catattactc cacaccttt    2340 atgaatcaaa tatgattttt ttgttgttgt taagacagag tctcactttg cacccaggc    2400 tggagtgcag tggtgccatc accacggctc actgcagcct cagcgtcctg ggctcaaatg   2460
atcctcccac ctcagcctcc tgagtagctg ggactacagg ctcatgccat catgcccagc   2520
taatattttt ttattttcgt ggagacgggg cctcactatg ttgcctaggc tggaaatagg   2580
attttgaacc caaattgagt ttaacaataa taaaaagttg ttttacgcta aagatggaaa   2640
agaactagga ctgaactatt ttaaataaaa tattggcaaa agaaaaaaaa aaaaaaaaa    2700 aaaaaaa                                                              2707

<210> SEQ ID NO 56
<211> LENGTH: 1584
<212> TYPE: DNA
<213> ORGANISM: Homo sapiens

<400> SEQUENCE: 56
ggggagagga agagtggtag ggggagggag agagagagga agagtttcca aacttgtctc     60
cagtgacagg agacatttac gttccacaag ataaaactgc cacttagagc ccagggaagc    120
taaaccttcc tggcttggcc taggagctcg agcggagtca tgggctctct ggtcctgaca    180
ctgtgcgctc ttttctgcct ggcagcttac ttggtttctg gcagccccat catgaaccta    240
gagcagtctc ctctggaaga agatatgtcc ctctttggtg atgttttctc agagcaagac    300
ggtgtcgact ttaacacact gctccagagc atgaaggatg agtttcttaa gacactaaac    360
ctctctgaca tccccacgca ggattcagcc aaggtggacc accagagta catgttggaa    420 ctctacaaca aatttgcaac agatcggacc tccatgccct ctgccaacat cattaggagt    480
ttcaagaatg aagatctgtt tcccagccg gtcagtttta tgggctccg aaaatacccc    540 ctcctcttca atgtgtccat tcctcaccat gaagaggtca tcatggctga acttaggcta    600
tacacactgg tgcaaaggga tcgtatgata tacgatggag tagaccggaa aattaccatt    660
tttgaagtgc tggagagcaa agggggataat gagggagaaa gaaacatgct ggtcttggtg    720
tctggggaga tatatggaac caacagtgag tgggagactt tgatgtcac agatgccatc    780 agacgttggc aaaagtcagg ctcatccacc caccagctgg aggtccacat tgagagcaaa    840
cacgatgaag ctgaggatgc cagcagtgga cggctagaaa tagataccag tgcccagaat    900
```

```
aagcataacc ctttgctcat cgtgtttcct gatgaccaaa gcagtgacaa ggagaggaag    960
gaggaactga atgaaatgat ttcccatgag caacttccag agctggacaa cttgggcctg   1020
gatagctttt ccagtggacc tggggaagag gctttgttgc agatgagatc aaacatcatc   1080
tatgactcca ctgcccgaat cagaaggaac gccaaaggaa actactgtaa gaggaccccg   1140
ctctacatcg acttcaagga gattgggtgg gactcctgga tcatcgctcc gcctggatac   1200
gaagcctatg aatgccgtgg tgtttgtaac taccccctgg cagagcatct cacacccaca   1260
aagcatgcaa ttatccaggc cttggtccac ctcaagaatt cccagaaagc ttccaaagcc   1320
tgctgtgtgc ccacaaagct agagcccatc tccatcctct atttagacaa aggcgtcgtc   1380
acctacaagt ttaaatacga aggcatggcc gtctccgaat gtggctgtag atagaagaag   1440
agtcctatgg cttatttaat aactgtaaat gtgtatattt ggtgttccta tttaatgaga   1500
ttatttaata agggtgtaca gtaatagagg cttgctgcct tcaggaaatg gacaggtcag   1560
tttgttgtag gaaatgcata tttt                                         1584

<210> SEQ ID NO 57
<211> LENGTH: 4134
<212> TYPE: DNA
<213> ORGANISM: Homo sapiens

<400> SEQUENCE: 57
aggcctccct cgccagcggg gtgtggctcc cctccaaaga cggtcggctg acaggctcca     60
cagagctcca ctcacgctca gccctggacg acaggcagt ccaacggaac agaaacatcc    120
ctcagcccac aggcacgatc tgttcctcct gggaagatgc agaggctcat gatgctcctc    180
gccacatcgg gcgcctgcct gggcctgctg gcagtggcag cagtggcagc agcaggtgct    240
aaccctgccc aacgggacac ccacagcctg ctgcccaccc accggcgcca aaagagagat    300
tggatttgga accagatgca cattgatgaa gagaaaaaca cctcacttcc ccatcatgta    360
ggcaagatca agtcaagcgt gagtcgcaag aatgccaagt acctgctcaa aggagaatat    420
gtgggcaagg tcttccgggt cgatgcagag acaggagacg tgttcgccat tgagaggctg    480
gaccgggaga atatctcaga gtaccacctc actgctgtca ttgtggacaa ggacactggc    540
gaaaacctgg agactccttc cagcttcacc atcaaagttc atgacgtgaa cgacaactgg    600
cctgtgttca gcatcggtt gttcaatgcg tccgtgcctg agtcgtcggc tgtgggacc    660
tcagtcatct ctgtgacagc agtggatca gacgacccca ctgtgggaga ccacgcctct   720
gtcatgtacc aaatcctgaa ggggaaagag tattttgcca tcgataattc tggacgtatt   780
atcacaataa cgaaaagctt ggaccgagag aagcaggcca ggtatgagat cgtggtggaa   840
gcgcgagatg cccagggcct ccggggggac tcgggcacgg ccaccgtgct ggtcactctg   900
caagacatca atgacaactt ccccttcttc acccagacca agtacacatt tgtcgtgcct   960
gaagacaccc gtgtgggcac ctctgtgggc tctctgtttg ttgaggaccc agatgagccc  1020
cagaaccgga tgaccaagta cagcatcttg cggggcgact accaggacgc tttcaccatt  1080
gagacaaacc ccgcccacaa cgagggcatc atcaagccca tgaagcctct ggattatgaa  1140
tacatccagc aatacagctt catcgtcgag gccacagacc ccaccatcga cctccgatac  1200
atgagccctc ccgcgggaaa cagagcccag gtcattatca acatcacaga tgtggacgag  1260
ccccccattt tccagcagcc tttctaccac ttccagctga aggaaaacca gaagaagcct  1320
ctgattggca cagtgctggc catggaccct gatgcggcta gcatagcat tggatactcc  1380
atccgcagga ccagtgacaa gggccagttc ttccgagtca caaaaaaggg ggacatttac  1440
```

-continued

```
aatgagaaag aactggacag agaagtctac ccctggtata acctgactgt ggaggccaaa    1500
gaactggatt ccactggaac ccccacagga aaagaatcca ttgtgcaagt ccacattgaa    1560
gttttggatg agaatgacaa tgccccggag tttgccaagc cctaccagcc caaagtgtgt    1620
gagaacgctg tccatggcca gctggtcctg cagatctccg caatagacaa ggacataaca    1680
ccacgaaacg tgaagttcaa attcatcttg aatactgaga acaactttac cctcacggat    1740
aatcacgata cacggccaa catcacagtc aagtatgggc agtttgaccg ggagcatacc    1800
aaggtccact tcctacccgt ggtcatctca gacaatggga tgccaagtcg cacgggcacc    1860
agcacgctga ccgtggccgt gtgcaagtgc aacgagcagg gcgagttcac cttctgcgag    1920
gatatggccg cccaggtggg cgtgagcatc caggcagtgg tagccatctt actctgcatc    1980
ctcaccatca cagtgatcac cctgctcatc ttcctgcggc ggcggctccg gaagcaggcc    2040
cgcgcgcacg gcaagagcgt gccggagatc cacgagcagc tggtcaccta cgacgaggag    2100
ggcggcggcg agatggacac caccagctac gatgtgtcgg tgctcaactc ggtgcgccgc    2160
ggcggggcca agcccccgcg gccgcgctg acgcccggc cttccctcta tgcgcaggtg    2220
cagaagccac cgaggcacgc gcctggggca cacggagggc ccggggagat ggcagccatg    2280
atcgaggtga agaaggacga ggcggaccac gacggcgacg gccccccta cgacacgctg    2340
cacatctacg gctacgaggg ctccgagtcc atagccgagt ccctcagctc cctgggcacc    2400
gactcatccg actctgacgt ggattacgac ttccttaacg actggggacc caggtttaag    2460
atgctggctg agctgtacgg ctcggacccc cgggaggagc tgctgtatta ggcggccgag    2520
gtcactctgg gcctggggac ccaaaccccc tgcagcccag gccagtcaga cgccaggcac    2580
cacagcctcc aaaatggca gtgactccc agcccagcac ccttcctcg tgggtcccag    2640
agacctcatc agccttggga tagcaaactc caggttcctg aaatatccag gaatatatgt    2700
cagtgatgac tattctcaaa tgctggcaaa tccaggctgg tgttctgtct gggctcagac    2760
atccacataa ccctgtcacc cacagaccgc cgtctaactc aaagacttcc tctggctccc    2820
caaggctgca aagcaaaaca gactgtgttt aactgctgca gggtcttttt ctagggtccc    2880
tgaacgccct ggtaaggctg gtgaggtcct ggtgcctatc tgcctggagg caaaggcctg    2940
gacagcttga cttgtggggc aggattctct gcagcccatt cccaaggggag actgaccatc    3000
atgccctctc tcgggagccc tagccctgct ccaactccat actccactcc aagtgcccca    3060
ccactcccca acccctctcc aggcctgtca agagggagga aggggcccca tggcagctcc    3120
tgaccttggg tcctgaagtg acctcactgg cctgccatgc cagtaactgt gctgtactga    3180
gcactgaacc acattcaggg aaatggctta ttaaactttg aagcaactgt gaattcattc    3240
tggaggggca gtggagatca ggagtgacag atcacaggg gagggccacc tccacaccca    3300
cccctctgg agaaggcctg gaagagctga ccttgctt tgagactcct cagcacccct    3360
ccagttttgc ctgagaaggg gcagatgttc ccggagcaga agacgtctcc ccttctctgc    3420
ctcacctggt cgccaatcca tgctctcttt cttttctctg tctactcctt atcccttggt    3480
ttagaggaac ccaagatgtg gcctttagca aaactggaca atgtccaaac ccactcatga    3540
ctgcatgacg gagccgagcc atgtgtcttt acacctcgct gttgtcacat ctcagggaac    3600
tgaccctcag gcacaccttg cagaaggcaa ggccctgccc tgcccaacct ctgtggtcac    3660
ccatgcatct tccactggaa cgtttcactg caaacacacc ttggagaagt ggcatcagtc    3720
aacagagagg ggcagggaag gagacaccaa gctcacccctt cgtcatggac cgaggttccc    3780
```

| | |
|---|---|
| actctgggca aagcccctca cactgcaagg gattgtagat aacactgact tgtttgtttt | 3840 |
| aaccaataac tagcttctta taatgatttt tttactaatg atacttacaa gtttctagct | 3900 |
| ctcacagaca tatagaataa gggttttttgc ataataagca ggttgttatt taggttaaca | 3960 |
| atattaattc aggtttttta gttggaaaaa caattcctgt aaccttctat tttctataat | 4020 |
| tgtagtaatt gctctacaga taatgtctat atattggcca aactggtgca tgacaagtac | 4080 |
| tgtattttt tatacctaaa taaagaaaaa tctttagcct gggcaacaaa aaaa | 4134 |

```
<210> SEQ ID NO 58
<211> LENGTH: 2370
<212> TYPE: DNA
<213> ORGANISM: Homo sapiens

<400> SEQUENCE: 58
```

| | |
|---|---|
| ctccaaccat tggtgtctgt gtcattacta atagagtctt gtaaacactc gttaatcacg | 60 |
| gaaggccgcc ggcctggggc tccgcacgcc agcctgtggc gggtcttccc cgcctctgca | 120 |
| gcctagtggg aaggaggtgg gaggaaagaa ggaagaaagg gagggaggga ggaggcaggc | 180 |
| cagagggagg gaccgcctcg gaggcagaag agccgcgagg agccagcgga gcaccgcggg | 240 |
| ctggggcgca gccacccgcc gctcctcgag tcccctcgcc cctttccctt cgtgcccccc | 300 |
| ggcagcctcc agcgtcggtc cccaggcagc atggtgaggt ctgctcccgg accctcgcca | 360 |
| ccatgtacgt gagctacctc ctggacaagg acgtgagcat gtaccctagc tccgtgcgcc | 420 |
| actctggcgg cctcaacctg gcgccgcaga acttcgtcag ccccccgcag tacccggact | 480 |
| acggcggtta ccacgtggcg gccgcagctg cagcggcagc gaacttggac agcgcgcagt | 540 |
| ccccgggggcc atcctggccg gcagcgtatg gcgccccact ccgggaggac tggaatggct | 600 |
| acgcgcccgg aggcgccgcg gccgccgcca acgccgtggc tcacgccctc aacggtggct | 660 |
| cccccggccgc agccatgggc tacagcagcc ccgcagacta ccatccgcac caccacccgc | 720 |
| atcaccaccc gcaccacccg gccgccgcgc cttcctgcgc ttctgggctg ctgcaaacgc | 780 |
| tcaaccccgg ccctcctggg cccgccgcca ccgctgccgc cgagcagctg tctcccggcg | 840 |
| gccagcggcg gaacctgtgc gagtggatgc ggaagccggc gcagcagtcc ctcggcagcc | 900 |
| aagtgaaaac caggacgaaa gacaaatatc gagtggtgta cacggaccac cagcggctgg | 960 |
| agctggagaa ggagtttcac tacagtcgct acatcaccat ccggaggaaa gccgagctag | 1020 |
| ccgccacgct ggggctctct gagaggcagg ttaaaatctg gttcagaac cgcagagcaa | 1080 |
| aggagaggaa aatcaacaag aagaagttgc agcagcaaca gcagcagcag ccaccacagc | 1140 |
| cgcctccgcc gccaccacag cctccccagc tcagccagg tcctctgaga agtgtcccag | 1200 |
| agcccttgag tccggtgtct tccctgcaag cctcagtgtc tggctctgtc cctgggttc | 1260 |
| tggggccaac tgggggggtg ctaaacccca ccgtcaccca gtgacccacc gggttctgca | 1320 |
| gcggcagagc aattccaggc tgagccatga ggagcgtgga ctctgctaga ctcctcagga | 1380 |
| gagacccctc cctcccacc cacagccata gacctacaga cctggctctc agaggaaaaa | 1440 |
| tgggagccag gagtaagaca agtgggattt ggggcctcaa gaaatatact ctcccagatt | 1500 |
| tttacttttt cccatctggc ttttttctgcc actgaggaga cagaaagcct ccgctgggct | 1560 |
| tcattccgga ctggcagaag cattgcctgg actgaccaca ccaaccaggc cttcatcctc | 1620 |
| ctccccagct cttctcttcc tagatctgca ggctgcacct ctggctagag ccgaggggag | 1680 |
| agagggactc aagggaaagg caagcttgag gccaagatgg ctgctgcctg ctcatggccc | 1740 |
| tcggaggtcc agctgggcct cctgcctccg ggcaggcaag gtttacactg cggaagccaa | 1800 |

```
aggcagctaa gatagaaagc tggactgacc aaagactgca gaaccccccag gtggcctgcg    1860 tcttttttct cttcccttcc cagaccagga aaggcttggc tggtgtatgc acagggtgtg    1920
gtatgagggg gtggttattg gactccaggc ctgaccaggg ggcccgaaca gggacttgtt    1980
tagagagcct gtcaccagag cttctctggg ctgaatgtat gtcagtgcta taaatgccag    2040
agccaacctg gacttcctgt cattttcaca atcttggggc tgatgaagaa gggggtgggg    2100
ggagtttgtg ttgttgttgc tgctgttttgg gttgttggtc tgtgtaacat ccaagccaga    2160 gttttttaaag ccttctggat ccatgggggg agaagtgata tggtgaaggg aagtggggag    2220
tatttgaaca cagttgaatt ttttctaaaa agaaaaagag ataaatgagc tttccagatt    2280
tcagattctg tatttatctt cagattttgt ctgcaactat tttttatttt ttaaagaaat    2340
gaaatatctt caaaaaaaaa aaaaaaaaaa                                     2370

<210> SEQ ID NO 59
<211> LENGTH: 1708
<212> TYPE: DNA
<213> ORGANISM: Homo sapiens

<400> SEQUENCE: 59
aaatacttcc ccttcttccc caaagcagga ggttttattt aaaataaagc tgtttatttg      60
gcatttctgg gagaccctttt tctgaggaac cacagcaatg aatggctttg catccttgct    120
tcgaagaaac caatttatcc tcctggtact atttctttttg caaattcaga gtctgggtct    180
ggatattgat agccgtccta ccgctgaagt ctgtgccaca cacacaattt caccaggacc    240
caaaggagat gatggtgaaa aaggagatcc aggagaagag ggaaagcatg gcaaagtggg    300
acgcatgggg ccgaaaggaa ttaaggaga actgggtgat atgggagatc agggcaatat    360
tggcaagact gggcccattg gaagaaggg tgacaaaggg gaaaaaggtt tgcttggaat    420
acctggagaa aaaggcaaag caggtactgt ctgtgattgt ggaagatacc ggaaatttgt    480
tggacaactg gatattagta ttgctcggct caagacatct atgaagtttg tcaagaatgt    540
gatagcaggg attagggaaa ctgaagagaa attctactac atcgtgcagg aagagaagaa    600
ctacagggaa tccctaaccc actgcaggat tcggggtgga atgctagcca tgcccaagga    660
tgaagctgcc aacacactca tcgctgacta tgttgccaag agtggcttct ttcgggtgtt    720
cattggcgtg aatgaccttg aaagggaggg acagtacatg ttcacagaca acactccact    780
gcagaactat agcaactgga atgaggggga acccagcgac ccctatggtc atgaggactg    840
tgtggagatg ctgagctctg gcagatgaa tgacacagag tgccatctta ccatgtactt    900
tgtctgtgag ttcatcaaga agaaaagta acttccctca tcctacgtat ttgctatttt    960
cctgtgaccg tcattacagt tattgttatc catccttttt ttcctgattg tactacattt   1020
gatctgagtc aacatagcta gaaaatgcta aactgaggta tggagcctcc atcatcatgc   1080
tcttttgtga tgattttcat attttcacac atggtatatt attgacccaa taactcgcca   1140
ggttacatgg gtcttgagag agaattttaa ttactaattg tgcacgagat agttggttgt   1200
ctatatgtca aatgagttgt tctcttggta tttgctctac catctctccc tagagcactc   1260
tgtgtctatc ccagtggata atttcccagt ttactgtga tgattaggaa ggttgttgat   1320
ggttaggcta acctgccctg gcccaaagcc agacatgtac aagggctttc tgtgagcaat   1380
gataagatct ttgaatccaa gatgcccaga tcttttacca gtcacaccct atggccatgg   1440
ctatacttgg aagttctcct tgttggcaca gacatagaaa tgctttaacc ccaaaccttt   1500
```

| | |
|---|---|
| atatgggga cttctagctt tgtgtcttgt ttcagaccat gtggaatgat aaatactctt | 1560 |
| tttgtgcttc tgatctatcg atttcactaa catataccaa gtaggtgctt tgaaccccct | 1620 |
| tctgtaggct cacaccttaa tctcaggccc ctatatagtc acactttgat ttaagaaaaa | 1680 |
| tggagctctt gaaatcaaaa gaaaaaaa | 1708 |

<210> SEQ ID NO 60
<211> LENGTH: 2089
<212> TYPE: DNA
<213> ORGANISM: Homo sapiens

<400> SEQUENCE: 60

| | |
|---|---|
| agtttggacg gctgcttccc accagcaaag accacgactg gagagccgag ccggaggcag | 60 |
| ctgggaaaca tgaagagcgt cttgctgctg accacgctcc tcgtgcctgc acacctggtg | 120 |
| gccgcctgga gcaataatta tgcggtggac tgccctcaac actgtgacag cagtgagtgc | 180 |
| aaaagcagcc cgcgctgcaa gaggacagtg ctcgacgact gtggctgctg ccgagtgtgc | 240 |
| gctgcagggc ggggagaaac ttgctaccgc acagtctcag gcatggatgg catgaagtgt | 300 |
| ggcccggggc tgaggtgtca gccttctaat ggggaggatc cttttggtga agagtttggt | 360 |
| atctgcaaag actgtcccta cggcaccttc gggatggatt gcagagagac ctgcaactgc | 420 |
| cagtcaggca tctgtgacag ggggacggga aaatgcctga attccccctt cttccaatat | 480 |
| tcagtaacca agtcttccaa cagatttgtt tctctcacgg agcatgacat ggcatctgga | 540 |
| gatggcaata ttgtgagaga agaagttgtg aaagagaatg ctgccgggtc tcccgtaatg | 600 |
| aggaaatggt taaatccacg ctgatcccgg ctgtgatttc tgagagaagg ctctatttc | 660 |
| gtgattgttc aacacacagc caacatttta ggaactttct agattatagc ataaggacat | 720 |
| gtaattttg aagaccaaat gtgatgcatg gtggatccag aaaacaaaaa gtaggatact | 780 |
| tacaatccat aacatccata tgactgaaca cttgtatgtg tttgttaaat attcgaatgc | 840 |
| atgtagattt gttaaatgtg tgtgtatagt aacactgaag aactaaaaat gcaatttagg | 900 |
| taatcttacg tggagacagg tcaaccaaag agggagctag gcaaagctga agaccgcagt | 960 |
| gagtcaaatt agttctttga ctttgatgta cattaatgtt gggatatgga atgaagactt | 1020 |
| aagagcagga gaagatgggg aggggtggg agtgggaaat aaaatattta gcccttcctt | 1080 |
| ggtaggtagc ttctctagaa tttaattgtg cttttttttt ttttttttggc tttgggaaaa | 1140 |
| gtcaaaataa acaaccaga aaaccccctga aggaagtaag atgtttgaag cttatggaaa | 1200 |
| tttgagtaac aaacagcttt gaactgagag caatttcaaa aggctgctga tgtagttccc | 1260 |
| gggttacctg tatctgaagg acggttctgg ggcataggaa acacatacac ttccataaat | 1320 |
| agctttaacg tatgccacct cagagataaa tctaagaagt attttaccca ctggtggttt | 1380 |
| gtgtgtgtat gaaggtaaat atttatatat ttttataaat aaatgtgtta gtgcaagtca | 1440 |
| tcttccctac ccatatttat catcctcttg aggaaagaaa tctagtatta tttgttgaaa | 1500 |
| atggttagaa taaaactatg actctataag gttttcaaac atctgaggca tgataaattt | 1560 |
| attatccata attatagtaa taataacctt aataagcata agaaaaacag agtcactctg | 1620 |
| gatttcaaaa atgtcaaaaa atgagcaaca gagggtcctt atttaaacat aagtgctgtg | 1680 |
| acttaggtga attttcaatt taaggtagaa aataagtttt taggaggttt gtaaaagaag | 1740 |
| aatcaatttt cagcagaaaa catgtcaact ttaaaatata gtttattttc atattttttt | 1800 |
| cttttaaact tggttgataa gtggaattag gagtatattt gaaagaatct tagcacaaac | 1860 |
| aggactgttg tactagatgt tcttaggaaa tatctcagaa gtattttatt tgaagtgaag | 1920 |

-continued

| | |
|---|---|
| aacttattta agaattattt cagtatttac ctgtatttta ttcttgaagt tggccaacag | 1980 |
| agttgtgaat gtgtgtggga aggcctttga atgtaaagct gcataagctg ttaggttttg | 2040 |
| ttttaaaagg acatgtttat tattgttcaa taaaaaagaa caagataca | 2089 |

<210> SEQ ID NO 61
<211> LENGTH: 1059
<212> TYPE: DNA
<213> ORGANISM: Homo sapiens

<400> SEQUENCE: 61

| | |
|---|---|
| agcaagatgg atctactgtg gatcctgccc tccctgtggc ttctcctgct tgggggggcct | 60 |
| gcctgcctga agacccagga acaccccagc tgcccaggac ccagggaact ggaagccagc | 120 |
| aaagttgtcc tcctgcccag ttgtcccgga gctccaggaa gtcctgggga aagggagcc | 180 |
| ccaggtcctc aagggccacc tggaccacca ggcaagatgg gccccaaggg tgagccagga | 240 |
| gatccagtga acctgctccg gtgccaggaa ggccccagaa actgccggga gctgttgagc | 300 |
| cagggcgcca ccttgagcgg ctggtaccat ctgtgcctac ctgagggcag ggccctccca | 360 |
| gtcttttgtg acatggacac cgagggggc ggctggctgg tgtttcagag cgccaggat | 420 |
| ggttctgtgg atttcttccg ctcttggtcc tcctacagag caggttttgg gaaccaagag | 480 |
| tctgaattct ggctgggaaa tgagaatttg caccagctta ctctccaggg taactgggag | 540 |
| ctgcgggtag agctggaaga cttttaatggt aaccgtactt tcgcccacta tgcgaccttc | 600 |
| cgcctcctcg gtgaggtaga ccactaccag ctggcactgg gcaagttctc agagggcact | 660 |
| gcaggggatt ccctgagcct ccacagtggg aggccttta ccacctatga cgctgaccac | 720 |
| gattcaagca acagcaactg tgcagtgatt gtccacggtg cctggtggta tgcatcctgt | 780 |
| taccgatcaa atctcaatgg tcgctatgca gtgtctgagg ctgccgccca caaatatggc | 840 |
| attgactggg cctcaggccg tggtgtgggc caccccctacc gcagggttcg gatgatgctt | 900 |
| cgatagggca ctctggcagc cagtgccctt atctctcctg tacagcttcc ggatcgtcag | 960 |
| ccaccttgcc tttgccaacc acctctgctt gcctgtccac atttaaaaat aaaatcattt | 1020 |
| tagcccttc aaaaaaaaaa aaaaaaaaaa aaaaaaaa | 1059 |

<210> SEQ ID NO 62
<211> LENGTH: 2579
<212> TYPE: DNA
<213> ORGANISM: Homo sapiens

<400> SEQUENCE: 62

| | |
|---|---|
| gcagagcagc ggcggcagcg gcggcggcgg cagcagccac ccgatgtctt cggcgcccga | 60 |
| gaagcagcag ccaccgcacg gcggcggcgg cggcggcggc gggggaggcg gcgcggccat | 120 |
| ggaccccgcg tcgtccggcc cgtccaaggc caagaagacc aacgccggca tccggcgccc | 180 |
| ggagaagccg ccctattcct acatcgcgct catcgtcatg gccatccaga gttcacccac | 240 |
| caagcgcctg acgctgagcg agatctacca gttcctgcag agccgcttcc ccttcttccg | 300 |
| gggctcctac cagggctgga gaactccgt gcgccacaac ctctcgctca acgagtgctt | 360 |
| catcaagcta cccaagggcc ttgggcggcc cggcaagggc cactactgga ccatcgaccc | 420 |
| ggccagcgag ttcatgttcg aggagggctc cttcggcgg cggccgcgcg gcttccgaag | 480 |
| gaaatgccag gcgctcaagc ccatgtacag catgatgaac gggctcggct tcaaccacct | 540 |
| cccggacacc tacggcttcc agggctcggc cggcggcctc tcgtgccgc ccaacagcct | 600 |

| | | |
|---|---|---|
| ggcgctggag ggcggcctgg gcatgatgaa cggccacttg ccgggcaacg tggacggcat | 660 | |
| ggccctgccc agccactcgg tgccccacct gccttccaac ggcggccact cgtacatggg | 720 | |
| cggctgcggc ggcgcggcgg ccggcgagta cccgcaccac gacagctcgg tgcccgcctc | 780 | |
| cccgctgctg cccaccggcg ccggtggggt catggagccg cacgccgtct actcgggctc | 840 | |
| ggcggcggcc tggccgccct cggcgtccgc ggcgctcaac agcggcgcct cttatatcaa | 900 | |
| gcagcagccc ctgtcccct gtaacccgc ggccaacccc ctgtccggca gcctctccac | 960 | |
| gcactccctg gagcagccgt atctgcacca gaacagccac aacgcccag ccgagctgca | 1020 | |
| aggcatcccg cggtatcact cgcagtcgcc cagcatgtgt gaccgaaagg agtttgtctt | 1080 | |
| ctctttcaac gccatggcgt cctcttccat gcactcggcc ggcggggct cctactacca | 1140 | |
| ccagcaggtc acctaccaag acatcaagcc ttgcgtgatg tgaggctgcc gccgcaggcc | 1200 | |
| ctcctggtgc aggcaggcgg gtcacaggga ccctggaccg gcacaagaaa ctgctttctt | 1260 | |
| ctcgaggtat aaccgtcggc agaagaaaag ggttccacct ctccccaacc ggagttttg | 1320 | |
| gcaaggagtc cccaatgcaa agacacgcg ctgcggttgg cacctccttc ctcactcctt | 1380 | |
| caaaattgtt aagaaatgtt agtggtgggt ctgatctgac tgcagccatc ggtaaataaa | 1440 | |
| agtttttgat cctgttgaac ccgcctgaga cggtgctgtg caggggaaag cccccgcacc | 1500 | |
| cacacaggaa ttctgctgag gtccccctc cttccggcca atggcagaag tgggggaaaa | 1560 | |
| tttttagaag aaaagcaaac atgtgagacc aatcattatc aaatactttt atttttggt | 1620 | |
| tgagtattta tctttttatt ttttattttt tttttgaaag aatgtcttgg aatgcgcaag | 1680 | |
| tctccctta gagccgtctt ttgcaggag cgggaagtga caagagctca gatctccctc | 1740 | |
| ccgatctccc tccccacctc cgaagtctcc tccgtggacc acaggtggat ctttgtgcga | 1800 | |
| acaacttgca tttcggaagc cactgtccgt ctttaaacag aaagtcaaag gagccacgaa | 1860 | |
| gcaagcggcc gtccgggcgt ccgcctccgt cccttccat gttcctcctc ttccttcgct | 1920 | |
| tcagcctctt ctgttatgtt ttgtcttgaa ttttatttag acttttcag tgggtatttt | 1980 | |
| tctgtctccc aacctctact gtaaactttc tggtccgaga cgagccgaa cacagcgcga | 2040 | |
| cgcagggact aggacggccc ggtgaccgcg cggattcagg attgcgggga cgcagaaagg | 2100 | |
| ttaaggcact tttaaaaact atagcaaggc tcctgtttat ttattctact ttctttccct | 2160 | |
| aataatcaaa acaccgcgta ggctcctccg tttatcagta ttaatggtgt aactttgttg | 2220 | |
| gcaatatttg ccgtgtagaa ttttttttag atatccattg taaatttgaa acaaagaccg | 2280 | |
| atctgtgtaa aaacaaattt ccatatgttt tatataaata tatatataat atgaaggact | 2340 | |
| accctccttt ttttttttg tattttggct gctagagtgc agcatttgtg acacgtattt | 2400 | |
| gaaatttgaa atttccttct gcactgtata aaaggaccat ttgaggatgt tttgcctttt | 2460 | |
| gtgtattttt tcctaaaaaa agaacaaaaa taaaaatgta taacatttgt acatggcctt | 2520 | |
| taaaattgta tcaactagaa ataaaattgc atgagtattt taaaaaaaaa aaaaaaaa | 2579 | |

<210> SEQ ID NO 63
<211> LENGTH: 1749
<212> TYPE: DNA
<213> ORGANISM: Homo sapiens

<400> SEQUENCE: 63

| | | |
|---|---|---|
| gcggtcttat ataagccaga tccgcagggg agtccgcaga agggttaaac aggtctttgg | 60 | |
| gcttcggcga cctcgcccgc ggcagaaacc ggtaagaaga cagtgggctg cgcgtctcat | 120 | |
| tttcagcctt gcccggactc tcccaaagcc ggcgcccagt agtggctcca gagcccacag | 180 | |

```
gtggccccg gcagtctctg gggcgcatgg agcggcgtta ataggggctgg cggcgcaggc    240 cagtagccgc tccaacatga acctcgtggg cagctacgca caccatcacc accatcacca    300
cccgcaccct gcgcacccca tgctccacga accttcctc ttcggtccgg cctcgcgctg     360
tcatcaggaa aggccctact tccagagctg gctgctgagc ccggctgacg ctgccccgga    420
cttccctgcg ggcgggccgc cgcccgcggc cgctgcagcc gccaccgcct atggtcctga    480
cgccaggcct gggcagagcc ccgggcggct ggaggcgctt ggcggccgtc ttggccggcg    540
gaaaggctca ggacccaaga aggagcggag acgcactgag agcattaaca gcgcattcgc    600
ggagttgcgc gagtgcatcc ccaacgtgcc ggccgacacc aagctctcca agatcaagac    660
tctgcgccta gccaccagct acatcgccta cctgatggac gtgctggcca aggatgcaca    720
gtctggcgat cccgaggcct tcaaggctga actcaagaag gcggatggcg gccgtgagag    780
caagcggaaa agggagctgc agcagcacga aggttttcct cctgccctgg gcccagtcga    840
gaagaggatt aaaggacgca ccggctggcc gcagcaagtc tgggcgctgg agttaaacca    900
gtgagccgag gcccgcgccg aggacctggc caggccagcc actcctgaag ccccgggagg    960
agaggaaggc agcggcgaac gccaggctct gggctccggc gactggtgct acgcatcccg   1020
cggagcttct gctgagcgcc ggcaggtcgt cggctgcaac cacacacttg gatcgcacgt   1080
gcaatgtcct ttgattttttt ttaatacatt aagagaaaga gaatatata tatatccacc   1140 cccagcccaa ccgagggcgg cccttggcgg caacatgcaa gaaggaggga ctgtcgaacc   1200
caagggctca aagacgcact cttccaccct tttggagcga atttagaacc tcagccctat   1260
ctccatttcc ctatctggct cttttctctct tgtccctcca tatgatccgc ccgacgccg   1320 tcttctctaa ttaaaatgca ataaggaatc aattcttttc tgcctgagaa agagaaccag   1380
acgcaggaag atgaaaggct gcccttttgtt cttcgaatcg tggtggtttt atttttatttt   1440 tcttttttgtc gctgcacttc ctgtttagtt ccaagggaaa cactttctct ctttctctgt   1500
ctctctcttt tcttccttct tttccttcct ttttgtttct atctaaataa aagctttccc   1560
tgtgttggaa agtttttatg tatttaaact acctaccatg cctgttgtgc tcaggtgttt   1620
gttcatcctg ccatccccaa ccctttctta cctcaagtct gtgtgaccac tcacagcccc   1680
cctcccttcg ccaaagcagt gtctatgctc ttgattaata aaacatttttc tgaaatcaaa   1740 aaaaaaaaa                                                           1749
```

<210> SEQ ID NO 64
<211> LENGTH: 2368
<212> TYPE: DNA
<213> ORGANISM: Homo sapiens

<400> SEQUENCE: 64

```
ctgtacatgg agatcttgct gggaaaatcc gcttgctccc ctcacgtcgt ccagcccagg     60
agaaccaccg ccgtcacccc ggagcttcct cggccaccgc gcagagccct ccgagagccc    120
gagccgcggt cttcgagctc caaggctcat tcagggcccc agatccttgc cccgaaagga    180
gaggatctga gaaaatggat gcactgagac ctctctgaaa accctccgag agagcgcgag    240
aggagcgagg acacgttact cgcagctaaa atcacattta aggaccaaaa caacaacaac    300
caaaaatttc attaaaacaa taagcgccca agaacccaga tcgggctggt ggggggaggg    360
gaagaggcgg gaaggggagg gtcgcacgga ggtagctttg cagtgagcag tcgacccgc    420 cgccccccgg cacagctgga ccggctcctc cagccgcggc tcagactcgc ccctggattc    480
```

| | |
|---|---|
| cgggttagct tcggtgccag gaccgcggcc cgggcttgga ttcccgagac tccgcgtacc | 540 |
| agcctcgcgg gagccccggc acctttgtat gagcacgaga ggattctgcc tccgcgcagc | 600 |
| agcccgggaa gcaggagccg aagcgcgggc cgtggagcaa ggcgggaacc ggaggcggcg | 660 |
| gcggcggcgg ccaggggcgc acggtgccag gaccagctcg ccgcgcccca tggggagccg | 720 |
| gcggccgcag cgctgctgag gcgggcccgg ctggccaggc gggggacgg ggcccgggct | 780 |
| gcagcagccc cctctgcggc tgccgggcgg gcccgggcgc ccggggctg ggggtgggg | 840 |
| ggtgggggag gacgccgagc gctgaggcag gggcccgggc cgagggcgcg gcggggctgc | 900 |
| gcgcacgctg gggcgcgtgg aggggcgcgg agggcgaaat gagtctggta ggtggttttc | 960 |
| cccaccaccc ggtggtgcac cacgagggct acccgtttgc cgccgccgcc gccgcagctg | 1020 |
| ccgccgccgc cgccagccgc tgcagccatg aggagaaccc ctacttccat ggctggctca | 1080 |
| tcggccaccc cgagatgtcg ccccccgact acagcatggc cctgtcctac agccccgagt | 1140 |
| atgccagcgg cgccgccggc ctggaccact cccattacgg gggggtgccg ccgggcgccg | 1200 |
| ggcccccggg cctgggggg ccgcgcccgg tgaagcgccg aggcaccgcc aaccgcaagg | 1260 |
| agcggcgcag gactcagagc atcaacagcg ccttcgccga actgcgcgag tgcatcccca | 1320 |
| acgtacccgc cgacaccaaa ctctccaaaa tcaagaccct cgcctggcc accagctaca | 1380 |
| tcgcctacct catggacctg ctggccaagg acgaccagaa tggcgaggcg gaggccttca | 1440 |
| aggcagagat caagaagacc gacgtgaaag aggagaagag gaagaaggag ctgaacgaaa | 1500 |
| tcttgaaaag cacagtgagc agcaacgaca agaaaaccaa aggccggacg ggctggccgc | 1560 |
| agcacgtctg ggccctggag ctcaagcagt gaggaggagg agaaggagga ggaggagagc | 1620 |
| gcgagtgagc aggggccaag gcgccagatg cagacccagg actccggaaa agccgtccgc | 1680 |
| gctccgctct gaggactcct tgcatttgga atcatccggt ttatttatgt gcaatttcct | 1740 |
| tcccctctct ttgacccct ttgaggcatc tgctccccgt ctcccctcc aaaaaaaaag | 1800 |
| tggatatttg aagaaaagca ttccatattt taatacgaag aggacactcc cgtgtggtaa | 1860 |
| gggatcccgt cgtctcatag attctgtgtg cgtgaatgtt ccctcttggc tgtgtagaca | 1920 |
| ccagcgttgc cccccgccaa cctactcaac cccttccaga taaagacagt gggcactagt | 1980 |
| gcgtttgtga agtgtatctt taatacttgg cctttggata taaatattcc tgggtattat | 2040 |
| aaagttttat ttcaaagcag aaaacagggc cgctaacatt tccgttgggg tcggtatcta | 2100 |
| gtgctatcca ttcatctgtg gtcgttccct ctttgaagat gtttccaaca gccacttgtt | 2160 |
| ttgtgcactt ccgtcctcta aaactaaatg gaatttaatt aatattgaag gtgtaaacgt | 2220 |
| tgtaagtatt caataaacca ctgtgttttt tttttacaaa aaccttaatc ttttaatggc | 2280 |
| tgatacctca aaagagtttt gaaaacaaag ctgttatact tgttttcgta atatttaaaa | 2340 |
| tattcagaag taaactaaat tatcatga | 2368 |

<210> SEQ ID NO 65
<211> LENGTH: 2319
<212> TYPE: DNA
<213> ORGANISM: Homo sapiens

<400> SEQUENCE: 65

| | |
|---|---|
| ttccccactc ccccgccctc cccagggccc tgggaagggg ctcagcgtgg gaaaggatgg | 60 |
| ttgagtttta accagaggca aagcgtgagc gggatcagtg tgtgcggaac gcaagcagcc | 120 |
| gagagcggag aggcgccgct gtagttaact cctccctgcc cgccgcgccg accctccca | 180 |
| ggaaccccca gggagccagc atgaagcgag ctcacccga gtacagctcc tcggacagcg | 240 |

```
agctggacga gaccatcgag gtggagaagg agagtgcgga cgagaatgga aacttgagtt    300
cggctctagg ttccatgtcc ccaactacat cttcccagat tttggccaga aaagacgga    360 gaggaataat tgagaagcgc cgacgagacc ggatcaataa cagtttgtct gagctgagaa    420
ggctggtacc cagtgctttt gagaagcagg gatctgctaa gctagaaaaa gccgagatcc    480
tgcagatgac cgtggatcac ctgaaaatgc tgcatacggc aggagggaaa ggttactttg    540
acgcgcacgc ccttgctatg gactatcgga gtttgggatt cgggaatgc ctggcagaag    600 ttgcgcgtta tctgagcatc attgaaggac tagatgcctc tgacccgctt cgagttcgac    660
tggtttcgca tctcaacaac tacgcttccc agcgggaagc cgcgagcggc gcccacgcgg    720
gcctcggaca cattccctgg gggaccgtct tcggacatca cccgcacatc gcgcacccgc    780
tgttgctgcc ccagaacggc cacgggaacg cgggcaccac ggcctcaccc acggaaccgc    840
accaccaggg caggctgggc tcggcacatc cggaggcgcc tgctttgcga gcgcccccta    900
gcggcagcct cggaccggtg ctccctgtgg tcacctccgc ctccaaactg tcgccgcctc    960
tgctctcctc agtggcctcc ctgtcggcct tccccttctc tttcggctcc ttccacttac   1020
tgtctcccaa tgcactgagc ccttcagcac ccacgcaggc tgcaaacctt ggcaagccct   1080
atagaccttg ggggacggag atcggagctt tttaaagaac tgatgtagaa tgagggaggg   1140
gaaagtttaa atcccagct gggctggact gttgccaaca tcaccttaaa gtcgtcagta   1200
aaagtaaaaa ggaaaaaggt acactttcag ataatttttt ttttaaagac taaaggtttg   1260
ttggtttact tttatctttt ttaatgtttt tttcatcatg tcatgtatta gcagttttta   1320
aaaactagtt gttaaatttt gttcaagaca ttaaattgaa atagtgagta taagccaaca   1380
ctttgtgata ggtttgtact gtgcctaatt tactttgtaa accagaatga ttccgttttt   1440
gcctcaaaat ttggggaatc ttaacattta gtattttgg tctgttttc tccttgtata   1500 gttatggtct gttttagaa ttaattttcc aaaccactat gcttaatgtt aacatgattc   1560
tgtttgttaa tattttgaca gattaaggtg ttgtataaat aatattcttt tgggggagg   1620 ggaactatat tgaattttat atttctgagc aaagcgttga caaatcagat gatcagcttt   1680
atccaagaaa gaagactagt aaattgtctg cctcctatag cagaaaggtg aatgtacaaa   1740
ctgttggtgg ccctgaatcc atctgaccag ctgctggtat ctgccaggac tggcagttct   1800
gatttagtta ggagagagcc gctgataggt taggtctcat ttggagtgtt ggtggaaagg   1860
aaactgaagg taattgaata gaatacgcct gcatttacca gccccagcaa cacaagaat   1920 ttttaatcac acggatctca aattcacaaa tgttaacatg gataagtgat catggtgtgc   1980
gagtggtcaa ttgagtagta cagtggaaac tgttaaatgc ataacctaat ttcctggga   2040 ctgccatatt ttctttaac tggaaatttt tatgtgagtt ttccttttgg tgcatggaac   2100
tgtggttgcc aaggtattta aaagggcttt cctgcctcct tctctttgat ttatttaatt   2160
tgatttgggc tataaaatat catttttcag gtttattctt ttagcaggtg tagttaaacg   2220
acctccactg aactgggttt gacctctgtt gtactgatgt gttgtgacta aataaaaaag   2280
aaagaacaaa gtaaaaaaaa aaaaaaaaa aaaaaaaa                           2319
```

<210> SEQ ID NO 66
<211> LENGTH: 1198
<212> TYPE: DNA
<213> ORGANISM: Homo sapiens

<400> SEQUENCE: 66

| | |
|---|---|
| gagacagaag gccgcctacc ggggaggccg gaggccggct agtcgcggac tcgggcgaac | 60 |
| ccaccctcgc gatctgtcaa gtctgtcccc aggggaggtc cccctttcgg gaggaagttt | 120 |
| ttaaggggat ttctcaaaat caccccccgcg cttccttcac tccttcctta gagccggagg | 180 |
| tcggtgaggg cccgcggaat catctatctc gccccgtcg cagcgcgcag ggaccatgtc | 240 |
| ggcggagacc gcgagcggcc ccacagagga ccaggtggaa atcctggagt acaacttcaa | 300 |
| caaggtcgac aagcacccgg attccaccac gctgtgcctc atcgcggccg aggcaggcct | 360 |
| ttccgaggag gagacccaga atggttttaa gcagcgcctg gcaaagtggc ggcgctcaga | 420 |
| aggcctgccc tcagagtgca gatccgtcac agactaagga gatggcaggc attgacagct | 480 |
| tcactccatg aaggccatct ctgtttctct cctccgctta accaagctgt tgtggttttt | 540 |
| cagcatagtg ttgtatgttc cattgctagc tgtcctgctg tttaacacag tgttgtattt | 600 |
| tttttctaaa tgtacataat tagaaaagaa ataacaata ggaagctatg tgtatcttct | 660 |
| gtgtaaagca gtggcttcac tggaaaaatg gtgtggctag catttccctt tgagtcatga | 720 |
| tgacagatgg tgtgaaaacc atctaagttt gcttttgacc atcacctccc agtagcaatt | 780 |
| tgctttcata atccatttag caatccaggc ctctgttgaa aagataatat gagggagaag | 840 |
| ggaacacatt tccttctgaa cttacttccc taagtcactt tccttatgta tcatctaata | 900 |
| caatgatggt tgagtgaaaa tacagaaggg gtgtttgagt attcagattt cataaaacac | 960 |
| ttccttggaa tatagctgca ttaacttgga aagaagcctg ttgggccaga agacagaaac | 1020 |
| tccaactggc aaaaaagcaa gcatctaaga aaaaaaacca ccaaagttct tgaatttact | 1080 |
| atatttaaat gcattggtta agtttatttt gctaaataaa gtgaactgct ttttgtctct | 1140 |
| aaaatgatat tctaaataaa accttaactt tttgttgaag atgcactgaa aaaaaaaa | 1198 |

<210> SEQ ID NO 67
<211> LENGTH: 8988
<212> TYPE: DNA
<213> ORGANISM: Homo sapiens

<400> SEQUENCE: 67

| | |
|---|---|
| actggggtgg cgcgctacct ctgcggagaa ggatctgaca gtgttccgga gccggggcga | 60 |
| gcagccaaaa ggcccgcgga gtcgcgctgg gccgccccgg cgcagctgaa ccgggggccg | 120 |
| cgcctgccag gccgacgggt ctggcccagc ctggcgccaa ggggtcgtg cgctgtggag | 180 |
| acgcggaggg tcgaggcggc gcggcctgag tgaaacccaa tggaaaaagc atgacattta | 240 |
| gaagtagaag acttagcttc aaatcccctac tccttcactt actaattttg tgatttggaa | 300 |
| atatccgcgc aagatgttga cgttgcagac ttggctagtg caagccttgt ttatttcct | 360 |
| caccactgaa tctacaggtg aacttctaga tccatgtggt tatatcagtc ctgaatctcc | 420 |
| agttgtacaa cttcattcta atttcactgc agtttgtgtg ctaaaggaaa aatgtatgga | 480 |
| ttattttcat gtaaatgcta attacattgt ctggaaaaca aaccatttta ctattcctaa | 540 |
| ggagcaatat actatcataa acagaacagc atccagtgtc acctttacag atatagcttc | 600 |
| attaaatatt cagctcactt gcaacattct tacattcgga cagcttgaac agaatgttta | 660 |
| tggaatcaca ataatttcag gcttgcctcc agaaaaacct aaaaatttga gttgcattgt | 720 |
| gaacgagggg aagaaaatga ggtgtgagtg ggatggtgga agggaaacac acttggagac | 780 |
| aaacttcact ttaaaatctg aatgggcaac acacaagttt gctgattgca aagcaaaacg | 840 |
| tgacaccccc acctcatgca ctgttgatta ttctactgtg tattttgtca acattgaagt | 900 |
| ctgggtagaa gcagagaatg cccttgggaa ggttacatca gatcatatca attttgatcc | 960 |

```
tgtatataaa gtgaagccca atccgccaca taatttatca gtgatcaact cagaggaact   1020
gtctagtatc ttaaaattga catggaccaa cccaagtatt aagagtgtta taatactaaa   1080
atataacatt caatatagga ccaaagatgc ctcaacttgg agccagattc ctcctgaaga   1140
cacagcatcc acccgatctt cattcactgt ccaagacctt aaacctttta cagaatatgt   1200
gtttaggatt cgctgtatga aggaagatgg taagggatac tggagtgact ggagtgaaga   1260
agcaagtggg atcacctatg aagataacat tgcctccttt tgaagccaat ggaaaaatct   1320
tggattatga agtgactctc acaagatgga aatcacattt acaaaattac acagttaatg   1380
ccacaaaact gacagtaaat ctcacaaatg atcgctatct agcaacccta acagtaagaa   1440
atcttgttgg caaatcagat gcagctgttt taactatccc tgcctgtgac tttcaagcta   1500
ctcaccctgt aatggatctt aaagcattcc ccaaagataa catgctttgg gtggaatgga   1560
ctactccaag ggaatctgta aagaaatata tacttgagtg gtgtgtgtta tcagataaag   1620
caccctgtat cacagactgg caacaagaag atggtaccgt gcatcgcacc tatttaagag   1680
ggaacttagc agagagcaaa tgctatttga taacagttac tccagtatat gctgatggac   1740
caggaagccc tgaatccata aaggcatacc ttaaacaagc tccaccttcc aaaggaccta   1800
ctgttcggac aaaaaaagta gggaaaaacg aagctgtctt agagtgggac caacttcctg   1860
ttgatgttca gaatggattt atcagaaatt atactatatt ttatagaacc atcattggaa   1920
atgaaactgc tgtgaatgtg gattcttccc acacagaata tacattgtcc tctttgacta   1980 gtgcacatt gtacatggta cgaatggcag catacacaga tgaaggtggg aaggatggtc   2040
cagaattcac ttttactacc ccaaagtttg ctcaaggaga aattgaagcc atagtcgtgc   2100
ctgtttgctt agcattccta ttgacaactc ttctgggagt gctgttctgc tttaataagc   2160
gagacctaat taaaaaacac atctggccta atgttccaga tccttcaaag agtcatattg   2220
cccagtggtc acctcacact cctccaaggc acaattttaa ttcaaaagat caaatgtatt   2280
cagatggcaa tttcactgat gtaagtgttg tggaaataga agcaaatgac aaaaagcctt   2340
ttccagaaga tctgaaatca ttggaccgtt tcaaaaagga aaaaattaat actgaaggac   2400
acagcagtgg tattgggggg tcttcatgca tgtcatcttc taggccaagc atttctagca   2460
gtgatgaaaa tgaatcttca caaaacactt cgagcactgt ccagtattct accgtggtac   2520
acagtggcta cagacaccaa gttccgtcag tccaagtctt ctcaagatcc gagtctaccc   2580
agcccttgtt agattcagag gagcggccag aagatctaca attagtagat catgtagatg   2640
gcggtgatgg tattttgccc aggcaacagt acttcaaaca gaactgcagt cagcatgaat   2700
ccagtccaga tatttcacat tttgaaaggt caaagcaagt ttcatcagtc aatgaggaag   2760
attttgttag acttaaacag cagatttcag atcatatttc acaatcctgt ggatctgggc   2820
aaatgaaaat gtttcaggaa gtttctgcag cagatgcttt tggtccaggt actgagggac   2880
aagtagaaag atttgaaaca gttggcatgg aggctgcgac tgatgaaggc atgcctaaaa   2940
gttacttacc acagactgta cggcaaggcg gctacatgcc tcagtgaagg actagtagtt   3000
cctgctacaa cttcagcagt acctataaag taaagctaaa atgatttttat ctgtgaattc   3060 agattttaaa aagtcttcac tctctgaaga tgatcatttg cccttaagga caaaaatgaa   3120
ctgaagtttc acatgagcta tttccattcc agaatatctg ggattctact taagcacta   3180 cataaactga ctttatcctc agactagctg aatgattttg tgctgtttca ggatgtttgc   3240
actgaagaaa aacagaaagc ttatctgaaa tttataaaac ttttttgtttt gctacataga   3300
```

-continued

```
aaacagaagg tatttgaata ataagcagtg atatgcttag tgagcacagc tatactgatt    3360
ttgattagaa tagtcatcag agtggcttag ggacagttaa tataaaagag gagcaaggtg    3420
tagaccatca tctacttctg ctaaaataac ttaaaaagag gtccataggc cataactaca    3480
tgagcccagc ttttgtaatc tgacaaaaaa atgaggagca gcttcgtgta tatcagtgta    3540
cacggtattc cttaggtccc ttccattggt agtgatgctg cgagttatta ctggagaaaa    3600
ggaattctag agctttaact tggcagatta aaagtactca tttttattc atcaataatt      3660 agtaatctca ctagttttca aaaatttgca tattattgac aacctctttg aagatgcatt    3720
tcacaaactc aacagagtgc catgataaga gctagggatc ccccaaacta tctcaagcat    3780
ctaaaaaatt gccatttta aaggcttaaa ttgtagtagt aaaggggaaa acaggaagta     3840
gtagtaaagg ggaaaaaaaa ccaataaagc atctaaaaaa ttggcatgtt aaaaggctta    3900
aattgctaat gtgtgtatat atatatatat atatacacac acatatcatt gacttttctt    3960
aagacttcag agtactgggt agatgaacac tttatacagt atatatcttc agcttaaatt    4020
tgttttgagt atttttttta ttttaaata agtaggcaaa gatttaaatt ttttatttt       4080 tagtaaatgt ttgaggcaca ctaagacaac ttgggcaata tttgccaaaa caaaacagaa    4140
ccccaaaaaa tgtacatctt gttcttagca aatatcatta ttgtagagac acttaataaa    4200
gagatggtat tttaatgtct gcagttctga ggtagggtgg aacttagttc tacattgtga    4260
tttaggaatt ttaaaacct tttttcttca agggagaagt gacccaggcc tcgagtttag      4320
tgctaaagcc gctagtgtac ttatgctgtc ccctaaccac cacgtgcgat atggaagcag    4380
atgctaaata taggggttt cttagaaagt aagaggaaat tagcaagcgt tattagtgat     4440
tgactactgc tatcaagtga attcaaagga aacaggtttt tatgccatat ttaagttaca    4500
gaaaccaggc atgcttagaa tagtttctag aggttattgg agaatagaaa gctaagaaaa    4560
cttggtatac atttacaatg gaaatataat tacacttttt actctcagaa tattgttcac    4620
attagacttc ctgtttatct tttatattct tgcatttata taatgcctca tccttttcaaa   4680 gttctttcac atattatatg atcttcttta tgaaaaaaat agatgtttca ttctgatata    4740
ttcagttccc cactttaggc aaaagtagat taatagaatg acgaattcaa agtgatgag     4800 gaaaatcagg cacagagaag taaggtagg gatagaccca aatttacaca acaagataat     4860
gacatctcca gcttttaagt tgatcatcaa aggctgggct ggattgtct tgctgtatgt     4920 gtcaggaaat ttatacctat tacatttcc attttctcaa aatttaagtc acatgactaa     4980
tatttagctg caacttttcct cataacaaat agtgtcatga agaatgttgt agtgtgaagt   5040
ttgtacattt cagggtcaga tatacaatat gaactcttaa tctacaggaa tgagaatgga    5100
ggatcattga aggccatgat ataaacaaat ttgcatgttg aagcctgtat aaaacatggt    5160
acagtgagtg aatatacccc catccccaag aacactttat acatattaaa tggatatatg    5220
attactgtgc aaaaattcat tctgaaaatg aacatatatt tgagcactaa tatgtaatgt    5280
acacctgccc taaggagaaa ataaattata aaactttta cattcaaaat tactttccca     5340
agcatgtctt agaataatct atgtgttgat gcatgtaaat tgtactttag gtaggcaaag    5400
aaatctggtt atttatgtaa aaactagtct aataagtta gttagtggct ttatcacttt      5460
aaatctttag tgtccaaaag tggtgtttaa agtaatagca catcagaaaa ccttgtctgg    5520
acaaaactag ttcactcact gcttctgcac ctgcagttgc tccctttagg gttataaaat    5580
aatgacccaa atgttacatg tgttgatatt taacttgtc agttactgat gtctgtggta      5640 tcctacccctc atctctgaaa gggataatac tgaataatta ttagaaaact ataaaacttc   5700
```

```
acactttgta ccattaaaac ctaaaatttt aatcttgtcc ttttttacta tggatcagtc   5760
ggcactcggg aacagcagca aggaaaaaaa gcaaatttca ttcacatgtt ctgtgttcat   5820
acctcttctc tacctaattg ttcatttaaa tttcagcctt attccttgat aagggatttt   5880
accacatgaa gtcatccagt gaccctagct cttattgtga agttagtgga gtatacttag   5940
aaatgttaca actttaaaat gttacaaaac attcattaaa gctcatattt aaagtagagc   6000
atctagtttg agaaatagaa atcaattatt aaagatgtct ttttctacc catttaacta   6060 gttaaaacca tgacatgtaa atgtagaagt agaataatca tagaattccc taaaatattt   6120
ctgtttacta acatatattg accaagtaca tcaagcagga gagatcttcc ttcattctgt   6180
tatagtccac atcattctaa ttttgctcag ttgttattaa gagcatattc ctaaaccata   6240 cactttgtt tcaataaagt tttatttgt tgagatgaat aaaataacaa agttataagc   6300
tgcataagac aaaagttcaa ttgttcaaaa aaaatttact gggatagctt tctattacag   6360
gtattgttag attatattgt gctgataaga ttactttcta aaaaatttgt acttttctgt   6420
aaattaaaag aatatggagt cataaaatgg caagtgtttt aggattagcc taaaattgga   6480
cattgtcatt gatttcaaag aaggtatgaa ctagcagtct tacagcctaa ttcttctttg   6540
gactggtcct tggcagcagt tccttttcag actcgataaa cagaattcag atgatgtaag   6600
tcaaaacaaa actttacaaa gccaagcgta ttatcttttg cattaaccta tttttttcca   6660
tcatacatgc tactagtatg tgcattagca tgatattctc atatacattg cattaaaaat   6720
taaaaggtgg cagctcaggg tgagctcttc tgttgctcat ttgttcctaa attttttaagg   6780 gcttttctc agtcaatagt ttgtacaaac tggttagttt aacttcatta cccatttcat   6840
taaagttgat gggtcgtgtg atgagatgca tttaaggccg atagtgatag atgttttttt   6900
tatttcttga acacaggctt tgtctgaatg atgttctttt atctcttgaa cacaagcttt   6960
gaatgataac tacaggtttt aagtgctgtt acattaatac cataatgtga tgtgttagaa   7020
acaaagggat atttcaaagg tagatatttg aaaattctct agtctcaata tgtatgtgta   7080
ttgaatatac tctaaaaata aatgtgcaat ttgctagtag gacaatgcag tgactgacta   7140
gcattaggta tgtttctttt atatcctagc tatgtcccac tttcttctaa gtgcaatcct   7200
ttcatgttca cttgctgttt taccccatct actctaactt catttggaag gcttgtctag   7260
agtatagcat gtattttac ctttgcagtg aattgcatgt gctaattgta accacagcta   7320
tttttatgtt gacataactc caaatgttat attaaatgtt ctattatata ttagctctaa   7380 tccctaagt aaatttaag aaataaatac ttgttcaaat ttttttctg tatgtggtta   7440 ctatcatctg actatgcata tttgtaacag catttatcat tagtggtgtt agctaaataa   7500
gcatcttagt gtaaatgaga tgcttcgtgt gggttttgtg acatttaaa tgacataatg   7560 gaatgtgatt taaagaaaa ccagtacact atcttggtct taataacata gaatggagat   7620
ggcaaattta tccactagtt ttccagattt actatttaat agctgaggtc tgaaatcgta   7680
gcatcctccc tcctagtgga cattaaaaaa aaaaaaaaaa aaaaaaacct acttggttgt   7740
caagagccca agtatggagg tgctgcgcca tcttgtggcc tgtctgtgcc caccctgcac   7800
tctgctggag tctccatcct tgttgcagtg agacttgaag ttcaagattg atacatggca   7860
tcctcctgct acttcttgag gttactaagt agtatatgaa actaatcagt cagcaagtcc   7920
acctggaagg aaaagaaaat ctcaactatt aatgtgcctt cacattgtga ttttgtctaa   7980
aaaaatgtag tgagtcaaaa aacccacaag ccagccaaca gtaactcctt cacatatata   8040
```

| | |
|---|---|
| ccagagttta tagaaataac atgtcagctt tgggctatgt gctcctttgt ttaaaatctt | 8100 |
| ctatttggtt atggcttgta taggctcaag cctgatttct ttaaggtgtg gtggctcatc | 8160 |
| ttatcctaat gtgtatgata gatacagtcc atcctgcttt ggaaaagatt atgtaactcc | 8220 |
| ttgagagcat actctttctc tagcccaaag gcagtgagag agttttcttg ttcaggattg | 8280 |
| cttaactttc catttaagct ttttcttttt aaattaatac aaacttctac actttcaaaa | 8340 |
| tacgaaatat attacaactg cgtataggct cttccatact taagtccagt gcttgggcaa | 8400 |
| gttaatggag tgaaagacta caagcaaaga ggaactgagg tagaaaaaga agaatgtgtg | 8460 |
| aaagcagcag gaagctcagc caactcgaaa gcagggtgaa cagcttgagt cctgttgctg | 8520 |
| ctgatcgggg ttggctcttg gacaacttag taagatcatg gaaaggctgc ttgggttctc | 8580 |
| catagaaaag ttctgtctcc atcaagggag gaaaatgtac cttcaactc aaaattcaat | 8640 |
| atttgttttt aaatatagct attttcccca accgctaaag attttcaaca gatacgaagc | 8700 |
| cagagcttag ttttagaaac ctgtggacat tcaaacctga ttctttattc cctgtgacta | 8760 |
| tggttatgtc attttacatg tcaaaaaagt gtatctagaa ttgtcatttc ttatttttga | 8820 |
| gcttttttta gtgagaatta tcccctcact taaatggctt tttatttaaa catctgtgca | 8880 |
| ttctgtatga aattgtagtc tttctgggat aacatggtga gctatatggt ggtaatccac | 8940 |
| acacacaaaa ataaaagcca aaaaaaaacc aaaaaaaaaa aaaaaaaa | 8988 |

<210> SEQ ID NO 68
<211> LENGTH: 1669
<212> TYPE: DNA
<213> ORGANISM: Homo sapiens

<400> SEQUENCE: 68

| | |
|---|---|
| gctcctgtca tcgaggcccc tggcccaatg gcaggctgag tcccctcct ctggcctggt | 60 |
| cccgcctctc ctgccccttg tgctcagcgc tacctgctgc ccggacacat ccagagctgg | 120 |
| ccgacgggtg cgcgggcggg cggcggcacc atgcagggaa gctgccaggg gccgtgggca | 180 |
| gcgccgcttt ctgccgccca cctggcgctg tgagactggc gctgccacca tgttccccag | 240 |
| ccctgctctc acgcccacgc ccttctcagt caaagacatc ctaaacctgg aacagcagca | 300 |
| gcgcagcctg gctgccgccg gagagctctc tgcccgcctg gaggcgaccc tggcgccctc | 360 |
| ctcctgcatg ctgccgcct tcaagccaga ggcctacgct gggcccgagg cggctgcgcc | 420 |
| gggcctccca gagctgcgcg cagagctggg ccgcgcgcct tcaccggcca agtgtgcgtc | 480 |
| tgcctttccc gccgccccg ccttctatcc acgtgcctac agcgaccccg acccagccaa | 540 |
| ggaccctaga gccgaaaaga aagagctgtg cgcgctgcag aaggcggtgg agctggagaa | 600 |
| gacagaggcg gacaacgcgg agcggccccg ggcgcgacgg cggaggaagc cgcgcgtgct | 660 |
| cttctcgcag gcgcaggtct atgagctgga gcggcgcttc aagcagcagc ggtacctgtc | 720 |
| ggcccccgaa cgcgaccagc tggccagcgt gctgaaactc acgtccacgc aggtcaagat | 780 |
| ctggttccag aaccggcgct acaagtgcaa gcggcagcgg caggaccaga ctctggagct | 840 |
| ggtggggctg ccccgccgc cgccgccgcc tgcccgcagg atcgcggtgc cagtgctggt | 900 |
| gcgcgatggc aagccatgcc taggggactc ggcgccctac gcgcctgcct acggcgtggg | 960 |
| cctcaatccc tacggttata cgcctaccc cgcctatccg ggttacggcg gcgcggcctg | 1020 |
| cagccctggc tacagctgca ctgccgctta ccccgccggg ccttcccag cgcagccggc | 1080 |
| cactgccgcc gccaacaaca acttcgtgaa cttcggcgtc gggggacttga atgcggttca | 1140 |
| gagccccggg attccgcaga gcaactcggg agtgtccacg ctgcatggta tccgagcctg | 1200 |

```
gtagggaagg  gacccgcgtg  gcgcgaccct  gaccgatccc  acctcaacag  ctccctgact      1260
ctcgggggga  gaagggctc   ccaacatgac  cctgagtccc  ctggattttg  cattcactcc      1320
tgcggagacc  taggaacttt  ttctgtccca  cgcgcgtttg  ttcttgcgca  cgggagagtt      1380
tgtggcggcg  attatgcagc  gtgcaatgag  tgatcctgca  gcctggtgtc  ttagctgtcc      1440
ccccaggagt  gccctccgag  agtccatggg  caccccggt   tggaactggg  actgagctcg      1500
ggcacgcagg  gcctgagatc  tggccgccca  ttccgcgagc  cagggccggg  cgcccgggcc      1560
tttgctatct  cgccgtcgcc  cgcccacgca  cccacccgta  tttatgtttt  tacctattgc      1620
tgtaagaaat  gacgatcccc  ttcccattaa  agagagtgcg  ttgaccccg                   1669

<210> SEQ ID NO 69
<211> LENGTH: 1301
<212> TYPE: DNA
<213> ORGANISM: Homo sapiens

<400> SEQUENCE: 69
agatatatca  tacgaaaatg  aaaattataa  ttcttcttgg  attcctggga  gccacattgt       60 cagcccccact tatcccacag  cgtctcatgt  ctgccagcaa  tagcaatgag  ttacttctta      120
atcttaataa  tggtcaactt  tgccactac   aacttcaggg  cccacttaat  tcatggattc      180 caccttttctc tggaatttta  caacagcagc  agcaggctca  aattccagga  ctctcccagt      240
tctctttatc  agctctagac  cagtttgctg  gactgctccc  aaatcagata  cccttaacag      300
gagaggccag  ttttgcccaa  ggagcccagg  caggccaagt  tgatccctta  cagcttcaaa      360
caccgcctca  gacacaacca  ggccccagtc  acgtgatgcc  ctatgtattc  tccttcaaaa      420
tgcctcaaga  gcaaggacag  atgtttcaat  actatccagt  ttacatggtc  ctaccctggg      480
aacaacctca  gcaaacagtt  ccaaggtcac  ctcaacaaac  aagacagcaa  cagtatgagg      540
agcagatacc  attctatgct  caatttggat  acattccaca  actagcagaa  cctgctatat      600
caggaggaca  gcagcaacta  gcttttgatc  cccaactagg  cacagctcct  gaaattgctg      660
tgatgtcaac  aggagaagag  ataccatatt  tacaaaaaga  agcgatcaac  tttagacatg      720
acagtgcagg  agttttcatg  ccctcaactt  caccaaaacc  cagcacaacc  aatgttttca      780
cttctgctgt  agaccaaaact attacccag   agctcccaga  agagaaggac  aagactgaca      840
gcctaaggga  accataagaa  gttgccctga  tcattcagac  attttgggaa  aaagatgtgg      900
ccatgccttg  gatataattt  taggctatta  gcttcctcaa  tactagtatc  agttctttgg      960
aatacatgaa  atatcttgac  tcttctccta  aatttgtttt  tacttataca  tgttattaaa     1020
ctctttaaat  atgtcataga  aaataataca  atcatgtaat  gagtcttgtc  ttacaaaatt     1080
atatgtctct  tcaaatatcc  tatcattgta  taatatggaa  tataataaca  cagaataaag     1140
ctagtatcat  taaatcaatt  ggataattgc  attagtaaat  gatgcctctg  caaaatggta     1200
gtacccatga  agatatgtat  attgtcattg  gatgtatgat  gagtgttgtg  attggaactg     1260
atgaagtaaa  ataagtatct  agatttgaaa  aaaaaaaaa   a                          1301

<210> SEQ ID NO 70
<211> LENGTH: 6574
<212> TYPE: DNA
<213> ORGANISM: Homo sapiens

<400> SEQUENCE: 70
aagagcaaaa  agcgaaggcg  caatctggac  actgggagat  tcggagcgca  gggagtttga       60
```

| | |
|---|---|
| gagaaacttt tattttgaag agaccaaggt tgagggggggg cttatttcct gacagctatt | 120 |
| tacttagagc aaatgattag ttttagaagg atggactata acattgaatc aattacaaaa | 180 |
| cgcggttttt gagcccatta ctgttggagc tacagggaga gaaacagagg aggagactgc | 240 |
| aagagatcat tggaggccgt gggcacgctc tttactccat gtgtgggaca ttcattgcgg | 300 |
| aataacatcg gaggagaagt ttcccagagc tatgggggact tcccatccgg cgttcctggt | 360 |
| cttaggctgt cttctcacag ggctgagcct aatcctctgc cagctttcat taccctctat | 420 |
| ccttccaaat gaaatgaaa aggttgtgca gctgaattca tccttttctc tgagatgctt | 480 |
| tggggagagt gaagtgagct ggcagtaccc catgtctgaa gaagagagct ccgatgtgga | 540 |
| aatcagaaat gaagaaaaca acagcggcct ttttgtgacg gtcttggaag tgagcagtgc | 600 |
| ctcggcggcc cacacagggt tgtacacttg ctattacaac cacactcaga cagaagagaa | 660 |
| tgagcttgaa ggcaggcaca tttacatcta tgtgccagac ccagatgtag cctttgtacc | 720 |
| tctaggaatg acggattatt tagtcatcgt ggaggatgat gattctgcca ttataccttg | 780 |
| tcgcacaact gatcccgaga ctcctgtaac cttacacaac agtgaggggg tggtacctgc | 840 |
| ctcctacgac agcagacagg gctttaatgg gaccttcact gtagggccct atatctgtga | 900 |
| ggccaccgtc aaaggaaaga agttccgagac catcccattt aatgtttatg ctttaaaagc | 960 |
| aacatcagag ctggatctag aaatggaagc tcttaaaacc gtgtataagt caggggaaac | 1020 |
| gattgtggtc acctgtgctg tttttaacaa tgaggtggtt gaccttcaat ggacttaccc | 1080 |
| tggagaagtg aaaggcaaag gcatcacaat gctggaagaa atcaaagtcc catccatcaa | 1140 |
| attggtgtac actttgacgg tccccgaggc cacggtgaaa gacagtggag attacgaatg | 1200 |
| tgctgcccgc caggctacca gggaggtcaa agaaatgaag aaagtcacta tttctgtcca | 1260 |
| tgagaaaggt ttcattgaaa tcaaacccac cttcagccag ttggaagctg tcaacctgca | 1320 |
| tgaagtcaaa cattttgttg tagaggtgcg ggcctaccca cctcccagga tatcctggct | 1380 |
| gaaaaacaat ctgactctga ttgaaaatct cactgagatc accactgatg tggaaaaagat | 1440 |
| tcaggaaata aggtatcgaa gcaaattaaa gctgatccgt gctaaggaag aagacagtgg | 1500 |
| ccattatact attgtagctc aaaatgaaga tgctgtgaag agctatactt ttgaactgtt | 1560 |
| aactcaagtt ccttcatcca ttctggactt ggtcgatgat caccatggct caactggggg | 1620 |
| acagacggtg aggtgcacag ctgaaggcac gccgcttcct gatattgagt ggatgatatg | 1680 |
| caaagatatt aagaaatgta ataatgaaac ttcctggact attttggcca acaatgtctc | 1740 |
| aaacatcatc acggagatcc actcccgaga caggagtacc gtggagggcc gtgtgacttt | 1800 |
| cgccaaagtg gaggagacca tcgccgtgcg atgcctggct aagaatctcc ttggagctga | 1860 |
| gaaccgagag ctgaagctgg tggctcccac cctgcgttct gaactcacgg tggctgctgc | 1920 |
| agtcctggtg ctgttggtga ttgtgatcat ctcacttatt gtcctggttg tcatttggaa | 1980 |
| acagaaaccg aggtatgaaa ttcgctggag ggtcattgaa tcaatcagcc cagatggaca | 2040 |
| tgaatatatt tatgtggacc cgatgcagct gccttatgac tcaagatggg agtttccaag | 2100 |
| agatggacta gtgcttggtc gggtcttggg gtctggagcg tttgggaagg tggttgaagg | 2160 |
| aacagcctat ggattaagcc ggtcccaacc tgtcatgaaa gttgcagtga agatgctaaa | 2220 |
| acccacggcc agatccagtg aaaaacaagc tctcatgtct gaactgaaga taatgactca | 2280 |
| cctggggcca cattttgaaca ttgtaaactt gctgggagcc tgcaccaagt caggcccccat | 2340 |
| ttacatcatc acagagtatt gcttctatgg agatttggtc aactatttgc ataagaatag | 2400 |
| ggatagcttc ctgagccacc acccagagaa gccaaagaaa gagctggata tctttggatt | 2460 |

```
gaaccctgct gatgaaagca cacggagcta tgttatttta tcttttgaaa acaatggtga    2520
ctacatggac atgaagcagg ctgatactac acagtatgtc cccatgctag aaaggaaaga    2580
ggtttctaaa tattccgaca tccagagatc actctatgat cgtccagcct catataagaa    2640
gaaatctatg ttagactcag aagtcaaaaa cctcctttca gatgataact cagaaggcct    2700
tactttattg gatttgttga gcttcaccta tcaagttgcc cgaggaatgg agttttggc     2760
ttcaaaaaat tgtgtccacc gtgatctggc tgctcgcaac gtcctcctgg cacaaggaaa    2820
aattgtgaag atctgtgact ttggcctggc cagagacatc atgcatgatt cgaactatgt    2880
gtcgaaaggc agtacctttc tgcccgtgaa gtggatggct cctgagagca tctttgacaa    2940
cctctacacc acactgagtg atgtctggtc ttatggcatt ctgctctggg agatcttttc    3000
ccttggtggc accccttacc ccggcatgat ggtggattct actttctaca ataagatcaa    3060
gagtgggtac cggatggcca agcctgacca cgctaccagt gaagtctacg agatcatggt    3120
gaaatgctgg aacagtgagc cggagaagag accctccttt taccacctga gtgagattgt    3180
ggagaatctg ctgcctggac aatataaaaa gagttatgaa aaaattcacc tggacttcct    3240
gaagagtgac catcctgctg tggcacgcat gcgtgtggac tcagacaatg catacattgg    3300
tgtcacctac aaaaacgagg aagacaagct gaaggactgg gagggtggtc tggatgagca    3360
gagactgagc gctgacagtg gctacatcat tcctctgcct gacattgacc ctgtccctga    3420
ggaggaggac ctgggcaaga ggaacagaca cagctcgcag acctctgaag agagtgccat    3480
tgagacgggt tccagcagtt ccaccttcat caagagagag gacgagacca ttgaagacat    3540
cgacatgatg gatgacatcg gcatagactc ttcagacctg gtggaagaca gcttcctgta    3600
actggcggat tcgaggggtt ccttccactt ctggggccac ctctggatcc cgttcagaaa    3660
accactttat tgcaatgcag aggttgagag gaggacttgg ttgatgttta aagagaagtt    3720
cccagccaag ggcctcgggg agcgttctaa atatgaatga atgggatatt ttgaaatgaa    3780
ctttgtcagt gttgcctctt gcaatgcctc agtagcatct cagtggtgtg tgaagtttgg    3840
agatagatgg ataagggaat aataggccac agaaggtgaa ctttgtgctt caaggacatt    3900
ggtgagagtc caacagacac aatttatact gcgacagaac ttcagcattg taattatgta    3960
aataactcta accaaggctg tgtttagatt gtattaacta tcttctttgg acttctgaag    4020
agaccactca atccatccat gtacttccct cttgaaacct gatgtcagct gctgttgaac    4080
tttttaaaga agtgcatgaa aaaccatttt tgaaccttaa aaggtactgg tactatagca    4140
ttttgctatc tttttttagtg ttaaagagat aaagaataat aattaaccaa ccttgtttaa    4200
tagatttggg tcatttagaa gcctgacaac tcattttcat attgtaatct atgtttataa    4260
tactactact gttatcagta atgctaaatg tgtaataatg taacatgatt ccctccaga     4320
gaaagcacaa tttaaaacaa tccttactaa gtaggtgatg agtttgacag ttttttgacat    4380
ttatattaaa taacatgttt ctctataaag tatggtaata gctttagtga attaaattta    4440
gttgagcata gagaacaaag taaaagtagt gttgtccagg aagtcagaat ttttaactgt    4500
actgaatagg ttccccaatc catcgtatta aaaaacaatt aactgccctc tgaaataatg    4560
ggattagaaa caaacaaaac tcttaagtcc taaaagttct caatgtagag gcataaacct    4620
gtgctgaaca taacttctca tgtatattac ccaatggaaa atataatgat cagcaaaaag    4680
actggatttg cagaagtttt ttttttttttt ttcttcatgc ctgatgaaag ctttggcgac    4740
cccaatatat gtatttttg aatctatgaa cctgaaaagg gtcagaagga tgcccagaca    4800
```

| | |
|---|---|
| tcagcctcct tctttcaccc cttaccccaa agagaaagag tttgaaactc gagaccataa | 4860 |
| agatattctt tagtggaggc tggatgtgca ttagcctgga tcctcagttc tcaaatgtgt | 4920 |
| gtggcagcca ggatgactag atcctgggtt tccatccttg agattctgaa gtatgaagtc | 4980 |
| tgagggaaac cagagtctgt atttttctaa actccctggc tgttctgatc ggccagtttt | 5040 |
| cggaaacact gacttaggtt tcaggaagtt gccatgggaa acaaataatt tgaactttgg | 5100 |
| aacagggttg gcattcaacc acgcaggaag cctactattt aaatccttgg cttcaggtta | 5160 |
| gtgacattta atgccatcta gctagcaatt gcgaccttaa tttaactttc cagtcttagc | 5220 |
| tgaggctgag aaagctaaag tttggttttg acaggttttc caaagtaaa gatgctactt | 5280 |
| cccactgtat gggggagatt gaactttccc cgtctcccgt cttctgcctc ccactccata | 5340 |
| ccccgccaag gaaaggcatg tacaaaaatt atgcaattca gtgttccaag tctctgtgta | 5400 |
| accagctcag tgttttggtg gaaaaaacat tttaagtttt actgataatt tgaggttaga | 5460 |
| tgggaggatg aattgtcaca tctatccaca ctgtcaaaca ggttggtgtg ggttcattgg | 5520 |
| cattctttgc aatactgctt aattgctgat accatatgaa tgaaacatgg gctgtgatta | 5580 |
| ctgcaatcac tgtgctatcg gcagatgatg ctttggaaga tgcagaagca ataataaagt | 5640 |
| acttgactac ctactggtgt aatctcaatg caagccccaa ctttcttatc caacttttc | 5700 |
| atagtaagtg cgaagactga gccagattgg ccaattaaaa acgaaaacct gactaggttc | 5760 |
| tgtagagcca attagacttg aaatacgttt gtgtttctag aatcacagct caagcattct | 5820 |
| gtttatcgct cactctccct tgtacagcct tattttgttg gtgctttgca ttttgatatt | 5880 |
| gctgtgagcc ttgcatgaca tcatgaggcc ggatgaaact tctcagtcca gcagtttcca | 5940 |
| gtcctaacaa atgctcccac ctgaatttgt atatgactgc atttgtgtgt gtgtgtgtgt | 6000 |
| tttcagcaaa ttccagattt gtttccttt ggcctcctgc aaagtctcca gaagaaaatt | 6060 |
| tgccaatctt tcctactttc tattttatg atgacaatca agccggcct gagaaacact | 6120 |
| atttgtgact ttttaaacga ttagtgatgt ccttaaaatg tggtctgcca atctgtacaa | 6180 |
| aatggtccta tttttgtgaa gagggacata agataaaatg atgttataca tcaatatgta | 6240 |
| tatatgtatt tctatataga cttggagaat actgccaaaa catttatgac aagctgtatc | 6300 |
| actgccttcg tttatatttt tttaactgtg ataatcccca caggcacatt aactgttgca | 6360 |
| cttttgaatg tccaaaattt atattttaga aataataaaa agaaagatac ttacatgttc | 6420 |
| ccaaaacaat ggtgtggtga atgtgtgaga aaaactaact tgatagggtc taccaataca | 6480 |
| aaatgtatta cgaatgcccc tgttcatgtt tttgttttaa aacgtgtaaa tgaagatctt | 6540 |
| tatatttcaa taaatgatat ataatttaaa gtta | 6574 |

<210> SEQ ID NO 71
<211> LENGTH: 2317
<212> TYPE: DNA
<213> ORGANISM: Homo sapiens

<400> SEQUENCE: 71

| | |
|---|---|
| cggacgcgtg ggtgagcagg acggtgcac cggacggcgg gatcgagcaa atgggtctgg | 60 |
| ccatggagca cggagggtcc tacgctcggg cggggggcag ctctcgggc tgctggtatt | 120 |
| acctgcgcta cttcttcctc ttcgtctccc tcatccaatt cctcatcatc ctggggctcg | 180 |
| tgctcttcat ggtctatggc aacgtgcacg tgagcacaga gtccaacctg caggccaccg | 240 |
| agcgccgagc cgagggccta tacagtcagc tcctagggct cacggcctcc cagtccaact | 300 |
| tgaccaagga gctcaacttc accacccgcg ccaaggatgc catcatgcag atgtggctga | 360 |

```
atgctcgccg cgacctggac cgcatcaatg ccagcttccg ccagtgccag ggtgaccggg      420
tcatctacac gaacaatcag aggtacatgg ctgccatcat cttgagtgag aagcaatgca      480
gagatcaatt caaggacatg aacaagagct gcgatgcctt gctcttcatg ctgaatcaga      540
aggtgaagac gctggaggtg gagatagcca aggagaagac catttgcact aaggataagg      600
aaagcgtgct gctgaacaaa cgcgtggcgg aggaacagct ggttgaatgc gtgaaaaccc      660
gggagctgca gcaccaagag cgccagctgg ccaaggagca actgcaaaag gtgcaagccc      720
tctgcctgcc cctggacaag gacaagtttg agatggacct tcgtaacctg tggagggact      780
ccattatccc acgcagcctg acaacctggg gttacaacct ctaccatccc ctgggctcgg      840
aattggcctc catccgcaga gcctgcgacc acatgcccag cctcatgagc tccaaggtgg      900
aggagctggc ccggagcctc cgggcggata tcgaacgcgt ggcccgcgag aactcagacc      960
tccaacgcca gaagctggaa gcccagcagg gcctgcgggc cagtcaggag gcgaaacaga     1020
aggtggagaa ggaggctcag gcccgggagg ccaagctcca agctgaatgc tcccggcaga     1080
cccagctagc gctggaggag aaggcggtgc tgcggaagga acgagacaac ctggccaagg     1140
agctggaaga gaagaagagg gaggcggagc agctcaggat ggagctggcc atcagaaact     1200
cagccctgga cacctgcatc aagaccaagt cgcagccgat gatgccagtg tcaaggccca     1260
tgggccctgt ccccaacccc cagcccatcg acccagctag cctggaggag ttcaaggaga     1320
agatcctgga gtcccagagg ccccctgcag gcatccctgt agccccatcc agtggctgag     1380
gaggctccag gctgaggac caagggatgg cccgactcgg cggtttgcgg aggatgcagg     1440
gatatgctca cagcgcccga cacaaccccc tcccgccgcc cccaaccacc cagggccacc     1500
atcagacaac tccctgcatg caaacccta gtaccctctc acaccgcac ccgcgcctca     1560 cgatccctca cccagagcac acggccgcgg agatgacgtc acgcaagcaa cggcgctgac     1620
gtcacatatc accgtggtga tggcgtcacg tggccatgta gacgtcacga agagatatag     1680
cgatggcgtc gtgcagatgc agcacgtcgc acacagacat ggggaacttg gcatgacgtc     1740
acaccgagat gcagcaacga cgtcacgggc catgtcgacg tcacacatat taatgtcaca     1800
cagacgcggc gatggcatca cacagacggt gatgatgtca cacacagaca cagtgacaac     1860
acacaccatg acaacgacac ctatagatat ggcaccaaca tcacatgcac gcatgccctt     1920
tcacacacac tttctaccca attctcacct agtgtcacgt tcccccgacc ctggcacacg     1980
ggccaaggta cccacaggat cccatcccct cccgcacagc cctgggcccc agcacctccc     2040
ctcctccagc ttcctggcct cccagccact tcctcacccc cagtgcctgg acccggaggt     2100
gagaacagga agccattcac ctccgctcct tgagcgtgag tgtttccagg acccctcgg      2160 ggccctgagc cggggtgag ggtcacctgt tgtcggagg ggagccactc cttctccccc      2220
aactcccagc cctgcctgtg gcccgttgaa atgttggtgg cacttaataa atattagtaa     2280
atccttaaaa aaaaaaaaaa aaaaaaaaaa aaaaaaa                               2317

<210> SEQ ID NO 72
<211> LENGTH: 3371
<212> TYPE: DNA
<213> ORGANISM: Homo sapiens

<400> SEQUENCE: 72
attgggagtc agctcctaag taagctccag aattcctgct ggtacttttc cttccaggaa       60
gcaacttcct tgatattttt tttttacagg catatgaata aaaactatat tttgcagcat      120
```

```
tgtacactt ttttcctttt ctagaaattc taaacctctg acattggtgg agacattgag     180
tacatttttt cccatatccc tacttttcag aaggatttc tctgctcgtt cacttaacat     240
tgctgatgcg tcagtctttt cttcctcatc tctttcaggg gctggagagg cagagggaga    300
cagaggagct ggtactgcag agcggtcgtc tgattggctg gacggtcgta gctgggctat    360
aaaagagacc cctacaggct tagcaggaag acgctcagag gattctgaca atatctttac    420
cggagaagag gcaaagtacg ctcaaagccg aagccacagc tcctcctgcc gcatttcttt    480
cctgcttgcg aattccaagc tgttaaataa gatgtgcaaa gggcttgcag gtctgccggc    540
ttcttgcttg aggagtgcaa aagatatgaa acatcggcta ggtttcctgc tgcaaaaatc    600
tgattcctgt gaacacaatt cttcccacaa caagaaggac aaagtggtta tttgccagag    660
agtgagccaa gaggaagtca agaaatgggc tgaatcactg gaaaacctga ttagtcatga    720
atgtgggctg gcagctttca aagctttctt gaagtctgaa tatagtgagg agaatattga    780
cttctggatc agctgtgaag agtacaagaa aatcaaatca ccatctaaac taagtcccaa    840
ggccaaaaag atctataatg aattcatctc agtccaggca accaaagagg tgaacctgga    900
ttcttgcacc agggaagaga caagccggaa catgctagag cctacaataa cctgctttga    960
tgaggcccag aagaagattt tcaacctgat ggagaaggat tcctaccgcc gcttcctcaa   1020
gtctcgattc tatcttgatt tggtcaaccc gtccagctgt ggggcagaaa agcagaaagg   1080
agccaagagt tcagcagact gtgcttccct ggtccctcag tgtgcctaat tctcacctga   1140
aggcagaggg atgaaatgcc aagactctat gctctggaaa acctgaggcc aaatattgat   1200
ctgtattaag ctccagtgct ttatccacat tgtagcctaa tattcatgct gcctgccatg   1260
tgtgagtcac ttctacgcat aaactagata tagcttttgg tgtttgagtg ttcatcaggg   1320
tgggacccca ttccagtcca attttcctaa gtttctttga gggttccatg ggagcaaata   1380
tctaaataat ggcctggtag gtctggattt tcaaagattg ttggcagttt cctcctccca   1440
acagttttac ctcgggatgg ttggttagtg catgtcacat gacatccaca tgcacatgta   1500
ttctgttggc cagcacgttc tccagactct agatgtttag atgaggttga gctatgatat   1560
gtgcttgtgt gtatgtctat gtgtatatat tatatataca ttagacacac atatacatta   1620
tttctgtata tagatgtctg tgtatacata tgtatgtgtg agtgtatgta tacacacaca   1680
cacacacaca cacacacact tttgcaagag tgatgggaaa gaccctaggt gctcataact   1740
agagtatgtg tatgtactta catgggtgtt ttgatctctg ttctttcata ctacatttga   1800
acagggcaaa atgaactaac tgccatgtag gctaagaaag aaatgctaac ctgtggaaag   1860
ttggttttgt aaaattccat ggatcttgct ggagaagcat ccaaggaact tcatgcttga   1920
tttgaccact gacagcctcc accttgagca ctattctaag gagcaaatac cttagctccc   1980
ttgagctggt tttctctgat ggcacttttg agctcctaag ctgccagcct tcccttcttt   2040
tcctgggtgc tcagggcatg cttattagca gctgggttgg tatggagttg gcagacagga   2100
tgttcaactt aatgaagaaa tacagctaag gccttgccag caacacctgc cgtaagttac   2160
tggctgagtg agggcataga agttaaaggt tactgttttt atcctctatc cttttttcct   2220
ttcctgatca aggtgctctt ctcattttt cctgagaacc ttagccatca gatgaggctc   2280
cttagtttat tgtggttggt tgttttttct ttataatggc tctgggctat atgcctatat   2340
ttataaacca gcagcagggg aaagattata tttataaga gggaacaaat tttcacaatt   2400
tgaaaagccc acataagttt tctcttttaa ggtagaatct tgttaatttc attccaaaca   2460
tcggggctaa cagagactgg aggcatttct ttttaggctc tgagactaaa tgagaggaaa   2520
```

```
agaaaagaaa aaaaaaatga ttgtctaacc aattgtgaga attactgttt gaaacttttc    2580
aaggcacatt gaaatacttg aaaacttctc atttatgtta tttatgatgt tattttgtac    2640
gtgttattat tattatattg ttttataaat ggaggtacag gatatcacct gaattattaa    2700
tgaatgccca ggaagtaatt ttcttctcat tcttctaaaa ctactgcctt tcaaagtgca    2760
cacacacgcg tccacataca ctgcattcgt tgctccagta taaattacat gcatgagcac    2820 cttctggct tttaagccaa tataatgggc tgcaaaatga agacaccaga gtgtatgcat    2880
acaaatctca ctgtattaaa gatgcaggtt ttctaattgt acccttcttg tctctctggc    2940
aatcttgccc ttaatatccc tggagttcct catcagtgtc attttctgtt atacacagtt    3000
ccacaatttt gtctctagtt gacttcaaat gtgtaacttt attggtcttg ccctattata    3060
attgtcatga ctttcagatt gtatctgaac tcacagactg ctgtcttact aataggtctg    3120
gaaggtcacg ctgaatgaga agtaaattat tttatgtaat acattttga gtgtgttttt    3180 cagttgtatt tccctgttat ttcatcacta tttccaatgg tgagcttgcc tgctcatgct    3240
ccctggacag aatactcctt cctttttgcat gcctgtttct atcatgtgct tgataggcct    3300
caaagctaat gcttccagtg aaacacacgc atcttaataa taagggtaaa taaacgctcc    3360
atatgaaact a                                                        3371

<210> SEQ ID NO 73
<211> LENGTH: 2112
<212> TYPE: DNA
<213> ORGANISM: Homo sapiens

<400> SEQUENCE: 73
aaaacgggct cagttcgtaa aggagccggg tgacttcaga ggcgccggcc cgtccgtctg      60
ccgcacctga gcacggcccc tgcccgagcc tggcccgccg cgatgctgta gggaccgccg     120
tgtcctcccg ccggaccgtt atccgcgccg ggcgcccgcc agaccccgctg caagatgcc     180 gcgctccttc ctggtcaaga agcatttcaa cgcctccaaa aagccaaact acagcgaact     240
ggacacacat acagtgatta tttccccgta tctctatgag agttactcca tgcctgtcat     300
accacaacca gagatcctca gctcaggagc atacagcccc atcactgtgt ggactaccgc     360
tgctccattc cacgcccagc tacccaatgg cctctctcct ctttccggat actcctcatc     420
tttggggcga gtgagtcccc ctcctccatc tgacacctcc tccaaggacc acagtggctc     480
agaaagcccc attagtgatg aagaggaaag actacagtcc aagctttcag accccccatgc     540 cattgaagct gaaaagtttc agtgcaattt atgcaataag acctattcaa ctttttctgg     600
gctggccaaa cataagcagc tgcactgcga tgcccagtct agaaaatctt tcagctgtaa     660
atactgtgac aaggaatatg tgagcctggg cgccctgaag atgcatattc ggacccacac     720
attaccttgt gtttgcaaga tctgcggcaa ggcgttttcc agaccctggt tgcttcaagg     780
acacattaga actcacacgg gggagaagcc ttttcttgc cctcactgca acagagcatt     840
tgcagacagg tcaaatctga gggctcatct gcagacccat tctgatgtaa agaaatacca     900
gtgcaaaaac tgctccaaaa ccttctccag aatgtctctc ctgcacaaac atgaggaatc     960
tggctgctgt gtagcacact gagtgacgca atcaatgttt actcgaacag aatgcatttc    1020
ttcactccga agccaaatga caaataaagt ccaaaggcat tttctcctgt gctgaccaac    1080
caaataatat gtatagacac acacacatat gcacacacac acacacacac ccacagagag    1140
agagctgcaa gagcatggaa ttcatgtgtt taaagataat cctttccatg tgaagtttaa    1200
```

| | |
|---|---|
| aattactata tatttgctga tggctagatt gagagaataa aagacagtaa cctttctctt | 1260 |
| caaagataaa atgaaaagca cattgcatct tttcttccta aaaaaatgca aagatttaca | 1320 |
| ttgctgccaa atcatttcaa ctgaaaagaa cagtattgct ttgtaataga gtctgtaata | 1380 |
| ggatttccca taggaagaga tctgccagac gcgaactcag gtgccttaaa aagtattcca | 1440 |
| agtttactcc attacatgtc ggttgtctgg ttgccattgt tgaactaaag cctttttttg | 1500 |
| attacctgta gtgctttaaa gtatatttt aaaagggagg aaaaaaataa caagaacaaa | 1560 |
| acacaggaga atgtattaaa agtattttg ttttgttttg ttttgccaa ttaacagtat | 1620 |
| gtgccttggg ggaggaggga aagattagct ttgaacattc ctggcgcatg ctccattgtc | 1680 |
| ttactatttt aaaacatttt aataattttt gaaaattaat taaagatggg aataagtgca | 1740 |
| aaagaggatt cttacaaatt cattaatgta cttaaactat ttcaaatgca taccacaaat | 1800 |
| gcaataatac aatacccctt ccaagtgcct tttaaattg tatagttgat gagtcaatgt | 1860 |
| aaatttgtgt ttattttat atgattgaat gagttctgta tgaaactgag atgttgtcta | 1920 |
| tagctatgtc tataaacaac ctgaagactt gtgaaatcaa tgtttcttt ttaaaaaaca | 1980 |
| attttcaagt ttttttaca ataaacagtt ttgatttaaa atctcgtttg tatactatt | 2040 |
| tcagagactt tacttgcttc atgattagta ccaaaccact gtacaaagaa ttgtttgtta | 2100 |
| acaagaaaaa aa | 2112 |

<210> SEQ ID NO 74
<211> LENGTH: 665
<212> TYPE: DNA
<213> ORGANISM: Homo sapiens

<400> SEQUENCE: 74

| | |
|---|---|
| gggagacggt tgagagcaca caagccgctt taggagcgag gttcggagcc atcgctgctg | 60 |
| cctgctgatc cgcgcctaga gtttgaccag ccactctcca gctcggcttt cgcggcgccg | 120 |
| agatgctgtc ctgccgcctc cagtgcgcgc tggctgcgct gtccatcgtc ctggccctgg | 180 |
| gctgtgtcac cggcgctccc tcggacccca gactccgtca gtttctgcag aagtccctgg | 240 |
| ctgctgccgc ggggaagcag gaactggcca agtacttctt ggcagagctg ctgtctgaac | 300 |
| ccaaccagac ggagaatgat gccctggaac ctgaagatct gtcccaggct gctgagcagg | 360 |
| atgaaatgag gcttgagctg cagagatctg ctaactcaaa cccggctatg gcaccccgag | 420 |
| aacgcaaagc tggctgcaag aatttcttct ggaagacttt cacatcctgt agctttctt | 480 |
| aactagtatt gtccatatca gacctctgat ccctcgcccc cacacccat ctctcttccc | 540 |
| taatcctcca agtcttcagc gagacccttg cattagaaac tgaaactgt aaatacaaaa | 600 |
| taaaattatg gtgaaattat gaaaatgtg aaaaaaaaaa aaaaaaaaa aaaaaaaaa | 660 |
| aaaaa | 665 |

<210> SEQ ID NO 75
<211> LENGTH: 4814
<212> TYPE: DNA
<213> ORGANISM: Homo sapiens

<400> SEQUENCE: 75

| | |
|---|---|
| gaattctaga ggcggcggag ggtggcgagg agctctcgct ttctctcgct ccctccctct | 60 |
| ccgactccgt ctctctctct ctctctctct ctcccctccc tctctttccc tctgttccat | 120 |
| tttttccccc tctaaatcct ccctgccctg cgcgcctgga cacagattta ggaagcgaat | 180 |
| tcgctcacgt tttaggacaa ggaagagaga gaggcacggg agaagagccc agcaagattt | 240 |

```
ggattgaaac cgagacaccc tccggaggct cggagcagag gaaggaggag gagggcggcg    300
aacggaagcc agtttgcaat tcaagttttg atagcgctgg tagaaggggg tttaaatcag    360 atttttttt ttttaaagga gagagacttt ttccgctctc tcgctccctg ttaaagccgg     420
gtctagcaca gctgcagacg ccaccagcga gaaagaggga gaggaagaca gataggggc     480 gggggaagaa gaaaaagaaa ggtaaaaagt cttctaggag aacctttcac atttgcaaca    540
aaagacctag gggctggaga gagattcctg ggacgcaggg ctggagtgtc tatttcgagc    600
tcagcggcag ggctcgggcg cgagtcgaga ccctgctcgc tcctctcgct tctgaaaccg    660
acgttcagga gcggcttttt aaaaacgcaa ggcacaagga cggtcacccg cgcgactatg    720
tttgctgatt tttcgccttg ccctctttaa aagcggcctc ccattctcca aaagacactt    780
cccctcctcc ctttgaagtg cattagttgt gatttctgcc tccttttctt ttttcttctt    840
tttttgtttt gctttttccc ccctttttgaa ttatgtgctg ctgttaaaca acaacaaaaa   900
aacaacaaaa cacagcagct gcggacttgt cccccggctgg agcccagcgc ccgcctgga    960 gtggatgagc ctctccatga gagatccggt cattcctggg acaagcatgg cctaccatcc    1020
gttcctacct caccgggcgc cggacttcgc catgagcgcg gtgctgggtc accagccgcc    1080
gttcttcccc gcgctgacgc tgcctcccaa cggcgcggcg gcgctctcgc tgccgggcgc    1140
cctggccaag ccgatcatgg atcaattggt gggggcggcc gagaccggca tcccgttctc    1200
ctccctgggg cccccaggcgc atctgaggcc tttgaagacc atggagcccg aagaagaggt    1260
ggaggacgac cccaaggtgc acctggaggc taaagaactt tgggatcagt ttcacaagcg    1320
gggcaccgag atggtcatta ccaagtcggg aaggcgaatg tttcctccat ttaaagtgag    1380
atgttctggg ctggataaaa aagccaaata cattttattg atggacatta tagctgctga    1440
tgactgtcgt tataaatttc acaattctcg gtggatggtg gctggtaagg ccgaccccga    1500
aatgccaaag aggatgtaca ttcacccgga cagccccgct actggggaac agtggatgtc    1560
caaagtcgtc actttccaca aactgaaact caccaacaac atttcagaca acatggatt    1620 tactttggcc ttcccaagtg atcacgctac gtggcagggg aattatagtt ttggtactca    1680
gactatattg aactccatgc acaaatacca gccccggttc cacattgtaa gagccaatga    1740
catcttgaaa ctcccttata gtacatttcg gacatacttg ttccccgaaa ctgaattcat    1800
cgctgtgact gcataccaga atgataagat aacccagtta aaaatagaca acaacccttt    1860
tgcaaaaggt ttccgggaca ctggaaatgg ccgaagagaa aaagaaaac agctcaccct    1920 gcagtccatg agggtgtttg atgaaagaca caaaaggaa aatgggacct ctgatgagtc    1980
ctccagtgaa caagcagctt tcaactgctt cgcccaggct tcttctccag ccgcctccac    2040
tgtagggaca tcgaacctca agatttatg tcccagcgag ggtgagagcg acgccgaggc    2100
cgagagcaaa gaggagcatg gcccgaggc ctgcgacgcg gccaagatct ccaccaccac    2160
gtcggaggag ccctgccgtg acaagggcag ccccgcggtc aaggctcacc ttttcgctgc    2220
tgagcggccc cgggacagcg ggcggctgga caaagcgtcg cccgactcac gccatagccc    2280
cgccaccatc tcgtccagca ctcgcggcct gggcgcggag gagcgcagga gcccggttcg    2340
cgagggcaca gcgccggcca aggtggaaga ggcgcgcgcg ctcccgggca aggaggcctt    2400
cgcgccgctc acggtgcaga cggacgcggc gcccgcgcac ctggcccagg gcccctgcc    2460 tggcctcggc ttcgccccgg gcctggcggg ccaacagttc ttcaacggc acccgctctt    2520 cctgcacccc agccagtttg ccatgggggg cgccttctcc agcatggcgg ccgctggcat    2580
```

```
gggtccccte  ctggccacgg  tttctggggc  ctccaccggt  gtctcgggcc  tggattccac    2640
ggccatggcc  tctgccgctg  cggcgcaggg  actgtccggg  gcgtccgcgg  ccaccctgcc    2700
cttccacctc  cagcagcacg  tcctggcctc  tcagggcctg  gccatgtccc  ctttcggaag    2760
cctgttccct  taccectaca  cgtacatggc  cgcagcggcg  gccgcctcct  ctgcggcagc    2820
ctccagctcg  gtgcaccgcc  acccettect  caatctgaac  accatgcgcc  cgcggctgcg    2880
ctacagcccc  tactccatcc  cggtgccggt  cccggacggc  agcagtctgc  tcaccaccgc    2940
cctgccctcc  atggcggcgg  ccgcggggcc  cctggacggc  aaagtcgccg  ccctggccgc    3000
cagcccggcc  tcggtggcag  tggactcggg  ctctgaactc  aacagccgct  cctccacgct    3060
ctcctccagc  tccatgtcct  tgtcgcccaa  actctgcgcg  gagaaagagg  cggccaccag    3120
cgaactgcag  agcatccagc  ggttggttag  cggcttggaa  gccaagccgg  acaggtcccg    3180
cagcgcgtcc  ccgtagaccc  gtcccagaca  cgtcttttca  ttccagtcca  gttcaggctg    3240
ccgtgcactt  tgtcggatat  aaaataaacc  acgggcccgc  catggcgtta  gcccttcctt    3300
ttgcagttgc  gtctgggaag  gggccccgga  ctccctcgag  agaatgtgct  agagacagcc    3360
cctgtcttct  tggcgtggtt  tatatgtccg  ggatctggat  cagattctgg  gggctcagaa    3420
acgtcggttg  cattgagcta  ctgggggtag  gagttccaac  atttatgtcc  agagcaactt    3480
ccagcaaggc  tggtctgggt  ctctgcccac  caggcgggga  ggtgttcaaa  gacatctccc    3540
tcagtgcgga  tttatatata  tattttttcct  tcactgtgtc  aagtggaaac  aaaaacaaaa    3600
tctttcaaaa  aaaaaatcgg  gacaagtgaa  cacattaaca  tgattctgtt  tgtgcagatt    3660
aaaaacttta  tagggacttg  cattatcggt  tctcaataaa  ttactgagca  gctttgtttg    3720
gggagggaag  tccctaccat  ccttgtttag  tctatattaa  gaaaatctgt  gtctttttaa    3780
tattcttgtg  atgttttcag  agccgctgta  ggtctcttct  tgcatgtcca  cagtaatgta    3840
tttgtggttt  ttatttttgaa  cgcttgcttt  tagagagaaa  acaatatagc  ccctaccct    3900 tttcccaatc  ctttgccctc  aaatcagtga  cccaagggag  gggggatttt  aaagggaagg    3960
agtgggcaaa  acacataaaa  tgaatttatt  atatctaagc  tctgtagcag  gattcatgtc    4020
gttctttgac  agttctttct  cttccctgta  tatgcaataa  caaggttttta  aaaaaataat    4080 aaagaagtga  gactattaga  caaagtattt  atgtaattat  ttgataactc  ttgtaaatag    4140
gtggaatatg  aatgcttgga  aaattaaact  ttaatttatt  gacattgtac  atagctctgt    4200
gtaaatagaa  ttgcaactgt  caggttttgt  gttcttgttt  tcctttagtt  gggtttatttt   4260 ccaggtcaca  gaattgctgt  taacactaga  aaacacactt  cctgcaccaa  caccaatacc    4320 cttttcaaaag  agttgtctgc  aacattttttg  ttttcttttt  taatgtccaa  aagtggggga   4380
aagtgctatt  tcctatttttc  accaaaattg  gggaaggagt  gccactttcc  agctccactt    4440
caaattcctt  aaaatataac  tgagattgct  gtggggaggg  aggagggcag  aggctgcggt    4500 ttgactttttt  aatttttcttt  ttgttatttg  tatttgctag  tctctgatttt  cctcaaaacg   4560 aagtggaatt  tactactgtt  gtcagtatcg  gtgtttttgaa  ttggtgcctg  cctatagaga    4620
tatattcaca  gttcaaaagt  caggtgctga  gagatggttt  aaagacaaat  tcatgaaggt    4680
atattttgtg  ttatagttgt  tgatgagttc  tttggttttc  tgtattttttc  ccctctctt    4740 taaaacatca  ctgaaatttc  aataaatttt  tattgaaatg  tctaaaaaaa  aaaaaaaaaa    4800
aaaaaaaaaa  aaaa                                                         4814
```

<210> SEQ ID NO 76
<211> LENGTH: 1712

<212> TYPE: DNA
<213> ORGANISM: Homo sapiens

<400> SEQUENCE: 76

```
aagggcggga cattccccct gcctcttcgc accacagcca gagcctgcca ttaggaccaa        60
tgaaagcaaa gtacctcatc ccctcagtga ctaagaatcg cagtatttaa gaggtagcag       120
gaatgggctg agagtggtgt ttgctttctc caccagaagg gcacactttc atctaatttg       180
gggtatcact gagctgaaga caaagagaag ggggagaaaa cctagcagac caccatgtgc       240
tatgggaagt gtgcacgatg catcggacat tctctggtgg ggctcgccct cctgtgcatc       300
gcggctaata ttttgcttta ctttcccaat ggggaaacaa agtatgcctc cgaaaaccac       360
ctcagccgct tcgtgtggtt cttttctggc atcgtaggag gtggcctgct gatgctcctg       420
ccagcatttg tcttcattgg gctggaacag gatgactgct gtggctgctg tggccatgaa       480
aactgtggca acgatgtgc gatgctttct tctgtattgg ctgctctcat tggaattgca       540
ggatctggct actgtgtcat tgtggcagcc cttggcttag cagaaggacc actatgtctt       600
gattccctcg gccagtggaa ctacaccttt gccagcactg agggccagta ccttctggat       660
acctccacat ggtccgagtg cactgaaccc aagcacattg tggaatggaa tgtatctctg       720
ttttctatcc tcttggctct tggtggaatt gaattcatct tgtgtcttat tcaagtaata       780
aatggagtgc ttgaggcat atgtggcttt tgctgctctc accaacagca atatgactgc       840
taaaagaacc aacccaggac agagccacaa tcttcctcta tttcattgta atttatatat       900
ttcacttgta ttcatttgta aaactttgta ttagtgtaac atactcccca cagtctactt       960
ttacaaacgc ctgtaaagac tggcatcttc acaggatgtc agtgtttaaa tttagtaaac      1020
ttcttttttg tttgtttatt tgttttgtt ttttttaag gaatgaggaa acaaaccacc      1080
ctctggggt aatttacaga ctgagtgaca gtactcagta tatctgagat aaactctata      1140
atgttttgga taaaaataac attccaatca ctattgtata tatgtgcatg tattttttaa      1200
attaaagatg tctagttgct ttttataaga ccaagaagga gaaaatccga caacctggaa      1260
agatttttgt tttcactgct tgtatgatgt ttcccattca tacacctata aatctctaac      1320
aagaggccct ttgaactgcc ttgtgttctg tgagaaacaa atatttactt agagtggaag      1380
gactgattga gaatgttcca atccaaatga atgcatcaca acttacaatg ctgctcattg      1440
ttgtgagtac tatgagattc aaatttttct aacatatgga aagccttttg tcctccaaag      1500
atgagtacta gggatcatgt gtttaaaaaa agaaaggcta cgatgactgg gcaagaagaa      1560
agatgggaaa ctgaataaag cagttgatca gcatcattgg aacatgggga cgagtgacgg      1620
caggaggacc acgaggaaat accctcaaaa ctaacttgtt tacaacaaaa taaagtattc      1680
actaccatgt taaaaaaaaa aaaaaaaaa aa                                    1712
```

<210> SEQ ID NO 77
<211> LENGTH: 5748
<212> TYPE: DNA
<213> ORGANISM: Homo sapiens

<400> SEQUENCE: 77

```
gagaagaaag ccagtgcgtc tctgggcgca ggggccagtg gggctcggag gcacaggcac        60
cccgcgacac tccaggttcc ccgacccacg tccctggcag ccccgattat ttacagcctc       120
agcagagcac ggggcggggg cagaggggcc cgcccgggag gctgctact tcttaaaacc       180
tctgcgggct gcttagtcac agccccccct tgcttgggtgt gtccttcgct cgctccctcc       240
```

```
ctccgtctta ggtcactgtt ttcaacctcg aataaaaact gcagccaact tccgaggcag    300
cctcattgcc cagcggaccc cagcctctgc caggttcggt ccgccatcct cgtcccgtcc    360
tccgccggcc cctgccccgc gcccagggat cctccagctc ctttcgcccg cgccctccgt    420
tcgctccgga caccatggac aagttttggt ggcacgcagc ctgggactc tgcctcgtgc     480 cgctgagcct ggcgcagatc gatttgaata taacctgccg ctttgcaggt gtattccacg    540
tggagaaaaa tggtcgctac agcatctctc ggacggaggc cgctgacctc tgcaaggctt    600
tcaatagcac cttgcccaca atggcccaga tggagaaagc tctgagcatc ggatttgaga    660
cctgcaggta tgggttcata gaagggcacg tggtgattcc ccggatccac cccaactcca    720
tctgtgcagc aaacaacaca ggggtgtaca tcctcacatc caacacctcc cagtatgaca    780
catattgctt caatgcttca gctccacctg aagaagattg tacatcagtc acagacctgc    840
ccaatgcctt tgatggacca attaccataa ctattgttaa ccgtgatggc acccgctatg    900
tccagaaagg agaatacaga acgaatcctg aagacatcta ccccagcaac cctactgatg    960
atgacgtgag cagcggctcc tccagtgaaa ggagcagcac ttcaggaggt tacatctttt   1020 acacctttc tactgtacac cccatcccag acgaagacag tccctggatc accgacagca   1080
cagacagaat ccctgctacc actttgatga gcactagtgc tacagcaact gagacagcaa   1140
ccaagaggca agaaacctgg gattggtttt catggttgtt tctaccatca gagtcaaaga   1200
atcatcttca cacaacaaca caaatggctg gtacgtcttc aaataccatc tcagcaggct   1260
gggagccaaa tgaagaaaat gaagatgaaa gagacagaca cctcagtttt tctggatcag   1320
gcattgatga tgatgaagat tttatctcca gcaccatttc aaccacacca cgggcttttg   1380
accacacaaa acagaaccag gactggaccc agtggaaccc aagccattca aatccggaag   1440
tgctacttca gacaaccaca aggatgactg atgtagacag aaatggcacc actgcttatg   1500
aaggaaactg gaacccagaa gcacaccctc ccctcattca ccatgagcat catgaggaag   1560
aagagacccc acattctaca agcacaatcc aggcaactcc tagtagtaca acggaagaaa   1620
cagctaccca gaaggaacag tggtttggca cagatggca tgagggatat cgccaaacac   1680
ccaaagaaga ctcccattcg acaacaggga cagctgcagc ctcagctcat accagccatc   1740
caatgcaagg aaggacaaca ccaagcccag aggacagttc ctggactgat tccttcaacc   1800
caatctcaca ccccatggga cgaggtcatc aagcaggaag aaggatggat atggactcca   1860
gtcatagtat aacgcttcag cctactgcaa atccaaacac aggtttggtg aagatttgg    1920 acaggacagg acctctttca atgacaacgc agcagagtaa ttctcagagc ttctctacat   1980
cacatgaagg cttggaagaa gataaagacc atccaacaac ttctactctg acatcaagca   2040
ataggaatga tgtcacaggt ggaagaagag acccaaatca ttctgaaggc tcaactactt   2100
tactggaagg ttatacctct cattacccac acacgaagga aagcaggacc ttcatcccag   2160
tgacctcagc taagactggg tcctttggag ttactgcagt tactgttgga gattccaact   2220
ctaatgtcaa tcgttcctta tcaggagacc aagacacatt ccaccccagt gggggtccc    2280 ataccactca tggatctgaa tcagatggac actcacatgg gagtcaagaa ggtggagcaa   2340
acacaacctc tggtcctata aggacacccc aaattccaga atggctgatc atcttggcat   2400
ccctcttggc cttggctttg attcttgcag tttgcattgc agtcaacagt cgaagaaggt   2460
gtgggcagaa gaaaaagcta gtgatcaaca gtggcaatgg agctgtggag acagaaagc    2520 caagtggact caacgagag gccagcaagt ctcaggaaat ggtgcatttg gtgaacaagg   2580
agtcgtcaga aactccagac cagtttatga cagctgatga cacaaggaac ctgcagaatg   2640
```

```
tggacatgaa gattggggtg taacacctac accattatct tggaaagaaa caaccgttgg    2700
aaacataacc attacaggga gctgggacac ttaacagatg caatgtgcta ctgattgttt    2760
cattgcgaat cttttttagc ataaaatttt ctactcttt tgtttttgt gttttgttct      2820 ttaaagtcag gtccaatttg taaaaacagc attgctttct gaaattaggg cccaattaat   2880
aatcagcaag aatttgatcg ttccagttcc cacttggagg cctttcatcc ctcgggtgtg    2940
ctatggatgg cttctaacaa aaactacaca tatgtattcc tgatcgccaa cctttccccc   3000
accagctaag gacatttccc agggttaata gggcctggtc cctgggagga aatttgaatg    3060
ggtccatttt gccctccat agcctaatcc ctgggcattg cttccactg aggttggggg     3120 ttggggtgta ctagttacac atcttcaaca ccccctct agaaatttt cagatgcttc      3180 tgggagacac ccaaagggtg aagctattta tctgtagtaa actatttatc tgtgtttttg    3240
aaatattaaa ccctggatca gtcctttgat cagtataatt ttttaaagtt actttgtcag    3300
aggcacaaaa gggtttaaac tgattcataa taaatatctg tacttcttcg atcttcacct   3360
tttgtgctgt gattcttcag tttctaaacc agcactgtct gggtccctac aatgtatcag    3420
gaagagctga gaatggtaag gagactcttc taagtcttca tctcagagac cctgagttcc    3480
cactcagacc cactcagcca aatctcatgg aagaccaagg agggcagcac tgtttttgtt   3540
ttttgttttt tgtttttttt ttttgacact gtccaaaggt tttccatcct gtcctggaat    3600
cagagttgga agctgaggag cttcagcctc ttttatggtt taatggccac ctgttctctc    3660
ctgtgaaagg ctttgcaaag tcacattaag tttgcatgac ctgttatccc tggggcccta    3720
tttcatagag gctggcccta ttagtgattt ccaaaaacaa tatggaagtg ccttttgatg    3780
tcttacaata agagaagaag ccaatggaaa tgaaagagat tggcaaaggg gaaggatgat    3840
gccatgtaga tcctgtttga cattttatg gctgtatttg taaacttaaa cacaccagtg    3900
tctgttcttg atgcagttgc tatttaggat gagttaagtg cctggggagt ccctcaaaag    3960
gttaaaggga ttcccatcat tggaatctta tcaccagata ggcaagttta tgaccaaaca    4020
agagagtact ggcttatcc tctaacctca tattttctcc cacttggcaa gtcctttgtg    4080
gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
cacaaagcag aaagaagaag aaaagctcct gactaaatca gggctgggct tagacagagt    4320
tgatctgtag aatatcttta aaggagagat gtcaactttc tgcactattc ccagcctctg    4380
ctcctccctg tctaccctct cccctccctc tctccctcca cttcacccca caatcttgaa    4440
aaacttcctt tctcttctgt gaacatcatt ggccagatcc attttcagtg gtctggattt    4500 cttttttattt tcttttcaac ttgaaagaaa ctggacatta ggccactatg tgttgttact    4560
gccactagtg ttcaagtgcc tcttgttttc ccagagattt cctgggtctg ccagaggccc    4620
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaagaggc tgagacagga    4800 ggttattttc aattttattt tggaattaaa tactttttc cctttattac tgttgtagtc    4860
cctcacttgg atatacctct gttttcacga tagaaataag ggaggtctag agcttctatt    4920
ccttggccat tgtcaacgga gagctggcca agtcttcaca aacccttgca acattgcctg    4980
```

| | |
|---|---|
| aagtttatgg aataagatgt attctcactc ccttgatctc aagggcgtaa ctctggaagc | 5040 |
| acagcttgac tacacgtcat ttttaccaat gattttcagg tgacctgggc taagtcattt | 5100 |
| aaactgggtc tttataaaag taaaaggcca acatttaatt attttgcaaa gcaacctaag | 5160 |
| agctaaagat gtaatttttc ttgcaattgt aaatcttttg tgtctcctga agacttccct | 5220 |
| taaaattagc tctgagtgaa aaatcaaaag agacaaaaga catcttcgaa tccatatttc | 5280 |
| aagcctggta gaattggctt ttctagcaga acctttccaa aagttttata ttgagattca | 5340 |
| taacaacacc aagaattgat tttgtagcca acattcattc aatactgtta tatcagagga | 5400 |
| gtaggagaga ggaaacattt gacttatctg gaaaagcaaa atgtacttaa gaataagaat | 5460 |
| aacatggtcc attcacctttt atgttataga tatgtctttg tgtaaatcat ttgttttgag | 5520 |
| ttttcaaaga atagcccatt gttcattctt gtgctgtaca atgaccactg ttattgttac | 5580 |
| tttgactttt cagagcacac ccttcctctg gtttttgtat atttattgat ggatcaataa | 5640 |
| taatgaggaa agcatgatat gtatattgct gagttgaaag cacttattgg aaaatattaa | 5700 |
| aaggctaaca ttaaaagact aaaggaaaca gaaaaaaaaa aaaaaaaa | 5748 |

<210> SEQ ID NO 78
<211> LENGTH: 4293
<212> TYPE: DNA
<213> ORGANISM: Homo sapiens

<400> SEQUENCE: 78

| | |
|---|---|
| acccactccc gctgccccgt ccggcccgcg ccgcttcctc gcagcagctg ctcccggctc | 60 |
| cgcggccgca gcccgcgtgg acgctccgag cgccccccga cggacgggac cggctccctg | 120 |
| gcggtcgggc gagcgggcgg caacgctgcc cggccggcag cgctggggtt aagtggccca | 180 |
| agtaaaccta gctcggcgat cggcgccgga gattcgcgag cccagcgccc tgcacggccg | 240 |
| ccagccggcc tcccgccagc cagccccgac ccgcggctcc gccgcccagc cgcgccccag | 300 |
| ccagccctgc ggcaggaaag catgaaggga gacaccaggc atctcaatgg agaggaggac | 360 |
| gccggcggga gggaagactc gatcctcgtc aacggggcct gcagcgacca gtcctccgac | 420 |
| tcgcccccaa tcctggaggc tatccgcacc ccggagatca gaggccgaag atcaagctcg | 480 |
| cgactctcca gagggaggt gtccagtctg ctaagctaca cacaggactt gacaggcgat | 540 |
| ggcgacgggg aagatgggga tggctctgac accccagtca tgccaaagct cttccgggaa | 600 |
| accaggactc gttcagaaag cccagctgtc cgaactcgaa ataacaacag tgtctccagc | 660 |
| cgggagaggc acaggcctttc cccacgttcc acccgaggcc ggcagggccg caaccatgtg | 720 |
| gacgagtccc ccgtggagtt cccggctacc aggtccctga cggcgggc aacagcatcg | 780 |
| gcaggaacgc catggccgtc ccctcccagc tcttaccta ccatcgacct cacagacgac | 840 |
| acagaggaca cacatgggac gccccagagc agcagtaccc cctacgcccg cctagcccag | 900 |
| gacagccagc agggggcat ggagtccccg caggtggagg cagacagtgg agatggagac | 960 |
| agttcagagt atcaggatgg gaaggagttt ggaataggg acctcgtgtg gggaaagatc | 1020 |
| aagggcttct cctggtggcc cgccatggtg gtgtcttgga aggccacctc caagcgacag | 1080 |
| gctatgtctg gcatgcggtg ggtccagtgg tttggcgatg gcaagttctc cgaggtctct | 1140 |
| gcagacaaac tggtggcact ggggctgttc agccagcact ttaatttggc caccttcaat | 1200 |
| aagctcgtct cctatcgaaa agccatgtac catgctctgg agaaagctag ggtgcgagct | 1260 |
| ggcaagacct tccccagcag ccctggagac tcattggagg accagctgaa gcccatgttg | 1320 |
| gagtgggccc acggggcttt caagcccact gggatcgagg gcctcaaacc caacaacacg | 1380 |

```
caaccagaga acaagactcg aagacgcaca gctgacgact cagccacctc tgactactgc   1440
cccgcaccca agcgcctcaa gacaaattgc tataacaacg gcaaagaccg aggggatgaa   1500
gatcagagcc gagaacaaat ggcttcagat gttgccaaca acaagagcag cctggaagat   1560
ggctgtttgt cttgtggcag gaaaaacccc gtgtccttcc accctctctt tgagggggggg   1620
ctctgtcaga catgccggga tcgcttcctt gagctgtttt acatgtatga tgacgatggc   1680
tatcagtctt actgcactgt gtgctgcgag ggccgagagc tgctgctttg cagcaacacg   1740
agctgctgcc ggtgtttctg tgtggagtgc ctggaggtgc tggtgggcac aggcacagcg   1800
gccgaggcca agcttcagga gccctggagc tgttacatgt gtctcccgca gcgctgtcat   1860
ggcgtcctgc ggcgccggaa ggactggaac gtgcgcctgc aggccttctt caccagtgac   1920
acggggcttg aatatgaagc ccccaagctg taccctgcca ttcccgcagc ccgaaggcgg   1980
cccattcgag tcctgtcatt gtttgatggc atcgcgacag gctacctagt cctcaaagag   2040
ttgggcataa aggtaggaaa gtacgtcgct tctgaagtgt gtgaggagtc cattgctgtt   2100
ggaaccgtga agcacgaggg gaatatcaaa tacgtgaacg acgtgaggaa catcacaaag   2160
aaaaatattg aagaatgggg cccatttgac ttggtgattg gcggaagccc atgcaacgat   2220
ctctcaaatg tgaatccagc caggaaaggc ctgtatgagg gtacaggccg gctcttcttc   2280
gaattttacc acctgctgaa ttactcacgc cccaaggagg gtgatgaccg gccgttcttc   2340
tggatgtttg agaatgttgt agccatgaag gttggcgaca gagggacat ctcacggttc   2400
ctggagtgta atccagtgat gattgatgcc atcaaagttt ctgctgctca cagggcccga   2460
tacttctggg gcaacctacc cgggatgaac aggcccgtga tagcatcaaa gaatgataaa   2520
ctcgagctgc aggactgctt ggaatacaat aggatagcca agttaaagaa agtcacagaca   2580
ataaccacca agtcgaactc gatcaaacag gggaaaaacc aacttttccc tgttgtcatg   2640
aatggcaaag aagatgtttt gtggtgcact gagctcgaaa ggatctttgg cttttcctgtg   2700
cactacacag acgtgtccaa catgggccgt ggtgcccgcc agaagctgct gggaaggtcc   2760
tggagcgtgc ctgtcatccg acacctcttc gcccctctga aggactactt tgcatgtgaa   2820
tagttccagc caggccccaa gcccactggg gtgtgtggca gagccaggac ccaggaggtg   2880
tgattcctga aggcatcccc aggccctgct cttcctcagc tgtgtgggtc ataccgtgta   2940
cctcagttcc ctcttgctca gtgggggcag agccacctga ctcttgcagg ggtagcctga   3000
ggtgccgcct ccttgtgcac aaatcagacc tggctgcttg gagcagccta acacggtgct   3060
cattttttct tctcctaaaa cttttaaaact tgaagtaggt agcaacgtgg cttttttttt   3120
ttcccttcct gggtctacca ctcagagaaa caatggctaa gataccaaaa ccacagtgcc   3180
gacagctctc caatactcag gttaatgctg aaaaatcatc caagacagtt attgcaagag   3240
tttaatttt gaaaactggc tactgctctg tgtttacaga cgtgtgcagt tgtaggcatg   3300
tagctacagg acattttaa gggcccagga tcgttttttc ccaggcaag cagaagagaa   3360
aatgttgtat atgtctttta cccggcacat tcccctttgcc taaatacaag ggctggagtc   3420
tgcacgggac ctattagagt attttccaca atgatgatga tttcagcagg gatgacgtca   3480
tcatcacatt cagggctatt ttttccccca caaacccaag ggcaggggcc actcttagct   3540
aaatccctcc ccgtgactgc aatagaaccc tctggggagc tcaggaaggg gtgtgctgag   3600
ttctataata taagctgcca tatattttgt agacaagtat ggctcctcca tatctccctc   3660
ttccctagga gaggagtgtg aagcaaggag cttagataag acacccctc aaacccattc   3720
```

| | |
|---|---|
| cctctccagg agacctaccc tccacaggca caggtcccca gatgagaagt ctgctaccct | 3780 |
| catttctcat cttttttacta aactcagagg cagtgacagc agtcagggac agacatacat | 3840 |
| ttctcatacc ttccccacat ctgagagatg acagggaaaa ctgcaaagct cggtgctccc | 3900 |
| tttggagatt ttttaatcct ttttttattcc ataagaagtc gttttttaggg agaacgggaa | 3960 |
| ttcagacaag ctgcatttca gaaatgctgt cataatggtt tttaacacct tttactcttc | 4020 |
| ttactggtgc tattttgtag aataaggaac aacgttgaca agttttgtgg ggcttttttat | 4080 |
| acactttttta aaatctcaaa cttctatttt tatgtttaac gttttcatta aaatttttttt | 4140 |
| tgtaactgga gccacgacgt aacaaatatg gggaaaaaac tgtgccttgt ttcaacagtt | 4200 |
| tttgctaatt tttaggctga aagatgacgg atgcctagag tttaccttat gtttaattaa | 4260 |
| aatcagtatt tgtctaaaaa aaaaaaaaaa aaa | 4293 |

<210> SEQ ID NO 79
<211> LENGTH: 8761
<212> TYPE: DNA
<213> ORGANISM: Homo sapiens

<400> SEQUENCE: 79

| | |
|---|---|
| gccgaggagg aagaggttga tggcggcggc ggagctccga gagacctcgg ctgggcaggg | 60 |
| gccggccgtg gcgggccggg gactgcgcct ctagagccgc gagttctcgg gaattcgccg | 120 |
| cagcggacgc gctcggcgaa tttgtgctct tgtgccctcc tccgggcttg ggcccaggcc | 180 |
| cggcccctcg cacttgccct tacctttttct atcgagtccg catccctctc cagccactgc | 240 |
| gacccggcga agagaaaaag gaacttcccc caccccctcg ggtgccgtcg gagccccca | 300 |
| gcccacccct gggtgcggcg cggggacccc gggccgaaga agagatttcc tgaggattct | 360 |
| ggttttcctc gcttgtatct ccgaaagaat taaaaatggc cgagaatgtg gtggaaccgg | 420 |
| ggccgccttc agccaagcgg cctaaactct catctccggc cctctcggcg tccgccagcg | 480 |
| atggcacaga ttttggctct ctatttgact tggagcacga cttaccagat gaattaatca | 540 |
| actctacaga attgggacta accaatggtg gtgatattaa tcagcttcag acaagtcttg | 600 |
| gcatggtaca agatgcagct tctaaacata aacagctgtc agaattgctg cgatctggta | 660 |
| gttccccctaa cctcaatatg ggagttggtg gcccaggtca agtcatggcc agccaggccc | 720 |
| aacagagcag tcctggatta ggtttgataa atagcatggt caaaagccca atgacacagg | 780 |
| caggcttgac ttctcccaac atggggatgg gcactagtgg accaaatcag ggtcctacgc | 840 |
| agtcaacagg tatgatgaac agtccagtaa atcagcctgc catgggaatg aacacaggga | 900 |
| tgaatgcggg catgaatcct ggaatgttgg ctgcaggcaa tggacaaggg ataatgccta | 960 |
| atcaagtcat gaacggttca attggagcag gccgagggcg acagaatatg cagtacccaa | 1020 |
| acccaggcat gggaagtgct ggcaacttac tgactgagcc tcttcagcag ggctctcccc | 1080 |
| agatgggagg acaaacagga ttgagaggcc cccagcctct taagatggga atgatgaaca | 1140 |
| accccaatcc ttatggttca ccatatactc agaatcctgg acagcagatt ggagccagtg | 1200 |
| gccttggtct ccagattcag acaaaaactg tactatcaaa taacttatct ccatttgcta | 1260 |
| tggacaaaaa ggcagttcct ggtggaggaa tgcccaacat gggtcaacag ccagcccgc | 1320 |
| aggtccagca gccaggcctg gtgactccag ttgcccaagg gatgggttct ggagcacata | 1380 |
| cagctgatcc agagaagcgc aagctcatcc agcagcagct tgttctcctt ttgcatgctc | 1440 |
| acaagtgcca gcgccgggaa caggccaatg gggaagtgag gcagtgcaac cttccccact | 1500 |
| gtcgcacaat gaagaatgtc ctaaaccaca tgacacactg ccagtcaggc aagtcttgcc | 1560 |

```
aagtggcaca ctgtgcatct tctcgacaaa tcatttcaca ctggaagaat tgtacaagac    1620
atgattgtcc tgtgtgtctc cccctcaaaa atgctggtga taagagaaat caacagccaa    1680
ttttgactgg agcacccgtt ggacttggaa atcctagctc tctaggggtg ggtcaacagt    1740
ctgcccccaa cctaagcact gttagtcaga ttgatcccag ctccatagaa agagcctatg    1800
cagctcttgg actaccctat caagtaaatc agatgccgac acaacccag gtgcaagcaa     1860 agaaccagca gaatcagcag cctgggcagt ctccccaagg catgcggccc atgagcaaca    1920
tgagtgctag tcctatggga gtaaatggag gtgtaggagt tcaaacgccg agtcttcttt    1980
ctgactcaat gttgcattca gccataaatt ctcaaaaccc aatgatgagt gaaaatgcca    2040
gtgtgccctc cctgggtcct atgccaacag cagctcaacc atccactact ggaattcgga    2100
aacagtggca cgaagatatt actcaggatc ttcgaaatca tcttgttcac aaactcgtcc    2160
aagccatatt tcctacgccg gatcctgctg ctttaaaaga cagacggatg gaaaacctag    2220
ttgcatatgc tcggaaagtt gaaggggaca tgtatgaatc tgcaaacaat cgagcggaat    2280
actaccacct tctagctgag aaaatctata agatccagaa agaactagaa gaaaaacgaa    2340
ggaccagact acagaagcag aacatgctac caaatgctgc aggcatggtt ccagtttcca    2400
tgaatccagg gcctaacatg ggacagccgc aaccaggaat gacttctaat ggccctctac    2460
ctgacccaag tatgatccgt ggcagtgtgc caaaccagat gatgcctcga ataactccac    2520
aatctggttt gaatcaattt ggccagatga gcatggccca gccccctatt gtaccccggc    2580
aaacccctcc tcttcagcac catggacagt tggctcaacc tggagctctc aacccgccta    2640
tgggctatgg gcctcgtatg caacagcctt ccaaccaggg ccagttcctt cctcagactc    2700
agttcccatc acagggaatg aatgtaacaa atatcccttt ggctccgtcc agcggtcaag    2760
ctccagtgtc tcaagcacaa atgtctagtt cttcctgccc ggtgaactct cctataatgc    2820
ctccagggtc tcaggggagc acattcact gtccccagct tcctcaacca gctcttcatc     2880
agaattcacc ctcgcctgta cctagtcgta ccccccacccc tcaccatact ccccaagca    2940 taggggctca gcagccacca gcaacaacaa ttccagcccc tgttcctaca cctcctgcca    3000
tgccacctgg gccacagtcc caggctctac atccccctcc aaggcagaca cctacaccac    3060
caacaacaca acttccccaa caagtgcagc cttcacttcc tgctgcacct tctgctgacc    3120
agccccagca gcagcctcgc tcacagcaga gcacagcagc gtctgttcct accccaacag    3180
caccgctgct cctccgcag cctgcaactc cactttccca gccagctgta agcattgaag     3240
gacaggtatc aaatcctcca tctactagta gcacagaagt gaattctcag gccattgctg    3300
agaagcagcc ttcccaggaa gtgaagatgg aggccaaaat ggaagtggat caaccagaac    3360
cagcagatac tcagccggag gatatttcag agtctaaagt ggaagactgt aaaatggaat    3420
ctaccgaaac agaagagaga agcactgagt taaaaactga aataaaagag gaggaagacc    3480
agccaagtac ttcagctacc cagtcatctc cggctccagg acagtcaaag aaaaagattt    3540
tcaaaccaga agaactacga caggcactga tgccaacttt ggaggcactt taccgtcagg    3600
atccagaatc ccttcccttt cgtcaacctg tggaccctca gcttttagga atccctgatt    3660
actttgatat tgtgaagagc cccatggatc tttctaccat taagaggaag ttagacactg    3720
gacagtatca ggagccctgg cagtatgtcg atgatatttg gcttatgttc aataatgcct    3780
ggttatataa ccgaaaaaca tcacgggtat acaaatactg ctccaagctc tctgaggtct    3840
ttgaacaaga aattgaccca gtgatgcaaa gccttggata ctgttgtggc agaaagttgg    3900
```

```
agttctctcc acagacactg tgttgctacg gcaaacagtt gtgcacaata cctcgtgatg   3960
ccacttatta cagttaccag aacaggtatc atttctgtga gaagtgtttc aatgagatcc   4020
aaggggagag cgtttctttg ggggatgacc cttcccagcc tcaaactaca ataaataaag   4080
aacaattttc caagagaaaa aatgacacac tggatcctga actgtttgtt gaatgtacag   4140
agtgcggaag aaagatgcat cagatctgtg tccttcacca tgagatcatc tggcctgctg   4200
gattcgtctg tgatggctgt ttaaagaaaa gtgcacgaac taggaaagaa ataagttttc   4260
ctgctaaaag gttgccatct accagacttg gcacctttct agagaatcgt gtgaatgact   4320
ttctgaggcg acagaatcac cctgagtcag gagaggtcac tgttagagta gttcatgctt   4380
ctgacaaaac cgtggaagta aaaccaggca tgaaagcaag gtttgtggac agtggagaga   4440
tggcagaatc ctttccatac cgaaccaaag ccctctttgc ctttgaagaa attgatggtg   4500
ttgacctgtg cttctttggc atgcatgttc aagagtatgg ctctgactgc cctccaccca   4560
accagaggag agtatacata tcttacctcg atagtgttca tttcttccgt cctaaatgct   4620
tgaggactgc agtctatcat gaaatcctaa ttggatattt agaatatgtc aagaaattag   4680
gttacacaac agggcatatt tgggcatgtc caccaagtga gggagatgat tatatcttcc   4740
attgccatcc tcctgaccag aagatacccca agcccaagcg actgcaggaa tggtacaaaa   4800
aaatgcttga caaggctgta tcagagcgta ttgtccatga ctacaaggat atttttaaac   4860
aagctactga agatagatta acaagtgcaa aggaattgcc ttatttcgag ggtgatttct   4920
ggcccaatgt tctggaagaa agcattaagg aactggaaca ggaggaagaa gagagaaaac   4980
gagaggaaaa caccagcaat gaaagcacag atgtgaccaa gggagacagc aaaaatgcta   5040 aaagaagaa taataagaaa accagcaaaa ataagagcag cctgagtagg ggcaacaaga   5100
agaaacccgg gatgcccaat gtatctaacg acctctcaca gaaactatat gccaccatgg   5160
agaagcataa agaggtcttc tttgtgatcc gcctcattgc tggccctgct gccaactccc   5220
tgcctcccat tgttgatcct gatcctctca tcccctgcga tctgatggat ggtcgggatg   5280
cgtttctcac gctggcaagg gacaagcacc tggagttctc ttcactccga agagcccagt   5340
ggtccaccat gtgcatgctg gtggagctgc acacgcagag ccaggaccgc tttgtctaca   5400
cctgcaatga atgcaagcac catgtggaga cacgctggca ctgtactgtc tgtgaggatt   5460
atgacttgtg tatcacctgc tataacacta aaaaccatga ccacaaaatg gagaaactag   5520
gccttggctt agatgatgag agcaacaacc agcaggctgc agccacccag agcccaggcg   5580
attctcgccg cctgagtatc cagcgctgca tccagtctct ggtccatgct tgccagtgtc   5640
ggaatgccaa ttgctcactg ccatcctgcc agaagatgaa gcgggttgtg cagcatacca   5700
agggttgcaa acgaaaaacc aatggcgggt gccccatctg caagcagctc attgccctct   5760
gctgctacca tgccaagcac tgccaggaga caaatgccc ggtgccgttc tgcctaaaca   5820
tcaagcagaa gctccggcag caacagctgc agcaccgact acagcaggcc caaatgcttc   5880
gcaggaggat ggccagcatg cagcggactg gtgtggttgg gcagcaacag ggcctccctt   5940
cccccactcc tgccactcca acgacaccaa ctggccaaca gccaaccacc ccgcagacgc   6000
cccagcccac ttctcagcct cagcctaccc ctcccaatag catgccaccc tacttgccca   6060
ggactcaagc tgctggccct gtgtcccagg gtaaggcagc aggccaggtg accctccaa    6120 cccctcctca gactgctcag ccaccccttc cagggccccc acctgcagca gtggaaatgg   6180
caatgcagat tcagagagca gcggagacgc agcgccagat ggcccacgtg caaattttc    6240 aaaggccaat ccaacaccag atgccccga tgactcccat ggcccccatg ggtatgaacc    6300
```

```
cacctcccat gaccagaggt cccagtgggc atttggagcc agggatggga ccgacaggga    6360
tgcagcaaca gccaccctgg agccaaggag gattgcctca gccccagcaa ctacagtctg    6420
ggatgccaag gccagccatg atgtcagtgg cccagcatgg tcaacctttg aacatggctc    6480
cacaaccagg attgggccag gtaggtatca gcccactcaa accaggcact gtgtctcaac    6540
aagccttaca aaaccttttg cggactctca ggtctcccag ctctcccctg cagcagcaac    6600
aggtgcttag tatccttcac gccaaccccc agctgttggc tgcattcatc aagcagcggg    6660
ctgccaagta tgccaactct aatccacaac ccatccctgg gcagcctggc atgccccagg    6720
ggcagccagg gctacagcca cctaccatgc caggtcagca gggggtccac tccaatccag    6780
ccatgcagaa catgaatcca atgcaggcgg gcgttcagag ggctggcctg ccccagcagc    6840
aaccacagca gcaactccag ccacccatgg agggatgag ccccaggct cagcagatga    6900 acatgaacca caacaccatg ccttcacaat tccgagacat cttgagacga cagcaaatga    6960
tgcaacagca gcagcaacag ggagcagggc caggaatagg ccctggaatg gccaaccata    7020
accagttcca gcaaccccaa ggagttggct acccaccaca gcagcagcag cggatgcagc    7080
atcacatgca acagatgcaa caaggaaata tgggacagat aggccagctt ccccaggcct    7140
tgggagcaga ggcaggtgcc agtctacagg cctatcagca gcgactcctt cagcaacaga    7200
tggggtcccc tgttcagccc aaccccatga gccccagca gcatatgctc ccaaatcagg    7260
cccagtcccc acacctacaa ggccagcaga tccctaattc tctctccaat caagtgcgct    7320
ctccccagcc tgtcccttct ccacggccac agtcccagcc ccccactcc agtccttccc    7380 caaggatgca gcctcagcct tctccacacc acgtttcccc acagacaagt tccccacatc    7440
ctggactggt agctgcccag gccaacccca tggaacaagg gcattttgcc agcccggacc    7500
agaattcaat gctttctcag cttgctagca atccaggcat ggcaaacctc catggtgcaa    7560
gcgccacgga cctgggactc agcaccgata actcagactt gaattcaaac ctctcacaga    7620
gtacactaga catacactag agacaccttg tagtattttg ggagcaaaaa aattattttc    7680
tcttaacaag acttttttgta ctgaaaacaa tttttttgaa tctttcgtag cctaaaagac    7740
aattttcctt ggaacacata agaactgtgc agtagccgtt tgtggtttaa agcaaacatg    7800
caagatgaac ctgagggatg atagaataca aagaatatat ttttgttatg gctggttacc    7860
accagccttt cttccccttt gtgtgtgtgg ttcaagtgtg cactgggagg aggctgaggc    7920
ctgtgaagcc aaacaatatg ctcctgcctt gcacctccaa taggttttat tattttttt     7980 aaattaatga acatatgtaa tattaatagt tattatttac tggtgcagat ggttgacatt    8040
tttccctatt ttcctcactt tatggaagag ttaaaacatt tctaaaccag aggacaaaag    8100
gggttaatgt tactttaaaa ttacattcta tatatatata aatatatata aatatatatt    8160
aaaataccag ttttttttct ctgggtgcaa agatgttcat tcttttaaaa aatgtttaaa    8220
aaaaaaaaaa aactgccttt cttccccctca agtcaacttt tgtgctccag aaaattttct    8280
attctgtaag tctgagcgta aaacttcaag tattaaaata atttgtacat gtagagagaa    8340
aaatgacttt ttcaaaaata tacaggggca gctgccaaat tgatgtatta tatattgtgg    8400
tttctgtttc ttgaaagaat ttttttcgtt atttttacat ctaacaaagt aaaaaaatta    8460
aaaagagggt aagaaacgat tccggtggga tgatttaaac atgcaaaatg tccctggggg    8520
tttcttcttt gcttgctttc ttcctcctta ccctaccccc cactcacaca cacacacaca    8580
cacacacaca cacacacaca cacacactt ctataaaact tgaaaatagc aaaaaccctc    8640
```

-continued

```
aactgttgta aatcatgcaa ttaaagttga ttacttataa atatgaactt tggatcactg    8700
tatagactgt taaatttgat ttcttattac ctattgttaa ataaactgtg tgagacagac    8760
a                                                                    8761

<210> SEQ ID NO 80
<211> LENGTH: 2379
<212> TYPE: DNA
<213> ORGANISM: Homo sapiens

<400> SEQUENCE: 80
gacccccgag ctgtgctgct cgcggccgcc accgccgggc cccggccgtc cctggctccc      60
ctcctgcctc gagaagggca gggcttctca gaggcttggc gggaaaaaga acggagggag     120
ggatcgcgct gagtataaaa gccggttttc ggggctttat ctaactcgct gtagtaattc     180
cagcgagagg cagagggagc gagcgggcgg ccggctaggt ggaagagcc gggcgagcag      240 agctgcgctg cgggcgtcct gggaagggag atccggagcg aataggggc ttcgcctctg      300 gcccagccct cccgctgatc ccccagccag cggtccgcaa cccttgccgc atccacgaaa     360
ctttgcccat agcagcgggc gggcactttg cactggaact tacaacaccc gagcaaggac     420
gcgactctcc cgacgcgggg aggctattct gcccatttgg ggacacttcc ccgccgctgc     480
caggacccgc ttctctgaaa ggctctcctt gcagctgctt agacgctgga tttttttcgg     540
gtagtggaaa accagcagcc tcccgcgacg atgcccctca cgttagctt caccaacagg      600 aactatgacc tcgactacga ctcggtgcag ccgtatttct actgcgacga ggaggagaac     660
ttctaccagc agcagcagca gagcgagctg cagcccccgg cgcccagcga ggatatctgg     720
aagaaattcg agctgctgcc caccccgccc ctgtccccta gccgccgctc cgggctctgc     780
tcgccctcct acgttgcggt cacacccttc tcccttcggg gagacaacga cggcggtggc     840
gggagcttct ccacggccga ccagctggag atggtgaccg agctgctggg aggagacatg     900
gtgaaccaga gtttcatctg cgacccggac gacgagacct tcatcaaaaa catcatcatc     960
caggactgta tgtggagcgg cttctcggcc gccgccaagc tcgtctcaga aagctggcc    1020 tcctaccagc tgcgcgcaa agacagcggc agcccgaacc cgcccgcgg ccacagcgtc    1080 tgctccacct ccagcttgta cctgcaggat ctgagcgccg ccgcctcaga gtgcatcgac    1140
ccctcggtgg tcttccccta ccctctcaac gacagcagct cgcccaagtc ctgcgcctcg    1200
caagactcca gcgccttctc tccgtcctcg gattctctgc tctcctcgac ggagtcctcc    1260
ccgcagggca gccccgagcc cctggtgctc catgaggaga ccgcccac caccagcagc     1320 gactctgagg aggaacaaga agatgaggaa gaaatcgatg ttgtttctgt ggaaaagagg    1380
caggctcctg gcaaaaggtc agagtctgga tcaccttctg ctggaggcca cagcaaacct    1440
cctcacagcc cactggtcct caagaggtgc cacgtctcca cacatcagca caactacgca    1500
gcgcctcctt ccactcggaa ggactatcct gctgccaaga gggtcaagtt ggacagtgtc    1560
agagtcctga gacagatcag caacaaccga aaatgcacca gccccaggtc ctcggacacc    1620
gaggagaatg tcaagaggcg aacacacaac gtcttggagc gccagaggag aacgagcta    1680 aaacggagct ttttttgccct gcgtgaccag atccccgagt tggaaaacaa tgaaaaggcc    1740
cccaaggtag ttatccttaa aaaagccaca gcatacatcc tgtccgtcca agcagaggag    1800
caaaagctca tttctgaaga ggacttgttg cggaaacgac gagaacagtt gaaacacaaa    1860
cttgaacagc tacggaactc ttgtgcgtaa ggaaaagtaa ggaaaacgat tccttctaac    1920
agaaatgtcc tgagcaatca cctatgaact tgtttcaaat gcatgatcaa atgcaacctc    1980
```

```
acaaccttgg ctgagtcttg agactgaaag atttagccat aatgtaaact gcctcaaatt    2040
ggactttggg cataaaagaa cttttttatg cttaccatct ttttttttc tttaacagat    2100 ttgtatttaa gaattgtttt taaaaaattt taagatttac acaatgtttc tctgtaaata    2160
ttgccattaa atgtaaataa ctttaataaa acgtttatag cagttacaca gaatttcaat    2220
cctagtatat agtacctagt attataggta ctataaaccc taattttttt tatttaagta    2280
cattttgctt tttaaagttg atttttttct attgttttta gaaaaaataa aataactggc    2340
aaatatatca ttgagccaaa tcttaaaaaa aaaaaaaa                            2379

<210> SEQ ID NO 81
<211> LENGTH: 8758
<212> TYPE: DNA
<213> ORGANISM: Drosophila melanogaster

<400> SEQUENCE: 81
agttctgctg cgatcgcgcc actgcgcact acgtaacgct tcgggaatcg cacatccaga      60
tccagattca gatccacatc cagatatctg tgacattttg tcgagtgagt tgcgttctca     120
aagatacaag atacatccgt gcgcgtatgt gtgtgtttgc atgaatttcg gctcttttaa     180
tacccttttt ttttcgcgtg cactaagtgt tcctatgtgt gtgtgtgtgg agttgctttt     240
cagttggggc cgcaactgca acaataaaat gcaattaagc cgctcaaatc aacaataaat     300
tgaattaaag cgcgtgaaca cgcttaaca  acttcaacag cggcgattcg agcgaaatgt     360
gggtgagagt ttaaggctcc atcggttttg actttctgat tgtacaaata tgtatatata     420
tatactatag catacatacc ttcgactaat taatgcaaaa cgctggccgg cagcttttgc     480
ataatattct ctgaataact ttaatgcaat taatcccgct gtgatctttc gtgttttcac     540
tatttcgcgc ggtttattca atttgaattt caatttattt tcggttttc tgtttcattt      600 tgtttataca tatatatatt tgttcggtct agtctgctca tcgggcgatt taattaacat     660
tttccgtgct gctgtgctgt tgttgttgct gtttcgtttt cagtcaaatg cggcactaaa     720
atgttaattc agccaaagca aacaacgatt atcgagtgaa ataggaatcg aacgccacaa     780
atcgcgaact cggggtgaag atcgagtgcc tcgatgacta tgttttggca acaaaatgta     840
gaccaccagt cggatgagca ggacaaacag gcgaagggtg cggcgcccac aaagagattg     900
aacatcagct tcaatgtgaa gatcgcggtg aatgtgaata ccaagatgac caccacccac     960
atcaatcagc aggcacctgg cacctcctcc tcctcgtcga actcccagaa tgcctcaccc    1020
agcaagattg tggtccgcca gcagagcagc tccttcgatc tacgtcagca attggctcgc    1080
ttaggccgcc aattggccag tggccaggat ggccatggcg gcatatccac catactgatc    1140
atcaatcttc tcctgctcat tctactctcg atctgctgcg atgtctgccg atcgcacaac    1200
tatacggtgc accagagtcc cgaacccgtc tccaagacc aaatgcgcct gctgcgtccc     1260
aagctggaca gcgatgtggt cgagaaggtg gccatctggc acaagcacgc cgccgcagct    1320
ccgccaagca ttgtcgaggg catcgccatc agcagcaggc cacagtcaac gatggcccat    1380
catccagatg atcgagatcg ggatcgtgat ccttcggagg aacagcatgg cgtcgacgag    1440
cgaatggtcc tggaacgcgt gaccagggat tgtgtgcagc gctgcattgt tgaggaggat    1500
ctgtttctgg acgaatttgg aatacagtgc gaaaaggcgg acaatggcga gaagtgctac    1560
aaaacacgat gcaccaaggg ctgtgcccag tggtatcgcg ccctcaagga gctggagtcc    1620
tgccaggagg cctgcctgtc cctccagttc tacccgtacg acatgccctg catcggtgcc    1680
```

```
tgcgagatgg cccagcggga ctactggcac ctccagcgac tggccatcag ccacctggtg  1740
gagcggacgc agccgcagct ggagcgagct cctcgggcgg acggacagtc cacgccactg  1800
accatccgct gggcgatgca ctttccggaa cactacctgg ccagcagacc cttcaacatt  1860
cagtaccagt ttgtggatca ccacggcgag gagctggatc tcgagcagga agaccaggat  1920
gcatccggag agacgggttc cagtgcctgg tttaacttag ccgattacga ctgtgacgag  1980
tattatgtgt gcgagatact ggaggccctg ataccctaca cacaatacag gttccgattt  2040
gagttgcctt tcggcgagaa tagagacgaa gtcctctact ctccggccac gcccgcctac  2100
caaacgccac ccgagggcgc gcccatctcg gctccggtca tcgagcatct gatgggtctc  2160
gacgacagcc acctggctgt ccactggcat cccggtcgct tcaccaatgg acccatcgag  2220
ggttaccgcc tgcgtttgag ttcctcgagg ggaaacgcta caagtgaaca gctggttccg  2280
gccggacgag gtagctacat cttttcccag ctacaagccg gcaccaacta taccctggcg  2340
ctgagcatga tcaacaaaca gggtgagggt ccggtggcca agggatttgt gcagactcac  2400
tccgctcgaa atgaaaagcc tgccaaggat ctgacagaaa gtgtcctgct cgtcggacga  2460
agggctgtga tgtggcaatc gctggaaccg gctggtgaga actccatgat ctatcaatct  2520
caggaggaat tggctgatat cgcctggtca aagcgggagc aacaactgtg gctgctcaac  2580
gtccatggag agttgcgcag cttaaaattt gaatccggcc agatggtgag tccagcgcag  2640
cagctcaagc tggatctggg aaacatatcc agtggaagat gggttcctcg cagattgagc  2700
ttcgactggc tgcatcatcg actgtacttc gctatggagt cgccagagcg aaaccaatcc  2760
agctttcaga ttatcagcac agatttgctg ggtgaatcaa cgcagaaagt gggcgagtcc  2820
tttgatctgc ccgttgagca gttggaagtg gatgccctga atggctggat tttctggagg  2880
aacgaggagt cgctgtggcg tcaggatctg catggtcgaa tgatccatcg cctgttgagg  2940
atcaggcagc ccggttggtt cctggtgcag ccacaacact tcatcatcca tctaatgctt  3000
ccacaggagg gtaaattcct agagataagc tacgatggtg ggttcaagca tcccactgccg  3060
ctaccaccgc cttcgaatgg agctggaaat ggacctgcat ccagccattg gcaaagcttt  3120
gccctgttgg gtcgctccct gctcctgccc gattctggtc agctgatcct ggttgagcag  3180
cagggtcagg cagccagtcc cagtgcctca tggcctctaa gaacttgcc cgactgttgg  3240
gccgtgatac tcctggtgcc ggaaagccaa ccactgacca cgctggagg aaaaccgcac  3300
agcttgaagg ccttgctggg agcccaggcg gcaaagatct cgtggaagga gccggaacgc  3360
aatccctacc aatcggcgga tgcagcacgc agctggagct acgaactgga agtgcttgat  3420
gtggccagcc aaaagtgcct tagcattcgc aatattcgtg gacccatctt tggactgcag  3480
cgcctgcagc cggataatct ctatcaactg cgagttaggg caataaacgt ggatggagag  3540
ccgggcgagt ggactgaacc gttggctgcc cgcacctggc cactgggtcc acatcgcttg  3600
agatgggcca ccggcaggg aagcgtcatt cataccaacg agctgggcga gggcttggaa  3660
gtgcagcagg aacagttgga gcgactaccc ggacccatga ccatggtgaa tgaaagcgtg  3720
ggctactacg tcactggcga cggtctactg cactgcatca atctggtgca cagccagtgg  3780
ggatgcccaa tctcggagcc actgcagcac gtgggctcgg tgacttacga ctggcggggc  3840
ggaagagttt attggacgga tctggccagg aattgcgtgg tgcgcatgga tccatggtcg  3900
ggcagtcggg aactgttgcc cgtcttcgag gccaacttcc tggcattgga tccgcgtcaa  3960
ggccacctgt actatgccac cagctctcag ctgtcgcgac atggtccac gcccgatgaa  4020
gcggtcactt attatcgtgt taatgggctg gagggaagca tcgcctcctt tgtgctggac  4080
```

-continued

```
acccagcagg atcagctctt ctggcttgtt aaaggctctg gtgcactgcg tttgtatcgt    4140
gcgcccctga cagctggcgg ggattcactg cagatgatcc agcagattaa aggcgtcttt    4200
caggctgtcc cggacagttt gcagcttctg cggcccttgg gcgcacttct ttggctggag    4260
cggagtggca ggagagctcg cttggtccgc ctggctgctc ctctggatgt catggagcta    4320
ccgacaccgg accaggcctc tcctgcctcc gcattgcaat tattggaccc acaaccattg    4380
cctccgcggg atgagggggt tattccaatg accgtgctcc cggatagcgt gcgtctggac    4440
gatggccact gggacgactt ccatgtgcgc tggcagccat ccacttccgg tggcaatcac    4500
agcgtctcct atcgtctgct cctcgagttt ggccaaagac tacaaacctt ggatttgagc    4560
acaccatttg cccggctgac ccaattgccg caggctcaat tgcagctaaa gatcagcatc    4620
acaccgcgaa ccgcgtggcg aagtggagac accactcggg tgcagctcac caccccgccg    4680
gtggctccta gtcagcctcg tcgtctgcgc gtgttcgtgg agcgcttggc cactgccctg    4740
caggaggcta atgtgagtgc tgtgctccgc tgggatgcgc cggaacaggg tcaggaggcg    4800
ccgatgcagg cgctggagta tcacatcagc tgttgggtgg gctcagagct gcacgaggag    4860
ttgcgcctca atcagagtgc cctggaggcc cgcgtagagc acctgcaacc ggatcagacg    4920
taccacttcc aggtggaggc acgtgtggct gccacgggag cggcagcggg cgcagctagt    4980
catgccctcc atgtggcacc ggaggtgcag gcggtgccac gcgtactcta cgccaatgca    5040
gagtttattg gcgaactgga cctggacaca cggaatcgca ggcgactggt gcacacggcc    5100
agtccggttg agcatctggt ggggatcgag ggagagcagc gattgctgtg ggtcaacgag    5160
cacgtggagc tgctcaccca tgtcccggga tcagctccag caaagctggc cagaatgagg    5220
gccgaggtct tggcactggc cgtggactgg atacagcgta tcgtctactg gcggaactg    5280
gatgctactg caccgcaggc ggcgataatc tatcgcctgg atctgtgcaa ctttgaaggg    5340
aagatcctgc agggcgagcg ggtgtggagc actcccaggg gacggttgct gaaggatctg    5400
gtggccctgc cacaggcgca atctctgatc tggttggagt acgagcaggg atctccgaga    5460
aatggttcgc tccggggcag aaatctaacc gatggctcgg agctggagtg ggcaacggtt    5520
cagccgctaa tccgtctgca tgctggaagc ttagagcccg gatcggagac cttgaacctg    5580
gtggacaacc agggcaagct gtgtgtctac gatgtggccc gtcagctgtg cacggccagc    5640
gctttgcggg cacagctgaa cttgctgggc gaggactcca ttgctggtca gttggcccag    5700
gattcgggat cctttacgc cgtgaaaaac tggagcattc gtgcttatgg tcgccggcgc    5760
cagcagctgg agtatacggt ggaactggag ccggaagagg tgcgtctgct ccaggcacac    5820
aactatcagg cctatccgcc caagaactgt ctgctccttc cttcatccgg cggatccctt    5880
ttgaaagcta ccgattgtga ggagcagaga tgcctattac acttacccat gatcacagcc    5940
tccgaagatt gtccactgcc tattcctggc gttagatacc aactgaatct tacgttggcc    6000
aaggagccgg gatccgagga gcacgatcat gggatgagc ccctgggaca gtggctgctc    6060
ggtgctgggg aatcgttgaa tcttacagac ctgctgccct tcacccgtta tcgcgtgtct    6120
ggaattttga gcagctttta ccaaaagaag ttggcattac ccaccttggt gttggcacca    6180
ctggagctcc ttaccgcctc tgccacgccc tcgcctccaa ggaacttcag tgttcgtgtg    6240
cttagtccca gggaactgga ggtcagctgg ttgccgccgg agcagctgcg tagcgaaagt    6300
gtctactaca cgctccactg gcaacaggaa ctggatggtg aaaatgtcca ggatcggcgg    6360
gaatgggagg cacatgagcg gcgactggag acggcgggca ctcatcgatt gactggaatc    6420
```

```
aagccgggat ctgggtatag cctgtgggtt caggcccatg ccacgcccac caagagcaac    6480
agcagcgagc ggctgcatgt gcgtagtttc gccgaattac ccgagttgca gctcctggaa    6540
ctgggaccct attctctgag tctcacctgg gcgggaacac cggatccact gggatcgctg    6600
cagctcgaat gccgatcgtc ggctgagcaa ctgcgtcgca atgtggccgg aaatcacact    6660
aagatggtgg tggagccatt gcagccacgc acccgctacc agtgtcgcct gctcctgggc    6720
tatgcggcga cgccgggagc tccactgtac catggcactg cagaggtgta cgaaactctg    6780
ggagatgcgc ccagtcagcc gggcaagcca caattggagc acatcgctga ggaggttttc    6840
cgtgtcacct ggacggcggc ccgcggtaat ggagcaccca ttgctctcta caatctggag    6900
gcactccagg cgaggagcga cattcgccgg aggcgcagaa gaaggcgccg caatagcggt    6960
ggatcactag agcagttgcc gtgggctgag gaaccggtgg tcgtggagga tcagtggctg    7020
gacttctgca acaccaccga gctgagctgc attgtgaaga gtctgcattc gagcaggttg    7080
ctcctcttcc gtgtgcgtgc gcggagcttg agcacggat ggggaccta cagcgaggag      7140
agcgaacggg tggcggagcc cttcgtttcg ccggagaaga gaggatcact ggtcctggcc    7200
atcattgcgc cggctgccat cgtttccagc tgcgttctgg cattggtgct cgttcgaaaa    7260
gttcaaaagc gacgactgcg tgccaagaaa ctgcttcagc agagccgtcc cagcatctgg    7320
agcaacctgt ccaccttgca gacgcaacag cagctgatgg ccgtcaggaa tcgcgccttc    7380
tccaccacgc tgagtgatgc ggacatcgct ctgctgcccc aaattaattg gagtcaactg    7440
aagttgctcc gatttcttgg cagcggtgct tttggtgagg tatacgaggg tcagttgaag    7500
acggaggact ccgaggagcc gcaacgagtg gccatcaaga gcctgcgcaa gggagccagt    7560
gaatttgccg agctgcttca ggaggctcag ctgatgagca acttcaagca cgagaacatt    7620
gtgtgcctgg tgggaatctg cttcgacacc gagtccatat ctctgattat ggagcacatg    7680
gaagcgggcg acttgctaag ctacctacgt gccgccaggg ctaccagcac ccaggagcca    7740
caacccactg ctggactctc gctctccgag ctcctggcca tgtgcattga tgtgccaac    7800
ggctgcagtt atctggagga catgcacttt gtgcatcgcg acctggcctg ccggaactgt    7860
ttggtcacgg aatcgacggg cagcacggat cgtcggcgca ccgtgaagat tggtgacttc    7920
ggattggcga gggacatcta caagagcgac tactaccgaa aggagggcga gggcctgcta    7980
ccggtgcgct ggatgtcgcc ggagagtctc gtcgacgggt tgttcaccac acagtcggat    8040
gtgtgggcct ttggagtgct ctgctgggag atcctcacac tgggccagca gccgtatgcg    8100
gcgaggaaca acttcgaggt gctggcccat gtcaaggagg gcgacggct ccagcagccg     8160
cccatgtgta cggagaagct ttactccctg ctcctgcttt gctggcgaac ggatccgtgg    8220
gagcgaccca gttccggcg ctgctacaac acactccatg ccatcagcac cgatttgcgg     8280
cgcacccaaa tggcctcggc aactgcggat acggttgtca gctgctccag gccggagttc    8340
aaggtgcgat tcgatggcca gccgctggag gagcatagag agcacaatga gcggccggag    8400
gatgagaacc tgacgctgcg ggaagtgccg ctcaaggata agcaactgta tgcaaacgag    8460
ggagtctcgc gactttagaa aggtgactcc catgtccttc acaaaggtcg tctcaaaacg    8520
attagctttc catttaatct aagttctaag tttaatatgt acgagaatat aaaatggtcg    8580
atgaggatgg caagtttgta ttctatttca gattaagata cttttttttt tcttctcaga    8640
tacaggaatt atgggcaagc gcattgccta taagttttat ttgcaccgct atttatttat    8700
tttctttaat atttcaatta atggatagac ttaaatatat tataaaattt ttggtact     8758
```

<210> SEQ ID NO 82
<211> LENGTH: 2505
<212> TYPE: DNA
<213> ORGANISM: Homo sapiens

<400> SEQUENCE: 82

```
agtggggaga gatgagtgta gataaaagga gtgcagaagg cacgaggaag ccacagtgct      60
ccggatcctc caatcttcgc tcctccaatc tccgctcctc cacccagttc aggaacccgc     120
gaccgctcgc agcgctctct tgaccactat gagcctcctg tccagccgcg cggcccgtgt     180
ccccggtcct tcgagctcct tgtgcgcgct gttggtgctg ctgctgctgc tgacgcagcc     240
agggcccatc gccagcgctg gtcctgccgc tgctgtgttg agagagctgc gttgcgtttg     300
tttacagacc acgcaaggag ttcatcccaa aatgatcagt aatctgcaag tgttcgccat     360
aggcccacag tgctccaagg tggaagtggt agcctccctg aagaacggga aggaaatttg     420
tcttgatcca gaagccccctt ttctaaagaa agtcatccag aaaattttgg acggtggaaa     480
caaggaaaac tgattaagag aaatgagcac gcatggaaaa gtttcccagt cttcagcaga     540
gaagttttct ggaggtctct gaacccaggg aagacaagaa ggaaagattt tgttgttgtt     600
tgtttatttg ttttttccagt agttagcttt cttcctggat tcctcacttt gaagagtgtg     660
aggaaaacct atgtttgccg cttaagcttt cagctcagct aatgaagtgt ttagcatagt     720
acctctgcta tttgctgtta ttttatctgc tatgctattg aagttttggc aattgactat     780
agtgtgagcc aggaatcact ggctgttaat cttttcaaagt gtcttgaatt gtaggtgact     840
attatatttc caagaaatat tccttaagat attaactgag aaggctgtgg atttaatgtg     900
gaaatgatgt ttcataagaa ttctgttgat ggaaatacac tgttatcttc acttttataa     960
gaaataggaa atattttaat gtttcttggg gaatatgtta gagaatttcc ttactcttga    1020
ttgtgggata ctatttaatt atttcacttt agaaagctga gtgtttcaca ccttatctat    1080
gtagaatata tttccttatt cagaatttct aaaagtttaa gttctatgag ggctaatatc    1140
ttatcttcct ataattttag acattcttta tcttttttagt atggcaaact gccatcattt    1200
acttttaaac tttgatttta tatgctattt attaagtatt ttattaggag taccataatt    1260
ctggtagcta aatatatatt ttagatagat gaagaagcta gaaaacaggc aaattcctga    1320
ctgctagttt atatagaaat gtattctttt agttttttaaa gtaaaggcaa acttaacaat    1380
gacttgtact ctgaaagttt tggaaacgta ttcaaacaat ttgaatataa atttatcatt    1440
tagttataaa aatatatagc gacatcctcg aggccctagc atttctcctt ggataggga     1500
ccagagagag cttggaatgt taaaaacaaa acaaaacaaa aaaaaacaag gagaagttgt    1560
ccaagggatg tcaattttttt atccctctgt atgggttaga ttttccaaaa tcataatttg    1620
aagaaggcca gcatttatgg tagaatatat aattatatat aaggtggcca cgctggggca    1680
agttccctcc ccactcacag ctttggcccc tttcacagag tagaacctgg gttagaggat    1740
tgcagaagac gagcggcagc ggggagggca gggaagatgc ctgtcgggtt tttagcacag    1800
ttcatttcac tgggattttg aagcattttct gtctgaatgt aaagcctgtt ctagtcctgg    1860
tgggacacac tggggttggg ggtgggggaa gatgcggtaa tgaaaccggt tagtcagtgt    1920
tgtcttaata tccttgataa tgctgtaaag tttattttta caaatatttc tgtttaagct    1980
atttcacctt tgtttggaaa tccttccctt ttaaagagaa aatgtgacac ttgtgaaaag    2040
gcttgtagga aagctcctcc cttttttttct ttaaaccttt aaatgacaaa cctaggtaat    2100
taatggttgt gaatttctat ttttgctttg tttttaatga acatttgtct ttcagaatag    2160
```

```
gattctgtga taatatttaa atggcaaaaa caaaacataa ttttgtgcaa ttaacaaagc    2220
tactgcaaga aaaataaaac atttcttggt aaaaacgtat gtatttatat attatatatt    2280
tatatataat atatattata tatttagcat tgctgagctt tttagatgcc tattgtgtat    2340
cttttaaagg ttttgaccat tttgttatga gtaattacat atatattaca ttcactatat    2400
taaaattgta cttttttact atgtgtctca ttggttcata gtctttattt tgtcctttga    2460
ataaacatta aaagatttct aaacttcaaa aaaaaaaaa aaaaa                     2505

<210> SEQ ID NO 83
<211> LENGTH: 1182
<212> TYPE: DNA
<213> ORGANISM: Homo sapiens

<400> SEQUENCE: 83
ccacatttgt gcatcacttc tttagagaaa gttaagtctg tgttctgctt aggagagata     60 acacttttg tccctgtagg tggcccccct ggtgtagcca ttagttgcta attacttgca    120
aacaaataaa caattaactc cttaagctgc tggctgggca agtgttcatt gacatgctaa    180
aactttctaa gacaggattt taattagtga cgttctaaat ccagcccct tgtcagcgga    240 gctataaggt gaactgcagg aagatcccag ccctatacac gtggggcaga gccagcagag    300
gccagagctg ttgctctgtg cagaccacga gaggatgtct cccagccttc aggaaggcgc    360
tcagctcggg gaaaacaaac cctcaacttg ctccttttca attgagagaa tcttaggact    420
ggaccagaag aaagactgtg ttccattaat gaaaccccac aggccctggg cagacacctg    480
cagctcatca gggaaagatg gtaacttatg tctacatgtc ccaaatcctc ccagtgggat    540
ttcattccct agcgtggtgg atcacccaat gccagaagaa agagcttcga aatatgaaaa    600
ttacttttca gcctcagaaa gactgtcttt gaaaagagag ttgagttggt atagaggccg    660
aagaccaaga actgctttta ctcaaaacca gattgaagtg ttagaaaatg tctttagagt    720
aaactgctat cctggtatcg atattagaga agcttagct caaaaattga atctagagga    780
agacagaatc cagatttggt ttcaaaatcg gcgtgcaaaa ctgaaaaggt cccatagaga    840
atcacagttt ctaatggcga aaaaaaattt caacacaaat ctgctggaat agatagaaaa    900
ctaaacaagt gaaattatct tctaattgca gagcatgaag aatcagtgga aatattaagt    960
gttaaaatgt gatgttttct ttcctgcatt taatctgaat attgtcattt tttctgaaaa   1020
tatattgtaa atactattat agcatggtac atatttgggc acttttagtt atagtaaaga   1080
ccttttatat atattttaat aaacattttc agaaagatt gctatttttt aagtaagcca   1140
aattaatcta ataaattagt ttgttaaaat caaaaaaaaa aa                      1182

<210> SEQ ID NO 84
<211> LENGTH: 1944
<212> TYPE: DNA
<213> ORGANISM: Homo sapiens

<400> SEQUENCE: 84
aatttctcac tgcccctgtg ataaactgtg gtcactggct gtggcagcaa ctattataag     60
atgctctgaa aactcttcag acactgaggg gcaccagagg agcagactac aagaatggca    120
cacgctatgg aaaactcctg gacaatcagt aaagagtacc atattgatga agaagtgggc    180
tttgctctgc caaatccaca ggaaaatcta cctgattttt ataatgactg gatgttcatt    240
gctaaacatc tgcctgatct catagagtct ggccagcttc gagaaagagt tgagaagtta    300
aacatgctca gcattgatca tctcacagac cacaagtcac agcgccttgc acgtctagtt    360
```

```
ctgggatgca tcaccatggc atatgtgtgg ggcaaaggtc atggagatgt ccgtaaggtc      420
ttgccaagaa atattgctgt tccttactgc caactctcca agaaactgga actgcctcct      480
attttggttt atgcagactg tgtcttggca aactggaaga aaaggatcc taataagccc       540 ctgacttatg agaacatgga cgttttgttc tcatttcgtg atggagactg cagtaaagga      600
ttcttcctgg tctctctatt ggtggaaata gcagctgctt ctgcaatcaa agtaattcct      660
actgtattca aggcaatgca aatgcaagaa cgggacactt tgctaaaggc gctgttggaa      720
atagcttctt gcttggagaa agcccttcaa gtgtttcacc aaatccacga tcatgtgaac      780
ccaaaagcat ttttcagtgt tcttcgcata tatttgtctg gctggaaagg caaccccag       840 ctatcagacg gtctggtgta tgaagggttc tgggaagacc caaggagtt tgcaggggc       900 agtgcaggcc aaagcagcgt ctttcagtgc tttgacgtcc tgctgggcat ccagcagact      960
gctggtggag acatgctgc tcagttcctc caggacatga aagatatat gccaccagct       1020 cacaggaact tcctgtgctc attagagtca aatccctcag tccgtgagtt tgtcctttca      1080
aaaggtgatg ctggcctgcg ggaagcttat gacgcctgtg tgaaagctct ggtctccctg     1140
aggagctacc atctgcaaat cgtgactaag tacatcctga ttcctgcaag ccagcagcca     1200
aaggagaata agacctctga agaccttca aaactggaag ccaaaggaac tggaggcact      1260
gatttaatga atttcctgaa gactgtaaga agtacaactg agaaatccct tttgaaggaa     1320
ggttaatgta acccaacaag agcacatttt atcatagcag agacatctgt atgcattcct     1380
gtcattaccc attgtaacag agccacaaac taatactatg caatgtttta ccaataatgc     1440
aatacaaaag acctcaaaat acctgtgcat ttcttgtagg aaaacaacaa aaggtaatta     1500
tgtgtaatta tactagaagt tttgtaatct gtatcttatc attggaataa atgacattc     1560 aataaataaa aatgcataag atatattctg tcggctgggc gcggtggctc acgcctgtaa     1620
tcccagcact ttgggaggcc gaggcgggcg gatcacaagg tcaggagatc gagaccatct     1680
tggctaacac ggtgaaaccc cgtctctact aaaaatacaa aaattagcc gggcgcggtg      1740 gcgggcacct gtagtcccag ctactcggga ggctgaggca ggagaatggc gtgaacctgg     1800
gaggcggagc ttgcagtgag ccaagattgt gccactgcaa tccggcctgg gctaaagagc     1860
gggactccgt ctcaaaaaaa aaaaaaaaaa gatatattct gtcataataa ataaaaatgc     1920
ataagatata aaaaaaaaaa aaaa                                            1944
```

<210> SEQ ID NO 85
<211> LENGTH: 2119
<212> TYPE: DNA
<213> ORGANISM: Homo sapiens

<400> SEQUENCE: 85

```
aagtcagggt gggacgtggg cgcggggaga caggtggtgg ctacgacggc gaagggagct      60
gagactgtcc aggcagccag gttaggccag gaggaccatg tgaatgggc cagagggctc      120 ccgggctggg cagggaccat gggctgtggc tgcagctcac acccggaaga tgactggatg      180
gaaaacatcg atgtgtgtga gaactgccat tatcccatag tcccactgga tgcaagggc      240 acgctgctca tccgaaatgg ctctgaggtg cgggaccac tggttaccta cgaaggctcc      300
aatccgccgg cttccccact gcaagacaac ctggttatcg ctctgcacag ctatgagccc      360
tctcacgacg gagatctggg cttttgagaag ggggaacagc tccgcatcct ggagcagagc      420
ggcgagtggt ggaaggcgca gtccctgacc acgggccagg aaggcttcat ccccttcaat      480
```

```
tttgtggcca aagcgaacag cctggagccc gaaccctggt tcttcaagaa cctgagccgc    540
aaggacgcgg agcggcagct cctggcgccc gggaacactc acggctcctt cctcatccgg    600
gagagcgaga gcaccgcggg atcgttttca ctgtcggtcc gggacttcga ccagaaccag    660
ggagaggtgg tgaaacatta caagatccgt aatctggaca acgtggcttc tacatctcc    720 cctcgaatca cttttcccgg cctgcatgaa ctggtccgcc attacaccaa tgcttcagat    780
gggctgtgca cacggttgag ccgcccctgc cagacccaga agcccagaa gccgtggtgg     840 gaggacgagt gggaggttcc cagggagacg ctgaagctgg tggagcggct ggggctgga     900 cagttcgggg aggtgtggat ggggtactac aacgggcaca cgaaggtggc ggtgaagagc    960
ctgaagcagg gcagcatgtc cccggacgcc ttcctggccg aggccaacct catgaagcag   1020
ctgcaacacc agcggctggt tcggctctac gctgtggtca cccaggagcc catctacatc   1080
atcactgaat acatggagaa tgggagtcta gtggattttc tcaagacccc ttcaggcatc   1140
aagttgacca tcaacaaact cctggacatg gcagcccaaa ttgcagaagg catggcattc   1200
attgaagagc ggaattatat tcatcgtgac cttcgggctg ccaacattct ggtgtctgac   1260
accctgagct gcaagattgc agactttggc ctagcacgcc tcattgagga caacgagtac   1320
acagccagga ggggggccaa gtttcccatt aagtggacag cgccagaagc cattaactac   1380
gggacattca ccatcaagtc agatgtgtgg tcttttggga tcctgctgac ggaaattgtc   1440
acccacggcc gcatccctta cccagggatg accaacccgg aggtgattca gaacctggag   1500
cgaggctacc gcatggtgcg ccctgacaac tgtccagagg agctgtacca actcatgagg   1560
ctgtgctgga aggagcgccc agaggaccgg cccacctttg actacctgcg cagtgtgctg   1620
gaggacttct tcacggccac agagggccag taccagcctc agccttgaga ggccttgaga   1680
ggccctgggg ttctccccct ttctctccag cctgacttgg ggagatggag ttcttgtgcc   1740
atagtcacat ggcctatgca catatggact ctgcacatga atcccaccca catgtgacac   1800
atatgcacct tgtgtctgta cacgtgtcct gtagttgcgt ggactctgca catgtcttgt   1860
acatgtgtag cctgtgcatg tatgtcttgg acactgtaca aggtacccct ttctggctct   1920
cccatttcct gagaccacag agagagggga gaagcctggg attgacagaa gcttctgccc   1980
acctactttt cttccctcag atcatccaga agttcctcaa gggccaggac tttatctaat   2040
acctctgtgt gctcctcctt ggtgcctggc ctggcacaca tcaggagttc aataaatgtc   2100
tgttgatgac tgttgtaca                                                2119

<210> SEQ ID NO 86
<211> LENGTH: 2098
<212> TYPE: DNA
<213> ORGANISM: Homo sapiens

<400> SEQUENCE: 86
attataaatc tagagactcc aggattttaa cgttctgctg gactgagctg gttgcctcat     60
gttattatgc aggcaactca ctttatccca atttcttgat acttttcctt ctggaggtcc    120
tatttctcta acatcttcca gaaaagtctt aaagctgcct taaccttttt tccagtccac    180
ctcttaaatt ttttcctcct cttcctctat actaacatga gtgtggatcc agcttgtccc    240
caaagcttgc cttgctttga agcatccgac tgtaaagaat cttcacctat gcctgtgatt    300
tgtgggcctg aagaaaacta tccatccttg caaatgtctt ctgctgagat gcctcacacg    360
gagactgtct ctcctcttcc ttcctccatg gatctgctta ttcaggacag ccctgattct    420
tccaccagtc ccaaaggcaa acaacccact tctgcagaga agagtgtcgc aaaaaaggaa    480
```

```
gacaaggtcc cggtcaagaa acagaagacc agaactgtgt tctcttccac ccagctgtgt    540
gtactcaatg atagatttca gagacagaaa tacctcagcc tccagcagat gcaagaactc    600
tccaacatcc tgaacctcag ctacaaacag gtgaagacct ggttccagaa ccagagaatg    660
aaatctaaga ggtggcagaa aaacaactgg ccgaagaata gcaatggtgt gacgcagaag    720
gcctcagcac ctacctaccc cagcctttac tcttcctacc accagggatg cctggtgaac    780
ccgactggga accttccaat gtggagcaac cagacctgga caattcaac ctggagcaac    840 cagacccaga catccagtc tggagcaac cactcctgga cactcagac tggtgcacc    900 caatcctgga caatcaggc ctggaacagt cccttctata actgtggaga ggaatctctg    960
cagtcctgca tgcagttcca gccaaattct cctgccagtg acttggaggc tgccttggaa    1020
gctgctgggg aaggccttaa tgtaatacag cagaccacta ggtattttag tactccacaa    1080
accatggatt tattcctaaa ctactccatg aacatgcaac ctgaagacgt gtgaagatga    1140
gtgaaactga tattactcaa tttcagtctg gacactggct gaatccttcc tctcccctcc    1200
tcccatccct cataggattt ttcttgtttg gaaaccacgt gttctggttt ccatgatgcc    1260
catccagtca atctcatgga gggtggagta tggttggagc taatcagcg aggtttcttt    1320 tttttttttt ttcctattgg atcttcctgg agaaaatact tttttttttt ttttttttga    1380
aacggagtct tgctctgtcg cccaggctgg agtgcagtgg cgcggtcttg gctcactgca    1440
agctccgtct cccgggttca cgccattctc ctgcctcagc ctcccgagca gctgggacta    1500
caggcgcccg ccacctcgcc cggctaatat tttgtatttt tagtagagac ggggtttcac    1560
tgtgttagcc aggatggtct cgatctcctg accttgtgat ccacccgcct cggcctccct    1620
aacagctggg atttacaggc gtgagccacc gcgcccgcc tagaaaagac atttaataa    1680 ccttggctgc cgtctctggc tatagataag tagatctaat actagtttgg atatctttag    1740
ggtttagaat ctaacctcaa gaataagaaa tacaagtaca aattggtgat gaagatgtat    1800
tcgtattgtt tgggattggg aggctttgct tattttttaa aaactattga ggtaaagggt    1860
taagctgtaa catacttaat tgatttctta ccgttttttgg ctctgttttg ctatatcccc    1920
taatttgttg gttgtgctaa tctttgtaga aagaggctc gtatttgctg catcgtaatg    1980
acatgagtac tgctttagtt ggtttaagtt caaatgaatg aaacaactat ttttccttta    2040
gttgatttta ccctgatttc accgagtgtt tcaatgagta aatatacagc ttaaacat     2098
```

<210> SEQ ID NO 87
<211> LENGTH: 2075
<212> TYPE: DNA
<213> ORGANISM: Homo sapiens

<400> SEQUENCE: 87

```
ggaaaaaagg aaagtgcact tggaagagat ccaagtgggc aacttgaaga acaagtgcca     60
aatagcactt ctgtcatgct ggatgtcagg gctctttgtc cactttgtat agccgctggc    120
ttatagaagg tgctcgataa atctcttgaa tttaaaaatc aattaggatg cctctatagt    180 gaaaagata cagtaaagat gagggataat caatttaaaa aatgagtaag tacacacaaa    240
gcactttatc cattcttatg acacctgtta cttttttgct gtgtttgtgt gtatgcatgc    300
catgttatag tttgtgggac cctcaaagca agctggggag agtatatact gaatttagct    360
tctgagacat gatgctcttc cttttttaatt aacccagaac ttagcagctt atctatttct    420
ctaatctcaa aacatcctta aactgggggt gatacttgag tgagagaatt ttgcaggtat    480
```

| | |
|---|---|
| taaatgaact atcttctttt ttttttttct ttgagacaga gtcttgctct gtcacccagg | 540 |
| ctggagtgca gtggcgtgat ctcagctcac tgcaacctcc gcctcccggg ttcaagtgat | 600 |
| tctcctgcct cagcctcctg agtagctggg attacaggtg cgtgccaccg tgcccagcta | 660 |
| attttttgtgt ttttagtaga dacgggggttt caccatgttg gccatgctgg tcttgaactc | 720 |
| ctgacctcgt gatctgccca cctcggcctc ccaaagtgct ggaattatag gcgtgagcca | 780 |
| ccgcgcccag caaagaactt ctaaccttca taacctgaca ggtgttctcg aggccagggt | 840 |
| ctctctttct gtcctttcac gatgctctgc atcccttgga tgtgccagtt tctgggggaa | 900 |
| gagtagtcct ttgttacatg catgagtcag tgaacaggga atgggtgaat gacatttgtg | 960 |
| ggtaggttat ttctagaagt taggtgggca gcttggaagg cagaggcact tctacagact | 1020 |
| attccttggg gccacacgta ggttcttgaa tcccgaatgg aaaggggaga ttgataactg | 1080 |
| gtgtgtttat gttcttacaa gtcttctgcc ttttaaaatc cagtcccagg acatcaaagc | 1140 |
| tctgcagaaa gaactcgagc aatttgccaa gctcctgaag cagaagagga tcaccctggg | 1200 |
| atatacacag gccgatgtgg ggctcaccct gggggttcta tttgggaagg tattcagcca | 1260 |
| aacgaccatc tgccgctttg aggctctgca gcttagcttc aagaacatgt gtaagctgcg | 1320 |
| gcccttgctg cagaagtggg tggaggaagc tgacaacaat gaaaatcttc aggagatatg | 1380 |
| caaagcagaa accctcgtgc aggcccgaaa gagaaagcga accagtatcg agaaccgagt | 1440 |
| gagaggcaac ctggagaatt tgttcctgca gtgcccgaaa cccacactgc agcagatcag | 1500 |
| ccacatcgcc cagcagcttg ggctcgagaa ggatgtggtc cgagtgtggt tctgtaaccg | 1560 |
| gcgccagaag ggcaagcgat caagcagcga ctatgcacaa cgagaggatt ttgaggctgc | 1620 |
| tgggtctcct ttctcagggg gaccagtgtc ctttcctctg gccccagggc cccattttgg | 1680 |
| taccccagc tatgggagcc ctcacttcac tgcactgtac tcctcggtcc ctttccctga | 1740 |
| gggggaagcc tttcccccctg tctccgtcac cactctgggc tctcccatgc attcaaactg | 1800 |
| aggtgcctgc ccttctagga atgggggaca ggggagggg aggagctagg gaaagaaaac | 1860 |
| ctggagtttg tgccagggtt tttgggatta agttcttcat tcactaagga aggaattggg | 1920 |
| aacacaaagg gtgggggcag gggagtttgg ggcaactggt tggagggaag gtgaagttca | 1980 |
| atgatgctct tgattttaat cccacatcat gtatcacttt tttcttaaat aaagaagcct | 2040 |
| gggacacagt agatagacac acttaaaaaa aaaaa | 2075 |

<210> SEQ ID NO 88
<211> LENGTH: 2520
<212> TYPE: DNA
<213> ORGANISM: Homo sapiens

<400> SEQUENCE: 88

| | |
|---|---|
| ggatggttgt ctattaactt gttcaaaaaa gtatcaggag ttgtcaaggc agagaagaga | 60 |
| gtgtttgcaa aaggggggaaa gtagtttgct gcctctttaa gactaggact gagagaaaga | 120 |
| agaggagaga gaaagaaagg gagagaagtt tgagccccag gcttaagcct ttccaaaaaa | 180 |
| taataataac aatcatcggc ggcggcagga tcggccagag gaggagggaa gcgctttttt | 240 |
| tgatcctgat tccagtttgc ctctctcttt ttttccccca aattattctt cgcctgattt | 300 |
| tcctcgcgga gccctgcgct cccgacaccc ccgcccgcct cccctcctcc tctcccccg | 360 |
| cccgcggggcc cccaaagtc ccggccgggc cgagggtcgg cggccgcggg cgggccgggc | 420 |
| ccgcgcacag cgcccgcatg tacaacatga tggagacgga gctgaagccg ccgggcccgc | 480 |
| agcaaaacttc gggggggcggc ggcggcaact ccaccgcggc ggcggccggc ggcaaccaga | 540 |

```
aaaacagccc ggaccgcgtc aagcggccca tgaatgcctt catggtgtgg tcccgcgggc      600
agcggcgcaa gatggcccag gagaacccca agatgcacaa ctcggagatc agcaagcgcc      660
tgggcgccga gtggaaactt ttgtcggaga cggagaagcg gccgttcatc gacgaggcta      720
agcggctgcg agcgctgcac atgaaggagc acccggatta taaataccgg ccccggcgga      780
aaaccaagac gctcatgaag aaggataagt acacgctgcc cggcgggctg ctggcccccg      840
gcggcaatag catggcgagc ggggtcgggg tgggcgccgg cctgggcgcg ggcgtgaacc      900
agcgcatgga cagttacgcg cacatgaacg gctggagcaa cggcagctac agcatgatgc      960
aggaccagct gggctacccg cagcacccgg gcctcaatgc gcacggcgca gcgcagatgc     1020
agcccatgca ccgctacgac gtgagcgccc tgcagtacaa ctccatgacc agctcgcaga     1080
cctacatgaa cggctcgccc acctacagca tgtcctactc gcagcagggc acccctggca     1140
tggctcttgg ctccatgggt tcggtggtca agtccgaggc cagctccagc ccccctgtgg     1200
ttacctcttc ctcccactcc agggcgccct gccaggccgg ggacctccgg gacatgatca     1260
gcatgtatct ccccggcgcc gaggtgccgg aacccgccgc cccagcagaa cttcacatgt     1320
cccagcacta ccagagcggc ccggtgcccg gcacggccat taacggcaca ctgccccctct     1380 cacacatgtg agggccggac agcgaactgg aggggggaga aattttcaaa gaaaaacgag     1440
ggaaatggga ggggtgcaaa agaggagagt aagaaacagc atggagaaaa cccggtacgc     1500 tcaaaagaa aaggaaaaaa aaaaaatccc atcacccaca gcaaatgaca gctgcaaaag     1560
agaacaccaa tcccatccac actcacgcaa aaccgcgat gccgacaaga aaacttttat      1620
gagagagatc ctggacttct ttttggggga ctattttgt acagagaaaa cctggggagg      1680
gtggggaggg cggggaatg gaccttgtat agatctggag gaaagaaagc tacgaaaaac      1740
tttttaaaag ttctagtggt acggtaggag ctttgcagga gtttgcaaa agtctttacc       1800 aataatattt agagctagtc tccaagcgac gaaaaaatg ttttaatatt tgcaagcaac      1860
ttttgtacag tattacga gataaacatg gcaatcaaaa tgtccattgt ttataagctg      1920
agaatttgcc aatatttttc aaggagaggc ttcttgctga ttttgattc tgcagctgaa      1980 atttaggaca gttgcaaacg tgaaagaag aaaattattc aaatttggac atttttaattg     2040 tttaaaaatt gtacaaaagg aaaaaattag aataagtact ggcgaaccat ctctgtggtc     2100 ttgtttaaa agggcaaaag ttttagactg tactaaattt taacttac tgttaaaagc      2160 aaaaatggcc atgcaggttg acaccgttgg taatttataa agcttttgt tcgatcccaa      2220 cttttccattt tgttcagata aaaaaaacca tgaaattact gtgtttgaaa tattttctta      2280
tggtttgtaa tatttctgta aatttattgt gatattttaa ggttttcccc cctttatttt      2340
ccgtagttgt attttaaaag attcggctct gtattatttg aatcagtctg ccgagaatcc      2400
atgtatatat ttgaactaat atcatcctta taacaggtac attttcaact taagttttta     2460
ctccattatg cacagtttga gataaataaa ttttgaaat atggacactg aaaaaaaaaa     2520
```

<210> SEQ ID NO 89
<211> LENGTH: 3111
<212> TYPE: DNA
<213> ORGANISM: Homo sapiens

<400> SEQUENCE: 89

```
aaatattctt gcttgagtaa accacagtaa gaataaggaa gtagtgactg agtgccttgc       60
cagtacagca gatgctagaa cataatgtag cattactttc cccagggttt attgttatgt      120
```

```
aagttcttgt tcagcttcct ttgttttctt tcacttctga gaatttaact ttcgtttctc      180
actcagctcc tgtggggaaa ctcatttgtg gagaccagcc ctctggcttg gtgagtgaat      240
ctggtttaca ccggctcctg ccctgccttc actcttctcc cctgattcaa gactcctctg      300
ctttggactg aagcactgca ggagtttgtg accaagaact tcaagagtca agacagaagg      360
aagccaaggg agcagtgcaa tggatttctc agtaaaggta gacatagaga aggaggtgac      420
ctgccccatc tgcctggagc tcctgacaga acctctgagc ctagattgtg ccacagctt       480 ctgccaagcc tgcatcactg caaagatcaa ggagtcagtg atcatctcaa gaggggaaag      540
cagctgtcct gtgtgtcaga ccagattcca gcctgggaac ctccgaccta atcggcatct      600
ggccaacata gttgagagag tcaaagaggt caagatgagc ccacaggagg ggcagaagag      660
agatgtctgt gagcaccatg gaaaaaaact ccagatcttc tgtaaggagg atggaaaagt      720
catttgctgg gtttgtgaac tgtctcagga acaccaaggt caccaaacat tccgcataaa      780
cgaggtggtc aaggaatgtc aggaaaagct gcaggtagcc ctgcagaggc tgataaagga      840
ggatcaagag gctgagaagc tggaagatga catcagacaa gagagaaccg cctggaagaa      900
ttatatccag atcgagagac agaagattct gaaagggttc aatgaaatga gagtcatctt      960
ggacaatgag gagcagagag agctgcaaaa gctggaggaa ggtgaggtga atgtgctgga     1020
taacctggca gcagctacag accagctggt ccagcagagg caggatgcca gcacgctcat     1080
ctcagatctc cagcggaggt tgaggggatc gtcagtagag atgctgcagg atgtgattga     1140
cgtcatgaaa aggagtgaaa gctggacatt gaagaagcca aaatctgttt ccaagaaact     1200 aaaagagtgta ttccgagtac cagatctgag tgggatgctg caagttctta aagagctgac    1260
agatgtccag tactactggg tggacgtgat gctgaatcca ggcagtgcca cttcgaatgt     1320
tgctatttct gtggatcaga gacaagtgaa aactgtacgc acctgcacat ttaagaattc     1380
aaatccatgt gattttttctg cttttggtgt cttcggctgc caatatttct cttcggggaa    1440
atattactgg gaagtagatg tgtctggaaa gattgcctgg atcctgggcg tacacagtaa     1500
aataagtagt ctgaataaaa ggaagagctc tgggtttgct tttgatccaa gtgtaaatta     1560
ttcaaaagtt tactccagat atagacctca atatggctac tgggttatag gattacagaa     1620
tacatgtgaa tataatgctt ttgaggactc ctcctcttct gatcccaagg ttttgactct     1680
ctttatggct gtgcctccct gtcgtattgg ggtttcccta gactatgagg caggcattgt     1740
ctcatttttc aatgtcacaa accacggagc actcatctac aagttctctg gatgtcgctt     1800
ttctcgacct gcttatccgt atttcaatcc ttggaactgc ctagtcccca tgactgtgtg     1860
cccaccgagc tcctgagtgt tctcattcct ttacccactt ctgcatagta gcccttgtgc     1920
tgagactcag attctgcacc tgagttcatc tctactgaga ccatctcttc ctttctttcc     1980
ccttctttta cttagaatgt ctttgtattc atttgctagg gcttccatag caaagcatca     2040
tagattgctg atttaaactg taattgtatt gccgtactgt gggctggaaa tcccaaatct     2100
agattccagc agagttggtt cttttctgagg tctgcaagga agggctctgt tccatgcctc    2160
tctccttggc ttgtagaagg catcttgtcc ctatgactct tcacattgtc tttatgtaca     2220
tctctgtgcc caagttttcc cttttttatta agacaccagt catactggct cagggcccac    2280
cgctaatgcc ttaatgaaat cattttaaca ttatattctc tacaaagacc ttatttccaa     2340
ataagataat atttggaggt attgggaata aaaactccaa catataaatt tgaggaaggc     2400
acgatttcac tcataacaat cttacccttt cttgcaagag atgcttgtac attatttttcc    2460 taatacctttg gtttcactag tagtaaacat tattattttt tttatatttg caaaggaaac    2520
```

```
atatctaatc cttcctatag aaagaacagt attgctgtaa ttccttttct tttcttcctc    2580
atttcctctg cccCttaaaa gattgaagaa agagaaactt gtcaactcat atccacgtta    2640
tctagcaaag tacataagaa tctatcacta agtaatgtat ccttcagaat gtgttggttt    2700
accagtgaca ccccatattc atcacaaaat taaagcaaga agtccatagt aatttatttg    2760
ctaatagtgg attttaatg ctcagagttt ctgaggtcaa attttatctt ttcacttaca    2820
agctctatga tcttaaataa tttacttaat gtattttggt gtattttcct caaattaata    2880
ttggtgttca agactatatc taattcctct gatcactttg agaaacaaac ttttattaaa    2940
tgtaaggcac ttttctatga attttaaata taaaaataaa tattgttctg attattactg    3000
aaaagatgtc agccatttca atgtcttggg aaacaatttt ttgttttttgt tctgttttct    3060 ttttgcttca ataaaacaat agctggctct aaaaaaaaaa aaaaaaaaaa a             3111

<210> SEQ ID NO 90
<211> LENGTH: 1852
<212> TYPE: DNA
<213> ORGANISM: Homo sapiens

<400> SEQUENCE: 90
accgccgaga ccgcgtccgc cccgcgagca cagagcctcg cctttgccga tccgccgccc      60
gtccacaccc gccgccagct caccatggat gatgatatcg ccgcgctcgt cgtcgacaac     120
ggctccggca tgtgcaaggc cggcttcgcg ggcgacgatg ccccccgggc cgtcttcccc     180
tccatcgtgg ggcgcccag gcaccagggc gtgatggtgg gcatgggtca gaaggattcc     240
tatgtgggcg acgaggccca gagcaagaga ggcatcctca ccctgaagta ccccatcgag     300
cacggcatcg tcaccaactg ggacgacatg gagaaaatct ggcaccacac cttctacaat     360
gagctgcgtg tggctcccga ggagcacccc gtgctgctga ccgaggcccc cctgaacccc     420
aaggccaacc gcgagaagat gacccagatc atgtttgaga ccttcaacac cccagccatg     480
tacgttgcta tccaggctgt gctatccctg tacgcctctg gccgtaccac tggcatcgtg     540
atggactccg gtgacggggt cacccacact gtgcccatct acgaggggta tgccctcccc     600
catgccatcc tgcgtctgga cctggctggc cgggacctga ctgactacct catgaagatc     660
ctcaccgagc gcggctacag cttcaccacc acggccgagc gggaaatcgt gcgtgacatt     720
aaggagaagc tgtgctacgt cgccctggac ttcgagcaag agatggccac ggctgcttcc     780
agctcctccc tggagaagag ctacgagctg cctgacggcc aggtcatcac cattggcaat     840
gagcggttcc gctgccctga ggcactcttc cagccttcct tcctgggcat ggagtcctgt     900
ggcatccacg aaactacctt caactccatc atgaagtgtg acgtggacat ccgcaaagac     960
ctgtacgcca acacagtgct gtctggcggc accaccatgt accctggcat tgccgacagg    1020
atgcagaagg agatcactgc cctggcaccc agcacaatga agatcaagat cattgctcct    1080
cctgagcgca agtactccgt gtggatcggc ggctccatcc tggcctcgct gtccaccttc    1140
cagcagatgt ggatcagcaa gcaggagtat gacgagtccg gcccctccat cgtccaccgc    1200
aaatgcttct aggcggacta tgacttagtt gcgttacacc ctttcttgac aaaacctaac    1260
ttgcgcagaa aacaagatga gattggcatg ctttatttg tttttttgt tttgttttgg     1320 ttttttttt ttttttggct tgactcagga tttaaaact ggaacggtga aggtgacagc     1380
agtcggttgg agcgagcatc ccccaaagtt cacaatgtgg ccgaggactt tgattgcaca    1440
ttgttgtttt ttaatagtc attccaaata tgagatgcgt tgttacagga agtcccttgc     1500
```

| | | | | |
|---|---|---|---|---|
| catcctaaaa | gccaccccac | ttctctctaa | ggagaatggc | ccagtcctct cccaagtcca | 1560 |
| cacaggggag | gtgatagcat | tgctttcgtg | taaattatgt | aatgcaaaat ttttttaatc | 1620 |
| ttcgccttaa | tacttttta | ttttgtttta | ttttgaatga | tgagccttcg tgcccccct | 1680 |
| tccccctttt | ttgtccccca | acttgagatg | tatgaaggct | tttggtctcc ctggagtgg | 1740 |
| gtggaggcag | ccagggctta | cctgtacact | gacttgagac | cagttgaata aaagtgcaca | 1800 |
| ccttaaaaat | gaaaaaaaaa | aaaaaaaaa | aaaaaaaaa | aaaaaaaaa aa | 1852 |

<210> SEQ ID NO 91
<211> LENGTH: 2985
<212> TYPE: DNA
<213> ORGANISM: Homo sapiens

<400> SEQUENCE: 91

| | | | | |
|---|---|---|---|---|
| cccatgctgc | cctgcgccaa | cccctcccct | cacctttcct | ccccgccct ctactcgccg | 60 |
| cccggccggt | cccccaccc | gtcccttccc | ttatcagcac | ccgcggcccc ggcagcgccg | 120 |
| acgcaggcgc | actgcaccgc | gccgccgcca | ttttgtgtct | gagcctgtgg agcgattaaa | 180 |
| ccgtgcgcgg | agctgcttct | ttggcggcag | cggcggcggc | ggtggccggt gcggacgcgc | 240 |
| ggagctcgcc | ggagacgccg | ggtggccgga | gccgtggagc | ggcggcggag cgggcgccgc | 300 |
| gggggtgtg | gcgcggagaa | tgattacgga | cctgaagcca | agaacaaga tgcgctagtg | 360 |
| gacagattgc | tgaccagggg | cttgagagct | gggttctatt | ttccctcctc aaactgactt | 420 |
| tgcagccacg | gagaggtact | cgtcctcaca | agtgcccaga | ctgcgacatg gcctttgtga | 480 |
| ccagtggaga | attggttcgg | catcgtcgtt | acaaacacac | ccacgagaag ccattcaagt | 540 |
| gttccatgtg | cgattacgcc | agtgtagaag | tcagcaaatt | aaaacgtcac attcgctctc | 600 |
| atactggaga | gcgtccgttt | cagtgcagtt | tgtgcagtta | tgccagcagg gacacataca | 660 |
| agctgaaaag | gcacatgaga | acccattcag | gggaaaagcc | ttatgaatgt tatatttgtc | 720 |
| atgctcggtt | tacccaaagt | ggtaccatga | agatgcacat | tttacagaag cacacagaaa | 780 |
| atgtggccaa | atttcactgt | ccccactgtg | acacagtcat | agcccgaaaa agtgatttgg | 840 |
| gtgtccactt | gcgaaagcag | cattcctata | ttgagcaagg | caagaaatgc cgttactgtg | 900 |
| atgctgtgtt | tcatgagcgc | tatgccctca | tccagcatca | gaagtcacac aagaatgaga | 960 |
| agcgctttaa | gtgtgaccag | tgtgattacg | cttgtagaca | ggagaggcac atgatcatgc | 1020 |
| acaagcgcac | ccacaccggg | gagaagcctt | acgcctgcag | ccactgcgat aagaccttcc | 1080 |
| gccagaagca | gcttctcgac | atgcacttca | gcgctatca | cgaccccaac ttcgtccctg | 1140 |
| cggcttttgt | ctgttctaag | tgtgggaaaa | catttacacg | tcggaatacc atggcaagac | 1200 |
| atgctgataa | ttgtgctggc | ccagatggcg | tagaggggca | aaatggagga gaaacgaaga | 1260 |
| agagtaaacg | tggaagaaaa | agaaagatgc | gctctaagaa | agaagattcc tctgacagtg | 1320 |
| aaaatgctga | accagatctg | gacgacaatg | aggatgagga | ggagcctgcc gtagaaattg | 1380 |
| aacctgagcc | agagcctcag | cctgtgaccc | cagccccacc | acccgccaag aagcggagag | 1440 |
| gacgaccccc | tggcagaacc | aaccagccca | acagaaccca | gccaacagct atcattcagg | 1500 |
| ttgaagacca | gaatacaggt | gcaattgaga | acattatagt | tgaagtaaaa aaagagccag | 1560 |
| atgctgagcc | cgcagaggga | gaggaagagg | aggcccagcc | agctgccaca gatgccccca | 1620 |
| acggagacct | cacgcccgag | atgatcctca | gcatgatgga | ccggtgatgg cggagccttg | 1680 |
| tgcgtcgcca | ggacttctct | gggctgtgtt | taaacggccc | gcatcttaat tttctcccct | 1740 |
| tctttctttt | tttggctttg | ggaaaagcat | cattttacca | aacataccga gaacgaaaac | 1800 |

```
ttcaaggatg atgttagaaa aaaatgtgat ttaactagaa cttgctgtct gatgttagca   1860
aatcatggaa tgttctgagt ccctgagggt ttactgtgaa gtgctgagga cagtgttgac   1920
aactaactcg ttttcctaga tggaaacgga gacattgacc cctccctcca tgtggtaaac   1980
cactccagaa tggccaccag gcttcccaga gttctatggt cttcttccca agagagtttt   2040
taattgtaaa tgcatacttg ggaaggactt agagttttaa actgttttt gcttttgctt   2100 ttccctgact ccctttgctt ggagtcagct gcacaccagt agtatggcat gctacgatca   2160
ggttctgtcc tgaaagcttt gcctctttct tggcaaagtt tctggtatgg tcaagcttgt   2220
aaataacttt tttacattt taatcttttc cattaattaa gaggttgaaa agaagtgcag   2280
tgtaagaaaa cccagcattt taattacttg caaattaagt taccacagac tctgtagtgt   2340
gtaaatgttg acaaggaatt ggatcacaat catgtagcag aatggcaccc agaccactgc   2400
ccaccagtga cggacatgca cgtggcagat catgatttcc agcccacgga gccagcattt   2460
gaaccttgta taattaactt tcagttatga tttcccatcg acattttctt tgccctgttt   2520
gtagctgatt gttgtgtttt ataaatcttc tgttaaggca gaagggtgat tatgagtggt   2580
tcacagcagc ccttataagc tgggccagaa aatttcacta ggtcagtaat ttaaaccttg   2640
gatcttcaaa aaataaaata atgtgaagca aaccaacta aaaagtgatt cttgcacatg   2700
aactgtcaca tgtttaaaaa tgtgtttttt agagagcctc agtcttactg atttcaaaca   2760
cttttttctt ctgtgtattg cttttaagag agccatcagt tagctatcag actctaggtt   2820
gatgcatttt gtacttagct gtactgtgtg atattttca ttattttagg acgccaacat   2880
gagacctgta ataaaatatg taatgggggtt gaaagctggg gaggaggatc tactgctgta   2940
cagctaataa atcataacgg attaacaagt gctccaaaga aaaaa              2985
```

<210> SEQ ID NO 92
<211> LENGTH: 3946
<212> TYPE: DNA
<213> ORGANISM: Homo sapiens

<400> SEQUENCE: 92

```
cccatgctgc cctgcgccaa cccctcccct cacctttcct cccccgccct ctactcgccg    60
cccggccggt cccccaccc gtcccttccc ttatcagcac ccgcggcccc ggcagcgccg   120
acgcaggcgc actgcaccgc gccgccgcca ttttgtgtct gagcctgtgg agcgattaaa   180
ccgtgcgcgg agctgcttct ttggcggcag cggcggcggc ggtggccggt gcggacgcgc   240
ggagctcgcc ggagacgccg ggtggccgga gccgtggagc ggcggcggag cgggcgccgc   300 gggggggtgtg gcgcggagaa tgattacgga cctgaagcca agaacaaga tgcgctagtg   360 gacagattgc tgaccagggg cttgagagct gggttctatt ttccctcctc aaactgactt   420
tgcagccacg gagaggcagg ggaaatggaa ggtgatgcag tcgaagccat tgtggaggag   480
tccgaaactt ttattaaagg aaaggagaga aagacttacc agagacgccg gaaggggggc   540
caggaagaag atgcctgcca cttaccccag aaccagacgg atggggggtga ggtggtccag   600 gatgtcaaca gcagtgtaca gatggtgatg atggaacagc tggacccac ccttcttcag   660 atgaagactg aagtaatgga gggcacagtg gctccagaag cagaggctgc tgtggacgat   720
acccagatta taactttaca ggttgtaaat atggaggaac agcccataaa cataggagaa   780
cttcagcttg ttcaagtacc tgttcctgtg actgtacctg ttgctaccac ttcagtagaa   840
gaacttcagg gggcttatga aaatgaagtg tctaaagagg gccttgcgga aagtgaaccc   900
```

```
atgatatgcc acaccctacc tttgcctgaa gggtttcagg tggttaaagt gggggccaat    960
ggagaggtgg agacactaga acaagggaa cttccacccc aggaagatcc tagttggcaa    1020
aaagacccag actatcagcc accagccaaa aaacaaaga aaccaaaaa gagcaaactg    1080
cgttatacag aggagggcaa agatgtagat gtgtctgtct acgattttga ggaagaacag    1140
caggagggtc tgctatcaga ggttaatgca gagaaagtgg ttggtaatat gaagcctcca    1200
aagccaacaa aaattaaaaa gaaggtgta aagaagacat tccagtgtga gctttgcagt    1260
tacacgtgtc cacggcgttc aaatttggat cgtcacatga aaagccacac tgatgagaga    1320
ccacacaagt gccatctctg tggcagggca ttcagaacag tcaccctcct gaggaatcac    1380
cttaacacac acacaggtac tcgtcctcac aagtgcccag actgcgacat ggcctttgtg    1440
accagtggag aattggttcg gcatcgtcgt tacaaacaca cccacgagaa gccattcaag    1500
tgttccatgt gcgattacgc cagtgtagaa gtcagcaaat taaaacgtca cattcgctct    1560
catactggag agcgtccgtt tcagtgcagt ttgtgcagtt atgccagcag ggacacatac    1620
aagctgaaaa ggcacatgag aacccattca ggggaaaagc cttatgaatg ttatatttgt    1680
catgctcggt ttacccaaag tggtaccatg aagatgcaca ttttacagaa gcacacagaa    1740
aatgtggcca aatttcactg tccccactgt gacacagtca tagcccgaaa aagtgatttg    1800
ggtgtccact tgcgaaagca gcattcctat attgagcaag gcagaaatg ccgttactgt    1860
gatgctgtgt ttcatgagcg ctatgccctc atccagcatc agaagtcaca caagaatgag    1920
aagcgcttta gtgtgaccaa gtgtgattac gcttgtagac aggagaggca catgatcatg    1980
cacaagcgca cccacaccgg ggagaagcct tacgcctgca gccactgcga taagaccttc    2040
cgccagaagc agcttctcga catgcacttc aagcgctatc acgaccccaa cttcgtccct    2100
gcggcttttg tctgttctaa gtgtgggaaa acatttacac gtcggaatac catggcaaga    2160
catgctgata attgtgctgg cccagatggc gtagaggggg aaaatggagg agaaacgaag    2220
aagagtaaac gtgaagaaa aagaaagatg cgctctaaga aagaagattc ctctgacagt    2280
gaaaatgctg aaccagatct ggacgacaat gaggatgagg aggagcctgc cgtagaaatt    2340
gaacctgagc cagagcctca gcctgtgacc ccagccccac cacccgccaa gaagcggaga    2400
ggacgacccc ctggcagaac caaccagccc aaacagaacc agccaacagc tatcattcag    2460
gttgaagacc agaatacagg tgcaattgag aacattatag ttgaagtaaa aaagagcca    2520
gatgctgagc ccgcagaggg agaggaagag gaggcccagc cagctgccac agatgccccc    2580
aacgagacc tcacgcccga gatgatcctc agcatgatgg accggtgatg gcggagcctt    2640
gtgcgtcgcc aggacttctc tgggctgtgt taaacggcc cgcatcttaa ttttttctccc    2700
ttctttctt tttttggctt gggaaaagca tcattttacc aaacataccg agaacgaaaa    2760
cttcaaggat gatgttagaa aaaatgtga tttaactaga acttgctgtc tgatgttagc    2820
aaatcatgga atgttctgag tccctgaggg tttactgtga agtgctgagg acagtgttga    2880
caactaactc gttttcctag atggaaacgg agacattgac ccctcctcc atgtggtaaa    2940
ccactccaga atggccacca ggcttcccag agttctatgg tcttcttccc aagagagttt    3000
ttaattgtaa atgcatactt gggaaggact tagagtttta aactgttttt tgcttttgct    3060
tttccctgac tcccttgct tggagtcagc tgcacaccag tagtatggca tgctacgatc    3120
aggttctgtc ctgaaagctt tgcctctttc ttggcaaagt ttctggtatg gtcaagcttg    3180
taaataactt tttttacatt ttaatctttt ccattaatta agaggttgaa agaagtgca    3240
gtgtaagaaa acccagcatt ttaattactt gcaaattaag ttaccacaga ctctgtagtg    3300
```

```
tgtaaatgtt gacaaggaat tggatcacaa tcatgtagca gaatggcacc cagaccactg    3360
cccaccagtg acggacatgc acgtggcaga tcatgatttc cagcccacgg agccagcatt    3420
tgaaccttgt ataattaact ttcagttatg atttcccatc gacattttct ttgccctgtt    3480
tgtagctgat tgttgtgttt tataaatctt ctgttaaggc agaagggtga ttatgagtgg    3540
ttcacagcag cccttataag ctgggccaga aaatttcact aggtcagtaa tttaaacctt    3600
ggatcttcaa aaaataaaat aatgtgaagc aaaaccaact aaaaagtgat tcttgcacat    3660
gaactgtcac atgtttaaaa atgtgttttt tagagagcct cagtcttact gatttcaaac    3720
acttttttct tctgtgtatt gcttttaaga gagccatcag ttagctatca gactctaggt    3780
tgatgcattt tgtacttagc tgtactgtgt gatatttttc attattttag gacgccaaca    3840
tgagacctgt aataaaatat gtaatggggt tgaaagctgg ggaggaggat ctactgctgt    3900
acagctaata aatcataacg gattaacaag tgctccaaag aaaaaa                   3946

<210> SEQ ID NO 93
<211> LENGTH: 5612
<212> TYPE: DNA
<213> ORGANISM: Homo sapiens

<400> SEQUENCE: 93 gggcggggc gggggctgcc gcagagccgg gctgcggcgt gggaggagga agaggaggaa      60
gatgcgctcg gcctctgcct tccgctccgg agcgtcgcgc ttcccaccag gatgacagtg    120
atgggattcc gtggtcagaa gaacgggtgg tacgtaaagt cctttatttg tctctgaagg    180
agttcaagaa ttcccagaag aggcagcatg cggaaggcat tgctgggagc ctgaaaactg    240
tgaatgggct ccttggtaat gaccagtcta agggattagg accagcatca gaacagtcag    300
agaatgaaaa ggacgatgca tcccaagtgt cctccactag caacgatgtt agttcttcag    360
attttgaaga agggccgtcg aggaaaaggc ccaggctgca agcacaaagg aagtttgctc    420
agtctcagcc gaatagtccc agcacaactc cagtaaagat agtggagcca ttgctacccc    480
ctccagctac tcagatatca gacctctcta aaaggaagcc taagacagaa gattttctta    540
cctttctctg ccttcgaggt tctcctgcgc tgcccaacag catggtgtat tttggaagct    600
ctcaggatga ggaggaagtc gaggaggaag atgatgagac agaagacgtc aaaacagcca    660
ccaacaatgc ttcatcttca tgccagtcga cccccaggaa aggaaaaacc cacaaacatg    720
ttcaacacgg gcatgttttc aatggttcca gcaggtcaac acgggagaag gaacctgttc    780
aaaaacacaa aagcaaagag gccactcccg caaaggagaa gcacagcgat caccgggctg    840
acagccgccg ggagcaggct tcagctaacc ccccgcagc ggcccctcc acgggttcct    900 cggccaaggg gcttgctgcc acccatcacc acccccctct gcatcggtcg gctcaggact    960
tacggaaaca ggtttctaag gtaaacggag tcactcgaat gtcatctctg ggtgcaggtg    1020
taaccagtgc caaaaagatg cgcgaggtca gaccttcacc atccaaaact gtgaagtaca    1080
ctgccacggt gacgaagggg gctgtcacat acaccaaagc caagagagaa ctggtcaagg    1140
acaccaaacc caatcaccac aagcccagtt ccgctgtcaa ccacacaatc tcagggaaaa    1200
ctgaaagtag caatgcaaaa acccgcaaac aggtgctatc cctcgggggg cgtccaagt    1260 ccactgggcc cgccgtcaat ggcctcaagg tcagtggcag gttgaaccca aagtcatgca    1320
ctaaggaggt ggggggcgg cagctgcggg agggcctgca gctgcgggag gggctgcgga    1380
actccaagag gagactggaa gaggcacacc aggcggagaa gccgcagtcg cccccccaaga   1440
```

-continued

```
agatgaaagg ggcggctggc cccgccgaag gccctggcaa gaaggccccg gccgagagag      1500
gtctgctgaa cggacacgtg aagaaggaag tgccggagcg cagtctggag aggaatcggc      1560
cgaagcgggc cacggccggg aagagcacgc caggcagaca agcacatggc aaggcggaca      1620
gcgcctcctg tgaaaatcgt tctacctcgc aaccggagtc cgtgcacaag ccgcaggact      1680
cgggcaaggc cgagaagggc ggcggcaagg ccgggtgggc ggccatggac gagatccccg      1740
tcctcaggcc ctccgccaag gagttccacg atccgctcat ctacatcgag tcggtccgcg      1800
ctcaggtgga gaagttcggg atgtgcaggg tgatccccce tccggactgg cggcccgagt      1860
gcaagctcaa cgatgagatg cggttttgtca cgcagattca gcacatccac aagctgggcc      1920
ggcgctgggg ccccaacgtg cagcggctgg cctgcatcaa gaagcacctc aaatctcagg      1980
gcatcaccat ggacgagctc ccgctcatag ggggctgtga gctcgacctg gcctgctttt      2040
tccggctgat taatgagatg ggcggcatgc agcaagtgac tgacctcaaa aaatggaaca      2100
aactagcaga catgctgcgc atccccagaa ctgcccagga ccggctggcc aagctgcagg      2160
aggcctactg ccagtaccta ctctcctacg actccctgtc cccagaggag caccggcggc      2220
tggagaagga ggtgctgatg gagaaggaga tcctggagaa gcgcaagggg ccgctggaag      2280
gccacacaga gaacgaccac cacaagttcc accctctgcc ccgcttcgag cccaagaatg      2340
ggctcatcca cggcgtggcc cccaggaacg gcttccgcag caagctcaag gaggtgggcc      2400
aggcccagtt gaagactggc cggcggcgac tcttcgctca ggaaaaagaa gtggtcaagg      2460
aagaggagga ggacaaaggc gtcctcaatg acttccacaa gtgcatctat aagggaaggt      2520
ctgtttctct aacaactttt tatcgaacag cgaggaatat catgagcatg tgtttcagca      2580
aggagcctgc cccagccgaa atcgagcaag agtactggag gctagtggaa gagaaggact      2640
gccacgtggc agtgcactgc ggcaaggtgg acaccaacac tcacggcagt ggattcccag      2700
taggaaaatc agaacccttt tcgaggcatg gatggaacct caccgtcctc cccaataaca      2760
cagggtccat cctgcgtcac ctcggtgctg tgcctggagt gactattccc tggctaaata      2820
ttggcatggt cttttctacc tcatgctggt ctcgagacca aaatcacctt ccatacattg      2880
actacttaca cactggtgct gactgcattt ggtattgcat tcctgctgag gaggagaaca      2940
agctggaaga tgtggtccac accctgctgc aagccaatgg caccccaggg ctgcagatgc      3000
tggaaagcaa cgtcatgatc tccccggagg tgctgtgcaa agagggatc aaggtgcaca      3060
ggaccgtgca gcagagtggc cagtttgtcg tctgcttccc gggatccttt gtgtccaaag      3120
tgtgctgtgg gtacagcgtg tctgaaaccg tgcactttgc taccacccag tggacaagta      3180
tgggctttga gaccgccaag gaaatgaagc gtcgccatat agctaagcca ttctccatgg      3240
agaagttact ctaccagatt gcacaagcag aagcaaaaaa agaaaacggt cccactctca      3300
gtaccatctc agccctcctg gatgagctca gggatacaga gctgcggcag cgcaggcagc      3360
tgttcgaggc tggcctccac tcctccgcac gctatggcag ccacgatggc agcagcacgg      3420
tggcggacgg gaagaaaaag cctcgaaagt ggctgcagtt ggagacgtca gagaggaggt      3480
gtcagatctg ccagcacctg tgctacctgt ccatggtggt acaagagaac gaaaacgtcg      3540
tgttctgtct ggagtgtgct ctgcgccacg tggagaaaca gaagtcctgc cgagggctga      3600
agttgatgta ccgctacgat gaggaacaga ttatcagtct ggtcaatcag atctgcggca      3660
aagtgtctgg taaaaacggc agcattgaga actgtctcag taaacccaca ccaaaaagag      3720
gtccccgcaa gagagcgaca gtggacgtgc cccctcccg tctgtcagcc tccagttcat      3780
ccaaaagtgc ttcgagctca tcatgaagat gccaacgccc gtggtcgatt tatatatatt      3840
```

| | | | | |
|---|---|---|---|---|
| ttttttgtaat | tattatattc | tagtttggag | tacttgctgt | aggattcaag ctgtctttgc | 3900 |
| actagctcta | aagaagattt | tcttctggtt | ttagagaact | aatttttgttt tagcattaaa | 3960 |
| ctgttgaact | tttttttgta | cttagaaaac | ctagatactg | cagtcagatt ttggaaactg | 4020 |
| ccgtatagtc | actgttttaa | aaaccccgga | ggggctgtat | taatttgtat tgccccatgg | 4080 |
| ctgacaaaag | cctttttttt | tggttttgat | tttttttttt | ttgtaactgt tgggggaaa | 4140 |
| aaggcttttt | aacccatttt | tgaagagggt | gaagtttgga | gaacaaattt aaaaaccatc | 4200 |
| agtcatgtga | gcagattttt | tagaagggat | aggagacaca | cgcgcacaca cacacacaca | 4260 |
| cgaaacttga | aatggctttg | ctttggctgt | cgtcttctgc | cgtgtgccag atgagcttgt | 4320 |
| gatctgggaa | gccggggcac | ccccgttttg | tttctctggg | cggttgtggc agctgaaggc | 4380 |
| ggacgttgtt | tcctaaccat | aggtggaacg | aggagacggg | agcgagtggg ctctccacca | 4440 |
| gcacatcact | atgcatctgt | tccaggaaag | aagaaaagcg | agcgaggaag acggaaaaga | 4500 |
| ctgcctgcct | tggaggggtc | acatgaggga | gacctgtgcc | tgatttcatt aggaaatcca | 4560 |
| ttctgttatt | ttttggtgct | gttggctact | ttatcaaaaa | acccttcaat agcatcctta | 4620 |
| agatttaaaa | aaaaaaaaa | aaaaaaggaa | aaaaaagtga | tggaagccgt aagtgcttct | 4680 |
| ttgtcatcga | cgtgcaatct | ttctaacatt | ccatctccat | ctcaccgctt cttgtttgac | 4740 |
| accttcacaa | gtcagcatta | atctttcttt | taaaacttgt | ttcatttatg atcatgtaga | 4800 |
| gagccactag | gaggcctgca | gttatttttg | aatgtgaaaa | tgcatttgcg ttcatcttgt | 4860 |
| ctattttttc | tcttcatgtt | gtaacaaaaa | ggaaaaaaga | aaaaaaaatc ccatcccttt | 4920 |
| tgtacatatg | cctgtaaatt | gttttaaata | cttgagcctt | tttctcggtg ggggtgggg | 4980 |
| agggggggtga | gaagacaaga | tgaagaaaag | ccttacattt | cagtttcttc atcggttgga | 5040 |
| ttggatgctt | acagggtttt | tcttgtaaca | tttataagtg | ctgcttacat cactgaacaa | 5100 |
| caacaaaaaa | ataataatgg | agtagctgtt | gcccttctcc | ggttgtgtgt acagtatgtg | 5160 |
| tggaataaaa | aagggaaact | gttttcacaa | gctgttcttt | gtttcataat tggattcatc | 5220 |
| aatcccgtag | ctacccatat | tgcactgagc | ttgccagtgg | tgactgccag gaacgtccta | 5280 |
| tgatccactt | tgttggttgt | tgttgcagaa | gactgaactg | ttttggaata tttaacaatt | 5340 |
| acagaaacag | tcaagtgttt | tccaatgtgg | ttgtccggtt | tctatggcct tgctgtgtac | 5400 |
| tttccctctt | tttgacagta | aacttctgcc | tatggcttac | agtttgacat ttaatttatt | 5460 |
| agcgctgctc | tgcacccctc | ccttgggagg | gagacttcat | gtggtttatt gcgagttttt | 5520 |
| tgtttacttt | tcaggtttgt | actacaaggt | ttaataataa | aaacaaagtt ttttggacat | 5580 |
| ttgtctgtct | tgtggaaaaa | aaaaaaaaaa | aa | | 5612 |

<210> SEQ ID NO 94
<211> LENGTH: 6112
<212> TYPE: DNA
<213> ORGANISM: Homo sapiens

<400> SEQUENCE: 94

| | | | | |
|---|---|---|---|---|
| tggatagcct | ctctctcatt | ggttaggggg | cttggaaaaa | agagactcgg cgagccctcg | 60 |
| ctgtggtgct | gccgccgccg | ccgccgccgc | cgctggagtt | gactcttctg ctcgcactgc | 120 |
| tgctgcagca | caaacgtgac | ttccaacatt | ttttatttat | cttccccttt tcttttccaa | 180 |
| gatgtaacta | cggatcagac | actaaggacc | ttcacgtttc | gctgatgtag ttttggagg | 240 |
| aaaaagggggg | gggagtgaag | ggcgtcggtt | tttttttgtg | tgtgtgtgta tgtgtttcgg | 300 |

```
gggaaatttt ccattatgag tgttttacta aagtgaattt ttttttgttt gcttcgttcg    360
tctttggctc ttttttttc cttcccaatt tcggatttat ttcaaggcga atctggcttt    420
gggggaagag gaagaaaagt cggattacaa gatcaaccac caccaacaac aataaaaacc    480
accaggatat tttttttgcaa atttctgacg gctttaaatt catgaagcaa ttgtcccctt    540
ttgcaatcag catttggatc tcagaatgag caaggaaaga cccaagagga atatcattca    600
gaagaaatac gatgacagtg atgggattcc gtggtcagaa gaacgggtgg tacgtaaagt    660
cctttatttg tctctgaagg agttcaagaa ttcccagaag aggcagcatg cggaaggcat    720
tgctgggagc ctgaaaactg tgaatgggct ccttggtaat gaccagtcta agggattagg    780
accagcatca gaacagtcag agaatgaaaa ggacgatgca tcccaagtgt cctccactag    840
caacgatgtt agttcttcag attttgaaga agggccgtcg aggaaaaggc ccaggctgca    900
agcacaaagg aagtttgctc agtctcagcc gaatagtccc agcacaactc cagtaaagat    960
agtggagcca ttgctacccc ctccagctac tcagatatca gacctctcta aaaggaagcc   1020
taagacagaa gattttctta ccttctctg ccttcgaggt tctcctgcgc tgcccaacag   1080
catggtgtat tttggaagct ctcaggatga ggaggaagtc gaggaggaag atgatgagac   1140
agaagacgtc aaaacagcca ccaacaatgc ttcatcttca tgccagtcga cccccaggaa   1200
aggaaaaacc cacaaacatg ttcacaacgg gcatgtttc aatggttcca gcaggtcaac   1260
acgggagaag gaacctgttc aaaaacacaa aagcaaagag gccactcccg caaggagaa   1320 gcacagcgat caccgggctg acagccgccg ggagcaggct tcagctaacc accccgcagc   1380
ggccccctcc acgggttcct cggccaaggg gcttgctgcc acccatcacc accccctct    1440 gcatcggtcg gctcaggact tacggaaaca ggtttctaag gtaaacggag tcactcgaat   1500
gtcatctctg ggtgcaggtg taaccagtgc caaaaagatg cgcgaggtca gaccttcacc   1560
atccaaaact gtgaagtaca ctgccacggt gacgaagggg gctgtcacat acaccaaagc   1620
caagagagaa ctggtcaagg acaccaaacc caatcaccac aagcccagtt ccgctgtcaa   1680
ccacacaatc tcagggaaaa ctgaaagtag caatgcaaaa accgcaaac aggtgctatc    1740 cctcgggggg gcgtccaagt ccactgggcc cgccgtcaat ggcctcaagg tcagtggcag   1800
gttgaaccca aagtcatgca ctaaggaggt gggggggcgg cagctgcggg agggcctgca   1860
gctgcgggag gggctgcgga actccaagag gagactggaa gaggcacacc aggcggagaa   1920
gccgcagtcg ccccccaaga gatgaaagg ggcggctggc cccgccgaag ccctggcaa    1980 gaaggccccg gccgagagag gtctgctgaa cggacacgtg aagaaggaag tgccggagcg   2040
cagtctggag aggaatcggc cgaagcgggc cacggccggg aagagcacgc caggcagaca   2100
agcacatggc aaggcggaca cgcctcctg tgaaaatcgt tctacctcgc aaccggagtc   2160
cgtgcacaag ccgcaggact cgggcaaggc cgagaagggc ggcggcaagg ccgggtgggc   2220
ggccatggac gagatccccg tcctcaggcc ctccgccaag gagttccacg atccgctcat   2280
ctacatcgag tcggtccgcg ctcaggtgga gaagttcggg atgtgcaggg tgatccccc    2340 tccggactgg cggcccgagt gcaagctcaa cgatgagatg cggtttgtca cgcagattca   2400
gcacatccac aagctgggcc ggcgctgggg cccaacgtg cagcggctgg cctgcatcaa   2460
gaagcacctc aaatctcagg gcatcaccat ggacgagctc ccgctcatag ggggctgtga   2520
gctcgacctg gcctgcttt tccggctgat taatgagatg gcggcatgc agcaagtgac    2580 tgacctcaaa aaatgaaca aactagcaga catgctgcgc atcccagaa ctgcccagga    2640 ccggctggcc aagctgcagg aggcctactg ccagtaccta ctctcctacg actccctgtc   2700
```

```
cccagaggag caccggcggc tggagaagga ggtgctgatg gagaaggaga tcctggagaa    2760
gcgcaagggg ccgctggaag gccacacaga gaacgaccac cacaagttcc accctctgcc    2820
ccgcttcgag cccaagaatg ggctcatcca cggcgtggcc cccaggaacg gcttccgcag    2880
caagctcaag gaggtgggcc aggcccagtt gaagactggc cggcggcgac tcttcgctca    2940
ggaaaaagaa gtggtcaagg aagaggagga ggacaaaggc gtcctcaatg acttccacaa    3000
gtgcatctat aagggaaggt ctgtttctct aacaactttt tatcgaacag cgaggaatat    3060
catgagcatg tgtttcagca aggagcctgc cccagccgaa atcgagcaag agtactggag    3120
gctagtggaa gagaaggact gccacgtggc agtgcactgc ggcaaggtgg acaccaacac    3180
tcacggcagt ggattcccag taggaaaatc agaaccattt tcgaggcatg gatggaacct    3240
caccgtcctc cccaataaca cagggtccat cctgcgtcac ctcggtgctg tgcctggagt    3300
gactattccc tggctaaata ttggcatggt cttttctacc tcatgctggt ctcgagacca    3360
aaatcacctt ccatacattg actacttaca cactggtgct gactgcattt ggtattgcat    3420
tcctgctgag gaggagaaca agctggaaga tgtggtccac accctgctgc aagccaatgg    3480
caccccaggg ctgcagatgc tggaaagcaa cgtcatgatc tccccggagg tgctgtgcaa    3540 agagggatc aaggtgcaca ggaccgtgca gcagagtggc cagtttgtcg tctgcttccc    3600
gggatccttt gtgtccaaag tgtgctgtgg gtacagcgtg tctgaaaccg tgcactttgc    3660
taccacccag tggacaagta tgggctttga gaccgccaag gaaatgaagc gtcgccatat    3720
agctaagcca ttctccatgg agaagttact ctaccagatt gcacaagcag aagcaaaaaa    3780
agaaaacggt cccactctca gtaccatctc agccctcctg gatgagctca gggatacaga    3840
gctgcggcag cgcaggcagc tgttcgaggc tggcctccac tcctccgcac gctatggcag    3900
ccacgatggc agcagcacgg tggcggacgg gaagaaaaag cctcgaaagt ggctgcagtt    3960
ggagacgtca gagaggaggt gtcagatctg ccagcacctg tgctacctgt ccatggtggt    4020
acaagagaac gaaaacgtcg tgttctgtct ggagtgtgct ctgcgccacg tggagaaaca    4080
gaagtcctgc cgagggctga gttgatgta ccgctacgat gaggaacaga ttatcagtct    4140
ggtcaatcag atctgcggca agtgtctgg taaaaacggc agcattgaga actgtctcag    4200
taaacccaca ccaaaagag gtccccgcaa gagagcgaca gtggacgtgc ccccctcccg    4260
tctgtcagcc tccagttcat ccaaaagtgc ttcgagctca tcatgaagat gccaacgccc    4320
gtggtcgatt tatatatatt tttttgtaat tattatattc tagtttggag tacttgctgt    4380
aggattcaag ctgtctttgc actagctcta aagaagattt tcttctggtt ttagagaact    4440
aattttgttt tagcattaaa ctgttgaact ttttttgta cttagaaaac ctagatactg    4500
cagtcagatt ttgaaaactg ccgtatagtc actgttttaa aaaccccgga ggggctgtat    4560
taatttgtat tgccccatgg ctgacaaaag cctttttttt tggttttgat ttttttttt    4620 ttgtaactgt tgggggaaa aaggcttttt aacccatttt tgaagagggt gaagtttgga    4680
gaacaaattt aaaaaccatc agtcatgtga gcagattttt tagaagggat aggagacaca    4740
cgcgcacaca cacacacaca cgaaacttga aatggctttg cttggctgt cgtcttctgc    4800 cgtgtgccag atgagcttgt gatctgggaa gccggggcac ccccgttttg tttctctggg    4860
cggttgtggc agctgaaggc ggacgttgtt tcctaaccat aggtggaacg aggagacggg    4920
agcgagtggg ctctccacca gcacatcact atgcatctgt tccaggaaag aagaaaagcg    4980
agcgaggaag acgaaaaaga ctgcctgcct tggagggtc acatgaggga gacctgtgcc    5040
```

| | |
|---|---|
| tgatttcatt aggaaatcca ttctgttatt ttttggtgct gttggctact ttatcaaaaa | 5100 |
| acccttcaat agcatcctta agatttaaaa aaaaaaaaaa aaaaaaggaa aaaaaagtga | 5160 |
| tggaagccgt aagtgcttct ttgtcatcga cgtgcaatct ttctaacatt ccatctccat | 5220 |
| ctcaccgctt cttgtttgac accttcacaa gtcagcatta atctttcttt taaaacttgt | 5280 |
| ttcatttatg atcatgtaga gagccactag gaggcctgca gttattttg aatgtgaaaa | 5340 |
| tgcatttgcg ttcatcttgt ctattttttc tcttcatgtt gtaacaaaaa ggaaaaaaga | 5400 |
| aaaaaaatc ccatcccttt tgtacatatg cctgtaaatt gttttaaata cttgagcctt | 5460 |
| tttctcggtg gggggtgggg aggggggtga aagacaaga tgaagaaaag ccttacatt | 5520 |
| cagtttcttc atcggttgga ttggatgctt acagggtttt tcttgtaaca tttataagtg | 5580 |
| ctgcttacat cactgaacaa caacaaaaaa ataataatgg agtagctgtt gcccttctcc | 5640 |
| ggttgtgtgt acagtatgtg tggaataaaa aagggaaact gttttcacaa gctgttcttt | 5700 |
| gtttcataat tggattcatc aatcccgtag ctacccatat tgcactgagc ttgccagtgg | 5760 |
| tgactgccag gaacgtccta tgatccactt tgttggttgt tgttgcagaa gactgaactg | 5820 |
| ttttggaata tttaacaatt acagaaacag tcaagtgttt tccaatgtgg ttgtccggtt | 5880 |
| tctatggcct tgctgtgtac tttccctctt tttgacagta aacttctgcc tatggcttac | 5940 |
| agtttgacat ttaatttatt agcgctgctc tgcacccctc ccttgggagg gagacttcat | 6000 |
| gtggtttatt gcgagttttt tgtttacttt tcaggtttgt actacaaggt ttaataataa | 6060 |
| aaacaaagtt ttttggacat ttgtctgtct tgtggaaaaa aaaaaaaaaa aa | 6112 |

<210> SEQ ID NO 95
<211> LENGTH: 2880
<212> TYPE: DNA
<213> ORGANISM: Homo sapiens

<400> SEQUENCE: 95

| | |
|---|---|
| cactgcatgt gtattcgtga gttcgcggtt gaacaactgt tcctttactc tgctccctgt | 60 |
| ctttgtgctg actgggttac ttttttaaac actaggaatg gtaatttcta ctcttctgga | 120 |
| cttcaaacta agaagttaaa gagacttctc tgtaaataaa caaatctctt ctgctgtcct | 180 |
| tttgcatttg gagacagctt tatttcacca tatccaagga gtataactag tgctgtcatt | 240 |
| atgaatgtga caagtttatt ttcctttaca agtccagctg tgaagagact tcttgggtgg | 300 |
| aaacagggcg atgaagaaga aaaatgggca gagaaagctg ttgatgcttt ggtgaaaaaa | 360 |
| ctgaagaaaa agaaaggtgc catggaggaa ctggaaaagg ccttgagctg cccagggcaa | 420 |
| ccgagtaact gtgtcaccat tccccgctct ctggatggca ggctgcaagt ctcccaccgg | 480 |
| aagggactgc tcatgtcat ttactgccgt gtgtggcgct ggcccgatct tcagagccac | 540 |
| catgaactaa aaccactgga atgctgtgag tttccttttg gttccaagca aaggaggtc | 600 |
| tgcatcaatc cctaccacta taagagagta gaaagccctg tacttcctcc tgtgctggtt | 660 |
| ccaagacaca gcgaatataa tcctcagcac agcctcttag ctcagttccg taacttagga | 720 |
| caaaatgagc ctcacatgcc actcaacgcc acttttccag attctttcca gcaacccaac | 780 |
| agccaccgt tcctcactc tcccaatagc agttacccaa actctcctgg gagcagcagc | 840 |
| agcacctacc ctcactctcc caccagctca gacccaggaa gcccttccca gatgccagct | 900 |
| gatacgcccc cacctgctta cctgcctcct gaagaccca tgacccagga tggctctcag | 960 |
| ccgatggaca caaacatgat ggcgcctccc ctgccctcag aaatcaacag aggagatgtt | 1020 |
| caggcggttg cttatgagga accaaaacac tggtgctcta ttgtctacta tgagctcaac | 1080 |

```
aatcgtgtgg gtgaagcgtt ccatgcctcc tccacaagtg tgttggtgga tggtttcact      1140
gatccttcca acaataagaa ccgtttctgc cttgggctgc tctccaatgt taaccggaat      1200
tccactattg aaaacaccag gcggcatatt ggaaaaggag ttcatcttta ttatgttgga      1260
ggggaggtgt atgccgaatg ccttagtgac agtagcatct tgtgcaaag tcggaactgc       1320 aactaccatc atggatttca tcctactact gtttgcaaga tccctagtgg gtgtagtctg      1380 aaaatttta acaaccaaga atttgctcag ttattggcac agtctgtgaa ccatggattt       1440
gagacagtct atgagcttac aaaaatgtgt actatacgta tgagctttgt gaagggctgg      1500
ggagcagaat accaccgcca ggatgttact agcaccccct gctggattga gatacatctg      1560
cacggccccc tccagtggct ggataaagtt cttactcaaa tgggttcacc tcataatcct      1620
atttcatctg tatcttaaat ggccccaggc atctgcctct ggaaaactat tgagccttgc      1680
atgtacttga aggatggatg agtcagacac gattgagaac tgacaaagga gccttgataa      1740
tacttgacct ctgtgaccaa ctgttggatt cagaaattta acaaaaaaa aaaaaaaaca       1800 cacacacctt ggtaacatac tgttgatatc aagaacctgt ttagtttaca ttgtaacatt      1860
ctattgtaaa atcaactaaa attcagactt ttagcaggac tttgtgtaca gttaaaggag      1920
agatggccaa gccagggaca aattgtctat tagaaaacgg tcctaagaga ttctttggtg      1980
tttggcactt taaggtcatc gttgggcaga agtttagcat taatagttgt tctgaaacgt      2040
gttttatcag gtttagagcc catgttgagt cttctttca tgggttttca taatatttta       2100
aaactatttg tttagcgatg gtttttgttcg tttaagtaaa ggttaatctt gatgatatac     2160
ataataatct ttctaaaatt gtatgctgac catacttgct gtcagaataa tgctaggcat      2220 atgcttttg ctaaatatgt atgtacagag tatttgaag ttaagaattg attagactag        2280
tgaatttagg agtatttgag gtgggtgggg ggaagaggga aatgacaact gcaaatgtag      2340
actatactgt aaaaattcag tttgttgctt taaagaaaca aactgatacc tgaattttgc      2400
tgtgtttcca ttttttagag attttttatca tttttttctc tctcggcatt cttttttctc     2460
atactcttca aaaagcagtt ctgcagctgg ttaattcatg taactgtgag agcaaatgaa      2520
taattcctgc tattctgaaa ttgcctacat gtttcaatac cagttatatg gagtgcttga     2580
atttaataag cagttttttac ggagtttaca gtacagaaat aggctttaat ttcaagtga     2640 attttttgcc aaacttagta actctgttaa atatttggag gatttaaaga acatcccagt     2700
ttgaattcat ttcaaacttt ttaaatttt ttgtactatg tttggttta ttttccttct        2760 gttaatcttt tgtattcact tatgctctcg tacattgagt acttttattc caaaactagt     2820
gggttttctc tactggaaat tttcaataaa cctgtcatta ttgcttactt tgattaaaaa     2880
```

<210> SEQ ID NO 96
<211> LENGTH: 3056
<212> TYPE: DNA
<213> ORGANISM: Homo sapiens

<400> SEQUENCE: 96

```
ggcagctgag gagtggaggc tgggcagctc cgactccctg acgccagcgc gaccagatca        60
atccaggctc caggagaaag caggcggggcg ggcggagaaa ggagaggccg agcggctcaa      120
cccgggccga ggctcgggga gcggagagtg gcgcagcgcc cggccgtccg acccgggcc       180 gcgagacccc gctcgcccgg ccactcgtgc tcccacacgg acgggcgcgc cgccaacccg      240
gtgctgactg ggttactttt ttaaaacacta ggaatggtaa tttctactct tctggacttc     300
```

| | |
|---|---|
| aaactaagaa gttaaagaga cttctctgta aataaacaaa tctcttctgc tgtccttttg | 360 |
| catttggaga cagcttttatt tcaccatatc caaggagtat aactagtgct gtcattatga | 420 |
| atgtgacaag tttatttttcc tttacaagtc cagctgtgaa gagacttctt gggtggaaac | 480 |
| agggcgatga agaagaaaaa tgggcagaga agctgttga tgctttggtg aaaaaactga | 540 |
| agaaaaagaa aggtgccatg gaggaactgg aaaaggcctt gagctgccca gggcaaccga | 600 |
| gtaactgtgt caccattccc cgctctctgg atggcaggct gcaagtctcc caccggaagg | 660 |
| gactgcctca tgtcatttac tgccgtgtgt ggcgctggcc cgatcttcag agccaccatg | 720 |
| aactaaaacc actggaatgc tgtgagtttc cttttggttc caagcagaag gaggtctgca | 780 |
| tcaatcccta ccactataag agagtagaaa gccctgtact tcctcctgtg ctggttccaa | 840 |
| gacacagcga atataatcct cagcacagcc tcttagctca gttccgtaac ttaggacaaa | 900 |
| atgagcctca catgccactc aacgccactt ttccagattc tttccagcaa cccaacagcc | 960 |
| acccgttttcc tcactctccc aatagcagtt acccaaactc tcctgggagc agcagcagca | 1020 |
| cctaccctca ctctcccacc agctcagacc caggaagccc tttccagatg ccagctgata | 1080 |
| cgccccacc tgcttacctg cctcctgaag accccatgac ccaggatggc tctcagccga | 1140 |
| tggacacaaa catgatggcg cctcccctgc cctcagaaat caacagagga gatgttcagg | 1200 |
| cggttgctta tgaggaacca aaacactggt gctctattgt ctactatgag ctcaacaatc | 1260 |
| gtgtgggtga agcgttccat gcctcctcca caagtgtgtt ggtggatggt ttcactgatc | 1320 |
| cttccaacaa taagaaccgt ttctgccttg ggctgctctc caatgttaac cggaattcca | 1380 |
| ctattgaaaa caccaggcgg catattggaa aaggagttca tctttattat gttggagggg | 1440 |
| aggtgtatgc cgaatgcctt agtgacagta gcatctttgt gcaaagtcgg aactgcaact | 1500 |
| accatcatgg atttcatcct actactgttt gcaagatccc tagtgggtgt agtctgaaaa | 1560 |
| tttttaacaa ccaagaattt gctcagttat tggcacagtc tgtgaaccat ggatttgaga | 1620 |
| cagtctatga gcttacaaaa atgtgtacta tacgtatgag cttttgtgaag ggctggggag | 1680 |
| cagaatacca ccgccaggat gttactagca cccccctgctg gattgagata catctgcacg | 1740 |
| gccccctcca gtggctggat aaagttctta ctcaaatggg ttcacctcat aatcctattt | 1800 |
| catctgtatc ttaaatggcc ccaggcatct gcctctggaa aactattgag ccttgcatgt | 1860 |
| acttgaagga tggatgagtc agacacgatt gagaactgac aaaggagcct tgataatact | 1920 |
| tgacctctgt gaccaactgt tggattcaga aatttaaaca aaaaaaaaaa aaaacacaca | 1980 |
| caccttggta acatactgtt gatatcaaga acctgtttag tttacattgt aacattctat | 2040 |
| tgtaaaatca actaaaattc agacttttag caggactttg tgtacagtta aaggagagat | 2100 |
| ggccaagcca gggacaaatt gtctattaga aaacggtcct aagagattct ttggtgtttg | 2160 |
| gcactttaag gtcatcgttg gcagaagtt tagcattaat agttgttctg aaacgtgttt | 2220 |
| tatcaggttt agagcccatg ttgagtcttc ttttcatggg ttttcataat attttaaaac | 2280 |
| tatttgttta gcgatggttt tgttcgttta agtaaaggtt aatcttgatg atatacataa | 2340 |
| taatctttct aaaattgtat gctgaccata cttgctgtca gaataatgct aggcatatgc | 2400 |
| ttttttgctaa atatgtatgt acagagtatt tggaagttaa gaattgatta gactagtgaa | 2460 |
| tttaggagta tttgaggtgg gtgggggaa gagggaaatg acaactgcaa atgtagacta | 2520 |
| tactgtaaaa attcagtttg ttgctttaaa gaaacaaact gatacctgaa ttttgctgtg | 2580 |
| tttccatttt ttagagattt ttatcatttt tttctctctc ggcattcttt tttctcatac | 2640 |
| tcttcaaaaa gcagttctgc agctggttaa ttcatgtaac tgtgagagca atgaataat | 2700 |

```
tcctgctatt ctgaaattgc ctacatgttt caataccagt tatatggagt gcttgaattt    2760
aataagcagt ttttacggag tttacagtac agaaataggc tttaattttc aagtgaattt    2820
tttgccaaac ttagtaactc tgttaaatat ttggaggatt taaagaacat cccagtttga    2880
attcatttca aactttttaa attttttttgt actatgtttg gttttatttt ccttctgtta   2940
atcttttgta ttcacttatg ctctcgtaca ttgagtactt ttattccaaa actagtgggt    3000
tttctctact ggaaattttc aataaacctg tcattattgc ttactttgat taaaaa        3056
```

EARLY DEVELOPMENTAL GENOMIC ASSAY FOR CHARACTERIZING PLURIPOTENT STEM CELL UTILITY AND SAFETY

CROSS REFERENCE TO RELATED APPLICATIONS

This application is a 371 National Phase Entry of International Patent Application No. PCT/US2014/041513 filed on Jun. 9, 2014 which claims benefit under 35 U.S.C. § 119(e) of U.S. Provisional Application No. 61/833,092 filed on Jun. 10, 2013, the contents of each of which are incorporated herein by reference in their entirety.

This invention was made with government support under ES017155 awarded by the National Institutes of Health. The government has certain rights in the invention.

FIELD OF THE INVENTION

The present invention relates to arrays and methods for characterizing pluripotent stem cell populations to permit selection of pluripotent stem cell lines for further use.

SEQUENCE LISTING

The instant application contains a Sequence Listing which has been submitted electronically in ASCII format and is hereby incorporated by reference in its entirety. Said ASCII copy, created on Dec. 9, 2015, is named 002806-077891-PCT_SL.txt and is 436,312 bytes in size.

BACKGROUND OF THE INVENTION

One goal of regenerative medicine is to be able to convert pluripotent cells into other cell types for tissue repair and regeneration. Human pluripotent cell lines exhibit a level of developmental plasticity that is similar to the early embryo, enabling in vitro differentiation into all three embryonic germ layers (Rossant, 2008; Thomson et al., 1998). At the same time it is possible to maintain these pluripotent cell lines for many passages in the undifferentiated state (Adewumi et al., 2007). These unique characteristics render human embryonic stem (ES) and human induced pluripotent stem (iPS) cells a promising tool for biomedical research (Colman and Dreesen, 2009). ES cell lines have already been established as a model system for dissecting the cellular basis of monogenic human diseases.

However, several recent developments have greatly increased the need for an assay that can predict the behavior of pluripotent human cell lines. First, the continued derivation of human ES cell lines by many labs and the lifting of funding restrictions in the U.S. have substantially increased the number of ES cell lines from which investigators can choose. Additionally, it has become clear that not all human ES cell lines are equally suited for every purpose (Osafune et al., 2008). This suggests that any new research project should include a deliberate and informed selection of the cell lines that are most qualified for an application of interest.

The ability to reprogram somatic cells from patients into iPS cells has also led to a further increase in the number of pluripotent cell lines available to, and used by, the research community. As investigators gather together existing cell lines, or derive new ones for their application of interest, there is little information or guidance concerning how to select cell lines that are most appropriate for use.

Future applications of human pluripotent stem cell lines will likely include the study of common diseases that arise as the result of complex interactions between a person's genotype and their environment (Colman and Dreesen, 2009). In addition, pluripotent cells will eventually serve as a renewable source of both cells and tissue for transplantation medicine (Daley, 2010). Both of these proposed applications for pluripotent stem cells will require the selection of cell lines that reliably, reproducibly, efficiently and stably differentiate into disease-relevant cell types. However, a significant amount of variation has been reported in the efficiency by which different human ES cell lines or iPSC lines differentiate into different derivatives of the three embryonic germ layers (Di Giorgio et al., 2008; Osafune et al., 2008). Furthermore, it has been reported that iPS cells collectively deviate from ES cells in the expression of hundreds of genes (Chin et al., 2009), and their ability to differentiate down particular lineages (Hu et al., 2010). While some iPS cell lines can differentiate as efficiently as ES cells (Boland et al., 2009; Miura et al., 2009; Zhao et al., 2009), the published gene expression signatures of iPS cells are not reproducible (Stadtfeld et al., 2010). The long-term proliferation and differentiation potential of human pluripotent stem cells suggests that they can produce large quantities of various cell types for disease modeling and transplantation therapy. However, before embryonic stem (ES) cells or induced pluripotent stem (iPS) cells can be used with confidence in therapeutic application or disease modeling, or in drug screening or toxicity assays, the extent of variation between human pluripotent cell lines must be understood. In particular, it is necessary to establish a reference of normal variation among high-quality pluripotent cell lines, in order to provide a baseline against which variation from cell-line to cell-line can be identified and to permit systematic selection of a particular pluripotent stem cell best suited for a particular use.

Therefore, there is a need in the art for novel, effective and efficient methods for characterizing and validating cells, including pluripotent stem cell monitoring and validation, and for determining the quality of the, for example, pluripotent stem cell as well as its propensity to, for example, differentiate along a particular cell lineage, prior to its use, e.g., in therapeutic administration, disease modeling, drug development and screening and toxicity assays etc., to reduce administration of aberrant cells (e.g., non-pluripotent stem cells, or cells that are unlikely to differentiate along a desired lineage).

SUMMARY OF THE INVENTION

The present invention is directed to a set of early developmental gene biomarkers, or subsets thereof, which can be used to characterize cells. In one embodiment, these markers can be used to determine the differentiation potential of a pluripotent stem cell population. Aspects of the present invention relate to arrays, assays, systems, kits and methods to rapidly and inexpensively screen cells, including pluripotent cells, for their general quality (e.g., pluripotent capacity) and differentiation capacity. The present invention as disclosed herein therefore allows for a high throughput screening of the signature of gene expression of a set of early developmental genes, in a plurality of stem cell lines including, for example, pluripotent stem cell lines, to permit rapid identification and selection of cells, in some instances an automated selection of cells, which can be chosen for further use or for a particular utility. Accordingly, in one embodiment the present invention relates to a method of characterization of pluripotent stem cells, including induced pluripotent stem cells (iPSCs) by measuring the gene expression of a set of early developmental genes, or a subset thereof, which is highly predictive for how a specific cell line will perform in directed differentiation regimens and paradigms.

It is currently very difficult to predict how a pluripotent stem cell line will behave or which cell lineage the pluripotent stem cell line has a bias for differentiating into without either letting the pluripotent stem cell spontaneously differentiate, and/or differentiating the pluripotent stem cell along a variety of different cell lineages. Current systems to assess pluripotency, such as teratoma formation, are cumbersome, time consuming and very expensive, thus preventing these methods from becoming useful in a large scale characterization of stem cells. Additionally, teratoma formation is not able to predict which cell lineages the cell line will likely differentiate into, nor can these methods identify sub-optimal stem cell lines. Other gene expression analysis systems for characterizing stem cell lines require the pluripotent stem cell line to be cultured for a period of time (e.g., about 1 week) before analysis, or require the pluripotent stem cell to be differentiated (e.g., by directed differentiation) or to undergo spontaneous differentiation for a given period of time before analysis.

The inventors have surprisingly discovered as described herein that the expression of a subset of genes which are expressed in very early stages of development, herein referred to as "early developmental genes," can accurately predict whether the stem cell is still pluripotent, and/or whether the stem cell line has a propensity to differentiate along mesoderm, ectoderm and/or endoderm lineages. For example, the present invention is based on the discovery that the expression of an earlier set of developmental genes provides a meaningful insight into the cells' developmental and differentiation pathway.

For example, by measuring the gene expression of a set of early developmental genes in a stem cell line as disclosed herein, one is able to forecast the differentiation efficiency and pluripotency of a stem cell line being analyzed. For example, by measuring the expression level of a set of early developmental genes, the inventors have demonstrated the levels of these genes are highly predictive for determining the likely direction of the differentiation of the pluripotent stem cell line along particular lineages, e.g., mesoderm, ectoderm or endoderm lineages. Therefore, the invention as disclosed herein has broad utility and can be used to prospectively predict how well a given pluripotent stem cell will differentiate along any desired lineage, for example, hematopoietic lineage, endoderm lineage, pancreatic lineage, neuronal lineage such as a motor neuron lineage, and the like.

Accordingly, as the genes analyzed are expressed in very early stages of development, the invention as disclosed herein has a significant advantage over other gene expression systems used to characterize pluripotent stem cells in that it permits the characterization of the stem cell population at a much earlier time point than in previous assays, thus increasing the efficiency and reducing costs for such characterization. Accordingly, the invention as disclosed herein provides a rapid, inexpensive and quantitative approach for characterizing pluripotent stem cell lines. The methods described are highly efficient in predicting the differentiation ability of the cell as compared to traditional methods, and can identify stem cell lines which can be particularly suited for a particular purpose or use, or alternatively, unsuitable for a particular purpose or use. Additionally, the analysis of the expression of a set of early developmental genes is highly accurate at identifying the lineage propensity of the pluripotent stem cell on a single analysis, thus eliminating the need for replicates, further decreasing costs and effort required to characterize a stem cell population.

As demonstrated herein, the gene expression analysis of a set of early developmental genes in a pluripotent stem cell line can be performed on pluripotent stem cells at as early as embryonic day 2, which is reduced from analysis performed on cells at least 5-7 days of embryonic age. As little as 2 days in EB forming conditions is enough to obtain an accurate prediction of the likelihood that a given stem cell, e.g., ES cell or iPS cell line, will differentiate into a desired lineage or phenotype. Described herein is a set of markers that permit accurate prediction of the differentiation potential after as little as 2 days in EB forming conditions.

Accordingly, shortening the time prior to measuring gene expression is advantageous in that it decreases the time-to-results and also minimizes the logistical costs in terms of incubator space and need for media changes. Accordingly, in some embodiments, measurement of the gene expression of a set of early developmental genes permits one to determine the differentiation potential of a pluripotent stem cell population at a very early developmental stage, e.g., the gene expression analysis can be performed on a stem cell population that is at embryonic stage of at least about 2, or at least about 3, or at least about 4 or at least about 5 days. As discussed above, previously an investigator would have had to wait for the pluripotent stem cell line to reach embryonic stage 7 (Embryonic body 7 days; EB7) or greater, e.g., 16 days (EB16) and/or actually differentiate the cells before performing an analysis to determine the differentiation potential of the stem cell line.

Accordingly, in some embodiments, the ability of the pluripotent cell to differentiate into at least one of the mesoderm, endoderm and ectoderm lineages is determined by assessing the gene expression of a set of early developmental genes listed in Table 1 and/or Table 2 in a pluripotent stem cell line after less than one day in embryoid body (EB) forming conditions or supporting media. In some embodiments, the ability of the pluripotent cell to differentiate into at least one of the mesoderm, endoderm and ectoderm lineages is determined by measuring the gene expression of a set of at least 10, or at least 20 early developmental genes listed in Table 1 and/or Table 2 at anywhere between 0 days in EB forming conditions or supporting media, or between 0-14 days in EB forming conditions or supporting media, e.g., at least 1 day, or at least 2 days, or at least about 3 days, or at least about 4 days, or at least about 5 days, or at least about 6 days, or at least about 7 days, or more than about 7 days in EB forming conditions or supporting media, e.g., between 5-7 days in EB forming conditions or supporting media, or between about 7-10 days in EB forming conditions or supporting media, or between about 10-14 days in EB forming conditions or supporting media, or longer than 14 days in EB forming conditions or supporting media.

In some embodiments, the ability of the pluripotent cell to differentiate into at least one of the mesoderm, endoderm and ectoderm lineages is determined by measuring the gene expression of a set of at least 1, or at least 2 or at least 3 or at least 4 genes from the group of mesoderm early developmental genes, selected from the group consisting of: HAND1, ESM1, HAND2, HOPX, BMP10, FCN3 and GSC, and/or a set of endoderm early developmental genes selected from the group consisting of: LEFTY1, EOMES, NODAL and FOXA2, and/or a set of ectoderm early developmental genes selected from the group consisting of: TRPM8, POU4F1, OLFM3, WNT1, LMX1A and CDH9 and/or a set of early developmental selected from the group consisting of: IDO1, LCK, POU5F1 and HESX1 at anywhere between 0 days in EB forming conditions or supporting media, or between 0-14 days in EB forming conditions or supporting media, e.g., at least 1 day, or at least 2 days, or at least about 3 days, or at least about 4 days, or at least about 5 days, or at least about 6 days, or at least about 7 days, or more than about 7 days in EB forming conditions or supporting media, e.g., between 5-7 days in EB forming conditions or supporting media, or between about 7-10 days in EB forming conditions or supporting media, or between about 10-14 days in EB forming conditions or supporting media, or longer than 14 days in EB forming conditions or supporting media.

As disclosed herein, the measurement of the expression of a set of early developmental genes in a stem cell line can be preformed alone as a single indicator of the pluripotency and/or differentiation potential of the stem cell line. As demonstrated in the Examples, the inventors have optimized the set of early developmental genes to be measured so an array or assay is sufficiently sensitive to estimate the differentiation propensities and pluripotency of the stem cell line using RNA isolated directly from the undifferentiated pluripotent cell lines, e.g., the assays and arrays can detect low levels of cellular differentiation in an otherwise self-renewing culture media or conditions. Further, the expression analysis for a set of early developmental genes can be performed using a variety of different RNA preparation methods, culture media and the like. The inventors have also demonstrated that the gene expression of a set of early developmental genes in a stem cell line can be analyzed in a multiplex system, for example in a 96- or 384-well plate format, allowing multiple stem cell lines to be analyzed simultaneously, demonstrating the ability of this assay to be performed in a high-throughput system.

The expression of a set of early developmental genes can be measured to assess the differentiation potential of a variety of different stem cells selected from, but not limited to, a pluripotent, multipotent, unipotent, or somatic stem cell, including but not limited to precursor cells, embryonic stem (ES) cells, somatic stem cells, cancer stem cells, progenitor cells, induced pluripotent stem (iPS) cells, partially induced pluripotent (piPS) cells, reprogrammed cells, directly reprogrammed cells, etc., to determine the stem cell's propensity to differentiate into ectoderm, mesoderm and endoderm lineages and/or to predict if the stem cell line has the ability to differentiate along a desired and/or particular developmental pathway and into a specific cell lineage.

In some embodiments, while the present invention specifically contemplates using the arrays, assays and methods as disclosed herein to determine if a stem cell is pluripotent, any type of stem cell can be assessed. For simplicity, when referring to a pluripotent stem cell herein, this encompasses both pluripotent and non-pluripotent stem cells. In some embodiments, the stem cell is a pluripotent stem cell.

In some embodiments, the expression of a defined set of early developmental genes can be analyzed in a high throughput manner, e.g., to screen for particular stem cell characteristics in a plurality of pluripotent stem cell lines. The sets of early developmental genes can be any selected set of early developmental genes from Table 1, as disclosed herein. In some embodiments, a set of early developmental genes which are analyzed include at least 3 genes from the group disclosed in Table 2. In some embodiments, a set of early developmental genes which are analyzed include at least 3 genes from Table 2 and any combination of at least 10, or at least 20 genes as disclosed in Table 1 can be assessed in a differentiation propensity assay as disclosed herein. In some embodiments, a set of early developmental genes which are analyzed include at least 1, or at least 2, or at least 3, or at least 4 genes or more from the group of mesoderm early developmental genes, selected from the group consisting of: HAND1, ESM1, HAND2, HOPX, BMP10, FCN3 and GSC, and/or at least 1, or at least 2, or at least 3, or at least 4 genes or more from a set of endoderm early developmental genes selected from the group consisting of: LEFTY1, EOMES, NODAL and FOXA2, and/or at least 1, or at least 2, or at least 3, or at least 4 genes from a set of ectoderm early developmental genes selected from the group consisting of: TRPM8, POU4F1, OLFM3, WNT1, LMX1A and CDH9 and/or at least 1, or at least 2, or at least 3, or at least 4 genes from a set of early developmental selected from the group consisting of: IDO1, LCK, POU5F1 and HESX1.

In some embodiments, one can measure the expression of a set of early developmental genes and allow the automatic selection of a suitable pluripotent stem cell line or clones with desired characteristics (e.g., pluripotency and/or predisposition to differentiate along a desired lineage). Specifically, the present invention relates to the measurement of expression of a set of early developmental genes in a stem cell line, such that a stem cell deviating from a normal range of early differentiation gene expression pattern can be excluded, and the cells that fall within the normal ranges can be selected for further use. For example, one can screen for, or evaluate expression of a subset of early developmental genes as disclosed herein, and if a stem cell does not fit within the predetermined parameters for a pluripotent cell expressing the appropriate marker set, it can be discarded or not selected for further use. Statistical analysis methods can be used to automate the system. In some embodiments, the expression of a set of early developmental genes as disclosed in Table 1 is analyzed in a stem cell line at a pre-defined time point, e.g., at least 2 days in EB forming conditions but not longer than 5 days, or not longer than or 7 days, in EB forming conditions (e.g., self-renewing culture conditions).

Accordingly, by measuring the expression of a set of early developmental genes, the inventors have demonstrated an efficient and effective method to monitor and validate the differentiation propensity and pluripotency of a stem cell population in order to predict their therapeutic utility and safety profile, (e.g., determining if the pluripotent stem cell population is predisposed to continual self-renewal and/or has an increased efficiency to differentiate along a particular lineage which is important if the pluripotent stem cell is to be transplanted for therapeutic use), and also permits one to predict into which lineages and developmental pathways the pluripotent stem cell line will efficiently differentiate. As such, the invention as disclosed herein permits the user to select or choose a stem cell line with desirable characteristics, e.g., positively select for stem cells with similar characteristics to other pluripotent stem cells, or stem cells which have a predisposition to optimally differentiate into a desired cell type or along a specific cell lineage. Alternatively, the present invention permits one to negatively select, e.g., identify, and optionally discard, stem cells with undesirable characteristics, e.g., cells which are non-pluripotent and/or are likely to differentiate into a cell type which is not desired by the investigator. Accordingly, the present invention permits one to determine the likely direction of the differentiation of a stem cell line and thus permits one to identify and/or choose a particular stem cell population for its suitability for downstream applications, such as its suitability for therapeutic use, drug screening and toxicity assays, differentiation into a desired cell lineage, and the like. The ability to predict to which lineage a stem cell line will likely differentiate into prior to a therapeutic application and/or administration can avoid the introduction of aberrant cells (e.g., can avoid administering a non-pluripotent stem cell line and/or cells which are unlikely to differentiate along a specific desired lineage, or cells which have an increased propensity to differentiate along an undesired lineage).

Accordingly, one aspect of the present invention relates to an array composition for characterizing the differentiation potential of a pluripotent stem cell, comprising nucleic acids, e.g., oligonucleotides or primers (e.g., primer pairs), that amplify the mRNA of any combination of early developmental genes selected from those listed in Table 1. In some embodiments, the array comprises nucleic acids, e.g., oligonucleotides or primers, that amplify the mRNA of at least 3 early developmental genes selected from those listed in Table 1 or Table 2. In some embodiments, the amplified developmental genes are at least 90% identical to, or specifically hybridize with nucleic acids encoding genes selected from those listed in Table 1 and/or Table 2.

In some embodiments, the array comprises at least 10, or at least about 20, or at least about 30, or 30-60, or 60-90 or more than 90 different nucleic acids (e.g. oligonucleotides), or at least 10, or at least about 20, or at least about 30, or 30-60, or 60-90 or more than 90 pairs of nucleic acids (e.g., primers), that amplify the mRNA of a combination of early developmental genes selected from those listed in Table 1 or Table 2.

In some embodiments, the array comprises nucleic acids, e.g., oligonucleotides or primers, that amplify the mRNA of at least one pluripotent stem cell gene, at least one early mesoderm developmental gene, at least one ectoderm developmental gene, and at least one endoderm developmental gene selected from Table 1 and/or from Table 2. In some embodiments, the array comprises nucleic acids, e.g., oligonucleotides or primers, that amplify the mRNA of at least 4 pluripotent stem cell genes, at least 4 early mesoderm developmental genes, at least 4 ectoderm developmental genes, and at least 4 endoderm developmental genes selected from Table 1. In some embodiments, the array comprises nucleic acids, e.g., oligonucleotides or primers that amplify at least 1, or at least 2, or at least 3, or at least 4 genes or more from the group of mesoderm early developmental genes, selected from the group consisting of: HAND1, ESM1, HAND2, HOPX, BMP10, FCN3 and GSC, and/or at least 1, or at least 2, or at least 3, or at least 4 genes or more from a set of endoderm early developmental genes selected from the group consisting of: LEFTY1, EOMES, NODAL and FOXA2, and/or at least 1, or at least 2, or at least 3, or at least 4 genes from a set of ectoderm early developmental genes selected from the group consisting of: TRPM8, POU4F1, OLFM3, WNT1, LMX1A and CDH9 and/or at least 1, or at least 2, or at least 3, or at least 4 genes from a set of early developmental selected from the group consisting of: IDO1, LCK, POU5F1 and HESX1.

In some embodiments, the array comprises nucleic acids, e.g., oligonucleotides or primers, that amplify the mRNA corresponding to 1-10 control genes, such as, but not limited to control genes selected from the group consisting of: ACTB, JARID2, CTCF, SMAD1, GAPDH, β-actin, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLPO, PPIA, POLR2A, PGK1, IP08, HMBS, GUSB, B2M, HPRT1 or 18S.

In some embodiments, the array comprises no more than 100, or no more than 90, or no more than 50 nucleic acids, e.g., oligonucleotides or primers. In some embodiments, the nucleic acids present on the array are sets of primers. In some embodiments, the nucleic acids, e.g., oligonucleotides or primers are immobilized on, or within a solid support. As a non-limiting example, the nucleic acids can be immobilized on the solid surface by the 5' end of said oligonucleotides. In some embodiments, the solid surface is selected from a group of materials comprising silicon, metal, and glass. In some embodiments, the solid support comprises oligonucleotides at assigned positions defined by x and y coordinates.

In some embodiments, the array comprises nucleic acids, e.g., primers that can amplify the mRNA of the early developmental genes by a method comprising: polymerase chain reaction (PCR); strand displacement amplification (SDA); loop-mediated isothermal amplification (LAMP); rolling circle amplification (RCA); transcription-mediated amplification (TMA); self-sustained sequence replication (3SR); nucleic acid sequence based amplification (NASBA); or reverse transcription polymerase chain reaction (RT-PCR). In some embodiments, the array allows for real-time PCR amplification of the early developmental genes, or a real-time PCR amplification of the early developmental genes with detection by SYBR green or a MNAzyme detection method.

In some embodiments, the array as disclosed herein is, e.g., an OpenArray®, which is commercially available from Life Technologies, wherein the oligonucleotides or primers are immobilized within the wells of the OpenArray®. In some embodiments, the array is configured as a 96 or 384 well plate comprising primers to a set of early developmental genes selected from Table 1 and/or Table 2 dried in the wells, where each of the wells of the solid support of the plate has a hydrophobic top and bottom surface and a hydrophilic interior wall of each well permitting the primers and reaction mixture to remain in each individual well. In some embodiments, an array encompassed for use in the present invention comprises primers to a set of early developmental genes selected from Table 1 and/or Table and is configured as an OpenArray® as disclosed in U.S. Pat. Nos. 6,387,331; 6,743,633; 6,893,877; 7,332,271 and 7,547,556 which are incorporated herein in their entirety by reference.

Another aspect of the present invention relates to a method to determine the differentiation potential of a pluripotent stem cell comprising performing array amplification using the nucleic acid derived from a stem cell line and an array as disclosed herein. In some embodiments, after the array amplification, the data is analyzed using a web-based analysis tool which can output an indicator of the potential of the pluripotent stem cell to differentiate along different lineages selected from: mesoderm lineage, ectoderm lineage and endoderm lineage and/or the pluripotency of the pluripotent stem cell.

Another aspect of the present invention relates to a method of determining the differentiation potential of a test stem cell line comprising detecting and comparing the expression in the stem cell line of a set of early developmental genes selected from any listed in Table 1 and/or Table 2 to the expression of the same genes by a control pluripotent stem cell sample, and, based on this comparison, determining the differentiation potential of the test stem cell line. In some embodiments, the gene expression is assayed by real time amplification, or wherein the detection comprises SYBR Green based real-time PCR.

In some embodiments, the expression values (e.g., expression levels) of the early developmental genes plus at least one control gene are measured in the stem cell line and a ΔCt is calculated for each gene, and the ΔCt value of each early developmental gene is compared to the ΔCt value of each early developmental gene in a data pool that contains reference ΔCt values from a plurality of reference pluripotent stem cells, to provide a ΔΔCt value. In some embodiments, the expression values (e.g., expression levels) of the early developmental genes plus at least one control gene are measured in the stem cell line and the average ΔCt for the genes in each of the mesoderm, ectoderm and endoderm early developmental gene subgroups is calculated. In some embodiments, a ΔΔCt value is calculated by comparing the average ΔCt value of the genes in each of the mesoderm, ectoderm and endoderm early developmental gene subgroups with the average ΔCt value of the same genes in each of the mesoderm, ectoderm and endoderm early developmental gene subgroups in a data pool that contains reference average ΔCt values for the same genes in the mesoderm, ectoderm and endoderm early developmental gene subgroups from a plurality of reference pluripotent stem cells. In some embodiments, a t-test is used to identify statistically significant ΔΔCt values from the comparison of the average ΔCt value of the genes in each of the mesoderm, ectoderm and endoderm early developmental gene subgroups as compared to reference ΔCt value for genes in each of the mesoderm, ectoderm and endoderm early developmental gene subgroups from a plurality of reference pluripotent stem cells in the data pool.

In some embodiments, a stem cell line, e.g., a pluripotent stem cell line which differs by a statistically significant amount in the expression level of a set of mesoderm, ectoderm and endoderm early developmental genes is selected (e.g., chosen) for further use and/or research, or optionally discarded, depending on the investigators interest, on the basis of such a statistically significant difference(s) in early developmental gene expression.

In some embodiments, the method comprises detecting and comparing the expression levels of at least 10, or at least about 20, or at least about 30, or 30-60, or 60-90 or more than 90 early developmental genes selected from those listed in Table 1.

In some embodiments, the method comprises detecting and comparing the expression levels of at least one pluripotent stem cell gene, at least one early mesoderm developmental gene, at least one ectoderm developmental gene, and at least one endoderm developmental gene selected from Table 1 and/or from Table 2. In some embodiments, the method comprises detecting and comparing the expression levels of at least 4 pluripotent stem cell genes, at least 4 early mesoderm developmental genes, at least 4 ectoderm developmental genes, and at least 4 endoderm developmental genes selected from Table 1.

In some embodiments, the methods as disclosed herein permit a prediction of the response of a pluripotent stem cell line to signals directing differentiation along different lineages selected from: mesoderm lineage, ectoderm lineage and endoderm lineage. In some embodiments, the method as disclosed herein permits the evaluation of the pluripotency of a pluripotent stem cell line.

Another aspect of the present invention relates to an assay for choosing a stem cell line, e.g., a pluripotent stem cell line for a desired use by characterizing the differentiation potential of the stem cell line, the assay comprising: (a) measuring the level of expression of a plurality of early developmental genes in the stem cell line selected from the genes listed in Table 1; and comparing the measured level of expression with a reference gene expression level for the same plurality of early developmental genes; and (b) choosing a stem cell line on the basis of there being no statistically significant difference in the level of gene expression of the measured early developmental genes as compared to the reference gene expression level for the early developmental genes; or choosing a stem cell line on the basis of there being a statistically significant difference in the expression level in at least one desired early developmental gene as compared to the reference expression level of the early developmental genes.

In some embodiments, the assay measures a plurality of early developmental genes selected from at least 10, or at least about 20, or at least about 30, or 30-60, or 60-90 or more than 90 early developmental genes selected from those listed in Table 1. In some embodiments, the assay measures a plurality of early developmental genes selected from at least one pluripotent stem cell gene, at least one early mesoderm developmental gene, at least one ectoderm developmental gene, and at least one endoderm developmental gene selected from Table 1 and/or from Table 2. In some embodiments, the assay measures a plurality of early developmental genes selected from at least 4 pluripotent stem cell genes, at least 4 early mesoderm developmental genes, at least 4 ectoderm developmental genes, and at least 4 endoderm developmental genes selected from Table 1.

In some embodiments, the assay measures a plurality of early developmental genes in a pluripotent stem cell line that has been cultured for at least about 2 days as embryoid bodies (EB), or at least about 3 days, or at least about 4 days, or at least about 5 days as embryoid bodies (EB). In some embodiments, the assay measures a plurality of early developmental genes in pluripotent stem cell that has been cultured for no longer than about 2 days as EBs, or for no longer than about 3 or about 4 days as EBs, or in self-renewing culture conditions.

In some embodiments, the assay measures a plurality of early developmental genes in stem cells using any method commonly known by persons of ordinary skill in the art, e.g., a method selected from the group consisting of: polymerase chain reaction (PCR); strand displacement amplification (SDA); loop-mediated isothermal amplification (LAMP); rolling circle amplification (RCA); transcription-mediated amplification (TMA); self-sustained sequence replication (3SR); nucleic acid sequence based amplification (NASBA); or reverse transcription polymerase chain reaction (RT-PCR).

In some embodiments, the assay uses real-time PCR amplification, or a real-time PCR amplification method with detection by SYBR green or an MNAzyme detection method to measure the expression level of a plurality of early developmental genes.

In some embodiments, the assay further comprises measuring the level of expression of at least one control gene in the pluripotent stem cell, for example, a control gene selected from the group consisting of: ACTB, JARID2, CTCF, SMAD1, GAPDH, β-actin, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLPO, PPIA, POLR2A, PGK1, IP08, HMBS, GUSB, B2M, HPRT1 or 18S.

In some embodiments, the level of the expression of the control gene in a test stem cell line, e.g., a pluripotent stem cell line is compared with the level of the expression of an early developmental gene to provide the ΔCt of the level of gene expression of an early developmental gene measured in the test stem cell line. In some embodiments, the assay comprises comparing the level of gene expression of the same plurality of early developmental genes with a reference gene expression level of the same early developmental genes and comparing the ΔCt of the expression of an early developmental gene measured in the test stem cell with the average ΔCt of the gene expression of the same early developmental gene measured from a plurality of reference pluripotent stem cells.

In some embodiments, the assay can be used to choose a stem cell line, e.g., a pluripotent stem cell line which differs by a statistically significant amount in the expression level of at least one desired early developmental gene, by selecting a stem cell line which differs by a statistically significant amount (e.g., using a t-test or other appropriate statistical measurement) in the expression level of an early developmental gene which is a mesoderm developmental gene, an ectoderm developmental gene, or an endoderm developmental gene. In some embodiments, a statistical difference is a difference of at least 1, at least 2, or at least 3 standard deviations from the reference gene expression level for the early developmental gene.

In some embodiments, the reference gene expression level for an early developmental gene includes the range of normal variation for the expression of that early developmental gene in a plurality of pluripotent stem cells. In some embodiments, the reference gene expression level for an early developmental gene is an average of expression level for that early developmental gene, wherein the average is calculated from expression level of that early developmental gene in a plurality of pluripotent stem cell lines. In some embodiments, the plurality of pluripotent stem cell lines for a reference gene expression level is obtained from at least 5 or more pluripotent stem lines.

In some embodiments, the assay as disclosed herein can be used characterize the differentiation potential of a mammalian a stem cell line, e.g., a pluripotent stem cell, e.g., a human pluripotent stem cell. In some embodiments, the pluripotent stem cell is an ES cell, or an iPS cell, or a partial iPS cell (piPSC), an adult stem cell, or a stem cell produced by reprogramming a somatic stem cell to an earlier developmental state.

Another aspect of the present invention relates to a kit comprising an array as disclosed herein, and reagents to carry out amplification of the mRNA of the early developmental genes.

Another aspect of the present invention relates to use of an array as disclosed herein for characterizing the differentiation potential of a stem cell line, e.g., a pluripotent stem cell according to an assay as disclosed herein.

In some embodiments, the invention as disclosed herein is useful for screening a compound for an effect on the expression level of at least one early developmental gene selected from the group listed in Table 1 and/or Table 2. In some embodiments, such a screening comprises the steps of (i) contacting a pluripotent stem cell with a test compound for a pre-determined amount of time; (ii) performing the assay as disclosed herein; and (iii) determining an increase or decrease on the expression level of at least one early developmental gene in the presence of the compound as compared to the absence of the compound. In some embodiments, a test compound can be selected from the group consisting of a small organic molecule, a small inorganic molecule, a polysaccharide, a peptide, a protein, a nucleic acid, an extract made from biological materials such as bacteria, plants, fungi, animal cells, animal tissues, or any combination thereof. In some embodiments, a test compound is tested at concentrations in the range of about 0.01 nM to about 1000 mM. In some embodiments, the screening method is configured to be compatible with a high-throughput screening method.

The inventors have also demonstrated that the analyses of the gene expression of a set of early developmental genes can be used to provide a "lineage scorecard" that can be used to predict the differentiation propensities, pluripotency and utility of any stem cell line. In particular, the inventors have demonstrated that the gene expression of a set of early developmental genes from a plurality of pluripotent stem cell populations provide a reference level for the normal variation of early developmental gene expression levels among a variety of different pluripotent cell lines, which can be used to compare the gene expression levels of the same early developmental genes from a test stem cell line to permit one to predict the behavior (e.g., differentiation propensity and pluripotency) of the individual test stem cell population. Such a lineage scorecard therefore also provides a platform for systematic comparison between different classes of pluripotent stem cells, (e.g., ES cells versus iPS cells, or iPS cells versus partially induced iPS cells and other pluripotent or non-pluripotent stem cell lines and the like). Accordingly, the inventors demonstrate that use of datasets, or a standard or reference lineage scorecard and bioinformatics data tools permit high-throughput characterization of the differentiation propensity and pluripotency of human stem cell lines, e.g., pluripotent stem cell lines, such as iPS cells lines and embryonic cell lines.

Accordingly, another aspect of the present invention relates to a set of reference data or reference lineage scorecard, which refer to the average data or otherwise aggregated data of the expression of a set of early developmental genes from a number of different pluripotent stem cell lines. The reference data which constitute a "lineage scorecard" can be used by one of ordinary skill in the art to compare, for example using a computer algorithm or software, a stem cell line of interest to a normal, well-functioning stem cell or a known set of pluripotent stem cells. The comparison with the reference "lineage scorecard" can be used to effectively and accurately predict the utility of the stem cell line for a given application, as well as any specific characteristics (e.g., differentiation propensity and/or pluripotency) of the stem cell line of interest, e.g., an ES cell or iPS cell line etc.

In some embodiments, the lineage scorecard comprises a data set of gene expression for a range of early developmental genes (e.g., a subset or any combination of the genes listed in Table 1) from at least 5 stem cell populations to determine the differentiation propensity and pluripotency of the stem cell line to differentiate along ectoderm, mesoderm and endoderm lineages. In some embodiments, the data of the expression of the early developmental genes are connected to a data storage device, such as a data storage device which is a database located on a computer device.

Accordingly, another aspect of the present invention relates to a lineage scorecard of the differentiation potential and pluripotency of a stem cell line, e.g., a pluripotent stem cell line, the scorecard comprising a data set of the expression level of a plurality of early developmental genes from a plurality of stem cell lines.

In some embodiments, the lineage scorecard comprises a data set of the expression levels a plurality of early developmental genes selected from at least 10, or at least about 20, or at least about 30, or 30-60, or 60-90 or more than 90 early developmental genes selected from those listed in Table 1. In some embodiments, the lineage scorecard comprises a data set of the expression levels a plurality of early developmental genes selected from at least one pluripotent stem cell gene, at least one early mesoderm developmental gene, at least one ectoderm developmental gene, and at least one endoderm developmental gene selected from Table 1 and/or from Table 2. In some embodiments, the lineage scorecard comprises a data set of the expression levels a plurality of early developmental genes selected from at least 4 pluripotent stem cell genes, at least 4 early mesoderm developmental genes, at least 4 ectoderm developmental genes, and at least 4 endoderm developmental genes selected from Table 1.

In some embodiments, the data set of the expression levels of a plurality of early developmental genes are connected to a storage device, and the storage device is a database located on a computer.

In some embodiments, at least 5, or at least about 10, or at least about 15 reference pluripotent stem cell lines are used to generate an early developmental gene expression data set for the reference lineage scorecard. In some embodiments, an early developmental gene expression data set is obtained from at least 5 or more, or at least 6, or at least 7, or at least 8, or at least 9, or at least 10, or at least 11, or at least 12, or at least 13 or at least 14, or at least 15, or at least 16, or at least 17, or at least 18, or all 19 of the following reference pluripotent stem cells lines selected from the group; HUES64, HUES3, HUES8, HUES53, HUES28, HUES49, HUES9, HUES48, HUES45, HUES1, HUES44, HUES6, H1, HUES62, HUES65, H7, HUES13, HUES63, HUES66.

In some embodiments, the pluripotent stem cell populations used to generate an early developmental gene expression data set for a reference lineage scorecard are mammalian pluripotent stem cell populations, such as human pluripotent stem cell populations, or induced pluripotent stem (iPS) cell populations, or embryonic stem cell populations, or adult stem cell populations, or autologous stem cell populations, or embryonic stem (ES) stem cell populations.

In some embodiments, the lineage scorecard as disclosed herein can be used to validate and/or predict the behavior (e.g., differentiation propensity and/or pluripotency) of a stem cell line, e.g., a pluripotent stem cell population by predicting the optimal differentiation along a specific lineage and/or propensity to have undesirable characteristic, e.g., stem cell populations which have a predisposition to develop along lineages not desired by the investigator. Thus, in some embodiments, the lineage scorecard can be used in methods for, e.g., positive selection of a stem cell population with desirable characteristics (e.g., high differentiation potential along a specific lineage and/or pluripotent characteristics), and/or to negatively select cells (and optionally discard) stem cell lines with undesirable characteristics, e.g., stem cells with a predisposition to develop along lineages not desired by the investigator, or non-pluripotent stem cell lines.

In some embodiments, the lineage scorecard report provides an indication of suitable uses or applications for the pluripotent stem cell population, or in alternative embodiments, provide an indication of uses or applications that the pluripotent stem cell line is not suitable for.

Another aspect of the present invention relates to a method for generating a lineage score card comprising measuring the gene expression of a set of early differentiation genes in a plurality of pluripotent stem cell lines. In some embodiments, the method to generate a pluripotent stem cell score card can be used to generate a scorecard comprising the values of normal variations of the levels of gene expression of a set of early developmental genes from a plurality of pluripotent stem cell lines, for example, at least 5, or at least 6, or at least 7, or at least 8, or at least 9, or at least 10, or at least 15, or at least 20, or at least 30, or at least 40 or more than 40 different pluripotent stem cell populations.

Another aspect of the present invention relates to a method for selecting or choosing a stem cell line, e.g., a pluripotent stem cell population, comprising measuring the gene expression of a set of early developmental genes in a stem cell population and comparing the early developmental gene expression data with reference data for early developmental gene expression, and selecting a stem cell line which does not differ by a statistically significant amount in the expression of the early developmental genes expressed and thus in the stem cells' ability to differentiate along mesoderm, ectoderm and endoderm lineages as compared to a reference differentiation potential or reference pluripotent stem cell line. In some embodiments, a stem cell line is not selected if it differs by a statistically significant amount to the expression in the early developmental genes expressed and thus differs in its ability to differentiate along mesoderm, ectoderm and endoderm lineages as compared to a reference differentiation potential of a reference pluripotent stem cell line. In some embodiments, a stem cell line is also selected if it differs by a statistically significant amount to the expression in the early developmental genes expressed and thus identifies the stem cell line as one which is capable of differentiating along a desired cell lineage selected from: mesoderm, ectoderm and endoderm lineages, and can be selected based on it's propensity to differentiate along a particular lineage desired by the user.

Another aspect of the present invention relates to a computer system for generating a lineage scorecard of a pluripotent stem cell, comprising; (a) at least one memory containing at least one program comprising the steps of: (i) receiving gene expression data of a set of early developmental genes in the pluripotent stem cell line and comparing the expression data with a reference level of the same set of early developmental genes; (ii) generating a lineage scorecard based on the comparison of the expression of the early developmental genes as compared to reference levels of the same early developmental genes; and (b) a processor for running said program.

In some embodiments, the system further comprises an output or report-generating module for generating a stem cell lineage scorecard report based on the expression of the early developmental gene expression data set obtained from the test stem cell line. In some embodiments, the system comprises a memory, where the memory further comprises a database. In some embodiments, the database arranges the early developmental gene expression data set in a hierarchical manner, for example, where the database arranges the propensity of differentiation of the pluripotent stem cell of interest into different lineages in a hierarchical manner. In some embodiments, the memory of the system is connected to the first computer via a network, for example, a wide area network, or a world-wide network.

Another aspect of the present invention relates to a computer readable medium comprising instructions for generating a lineage scorecard of a test stem cell line, e.g., a pluripotent stem cell line, comprising: (i) receiving an early developmental gene expression data set from the test stem cell line and performing a comparison of the early developmental gene expression data set with a reference levels of the early developmental genes; (ii) generating a lineage scorecard based on the comparison of the early developmental gene expression data set as compared to reference levels of the early developmental genes.

Accordingly, another aspect of the present invention relates to a reference database comprising a lineage scorecard as disclosed herein. Another aspect of the present invention relates to a computer readable storage media comprising a reference database as disclosed herein. In some embodiments the computer readable storage medium is tangible, non-transitory storage media, for example, any available tangible or physical media that can be accessed by a computer. Computer readable medium do not encompass a signal, such as a carrier signal.

Another aspect of the present invention relates to a computer-readable, physical memory comprising computer-executable instructions for calculating the ΔCt for each early developmental gene measured, and wherein the ΔCt value of each early developmental gene is compared to the ΔCt value for each early developmental gene from a data pool that contains reference ΔCt values for each early developmental genes from a plurality of reference pluripotent stem cells, to provide a ΔΔCt value.

In some embodiments, the computer readable instructions enable calculation of the average ΔCt for the genes in each of the mesoderm, ectoderm and endoderm early developmental gene subgroups, and comparing the average ΔCt value of the genes in each of the mesoderm, ectoderm and endoderm early developmental gene subgroups with the average ΔCt value of the same genes in each of the mesoderm, ectoderm and endoderm early developmental gene subgroups from a data pool that contains reference average ΔCt values for the same genes in the mesoderm, ectoderm and endoderm early developmental gene subgroups from a plurality of reference pluripotent stem cells, to provide an average ΔΔCt value.

In some embodiments, the computer readable instructions further comprises instructions to perform a t-test to identify statistically significant ΔΔCt values from the comparison of the average ΔCt value of the genes in each of the mesoderm, ectoderm and endoderm early developmental gene subgroups as compared to average reference ΔCt value for genes in each of the mesoderm, ectoderm and endoderm early developmental gene subgroups from a plurality of reference pluripotent stem cells in the data pool.

In some embodiments, the gene expression of a set of early developmental genes is measured using RT-PCR, e.g., an RT-PCR assay comprising primers specific for a set of genes listed in Table 1 or at least 3 genes from Table 2. In some embodiments, the RT-PCR assay uses an array comprising primers for performing RT-PCR to amplify the mRNA of a set of early developmental genes from Table 1 and optionally can comprise primers for amplifying the mRNA of at least 3 early developmental genes from Table 2.

In some embodiments, the gene expression of a set of early developmental genes is measured using a microarray assay. In some embodiments, the RT-PCR array or microarray comprises a set of early developmental genes for analysis selected from at least about 20, or at least 30, or at least 40 selected from a subset of any combination of the genes listed in Table 1. In some embodiments, the RT-PCR array or microarray comprises a set of early developmental genes for analysis selected from at least about 3 or more genes from a subset of any combination of the genes listed in Table 2. In some embodiments, gene expression of a set of early developmental genes is determined using an RT-PCR array or microarray from a pluripotent stem cell line at about 2 days in culture (e.g., 2 days EB).

In some embodiments, the differentiation assay as disclosed herein is a high-throughput assay for assaying a plurality of different pluripotent stem cells, for example, permitting one to measure and assess the level of gene expression of a set of early developmental genes in a plurality of different induced pluripotent stem cells, wherein the stem cells are derived by reprogramming a somatic cell obtained from the same or a different subject, e.g., a mammalian subject or a human subject.

In some embodiments, measuring the gene expression of a set of early developmental genes in a stem cell line as disclosed herein can be used to identify and/or optimize and/or validate a differentiating media and/or differentiation factors which can increase the efficiency of a stem cell line to differentiate along a particular cell-type lineage. By way of an exemplary example only, in some embodiments, the arrays, assays and methods as disclosed herein can be used to confirm that mesoderm early developmental markers as disclosed herein are being expressed in a stem cell line cultured in a mesoderm induction medium. Alternatively, in some embodiments, the arrays, assays and methods as disclosed herein can be used to confirm that a pluripotent stem cell media maintains a stem cell line in a pluripotent state and does not induce the cell line to differentiate along a particular lineage.

Measurement of the gene expression of a set of early developmental genes can be performed using an array or assay which is configured for high-throughput analysis, for example using multiplex qRT-PCR and high-throughput sample processing for the rapid characterization of the differentiation propensity of hundreds or thousands of pluripotent stem cell lines (e.g., ES and/or iPS cell lines). For example, such a high-throughput array would be useful where it is desirable to characterize 100's and 1000's of stem cell lines in high-throughput centers. For example, this would be useful to identify and choose stem cell lines for utility in drug screening and/or for therapeutic use. Accordingly, the measurement of the expression of a set of early developmental genes as disclosed herein allow rapid and inexpensive characterization of large numbers of stem cell lines which would be highly expensive and impractical using traditional teratoma and/or other gene expression systems whereby the stem cells are required to undergo spontaneous or directed differentiation for a period of time prior to analysis. Alternatively, measurement of the expression of a set of early developmental genes as disclosed herein can be used on individual pluripotent stem cell lines to accelerate research and select those lines with desired lineage propensities to be used in research to address a research question of interest. For example, the expression of a set of early developmental genes as disclosed herein can be assessed in a stem cell line, e.g., a pluripotent stem cell line, as early as 2 days in EB in order to quickly identify the most suitable stem cell line (e.g., with the desired pluripotency and/or differentiation propensities) for further analysis or to address a research question of interest.

Another aspect of the present invention relates to a kit for measuring the gene expression of a set of early developmental genes, comprising reagents (e.g., oligonucleotide probes and/or primers and other reagents) necessary for measuring gene expression levels of a plurality of early developmental genes, e.g., a subset of any combination of the genes listed in Table 1 and/or Table 2. In some embodiments, the kit further comprises a lineage score card as disclosed herein. In some embodiments, the kit further comprises instructions for use. In some embodiments, the kit comprises a computer readable medium comprising instructions on a computer to compare the measured levels of the early developmental genes from the test stem cell line with reference levels of the same genes. In some embodiments, the kit comprises instructions to access to a software program available online (e.g., on a cloud) to compare the measured levels of the early developmental genes from the test stem cell line, e.g., pluripotent stem cell line, with reference levels of the same genes from reference pluripotent stem cell lines.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIGS. 1A-1D show prior art methods disclosed in WO2012/037456, which is incorporated herein in its entirety by reference, in which cell-line specific differentiation propensities can be measured by a quantitative EB assay. FIG. 1A shows a schematic outline of a prior art assay for quantifying cell-line specific differentiation propensities. The cell lines need to be differentiated for at least 7- to 14-days in culture before measuring lineage markers. Furthermore, the lineage markers were not early developmental genes. FIG. 1B shows a prior art lineage scorecard summarizing cell-line specific differentiation propensities of a set of low-passage human ES cell lines. The numbers indicate relative enrichment (positive values) or depletion (negative values) on a linear scale. They were calculated by performing moderated t-tests comparing all biological replicates for a given ES cell line to the ES-cell reference (consisting of biological replicates for all other ES cell lines), followed by a gene set enrichment analysis for sets of markers genes with relevance for the cellular lineage or germ layer of interest. All columns are centered on zero, such that an ES cell line will exhibit differentiation propensities of zero if it differentiates just like the average of all other ES cell lines that were used to calibrate the assay. Values should be interpreted relative to each other, with higher numbers indicating higher differentiation propensities and lower values indicating lower differentiation propensities, while the absolute values have no measurement unit and no direct biological interpretation. FIG. 1C shows prior art of a two-dimensional multidimensional scaling map of the transcriptional similarity of ES and iPS cell lines, ES-derived and iPS-derived EBs, and primary fibroblast cell lines. Gene expression of 500 lineage marker genes was measured using the nCounter system, and the normalized data were projected onto a plane such that the distance of the points to each other represents their distance in the 500-dimensional space of gene expression levels. Each point corresponds to a single biological replicate, and the projection was performed using multidimensional scaling. Two iPS cell lines were significantly impaired in their ability to form normal EBs (hiPS 15b, hiPS 29e, highlighted by an arrow and labeled as "impaired EBs"), and one iPS cell line completely failed to form normal EBs (hiPS 27e, highlighted by an arrow and labeled "failed EBs"), maintaining a gene expression profile that is reminiscent of pluripotent cells even after 16-day EB differentiation. All biological replicates of these three cell lines are highlighted by arrows, and all three cell lines also exhibit significantly reduced differentiation propensities according to the lineage scorecard (FIG. 1D). FIG. 1D shows a prior art lineage scorecard summarizing cell-line specific differentiation propensities of a set of human iPS cell lines. The scorecard was derived as described for FIG. 1B and normalized against the ES-cell reference. The scores were calculated across all biological replicates that were available fore each cell line. This scorecard required (i) pluripotent stem cells to be cultured for at least 7 or 14-days in culture, (ii) directed differentiation of the stem cell down a particular lineage, (iii) analysis of ~500 lineage markers and (iv) the gene expression analysis to be performed in replicates (e.g., duplicate or triplicate).

FIG. 2A shows that the PluriTest analysis of MicroArray data fails to distinguish Day 7 differentiated cells from undifferentiated cells and is limiting in just pluripotency assessment and not differentiation status. FIG. 2B shows that the lineage ScoreCard analysis of a focused set of 96 genes shows clear downregulation of pluripotent genes and upregulation of the differentiation genes classified into the three germ layers thus permitting assessment of both pluripotency as well as trilineage differentiation potential.

FIG. 3 is a comparison of the mean measured early developmental genes with the reference level expression levels. For each input sample (e.g., BJ fibroblasts, H9 ESCs and hNSC), and for each of six categories of early developmental genes (control, pluri, endo, mesendo, meso, ecto) the software reports mean (mu) and standard deviation of t-statistic (significance) and min and max p-value over the gene category.

FIG. 4 shows the expression levels of each category of early developmental gene relative to a reference standard for each category of early developmental genes. Using t-value as an indicator, a t-value of 0-1 indicates that the measured level of gene expression in that early developmental gene category is comparable with the reference gene expression level in the same category. A t-value of >1 indicates that the measured gene expression level in that early developmental gene category of the pluripotent cell line is higher than the reference gene expression level in the same category. A t-value of <0 indicates that the measured gene expression level in that early developmental gene category of the pluripotent cell line is lower than the reference gene expression level in the same category.

FIG. 5 shows pluripotent stem cells cultured at 2 and 4 days produce reliable results for levels of expression of each category of early developmental gene.

FIG. 6 shows that the expression of the early developmental genes of D4 and D7 is not affected if the pluripotent stem cells are cultured in an embryoid (EB) suspension or in a monolayer.

FIGS. 7A-7C show that the differentiation assay can identify outlier pluripotent stem cells, e.g., cell lines which are no-longer pluripotent, stem cell lines with an increased efficiency to differentiate along a particular cell lineage and/or pluripotent stem cells contaminated with mouse (e.g., MEF) cells. FIG. 7A shows an embodiment of a lineage scorecard to identify a bad clone or culture (e.g., BS4-iPS5 P8), when the pluripotent stem cell is compared to similar pluripotent stem cells lines at the same time point. FIG. 7B shows an embodiment of a lineage scorecard to identify a stem cell line which has a predisposition to differentiate along a particular lineage, showing that the hNSDup cell line has increased ectoderm levels indicating the cell line has a predisposition to differentiate along an ectoderm lineage. FIG. 7C shows an embodiment of a lineage scorecard to identify a stem cell line which is no longer pluripotent (e.g., see BJ fibroblasts and HJF fetal cells) which have a significant decrease in pluripotent genes, and that the contamination of a stem cell line with MEF has no effect on the expression levels of early developmental genes.

DETAILED DESCRIPTION OF THE INVENTION

Figure 1A:
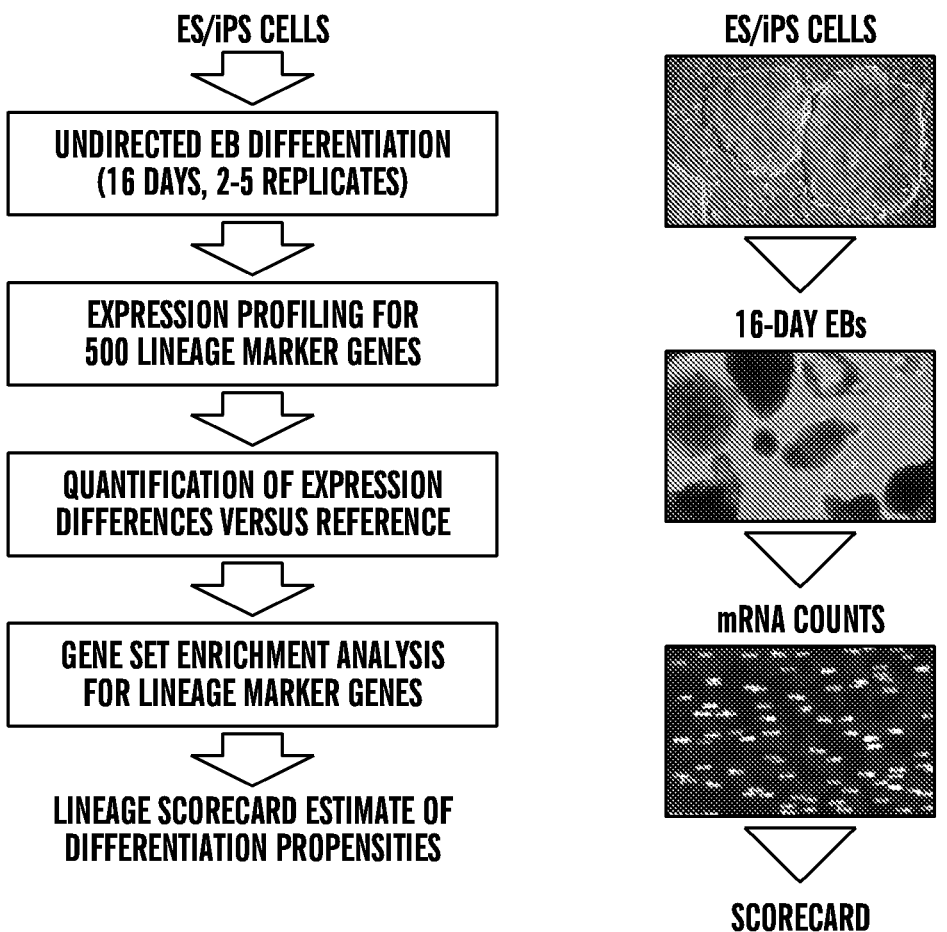
Figure 1C:
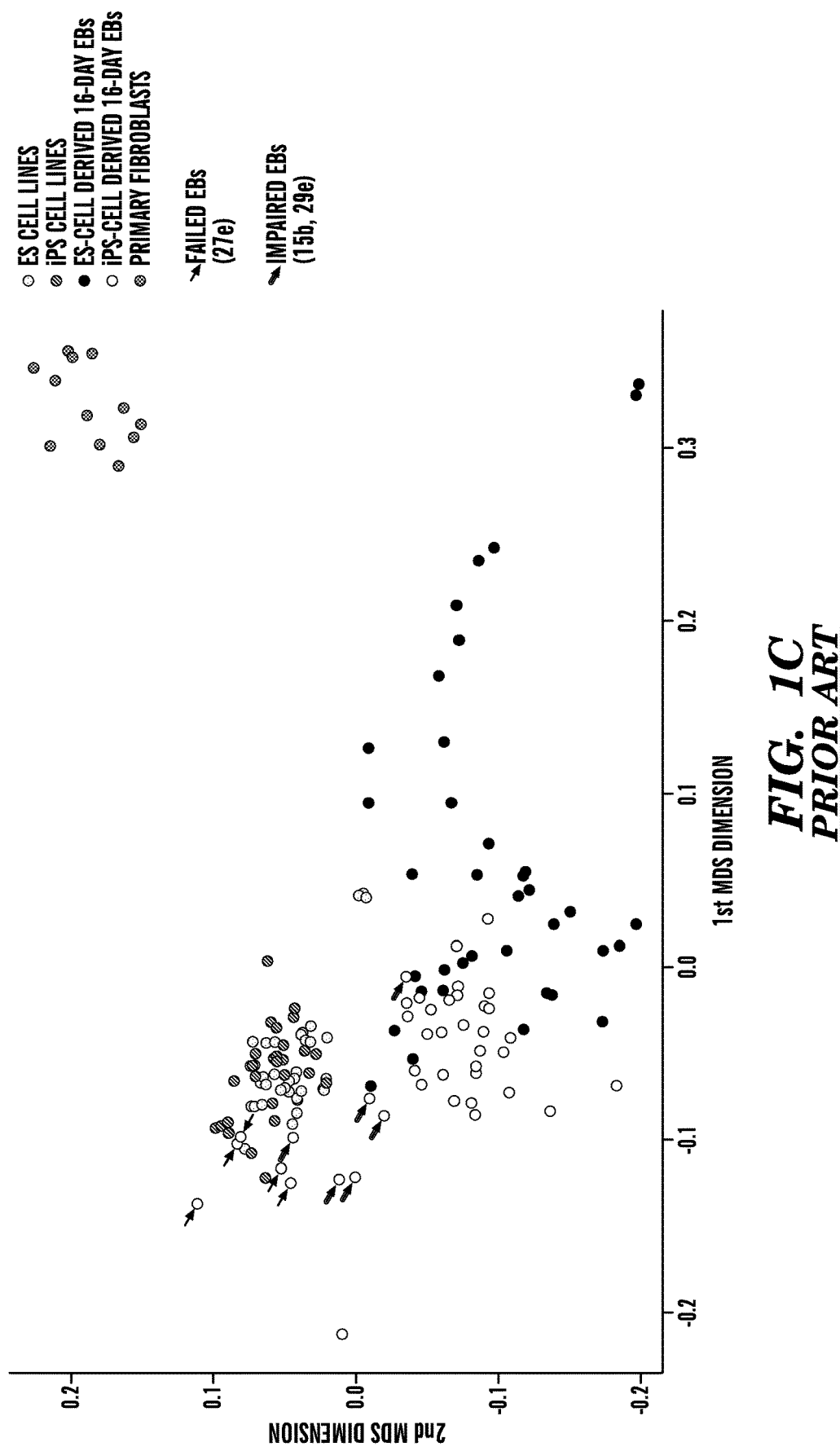
Figure 1D:

The present invention is directed a set of early developmental gene biomarkers, or subsets thereof, which can be used to characterize and determine the pluripotency and/or differentiation potential of a stem cell population. Aspects of the present invention relate to arrays, assays, systems, kits and methods to rapidly and inexpensively screen stem cell lines for their general quality (e.g., pluripotent capacity) and differentiation capacity.

As disclosed herein in the Examples, the inventors have surprisingly discovered that the expression of a subset of genes which are expressed in very early stages of development, herein referred to as "early developmental genes" can accurately predict if the stem cell line is pluripotent, and/or if the stem cell line has a propensity to differentiate along mesoderm, ectoderm and endoderm lineages, and/or if there is a favorable lineage that the stem cell line differentiates along. Thus, the set of early developmental genes disclosed herein provides meaningful insight into the cells' likely developmental and differentiation pathways at a very early stage of development, e.g., from about 2 days in EB culture conditions.

For example, by measuring the gene expression of a set of early developmental genes in a stem cell line, e.g., a pluripotent stem cell line as disclosed herein, one is able to forecast the differentiation efficiency of the stem cell line being analyzed. For example, the inventors have demonstrated that the levels of these genes are highly predictive for determining the likely direction of the differentiation of the stem cell line along particular lineages, e.g., mesoderm, ectoderm and endoderm lineages. Therefore, the present invention as disclosed herein has broad utility and can be used to prospectively predict how well a given stem cell will differentiate along any desired lineage, for example, hematopoietic lineage, endoderm lineage, pancreatic lineage, neuronal lineage such as a motor neuron lineage and the like.

Accordingly, the present invention generally relates to arrays, assays, methods, kits and systems for measuring a set of early developmental genes in a stem cell line, e.g., a pluripotent stem cell line, to predict the differentiation potential and/or pluripotency of the stem cell line. The present invention also relates to a reference database of the expression of a set of early developmental genes to produce a "lineage scorecard" for a stem cell line, where the gene expression of such a set of early developmental genes can predict the functionality and suitability of a stem cell line for a desired use, and can predict if the stem cell line will differentiate along a particular cell lineage, or differentiate with an increased efficiency along a particular cell lineage, such as neural stem cell, hematopoietic stem cell, pancreatic stem cell and other lineages. In some embodiments, a lineage scorecard further provides guidelines to determine if a stem cell line, e.g., a pluripotent stem cell of interest, falls within normal parameters of normal pluripotent stem cell variation and/or has a propensity to differentiate along a specific cell lineage. Such guidelines are preferably in a computer executable format.

In some embodiments, a lineage scorecard is a scorecard compiled from the expression data of a set of early developmental genes from a plurality of different pluripotent stem cells with desirable characteristics, for example, a pluripotent stem cell with propensity to differentiate into endoderm lineages, such as pancreatic lineages and the like, or other lineages, such as, for example, ectoderm or mesoderm lineages.

Another aspect of the present invention relates to a method for generating a lineage scorecard comprising performing a gene expression assay to predict the functionality and suitability of a stem cell line, e.g., a pluripotent stem cell line for a desired use. In some embodiments, a lineage scorecard reference data can be compared with the test stem cells' data to effectively and accurately predict the utility of the test stem cell line for a given application, as well as to identify specific characteristics of the stem cell line to determine their suitability for downstream applications, such as their suitability for therapeutic use, drug screening and toxicity assays, differentiation into a desired cell lineage, and the like.

In some embodiments, the gene expression of a set of early developmental genes measured in the methods, arrays, assays, kits and systems as disclosed herein includes at least 10, or at least 20 genes selected from any combination of the genes listed in Table 1. In some embodiments, the set of early developmental genes measured in the methods, arrays, assays, kits and systems as disclosed herein include at least 3 genes from any combination of the genes listed in Table 2.

In some embodiments, the differentiation assays, methods, systems and kits as disclosed herein can be used to characterize and determine the differentiation potential of a variety of stem cell lines, e.g., a pluripotent stem cell lines, such as, but not limited to embryonic stem cells, adult stem cells, autologous adult stem cells, iPS cells, and other pluripotent stem cell lines, such as reprogrammed cells, direct reprogrammed cells or partially reprogrammed cells. In some embodiments, a stem cell line is a human stem cell line. In some embodiments, a stem cell line, e.g., a pluripotent stem cell line is a genetically modified stem cell line. In some embodiments, where the stem cell line, e.g., a pluripotent stem cell line is for therapeutic use or for transplantation into a subject, a stem cell line is an autologous stem cell line, e.g., derived from a subject to which a population of stem cells will be transplanted back into, and in alternative embodiments, a stem cell line, e.g., a pluripotent stem cell line is an allogeneic pluripotent stem cell line.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "lineage scorecard" as disclosed herein refers to a listing of a summary of the gene expression differences of a plurality of early developmental genes in each category (e.g., pluripotent genes, early endoderm genes, early mesoderm genes, early ectoderm genes) in one or more pluripotent stem cell lines of interest as compared to a reference pluripotent stem cell line, and functions as record of the pluripotent stem cell's predicted performance, for example, differentiation ability and/or pluripotency capacity. A scorecard can exist in any form, for example, in a database, a written form, an electronic form and the like, and can be electronically or digitally recorded and stored in annotated databases. In some embodiments, a scorecard can be a graphical representation of a prediction of the pluripotent stem cell capabilities (e.g., differentiation capabilities, pluripotency etc.) as compared to a reference pluripotent cell line or plurality of lines. Accordingly, the scorecards as disclosed herein serve as an indicator or listing of the characteristics and potential of a pluripotent stem cell line and can be used to assist in fast and efficient selection of a particular pluripotent stem cell line for a particular use and/or to reach a specific objective.

The term "nucleic acid" or "nucleic acid sequence" as used herein is defined as a molecule comprised of two or more deoxyribonucleotides or ribonucleotides. The exact length of the sequence will depend on many factors, which in turn depends on the ultimate function or use of the sequence. The sequence can be generated in any manner, including chemical synthesis, DNA replication, reverse transcription, or a combination thereof. Due to the amplifying nature of the present invention, the number of deoxyribonucleotide or ribonucleotide bases within a nucleic acid sequence can be virtually unlimited. The term "oligonucleotide," as used herein, is interchangeably synonymous with the term "nucleic acid sequence".

As used herein, oligonucleotide sequences that are complementary to one or more of the genes described herein, refers to oligonucleotides that are capable of hybridizing under stringent conditions to at least part of the nucleotide sequence of said genes. Such hybridizable oligonucleotides will typically exhibit at least about 75% sequence identity at the nucleotide level to said genes, preferably about 80% or 85% sequence identity or more preferably about 90% or 95% or more sequence identity to said genes.

The term "primer" as used herein refers to a sequence of nucleic acid which is complementary or substantially complementary to a portion of the target early developmental gene of interest. Typically 2 primers (e.g., a 3' primer and a 5' primer) are complementary to different portions of the target early developmental gene of interest and can be used to amplify a portion of the mRNA of the early developmental gene by RT-PCR.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to" refers to the binding, duplexing or hybridizing of a molecule substantially to or only to a particular nucleotide sequence or sequences under stringent conditions when that sequence is present in a complex mixture (e.g., total cellular) DNA or RNA.

The term "biomarker" means any gene, protein, or an EST derived from that gene, the expression or level of which changes between certain conditions. Where the expression of the gene correlates with a certain condition, the gene is a biomarker for that condition.

"Biomarker-derived polynucleotides" means the RNA transcribed from a biomarker gene, any cDNA or cRNA produced therefrom, and any nucleic acid derived therefrom, such as synthetic nucleic acid having a sequence derived from the gene corresponding to the biomarker gene.

As used herein, the term "gene" has its meaning as understood in the art. However, it will be appreciated by those of ordinary skill in the art that the term "gene" can include gene regulatory sequences (e.g., promoters, enhancers, etc.) and/or intron sequences. It will further be appreciated that definitions of gene include references to nucleic acids that do not encode proteins but rather encode functional RNA molecules such as tRNAs. For clarity, the term gene generally refers to a portion of a nucleic acid that encodes a protein; the term can optionally encompass regulatory sequences. This definition is not intended to exclude application of the term "gene" to non-protein coding expression units but rather to clarify that, in most cases, the term as used in this document refers to a protein coding nucleic acid. In some cases, the gene includes regulatory sequences involved in transcription, or message production or composition. In other embodiments, the gene comprises transcribed sequences that encode for a protein, polypeptide or peptide. In keeping with the terminology described herein, an "isolated gene" can comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof.

The term "signature" as used herein refers to the differential expression pattern. It could be expressed as the number of individual unique probes whose expression is detected when a cRNA product is used in microarray analysis. It could also be expressed as the number of individual genes whose expression is detected with real time RT-PCR. A signature can be exemplified by a particular set of biomarkers.

The term a "similarity value" is a number that represents the degree of similarity between two things being compared. For example, a similarity value can be a number that indicates the overall similarity between a cell sample expression profile using specific phenotype-related biomarkers and a control specific to that template. The similarity value can be expressed as a similarity metric, such as a correlation coefficient, or a classification probability or can simply be expressed as the expression level difference, or the aggregate of the expression level differences, between a cell sample expression profile and a baseline template.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

As used herein, the terms "measuring expression levels," "obtaining expression level," and "detecting an expression level" and the like, includes methods that quantify a gene expression level of, for example, a transcript of a gene, or a protein encoded by a gene, as well as methods that determine whether a gene of interest is expressed at all. In some embodiments, the assay provides an indicator if the pluripotent stem cell can differentiate along a particular lineage, e.g., mesoderm, ectoderm or endoderm lineage. In some embodiments, the indicator is a numerical value (e.g., the value from a t-test from the comparison of the average ΔCt for each of the measured mesoderm, or ectoderm or endoderm early developmental genes in the pluripotent stem cell as compared to reference ΔCt of the same genes in a reference set of pluripotent stem cells, as disclosed herein in the Examples). In some embodiments, the assay can provide a "yes" or "no" result without necessarily providing quantification, indicating that the pluripotent can or cannot, respectively, differentiate along each of the mesoderm, ectoderm or endoderm lineages, or "yes" or "no" to indicate that the stem cell line tested is or is not pluripotent, respectively. Alternatively, a measured or obtained expression level can be expressed as any quantitative value, for example, a fold-change in expression, up or down, relative to a control gene or relative to the same gene in another sample, or a log ratio of expression, or any visual representation thereof, such as, for example, a "heatmap" where a color intensity is representative of the amount of gene expression detected. For example, in some embodiments, the assay can provide a heat map, with green indicator signals that pluripotent stem cell has a high propensity or likelihood of differentiating along a particular lineage (e.g., each of the mesoderm, ectoderm or endoderm lineages), a yellow indicator to signal that pluripotent stem cell has the ability to differentiate along a particular lineage and a red indicator to signal that pluripotent stem cell has a low propensity, or cannot differentiate along a particular lineage. In some embodiments, there is an indicator for each of: the pluripotency of the stem cell, the stem cell ability to differentiate along mesoderm lineage, the stem cells' ability to differentiate along a ectoderm lineage and a the stem cells' ability to differentiate along a endoderm lineage. The early developmental genes identified as being differentially expressed in the pluripotent stem cell line of interest can be used in a variety of nucleic acid or protein detection assays to detect or quantify the expression level of a gene or multiple genes in a given sample. Exemplary methods for detecting the level of expression of a gene include, but are not limited to, Northern blotting, dot or slot blots, reporter gene matrix (see for example, U.S. Pat. No. 5,569,588) nuclease protection, RT-PCR, microarray profiling, differential display, 2D gel electrophoresis, SELDI-TOF, ICAT, enzyme assay, antibody assay, MNAzyme-based detection methods (see U.S. Ser. No. 61/470,919, US 2011/0143338; US 2007/0231810; WO WO/2008/122084; WO/2007/041774; and Mokany et al., J Am Chem Soc. 2010 Jan. 27; 132(3): 1051-1059, each of which is incorporated by reference in its entirety), and the like. Optionally a gene whose level of expression is to be detected can be amplified, for example by methods that can include one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR). In the preferred embodiment gene expression will be detected by RT-PCR, preferably using SYBR green.

The term "gene profile" as used herein is intended to refer to the expression level of a gene, or a set of genes, in a pluripotent stem cell sample. In one embodiment of the invention the term "gene profile" refers to the expression levels or status of a gene or a set of genes listed in Table 1 or to that of any selection of the genes of Table 1, which are described herein.

The term "differential expression" in the context of the present invention means the gene is upregulated or down-regulated in comparison to its normal variation of expression in a pluripotent stem cell. Statistical methods for calculating differential expression of genes are discussed elsewhere herein.

"Genes of Table 1" is used interchangeably herein with "gene listed in Table 1" and refers to the gene products of genes listed under "Early Developmental genes" in Table 1. By "gene product" is meant any product of transcription or translation of the genes, whether produced by natural or artificial means. In some embodiments of the invention, the genes referred to herein are those listed in Table 1. The same applies to "genes of Table 2", but refers to the gene products of genes listed under early developmental genes in Table 2.

The term "hybridization" or "hybridizes" as used herein involves the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA, 46:453 (1960) and Doty et al., Proc. Natl. Acad. Sci. USA, 46:461 (1960) have been followed by the refinement of this process into an essential tool of modern biology.

The terms "complementary" or "substantially complementary" as used herein refer to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity. See M. Kanehisa, Nucleic Acids Res., 12:203 (1984), incorporated herein by reference. The term "at least a portion of" as used herein, refers to the complimentarity between a circular DNA template and an oligonucleotide primer of at least one base pair.

Partially complementary sequences will hybridize under low stringency conditions. This is not to say that conditions of low stringency are such that non-specific binding is permitted; low stringency conditions require that the binding of two sequences to one another be a specific (i.e., selective) interaction. The absence of non-specific binding can be tested by the use of a second target which lacks even a partial degree of complementarity (e.g., less than about 30% identity); in the absence of non-specific binding the probe will not hybridize to the second non-complementary target.

The term "stringency" refers to the degree of specificity imposed on a hybridization reaction by the specific conditions used for a reaction. When used in reference to nucleic acid hybridization, stringency typically occurs in a range from about $T_m$–5° C. (5° C. below the $T_m$ of the probe) to about 20° C., 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences. Suitably stringent hybridization conditions for nucleic acid hybridization of a primer or short probe include, e.g., 3×SSC, 0.1% SDS, at 50° C.

When used in reference to nucleic acid hybridization the art knows well that numerous equivalent conditions can be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution can be varied to generate conditions of either low or high stringency hybridization different from, but equivalent to, the above listed conditions.

The term "solid surface" as used herein refers to a material having a rigid or semi-rigid surface. Such materials will preferably take the form of chips, plates (e.g., microtiter plates), slides, small beads, pellets, disks or other convenient forms, although other forms can be used. In some embodiments, at least one surface of the solid surface will be substantially flat. In other embodiments, a roughly spherical shape is preferred.

The term "reprogramming" as used herein refers to a process that alters or reverses the differentiation state of a differentiated cell (e.g. a somatic cell). Stated another way, reprogramming refers to a process of driving the differentiation of a cell backwards to a more undifferentiated or more primitive type of cell. Complete reprogramming involves complete reversal of at least some of the heritable patterns of nucleic acid modification (e.g., methylation), chromatin condensation, epigenetic changes, genomic imprinting, etc., that occur during cellular differentiation as a zygote develops into an adult. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent.

The term "induced pluripotent stem cell" or "iPSC" or "iPS cell" refers to a cell derived from a complete reversion or reprogramming of the differentiation state of a differentiated cell (e.g. a somatic cell). As used herein, an iPSC is fully reprogrammed and is a cell which has undergone complete epigenetic reprogramming. As used herein, an iPSC is a cell which cannot be further reprogrammed to a more immature state (e.g., an iPSC cell is terminally reprogrammed).

The term "pluripotent" as used herein refers to a cell with the capacity, under different conditions, to differentiate to cell types characteristic of all three germ cell layers (endoderm, mesoderm and ectoderm). A pluripotent stem cell typically has the potential to divide in vitro for a long period of time, e.g., greater than one year or more than 30 passages.

The term "differentiated cell" refers to any primary cell that is not, in its native form, pluripotent as that term is defined herein. The term a "differentiated cell" also encompasses cells that are partially differentiated, such as multipotent cells, or cells that are stable non-pluripotent partially reprogrammed cells. It should be noted that placing many primary cells in culture can lead to some loss of fully differentiated characteristics. However, such cells are included in the term differentiated cells and the loss of fully differentiated characteristics does not render these cells non-differentiated cells (e.g. undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

As used herein, the term "adult cell" refers to a cell found throughout the body after embryonic development.

In the context of cell ontogeny, the term "differentiate", or "differentiating" is a relative term meaning a "differentiated cell" is a cell that has progressed further down the developmental pathway than its precursor cell. Thus in some embodiments, a reprogrammed cell as this term is defined herein, can differentiate to lineage-restricted precursor cells (such as a mesodermal stem cell), which in turn can differentiate into other types of precursor cells further down the pathway (such as an tissue specific precursor, for example, a cardiomyocyte precursor), and then to an end-stage differentiated cell, which plays a characteristic role in a certain tissue type, and can or cannot retain the capacity to proliferate further.

The term "embryonic stem cell" is used to refer to the pluripotent stem cells of the inner cell mass of the embryonic blastocyst (see U.S. Pat. Nos. 5,843,780, 6,200,806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "phenotype" refers to one or a number of total biological characteristics that define the cell or organism under a particular set of environmental conditions and factors, regardless of the actual genotype.

The term "cell culture medium" (also referred to herein as a "culture medium" or "medium") as referred to herein is a medium for culturing cells containing nutrients that maintain cell viability and support proliferation. The cell culture medium can contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "self-renewing media" or "self-renewing culture conditions" refers to a medium for culturing stem cells which contains nutrients that allow a stem cell line to propagate in an undifferentiated state. Self-renewing culture media is well known to those of ordinary skill in the art and is ordinarily used for maintenance of stem cells as embroid bodies (EBs), where the stem cells divide and replicate in an undifferentiated state.

The term "cell line" refers to a population of largely or substantially identical cells that has typically been derived from a single ancestor cell or from a defined and/or substantially identical population of ancestor cells. The cell line can have been or can be capable of being maintained in culture for an extended period (e.g., months, years, for an unlimited period of time). Cell lines include all those cell lines recognized in the art as such. It will be appreciated that cells acquire mutations and possibly epigenetic changes over time such that at least some properties of individual cells of a cell line can differ with respect to each other.

The term "lineages" as used herein describes a cell with a common ancestry or cells with a common developmental fate. By way of an example only, stating that a cell that is of endoderm origin or is of "endodermal lineage" means the cell was derived from an endodermal cell and can differentiate along the endodermal lineage restricted pathways, such as one or more developmental lineage pathways which give rise to definitive endoderm cells, which in turn can differentiate into liver cells, thymus, pancreas, lung and intestine.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2 SD) or greater difference in a value of the marker. The term refers to statistical evidence that there is a difference. It is defined as the probability of making a decision to reject the null hypothesis when the null hypothesis is actually true. Statistical significance can be determined by t-test or using a p-value.

As used herein, the term "DNA" is defined as deoxyribonucleic acid.

The term "differentiation" as used herein refers to the cellular development of a cell from a primitive stage towards a more mature (i.e. less primitive) cell.

The term "directed differentiation" as used herein refers to forcing differentiation of a cell from an undifferentiated (e.g. more primitive cell) to a more mature cell type (i.e. less primitive cell) via genetic and/or environmental manipulation. In some embodiments, a reprogrammed cell as disclosed herein is subject to directed differentiation into specific cell types, such as neuronal cell types, muscle cell types and the like.

The term "disease modeling" as used herein refers to the use of laboratory cell culture or animal research to obtain new information about human disease or illness. In some embodiments, a reprogrammed cell produced by the methods as disclosed herein can be used in disease modeling experiments.

The term "drug screening" as used herein refers to the use of cells and tissues in the laboratory to identify drugs with a specific function. In some embodiments, the present invention provides drug screening to identify compounds or drugs which alter (e.g., increase or decrease) the level of expression of a set of early developmental genes, as compared to in the absence of the compound or drug.

The term "marker" as used interchangeably with "biomarker" and describes the characteristics and/or phenotype of a cell. Markers can be used for selection of cells comprising characteristics of interest. Markers will vary with specific cells. Markers are characteristics, whether morphological, functional or biochemical (enzymatic) characteristics of the cell of a particular cell type, or molecules expressed by the cell type. Preferably, such markers are gene transcripts or their translation products (e.g., proteins). However, a marker can consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" can refer to any storage device used for storing data accessible by a computer, as well as any other means for providing access to data by a computer. Examples of a storage-device-type computer-readable medium include, but is not limited to: a magnetic hard disk; a floppy disk; an optical disk, such as a CD-ROM and a DVD; DATs, a USB drive, a magnetic tape; a memory chip. A computer-readable medium is a tangible media not a signal, and does not include carrier waves or other wave forms for data transmission.

The term "software" is used interchangeably herein with "program" and refers to prescribed rules to operate a computer. Examples of software include: software; code segments; instructions; computer programs; and programmed logic.

The term a "computer system" can refer to a system having a computer, where the computer comprises a computer-readable medium embodying software to operate the computer.

The phrase "displaying or outputting" or providing an "indication" of the result of the expression analysis of a set of early developmental genes, or a prediction result, means that the results of a gene expression are communicated to a user using any medium, such as for example, orally, writing, visual display, etc., computer readable medium or computer system. It will be clear to one skilled in the art that outputting the result is not limited to outputting to a user or a linked external component(s), such as a computer system or computer memory, but can alternatively or additionally be outputting to internal components, such as any computer readable medium. It will be clear to one skilled in the art that the various sample classification methods disclosed and claimed herein, can, but need not be, computer-implemented, and that, for example, the displaying or outputting step can be done by, for example, by communicating to a person orally or in writing (e.g., in handwriting).

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following, including the Examples, but the scope of the invention should not be limited thereto.

It is understood that the detailed description and the Examples that follow are illustrative only and are not to be taken as limitations upon the scope of the invention. Various changes and modifications to the disclosed embodiments, which will be apparent to those of skill in the art, can be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. All statements as to the date or representation as to the contents of these documents are based on the information available to the applicants and do not constitute any admission as to the correctness of the dates or contents of these documents.

Early Developmental Genes

One aspect of the present invention relates to measuring the gene expression of a set of early developmental genes to determine the differentiation potential and/or pluripotency of a stem cell line, e.g., a pluripotent stem cell line and/or for the production of a lineage scorecard for characterizing and/or comparing stem cell lines. A "lineage scorecard" is useful as a quantification of the differentiation potential and pluripotency of the stem cell line, e.g., a pluripotent stem cell of interest, and provides information of how efficiently the stem cell line of interest will differentiate into a particular lineage of interest as compared to previously established or reference pluripotent stem cell lines.

Accordingly, further aspects of the present invention provide a method for validating and/or monitoring a stem cell line, e.g., a pluripotent stem cell population, comprising generating a lineage score card of a stem cell line, by monitoring the gene expression of a set of early developmental genes and lineage marker genes, and to identify the characteristics of stem cell line, including predicting which stem cell lines are likely to differentiate along a desired cell lineage and/or which stem cell lines are pluripotent and which are non-pluripotent.

In some embodiments, for example, one can determine the differentiation propensity (or differentiation potential) for a given stem cell line by measuring the differentially expressed early developmental genes, followed by determining changes in gene expression levels of a set of early developmental target genes (e.g., some or a combination of genes listed in Tables 1) as compared to a reference or "standard" pluripotent stem cell line.

TABLE 1

List of early development target genes in each differentiation category (e.g., ectoderm early developmental genes, endoderm early developmental genes, mesoderm early developmental genes, pluripotent developmental genes) for determining the differentiation of a stem cell along a particular lineage as early as 2 days in culture, e.g., in self-renewing culture conditions or media.

| Assay ID/Name | Early Developmental Gene Target | Early Developmental Gene name | SEQ ID NO: | Accession number | Early Developmental gene category |
|---|---|---|---|---|---|
| Hs00940349_m1 | CDH9 | cadherin 9, type 2 (T1-cadherin) | 1 | NM_016279 | Ectoderm |
| Hs00264051_m1 | COL2A1 | collagen, type II, alpha 1 | 2 | NM_001844 | Ectoderm |
| Hs00542612_m1 | DMBX1 | diencephalon/mesencephalon homeobox 1 (OTX3) | 3 | NM_147192 | Ectoderm |
| Hs00609526_m1 | DRD4 | dopamine receptor D4 | 4 | NM_000797 | Ectoderm |
| Hs00154977_m1 | EN1 | engrailed homolog 1 | 5 | NM_001426 | Ectoderm |
| Hs00892663_m1 | LMX1A | LIM homeobox transcription factor 1, alpha | 6 | NM_177399 | Ectoderm |
| Hs00258900_m1 | MAP2 | microtubule-associated protein 2 | 7 | NM_031846 | Ectoderm |
| Hs00928272_m1 | MYO3B | myosin IIIB | 8 | NM_138995 | Ectoderm |
| Hs01075529_m1 | NOS2 | nitric oxide synthase 2A | 9 | NM_153292 | Ectoderm |
| Hs01354342_mH | NR2F1/NR2F2 | nuclear receptor subfamily 2, group F, member 1/member 2 | 10 | NM_005654 | Ectoderm |
| Hs00819630_m1 | NR2F2 | nuclear receptor subfamily 2, group F, member 2 | 11 | NM_021005 | Ectoderm |
| Hs00379238_m1 | OLFM3 | olfactomedin 3 | 12 | NM_058170 | Ectoderm |
| Hs00404545_m1 | PAPLN | papilin, proteoglycan-like sulfated glycoprotein | 13 | NM_173462 | Ectoderm |
| Hs00240950_m1 | PAX3 | paired box gene 3 | 14 | NM_181457 | Ectoderm |
| Hs00240871_m1 | PAX6 | paired box gene 6 | 15 | NM_000280 | Ectoderm |
| Hs00366711_m1 | POU4F1 | POU domain, class 4, transcription factor 1 | 16 | NM_006237 | Ectoderm |
| Hs00925195_m1 | PRKCA | protein kinase C, alpha | 17 | NM_002737 | Ectoderm |
| Hs00299807_m1 | SDC2 | syndecan 2 | 18 | NM_002998 | Ectoderm |
| Hs01057642_s1 | SOX1 | SRY (sex determining region Y)-box 1 | 19 | NM_005986 | Ectoderm |
| Hs00375481_m1 | TRPM8 | transient receptor potential cation channel, subfamily M, member 8 | 20 | NM_024080 | Ectoderm |
| Hs01011247_m1 | WNT1 | wingless-type MMTV integration site family, member 1 | 21 | NM_005430 | Ectoderm |
| Hs00957433_m1 | ZBTB16 | zinc finger and BTB domain containing 16 | 22 | NM_006006 | Ectoderm |
| Hs00173490_m1 | AFP | alpha-fetoprotein | 23 | NM_001134 | Endoderm |
| Hs00418197_m1 | CABP7 | calcium binding protein 7 | 24 | NM_182527 | Endoderm |
| Hs00230412_m1 | CDH2O | cadherin 20, type 2 | 25 | NM_031891 | Endoderm |
| Hs00221623_m1 | CLDN1 | claudin 1 | 26 | NM_021101 | Endoderm |
| Hs00932617_m1 | CPLX2 | complexin 2 | 27 | NM_001008220 | Endoderm |
| Hs00154959_m1 | ELAVL3 | ELAV (embryonic lethal, abnormal vision, *Drosophila*)-like 3 (Hu antigen C) | 28 | NM_032281 | Endoderm |
| Hs00270129_m1 | FOXA1 | forkhead box A1 | 29 | NM_004496 | Endoderm |
| Hs00232764_m1 | FOXA2 | forkhead box A2 | 30 | NM_153675 | Endoderm |
| Hs00362818_m1 | FOXP2 | forkhead box P2 | 31 | NM_014491 | Endoderm |
| Hs00171403_m1 | GATA4 | GATA binding protein 4 | 32 | NM_002052 | Endoderm |
| Hs00232018_m1 | GATA6 | GATA binding protein 6 | 33 | NM_005257 | Endoderm |
| Hs00242160_m1 | HHEX | hematopoietically expressed homeobox | 34 | NM_002729 | Endoderm |
| Hs01004769_m1 | HMP19 | HMP19 protein | 35 | NM_015980 | Endoderm |
| Hs01001602_m1 | HNF1B | transcription factor 2, hepatic (TF2); LF-B3; hepatocyte nuclear factor 1, beta | 36 | NM_000458 | Endoderm |
| Hs00230853_m1 | HNF4A | hepatocyte nuclear factor 4, alpha | 37 | NM_178849 | Endoderm |
| Hs00156145_m1 | KLF5 | Kruppel-like factor 5 (intestinal) | 38 | NM_001730 | Endoderm |

TABLE 1-continued

List of early development target genes in each differentiation category (e.g., ectoderm early developmental genes, endoderm early developmental genes, mesoderm early developmental genes, pluripotent developmental genes) for determining the differentiation of a stem cell along a particular lineage as early as 2 days in culture, e.g., in self-renewing culture conditions or media.

| Assay ID/Name | Early Developmental Gene Target | Early Developmental Gene name | SEQ ID NO: | Accession number | Early Developmental gene category |
|---|---|---|---|---|---|
| Hs00745761_s1 | LEFTY2 | left-right determination factor 2/endometrial bleeding associated factor (EBAF) | 39 | NM_003240 | Endoderm |
| Hs00243679_m1 | PHOX2B | paired-like homeobox 2b, NBPhox, Phox2b | 40 | NM_003924 | Endoderm |
| Hs00275987_s1 | POU3F3 | POU domain, class 3, transcription factor 3 | 41 | NM_006236 | Endoderm |
| Hs00153357_m1 | PRDM1 | PR domain containing 1, with ZNF domain | 42 | NM_182907 | Endoderm |
| Hs00199455_m1 | RXRG | retinoid X receptor, gamma | 43 | NM_006917 | Endoderm |
| Hs00751752_s1 | SOX17 | SRY (sex determining region Y)-box 17 | 44 | NM_022454 | Endoderm |
| Hs00172872_m1 | EOMES | Eomesodermin, T-box brain 2, TBR2 | 45 | NM_005442 | Mesendoderm |
| Hs00999691_m1 | FGF4 | fibroblast growth factor 4 | 46 | NM_002007 | Mesendoderm |
| Hs00220998_m1 | GDF3 | growth differentiation factor 3 | 47 | NM_020634 | Mesendoderm |
| Hs00764128_s1 | LEFTY1 | left-right determination factor 1/left-right determination, factor B (LEFTYB) | 48 | NM_020997 | Mesendoderm |
| Hs00415443_m1 | NODAL | nodal homolog (mouse) | 49 | NM_018055 | Mesendoderm |
| Hs01057466_g1 | NPPB | natriuretic peptide precursor B | 50 | NM_002521 | Mesendoderm |
| Hs00187067_m1 | NR5A2 | nuclear receptor subfamily 5, group A, member 2 | 51 | NM_205860 | Mesendoderm |
| Hs00174969_m1 | PTHLH | parathyroid hormone-like hormone | 52 | NM_198964 | Mesendoderm |
| Hs00610080_m1 | T | T, brachyury homolog (mouse) | 53 | NM_003181 | Mesendoderm |
| Hs00979594_m1 | ABCA4 | ATP-binding cassette, sub-family A (ABC1), member 4 | 54 | NM_000350 | Mesoderm |
| Hs00993765_g1 | ALOX15 | arachidonate 15-lipoxygenase | 55 | NM_001140 | Mesoderm |
| Hs00205566_m1 | BMP10 | bone morphogenetic protein 10 | 56 | NM_014482 | Mesoderm |
| Hs00901463_m1 | CDH5 | cadherin 5, type 2, VE-cadherin (vascular epithelium) | 57 | NM_001795 | Mesoderm |
| Hs01078080_m1 | CDX2 | caudal type homeo box transcription factor 2 | 58 | NM_001265 | Mesoderm |
| Hs00197571_m1 | COLEC10 | collectin sub-family member 10 (C-type lectin) | 59 | NM_006438 | Mesoderm |
| Hs00199831_m1 | ESM1 | endothelial cell-specific molecule 1 | 60 | NM_007036 | Mesoderm |
| Hs00892390_m1 | FCN3 | ficolin (collagen/fibrinogen domain containing) 3 | 61 | NM_003665 | Mesoderm |
| Hs00230962_m1 | FOXF1 | forkhead box F1 | 62 | NM_001451 | Mesoderm |
| Hs02330376_s1 | HAND1 | heart and neural crest derivatives expressed 1 | 63 | NM_004821 | Mesoderm |
| Hs00232769_m1 | HAND2 | heart and neural crest derivatives expressed 2 | 64 | NM_021973 | Mesoderm |
| Hs01114113_m1 | HEY1 | hairy/enhancer-of-split related with YRPW motif 1 | 65 | NM_012258 | Mesoderm |
| Hs04188695_m1 | HOPX | HOP homeobox, homeobox only domain, HOP, LAGY, NECC1, OB1, SMAP31 | 66 | NM_001145459 | Mesoderm |
| Hs00174360_m1 | IL6ST | interleukin 6 signal transducer (gp130, oncostatin M receptor) | 67 | NM_175767 | Mesoderm |

TABLE 1-continued

List of early development target genes in each differentiation category (e.g., ectoderm early developmental genes, endoderm early developmental genes, mesoderm early developmental genes, pluripotent developmental genes) for determining the differentiation of a stem cell along a particular lineage as early as 2 days in culture, e.g., in self-renewing culture conditions or media.

| Assay ID/Name | Early Developmental Gene Target | Early Developmental Gene name | SEQ ID NO: | Accession number | Early Developmental gene category |
|---|---|---|---|---|---|
| Hs00231763_m1 | NKX2-5 | NK2 transcription factor related, locus 5 (*Drosophila*) | 68 | NM_004387 | Mesoderm |
| Hs00215292_m1 | ODAM | APIN hypothetical protein FLJ20513/APin protein | 69 | NM_017855 | Mesoderm |
| Hs00998018_m1 | PDGFRA | platelet-derived growth factor receptor, alpha polypeptide | 70 | NM_006206 | Mesoderm |
| Hs00229941_m1 | PLVAP | plasmalemma vesicle associated protein | 71 | NM_031310 | Mesoderm |
| Hs01111690_g1 | RGS4 | regulator of G-protein signalling 4 | 72 | NM_005613 | Mesoderm |
| Hs00950344_m1 | SNAI2 | snail homolog 2 (*Drosophila*) | 73 | NM_003068 | Mesoderm |
| Hs00356144_m1 | SST | somatostatin | 74 | NM_001048 | Mesoderm |
| Hs00195612_m1 | TBX3 | T-box 3 (ulnar mammary syndrome) | 75 | NM_016569 | Mesoderm |
| Hs00371997_m1 | TM4SF1 | transmembrane 4 superfamily member 1 | 76 | NM_014220 | Mesoderm |
| Mm01277163m1 | CD44 | CD44R, chondroitin sulfate proteoglycan 8 (CSPG8), HCELL (hematopoietic cell E- and L-selectin ligand), IN, MC56, Pgp1 | 77 | NM_000610 | Other |
| Hs00171876_m1 | DNMT3B | DNA (cytosine-5-)-methyltransferase 3 beta | 78 | NM_175848 | Other |
| Hs00914223_m1 | EP300 | E1A binding protein p300 | 79 | NM_001429 | control |
| Hs00153408_m1 | MYC | v-myc myelocytomatosis viral oncogene homolog | 80 | NM_002467 | Other |
| Mr04269880_mr | SEV | sevenless | 81 | NM_078559.2 | Other |
| Hs01099660_g1 | CXCL5 | chemokine (C-X-C motif) ligand 5 | 82 | NM_002994 | Pluri |
| Hs00172696_m1 | HESX1 | homeobox, ES cell expressed 1, ANF, RPX | 83 | NM_003865 | Pluri |
| Hs00984148_m1 | IDO1 | indoleamine-pyrrole 2,3 dioxygenase | 84 | NM_002164 | Pluri |
| Hs00178427_m1 | LCK | lymphocyte-specific protein tyrosine kinase | 85 | NM_005356 | Pluri |
| Hs02387400_g1 | NANOG | Nanog homeobox | 86 | NM_024865.2 | Pluri |
| Hs00742896_s1 | POU5F1 | POU domain, class 5, transcription factor 1 | 87 | NM_203289 | Pluri |
| Hs01053049_s1 | SOX2 | SRY (sex determining region Y)-box 2 | 88 | NM_003106 | Pluri |
| Hs01001179_m1 | TRIM22 | tripartite motif-containing 22 | 89 | NM_006074 | Pluri |

In some embodiments, the present invention encompasses measuring the gene expression of a set of early developmental genes selected from at least 3 genes from Table 2.

TABLE 2

List of early development target genes for determining the differentiation of a stem cell along a particular lineage as early as 2 days in culture.

| Assay ID/Name Developmental | Early Developmental Gene Target | SEQ ID NO: | Early Developmental gene category |
|---|---|---|---|
| Hs00940349_m1 | CDH9 | 1 | Ectoderm |
| Hs00542612_m1 | DMBX1 | 3 | Ectoderm |
| Hs00609526_m1 | DRD4 | 4 | Ectoderm |
| Hs00928272_ml | MYO3B | 8 | Ectoderm |
| Hs01075529_m1 | NOS2 | 9 | Ectoderm |
| Hs00379238_m1 | OLFM3 | 12 | Ectoderm |
| Hs00404545_m1 | PAPLN | 13 | Ectoderm |
| Hs00375481_m1 | TRPM8 | 20 | Ectoderm |
| Hs01011247_m1 | WNT1 | 21 | Ectoderm |
| Hs00418197_m1 | CABP7 | 24 | Endoderm |
| Hs00230412_m1 | CDH20 | 25 | Endoderm |
| Hs00932617_m1 | CPLX2 | 27 | Endoderm |
| Hs00154959_m1 | ELAVL3 | 28 | Endoderm |
| Hs00362818_m1 | FOXP2 | 31 | Endoderm |

TABLE 2-continued

List of early development target genes for determining the differentiation of a stem cell along a particular lineage as early as 2 days in culture.

| Assay ID/Name Developmental | Early Developmental Gene Target | SEQ ID NO: | Early Developmental gene category |
| --- | --- | --- | --- |
| Hs01004769_m1 | HMP19 | 35 | Endoderm |
| Hs00243679_m1 | PHOX2B | 40 | Endoderm |
| Hs00197571_m1 | COLEC10 | 59 | Mesoderm |
| Hs00199831_m1 | ESM1 | 60 | Mesoderm |
| Hs00892390_m1 | FCN3 | 61 | Mesoderm |
| Hs00230962_m1 | FOXF1 | 62 | Mesoderm |
| Hs04188695_m1 | HOPX | 66 | Mesoderm |
| Hs00215292_m1 | ODAM | 69 | Mesoderm |
| Hs00229941_m1 | PLVAP | 71 | Mesoderm |
| Hs00371997_m1 | TM4SF1 | 76 | Mesoderm |
| Mr04269880_mr | SEV | 81 | Other |
| Hs00984148_m1 | IDO1 | 84 | Pluri |

In some embodiments, the present invention encompasses measuring the gene expression of at least one gene from the group of mesoderm early developmental genes, selected from the group consisting of: HAND1, ESM1, HAND2, HOPX, BMP10, FCN3 and GSC. In some embodiments, the present invention encompasses measuring the gene expression of at least one gene from the group of endoderm early developmental genes, selected from the group consisting of: LEFTY1, EOMES, NODAL and FOXA2. In some embodiments, the present invention encompasses measuring the gene expression of at least one gene from the group of ectoderm early developmental genes, selected from the group consisting of: TRPM8, POU4F1, OLFM3, WNT1, LMX1A and CDH9. In some embodiments, the present invention encompasses measuring the gene expression of at least one gene from the group of pluripotent genes, selected from the group consisting of: IDO1, LCK, POU5F1 and HESX1.

In some embodiments, the present invention encompasses measuring the gene expression of at least 2 or at least 3 or at least 4 genes from the group of mesoderm early developmental genes, selected from the group consisting of: HAND1, ESM1, HAND2, HOPX, BMP10, FCN3 and GSC. In some embodiments, the present invention encompasses measuring the gene expression of at least 2 or at least 3 or at least 4 genes from the group of endoderm early developmental genes, selected from the group consisting of: LEFTY1, EOMES, NODAL and FOXA2. In some embodiments, the present invention encompasses measuring the gene expression of at least 2 or at least 3 or at least 4 genes from the group of ectoderm early developmental genes, selected from the group consisting of: TRPM8, POU4F1, OLFM3, WNT1, LMX1A and CDH9. In some embodiments, the present invention encompasses measuring the gene expression of at least 2 or at least 3 or at least 4 genes from the group of pluripotent genes, selected from the group consisting of: IDO1, LCK, POU5F1 and HESX1.

In some embodiments, the present invention also encompasses measuring the gene expression of genes which identify if a stem cell line, e.g., a pluripotent stem cell line has the ability to differentiate along a neuronal lineages, pancreas lineages, cardiovascular lineages, hematopoietic and other lineages, e.g., bone, skin, liver, kidney, blood, lineages etc.

In some embodiments, the present invention also encompasses measuring the gene expression of at least one gene, or at least 2, or at least 3, or at least 4 more genes from a set of early developmental neuronal genes selected from the group consisting of: PAX3, PAX6, MAP2, LMX1A, SOX1, SOX2, SNAI2, EOMES, EN1 and NKX2-5. In some embodiments, the present invention also encompasses measuring the gene expression of at least one gene, or at least 2, or at least 3, genes from a set of early developmental hematopoietic genes selected from the group consisting of: ZBTB16, T and CDH5. In some embodiments, the present invention also encompasses measuring the gene expression of at least one gene, or at least 2, or at least 3, or at least 4 or more genes from a set of early developmental liver genes selected from the group consisting of: GATA4, HNF4A, HHEX, TBX3, AFP, HNF1B and FOXA2. In some embodiments, the present invention also encompasses measuring the gene expression of at least one gene, or at least 2, or at least 3, or at least 4 or more genes from a set of early developmental cardiac or cardiovascular genes selected from the group consisting of: ZBTB16, T, CDH5, GATA4 and HAND1. In some embodiments, the present invention also encompasses measuring the gene expression of at least one gene, or at least 2, or at least 3, or at least 4 or more genes from a set of early developmental pancreatic genes selected from the group consisting of: SST, PAX6, HHEX and FOXA2.

The gene SRY can also be used in the assay, methods and systems as disclosed herein as a sex determining gene and to aid identifying cell ID. In some embodiments, the assay, methods and systems can comprise software to analyze this gene. In some embodiments, the assay, methods and systems as disclosed herein can comprise SEV to detect Sendai dilution into CytoTune-derived iPSCs. In some embodiments, the assay, methods and systems as disclosed herein can comprise genes for exogenous versus endogenous reprogramming factors, e.g., Sox2, Oct4, c-myc, Klf4, as well as other known reprogramming genes or factors known by persons of ordinary skill in the art.

In some embodiments, a control gene is assayed, for example, one or more of the control genes listed in Table 3. In some embodiments, a control gene is selected from at least one from ACTB, CTCF, SMAD1 or EP300. In some embodiments, a control gene in Table 3 can be substituted with another control gene, e.g., a housekeeping gene, such as EP300, β-actin, HSP90, GAPDH and the like. A housekeeping gene is a constitutive gene that is required for the maintenance of basic cellular function, and is expressed in all cells of an organism under normal and patho-physiological conditions. Examples of other control genes which can be substituted for a control gene in Table 3 include, but are not limited to, EP300, APDH, β-actin, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLPO, PPIA, POLR2A, PGK1, IP08, HMBS, GUSB, B2M, HPRT1 or 18S.

In some embodiments, the control ACTB gene can be replaced with a species specific version for the particular pluripotent stem cell line being assessed (e.g., use a mouse ACTB gene for a mouse pluripotent stem cell line being assessed). In some embodiments, a control gene used in the assay and methods as disclosed herein is CD44 (Mm01277167_m1 or Mm01277164_m1), which is a mouse specific housekeeping gene and does not amplify genomic DNA and is ideal to detect residual MEF contamination).

TABLE 3

List of control genes for use in the assay, methods, kits and systems disclosed herein.

| Assay ID/Name | Control gene | SEQ ID NO: | Assay gene category |
|---|---|---|---|
| Hs01060665_g1 | ACTB | 90 | Controls |
| Hs99999903_m1 | ACTB | 90 | Controls |
| Hs00902008_m1 | CTCF | 91 & 92 | Controls |
| Hs01004460_m1 | JARID2 | 93 & 94 | Controls |
| Hs00195432_m1 | SMAD1 | 95 & 96 | Controls |

The differentiation assays, methods, systems and kits as disclosed herein have substantial utility for determining the quality and utility for various types of pluripotent stem cells and precursor cells (e.g., ES cell, somatic stem cells, hematopoietic stem cells, leukemic stem cells, skin stem cells, intestinal stem cells, gonadal stem cells, brain stem cells, muscle stem cells (muscle myoblasts, etc), mammary stem cells, neural stem cells (e.g., cerebellar granule neuron progenitors, etc.), etc), and for example the stem cell/precursor cells described in Table 1 of Sparmann & Lohuizen, Nature 6, 2006 (Nature Reviews Cancer, November 2006), incorporated herein by reference), as well as in vitro and in vivo derived stem cells, such as induced pluripotent stem cells (iPSC).

Arrays

One aspect of the present invention relates to an array composition for characterizing the differentiation potential and/or pluripotency of a stem cell line, e.g., a pluripotent stem cell, comprising nucleic acid sequences that amplify the mRNA of any combination of early developmental genes selected from those listed in Table 1. In some embodiments, the array comprises nucleic acid sequences, e.g., oligonucleotides or primers, that amplify the mRNA of at least 3 early developmental genes selected from those listed in Table 2. In some embodiments, the amplified developmental genes are at least 90% identical to or specifically hybridize to nucleic acids encoding genes selected from those listed in Table 1 and/or Table 2.

In some embodiments, the array comprises oligonucleotides (e.g., probes or primers) which specifically hybridize to the mRNA expressed by a set of early developmental genes selected from any combination of genes listed in Table 1 and/or Table 2. In some embodiments, the arrays can be present as part of a kit as disclosed herein, wherein the kits comprises reagents, in addition to the arrays which can be used for measuring the expression levels of a plurality of early developmental genes by PCR-based methods, e.g., RT-PCR In some embodiments, the kit can be used for carrying out a method as disclosed herein, comprises: an array and reagents for measuring the expression of a set of early developmental genes selected from a combination of the genes listed in Table 1 and/or table 2.

In some embodiments, the array and reagents for measuring the expression of a set of early developmental genes can be selected from at least 1, or at least 2 or at least 3 or at least 4 genes from the group of mesoderm early developmental genes, selected from the group consisting of: HAND1, ESM1, HAND2, HOPX, BMP10, FCN3 and GSC. In some embodiments, the array and reagents for measuring the expression of a set of early developmental genes can be selected from at least 1, or at least 2 or at least 3 or at least 4 genes from the group of endoderm early developmental genes, selected from the group consisting of: LEFTY1, EOMES, NODAL and FOXA2. In some embodiments, the array and reagents for measuring the expression of a set of early developmental genes can be selected from at least 1, or at least 2 or at least 3 or at least 4 genes from the group of ectoderm early developmental genes, selected from the group consisting of: TRPM8, POU4F1, OLFM3, WNT1, LMX1A and CDH9. In some embodiments, the array and reagents for measuring the expression of a set of early developmental genes can be selected from at least 1, or at least 2 or at least 3 or at least 4 genes from the group of pluripotent genes, selected from the group consisting of: IDO1, LCK, POU5F1 and HESX1.

In some embodiments, the array comprises at least 10, or at least about 20, or at least about 30, or 30-60, or 60-90 or more than 90 nucleic acid sequences (e.g. oligonucleotides), or at least 10, or at least about 20, or at least about 30, or 30-60, or 60-90 or more than 90 pairs of nucleic acid sequences (e.g., primers), that amplify the mRNA of a combination of 10 early developmental genes selected from those listed in Table 1.

In some embodiments, the array comprises nucleic acid sequences that amplify the mRNA of at least one pluripotent stem cell gene, at least one early mesoderm developmental gene, at least one ectoderm developmental gene, and at least one endoderm developmental gene selected from Table 1 and/or from Table 2. In some embodiments, the array comprises nucleic acid sequences, e.g., oligonucleotides or primers, that amplify the mRNA of at least 4 pluripotent stem cell genes, at least 4 early mesoderm developmental genes, at least 4 ectoderm developmental genes, and at least 4 endoderm developmental genes selected from Table 1.

In some embodiments, the array comprises nucleic acid sequences (e.g., oligonucleotides and/or primers) which specifically hybridize to the mRNA of at least one, or at least about 2, or at least about 3, or at least about 4, or at least about 5 or at least about 10, or at least about 20, or at least about 30, or more than 30 pluripotency genes, and/or probes for at least one, or at least about 2, or at least about 3, or at least about 4, or at least about 5 or at least about 10, or at least about 20, or at least about 30, or more than 30 early mesoderm genes, and/or probes for at least one, or at least about 2, or at least about 3, or at least about 4, or at least about 5 or at least about 10, or at least about 20, or at least about 30, or more than 30 early ectoderm genes, and/or probe for at least one, or at least about 2, or at least about 3, or at least about 4, or at least about 5, or at least about 10, or at least about 20, or at least about 30, or more than 30 early endoderm genes. Such early ectoderm genes, and/or early endoderm genes, and/or early mesoderm and/or pluripotent genes can be selected from any combination listed in Table 1 or in table 2. Alternatively, the early developmental genes can be from other genes not listed in Table 1, but are expressed in a cell which is at least 2 days EB, and where the cell has the ability to differentiate into that particular cell lineage at a later time point.

In some embodiments, the array comprises nucleic acid sequences (e.g., oligonucleotides and/or primers) which specifically hybridize to the mRNA of at least one, or at least about 2, or at least about 3, or at least about 4, or at least about 5 genes from Table 2. In some embodiments, the array comprises probes (e.g., oligonucleotides and/or primers) which specifically hybridize to the mRNA of at least one, or at least 2, or at least 3 genes from each lineage subtype (e.g., ectoderm, mesoderm and endoderm subtypes) as disclosed in Table 2.

In some embodiments, any of the genes listed in Table 1 and/or Table 2 can be substituted for alternative early developmental genes. For example, in some embodiments, in addition to comprising probes (e.g., oligonucleotides and/or primers) which specifically hybridize to the mRNA of at least 10, or at least 20 early developmental genes selected from Table 1, the array can comprise additional reagents (e.g., probes, e.g., oligonucleotides and/or primers) which specifically hybridize to the mRNA of other early development genes for measuring the expression of different early developmental genes not listed in Table 1. Such genes are known by persons of ordinary skill in the art and are envisioned for use in the assays, kits, methods, systems as disclosed herein. In some embodiments, for example, a mesoderm gene can be substituted for GSC (goosecoid homeobox) (the human mRNA corresponding to accession number NM_173849.2).

For example, in some embodiments alternative genes can include, but are not limited to markers for ectoderm germ cells include, but are not limited to, NCAM1, EN1, FGFR2, GATA2, GATA3, HAND1, MNX1, NEFL, NES, NOG, OTX2, PAX3, PAX6, PAX7, SNAI2, SOX10, SOX9, TDGF1, APOE, PDGFRA, MCAM, FUT4, NGFR, ITGB1, CD44, ITGA4, ITGA6, ICAM1, THY1, FAS, ABCG2, CRABP2, MAP2, CDH2, NES, NEUROG3, NOG, NOTCH1, SOX2, SYP, MAPT, TH. In some embodiments, alternative genes can include, but are not limited to markers for human endoderm germ cells include, but are not limited to APOE, CDX2, FOXA2, GATA4, GATA6, GCG, ISL1, NKX2-5, PAX6, PDX1, SLC2A2, SST, ITGB1, CD44, ITGA6, THY1, CDX2, GATA4, HNF1A, HNF1B, CDH2, NEUROG3, CTNNB1, SYP, and markers for mesoderm germ cells include, but are not limited to, CD34, DLL1, HHEX, INHBA, LEF1, SRF, T, TWIST1, ADIPOQ, MME, KIT, ITGAL, ITGAM, ITGAX, TNFRSF1A, ANPEP, SDC1, CDH5, MCAM, FUT4, NGFR, ITGB1, PECAM1, CDH1, CDH2, CD36, CD4, CD44, ITGA4, ITGA6, ITGAV, ICAM1, NCAM1, ITGB3, CEACAM1, THY1, ABCG2, KDR, GATA3, GATA4, MYOD1, MYOG, NES, NOTCH1, SPI1, STAT3. In mouse, markers of endoderm germ cells include, Gata4, FoxA2, PDX1, Nodal, Sox7 and Sox17. In mouse, markers of mesoderm germ cells include, Brachycury, GSC, LEF1, Mox1 and Tie1. In mouse, markers of ectoderm germ cells include cripto1, EN1, GFAP, Islet 1, LIM1 and Nestin. Accordingly, one can select specific sets of early developmental target genes (e.g., early mesoderm genes or early endoderm genes or early ectoderm genes) to develop a "customized array" for accurate characterization of a pluripotent stem cell line to identify particular desired or undesirable characteristics.

In some embodiments, the nucleic acid sequences in the array are primers, e.g., RT-PCR primers or hybridization probes that specifically hybridize to the mRNA of a subset of early developmental genes as disclosed in Table 1. In some embodiments, the nucleic acid sequences, e.g., primers (e.g., RT-PCR primers) can be immobilized on a solid support. In some embodiments, the array comprises nucleic acid sequences (e.g., oligonucleotides and/or primers) which specifically hybridize to the mRNA of at least 1, or at least 2, or at least 3, or at least 4 or least 5 control genes. Control genes include those listed in Table 3, but are not limited to ACTB, JARID2, CTCF, SMAD1, β-actin, GAPDH and the like. In some embodiments, nucleic acid sequences that amplify a control gene can be present at multiple locations in the same array.

In some embodiments, the array comprises nucleic acid sequences, e.g., oligonucleotides or primers, that amplify the mRNA of at least sequences corresponding to 1-10 control genes, such as, but not limited to the control genes selected from the group consisting of: ACTB, JARID2, CTCF, SMAD1, GAPDH, β-actin, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLPO, PPIA, POLR2A, PGK1, IP08, HMBS, GUSB, B2M, HPRT1 or 18S.

In some embodiments, the array comprises no more than 100, or no more than 90, or no more than 50 nucleic acid sequences, e.g., oligonucleotides or primers. In some embodiments, the nucleic acid sequences present on the array are sets of primers. In some embodiments, the nucleic acid sequences, e.g., oligonucleotides or primers are immobilized on, or within a solid support. Nucleic acid sequences can be immobilized on the solid support by the 5' end of said oligonucleotides. In some embodiments, the solid support is selected from a group of materials comprising silicon, metal, and glass. In some embodiments, the solid support comprises oligonucleotides at assigned positions defined by x and y coordinates.

In some embodiments, the array comprises nucleic acid sequences, e.g., primers that can amplify the mRNA of the early developmental genes by a method comprising: polymerase chain reaction (PCR); strand displacement amplification (SDA); loop-mediated isothermal amplification (LAMP); rolling circle amplification (RCA); transcription-mediated amplification (TMA); self-sustained sequence replication (3SR); nucleic acid sequence based amplification (NASBA) or reverse transcription polymerase chain reaction (RT-PCR). In some embodiments, the array allows for real-time PCR amplification of the early developmental genes, or a real-time PCR amplification of the early developmental genes with detection by SYBR green method or an MNAzyme detection method.

In some embodiments, the array as disclosed herein is an OpenArray®, e.g., which is commercially available from Life Technologies, wherein the nucleic acid sequences, e.g., oligonucleotides or primers are immobilized within the wells of the OpenArray®. In some embodiments, an array encompassed for use in the present invention comprises primers to a set of early developmental genes selected from Table 1 and/or Table and is configured as an OpenArray® as disclosed in U.S. Pat. Nos. 6,387,331; 6,743,633; 6,893,877; 7,332,271 and 7,547,556 which are incorporated herein in their entirety by reference. In some embodiments, the array is any array using primers for RT-PCR. In some embodiments, the array is a hybridization array such as a microarray.

Accordingly, the present invention contemplates a method of generating an array, comprising providing a solid support comprising a plurality of positions for oligonucleotides, the positions defined by x and y coordinates; a plurality of different oligonucleotides (or primer pairs), each comprising a sequence which is complementary to at least a portion of the sequence of an early developmental gene being measured, where each oligonucleotide (or primer pair) is placed in a known position on the solid support to create an ordered array.

In one embodiment of the present invention, oligonucleotides that are immobilized by the 5' end on a solid surface by a chemical linkage are contemplated. In some embodiments, the oligonucleotides are primers, and can be approximately 17 bases in length, although other lengths are also contemplated.

In another embodiment of the present invention, a method of hybridizing target nucleic acid fragments is contemplated which comprises providing an ordered array of immobilized oligonucleotides representing sequences in Table 1 and/or Table 2 and/or Table 3 and providing a plurality of fragments of a target nucleic acid; and bringing the fragments of the target nucleic acid into contact with the array under conditions such that at least one of the fragments hybridizes to one of the immobilized oligonucleotides on the array.

In another embodiment of the present invention, a method of generating an array capable of hybridizing to fragments of a target early developmental gene nucleic acid is contemplated, comprising providing a solid support comprising positions for oligonucleotides, the positions defined by x and y coordinates; a plurality of oligonucleotides, each oligonucleotide comprising a sequence complementary to a different portion of the early developmental gene target nucleic acid.

The arrays as disclosed herein allow for amplification of the mRNA of a set of early developmental genes as disclosed herein from a stem cell line, e.g., a pluripotent cell line of interest. Methods for preparing total and poly(A)+ RNA are well known and are described generally in Sambrook et al., MOLECULAR CLONING—A LABORATORY MANUAL (2ND ED.), Vols. 1-3, Cold Spring Harbor Laboratory, Cold Spring Harbor, N.Y. (1989)) and Ausubel et al., CURRENT PROTOCOLS IN MOLECULAR BIOLOGY, vol. 2, Current Protocols Publishing, New York (1994)).

RNA can be isolated from eukaryotic cells by procedures that involve lysis of the cells and denaturation of the proteins contained therein. Stem cells of interest include pluripotent stem cells, including but not limited to ES cells, adult stem cells and iPSC cells, from mammals including human species. Additional steps can be employed to remove DNA. Cell lysis can be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979)). Poly(A)+ RNA is isolated by selection with oligo-dT cellulose (see Sambrook et al, MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors can be added to the lysis buffer. Likewise, for certain cell types, it can be desirable to add a protein denaturation/digestion step to the protocol.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or Sephadex. (see Ausubel et al., CURRENT PROTOCOLS IN MOLECULAR BIOLOGY, vol. 2, Current Protocols Publishing, New York (1994)).

Once bound, poly(A)+ mRNA is eluted from the affinity column using 2 mM EDTA/0.1% SDS.

The sample of RNA can comprise a plurality of different mRNA molecules, each different mRNA molecule having a different nucleotide sequence. In a specific embodiment, the mRNA molecules in the RNA sample comprise at least 100 different nucleotide sequences. More preferably, the mRNA molecules of the RNA sample comprise mRNA molecules corresponding to each of the early developmental biomarker genes. In another specific embodiment, the RNA sample is a mammalian RNA sample.

In a specific embodiment, total RNA or mRNA from the pluripotent stem cell population is used in the assays and methods as disclosed herein. The source of the RNA can be pluripotent cells or stem cells of an animal, human, mammal, primate, non-human animal, dog, cat, mouse, rat, bird, etc. In specific embodiments, the methods of the invention are used with a sample containing mRNA or total RNA from $1 \times 10^6$ cells or less. In another embodiment, proteins can be isolated from the foregoing sources, by methods known in the art, for use in expression analysis at the protein level.

Probes to the homologs of the early developmental gene biomarker sequences disclosed herein can be employed preferably wherein non-human nucleic acid is being assayed.

Methods to Determine the Differentiation Potential of Pluripotent Stem Cells

Another aspect of the present invention relates to a method of to determine the differentiation potential of a pluripotent stem cell comprising performing array amplification using the nucleic acid derived from a pluripotent stem cell and an array as disclosed herein. In some embodiments, after the array amplification, the data are analyzed using a web based analysis tool which can output an indicator that is used to determine the differentiation potential of the pluripotent stem cell to differentiate along different lineages selected from: mesoderm lineage, ectoderm lineage and endoderm lineage and/or the pluripotency of the pluripotent stem cell.

Another aspect of the present invention relates to a method of determining the differentiation potential of a pluripotent stem cell line comprising detecting and comparing the expression in the pluripotent stem cell line of a set of early developmental genes selected from those listed in Table 1 and/or Table 2 to the expression of the same genes by a control pluripotent stem cell sample, and based on this comparison, determining the differentiation potential of the pluripotent stem cell line. In some embodiments, the gene expression is assayed by real time amplification, or the detection comprises SYBR Green based real-time PCR.

In some embodiments, the expression values (e.g., expression levels) of the early developmental genes plus at least one control gene are measured in the pluripotent stem cell line and a ΔCt is calculated for each gene, and the ΔCt value of each early developmental gene is compared to the ΔCt value of that early developmental gene in a data pool that contains reference ΔCt values from a plurality of reference pluripotent stem cells, to provide a ΔΔCt value. In some embodiments, the expression values (e.g., expression levels) of the early developmental genes plus at least one control gene are measured in the pluripotent stem cell line and the average ΔCt for the genes in each of the mesoderm, ectoderm and endoderm early developmental gene subgroups is calculated. A ΔΔCt value is calculated by subtracting the average ΔCt value of the genes in each of the subgroups with the average ΔCt value of the same genes in each of the subgroups in a data pool that contains reference average ΔCt values for the same genes in each subgroups from a plurality of reference pluripotent stem cells. In some embodiments, a t-test is used to identify statistically significant ΔΔCt values from the comparison of the average ΔCt value of the genes in each of the mesoderm, ectoderm and endoderm early developmental gene subgroups as compared to reference ΔCt value for genes in each of the mesoderm, ectoderm and endoderm early developmental gene subgroups from a plurality of reference pluripotent stem cells in the data pool.

In some embodiments, a pluripotent stem cell line which differs by a statistically significant amount in the expression level of a set of mesoderm, ectoderm and endoderm early developmental genes is selected (e.g., chosen) or discarded for further use on the basis of such statistically significant differences in early developmental gene expression.

Assays to Determine the Differentiation Potential of Pluripotent Stem Cells

In some embodiments, the present invention provides a method for selecting a stem cell line, e.g., a pluripotent stem cell line, comprising measuring the differentiation potential of the stem cell line by detecting the level of gene expression of a set of early developmental and lineage marker genes selected from a combination of the genes listed in Table 1 and/or Table 2; and comparing the levels of the gene expression of the early developmental genes with a reference level of the early developmental genes. A stem cell line which does not differ by a statistically significant amount (e.g., about 2SD) in the level of the gene expression of the early developmental genes can be selected or chosen as one for which the differentiation potential and propensity to differentiate along mesoderm, ectoderm and endoderm lineages will be similar to that of a reference pluripotent stem cell line having that pattern of early developmental gene expression. Under this method, a stem cell line which differs by a statistically significant amount in the level of the expression of the early developmental genes as compared to the reference set can be discarded as likely having a different potential for differentiation relative to a reference pluripotent stem cell line. In alternative embodiments, a stem cell line which differs by a statistically significant amount in the level of the expression of the early developmental genes as compared to the reference set can be selected as having an increased propensity to differentiate along a particular lineage that is desired by the user.

In some embodiments, the reference gene expression level for an early developmental gene is a range of normal variation for that early developmental target gene, and in some embodiments the reference level is an average of expression level for that early developmental target gene, wherein the average is calculated from expression level of that early developmental target gene in a plurality of pluripotent stem cell lines, for example, at least 5 or more different pluripotent stem cell lines.

In some embodiments, the gene expression level of a set of early developmental genes, e.g., those or a subset of those listed in Table 1, provides information on the stem cells' ability to differentiate into a lineage selected from the group consisting of mesoderm, endoderm, ectoderm, neuronal, hematopoietic lineages, and any combinations thereof, where the reference gene expression level of a set of early developmental genes is generated from a plurality of pluripotent stem cell lines, for example, at least 5 different pluripotent stem cell lines. In some embodiments, the gene expression level of a set of early developmental genes from a test pluripotent stem cell and/or a reference pluripotent stem cell is determined by measuring the gene expression of a set of early developmental genes, e.g., those or a subset of those listed in Table 1, as disclosed herein.

In some embodiments, a set of early developmental genes are selected from any of about 20, or at least about 30, or at least about 40 or at least about 50, or at least about 60, or at least about 70, or at least about 80 or at least about 90 or more than 90 genes from any combination from the list in Table 1, are measured in the pluripotent cell line, and compared to the reference early developmental gene level of the same set. In some embodiments, a set of early developmental genes are selected from any of about 2, or 3, or 4 or 5 or more than 5 genes from any combination from the list in Table 2, are measured in the pluripotent cell line, and compared to the reference early developmental gene level of the same set.

Accordingly, another aspect of the present invention relates to an assay for choosing a stem cell line, e.g., a pluripotent stem cell line for a desired use by characterizing the differentiation potential of the stem cell, the assay comprising: (a) measuring the level of expression of a plurality of early developmental genes in the pluripotent stem cell line selected from the genes listed in Table 1; and comparing the level of gene expression of the plurality of early developmental genes in the pluripotent stem cell with a reference gene expression level for the same plurality of early developmental genes; and (b) choosing a stem cell line on the basis of there being no statistically significant difference in the level of gene expression of the measured early developmental genes as compared to the reference gene expression level for the early developmental genes; or choosing a stem cell line on the basis of there being a statistically significant difference in the expression level in at least one desired early developmental gene as compared to the reference expression level of the early developmental genes.

In some embodiments, the assay measures a plurality of early developmental genes in a stem cell line, e.g., a pluripotent stem cell line, that has been cultured for at least about 2 days in self-renewing culture conditions, e.g., as embryoid bodies (EB) under EB forming conditions, or at least about 3 days, or at least about 4 days, or at least about 5 days as embryoid bodies (EB) and/or under EB forming conditions (e.g., in self-renewing culture media). In some embodiments, the assay measures a plurality of early developmental genes in a stem cell line that has been cultured for no longer than about 2 days in EB forming conditions, or for no longer than about 3 or about 4 days in EB forming conditions. In some embodiments, the assay is performed on a stem cell which is at least about 0 days or at least about 1 day or at least about 2 days or at least about 3 days or more than 3 days of culturing the EB. As disclosed herein in the Examples, the differentiation assay can be performed as early as 2 days of culturing the EBs with meaningful results in predicting the differentiation potential and/or pluripotency of the stem cell line and/or determining if the stem cell is no longer pluripotent.

In some embodiments, the level of the expression of the control gene in a stem cell line, e.g., a pluripotent stem cell is compared with the level of the expression of an early developmental gene to provide the ΔCt of the level of gene expression of an early developmental gene measured in the stem cell line. In some embodiments, the assay comprises comparing the level of gene expression of the same plurality of early developmental genes with a reference gene expression level of the same early developmental genes comprises comparing the ΔCt of the level of gene expression of an early developmental gene measured in the pluripotent stem cell with the average ΔCt of the level of gene expression of the same early developmental gene measured from a plurality of reference pluripotent stem cells.

In some embodiments, the assay can be used to choose a stem cell line, e.g., a pluripotent stem cell line which differs by a statistically significant amount in the expression level of at least one desired early developmental gene, by selecting a stem cell line which differs by a statistically significant amount (e.g., using a t-test or other appropriate statistical measurement) in the expression level of an early developmental gene which is a mesoderm developmental gene, an ectoderm developmental gene, or an endoderm developmental gene. In some embodiments, a statistical difference is a difference of at least 1, at least 2, or at least 3 standard deviations from the reference gene expression level for the early developmental gene.

In some embodiments, the reference gene expression level for an early developmental gene is the range of normal variation for the expression of that early developmental gene in a plurality of pluripotent stem cells. In some embodiments, the reference gene expression level for an early developmental gene is an average of expression level for that early developmental gene, wherein the average is calculated from expression level of that early developmental gene in a plurality of pluripotent stem cell lines. In some embodiments, the plurality of pluripotent stem cell lines for a reference gene expression level is obtained from at least 5 or more pluripotent stem lines.

In some embodiments, the assay as disclosed herein can be used to characterize the differentiation potential of a mammalian pluripotent stem cell, e.g., a human pluripotent stem cell. In some embodiments, the pluripotent stem cell is an ES cell, or an iPS cell, or a partial iPS cell (piPSC), or an adult stem cell.

In some embodiments, if the level of expression of at least one or at least 2 or at least 3 or more than 3 early developmental genes selected from Table 1 and/or Table 2 which are measured in the stem cell line is expressed at a statistically significant different increased level as compared to a reference level of gene expression of the same early developmental gene, it indicates that the stem cell line will differentiate down a particular cell lineage, and/or not be pluripotent.

In some embodiments, a stem cell line, e.g., a pluripotent stem cell line is a mammalian pluripotent stem cell line, such as a human pluripotent stem cell line.

In some embodiments, the assay is a high-throughput assay for assaying a plurality of different stem cell lines, for example, but not limited to permitting one to assess a plurality of different induced pluripotent stem cells derived from reprogramming a somatic cell obtained from the same or a different subject, e.g., a mammalian subject or a human subject. In some embodiments, the assay is a 96-well format, and in some embodiments, the assay is in a 384-well format, permitting multiple pluripotent stem cell lines to be assayed at the same time. In some embodiments, the assay is an automated format, enabling high-throughput analysis of 96- and/or 384-well plates.

In some embodiments, the assay as disclosed herein can be used to generate a lineage scorecard as disclosed herein from at least one, or a plurality of stem cell lines.

In some embodiments, in the differentiation assay and methods as disclosed herein, the expression level in a set of early developmental genes is measured before the stem cell has been cultured in a differentiation medium, where the results of the expression levels of a set of early developmental genes permits one to predict the linage differentiation bias of the stem cell line. Importantly, the differentiation assay can be performed on a stem cell line as early as at least about 2 days, or at least 3 days or at least about 4 days or more than 4 days in self-renewing culture conditions. In some embodiments, the levels of early developmental genes can be measured in a differentiation assay which is performed on a stem cell line which has been cultured less than 1 day, or for about 1 day, or about 2 days, or about 3 days, or about 4 days, or about 5 days, or about 6 days, or about 7 days.

In alternative embodiments, the expression level of a set of early developmental genes as disclosed herein is measured after a stem cell line, e.g., a pluripotent stem cell line, has been cultured for at least 2 days, where the results of the expression levels of a set of early developmental genes permits one to predict the pluripotency and/or lineage differentiation bias of the stem cell line. In some embodiments, the stem cell line, e.g., a pluripotent stem cell line has not been allowed to spontaneously differentiate. After a pre-defined period of time of the stem cell line in culture (e.g., at least 2 days, but no longer than 7 days), the nucleic acid material from the cells is collected and the mRNA is used as starting material for gene expression analysis of the early developmental genes as disclosed herein.

In alternative embodiments, the stem cell line, e.g., pluripotent stem cell line has been allowed to spontaneously differentiate for a pre-defined period of time. In some embodiments, the expression level of a set of early developmental genes is measured in the stem cell line after directed differentiation along a particular lineage. For example, the differentiation assay can be performed on stem cells that have undergone direct differentiation along a specific lineage (e.g., neuronal lineage, pancreatic lineage, cardiac lineage etc.) for a pre-defined period of time, after which the nucleic acid material from the differentiated cells is collected and used as starting material for gene expression of the early developmental genes. In some embodiments, the differentiation assay is performed on a stem cell line after spontaneous or direct differentiation for at least 0 days, or for about 1 day, or about 2 days, or about 3 days, or about 4 days, or about 5 days, or about 6 days, or about 7 days. In some embodiments, a stem cell line is directed to be differentiated along one or more different lineages. In some embodiments, the differentiation of the stem cell line can be assessed by the differentiation assay as disclosed herein.

In additional aspects, the stem cell line, e.g., pluripotent stem cells are cultured under different conditions and in different culture media and analyzed for their expression of early developmental genes. As disclosed herein in the Examples, different culture media, culture techniques and RNA extraction methods do not affect the results of the gene expression of early developmental genes. For example, maintenance in suboptimal culture conditions, such as the cultivation to high density, does not affect the results.

While the measurement of gene expression as described above focuses mostly on the effect of single genes, in some embodiments, the lineage scorecard measures the gene expression of a combination of early developmental target genes (e.g., any combination of genes listed in Tables 1 and in some embodiments, alternative early developmental genes not listed in Table 1), to predict a cell line's quality (e.g., is no longer pluripotent) and utility (e.g., likely to differentiate, or not, along specific lineages of interest). In some embodiments, alternative genes can include, but are not limited to markers for ectoderm germ cells include, but are not limited to, NCAM1, EN1, FGFR2, GATA2, GATA3, HAND1, MNX1, NEFL, NES, NOG, OTX2, PAX3, PAX6, PAX7, SNAI2, SOX10, SOX9, TDGF1, APOE, PDGFRA, MCAM, FUT4, NGFR, ITGB1, CD44, ITGA4, ITGA6, ICAM1, THY1, FAS, ABCG2, CRABP2, MAP2, CDH2, NES, NEUROG3, NOG, NOTCH1, SOX2, SYP, MAPT, TH. In some embodiments, alternative genes can include, but are not limited to markers for human endoderm germ cells include, but are not limited to, APOE, CDX2, FOXA2, GATA4, GATA6, GCG, ISL1, NKX2-5, PAX6, PDX1, SLC2A2, SST, ITGB1, CD44, ITGA6, THY1, CDX2, GATA4, HNF1A, HNF1B, CDH2, NEUROG3, CTNNB1, SYP, and markers for mesoderm germ cells include, but are not limited to, CD34, DLL1, HHEX, INHBA, LEF1, SRF, T, TWIST1, ADIPOQ, MME, KIT, ITGAL, ITGAM, ITGAX, TNFRSF1A, ANPEP, SDC1, CDH5, MCAM, FUT4, NGFR, ITGB1, PECAM1, CDH1, CDH2, CD36, CD4, CD44, ITGA4, ITGA6, ITGAV, ICAM1, NCAM1, ITGB3, CEACAM1, THY1, ABCG2, KDR, GATA3, GATA4, MYOD1, MYOG, NES, NOTCH1, SPI1, STAT3. In mouse, markers of endoderm germ cells include, Gata4, FoxA2, PDX1, Nodal, Sox7 and Sox17. In mouse, markers of mesoderm germ cells include, Brachycury, GSC, LEF1, Mox1 and Tie1. In mouse, markers of ectoderm germ cells include cripto1, EN1, GFAP, Islet 1, LIM1 and Nestin. In some embodiments, a partially reprogrammed cell is an undifferentiated cell. Accordingly, one can select specific sets of early developmental target genes (e.g., early mesoderm genes or early endoderm genes or early ectoderm genes) to develop a "customized scorecard" for sensitive and accurate characterization of a pluripotent stem cell line to identify particular desired or undesirable characteristics. This is one of the key advantages of use of the scorecard as disclosed herein to determine the quality and utility of a particular pluripotent stem cell line.

In some embodiments, the differentiation assay can be configured to be automated e.g., to be run by a robot. In some embodiments, a robot can also perform RNA extraction of an entire multiwell plate, and pipettes the RNA from each well into separate qPCR plates (e.g., when using 96-well qPCR plates) or into ¼ of a plate (e.g., when using 384-well qPCR plates). For example, where one stem cell line is to be analyzed, the RNA from the stem cell line can be pipetted into each well of a 96-well plate, and each well of the 96-well plate used to measure a different early development gene and/or control. In some embodiments, were multiple stem cell lines are to be analyzed, the RNA from each stem cell line can be plated into ¼ of the individual wells of a 384-well plate, where a 384-well plate can be used for the analysis of 4 stem cell lines at the same time. Reverse transcription is performed in the same plate, and barcoded Ct tables are transferred to the computer.

Another aspect of the present invention relates to the use of a stem cell line, e.g., a pluripotent stem cell line, which has been validated and characterized using the methods and lineage scorecards as disclosed herein, for treatment of a subject by administering to a subject a stem cell population, for example a treatment of a mammalian subject, e.g., a mouse or rodent animal model or a human subject, such as for regenerative medicine and cell replacement/enhancement therapy. In some embodiments, a subject suffers from or is diagnosed with a disease or condition selected from the group consisting of cancer, diabetes, cardiac failure, muscle damage, Celiac Disease, neurological disorder, neurodegenerative disorder, lysosomal storage disease, and any combinations thereof. In some embodiments, the pluripotent stem cell is administered locally, or alternatively, administration is transplantation of the pluripotent stem cell into the subject.

In some embodiments, a stem cell line, e.g., a pluripotent stem cell is differentiated before administering the stem cell population, or differentiated progeny thereof to the subject, for example, a stem cell population can be differentiated along a lineage selected from the group consisting of mesoderm, endoderm, ectoderm, neuronal, hematopoietic lineages, and any combinations thereof, or differentiated into an insulin producing cell (pancreatic cell, beta-cell, etc.), neuronal cell, muscle cell, skin cell, cardiac muscle cell, hepatocyte, blood cell, adaptive immunity cell, innate immunity cell and the like.

In some embodiments, the differentiation assay is a high-throughput assay for assaying a plurality of different stem cell lines, e.g., a pluripotent stem cell lines, including a plurality of different induced pluripotent stem cells from a subject, such as a human or other mammalian subject.

Another aspect of the present invention relates to the use of the assay as disclosed herein to generate a lineage scorecard from at least one or a plurality of stem cell lines, e.g., pluripotent stem cell lines.

In some embodiments, the methods, assays, arrays and systems as disclosed herein can be performed by a service provider, for example, where an investigator can have one or more samples (e.g., an array of samples) each sample comprising a stem cell line, or a different population of stem cells, for assessment using the methods, differentiation assays, kits and systems as disclosed herein in a diagnostic laboratory operated by the service provider. In such an embodiment, after performing the assays of the invention as disclosed, the service provider performs the analysis and provide the investigator a report, e.g., a lineage scorecard of the characteristics of each stem cell line analyzed. In alternative embodiments, the service provider can provide the investigator with the raw data of the assays and leave the analysis to be performed by the investigator. In some embodiments, the report is communicated or sent to the investigator via electronic means, e.g., uploaded on a secure web-site, or sent via e-mail or other electronic communication means. In some embodiments, the investigator can send the samples to the service provider via any means, e.g., via mail, express mail, etc., or alternatively, the service provider can provide a service to collect the samples from the investigator and transport them to the diagnostic laboratories of the service provider. In some embodiments, the investigator can deposit the samples to be analyzed at the location of the service provider diagnostic laboratories. In alternative embodiments, the service provider provides a stop-by service, where the service provider send personnel to the laboratories of the investigator and also provides the kits, apparatus, and reagents for performing the assays on the investigators stem cell lines in the investigators laboratories, and analyze the results and provides a report to the investigator of the characteristics of each stem cell line analyzed, or plurality of stem cell lines analyzed.

Lineage Scorecard

In some aspects of the invention, the invention relates to generating a lineage scorecard of a stem cell line, e.g., a pluripotent stem cell line, for validating and monitoring and to serve as a general quality control of the stem cell line, by monitoring the of expression of a set of early developmental genes and lineage marker genes to allow identification of characteristics of the stem cell line and to accurately and quickly predict which pluripotent stem cell lines are likely to be pluripotent (or likely not be pluripotent) and/or differentiate along a range of cell lineages.

One aspect of the present invention relates to a lineage scorecard of the differentiation propensity of a stem cell line, e.g., a pluripotent stem cell, the scorecard comprising a data set comprising the gene expression levels for a plurality of early developmental target genes from at least 5 stem cell populations In some embodiments, the plurality of early developmental target genes is at least about 20, or at least about 30, or at least about 40, or at least about 50, or at least about 60, or at least about 70, or at least about 80, or at least about 90 or more than 90 early developmental genes selected from any combination listed in Table 1. In some embodiments, some of the genes listed in Table 1 can be substituted for alternative early developmental genes. For example, in some embodiments, the plurality of early developmental genes include at least about 20, or at least about 30, or more than 30 genes selected from Table 1 and can include at least 1 or at least about 5, or at least about 10, or at least about 20 or more than 20 different early developmental genes which are not listed in Table. In some embodiments, the plurality of early developmental target genes is at least about 10, or at least about 20, or at least about 30, or more than 30 pluripotent genes, and/or probes for at least about 10, or at least about 20, or at least about 30, or more than 30 early mesoderm genes, and/or probes for at least about 10, or at least about 20, or at least about 30, or more than 30 early ectoderm genes, and/or probes for at least about 10, or at least about 20, or at least about 30, or more than 30 early endoderm genes.

In some embodiments, a data set of the level of expression of a set of early developmental genes can be connected to, or sent to, a data storage device, such as a data storage device comprising a database located on a computer device.

In some embodiments, at least 15 pluripotent stem cells lines are used to generate a data set of the expression of early developmental genes for a reference lineage scorecard. In some embodiments, a data set of the expression of early developmental genes are obtained from at least 5 or more, or at least 6, or at least 7, or at least 8, or at least 9, or at least 10, or at least 11, or at least 12, or at least 13 or at least 14, or at least 15, or at least 16, or at least 17, or at least 18, or all 19 of the following pluripotent stem cells lines selected from the group; HUES64, HUES3, HUES8, HUES53, HUES28, HUES49, HUES9, HUES48, HUES45, HUES1, HUES44, HUES6, H1, HUES62, HUES65, H7, HUES13, HUES63, HUES66.

In some embodiments, the pluripotent stem cell populations used to generate the data sets for the reference lineage scorecard can be mammalian pluripotent stem cell populations, such as human pluripotent stem cell populations, or induced pluripotent stem (iPS) cell populations, or embryonic stem cell populations, or adult stem cell populations, or autologous stem cell populations, or embryonic stem (ES) stem cell populations.

In some embodiments, the lineage scorecard as used herein can be used in methods to select for, e.g., positive selection of a stem cell population with desirable characteristics (e.g., high differentiation potential along a specific lineage and/or pluripotency), and/or to negatively select, e.g., identify and optionally discard, stem cell lines with undesirable characteristics, e.g., cells which are no longer pluripotent, and/or do not differentiate along a desired cell lineage.

Another aspect of the present invention relates to a method for generating a stem cell lineage scorecard comprising measuring the gene expression of a set of early developmental target genes in a plurality of stem cell lines. In some embodiment, if the method is done in replicates (e.g., duplicate, triplicate etc.), the method further comprises calculating an average gene expression level for each early developmental target gene measured. In some embodiments, the methods are sufficiently reliable such that only one (e.g., a single) measurement of the gene expression of early developmental genes is required to create a lineage scorecard, thus eliminating the time and expense of duplicates and triplicate experiments, as well as calculating the average gene expression for each early developmental gene measured.

In some embodiments, a data set of the measured expression levels of the early developmental genes are connected to a data storage device, for example, a data storage device which is a database located on a computer device. In some embodiments, the database is located on a network, for example, a remote network accessible for example, via the network (e.g., a cloud) or similar web accessible network.

In some embodiments, stem cell lines for generating a lineage score card as disclosed herein are mammalian pluripotent stem cell lines, e.g., human pluripotent stem cell line, including embryonic stem cells and/or induced pluripotent stem (iPS) cell lines, and/or adult stem cells, or somatic stem cells, or autologous stem cells.

Another aspect of the present invention relates to the use of the lineage scorecard as disclosed herein to distinguish an induced pluripotent stem cell from an embryonic stem cell line. In some embodiments, a lineage scorecard as disclosed herein can distinguish a pluripotent stem cell line from a non-pluripotent stem cell, or a stem cell line which has lost its pluripotency. In some embodiments, a lineage scorecard as disclosed herein can be used to distinguish a stem cell line, e.g., a pluripotent stem cell line, which has an increased efficiency to differentiate along neuronal lineages or a stem cell line, e.g., a pluripotent stem cell line, which has an increased efficiency to differentiate along mesoderm lineages, and/or ectoderm lineages and/or endoderm lineages.

In some embodiments, a stem cell line where the average ΔCt for the gene expression level of a subgroup of early developmental genes (e.g., subgroups of mesoderm, ectoderm, endoderm and pluripotent early developmental gene subgroups) is statistically significantly different to the reference average ΔCt for that category, as determined by a t-test, will be considered an outliner stem cell line, which is unlikely to differentiate along the same lineages as a reference pluripotent stem cell line.

As discussed above, in each defined group or category (e.g., control, pluripotent gene, early endoderm developmental genes, early mesendoderm developmental gene, early mesoderm developmental genes, early ectoderm developmental gene), the ΔCt is averaged and the averaged ΔCt is compared using a t-test to the reference ΔCt for that category to provide a t-value. A t-value of 0-1 indicates that the measured level of gene expression in that early developmental gene category is comparable with the reference gene expression level in the same category. A t-value of >1 indicates that the measured gene expression level in that early developmental gene category of the pluripotent cell line is higher than the reference gene expression level in the same category. A t-value of <0 indicates that the measured gene expression level in that early developmental gene category of the pluripotent cell line is lower than the reference gene expression level in the same category. Accordingly, the t-values can be used to negatively select a stem cell line, (e.g., isolate and optionally discard the cells with undesirable characteristics, e.g., cells which have been identified as unlikely to differentiate along particular lineages), and/or positively select for stem cell lines as those identified to have an increased efficiency or potential to differentiate along a particular cell lineage, or positively select a stem cell line which has a t-value indicating that it does not statistically differ from a reference pluripotent stem cell line.

In some embodiments, a stem cell line in which a gene expression level of an early developmental target gene which is statistically significantly different (FDR <10%), and/or which as an absolute difference of >1 fold change of level of gene expression as compared to the normal variation of gene expression for that gene (e.g., the normal reference value) in a reference pluripotent stem cell line would be considered a gene expression outlier. A stem cell line which has numerous, e.g., at least about 5, or at least about 6, or at least about 7, or at least about 8, or at least about 5-10, or at least about 10-15, or at least about 10-50, or at least about 50-100 or more total outlier gene expression genes (as determined by t-test) as compared to a reference pluripotent stem cell will be considered an outlier stem cell line. In some embodiments, such a stem cell line would be identified as a stem cell line that has an increased propensity to differentiate along a specific lineage. For example, if the expression of at least about 2, or at least about 3 or more early mesoderm genes expressed in the stem cell line are statistically different and/or absolutely different by >1 as compared to a reference level for the same early developmental gene, the stem cell line is identified as having an increased or decreased propensity to differentiate along a mesoderm cell lineage as compared to other stem cell lines. Accordingly, such a stem cell line can be either positively selected, or alternatively negatively selected, (e.g., isolated and optionally discarded as a stem cell line with undesirable characteristics) depending on the desired use or utility of the stem cell line.

In some embodiments, a stem cell line which has a gene expression level of an early developmental gene which is statistically significantly different (FDR <5%) and/or has an absolute difference of >1 log-2 fold change of level of the early developmental gene expression as compared to the normal variation of gene expression for that early developmental gene (e.g., the normal reference value) in a reference pluripotent stem cell line would be considered a differentiation outlier gene. A stem cell which has numerous, e.g., at least about 5, or at least about 6, or at least about 7, or at least about 8, or at least about 5-10, or at least about 10-15, or at least about 10-50, or at least about 50-100 or more total outlier lineage gene expression genes as compared to a reference pluripotent stem cell line would be considered an outlier stem cell line, which would be identified as not able, or unlikely to differentiate along the same lineages as a reference pluripotent stem cell line. Accordingly, such a stem cell line can be negatively selected, e.g., isolate and optionally discard the cells with undesirable characteristics, e.g., stem cells which are unlikely to differentiate along particular lineages, and/or alternatively positively selected as a stem cell line which is indicated to have an increased efficiency or potential to differentiate along a particular cell lineage.

Kits

Another aspect of the present invention relates to kits for characterizing the differentiation potential of a stem cell line, e.g., a pluripotent cell line, comprising an array as disclosed herein. In some embodiments, a kit comprises an array as disclosed herein and reagents for measuring the expression levels of a plurality of early developmental genes by RT-PCR. The kit can further comprise instructions for use.

In some embodiments, the kit for carrying out the methods as disclosed herein comprises probes (e.g., oligonucleotides and/or primers) which specifically hybridize to the mRNA of at least about 20, or at least about 30, or at least about 40, or at least about 50, or at least about 60, or at least about 70, or at least about 80, or at least about 90 or more than 90 early developmental genes selected from those listed in Table 1. In some embodiments, the kit comprises probes (e.g., oligonucleotides and/or primers) which specifically hybridize to the mRNA of at least about 3 or more genes selected from Table 2.

Another aspect of the present invention relates to a kit for carrying out a methods and assays as disclosed herein, where the kit comprises: reagents for measuring the expression of a set of early developmental genes selected from at least 20 or at least 30 from the genes listed in Table 1. In some embodiments, the reagents are probes, e.g., RT-PCR primers or hybridization probes that specifically hybridize to a set of early developmental genes selected from a subset of at least 20 from the genes listed in Table 1. In some embodiments, the probes, e.g., RT-PCR probes can be immobilized on a solid support. In some embodiments, in addition to comprising probes for at least 20 early developmental genes selected from Table 1, the kit can comprise additional reagents for measuring the expression of different early developmental genes not listed in Table 1. In some embodiments, the kit also comprises probes for at least 1, or at least 2, or at least 3, or at least 4 or least 5 control genes. Control genes include, but are not limited those listed in Table 3 and/or any from the combination of: ACTB, JARID2, CTCF, SMAD1, β-actin, GAPDH, EIF2B, RPL37A, CDKN1B, ABL1, ELF1, POP4, PSMC4, RPL30, CASC3, PES1, RPS17, RPSL17L, CDKN1A, MRPL19, MT-ATP6, GADD45A, PUM1, YWHAZ, UBC, TFRC, TBP, RPLPO, PPIA, POLR2A, PGK1, IP08, HMBS, GUSB, B2M, HPRT1 or 18S and the like. In some embodiments, a probe for a control gene can be present multiple times in the same assay or kit. In some embodiments, the kit and/or assay as disclosed herein comprises probes for at least about 10, or at least about 20, or at least about 30, or more than 30 pluripotent genes, and/or probes for at least about 10, or at least about 20, or at least about 30, or more than 30 early mesoderm genes, and/or probes for at least about 10, or at least about 20, or at least about 30, or more than 30 early ectoderm genes, and/or probes for at least about 10, or at least about 20, or at least about 30, or more than 30 early endoderm genes.

Accordingly, the present invention relates to a kit for determining the differentiation potential of a stem cell line, comprising reagents (e.g., probes and other reagents) necessary for measuring gene expression levels of a plurality of early developmental genes, e.g., such as any combination of genes listed in Table 1. In some embodiments, the kit further comprises a lineage score card as disclosed herein. In some embodiments, the kit further comprises instructions for use. In some embodiments, the kit comprises a computer readable medium comprising instructions encoded thereupon for running a software program on a computer to compare the levels of the early developmental genes measured in the test stem cell line with reference levels of the same early developmental genes. In some embodiments, the kit comprises instructions to access a software program available online (e.g., on a cloud) to compare the measured levels of the early developmental genes from the test pluripotent stem cell with reference levels of the early developmental genes for pluripotent stem cells.

In some embodiments, the kit reagents include probes e.g., RT-PCR primers or hybridization probes that specifically hybridize to a set of early developmental genes selected from a subset of at least 20 from the genes listed in Table 1. In some embodiments, the probes, e.g., RT-PCR probes can be immobilized on a solid support. In some embodiments, the kit and/or assay as disclosed herein comprises probes for at least about 10, or at least about 20, or at least about 30, or more than 30 pluripotency genes, and/or probes for at least about 10, or at least about 20, or at least about 30, or more than 30 early mesoderm genes, and/or probes for at least about 10, or at least about 20, or at least about 30, or more than 30 early ectoderm genes, and/or probes for at least about 10, or at least about 20, or at least about 30, or more than 30 early endoderm genes.

In some embodiments, the kit is in a 96-well or 384-well format and comprises probes to hybridize with a set of early developmental genes, e.g., a subset or all of those listed in Table 1. In some embodiments, the kit can be configured to be automated e.g., to be run by a robot. For example, samples can be added to the array of the kit using a robot etc., and the robot can perform the RT-PCR protocol and readout of the levels of the expression of the measured early developmental genes.

In some embodiments, a kit further comprises the reagents for reprogramming a somatic cell or differentiated cell into an induced pluripotent stem cell (iPSC) and also comprises the reagents for quality-assessing the generated iPS cell lines. Examples of reagents used to reprogram a somatic cell into an induced pluripotent stem (iPS) cell are well known to persons of ordinary skill in the art, and include those as discussed herein, for example, but not limited to the methods and reagents for reprogramming a somatic cell to an iPS cell or an piPS cell, as disclosed in International patent applications; WO2007/069666; WO2008/118820; WO2008/124133; WO2008/151058; WO2009/006997; and U.S. Patent Applications US2010/0062533; US2009/0227032; US2009/0068742; US2009/0047263; US2010/0015705; US2009/0081784; US2008/0233610; U.S. Pat. No. 7,615,374; U.S. patent application Ser. No. 12/595,041, EP2145000, CA2683056, AU8236629, 12/602,184, EP2164951, CA2688539, US2010/0105100; US2009/0324559, US2009/0304646, US2009/0299763, US2009/0191159, the contents of which are incorporated herein in their entirety by reference. In some embodiments, the kit comprises the reagents for virally-induced or chemically induced generation of reprogrammed cells e.g., iPS cells, as disclosed in EP1970446, US2009/0047263, US2009/0068742, and 2009/0227032, which are incorporated herein in their entirety by reference. In some embodiments, iPS cells can be reprogrammed using modified RNA (mod-RNA) as disclosed in US2012/0046346, which is incorporated herein in its entirety by reference.

In some embodiments, a kit as disclosed herein also comprises at least one reagent for selecting a desired stem cell line, e.g., a pluripotent stem cell line among many cell lines, e.g., reagents to select one or more appropriate stem cell lines for the intended use of the stem cell line. Such agents are well known in the art, and include without limitation, labeled antibodies to select for cell-specific lineage markers and the like. In some embodiments, the labeled antibodies are fluorescently labeled, or labeled with magnetic beads and the like. In some embodiments, a kit as disclosed herein can further comprise at least one or more reagents for profiling and annotating an existing ES cell and/or iPS cell bank in high throughput, according to the methods as disclosed herein.

In one aspect the invention provides a kit comprising a pluripotent stem cell selected by a differentiation assay, method, or system of the invention. In addition to the above mentioned component(s), the kit can also include informational material. The informational material can be descriptive, instructional, marketing or other material that relates to the methods described herein and/or the use of the components for the assays, methods and systems described herein. For example, the informational material can describe methods for selecting a pluripotent stem cell, for characterizing a plurality of properties of a pluripotent cell, or generating a scorecard according to the invention. Without limitations, if a kit includes material suitable for administering to a subject, the kit can optionally include a delivery device.

Alternative Assays for Measuring Gene Expression Levels of Early Developmental Genes In some embodiments, the assays, systems and methods comprise a quantitative gene profiling assay of a set of early developmental genes, such as via RT-PCT and/or a microarray or the like. Any method for determining gene expression levels commonly known to persons of ordinary skill in the art are encompassed for use in the methods, systems and assays as disclosed herein, and include Affymetrix gene expression systems, microarray methods, and other methods to measure DNA or transcript expression. In some embodiments, gene expression is measured using cDNA and RNA sequencing, imaging-based methods such as Nano String and a wide range of methods that use PCR as well as qPCR. Normalization for these methods has been widely described. In some embodiments, a gcRMA algorithm for normalizing Affymetrix microarray data can be used. In some embodiments, commercially available assays available from Life Technologies Inc., can be used to measure the gene expression of a set of early developmental genes.

In some embodiments, gene expression is determined on any gene level, for example, the expression of non-coding genes, as well as non-coding transcripts e.g., natural antisense transcripts (NATs), microRNA (miRNAs) genes and all other types of nucleic acid and/or RNA transcripts that are normally or abnormally present in pluripotent and differentiated cells.

In some embodiments, the level of gene expression measured is the level of gene transcript, e.g., at the level of messenger RNA (mRNA). In some embodiments, detection uses nucleic acid or nucleic acid analogues, for example, but not limited to, nucleic acid analogues including DNA, RNA, PNA, pseudo-complementary DNA (pcDNA), locked nucleic acid and variants and homologues thereof. In some embodiments, gene transcript expression can be assessed by reverse-transcription polymerase-chain reaction (RT-PCR) or quantitative RT-PCR by methods known to persons of ordinary skill in the art.

In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

In an alternative embodiment, expression of a target gene can be measured by reverse-transcription (RT) PCR and by quantitative RT-PCR (QRT-PCR) or real-time PCR methods. Methods of RT-PCR and QRT-PCR are well known in the art, and are described in more detail below.

Real time PCR is an amplification technique that can be used to determine levels of mRNA expression. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For mRNA levels, mRNA is extracted from a biological sample, e.g. a tumor and normal tissue, and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes can be obtained commercially from, for example, Perkin Elmer/Applied Biosystems (Foster City, Calif.). To quantitate the amount of the specific nucleic acid of interest in a sample, a standard curve is generated using a control. Standard curves can be generated using the Ct values determined in the real-time PCR, which are related to the initial concentration of the nucleic acid of interest used in the assay. Standard dilutions ranging from 10-$10^6$ copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan® probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994.

The TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq®, results in the cleavage of the TaqMan probe. This cleavage separates the 5' fluorescent dye and the 3' quenching agent, thereby resulting in an increase in fluorescence as a function of amplification (see, for example, at the world-wide web site: "perkin-elmer-dot-com").

In another embodiment, detection of RNA transcripts can be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

Detection of RNA transcripts can further be accomplished using known amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). One suitable method for detecting enzyme mRNA transcripts is described in reference Pabic et. al. Hepatology, 37(5): 1056-1066, 2003, which is herein incorporated by reference in its entirety.

Other known amplification methods which can be utilized in the methods described herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO 9322461.

In situ hybridization visualization can also be employed, wherein a radioactively labeled antisense RNA probe is hybridized with a thin section of a biopsy sample, washed, cleaved with RNase and exposed to a sensitive emulsion for autoradiography. The samples can be stained with haematoxylin to demonstrate the histological composition of the sample, and dark field imaging with a suitable light filter shows the developed emulsion. Non-radioactive labels such as digoxigenin can also be used.

Alternatively, mRNA expression can be detected on a DNA array, chip or a microarray. In such an embodiment, probes can be affixed to surfaces for use as "gene chips." Such gene chips can be used to detect genetic variations by a number of techniques known to one of skill in the art. In one technique, oligonucleotides are arrayed on a gene chip for determining the DNA sequence by the sequencing by hybridization approach, such as that outlined in U.S. Pat. Nos. 6,025,136 and 6,018,041. The probes also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999) Nucleic Acids Res. 27:4830-4837.

Oligonucleotides corresponding to a target gene are immobilized on a chip which is then hybridized with labeled nucleic acids of a test sample obtained from a pluripotent stem cell or putative pluripotent stem cell. A positive hybridization signal is obtained with a sample containing a target gene mRNA transcript. Methods of preparing DNA arrays and their use are well known in the art. (See, for example U.S. Pat. Nos. 6,618,6796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug discovery Today 5: 59-65, which are herein incorporated by reference in their entirety). Serial Analysis of Gene Expression (SAGE) can also be performed (See for example U.S. Patent Application 20030215858).

Microarrays

In some embodiments, the assays and kits as described herein for measuring a set of early developmental genes include use of a microarray. A microarray is an array in which probes, typically nucleic acids such as oligonucleic acid hybridization probes, which are arranged at discrete locations, which are separate from one another and are typically arrayed at a density of between, about 100/cm$^2$ to 1000/cm$^2$, but can be arrayed at greater densities such as 10000/cm$^2$. The principle of a microarray experiment is that mRNA from a given cell line or tissue is used to generate a labeled sample typically labeled cDNA, termed the 'target', which is hybridized in parallel to a large number of nucleic acid sequences, typically DNA sequences, immobilized on a solid surface in an ordered array.

Tens of thousands of transcript species can be detected and quantified simultaneously. Although many different microarray systems have been developed, the most commonly used systems today can be divided into two groups, according to the arrayed material: complementary DNA (cDNA) and oligonucleotide microarrays. The arrayed material has generally been termed the probe since it is equivalent to the probe used in a northern blot analysis. Probes for cDNA arrays are usually products of the polymerase chain reaction (PCR) generated from cDNA libraries or clone collections, using either vector-specific or gene-specific primers, and are printed onto glass slides or nylon membranes as spots at defined locations. Spots are typically 10-300 µm in size and are spaced about the same distance apart. Using this technique, arrays consisting of more than 30,000 cDNAs can be fitted onto the surface of a conventional microscope slide. For oligonucleotide arrays, short 20-25 mers are synthesized in situ, either by photolithography onto silicon wafers (high-density-oligonucleotide arrays from Affymetrix or by ink-jet technology (developed by Rosetta Inpharmatics, and licensed to Agilent Technologies).

Alternatively, presynthesized oligonucleotides can be printed onto glass slides. Methods based on synthetic oligonucleotides offer the advantage that because sequence information alone is sufficient to generate the DNA to be arrayed, no time-consuming handling of cDNA resources is required. Also, probes can be designed to represent the most unique part of a given transcript, making the detection of closely related genes or splice variants possible. Although short oligonucleotides can result in less specific hybridization and reduced sensitivity, the arraying of presynthesized longer oligonucleotides (50-100 mers) has recently been developed to counteract these disadvantages.

Thus in performing a microarray to ascertain the level of gene expression of target genes in pluripotent stem cells, the following steps can be performed: obtain mRNA from the sample comprising pluripotent stem cells and prepare nucleic acids targets, contact the array under conditions, typically as suggested by the manufactures of the microarray (suitably stringent hybridization conditions such as 3×SSC, 0.1% SDS, at 50° C.) to bind corresponding probes on the array, wash if necessary to remove unbound nucleic acid targets and analyze the results.

It will be appreciated that the mRNA can be enriched for sequences of interest such as those present in a gene profile as described herein by methods known in the art, such as primer specific cDNA synthesis. The population can be further amplified, for example, by using PCR technology. The targets or probes are labeled to permit detection of the hybridization of the target molecule to the microarray. Suitable labels include isotopic or fluorescent labels which can be incorporated into the probe.

The Affymetrix HG-U133.Plus 2.0 gene chips can be used and hybridized, washed and scanned according to the standard Affymetrix protocols. Some RNAs can be replicated on arrays, making 96 the total number of available hybridizations for subsequent analysis.

To monitor mRNA levels, for example, mRNA is extracted from the sample comprising pluripotent stem cells to be tested, reverse transcribed, and fluorescent-labeled cDNA probes are generated. The microarrays capable of hybridizing to gene expression target cDNA's are then probed with the labeled cDNA probes, the slides scanned and fluorescence intensity measured. This intensity correlates with the hybridization intensity and expression levels.

Methods of "quantitative" amplification are well known to those of skill in the art. For example, one approach to quantitative PCR involves simultaneously co-amplifying a known quantity of a control sequence using the same primers. This provides an internal standard that can be used to calibrate the PCR reaction. Detailed protocols for quantitative PCR are provided, for example, in Innis et al. (1990) PCR Protocols, A Guide to Methods and Applications, Academic Press, Inc. N.Y.

Although the same procedures and hardware described by Affymetrix could be employed in connection with the present invention, other alternatives are also available. Many reviews have been written detailing methods for making microarrays and for carrying out assays (see, e.g., Bowtell, Nature Genetics Suppl. 27:25-32 (1999); Constantine, et al, Life ScL News 7:11-13 (1998); Ramsay, Nature Biotechnol. 16:40-44 (1998)). In addition, patents have issued describing techniques for producing microarray plates, slides and related instruments (U.S. Pat. Nos. 6,902,702; 6,594,432; 5,622,826, which are incorporated herein in their entirety by reference) and for carrying out assays (U.S. Pat. Nos. 6,902,900; 6,759,197 which are incorporated herein in their entirety by reference). The two main techniques for making plates or slides involve either polylithographic methods (see U.S. Pat. Nos. 5,445,934; 5,744,305 which are incorporated herein in their entirety by reference) or robotic spotting methods (U.S. Pat. No. 5,807,522 which is incorporated herein in its entirety by reference). Other procedures can involve inkjet printing or capillary spotting (see, e.g., WO 98/29736 or WO 00/01859 which are incorporated herein in their entirety by reference).

The substrate used for microarray plates or slides can be any material capable of binding to and immobilizing oligonucleotides including plastic, metals such a platinum and glass. A preferred substrate is glass coated with a material that promotes oligonucleotide binding such as polylysine (see Chena, et al, Science 270:467-470 (1995)). Many schemes for covalently attaching oligonucleotides have been described and are suitable for use in connection with the present invention (see, e.g., U.S. Pat. No. 6,594,432 which is incorporated herein in its entirety by reference). The immobilized oligonucleotides should be, at a minimum, 20 bases in length and should have a sequence exactly corresponding to a segment in the gene targeted for hybridization.

Computer Systems

Another aspect of the present invention relates to a computer system for generating a lineage scorecard of a pluripotent stem cell, comprising: (i) at least one memory containing at least one program comprising the steps of: (a) receiving gene expression data of a set of early developmental genes selected from a combination of at least 20 from the list in Table 1 and performing a comparison of the gene expression levels of the early developmental genes with a reference gene expression level of the same target genes; (b) generating a lineage scorecard based on the comparison of the expression of the early developmental gene as compared to the reference gene expression levels for the same set of early developmental genes; and (ii) a processor for running said program. In some embodiments, the system further comprises a report generating module which generates a lineage scorecard report based on differentiation propensity of the pluripotent stem cell line tested. In some embodiments, the system comprises a memory, wherein the memory comprises a database. In some embodiments, the database arranges the gene expression of the set of early developmental genes in a hierarchical manner, e.g., the levels of expression the early developmental genes clustered according to group, e.g., expression levels of pluripotent genes, early mesoderm genes, early ectoderm genes or early endoderm genes. In some embodiments, the memory is connected to the first computer via a network, e.g., a local network (LAN) or a wide area network, such as the internet, where access to the network is via a secure site or via password access.

In some embodiments, the system as disclosed herein provides a lineage scorecard which provides an indication of suitable uses, utility or applications of the pluripotent stem cell line tested.

Another aspect of the present invention relates to a computer readable medium comprising instructions for generating a lineage scorecard of a pluripotent stem cell line, comprising: (i) receiving gene expression data of a set of early developmental genes selected from a combination of at least 20 from the list in Table 1 and performing a comparison of the gene expression levels of the early developmental genes with a reference gene expression level of the same target genes, and (ii) generating a lineage scorecard based on the comparison of the expression of the early developmental gene as compared to the reference gene expression levels for the same set of early developmental genes.

One aspect of the present invention relates to a computerized system for processing the differentiation assay data and generating a measure or rating of the pluripotent stem cell as propensity to differentiate along one or more cell lineages, and/or generating a lineage scorecard as disclosed herein.

In some embodiments, a computer system for generating a lineage scorecard of a pluripotent stem cell, comprising: (i) at least one memory containing at least one program comprising the steps of: (a) receiving gene expression data of a set of early developmental genes selected from a combination of at least 20 from any combination of genes listed in Table 1, and performing a comparison of the gene expression levels of the early developmental genes with a reference gene expression level of the same target genes; (b) generating a lineage scorecard based on the comparison of the expression of the early developmental gene as compared to the reference gene expression levels for the same set of early developmental genes; and (ii) a processor for running said program. In some embodiments, the system further comprises a report generating module which generates a lineage scorecard report based on differentiation propensity of the pluripotent stem cell line tested. In some embodiments, the system comprises a memory, wherein the memory comprises a database. In some embodiments, the database arranges the gene expression of the set of early developmental genes in a hierarchical manner, e.g., the levels of expression the early developmental genes clustered according to group, e.g., expression levels of pluripotent genes, early mesoderm genes, early ectoderm genes or early endoderm genes. In some embodiments, the memory is connected to the first computer via a network, e.g., a local network (LAN) or a wide area network, such as the internet, where access to the network is via a secure site or via password access.

In some embodiments, the system as disclosed herein provides a lineage scorecard which provides an indication of suitable uses, utility or applications of the pluripotent stem cell line tested.

In some embodiments, the computer program is adapted to control the operation of the computer system to implement a method that further includes: (i) receiving gene expression data (e.g., gene expression levels) of the early developmental genes expressed in the pluripotent stem cell line of interest and comparing the gene expression data (e.g., gene expression levels) with a reference early developmental gene expression data (e.g., gene expression levels of the same second set of early developmental target genes in a control pluripotent stem cell line or a plurality of pluripotent stem cell lines); (ii) generating a lineage scorecard based on the comparison of the gene expression data (e.g., gene expression levels of the early developmental genes) as compared to reference gene expression data (e.g., reference early developmental gene expression levels in reference pluripotent stem cell line(s)).

Another aspect of the present invention relates to a computer readable medium comprising instructions for generating a lineage scorecard of a pluripotent stem cell line, comprising: (i) receiving gene expression data of a set of early developmental genes selected from a combination of at least 20 from any combination of genes listed in Table 1 and performing a comparison of the gene expression levels of the early developmental genes with a reference gene expression level of the same target genes, and (ii) generating a lineage scorecard based on the comparison of the expression of the early developmental gene as compared to the reference gene expression levels for the same set of early developmental genes.

The computer system can include one or more general or special purpose processors and associated memory, including volatile and non-volatile memory devices. The computer system memory can store software or computer programs for controlling the operation of the computer system to make a special purpose system according to the invention or to implement a system to perform the methods according to the invention. The computer system can include an Intel or AMD x86 based single or multi-core central processing unit (CPU), an ARM processor or similar computer processor for processing the data. The CPU or microprocessor can be any conventional general purpose single- or multi-chip microprocessor such as an Intel Pentium processor, an Intel 8051 processor, a RISC or MISS processor, a Power PC processor, or an ALPHA processor. In addition, the microprocessor can be any conventional or special purpose microprocessor such as a digital signal processor or a graphics processor. The microprocessor typically has conventional address lines, conventional data lines, and one or more conventional control lines. As described below, the software according to the invention can be executed on dedicated system or on a general purpose computer having a DOS, CPM, Windows, Unix, Linix or other operating system. The system can include non-volatile memory, such as disk memory and solid state memory for storing computer programs, software and data and volatile memory, such as high speed ram for executing programs and software.

Computer-readable physical storage medium useful in various embodiments of the invention can include any physical computer-readable storage medium, e.g., solid state memory (such as flash memory), magnetic and optical computer-readable storage media and devices, and memory that uses other persistent storage technologies. In some embodiments, a computer readable medium can be any tangible media that allows computer programs and data to be accessed by a computer. Computer readable medium can include volatile and nonvolatile, removable and non-removable tangible media implemented in any method or technology capable of storing information such as computer readable instructions, program modules, programs, data, data structures, and database information. In some embodiments of the invention, computer readable medium includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store information and which can read by a computer including and any suitable combination of the foregoing.

Computer-readable physical storage medium is also commonly referred to as storage devices, Carrier waves and other signal-based storage or transmission media are not included within the scope of storage devices or physical computer-readable storage medium encompassed by the term and useful according to the invention. The storage device can be adapted or configured for having recorded thereon the reference data of levels of expression of early developmental genes from a plurality of pluripotent stem cells (e.g., including ΔCt levels for individual early developmental genes of Table 1 and/or Table 2, as well as average ΔCt levels for subgroups of early developmental genes). Such information can be provided in digital form that can be transmitted and read electronically, e.g., via the Internet, on diskette, via USB (universal serial bus) or via any other suitable mode of communication.

The present invention can be implemented on a stand-alone computer or as part of a networked computer system. In a stand-alone computer, all the software and data can reside on local memory devices, for example an optical disk or flash memory device can be used to store the computer software for implementing the invention as well as the data. In alternative embodiments, the software or the data or both can be accessed through a network connection to remote devices. In one networked computer system embodiment, the invention use a client-server environment over a public network, such as the internet or a private network to connect to data and resources stored in remote and/or centrally located locations. In this embodiment, a server including a web server can provide access, either open access, pay as you go or subscription based access to the information provided according to the invention. In a client server environment, a client computer executing a client software or program, such as a web browser, connects to the server over a network. The client software or web browser provides a user interface for a user of the invention to input data and information and receive access to data and information. The client software can be viewed on a local computer display or other output device and can allow the user to input information, such as by using a computer keyboard, mouse or other input device. The server executes one or more computer programs that enable the client software to input data, process data according to the invention and output data to the user, as well as provide access to local and remote computer resources. For example, the user interface can include a graphical user interface comprising an access element, such as a text box, that permits entry of data from the assay, e.g., the DNA methylation data levels or DNA gene expression levels of target genes of a reference pluripotent stem cell population and/or pluripotent stem cell population of interest, as well as a display element that can provide a graphical read out of the results of a comparison with a score card, or data sets transmitted to or made available by a processor following execution of the instructions encoded on a computer-readable medium.

Embodiments of the invention also provide for systems (and computer readable medium for causing computer systems) to perform a method for determining quality assurance of a pluripotent stem cell population according to the methods as disclosed herein.

In some embodiments of the invention, the computer system software can include one or more functional modules, which can be defined by computer executable instructions recorded on computer readable medium and which cause a computer to perform a method according to the invention, when executed. The modules can be segregated by function for the sake of clarity, however, it should be understood that the modules need not correspond to discreet blocks of code and the described functions can be carried out by the execution of various software code portions stored on various media and executed at various times. Furthermore, it should be appreciated that the modules can perform other functions, thus the modules are not limited to having any particular function or set of functions. In some embodiments, functional modules for producing a deviation score card are, for example, but are not limited to, a storage module, a gene mapping module, a reference comparison module, a normalization module, a relevance filter module, a gene set module, and a scorecard display module to display the deviation scorecard. Functional modules for producing a lineage scorecard are, for example, but are not limited to, a storage device, an assay normalization module, a sample normalization module, a reference comparison module, a gene set module, an enrichment analysis module, and a scorecard display module to display the lineage scorecard. The functional modules can be executed using one or multiple computers, and by using one or multiple computer networks.

The information embodied on one or more computer-readable medium can include data, computer software or programs, and program instructions, that, as a result of being executed by a computer, transform the computer to a special purpose machine and can cause the computer to perform one or more of the functions described herein. Such instructions can be originally written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable medium on which such instructions are embodied can reside on one or more of the components of a computer system or a network of computer systems according to the invention.

In some embodiments, a computer-readable medium can be transportable such that the instructions stored thereon can be loaded onto any computer resource to implement the aspects of the present invention discussed herein. In addition, it should be appreciated that the instructions stored on computer readable medium are not limited to instructions embodied as part of an application program running on a host computer. Rather, the instructions can be embodied as any type of computer code (e.g., object code, software or microcode) that can be employed to program a computer to implement aspects of the present invention. The computer executable instructions can be written in a suitable computer language or combination of several languages. Basic computational biology methods are known to those of ordinary skill in the art and are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

In some embodiments, a system as disclosed herein, can receive gene expression level data of the set of developmental genes measured from an automated gene expression analysis system, e.g., an automated protein expression analysis including but not limited to mass spectrometry systems including MALDI-TOF, or Matrix Assisted Laser Desorption Ionization—Time of Flight systems; SELDI-TOF-MS ProteinChip array profiling systems, e.g. Machines with Ciphergen Protein Biology System II™ software; systems for analyzing gene expression data (see for example U.S. 2003/0194711); systems for array based expression analysis, for example HT array systems and cartridge array systems available from Affymetrix (Santa Clara, Calif. 95051) AutoLoader, Complete GeneChip® Instrument System, Fluidics Station 450, Hybridization Oven 645, QC Toolbox Software Kit, Scanner 3000 7G, Scanner 3000 7G plus Targeted Genotyping System, Scanner 3000 7G Whole-Genome Association System, GeneTitan™ Instrument, GeneChip® Array Station, HT Array; an automated ELISA system (e.g. DSX® or DK® form Dynax, Chantilly, Va. or the ENEASYSTEM III®, Triturus®, The Mago® Plus); Densitometers (e.g. X-Rite-508-Spectro Densitometer®, The HYRYS™ 2 densitometer); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, Becton Dickinson); radio isotope analyzers (e.g. scintillation counters).

In some embodiments of the present invention, the reference data can be electronically or digitally recorded, annotated and retrieved from databases including, but not limited to GenBank (NCBI) protein and DNA databases such as genome, ESTs, SNPS, Traces, Celara, Ventor Reads, Watson reads, HGTS, etc.; Swiss Institute of Bioinformatics databases, such as ENZYME, PROSITE, SWISS-2DPAGE, Swiss-Prot and TrEMBL databases; the Melanie software package or the ExPASy WWW server, etc., the SWISS-MODEL, Swiss-Shop and other network-based computational tools; the Comprehensive Microbial Resource database (The institute of Genomic Research). The resulting information can be stored in a relational data base that can be employed to determine homologies between the reference data or genes or proteins within in and among genomes.

In some embodiments, the gene expression levels of early developmental target genes in a pluripotent stem cell can be received from a memory, a storage device, or a database. The memory, storage device or database can be directly connected to the computer system retrieving the data, or connected to the computer through a wired or wireless connection technology and retrieved from a remote device or system over the wired or wireless connection. Further, the memory, storage device or database, can be located remotely from the computer system from which it is retrieved.

Examples of suitable connection technologies for use with the present invention include, for example parallel interfaces (e.g., PATA), serial interfaces (e.g., SATA, USB, Firewire,), local area networks (LAN), wide area networks (WAN), Internet, Intranet, and Extranet, and wireless (e.g., Blue Tooth, Zigbee, WiFi, WiMAX, 3G, 4G) communication technologies As used herein, "stored" refers to a process for recording information, e.g., data, programs and instructions, on the storage device, that can be read back at a later time. Those skilled in the art can readily adopt any of the presently known methods for recording information on known media to contribute to a reference scorecard data, e.g., the level of DNA methylation, and/or gene expression level, and/or differentiation propensity data of a pluripotent stem cell as disclosed in the methods herein.

A variety of software programs and formats can be used to store the lineage scorecard data and/or level of expression of early developmental genes and information on the storage device. Any number of data processor structuring formats (e.g., text file or database) can be employed to obtain or create a medium having recorded scorecard thereon.

In one embodiment, the reference scorecard data can be electronically or digitally recorded and annotated from databases including, but not limited to protein expression databases commonly known in the art, such as Yale Protein Expression Database (YPED), as well as GenBank (NCBI) protein and DNA databases such as genome, ESTs, SNPS, Traces, Celara, Ventor Reads, Watson reads, HGTS, and the like; Swiss Institute of Bioinformatics databases, such as ENZYME, PROSITE, SWISS-2DPAGE, Swiss-Prot and TrEMBL databases; the Melanie software package or the ExPASy WWW server, and the like; the SWISS-MODEL, Swiss-Shop and other network-based computational tools; the Comprehensive Microbial Resource database (available from The Institute of Genomic Research). The resulting information of the level of DNA methylation, and/or Gene expression level, and/or differentiation propensity data of a pluripotent stem cell line can be stored in a relational database that can be employed to determine differences as compared to different pluripotent stem cell populations, or compared to reference DNA methylation levels, reference Gene expression levels and reference propensity differentiation data between different pluripotent stem cell populations, e.g., ES cells, and iPS cells and piPS cells, and somatic stem cells, or among pluripotent stem cells of the same type (e.g., iPS cells) from different genomes, species and different populations of individuals.

In some embodiments, the system has a processor for running one or more programs, e.g., where the programs can include an operating system (e.g., UNIX, Windows), a relational database management system, an application program, and a World Wide Web server program. The application program can be a World Wide Web application that includes the executable code necessary for generation of database language statements (e.g., Structured Query Language (SQL) statements). The executables can include embedded SQL statements. In addition, the World Wide Web application can include a configuration file which contains pointers and addresses to the various software entities that provide the World Wide Web server functions as well as the various external and internal databases which can be accessed to service user requests. The Configuration file can also direct requests for server resources to the appropriate hardware devices, as can be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers. In other embodiments of the invention, other interfaces, such as HTTP, FTP, SSH and VPN based interfaces can be used to connect to the Internet databases.

In one embodiment, the system as disclosed herein can be used to compare gene expression profiles (e.g., gene expression profiles or levels of gene expression of a plurality of early developmental target genes). For example, the system can receive onto its memory gene expression profiles or data of the test pluripotent stem cell line and compare it with one or more stored gene expression profiles (e.g. the normal variation of early developmental gene expression in one or more reference pluripotent stem cell lines), or compare with one or more early developmental gene expression profiles from the pluripotent stem cell line previously analyzed at an earlier time point. In some embodiments, gene expression profiles can be obtained using Affymetrix Microarray Suite software version 5.0 (MAS 5.0) (available from Affymetrix, Santa Clara, Calif.) to analyze the relative abundance of a gene or genes on the basis of the intensity of the signal from probe sets, and the MAS 5.0 data files can be transferred into a database and analyzed with Microsoft Excel and Gene-Spring 6.0 software (available from Agilent Technologies, Santa Clara, Calif.). In some embodiments, a comparison algorithm of MAS 5.0 software can be used to obtain a comprehensive overview of how many transcripts are detected in given samples and allows a comparative analysis of 2 or more microarray data sets. In some embodiments however, only one data set is required (e.g., a set of early developmental genes is measured only once in a given pluripotent stem cell line, eliminating the cost, time and resources required for duplicate and triplicate data sets).

In some embodiments of this aspect and all other aspects of the present invention, the system can compare the data in a "comparison module" which can use a variety of available software programs and formats for the comparison operative to compare sequence information determined in the determination module to reference data. In one embodiment, the comparison module is configured to use pattern recognition techniques to compare sequence information from one or more entries to one or more reference data patterns. The comparison module can be configured using existing commercially-available or freely-available software for comparing patterns, and can be optimized for particular data comparisons that are conducted. The comparison module can also provide computer readable information related to the sequence information that can include, for example, determination of the concentration of a sequence in the sample (e.g. amino acid sequence/protein expression levels, or nucleotide (RNA or DNA) expression levels), or determination of a Gene expression profile.

In some embodiments, the system comprises comparison software which is used to determine whether the gene expression level data of early developmental genes for a pluripotent stem cell of interests falls outside a reference gene expression levels for that early developmental gene as disclosed herein, e.g., outside the normal variation of gene expression levels for the early developmental target genes) for a plurality of pluripotent stem cells. For example, where the gene expression level of an early developmental gene for a pluripotent stem cell of interest expression is higher by a statically significantly amount above a reference gene expression level for that early developmental gene, it indicates likelihood of expression of the early developmental target gene, and the software can be configured to signal (or otherwise indicate) the likelihood of optimal differentiation along that cell lineage.

By providing gene expression level data of early developmental genes in computer-readable form, one can use the gene expression level data for a pluripotent stem cell to compare with gene expression levels of early developmental genes of other pluripotent stem cells within the storage device. For example, search programs can be used to identify relevant reference data (i.e. reference expression levels of early developmental genes) that match the expression level of a same early developmental target gene for the pluripotent stem cell of interest. The comparison made in computer-readable form provides computer readable content which can be processed by a variety of means. The content can be retrieved from the comparison module, the retrieved content.

In some embodiments, the comparison module provides computer readable comparison result that can be processed in computer readable form by predefined criteria, or criteria defined by a user, to provide a report which comprises content based in part on the comparison result that can be stored and output as requested by a user using a display module. In some embodiments, a display module enables display of a content based in part on the comparison result for the user, wherein the content is a report indicative of the results of the comparison of the pluripotent stem cell of interest with a scorecard, or the utility of the pluripotent stem cell, e.g., expression levels of specific early developmental genes, e.g., early mesoderm genes and/or early ectoderm genes, and/or early endoderm genes, as well as expression of pluripotent stem cells.

In some embodiments, the display module enables display of a report or content based in part on the comparison result for the end user, wherein the content is a report indicative of the results of the comparison of the pluripotent stem cell of interest with a lineage scorecard, or the utility of the pluripotent stem cell, e.g., expression levels of specific early developmental genes, e.g., early mesoderm genes and/or early ectoderm genes, and/or early endoderm genes, as well as expression of pluripotent stem cells.

The computer instructions can be implemented in software, firmware or hardware and include any type of programmed step undertaken by modules of the information processing system. The computer system can be connected to a local area network (LAN) or a wide area network (WAN). One example of the local area network can be a corporate computing network, including access to the Internet, to which computers and computing devices comprising the data processing system are connected. In one embodiment, the LAN uses the industry standard Transmission Control Protocol/Internet Protocol (TCP/IP) network protocols for communication. Transmission Control Protocol Transmission Control Protocol (TCP) can be used as a transport layer protocol to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions, and multiplexing multiple connections through a single network connection. Finally, TCP is responsible for encapsulating information into a datagram structure. In alternative embodiments, the LAN can conform to other network standards, including, but not limited to, the International Standards Organization's Open Systems Interconnection, IBM's SNA, Novell's Netware, and Banyan VINES.

In some embodiments, the computer system as described herein can include any type of electronically connected group of computers including, for instance, the following networks: Internet, Intranet, Local Area Networks (LAN) or Wide Area Networks (WAN). In addition, the connectivity to the network can be, for example, remote modem, Ethernet (IEEE 802.3), Token Ring (IEEE 802.5), Fiber Distributed Datalink Interface (FDDI) or Asynchronous Transfer Mode (ATM). The computing devices can be desktop devices, servers, portable computers, hand-held computing devices, smart phones, set-top devices, or any other desired type or configuration. As used herein, a network includes one or more of the following, including a public internet, a private internet, a secure internet, a private network, a public network, a value-added network, an intranet, an extranet and combinations of the foregoing.

In one embodiment of the invention, the computer system can comprise a pattern comparison software can be used to determine whether the patterns of gene expression levels in a pluripotent stem cell line of interest are indicative of that cell line being an outlier and predictive of a stem cell line functioning outside the normal characteristics of reference pluripotent stem cell lines, or the likelihood of the pluripotent stem cell line having a low efficiency or increased efficiency of differentiating along a particular cell line of interest or having lost is pluripotent state. In this embodiment, the pattern comparison software can compare at least some of the data (e.g., gene expression levels of early developmental genes) of the pluripotent stem cell of interest with predefined patterns of gene expression levels (gene expression levels of early developmental target genes) of reference pluripotent stem cell lines to determine how closely they match. The matching can be evaluated and reported in portions or degrees indicating the extent to which all or some of the pattern matches.

In some embodiments of this aspect and all other aspects of the present invention, a comparison module provides computer readable data that can be processed in computer readable form by predefined criteria, or criteria defined by a user, to provide a retrieved content that can be stored and output as requested by a user using a display module.

Display Module

In accordance with some embodiments of the invention, the computerized system can include or be operatively connected to a display module, such as computer monitor, touch screen or video display system. The display module allows user instructions to be presented to the user of the system, to view inputs to the system and for the system to display the results to the user as part of a user interface. Optionally, the computerized system can include or be operative connected to a printing device for producing printed copies of information output by the system. In some embodiments, the display module is a computer screen present at the location of the end user, which is connected to a system or computer which is processed on a comparison module or computer located at a different location, e.g., on a server at a remote location, which is accesable to the user using a secure access via the internet or world wide web etc.

In some embodiments, the results can be displayed on a display module or printed in a report, e.g., a lineage scorecard report to indicate the utility of the pluripotent stem cell of interest, e.g., utility for a particular therapeutic use based on the likelihood of differentiating along a certain cell line lineage based on the data from the level of gene expression of early developmental genes in the pluripotent stem cell.

In some embodiments, the scorecard report is a hard copy printed from a printer. In alternative embodiments, the computerized system can use light or sound to report the scorecard, e.g., to indicate the quality and utility of a pluripotent stem cell line of interest. For example, in all aspects of the invention, the scorecard produced by the methods, differentiation assays, systems and present in the kits as disclosed herein can comprise a report which is color coded to signal or indicate the quality of the pluripotent stem cell of interest as compared to one or more reference pluripotent stem cell lines (e.g., the standard human ES cell lines and iPS cells as tested herein), or compared to another "gold" standard pluripotent stem cell line of the investigators' choice.

For example, a red color or other predefined signal can indicate that the pluripotent stem cell line is an outlier pluripotent stem cell line, and has one or more early developmental genes vary by a statistically significant amount as compared to levels in one or more reference pluripotent stem cell lines, thus signaling that the pluripotent stem cell line has different characteristics to the reference pluripotent stem cell lines, e.g., can have an increased or decreased predisposition to differentiate into a particular cell lineage. In another embodiment, a yellow or orange color or other predefined signal can indicate that the pluripotent stem cell line can have one early developmental genes which varies by a statistically significant amount as compared to levels in one or more reference pluripotent stem cell lines, thus signaling that the pluripotent stem cell line has slightly different characteristic to the reference pluripotent stem cell line(s), but that difference can not be important to the function, e.g., the pluripotent stem cell line of interest is still of the characteristic quality to be used, and does not have an altered predisposition to differentiate along a particular cell lineage etc. In another embodiment, a green color or other predefined signal can indicate that the pluripotent stem cell line is of high quality and the level of expression of the majority of a set of early developmental genes does not vary by a statistically significant amount as compared to levels in one or more reference pluripotent stem cell lines, thus signaling that the pluripotent stem cell line is of high quality and likely to have similar characteristic to the reference pluripotent stem cell line(s). In alternative embodiments, other signals or colors can be used to signal that a pluripotent stem cell has an increased propensity to differentiate along a particular cell lineage, e.g., a mesoderm lineage, or an ectoderm lineage or an endoderm lineage. Different signals or colors can be used to signal likely differentiation along each lineage.

In some embodiments, a "heat map" or gradient color scheme can be used in the report, e.g., scorecard report to signal the quality of the pluripotent stem cell line, for example, where the gradient is a red to yellow to green gradient, where a red signal will signal an inferior and/or poor quality, and a yellow signal will indicate a good quality and a green signal will indicate a high quality pluripotent stem cell of interest as compared to one or more reference pluripotent stem cell line(s). Colors between red and yellow and yellow and green will signal the characteristics of the pluripotent stem cell line with respect to a red-yellow-green scale. Other color schemes and gradient schemes in the report are also encompassed.

In some embodiments, the report indicates a plurality oft values for the expression level of a plurality of early developmental gene relative to a reference gene expression level for that early developmental gene. A t-value of 0-1 between the measured early developmental gene and the reference expression level for that early developmental gene indicates that the expression levels are comparable and not statistically significant. A t-value of >1 between the measured early developmental gene in the pluripotent stem cell and the reference expression level for that early developmental gene indicates that the expression level of the early developmental gene is higher in the pluripotent stem cell as compared to the reference expression level for that gene. A t-value of <0 between the measured early developmental gene in the pluripotent stem cell and the reference expression level for that early developmental gene indicates that the expression level of the early developmental gene is lower in the pluripotent stem cell as compared to the reference expression level for that gene.

In some embodiments, a report indicates a green signal or similar signal (e.g., upward arrow) where the t-value for the early developmental gene is >1, indicating that the level of the early developmental gene in the pluripotent stem cell is higher as compared to the reference level for that early developmental gene. In some embodiments, the report indicates a yellow signal or similar signal (e.g., horizontal arrow, an 45° upward or downward angled arrow) where the t-value for the early developmental gene is between 0-1, indicating that the level of the early developmental gene in the pluripotent stem cell is comparable with the reference level for that early developmental gene. In some embodiments, a report indicates a red signal or similar signal (e.g., downward arrow) where the t-value for the early developmental gene is <0, indicating that the level of the early developmental gene in the pluripotent stem cell is lower as compared to the reference level for that early developmental gene. In some embodiments, the report indicates the t-values, and/or a symbol (e.g., directional arrows) for each early developmental gene measured in the differentiation assay. In alternative embodiments, the report indicates a summary of the t-values for the pluripotent stem cell measured, for example, the median or average t-values for the early developmental genes in each category, e.g., pluripotent stem cell genes, early mesoderm genes, early ectoderm genes, early endoderm genes and the like.

Any method or t-test to calculate t values is encompassed for use in the methods and assays and systems as disclosed herein. In some embodiments, the ΔCt of the early developmental gene is compared with the reference ΔCt for the same early developmental gene in a t-test. The ΔCt for each early developmental gene expressed in the pluripotent stem cell line is determined by comparing the Ct level of the early developmental gene measured in the pluripotent stem cell line with the median Ct value for a control gene (e.g., ACTB) measured in the same pluripotent stem cell line.

In some embodiments, the report, e.g., lineage scorecard can display the total %, and/or absolute total number of early developmental genes which have a different level of gene expression as compared to the normal variation of early developmental gene expression. As an illustrative example only, the score card can indicate that the test pluripotent stem cell has 21% genes of the genes assessed expressed at a different level as compared to the normal variation, and also indicate that the normal variation (e.g., in a plurality of reference pluripotent stem cell lines).

In some embodiments, the report, e.g., scorecard, can display the normalized values of the test pluripotent stem cell line, which are normalized to a reference pluripotent stem cell line (e.g., a selected "gold" standard line of the investigators choice) or the normal variation in reference pluripotent stem cell lines. Accordingly, a scorecard can display the % difference, and/or the change in absolute number of early developmental genes which are differentially expressed as compared to the normal variation of early developmental gene expression levels. As an illustrative example only, the lineage scorecard can indicate that the test pluripotent stem cell has 20 total (or 22%) of the 90 early developmental genes assessed that have increased gene expression (e.g., a t-value of >1) as compared to the normal variation of the early developmental genes. In some embodiments, this can be broken up, such as in an exemplary example, to indicate that 12 of the 20 genes which are increased are characterized as mesoderm early developmental genes, 4 are characterized as endoderm early developmental genes, and 4 are characterized as ectoderm early developmental genes.

In an alternative embodiment, the report, e.g., lineage scorecard can display the % or relative differentiation propensities to differentiate along specific lineages, e.g., neuronal, endoderm, ectoderm, mesoderm, pancreatic, cardiac lineages etc.

In some embodiments, the report, e.g., scorecard can also present text, either verbally or written, giving a recommendation of which applications and/or utility the pluripotent cell line is appropriate for, and/or which applications and/or utility the pluripotent cell line is not appropriate for.

In some embodiments of this aspect and all other aspects of the present invention, the report data, e.g., a lineage scorecard from the comparison module can be displayed on a computer monitor as one or more pages of the printed report, e.g., scorecard. In one embodiment of the invention, a page of the retrieved content can be displayed through printable media. The display module can be any device or system adapted for display of computer readable information to a user. The display module can include speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc.

In some embodiments of the present invention, a World Wide Web browser can be used to provide a user interface to allow the user to interact with the system to input information, construct requests and to display retrieved content. In addition, the various functional modules of the system can be adapted to use a web browser to provide a user interface. Using a Web browser, a user can construct requests for retrieving data from data sources, such as data bases and interact with the comparison module to perform comparisons and pattern matching. The user can point to and click on user interface elements such as buttons, pull down menus, scroll bars, etc. conventionally employed in graphical user interfaces to interact with the system and cause the system to perform the methods of the invention. The requests formulated with the user's Web browser can be transmitted over a network to a Web application that can process or format the request to produce a query of one or more database that can be employed to provide the pertinent information related to the DNA methylation levels and gene expression levels, the retrieved content, process this information and output the results, e.g. at least one of any of the following: (i) display of the average or median t-value (and optionally a directional arrow) for early developmental genes in each category (e.g., pluripotent stem cell genes, early mesoderm genes, early ectoderm genes, early endoderm genes and the like); (ii) display of the t-value for each early developmental gene assessed (and optionally a directional arrow); (iii) display of number of early developmental genes (% and/or absolute numbers) with an t-value of >1 (e.g., higher expression as compared to the reference early gene expression level); (iv) display of number of early developmental genes (% and/or absolute numbers) with an t-value of <0 (e.g., lower expression as compared to the reference early gene expression level); (v) display of number of early developmental genes (% and/or absolute numbers) with an t-value of between 0-1 (e.g., comparable expression as compared to the reference early gene expression level)). In one embodiment, the gene expression level of early developmental genes of one or more reference pluripotent stem cell lines can also displayed.

Example Workflow of a High-Throughput Sample Processing to Produce a Deviation or Lineage Scorecard As an exemplary example, but by no way a limitation, a lineage scorecard workflow is illustrated by the following case study: An individual researcher or a large company (or foundation) plans to establish a stem cell bank providing HLA-matched iPS cell lines for X % of the US population, which requires 10,000 iPS cell lines. All cell lines will be commercially available, and to make the resource most valuable to researchers and companies, it is planned to publish scorecard characterizations for each cell line. To facilitate automatization, all iPS cell lines are grown in 96-well plates or 384-well plates. Most sample processing is robotized, and all cell lines are barcoded and tracked by a central LIMS. The scorecard characterization is performed as follows:

(1) Deviation scorecard/confirmation of pluripotency: A researcher loads a liquid-handling robot as follows: (i) one 96-well or 384-well plate with one iPS cell line per well; (ii) 96-well or 384-well mRNA extraction kit, (iii) custom qPCR plates (96-well or 384-well) with pre-spotted probes (e.g., oligonucleotides and/or primers) that are specific to at least 20-genes listed in Table 1 and at least 1 oligonucleotide (or primer pair) that is specific for at least one control gene.

(2) A robot performs RNA extraction of the entire plate and pipettes the RNA from each well into separate qPCR plates (when using 96-well qPCR plates) or into ¼ of a plate (when using 384-well qPCR plates). Reverse transcription is performed in the same plate, and barcoded Ct tables are transferred to computer readable media on the computer.

(3) Lineage scorecard/quantification of differentiation potential: For example, starting from a 96-well plate with one iPS cell line per well, a researcher will harvest the cells from each well and plate them into a new 96-well plate.

(4) After a defined period of time (e.g. n days) of culture of the pluripotent stem cells, the plates are loaded into a liquid-handling robot and qPCR analysis is performed as described in steps 1 and 2, with the only exception that custom qPCR plates with early differentiation-specific marker genes are used.

(5) Upon completion of the experiments, the researcher loads the unprocessed Ct values into a custom lineage scorecard software. This software imports the output data format from any of the common qPCR machines, performs relative normalization using a number of house-keeping genes and calculates the scorecard prediction.

(6) Gene set selection. As disclosed herein, the lineage scorecard requires the measurement of the expression level of a set of early developmental markers. In some embodiments, the assay for generation of data for the deviation scorecard can consist of a single 96-well qPCR plate (or in some embodiments, four samples on a 384-well qPCR plate) with the most relevant genes for determining whether or not a given cell line classifies as pluripotent. In some embodiments, the assay for generation of data for the lineage scorecard can consist of two 96-well plates (or in some embodiments, two samples on a 384-well qPCR plate) with the most relevant genes for quantifying the differentiation propensities of a given cell line.

In some embodiments, the optimal gene selection of the early developmental genes for the lineage scorecards using a multiplex qPCR assay can be further validated and optimized. While replicates are not necessary in the present invention, in some embodiments, multiple plates are used for the differentiation assay of each cell line, which includes plates for each biological stem cell line of interest in replicate, plates for a stem cell line in its pluripotent state and one for the stem cell line in its EB state. In some embodiments, genes to be included in such a 384-well qPCR plate ("tech-dev plate") can be selected using the following gene set selection:

1. Normalization: Each plate contains at least 1 normalization gene. These can be in duplicate, can be a positive control or negative control. Control normalization genes which can be used can be selected from, for example, ACTB, JARID2, CTCF, SMAD1, GAPDH and β-actin. In some embodiments, the plate comprises at least 2 control genes.

2. Supported cell types/lineages: Early developmental genes can be selected which are expressed after at least 2 days of the pluripotent stem cell in culture (e.g., 2D EB) and identify subsequent differentiation of the pluripotent stem cell into ectoderm, mesoderm and endoderm germ layers as well as the neural and hematopoietic lineages. In some embodiments, these genes are selected from those listed in Table 1, and can optionally include additional early developmental genes not in Table 1. In some embodiments, a subset of the early developmental genes assessed is the same as those on the NanoString nCounter Gene Expression Code Assay (available from NanoString Technologies) for the qPCR-based scorecard (ectoderm, mesoderm and endoderm germ layers as well as the neural and hematopoietic lineages). In addition, in some embodiments, the list of early developmental genes can comprise additional categories of early developmental gene sets, including but not limited to early developmental genes for a: pluripotent cell signature, epidermis, mesenchymal stem cells, bone, cartilage, fat, muscle, blood vessel, heart, lymphoid cells, myeloid cells, liver, pancreas, epithelium, motor neurons, monocytes-macrophages.

Validation: In some embodiments, one can validate a qPCR plate for assays for producing data for a lineage scorecard. Validation can be performed in three phases. During an initial validation phase, one will assess the qPCR plate to determine if it provides similar accuracy and predictive power as the NanoString nCounter Gene Expression Code Assay (available from NanoString Technologies). A second biological validation phase can be performed which will assess and confirm the predictiveness of the qPCR-based lineage scorecard for many more pluripotent stem cell lines and the propensity of the stem cell assessed to differentiate into a variety of different lineages of interest. A final assay validation can be performed which will optimize the qPCR plate for technical consistency with all earlier data. More specifically, in some embodiments, a validation phases will be conducted as follows:

1. Technical qPCR assay validation. One can directly compare the results from a NanoString-based scorecard with a qPCR-based lineage scorecard as disclosed herein, comparing the accuracy, sensitivity and robustness of each gene between the NanoString and the qPCR platform. Furthermore, one can also confirm that the qPCR-based lineage scorecard is able to predict cell-line specific differences in the efficiency of, for example, directed differentiation on a particular lineage (e.g., ectoderm, endoderm or mesoderm lineage).

2. Biological qPCR assay validation and extension of scope. The inventors have extensively validated the lineage scorecard for predicting the differentiation of pluripotent stem cells into all three germ lines by at least 2 days in culture (e.g., 2D EB). Accordingly, one can validate the lineage scorecard predictability using several different culture media, as well as RNA preparations, culture conditions etc., to quantitatively determine the efficiencies and consistency predicting the differentiation potential of pluripotent stem cells into various different lineages. Furthermore, one can validate the qPCR differentiation assays using at least about 100 or more pluripotent stem cell lines, for example, selected from but not limited to, human pluripotent cell lines, partially reprogrammed cell lines, embryonic cancer cell lines etc., in order to calibrate the lineage scorecard. Such validation can be used to optimize and redesign the qPCR-based lineage scorecard assay for large-scale production, and for example, tailor it to a particular stem cell line or lineage preference.

3. Technical validation. In some embodiments, further validation can be desired to validate software and assay handling for a qPCR differentiation assay. For example, stability of the plates, ease of reading the output from the qPCR plates and the like can be optimized. Approaches for such validation and optimization are known by persons of ordinary skill in the art.

Algorithm and Methods of Bioinformatic Analysis for Producing a Score Card for a Pluripotent Stem Cell Line.

As discussed herein, the lineage scorecard as disclosed herein relates to the expression of a plurality of early developmental genes in an differentiation expression assay (e.g., identifying the differentially regulated (e.g., unregulated and/or downregulated) early developmental genes in a stem cell line, e.g., a pluripotent stem cell line, as compared to the normal variation of expression level for the set of early developmental genes in reference pluripotent cell lines.

Many different ways to determine the extent of the different gene expression of early developmental genes as compared to the reference level of the early developmental gene expression are encompassed for use in the methods and systems as disclosed herein. Accordingly, different bioinformatic methods in order to obtain a practically useful indication of a pluripotent cell line's quality and utility are encompassed.

For example, in some embodiments, the differentiation assay need not be done in replicate. For instance, a t-test can be used to calculate t values of the differential expression of an early expression gene in the pluripotent stem cell as compared to the reference level of expression of the early developmental gene. Accordingly, in some embodiments, the $\Delta Ct$ of the early developmental gene is compared with the reference $\Delta Ct$ for the same early developmental gene in a t-test. Any method to calculate the t-value is encompassed for use in the methods and assays and systems as disclosed herein. Other statistical tests can also be used (e.g. Fisher's exact test, ANOVA). The $\Delta Ct$ for each early developmental gene expressed in the pluripotent stem cell line is determined by comparing the Ct of the early developmental gene measured in the pluripotent stem cell line with the median Ct value for a control gene (e.g., ACTB) measured in the same pluripotent stem cell line.

As disclosed in the Examples, a scorecard as disclosed herein summarizes if one or more stem cell lines of interest, e.g., a pluripotent stem cell lines, deviates from one or more reference pluripotent cell lines with respect to expression of early developmental genes. As used herein, a reference pluripotent cell line can be any number of ES cells of interest. In alternative embodiments, a reference pluripotent cell line is used as a basis of the gene expression levels of early developmental genes for normal ranges for a number of iPSC and/or ES cells, for example, at least about 10- or at least about 20 low passage ES cell lines as used herein in the Examples.

Lineage Scorecard Calculation

A lineage scorecard as disclosed herein quantifies the differentiation propensity and/or pluripotency of a stem cell line of interest relative to one or more reference pluripotent stem cell lines, e.g., high quality and/or low-passage pluripotent stem cell lines, such as the reference values for the 19 low-passage ES cell lines as used herein in the Examples. One algorithm for calculating the lineage scorecard uses a combination of moderated t-tests (Smyth, 2004) and gene set enrichment analysis performed on t-scores (Nam and Kim, 2008; Subramanian et al., 2005).

To provide a biological basis for quantifying lineage-specific differentiation propensities, the inventors created several sets of early developmental genes for each of the three germ layers (ectoderm, mesoderm, endoderm) as well as for the neural and hematopoietic lineages. In some instances, Bioconductor's Limma™ package can be used to perform moderated t-tests comparing the gene expression in the EBs obtained for the cell line of interest to the EBs obtained for the ES cell reference, and the mean t-scores were calculated across all genes that contribute to a relevant gene set. High mean t-scores (e.g., >1) indicate increased expression of the gene set's genes in the tested EBs and are considered indicative of a high differentiation propensity for the corresponding lineage. In contrast, low mean t-scores (e.g., <0) indicate decreased expression of relevant genes and are considered indicative of a low differentiation propensity for the corresponding lineage. To increase the robustness of the analysis, the mean t-scores can be averaged over all gene sets assigned to a given lineage. The lineage scorecard diagrams (FIG. 4-7) list these "means of gene-set mean t-scores" as quantitative indicators of cell-line specific differentiation propensities. The lineage scorecard analyses and validations can be performed using custom R scripts (see the world wide web at "r-project.org/").

As demonstrated herein in the Examples section, expression of early developmental genes can be used as a reliable and robust test for predicting the differentiation potential of a pluripotent stem line into a particular cell lineage.

An algorithm for calculating the lineage scorecard includes the following steps:

(i) Data Import:

Import gene expression data of at least 20 early developmental genes selected from any combination of genes listed in Table 1 from (i) at least 2 day embryoid bodies (2D EBs) of the pluripotent stem cell of interest, and (ii) at least one, or at least about 5, or at least about 10 or more embryoid bodies at the same time point (e.g., 2 day embryoid bodies (2D EBs)) from reference pluripotent stem cell lines (e.g., pluripotent stem cell lines which are used as high quality reference pluripotent stem cell control cell lines). In some embodiments, the gene expression data is microarray data.

(ii) Optional Step of Assay Normalization:

Use positive spike-in controls to calculate an assay normalization factor and rescale the data accordingly. In some embodiments the spike-in normalization is needed for each experiment or replicate experiment.

(iii) Sample Normalization:

Perform variance stabilization and normalization across all experiments. In some embodiments, variance stabilization and normalization can be performed by readily available software by one of ordinary skill in the art, such as Bioconductor's VSN package).

(iv) Reference Comparison:

Compare the normalized gene expression values for each early developmental gene (e.g., from any combination of genes listed in Table 1) of EBs from each pluripotent stem cell line of interest with the and normalized gene expression values for the same early developmental genes in the EBs of the reference pluripotent stem cell lines at the same time point (e.g., at least 2 days in EB; 2D EBs). In some embodiments, statistical analysis is used for the comparison, for example use of a moderated t-test for each marker gene to compare the level of the expression of the early developmental gene in pluripotent stem cell lines of interest with the reference expression levels of the same set of early developmental genes values obtained from a plurality of reference high-quality EBs. In some embodiments, a statistical package such as, for example, using Bioconductor's limma package can be used.

(v) Gene Sets:

Load early developmental gene sets containing relevant genes that are characteristic and predictive of the pluripotent stem cell differentiating along a specific cellular lineage or germ layer of interest.

(vi) Enrichment Analysis:

For each early developmental gene set, calculate the mean t-scores of all marker genes that belong to each set.

(vii) Lineage Scorecard Report:

For each pluripotent stem cell line of interest, list the mean of the t-scores for all the relevant early development gene sets (e.g., early mesoderm genes, early endoderm genes, early ectoderm genes), to provide a lineage scorecard estimate for the lineage that the pluripotent stem cell will differentiate into (See FIGS. 4, 5, 6 and 7A-7C for example).

Bioinformatics Analysis and Data Access

In addition to method-specific data normalization and the calculation of the scorecard (described above), bioinformatics analyses of the data set can be conducted as follows:

(i) Hierarchical Clustering.

Hierarchical clustering can be performed as disclosed herein using the gene expression levels (e.g., for each Ensembl gene by averaging over all associated probes on the microarray). Prior to hierarchical clustering, one can separately normalize each of the two datasets separately to zero mean and unit variance in order to give equal weight to both datasets.

(ii) Annotation Clustering and Promoter Characteristics.

One can identify common characteristics among the most variable genes using commonly available software packages, such as, for example, DAVID (Huang et al., 2007) and EpiGRAPH (Bock et al., 2009) with default parameters and based on Ensembl gene annotations (promoters were defined as the −5 kb to +1 kb sequence window surrounding the transcription start site).

(iii) Classification of ES Vs. iPS Cell Lines.

One can easily validate ES and iPS gene signatures using the mean expression levels of the early developmental genes in a given signature. Logistic regression can be used to select a discriminatory threshold, and the predictiveness of each signature can be evaluated by leave-one-out cross-validation. To derive new classifiers, support vector machines can be trained on, e.g., gene expression data.

(iv) Linear Models of Epigenetic Memory.

One can also generate linear models of early developmental gene expression levels. For example, as disclosed herein, two alternative linear models can be constructed for gene expression. One model can be used to regress the iPS-cell specific mean gene expression levels of each gene on the ES-cell specific mean gene expression levels. A second model regresses the iPS-cell specific mean gene expression levels of each gene on the ES-cell specific and the fibroblast-specific mean gene expression levels.

Gene expression analysis can also be performed by a number of methods. Typical example include, but are not limited to, gene expression microarrays, cDNA and RNA sequencing, imaging-based methods such as NanoString and a wide range of methods that use PCR as well as qPCR. Normalization for these methods has been widely described. In some embodiments, a gcRMA algorithm can be used for normalizing Affymetrix microarray data. In some embodiments one can use a VSN algorithm for normalizing NanoString data or the data from an array as disclosed herein.

In some embodiments, gene expression is determined on any gene level, for example, the expression of non-coding genes, microRNA genes and all other types of RNA transcripts that are normally or abnormally present in pluripotent and differentiated cells.

Once the gene expression data are normalized, genes of relevance for cell line quality and utility are identified using standard methods for detecting differential gene expression between samples and/or groups of samples. Examples include t-test and its variants, non-parametric alternatives of the t-test, and ANOVA. In some embodiments, the limma package is encompassed for use in the methods and systems as disclosed herein, which implements a moderated t statistic.

While the differentiation gene expression assay as described above focuses mostly on the effect of single genes, in some embodiments, the lineage scorecard uses the combination of data for multiple genes to predict a cell line's quality and utility. This is the most critical and bioinformatically complex step for the creation of a lineage scorecard.

In some embodiments, the information from multiple genes is currently aggregated by mean and standard deviation calculations; however, by using statistical learning methods such as support vector machines, linear and logistic regression, hierarchical models, Bayesian algorithms and the like the effect of aggregation can be reduced. Any mathematical function that takes multiple measurements of candidate gene expression into account to produce a numeric or categorical value that describes an aspect of pluripotent cell quality and utility could be considered a predictor and an element of the scorecard as disclosed herein.

Importantly, these mathematical functions will in many cases take prior biological knowledge into account. In particular, the inventors have curated a substantial number of early developmental gene sets from the literature, from public databases and from functional genomics data to inform these predictors. In one embodiment of the lineage scorecard, one can use gene expression data from either the pluripotent cell or its differentiating progeny to assign differential expression scores to each gene, and then use the resulting t-scores to perform a (parametric or non-parametric) gene set enrichment analysis for sets of early developmental genes that represent the three germ layers as well as other interesting cell types, cellular pathways and networks, as well as other functionally or otherwise defined sets of genes.

While the bioinformatic methods described above were applied in the Examples herein, they can also be applied directly to the gene expression analysis of early developmental genes of pluripotent cells, and it is also possible to induce the pluripotent cell lines to differentiate such that certain aspects of their quality and utility become more evident. This can be performed using a wide range of perturbations, from simple growth factor withdrawal and physical manipulation (as used herein for undirected embryoid body differentiation) over a wide range of chemical, peptide and protein treatments (often in combination) to the plating on dedicated surfaces and the induced expression of specific genes.

One can analyze the gene expression data of a plurality of early developmental genes using a variety of methods, for example, as disclosed in Harr et al., Nucleic acid research, 2006; 34(2): e8, "Comparison of algorithms for the analysis of Affymetrix microarray data as evaluated by co-expression of genes in known operons", and in the book entitled "Methods in microarray normalization" Edited By Phillip Stafford, Drug Discovery Series/10, published by CRC Press (which are incorporated herein in its entirety by reference). The gcRMA algorithm (GC [GC content} robust multichip analysis (RMA)) uses both the quantile normalization and medium polish summarization methods of the RMA algorithm. A stochastic model can be used to describe the observed PM and MM probe signals for each probe pair on an array. One particular models is:

$$PM_{\mu i} = 0_{ni} + N_{1ni} + S_{ni}$$

$$NM_{ni} = 0_{ni} + N_{2ni}$$

Where $0_{ni}$ represents the optical noise, $N_1$ and $N_2$ represents nonspecific binding, and $S_{nj}$ is a quantity proportion to the RNA expression in the sample. In addition, the model assumes O follows a normal distribution $N(\mu 0, \sigma^2_0)$ and that $\log_2 (N_{1ni})$ and $\log_2 (N_{2ni})$ follow a bivariate-normal distribution with equal variances $\sigma^2_N$ and correlation 0.7, constant across probe pairs. The means of the distribution for the nonspecific binding terms are dependent on the probe sequence. The optical noise and nonspecific binding terms are assumed to be independent.

The method by which gcRMA includes information about the probe sequence is to compare an affinity based on the sum of position-dependent base affinities. In particular, the affinity of a probe is given by:

$$A = \sum_{k=1}^{25} \sum_{b \in (A,C,G,T)} \mu b(k) 1 \beta_k = j$$

where the $\mu_b(k)$ are modeled as spline functions with 5 degrees of freedom. In practice, µb(k) for a single microarray (e.g., U113A microarray chips) are either estimated using the observed data for all chips in an experiment or based on some hard-coded estimates from a specific NSB experiment carried out by the creators of gcRMA. This means for the $N_1$ and $N_2$ random variables in the gcRMA model are modeled using a smooth function h of the probe affinities.

The optical noise parameters $\mu_o$, $\sigma^2_o$ are estimated as follows: The variability due to optical noise is so much smaller than the variability due to the nonspecific binding and thus effectively constant. For simplicity this is set to 0. The mean values are estimated using the lowest PM or MM probe intensities on the array, with a correlation factor to avoid negatives. Next, all probe intensities are correlated by subtracting this constant $\mu_o$. To estimate $h(A_{ni})$ a Loess curve fit to a scatterplot is used relating the corrected log(MM) intensities to all the MM probe affinities. The negative residuals from this Loess plot are used to estimate $\sigma^2_N$. Finally, the background adjustment procedure for gcRMA is to compute the expected value of S given the observed PM, MM and model parameters. Note, that although gcRMA uses the medium polish summarization of RMA, the PLM summarization approach should not be used in its place if one wants to carry out quality assessment, although the expression estimates generated in this way are otherwise satisfactory.

In some embodiments, one can also use other methods for gene expression normalization, for example, the MAS5.0 algorithm (Microarray suite 5.0) or the RMA algorithm (robust multichip analysis), which are explained in detail in the "Method for microarray normalization" edited by Phillip Stafford.

Statistical Methods

Methods for statistical clustering and software for the same are discussed below. For example, one parameter used in quantifying the differential expression of early developmental genes is the fold change, which is a metric for comparing a gene's mRNA-expression level between two distinct experimental conditions. Its arithmetic definition differs between investigators. However, the greater the fold change the more likely that the differential expression of the relevant genes will be adequately separated, rendering it easier to decide which category the pluripotent stem cell falls into.

The fold change for an upregulated gene can be, for example, at least 1.4, at least 1.5, at least 1.6, at least 1.7, at least 1.8, at least 1.9 or at least 2.0 or more log-2 change. In one embodiment, in which the expression level is measured using PCR, the fold change is at least 2.0.

The fold change for a down-regulated gene can be 0.6 or less than 0.6, for example it can be 0.5 or less than 0.5, 0.4 or less than 0.4, 0.3 or less than 0.3, 0.2 or less than 0.2 or can be 0.1 or less than 0.1 log-2 change. Accordingly, a fold change of 0.1 indicates that the expression of a gene is down-regulated 10 times. A fold change of 2.0 indicates that the expression of a gene is upregulated 2 times.

For example: If the fold change of the expression of an early developmental target gene in a pluripotent stem cell is =2.0 (as compared to the normal variation of gene expression of that gene), it indicates that the gene is an "outlier" gene. Similarly, if the fold change of the expression of an early developmental target gene in a pluripotent stem cell is =0.5 (as compared to the normal variation of gene expression of that gene) of a gene=0.5, it indicates that the gene is an outlier gene. The higher number of early developmental genes in the test pluripotent stem cell line which are "outlier" genes indicates that the pluripotent stem cell line can have particular propensity to differentiate along specific lineages. For example, if the test pluripotent stem cell has at least about 10 outlier early developmental genes, the pluripotent stem cell line is identified as being an outlier pluripotent stem cell line and can have an increased efficiency or low efficiency to differentiate along a particular lineage.

Alternatively, if the fold change of the expression of an early developmental target gene in a pluripotent stem cell indicates a t-value of 0-1, the pluripotent stem cell is comparable with the pluripotent stem cell. A t-value of >1 indicates that expression of the measured early developmental gene is higher than the reference gene expression level of the same gene or group of genes in the same category, and that the pluripotent stem cell differs from a reference pluripotent stem cell line (e.g., is an outlier pluripotent stem cell). Such a pluripotent stem cell line will likely differentiate along the lineage of the category to which the early developmental gene belongs (e.g., endoderm, ectoderm or mesoderm lineages). A t-value of <0 indicates that expression of the measured early developmental gene is lower than the reference gene expression level of the same gene or group of genes in the same category, and that the pluripotent stem cell is an outlier in that it differs from a reference pluripotent stem cell line. Such a pluripotent stem cell line will likely not differentiate along the lineage of the category to which the early developmental gene belongs (e.g., endoderm, ectoderm or mesoderm lineages). The particular propensity of a pluripotent stem cell can be determined on the basis of exactly which genes or subgroups of genes are outliers.

Another parameter also used to quantify differential expression is the "p" value. It is thought that the lower the p value the more differentially expressed the gene is likely to be, indicating that the gene is an outlier gene as compared to the normal variation of gene expression in a pluripotent stem cell. p values can for example include 0.1 or less, such as 0.05 or less, in particular 0.01 or less. p values as used herein include corrected p values and/or also uncorrected p values.

Uses of the Scorecards.

In some embodiments, the methods, differentiation assays, systems, kits and lineage scorecards as disclosed herein can be used in a variety of ways clinically and in research applications. For instance, methods, differentiation assays, systems, kits and lineage scorecards as disclosed herein are useful for identifying the propensity of a pluripotent stem cell line to differentiate along a particular lineage in response to a drug, or for selecting a plurality of stem cell lines, e.g., a pluripotent stem cell lines that have the same properties to be used in a drug screen, which is useful to ensure the quality of the drug screen and ensure that any potential hits are the effect of the drug rather than due to variations in the different stem cell lines. In some embodiments, the aspects as disclosed herein are useful for identifying and selecting a stem cell line, e.g., a pluripotent stem cell line which would be suitable for therapeutic use, e.g., stem cell therapy or other regenerative medicine, to ensure that the stem cell line has the propensity to differentiate along a desired cell lineage and not differentiate along an undesired cell lineage. Similarly, aspects as disclosed herein are useful for characterizing and validating an iPSC generated from a mammal, e.g., a human, to ensure that the iPSC possesses desired qualities, and can be compared to other pluripotent stem cells.

In some embodiments, the methods, differentiation assays, systems, kits and lineage scorecards as disclosed herein can be used in clinics to determine clinical safety and utility of a particular pluripotent stem cell line.

In some embodiments, the methods, differentiation assays, systems, kits and lineage scorecards as disclosed herein can be used as a quality control to monitor the characteristics of a stem cell line, e.g., a pluripotent stem cell line, over multiple passages and/or before and after cryopreservation procedures, for example, to ensure that no significant epigenetic or functional genomic changes have occurred over time (e.g., over passages and after cryopreservation). For example, the methods, systems, kits and scorecards as disclosed herein can be used to characterize all stem cells in a stem cell bank, to catalogue each stem cell line which is placed in the bank, and to ensure that the stem cells have the same properties after thawing as they did prior to cryopreservation.

In some embodiments, the raw data (e.g., early developmental gene expression data) and/or lineage scorecard data for each stem cell line can be stored in a centralized database, where the data and/or scorecard can be used to select a pluripotent stem cell line for a particular use or utility. Accordingly, one aspect of the present invention relates to a database comprising at least one of: early developmental gene expression data, and lineage scorecard for a plurality of stem cell lines, e.g., pluripotent stem cell lines, and in some embodiments, the database comprises the early developmental gene expression data, and/or lineage scorecard for a plurality of stem cell lines, e.g., pluripotent stem cell lines in a stem cell bank.

In some embodiments, the methods, differentiation assays, systems, kits and lineage scorecards as disclosed herein can be used in research to monitor functional genomic changes as a stem cell line, e.g., a pluripotent stem cell line, differentiates along different lineages. In some embodiments, aspects as disclosed herein can be used to monitor and determine the characteristics of stem cell lines from subjects with particular diseases, e.g., one can monitor stem cell lines, e.g., pluripotent stem cell lines from subjects with genetic defects or particular genetic polymorphisms, and/or having a particular disease. For example, one can monitor and determine the functional genomic differences between an iPSC cell derived from a subject with a neurodegenerative disease, such as ALS, as compared to a normal iPSC cell from a healthy subject (or a non-ALS subject), such as a healthy sibling. Similarly, one can determine if iPS cells are comparable in functional genomics and/or differentiation propensity as compared to ES cells or other pluripotent stem cells. Additionally, the aspects as disclosed herein can fully characterize the pluripotency of a stem cell line without the need for teratoma assays and/or generation of chimera mice, therefore significantly increasing the high-throughput ability of characterizing pluripotent stem cell lines.

In some embodiments, the lineage scorecard can be included in an "all-included" kit for making and validating patient-specific iPS-cell lines. For example, in such an embodiment, the kit can comprise (i) a sample collection device, e.g., needle or tube as required for collecting patient somatic or differentiated cells, and in some embodiments, a patient consent form, (ii) reagents for reprogramming the patients' collected somatic or differentiated cell into an iPS cell, e.g., where the kit comprises any number or combination of reprogramming factors, such as virus/DNA/RNA/protein as described herein, and ES-cell media), and (iii), the differentiation assays for generating a lineage scorecard as disclosed herein, e.g., reagents for measuring the gene expression of a plurality of early developmental genes. In some embodiments, the kit can comprise one or more reference pluripotent stem cell lines, which can be used as a positive control (or a negative control, e.g., where the pluripotent stem cell line has been identified with an undesirable characteristic) as a quality control for the kit. In some embodiments, the kit can also comprise a reference lineage scorecard of one or more reference pluripotent stem cell lines to be used, for example, for comparison purposes for with the stem cell line being tested, e.g., a patient iPS cell line being assessed. In some embodiments, the "all-included" kit can be used for utility prediction of the patient iPS cell line based on the results from the quality control (e.g., as determined by the bioinformatic determination as disclosed herein). In some embodiments, an "all-included" kit can also additionally comprise the materials, reagents and protocols for directed differentiation of the newly generated patient iPS cell line into a particular cell type of interest (e.g., cardiomyocytes, beta cells, hepatocytes, hair follicle stem cells, cartilage, pancreatic cells (including beta-cells), hematopoietic cells, and the like).

In some embodiments, the methods, differentiation assays, systems, kits and lineage scorecards as disclosed herein can be used to provide a service, such as a "cell-to-quality assured pluripotent stem cell line" service, which can be carried out, for example, directly in a clinic, or in a clinical diagnostics lab, or as a mail-in service carried out by a dedicated facility. For example, such a service would operate in which an investigator, or a patient sends a pluripotent stem cell or, in some embodiments, somatic cells (e.g., differentiated cells) into the service provider, whereby if somatic cells are sent, the service provider generates iPS cell lines from the somatic cells using commonly known methods as disclosed herein. The service provider performs methods, differentiation assays, systems, kits and lineage scorecards as disclosed herein on the investigator-provided, or generated pluripotent iPS cell lines, for example, the service provider will perform (i) the differentiation assay (e.g., measure the gene expression of a plurality of early developmental genes), and subsequently perform the analysis to generate a lineage scorecard for each individual iPS cell analyzed. The service provider can also optionally suggest the suitability of one or more selected iPS cell lines for a particular use, e.g., the service provider can suggest "iPS cell line 1" which was identified to have a high efficiency of differentiating along endoderm differentiation pathways would be suitable for differentiation into pancreatic cells, or similarly the service provider can suggest "iPS cell line 2" which was identified to have a high efficiency of differentiating along hepatic lineages would be suitable for differentiation into liver cells for use in liver cell regenerative medicine. Similarly, the service provider can suggest "iPS cell line 6" which was identified to have decreased pluripotent stem cell genes, can not be suitable for therapeutic uses in regenerative medicine due to a risk of potential cancer formation. In some embodiments, the service provider does not make a recommendation, but rather provide a report of the scorecard for each iPS cell line generated and analyzed by the service provider. In some embodiments, the service provider returns the iPS cell lines to the investigator, or patient with a copy of the report scorecard.

In some embodiments, the methods, differentiation assays, systems, kits and lineage scorecards as disclosed herein can be used in creating a database, where such a database would be useful in organizing and cataloguing a pluripotent stem cell repository, e.g., a central repository (e.g., a tissue and/or cell bank) containing a large number of quality-controlled and utility-predicted pluripotent cell lines, such that one can use a database comprising the data of each scorecard for each pluripotent stem cell line in the bank to specifically select a particular pluripotent stem cell line for the investigators' intended use. For example, a user of the database can click a "suggest best cell line for my application" button on the website linked to the database, and obtain information and the identity of a number useful cell lines for the investigator's particular use. In some embodiments, the use of such a database can be easily extended such that a user can upload the data from the array or assays as disclosed herein (e.g., gene expression data) for a particular pluripotent stem cell type of interest. This data can be run through the scorecard algorithm as disclosed herein and the results compared with the database scorecard results for the pluripotent stem cell bank. In a simple analogy, the database could function similar to Google's "search for similar sites", whereby the database could be used as an efficient way to select useful cell lines for novel and/or mixed tissue types, or to identify pluripotent stem cell lines in a cell bank that can have potential to differentiate into a desired differentiated stem cell line.

In some embodiments, the methods, differentiation assays, systems, kits and lineage scorecards as disclosed herein can be used for identification and selection of a desired stem cell line, e.g., a pluripotent stem cell line for mass production, for example use of the methods, assays and scorecards as disclosed herein to identify and characterize and validate the quality of stem cell lines that grow well and/or efficiently in large quantities, e.g., large batch cultures or in bioreactors, and selection of stem cell lines that can be differentiated efficiently in bulk cultures into a specific cell type.

In another embodiment, methods, differentiation assays, systems, kits and lineage scorecards as disclosed herein can be used for selection of a stem cell line based on properties of pluripotent robustness. For example, the methods, differentiation assays, systems, kits and lineage scorecards as disclosed herein can be used to identify a stem cell line, e.g., a pluripotent stem cell line which is easy to culture in vitro (e.g., require little attention, and/or do not readily spontaneously differentiate, and/or maintain the pluripotency properties). For example, in some embodiments, a stem cell line can be assessed using the methods, assays and lineage scorecards prior to culturing, and then at different time points during and/or after culturing, and under different culture conditions and/or media conditions to identify one or more stem cell lines which maintain their initial qualities in short- and/or long-term culture conditions.

In another embodiment, the methods, differentiation assays, systems, kits and lineage scorecards as disclosed herein can be used for selection of a stem cell line, e.g., a pluripotent stem cell line for drug responsiveness, for example, a stem cell line can be assessed using the methods, assays and scorecards as disclosed herein prior to, during, and after contacting with a drug or other agent or stimulus (e.g., electric stimuli for cardiac pluripotent progenitors) to generate a drug metabolism and/or pharmacogenomics signature of the stem cell line. This can be used to identify stem cell lines which can be particularly useful for drug screening and drug discovery, including, for example drug toxicity assays.

In another embodiment, the methods, differentiation assays, systems, kits and lineage scorecards as disclosed herein can be used for selection of a stem cell line, e.g., a pluripotent stem cell line, based on its safety profile. For example, a stem cell line can be assessed using the methods, differentiation assays, systems, kits and lineage scorecards as disclosed herein to identify its likelihood the stem cell will differentiate into a particular cell type, or likelihood to dedifferentiate, which is very useful in validating the safety of a stem cell line or its differentiated progeny in clinical applications, such as cell replacement therapy and regenerative medicine.

In another embodiment, the methods, differentiation assays, systems, kits and lineage scorecards as disclosed herein can be used for selection of a stem cell line, e.g., a pluripotent stem cell line for efficacy. For example, one can use a lineage scorecard prediction of a particular pluripotent stem cell line to predict whether, and/or how well (e.g., how efficiently) differentiated cells derived from the stem cell line will continue to differentiate along a particular desired cell lineage, and/or if they will proliferate once implanted into a subject, e.g., a human patient or in an animal model (e.g., a rat or mouse disease model etc.). More generally, in some embodiments, a lineage scorecard can be used to predict not only the behavior of a stem cell line, but also that of differentiated cells that are directly or indirectly derived from the stem cell line.

In another embodiment, the methods, differentiation assays, systems, kits and lineage scorecards as disclosed herein can be used for selection of a stem cell line, e.g., a pluripotent stem cell line which has the same or very similar characteristics of a pluripotent stem cell in vivo (e.g., to select pluripotent stem cell which are a truthful representation of the cell in an in vivo environment). For example, a stem cell line can be assessed using the methods, differentiation assays, systems, kits and lineage scorecards as disclosed herein to identify a stem cell line suitable for disease modeling, as it is important to use stem cell lines that closely resemble their corresponding cells in vivo. Accordingly, one of ordinary skill in the art can use the lineage scorecard as disclosed herein to predict which stem cell line, e.g., which pluripotent cell line best resembles their corresponding cells in vivo, e.g. by comparing the properties (listed on the scorecard) of the stem cell line with corresponding cells harvested from a subject (e.g. an animal model, or disease model such as a rodent disease model), to minimize deviations from the stem cell line as compared to how the cell behaves in vivo.

In another embodiment, the methods, differentiation assays, systems, kits and lineage scorecards as disclosed herein can be used for selection and/or quality control, and/or validation of a stem cell line in different or new states of pluripotency or multipotency, for example to provide information regarding which stem cell lines are useful for differentiating and making cell types in vitro but do not fall under the usual definition of human ES cell lines (e.g., human ground-state ES cell and partially reprogrammed cell lines, e.g., partially induced pluripotent stem (piPS) cells, which are capable of being reprogrammed further to a pluripotent stem cell).

It has been shown that continued in vitro culture and passaging improves the quality of iPS cell lines (see Polo et al., Nat Biotechnol. 2010 August; 28(8):848-55, and Nat Rev Mol Cell Biol. 2010 September; 11(9):601, and Nat Rev Genet. 2010 September; 11(9):593). On the other hand, continued passaging is expensive. Accordingly, in some embodiments, the methods, differentiation assays, systems, kits and lineage scorecards as disclosed herein can be used for measuring how much passaging is sufficient for improving the quality of the stem cell line, e.g., the pluripotent stem cell line.

In further embodiments, the methods, differentiation assays, systems, kits and lineage scorecards as disclosed herein can be used in a variety of different research and clinical uses to characterize, monitor and validate stem cell lines, e.g., pluripotent stem cell lines. For example, typical application includes in areas such as, but not limited to, (i) labs and/or companies interested in disease mechanisms (e.g., using the kits or services as disclosed herein to reduce the complexity of generating iPS cell lines, as well as differentiated cells for disease modeling and small-scale drug screening, (ii) labs and/or companies trying to identify small molecules and/or biologicals for a given disease target (e.g., using the kits and/or services as disclose herein to enable the production of large numbers of highly standardized cells for drug screening), (iii) clinical and pre-clinical research groups for quality control and validating stem cell lines where they are interested in producing cells for implantation into humans or animals (e.g., using a kit and/or service as disclosed herein to permits quality control at a level of accuracy that will be sufficient for regulatory approval, e.g., FDA approval), (iv) tissue banks that desire to give their customers information, including advice and data about the performance, quality and utility of the stem cell lines, e.g., pluripotent stem cell lines on offer (e.g., using a kit and/or service as disclosed herein to provide unbiased assessment of the quality and/or utility of a large number of pluripotent cell lines, in an inexpensive high throughput manner, —it is contemplated that the assays can ultimately be performed on 1,000-100,000s of pluripotent stem cell lines to cover the whole population of cell lines stored in the cell bank), (v) private consumers who desire to generate, and optionally, bank at least one or more stem cell lines, e.g., pluripotent stem cell lines, e.g., iPS cell lines (or piPS cell lines) generated from their somatic differentiated cells, either for themselves and/or their children or other offspring, for example, as a type of health insurance policy for future regenerative medicine purposes.

Stem Cells for Analysis of Early Developmental Gene Expression and for Generating a Reference Lineage Scorecard.

As disclosed herein, the gene expression of a set of early developmental genes can be used to validate and monitor any stem cell line, from any species, e.g. a mammalian species, such as a human. In some embodiments, the present invention specifically contemplates using the arrays, assays and methods as disclosed herein to determine if a stem cell is pluripotent. Any type of stem cell can be assessed. For simplicity, when referring to analysis of a pluripotent stem cell herein, this encompasses analysis of both pluripotent and non-pluripotent stem cells.

In some embodiments, the stem cell is a pluripotent stem cell. Generally, a pluripotent stem cell to be analyzed according to the methods described herein can be obtained or derived from any available source. Accordingly, a pluripotent cell can be obtained or derived from a vertebrate or invertebrate. In some embodiments, the pluripotent stem cell is mammalian pluripotent stem cell. In all aspects as disclosed herein, pluripotent stem cells for use in the methods, assays and to generate scorecards or to compare with an existing scorecard as disclosed herein can be any pluripotent stem cell.

In some embodiments, the pluripotent stem cell is a primate or rodent pluripotent stem cell. In some embodiments, the pluripotent stem cell is selected from the group consisting of chimpanzee, cynomologous monkey, spider monkey, macaques (e.g. Rhesus monkey), mouse, rat, woodchuck, ferret, rabbit, hamster, cow, horse, pig, deer, bison, buffalo, feline (e.g., domestic cat), canine (e.g. dog, fox and wolf), avian (e.g. chicken, emu, and ostrich), and fish (e.g., trout, catfish and salmon) pluripotent stem cell.

In some embodiments, the pluripotent stem cell is a human pluripotent stem cell. In some embodiments, the pluripotent stem cell is a human stem cell line known in the art. In some embodiments, the pluripotent stem cell is an induced pluripotent stem (iPS) cell, or a stably reprogrammed cell which is an intermediate pluripotent stem cell and can be further reprogrammed into an iPS cell, e.g., partial induced pluripotent stem cells (also referred to as "piPS cells"). In some embodiments, the pluripotent stem cell, iPSC or piPSC is a genetically modified pluripotent stem cell.

In some embodiments, the pluripotent state of a pluripotent stem cell used in the present invention can be confirmed by various methods. For example, the pluripotent stem cells can be tested for the presence or absence of characteristic ES cell markers. In the case of human ES cells, examples of such markers include SSEA-4, SSEA-3, TRA-1-60, TRA-1-81 and OCT 4, and are known in the art.

While the methods of the present invention allow the pluripotency (or lack thereof) to be assessed by measuring the level of expression of a subset of early pluripotent genes listed in Table 1 of a stem cell which is at least 2 days in culture, if necessary, the pluripotency of a stem cell line can also be confirmed by injecting the cells into a suitable animal, e.g., a SCID mouse, and observing the production of differentiated cells and tissues. Still another method of confirming pluripotency is using the subject pluripotent cells to generate chimeric animals and observing the contribution of the introduced cells to different cell types. Methods for producing chimeric animals are well known in the art and are described in U.S. Pat. No. 6,642,433, which is incorporated by reference herein.

Yet another method of confirming pluripotency is to observe ES cell differentiation into embryoid bodies and other differentiated cell types when cultured under conditions that favor differentiation (e.g., removal of fibroblast feeder layers). This method has been utilized and it has been confirmed that the subject pluripotent cells give rise to embryoid bodies and different differentiated cell types in tissue culture.

In this regard, it is known that some mouse embryonic stem (ES) cells have a propensity of differentiating into some cell types at a greater efficiency as compared to other cell types. Similarly, human pluripotent (ES) cells can possess selective differentiation capacity. Accordingly, the present invention can be used to identify and select a pluripotent stem cell with desired characteristics and differentiation propensity for the desired use of the pluripotent stem cell. For example, where the pluripotent cell line has been screened according to the methods of the invention, a pluripotent stem cell can be selected due to its increased efficiency of differentiating along a particular cell line, and can be induced to differentiate to obtain the desired cell types according to known methods. For example, a human pluripotent stem cell, e.g., a ES cell or iPS cell can be induced to differentiate into hematopoietic stem cells, muscle cells, cardiac muscle cells, liver cells, islet cells, retinal cells, cartilage cells, epithelial cells, urinary tract cells, etc., by culturing such cells in differentiation medium and under conditions which provide for cell differentiation, according to methods known to persons of ordinary skill in the art. Medium and methods which result in the differentiation of ES cells are known in the art as are suitable culturing conditions.

One can use any method for reprogramming a somatic cell to an iPS cell or an piPS cell, for example, as disclosed in International patent applications; WO2007/069666; WO2008/118820; WO2008/124133; WO2008/151058; WO2009/006997; and U.S. Patent Applications US2010/0062533; US2009/0227032; US2009/0068742; US2009/0047263; US2010/0015705; US2009/0081784; US2008/0233610; U.S. Pat. No. 7,615,374; U.S. patent application Ser. No. 12/595,041, EP2145000, CA2683056, AU8236629, 12/602,184, EP2164951, CA2688539, US2010/0105100; US2009/0324559, US2009/0304646, US2009/0299763, US2009/0191159, the contents of which are incorporated herein in their entirety by reference. In some embodiments, an iPS cell for use in the methods as described herein can be produced by any method known in the art for reprogramming a cell, for example virally-induced or chemically induced generation of reprogrammed cells, as disclosed in EP1970446, US2009/0047263, US2009/0068742, and 2009/0227032, which are incorporated herein in their entirety by reference. In some embodiments, iPS cells can be reprogrammed using modified RNA (mod-RNA) as disclosed in US2012/0046346, which is incorporated herein in its entirety by reference.

In some embodiments, an iPS cell for use in the methods, differentiation assays and to generate lineage scorecards or to compare with an existing lineage scorecard as disclosed herein can be produced from the incomplete reprogramming of a somatic cell by chemical reprogramming, such as by the methods as disclosed in WO2010/033906, the content of which is incorporated herein in its entirety by reference. In alternative embodiments, the stable reprogrammed cells disclosed herein can be produced from the incomplete reprogramming of a somatic cell by non-viral means, such as by the methods as disclosed in WO2010/048567 the contents of which is incorporated herein in its entirety by reference.

Other stem cells for use in the methods as disclosed herein can be any stem cell known to persons of ordinary skill in the art. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including methods for isolating and culturing them, can be found in, among other places, Embryonic Stem Cells, Methods and Protocols, Turksen, ed., Humana Press, 2002; Weisman et al., Annu. Rev. Cell. Dev. Biol. 17:387 403; Pittinger et al., Science, 284:143 47, 1999; Animal Cell Culture, Masters, ed., Oxford University Press, 2000; Jackson et al., PNAS 96(25): 14482 86, 1999; Zuk et al., Tissue Engineering, 7:211 228, 2001 ("Zuk et al."); particularly Chapters 33 41; and U.S. Pat. Nos. 5,559,022, 5,672,346 and 5,827,735. Descriptions of stromal cells, including methods for isolating them, can be found in, among other places, Prockop, Science, 276:71 74, 1997; Theise et al., Hepatology, 31:235 40, 2000; Current Protocols in Cell Biology, Bonifacino et al., eds., John Wiley & Sons, 2000 (including updates through March, 2002); and U.S. Pat. No. 4,963,489.

Additional pluripotent stem cells for use in the methods, differentiation assays and to generate lineage scorecards or to compare with an existing lineage scorecard as disclosed herein can be any cells derived from any kind of tissue (for example embryonic tissue such as fetal or pre-fetal tissue, or adult tissue), which stem cells have the characteristic of being capable under appropriate conditions of producing progeny of different cell types that are derivatives of all of the 3 germinal layers (endoderm, mesoderm, and ectoderm). These cell types can be provided in the form of an established cell line, or they can be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). In some embodiments, an embryo has not been destroyed in obtaining a pluripotent stem cell for use in the methods, assays, systems and to generate scorecards or to compare with an existing scorecard as disclosed herein.

In another embodiment, the stem cells, e.g., adult or embryonic stem cells can be isolated from tissue including solid tissues (the exception to solid tissue is whole blood, including blood, plasma and bone marrow) which were previously unidentified in the literature as sources of stem cells. In some embodiments, the tissue is heart or cardiac tissue. In other embodiments, the tissue is for example but not limited to, umbilical cord blood, placenta, bone marrow, or chondral villi.

Stem cells of interest for use in the methods, assays, systems and to generate scorecards or to compare with an existing scorecard as disclosed herein also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2): 205-16; etc.).

Therapeutic Uses

Various disease and disorders have been suggested as potential targets for stem cell therapy, such as cancer, diabetes, cardiac failure, muscle damage, Celiac Disease, neurological disorder, neurodegenerative disorder, and lysosomal storage diseases, as well as, any of the following diseases, ALS, Parkinson, monogenetic diseases and Mendelian diseases, ageing, general wear and tear of the human body, rheumatic arthritis and other inflammatory diseases, birth defects, etc. Accordingly, the assays, methods, systems and kits of the invention can be used to select a stem cell line, e.g., a pluripotent stem cell line, for administering to a subject for treatment or for development of fully or partially differentiated cells for transplantation.

Therefore, in one aspect the invention provides for a method of treatment, prevention, or amelioration of disease or disorder in a subject, the method comprising administering to the subject a pluripotent stem cell, or fully or partially differentiated cells derived from pluripotent cells, and differentiated cells obtained by other methods that involve reprogramming (e.g. transdifferentiation), wherein the stem cell is selected by methods and assays that measure the gene expression of a set of early developmental genes as disclosed herein. Without limitation, a pluripotent stem cell can be treated for differentiation along a specific lineage before administration to a subject.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but can not be a complete cure for the disease. As used herein, the term "treatment" includes prophylaxis. Alternatively, treatment is "effective" if the progression of a disease is reduced or halted. In some embodiments, the term "treatment" can also mean prolonging survival as compared to expected survival if not receiving treatment. Those in need of treatment include those already diagnosed with a disease or condition, as well as those likely to develop a disease or condition due to genetic susceptibility or other factors which contribute to the disease or condition, such as a non-limiting example, weight, diet and health of a subject are factors which can contribute to a subject likely to develop diabetes mellitus. Those in need of treatment also include subjects in need of medical or surgical attention, care, or management. The subject is usually ill or injured, or at an increased risk of becoming ill relative to an average member of the population and in need of such attention, care, or management.

Routes of administration suitable for the methods of the invention include both local and systemic administration or transplantation. Generally, local administration results in of the cells being delivered to a specific location as compared to the entire body of the subject, whereas, systemic administration results in delivery of the cells to essentially the entire body of the subject. Exemplary modes of administration include, but are not limited to, injection, infusion, instillation and inhalation. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

One preferred method of administration is transplantation of such a pluripotent cell, or differentiated progeny derived from the pluripotent stem cell, in a subject. The term "transplantation" includes, e.g., autotransplantation (removal and transfer of cell(s) from one location on a patient to the same or another location on the same patient), allotransplantation (transplantation between members of the same species), and xenotransplantation (transplantations between members of different species). The ordinary skilled artisan is well aware of methods for implanting or transplantation of cells for treatment of various disease, which are amenable to the present invention.

As used herein, the terms "administering," "introducing" and "transplanting" are used interchangeably in the context of the placement of reprogrammed cells as disclosed herein, or their differentiated progeny into a subject, by a method or route which results in at least partial localization of the reprogrammed cells, or their differentiated progeny at a desired site. The reprogrammed cells, or their differentiated progeny can be administered directly to a tissue of interest, or alternatively be administered by any appropriate route which results in delivery to a desired location in the subject where at least a portion of the reprogrammed cells or their progeny or components of the cells remain viable. The period of viability of the reprogrammed cells after administration to a subject can be as short as a few hours, e.g. twenty-four hours, to a few days, to as long as several years.

In the context of administering a pluripotent stem cell, the term "administering" also include transplantation of such a cell in a subject. As used herein, the term "transplantation" refers to the process of implanting or transferring at least one cell to a subject. The term "transplantation" includes, e.g., autotransplantation (removal and transfer of cell(s) from one location on a patient to the same or another location on the same patient), allotransplantation (transplantation between members of the same species), and xenotransplantation (transplantations between members of different species).

For administration to a subject, the pluripotent stem cells can be provided in pharmaceutically acceptable compositions. These pharmaceutically acceptable compositions comprise one or more of the pluripotent cells, formulated together with one or more pharmaceutically acceptable carriers (additives) and/or diluents.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), involved in carrying or transporting the stem cell from one organ, or portion of the body, to another organ, or portion of the body. Each carrier must be "acceptable" in the sense of being compatible with the other ingredients of the formulation and not injurious to the patient. The terms such as "excipient", "carrier", "pharmaceutically acceptable carrier" or the like are used interchangeably herein.

The pluripotent stem cell, or its differentiated progeny, can be administrated to a subject in combination with a pharmaceutically active agent. As used herein, the term "pharmaceutically active agent" refers to an agent which, when released in vivo, possesses the desired biological activity, for example, therapeutic, diagnostic and/or prophylactic properties in vivo. It is understood that the term includes stabilized and/or extended release-formulated pharmaceutically active agents. Exemplary pharmaceutically active agents include, but are not limited to, those found in *Harrison's Principles of Internal Medicine*, $13^{th}$ Edition, Eds. T. R. Harrison et al. McGraw-Hill N.Y., NY; Physicians Desk Reference, $50^{th}$ Edition, 1997, Oradell N.J., Medical Economics Co.; Pharmacological Basis of Therapeutics, $8^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

As used herein, a "subject" means a human or animal. A subject can be one who has been previously diagnosed with or identified as suffering from or having a disorder characterized with a disease for which a stem cell based therapy would be useful. A subject can be one who is not currently being treated with a stem cell based therapy.

In some embodiments of the aspects described herein, the method further comprising selecting a subject with a disease that would benefit from a stem cell based therapy.

As used herein, the term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuro-inflammatory and demyelinating states or diseases such as leukoencephalopathies, and leukodystrophies. Exemplary, neurodegenerative disorders include, but are not limited to, AIDS dementia complex, Adrenoleukodystrophy, Alexander disease, Alpers' disease, Alzheimer's disease, Amyotrophic lateral sclerosis, Ataxia telangiectasia, Batten disease, Bovine spongiform encephalopathy, Canavan disease, Corticobasal degeneration, Creutzfeldt-Jakob disease, Dementia with Lewy bodies, Fatal familial insomnia, Frontotemporal lobar degeneration, Huntington's disease, Infantile Refsum disease, Kennedy's disease, Krabbe disease, Lyme disease, Machado-Joseph disease, Multiple sclerosis, Multiple system atrophy, Neuroacanthocytosis, Niemann-Pick disease, Parkinson's disease, Pick's disease, Primary lateral sclerosis, Progressive supranuclear palsy, Refsum disease, Sandhoff disease, Diffuse myelinoclastic sclerosis, Spinocerebellar ataxia, Subacute combined degeneration of spinal cord, Tabes dorsalis, Tay-Sachs disease, Toxic encephalopathy, and Transmissible spongiform encephalopathy.

Drug Screening and Other Uses

The characterization of the differentiation potential of a plurality of stem cell lines, e.g., pluripotent stem cell lines, by measuring the gene expression of a set of early developmental genes as disclosed herein can be used to develop in vitro assays based on such characterized pluripotent stem cell lines. Existing assays for drug screening/testing and toxicology studies have several shortcomings because they can include pluripotent stem cells which are poorly characterized and/or pluripotent stem cell lines which are abnormal or deviate from a typical pluripotent stem cell line in terms of its differentiation capacity and potential. Accordingly, by measuring the gene expression of a set of early developmental genes as disclosed herein, one can identify and choose and/or validate a stem cell line suitable for use in the assay that can differentiate along a lineage which is phenotypic of a disease. In addition to, or alternatively, measuring the gene expression of a set of early developmental genes in a pluripotent stem cell line as disclosed herein can be used to identify and/or validate the stem cell line as one that can differentiate into an organ, and/or tissue lineage, or a part thereof. Such identified stem cells then can be chosen for use in screening assays to screen a test compound and or in disease modeling assays.

Furthermore, the flurry of new information now available on the molecular and cellular level related to human diseases makes it crucial to develop and test hypotheses about pathogenetic interrelations. The experimental access to specific cell types from all developmental stages and even from blastocysts deemed to harbor pathology based on pre-implantation genetic diagnosis can be useful in modeling and understanding aspects of human disease. Thus, such cell lines would also be valuable for the testing of drugs.

Accordingly, the present invention provides methods and assays for screening a test compound for biological activity, the method comprising: (a) obtaining a stem cell, e.g., a pluripotent stem cell, wherein the stem cell is identified and validated for differentiation along a specific lineage; (b) optionally causing or permitting the stem cell to differentiate to the desired specific lineage; (c) contacting the stem cell with a test compound; and (d) determining any effect of the compound on the level of gene expression of a set of early developmental genes in the stem cell as compared to in the absence of the compound. The effect on the stem cell can be one that is observable directly or indirectly by use of reporter molecules.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell morphology, or a combination thereof. In some instances, a biological activity can refer to the ability of a test compound to produce a toxic effect in a biological sample.

As discussed above, the specific lineage can be a lineage which is phenotypic and/or genotypic of a disease. Alternatively, the specific lineage can be lineage which is phenotypic and/or genotypic of an organ and/or tissue or a part thereof.

As used herein, the term "test compound" refers to the collection of compounds that are to be screened for their ability to have an effect on the cell. Test compounds can include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and commercially available. A comprehensive list of compound libraries can be found at http://www.broad.harvard.edu/chembio/platform/screening/compound_libraries/index.htm. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Without limitation, the compounds can be tested at any concentration that can exert an effect on the cells relative to a control over an appropriate time period. In some embodiments, compounds are tested at concentration in the range of about 0.01 nM to about 1000 mM, about 0.1 nM to about 500 µM, about 0.1 µM to about 20 µM, about 0.1 µM to about 10 µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a pharmaceutical company can perform as many as 100,000 assays per day in parallel.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Uses to Optimize Differentiating Media and Differentiation Factors.

In some embodiments, the characterization of the differentiation potential of a plurality of stem cell lines, e.g., pluripotent stem cell lines, by measuring the gene expression of a set of early developmental genes as disclosed herein can be used to develop in vitro assays based on such characterized stem cell lines. Accordingly, by measuring the gene expression of a set of early developmental genes as disclosed herein, one can identify and choose and/or validate and/or optimize a differentiation media and/or or differentiation factors which increase the efficiency of a stem cell line to differentiate along a particular cell-type lineage. By way of an exemplary example only, in some embodiments, the arrays, assays and methods as disclosed herein can be used to confirm that mesoderm early developmental markers as disclosed herein are being expressed in a stem cell line cultured in a mesoderm induction medium. Such identified media and/or differentiation factors then can be chosen for use in differentiation protocols to differentiate stem cell line along a particular lineage. Alternatively, in some embodiments, the arrays, assays and methods as disclosed herein can be used to confirm that a stem cell media, e.g., a pluripotent stem cell media maintains a stem cell in a pluripotent state and does not induce the cell line to differentiate along a particular lineage, for example, by measuring a set of early gene expression markers in the stem cell line cultured in the test pluripotent media as disclosed herein and checking that the levels of the measured early developmental markers do not differ by a statistically significant amount as compared to a reference level for the measured early developmental markers, or the mean level of measured early developmental markers in a plurality of reference pluripotent stem cell lines.

EXAMPLES

Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

The developmental potential of human pluripotent stem cells suggests that they can produce disease-relevant cell types for biomedical research as well as cells for transplantation to address a disease. However, substantial variation has been reported among pluripotent cell lines, which could affect their utility and clinical safety. Such cell-line specific differences must be better understood before one can confidently use embryonic stem (ES) or induced pluripotent stem (iPS) cells in translational research. Towards this goal, the inventors have established genome-wide reference maps of developmental gene expression for 20 previously derived human ES lines and 12 human iPS cell lines, and have measured the in vitro differentiation propensity of these cell lines. This resource enabled the inventors to assess the epigenetic and transcriptional similarity of ES and iPS cells and to predict the differentiation efficiency of individual cell lines. The combination of assays yields a scorecard for quick and comprehensive characterization of pluripotent cell lines.

Pluripotent cell lines are valuable tools for disease modeling, drug screening and regenerative medicine. However, current validation assays of the differentiation potential of human pluripotent cell lines are cumbersome and not always accurate, take a long time and cannot be performed before about 7 days of embryonic age, which tends to slow down research and has led to some confusion about the potency of human iPS cells. To systematically address these issues, the inventors have established a set of early differentiation marker genes to identify the differentiation potential of a stem cell population at a very early stage of development. Such a quantitative differentiation assay assesses the differentiation propensities of these cell lines as early as 2-days in EB forming conditions (e.g., EB day 2). Using this dataset, the inventors quantified the deviation of each ES or iPS cell line from the ES-cell reference, giving rise to a scorecard of cell line quality and utility, particularly with respect to the stem cell line's differentiation capacity and the lineage the cell line is most applicable for. The inventors validated this scorecard by showing that it accurately predicts cell-line specific differences in the expression of early developmental markers for endoderm, ectoderm and mesoderm cell lineages, as well as decrease in pluripotent stem cell markers at a developmental stage as early as 2 days. In summary, the inventors have developed methods, systems and kits for a rapid, cost effective, high-throughput characterization of the differentiation potential of human pluripotent cell lines using gene expression of early developmental markers on a stem cell line as early as developmental stage of 2 days.

Methods

ES and iPSC Cell Lines and Culture Conditions

A total of 20 human ES cell lines, 13 human iPS cell lines and 6 primary fibroblast cell lines were included in the current study. The ES cell lines were obtained from the Human Embryonic Stem Cell Facility of the Harvard Stem Cell Institute (17 ES cell lines) and from WiCell (3 ES cell lines). The iPS cell lines were derived by retroviral transduction of OCT4, SOX2 and KLF4 in dermal fibroblasts. The fibroblasts were derived by skin puncture from the forearm of each respective donor and grown as previously described (Dimos et al., 2009). All pluripotent cell lines have been characterized by conventional methods (Chen et al., 2009; Cowan et al., 2004, Boulting et al., submitted), confirming that they qualify as pluripotent according to established standards (Maherali and Hochedlinger, 2008). The pluripotent stem cells were grown in human ES media consisting of KO-DMEM (Invitrogen), 10% KOSR (Invitrogen), 10% plasmanate (Talecris), 1% glutamax or L-glutamin, non-essential amino acids, penicillin/streptomycin, 0.1% 2-mercaptoethanol and 10-20 ng/ml bFGF. Cultures were grown on a monolayer of irradiated CF1-MEFs (GlobalStem) and passaged using trypsin (0.05%) or dispase (Invitrogen). Before collection of DNA and RNA for analysis, ES and iPS cells were either isolated by trypsin (0.05%) or dispase treatment, or plated on matrigel (BD Biosciences) for one passage and fed with human ES media conditioned in CF1-MEFs for 24 h.

Differentiation Protocols

A total of five ES/iPS cell differentiation protocols were used in the current study:

(i) Non-Directed EB Differentiation.

Undifferentiated cells were harvested using dispase or trypsin and plated in suspension in low-adherence plates in the presence of human ES cell culture media without bFGF and plasmanate. Cell aggregates (EBs) were allowed to grow for a total of 16 days, refreshing media every 48 h.

(ii) Monocyte/Macrophage Differentiation.

Undifferentiated cells were treated with multiple recombinant proteins following a published protocol for hematopoietic differentiation (Grigoriadis et al., 2010). Briefly, feeder depleted pluripotent cells were grown as small aggregates in suspension in 6-well low attachment plates (Corning) in StemPro-34 medium (Invitrogen) containing penicillin/streptomycin, glutamine (2 mM), monothioglycerol (0.0004M), ascorbic acid (50 m/ml) (Sigma-Aldrich) and BMP4 (10 ng/ml) (R&D Systems) for 24 h. To induce primitive streak/mesoderm formation, EBs were washed and cultured further in the StemPro-34 differentiation medium, supplemented with human recombinant bFGF (5 ng/ml) (Millipore) for another 3 days. At day 4, EBs were harvested again and cultured in the differentiation medium described above, additionally containing hVEGF (10 ng/ml) (PeproTech), hbFGF (1 ng/ml), hIL-6 (10 ng/ml) (PeproTech), hIL-3 (40 ng/mL) (PeproTech), hIL-11 (5 ng/mL) (PeproTech), and human recombinant SCF (100 ng/mL) (PeproTech) for another 4 days to induce hematopoietic specification. From day 8 onwards, cells were further cultured in StemPro-34 medium, containing hVEGF (10 ng/ml), human erythropoietin (4 U/ml) (Cell Sciences), human thrombopoietin (50 ng/ml) (Cell Sciences), and human stem cell factor, hIL-6, hIL-11, and hIL-3 to promote hematopoietic cell maturation and expansion.

(iii) Mesoderm Differentiation.

Undifferentiated cells were treated with Activin A and BMP4 according to a published protocol that fosters mesoderm differentiation (Laflamme et al., 2007). Briefly, cells were harvested by incubation with collagenase IV (Invitrogen) and plated onto a Matrigel-coated cell culture dish. To induce mesoderm differentiation, cells were cultured in RPMI-B27 medium (Invitrogen) supplemented with human recombinant Activin A (100 ng/ml) (R&D Systems) for 24 h. Human recombinant BMP4 (10 ng/ml) was added to the medium for four days, after which cells were fed further with supplement-free RBMI-B27 medium.

(iv) Ectoderm Differentiation.

Undifferentiated cells were harvested by incubation with collagenase IV (Invitrogen) and plated onto a Matrigel-coated cell culture dish. Cells were grown in KO-DMEM (Invitrogen) medium, containing knockout serum replacement (Invitrogen), supplemented with Noggin (500 ng/ml) (R&D Systems) and SB431542 (10 µM) (Tocris).

(v) Motor Neuron Differentiation.

Undifferentiated cells were differentiated following a published protocol (DiGiorgio et al., 2008), as described in more detail by Boulting et al. (submitted).

Gene Expression Profiling

Gene Expression of the set of genes in Table 1 was performed by RT-PCR analysis. To identify gene in which a given cell line deviates from the reference of all human ES cell lines sample, the inventors performed a moderated t-test as implemented in the limma package (Smyth, 2005), comparing the cell line of interest to the reference of all human ES cell lines included in this study (but excluding the cell line that is being tested). All statistical analyses were performed using the R statistics package (world-wide web at: r-project.org/) and the source code is available on request from the authors.

Quantitative RT-PCR Analysis

Total RNA was isolated using RNeasy kit (Qiagen) according to manufacturer's recommendation followed by cDNA synthesis using standard protocols. Briefly, cDNA was synthesized using Superscript II Reverse Transcriptase (Invitrogen) and Random Hexamers (Invitrogen) with 500 ng of total RNA input. SYBR Green PCR master mix (Applied Biosystems) was used for qPCR analysis, which was done on a StepOnePlus real time PCR system (Applied Biosystems). PCR conditions were as follow: 94° C. initial denaturation for 5 min, 94° C. 15 s, 60° C. 15 s, 72° C. 30 s for 40 cycles, and 72° C. for 10 min Relative quantification was calculated using the comparative threshold cycle ($\Delta\Delta$ Ct) method.

Quantitative Embryoid Body Assay and Lineage Scorecard

For embryoid body differentiation, ES/iPS cells were treated with dispase or trypsin and plated in suspension in low-adherence plates in the presence of human ES culture media without bFGF and plasmanate. Cell aggregates or embryoid bodies were allowed to grow for at least 2 days, refreshing media every 48 h. After 2 days, cells were lysed and total RNA was extracted using Trizol (Invitrogen), followed by column clean-up using RNeasy kit (Qiagen). Subsequently, 300 to 500 ng of RNA was used for analysis on the NanoString nCounter system according to manufacturer's instructions. 100 genes that were selected for their ability to monitor cell state, pluripotency and differentiation into mesoderm, ectoderm and endoderm lineages at an early developmental stage were selected. Data analysis was performed in much the same way as normal quantitative PCR using TaqMan assay is performed. Specifically, the inventors used a moderated t-test to compare the gene expression in the embryoid bodies for the cell line of interest to the reference of all ES-cell derived embryoid bodies included in this study (but excluding the cell line that is being tested). To prepare for gene set testing, the inventors calculated the mean and standard deviation of the t-scores over the early developmental genes in each subgroup (e.g., ectoderm, endoderm and mesoderm lineage subgroups). Next, the inventors calculated the mean t-score separately for all gene sets that were defined a priori, and the inventors performed a parametric test against the mean over all genes as described previously (Kim 2005). For the lineage scorecard diagram, the inventors plotted the signed difference between the gene test mean and the global mean of the t-scores independent of significance, averaged over all contributing gene sets.

Lineage Scorecard Calculation

The lineage scorecard quantifies the differentiation propensity of a cell line of interest relative to a reference constituted by 19 low-passage ES cell lines (Table 4). The algorithm for calculating the lineage scorecard uses a combination of moderated t-tests (Smyth, 2004) and gene set enrichment analysis performed on t-scores (Nam and Kim, 2008; Subramanian et al., 2005). To provide a biological basis for quantifying lineage-specific differentiation propensities, several sets of early developmental marker genes for each of the three germ layers (ectoderm, mesoderm, endoderm). Bioconductor's limma package can also be used to perform moderated t-tests comparing the gene expression in the EBs obtained for the cell line of interest to the EBs obtained for the ES cell reference, and the mean t-scores were calculated across all genes that contribute to a relevant gene set. High mean t-scores (e.g., >1) indicate increased expression of the gene set's genes in the tested EBs and are considered indicative of a high differentiation propensity for the corresponding lineage. In contrast, low mean t-scores (e.g., <0) indicate decreased expression of relevant genes and are considered indicative of a low differentiation propensity for the corresponding lineage. To increase the robustness of the analysis, the mean t-scores were averaged over all gene sets assigned to a given lineage. The lineage scorecard diagrams (FIG. 3-7) list these "means of gene-set mean t-scores" as quantitative indicators of cell-line specific differentiation propensities. The lineage scorecard analyses and validations were performed using custom R scripts (available from world-wide web: r-project.org/).

Example 1

Variation in Gene Expression Between hES Cell Lines

There are many properties of a given ES cell line that could influence its early developmental gene expression profile and its potential differentiation. These could include the genetic background of a cell line, the way in which a line is cultured, selective pressure applied by extended in vitro growth, or unexplained stochastic noise. Before one can attempt to study the potential underlying causes of the variance in pluripotent stem cell line behavior, it is crucial to first determine both the nature and extent of variation that exists within a substantial cohort of lines.

Table 4:

Summary of cell lines used in the high-throughput experiments. *verified by presence/absence of chrY and evidence of X-chromosome inactivation in the RRBS, microarray and/or NanoString data.

TABLE 4

| Cell Line | Reference | Donor Age | Donor Sex* | Sibling Pairs (ES)/ Donor (iPS) | Passage No. for RRBS | Passage No. for Microarray | Passage No. for Lineage Scorecard |
|---|---|---|---|---|---|---|---|
| HUES1 | Cowan et al. 2004 | NA | female | | 22 | 26 | 26, 26 |
| HUES3 | Cowan et al. 2004 | NA | male | | 27 | 27 | 27, 28 |
| HUES6 | Cowan et al. 2004 | NA | female | | 23 | 23 | 19, 21 |
| HUES8 | Cowan et al. 2004 | NA | male | | 27 | 27 | 25, 26 |

TABLE 4-continued

| Cell Line | Reference | Donor Age | Donor Sex* | Sibling Pairs (ES)/ Donor (iPS) | Passage No. for RRBS | Passage No. for Microarray | Passage No. for Lineage Scorecard |
|---|---|---|---|---|---|---|---|
| HUES9 | Cowan et al. 2004 | NA | female | | 21 | 21 | 19, 18 |
| HUES13 | Cowan et al. 2004 | NA | male | | 47 | 47 | NA |
| HUES28 | Chen et al. 2009 | NA | female | | 17 | 17 | 13, 15 |
| HUES44 | Chen et al. 2009 | NA | female | | 18 | 18 | 15, 16 |
| HUES45 | Chen et al. 2009 | NA | female | | 20 | 20 | 17, 19 |
| HUES48 | Chen et al. 2009 | NA | female | | 19 | 19 | 16, 17 |
| HUES49 | Chen et al. 2009 | NA | female | | 17 | 17 | 14, 14 |
| HUES53 | Chen et al. 2009 | NA | male | A | 17 | 18 | 17, 18 |
| HUES62 | Chen et al. 2009 | NA | female | B | 14 | 17 | 15, 16, 16, 16, 18 |
| HUES63 | Chen et al. 2009 | NA | male | B | 19 | 14 | 19, 17 |
| HUES64 | Chen et al. 2009 | NA | male | B | 19 | 19 | 18, 20 |
| HUES65 | Chen et al. 2009 | NA | male | | 19 | 19 | 16, 17 |
| HUES66 | Chen et al. 2009 | NA | female | A | 20 | 20 | 15, 15 |
| H1 | Thomson et al. 1998 | NA | male | | 34 | 34 | 33, 34 |
| H7 | Thomson et al. 1998 | NA | female | | 48 | 48 | NA |
| H9 | Thomson et al. 1998 | NA | female | | NA | 58 | 57, 58 |
| hiPS 11a | Boulting et al. | 36 | male | 11 | 22 | 22 | 14, 18, 27, 29 |
| hiPS 11b | Boulting et al. | 36 | male | 11 | 13 | 13 | 15, 18, 25, 31 |
| hiPS 15b | Boulting et al. | 48 | female | 15 | 27 | 16 | 29, 30, 41, 44 |
| hiPS 17a | Boulting et al. | 71 | female | 17 | 14 | 12 | 10, 16, 17, 19 |
| hiPS 17b | Boulting et al. | 71 | female | 17 | 32 | 32 | 18, 20, 38 |
| hiPS 18a | Boulting et al. | 48 | female | 18 | 30 | 30 | 31, 32, 46 |
| hiPS 18b | Boulting et al. | 48 | female | 18 | 27 | 27 | 20, 37 |
| hiPS 18c | Boulting et al. | 48 | female | 18 | 36 | 27 | 30, 32 |
| hiPS 20b | Boulting et al. | 55 | male | 20 | 43 | 43 | 26, 31, 46, 50 |
| hiPS 27b | Boulting et al. | 29 | female | 27 | 31 | 31 | 27, 28 |
| hiPS 27e | Boulting et al. | 29 | female | 27 | 32 | 30 | 30, 31, 32, 32, 35 |
| hiPS 29d | Boulting et al. | 82 | female | 29 | NA | NA | 14, 15 |
| hiPS 29e | Boulting et al. | 82 | female | 29 | NA | NA | 25, 27 |
| hFib__11 | Boulting et al. | 36 | male | 11 | 8 | 8 | 7, 8 |
| hFib__15 | Boulting et al. | 48 | female | 15 | 7 | 7 | 6, 7 |
| hFib__17 | Boulting et al. | 71 | female | 17 | 7 | 7 | 6, 7 |
| hFib__18 | Boulting et al. | 48 | female | 18 | 7 | 7 | 6, 7 |
| hFib__20 | Boulting et al. | 55 | male | 20 | 7 | 7 | 6, 7 |
| hFib__27 | Boulting et al. | 29 | female | 27 | 7 | 7 | 6, 7 |

*verified by presence/absence of chrY and evidence of X-chromosome inactivation in the RRBS, microarray and/or NanoString data Any appropriate method for positive selection of cell lines should be simple to perform in a short period of time, be inexpensive and be predictive for applications in differentiation down as many distinct lineages as possible. The inventors assessed if the differentiation of a given cell-line was initiated in a relatively unbiased manner, then its natural differentiation propensities might be predictive of its performance in directed differentiation protocols. In other words, the inventors assessed if a cell line that had a natural propensity to form ectoderm or cells of the neural lineage would also perform optimally in for example motor neuron directed differentiation. To assess this, the inventors designed a simple, rapid, and inexpensive assay for pluripotent cell line differentiation propensities (FIGS. 3-7C).

The inventors initial results demonstrated that a simple transcriptional assay using early developmental genes can predict the reproducible behavior of a given ES cell line. The inventors assessed whether this "lineage scorecard" could be used to predict the behavior of iPS cells. To this end, the inventors selected several well characterized iPS cell lines (Boulting et al), performed standard EB differentiation, collected RNAs, analyzed them using the an array of early developmental genes as disclosed in Table 1 and normalized the resulting data to the "reference" ES cell-derived EBs. The result was a lineage "scorecard" for the behavior of the selected iPS cell lines (FIG. 4).

Example 2

Toward High-Throughput Evaluation of Pluripotent Cell Quality and Utility

The inventors have demonstrated use of the differentiation assays as disclosed herein to design a "lineage scorecard" that can predict the differentiation propensities of any pluripotent cell line. The scorecard output provides a systematic estimate of a cell line's differentiation propensities.

Here, the inventors demonstrate that only one differentiation gene expression assay of early developmental genes is required to quantitative and characterize a stem cell without compromising the accuracy of the score-card relative to methods involving more than one type of assay, e.g., methylation assay, gene expression assay and a differentiation assay, or gene expression on differentiated or spontaneously differentiated stem cells.

As disclosed herein, the quantitative differentiation assay could be performed alone as a single indicator of the differentiation potential of the stem cells line. Additionally, the inventors demonstrate by assessing the expression of a distinct range of early developmental genes, a significant reduction the total length of time required to perform the quantitative differentiation assay. Effectively, the inventors have demonstrated that the early gene expression analysis can be performed on embryonic stem cells at embryonic day 2, reduced from analysis performed at least at 5-days or 7-days of embryonic age. By "embryonic day n" is meant n days in culture in EB forming conditions. Accordingly, shortening the duration of the assay is advantageous as it decreases the time-to-results and also minimizes the logistical costs in terms of incubator space and need for media changes. The inventors optimized the quantitative differentiation assay so it is sensitive enough to estimate differentiation propensities using RNA isolated directly from the undifferentiated pluripotent cell lines, most likely by detecting low levels of cellular differentiation in otherwise self-renewing cultures. Additionally, the inventors have demonstrated that the differentiation assay performed only once is sufficient to determine the differentiation propensity of the stem cell line, thus eliminating the expense and time required for duplicate and triplicate assays. Further, the differentiation assay can be performed using a variety of different RNA preparation methods, culture media and the like. The inventors have also demonstrated that the differentiation assay can be performed in multiplex for high-throughput analysis, for example in a 96- and 384-well plates, allowing multiple stem cell lines to be analyzed simultaneously.

Example 3

The inventors also investigated how robust and reproducible the results from the "scorecard" remained when the inventors compared the same pluripotent stem lines across several passages and between independent labs. Because the inventors' methods for analyzing DNA methylation and transcription have been shown to be reproducible (Gu et al., 2010; Irizarry et al., 2005) and because the inventors have already investigated how these measures change with passage (data not shown), the inventors focused on the reproducibility of the quantitative differentiation assay. Because differentiation of ES cells in EBs is likely to be sensitive to differences in such parameters as physical handling, media renewal and plasticware, the inventors assessed how predictive the results from the differentiation assay would be of cell line behavior in another lab and with a distinct investigator.

To further confirm the robustness and reproducibility of the scorecard for predicting the behavior of iPS cell lines, the inventors performed a variety of quality control experiments using different culture and sample preparation and gene expression methodology. The inventors therefore performed a systematic comparison in which two different cell lines (H9 ESC and BS3-C iPSC) were evaluated by two different investigators in two different labs, performing the EB assay separately and independently.

The focused set of early developmental genes listed in Table 1 is a good indicator of cell state. Thus, the assay as disclosed herein can cluster the cell lines by cell state, which is not achievable by other methods, such as the TaqMan Open Array (data not shown).

Figure 2A:
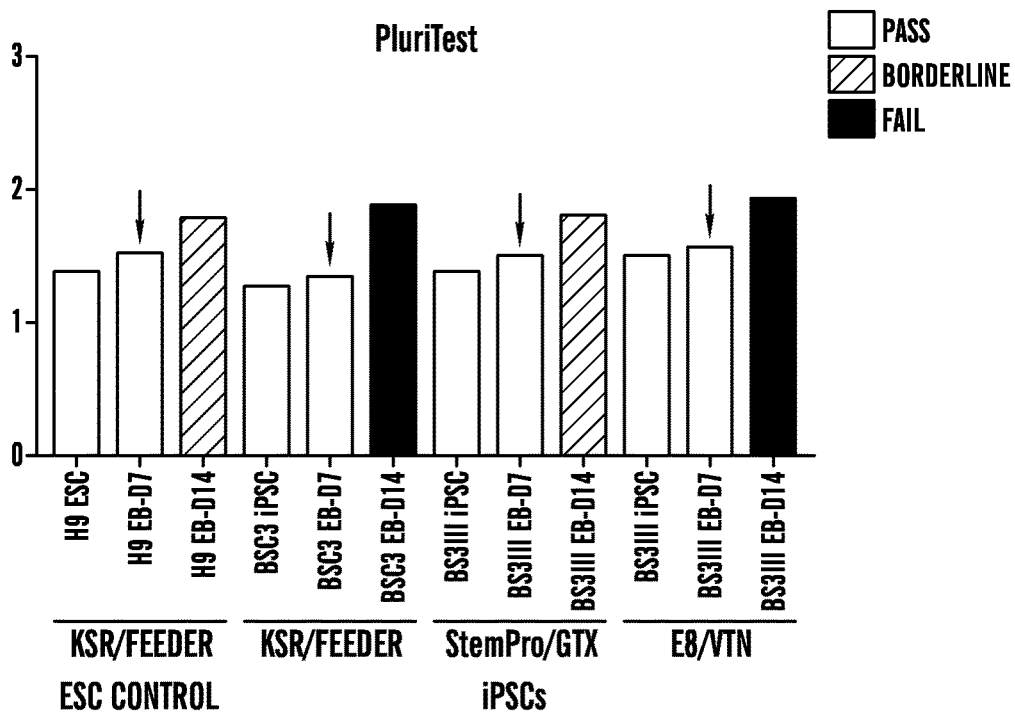
FIG. 2A-2B.
Figure 2B:
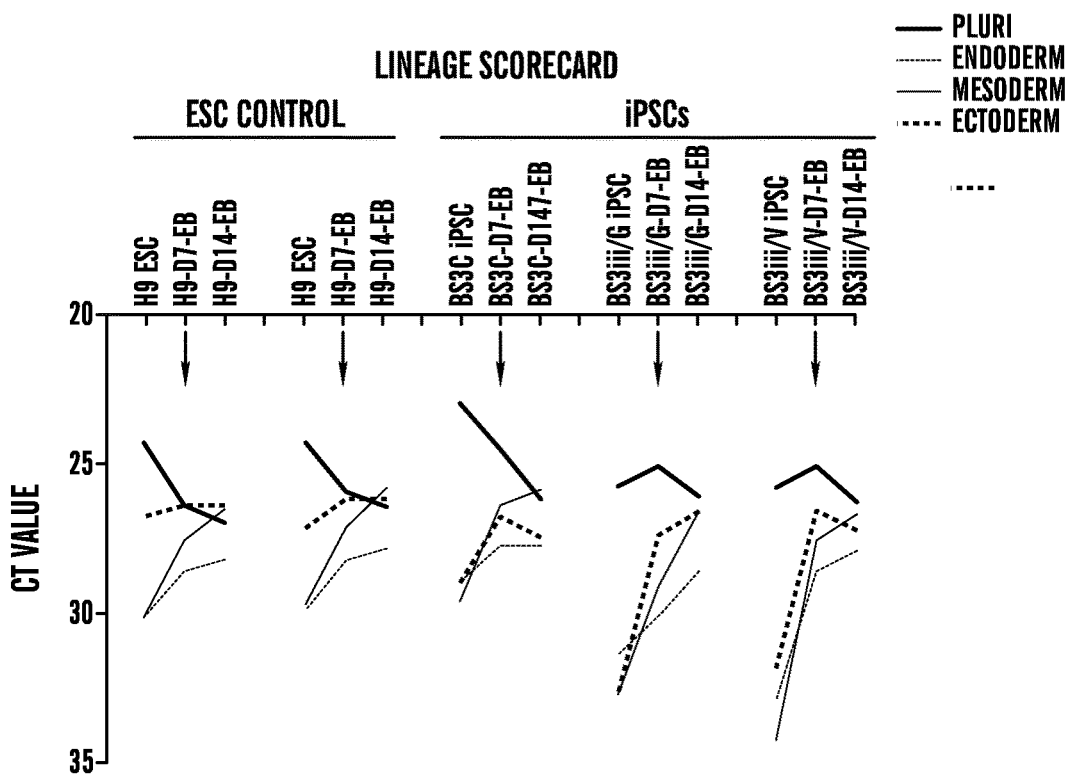
Figure 8:
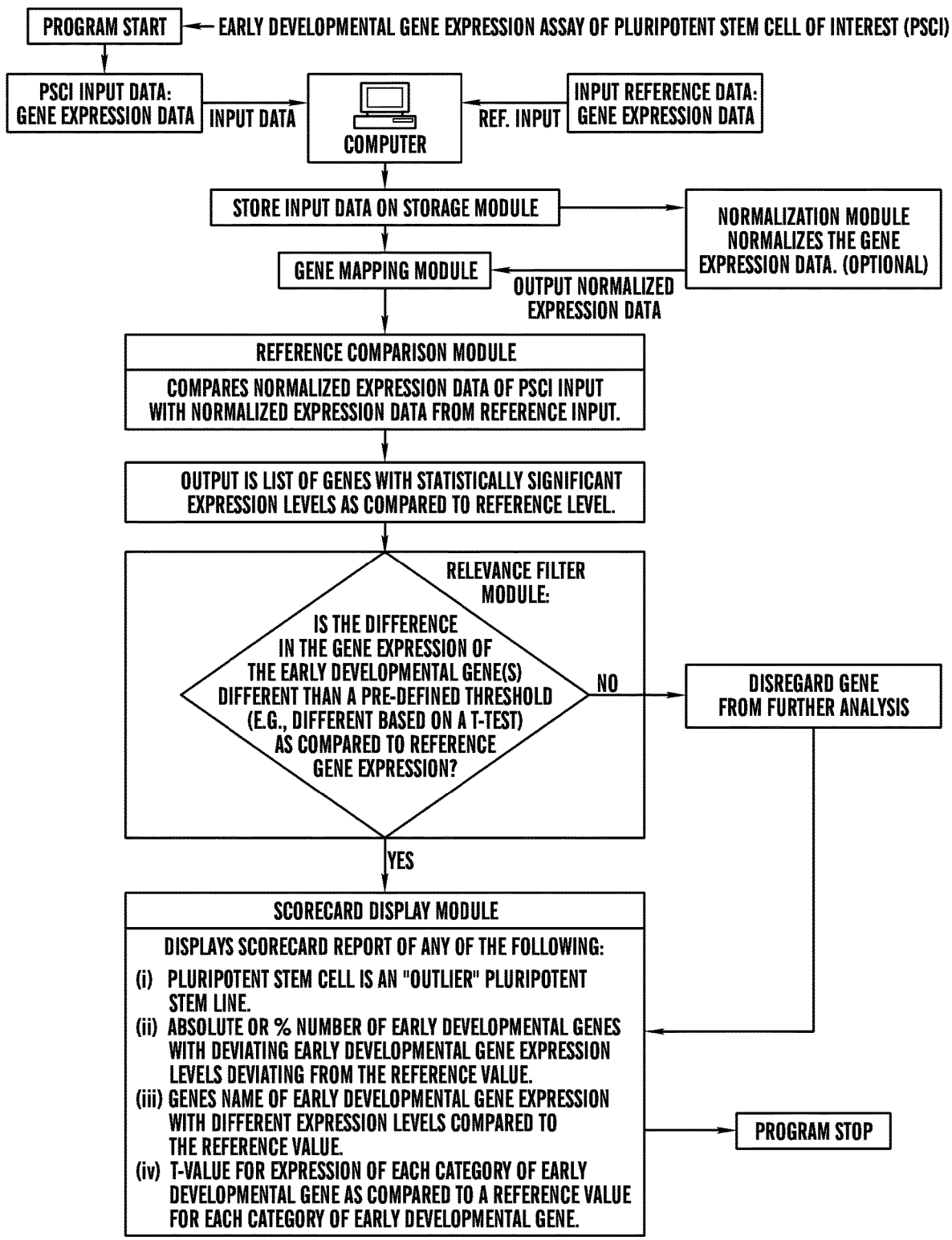
FIG. 8 shows a flow chart of an embodiment of instructions for a computer program for producing a lineage scorecard as disclosed herein for a pluripotent stem cell line of interest. The data are inputted into a computer comprising a processor and associated memory or storage device, and a gene mapping module, a reference comparison module, a normalization module a relevance filter module a gene set module and a scorecard display module to display the deviation scorecard.
Figure 9:
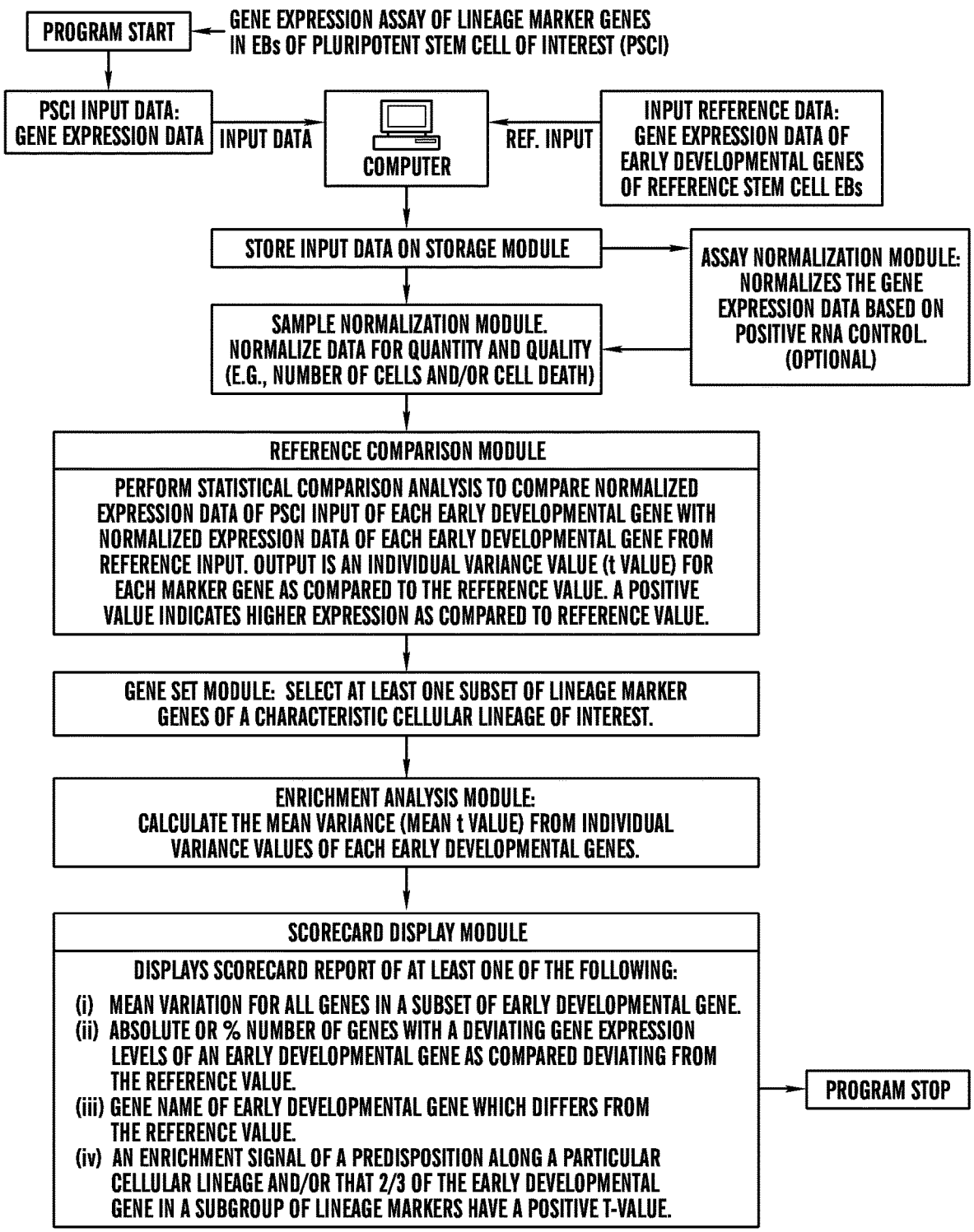
FIG. 9 shows a flow chart of one embodiment of instructions for a computer program for producing a lineage scorecard for a pluripotent stem cell line of interest. The data obtained for the generation of the deviation scorecard are gene expression data of early developmental genes for the pluripotent stem cell line of interest. The data are inputted into a computer comprising a processor and associated memory and/or storage device, and an assay normalization module. A sample normalization module, a reference comparison module, a gene set module, an enrichment analysis module and a scorecard display module to display the lineage scorecard.
Figure 10:
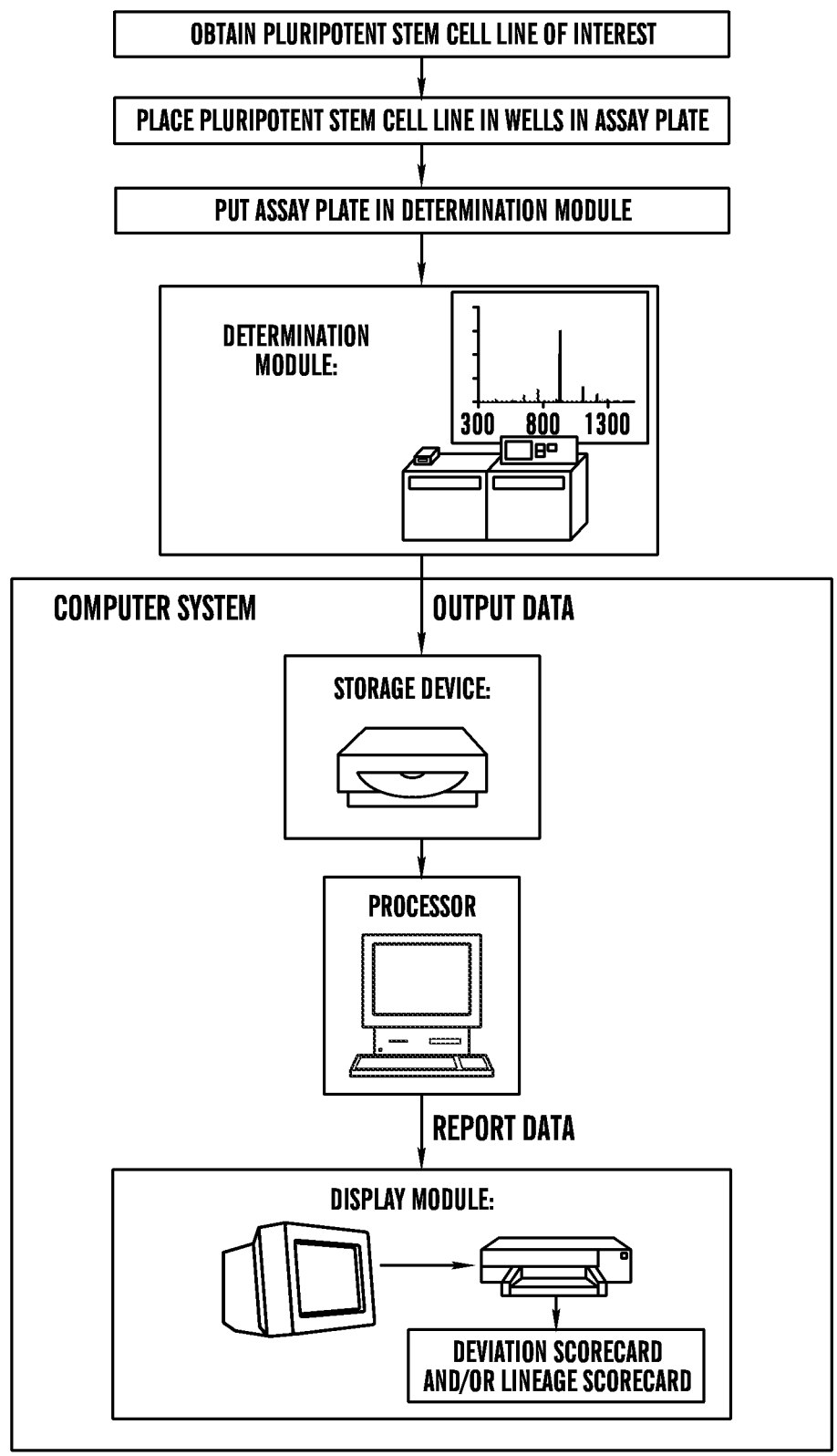
FIG. 10 shows a simplified block diagram of an embodiment of the present invention which relates to a high-throughput system for characterizing the differentiation propensity of a pluripotent stem cell of interest and producing a lineage scorecard. The determination module can be any apparatus or machine for measuring gene expression.
Figure 11:
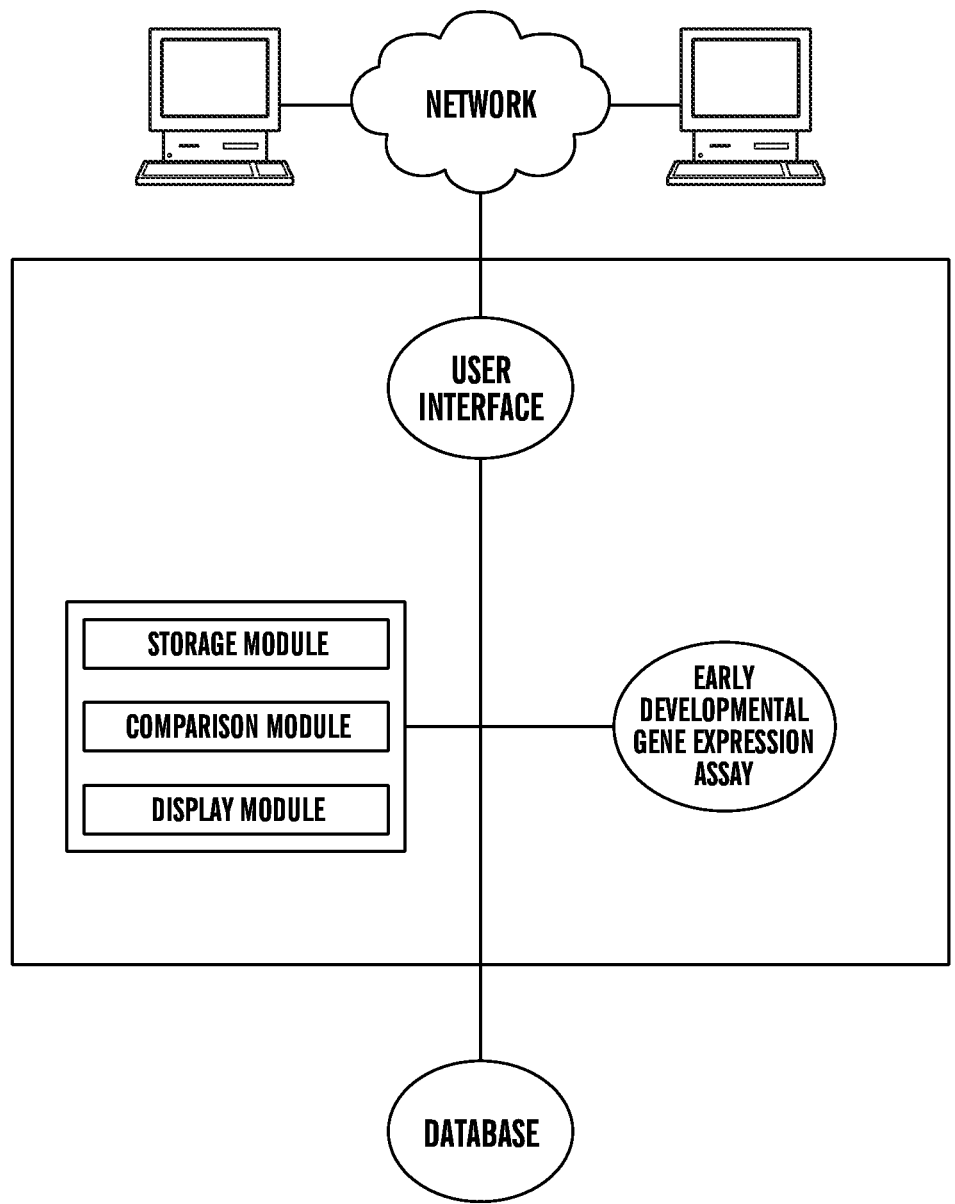
FIG. 11 shows a simplified block diagram of an embodiment of the present invention which permits the data gene expression differentiation assays to be configured to be processed by a computer system at any location and accessible through a user interface, where the data for each pluripotent stem cell are stored in a database.

In a direct comparison with other assays, the lineage scorecard as disclosed herein was demonstrated to be superior and more accurate than other assays, such as the PluriTest™ (Franz-Josef Müller et al., A bioinformatic assay for pluripotency in human cells, Nature Methods, 2011, 8; 315-317), in identifying pluripotent stem cells. As shown in FIG. 2A, while the Pluritest™ indicated that the stem cell line was not pluripotent at 14 days, but indicated that the stem cell line was pluripotent at 7 days. In contrast, FIG. 2B shows that the assay used herein was more sensitive, indicating that at 7 days, the expression of pluripotent genes was down and the expression of differentiation genes was increased. Accordingly, the assays as disclosed herein are more sensitive to determine the pluripotency of a stem cell line (or lack of pluripotency) at 7 days or earlier, e.g., by 5 days in culture.

Quality Control Experiments Demonstrate Consistency in the Measured Levels of Expression of the Early Developmental Genes Regardless User Differences, Culture Method, RNA Isolation Methods and PCR Mixes.

Different users in different labs demonstrate a high accuracy of predictability of pluripotency and differentiation potential using the assay as demonstrated herein. For example, different users, using different culturing methods and different stem cell culture media (e.g., conditioned media, StemPro/Geltrex and essential8/vitronectin), as well as different cell and RNA preparation showed little variability in the levels of expression of the early developmental genes of the assay in the same cell lines at the same timepoint (data not shown), demonstrating consistency and accuracy of the assay. Additionally, no significant difference in RNA quality was observed with different RNA isolation methods (e.g., Trizol PureLink™ or Trizol™), and resulted in high RNA purity and little variability in RNA yields (data not shown). Furthermore, the levels of expression of the early developmental genes was not affected by the different PCR master mixes (e.g. TaqMan® Universal master mix, TaqMan® Gene Expression Mix, TaqMan® Fast Advanced Master Mix, TaqMan® Genotyping Master Mix) used for amplification of the early developmental genes in the differentiation assay (data not shown).

Different lots of plates performed comparably for pluripotent samples (e.g., pluripotent cells cultured to the same time point, e.g., 3-days or 4-days or 5-days in EB), but with less consistency and higher variability with differentiated stem cell lines (data not shown). Accordingly, the assay plates are consistent from lot to lot and thus a pluripotent stem cell line can be assayed a single time, and does not need to be assayed in replicates. Different instruments (e.g., Viia7, QuantStudio and StepOne Plus) for the RT-PCR resulted in high correlation in the level of expression of the early developmental genes measured in the assay.

Accordingly, Trizol and PureLink isolated RNA have quality with in the acceptable range. TaqMan Gene expression Master mix and Universal Master Mix II both can be used as PCR master mixes under Standard PCR conditions (not Fast). Undifferentiated pluripotent samples harvested by different methods all show high level of correlation in gene expression when normalized to housekeeping gene. A clear change in gene expression pattern was observed between undifferentiated and differentiated EB samples and clustered away form the pluripotent cells. The majority of the gene assays show predicted expression in pluripotent and differentiated cells.

Example 4

Algorithm and Data Analysis

For each input sample and each of six categories of genes (control, pluri, endo, mesendo, meso, ecto) the software reports mean (mu) and standard deviation of t-statistic (significance) and min and max p-value over the gene category. The Reference Gene is calculated as follows: The median Ct value across ACTB will be used as a base to compute $\Delta$Ct values. The Reference Sample value provides a base $\Delta$Ct and is calculated as follows: T- and P-values are computed between the distribution defined by this group of samples (6 replicates of PSC—data comprised of 1 ESC and 1iPSC line prepared using two different methods by two users) and each unknown sample. There is a reference based on gene expression levels at in at least about 20 cell lines which are both differentiated and undifferentiated.

Accordingly, the ΔCt is determined for all early developmental genes measured in the pluripotent stem cell. In each defined group or category (e.g., control, pluripotent gene, early endoderm developmental genes, early mesendoderm developmental gene, early mesoderm developmental genes, early ectoderm developmental gene), the ΔCt is averaged and the averaged ΔCt is compared using a t-test to the reference ΔCt for that category (FIG. 3). Using t-value as an indicator (see FIG. 3), a t-value of 0-1 indicates that the measured level of gene expression in that early developmental gene category is comparable with the reference gene expression level in the same category. A t-value of >1 indicates that the measured gene expression level in that early developmental gene category of the pluripotent cell line is higher than the reference gene expression level in the same category. A t-value of <0 indicates that the measured gene expression level in that early developmental gene category of the pluripotent cell line is lower than the reference gene expression level in the same category.

Example 5

Analysis of Undifferentiated and Differentiated Pairs

The results of the differentiation assay which measured the levels of the early developmental genes can be displayed in a number of different ways. As demonstrated in FIG. 4, the t-value of each category of developmental gene can be displayed (e.g., the t-value comparison of the average ΔCt for all the genes in each category is compared with the average ΔCt for the same set of genes in the reference pluripotent stem cell lines). If the t-value is between 0-1, a signal, e.g., yellow signal or an arrow (e.g., horizontal or directional 45° upward or downward arrow) indicates that the measured level of gene expression in that early developmental gene category is comparable with the reference gene expression level in the same category. If the t-value is >1, a signal, e.g., green color or an upwards arrow indicates that the measured gene expression level in that early developmental gene category of the pluripotent cell line is higher than the reference gene expression level in the same category. If the t-value is <0, a signal, e.g., a red color or downwards arrow indicates that the measured gene expression level in that early developmental gene category of the pluripotent cell line is lower than the reference gene expression level in the same category. As shown in FIG. 3, the differentiation potential of a pluripotent stem cell can be determined by looking at the pluripotent genes and the three germ line early developmental genes (e.g., meso, endo, and ecto). For example, the analysis of the BS3C cells, shows the BS3C iPSC have comparable levels of pluripotent genes, mesoderm genes, endoderm genes and ectoderm genes as compared to the reference standard, whereas 7D and 14D BS3C cells have decreased pluripotent stem cells and increased expression levels for the mesoderm genes, endoderm genes and ectoderm genes, indicating that the genes are no longer pluripotent and have begun to differentiate.

Example 6

Differentiated Times and Methods

The inventors assessed whether the duration of the differentiation assay could be reduced from being performed on pluripotent stem cells at 7 days to cells which were at least 2 days. In this case, the inventors demonstrated an excellent agreement between the expression of early developmental genes in each category (e.g., pluripotent, mesoderm, ectoderm and endoderm) on a representative iPS cell lines (FIG. 5), demonstrating that it is possible to reduce the duration at which the time of the differentiation assay is performed without jeopardizing its accuracy. This was a surprising finding allowing reduced cost associated with a quicker determination of the characterization of the differentiation potential of a pluripotent stem cell line.

Accordingly, herein the inventors demonstrate that the assays, methods and systems can be performed on pluripotent stem cells as early as 2 days in culture (e.g., EB Day 2). As demonstrated in FIG. 5, pluripotent stem cells cultured at 2 and 4 days produce reliable results for levels of expression of early developmental genes. Furthermore, the assay, methods and systems can be performed on pluripotent stem cells in EB suspension or in a monolayer, as demonstrated in FIG. 6. As shown in FIG. 7A, the differentiation assays, methods and systems as disclosed herein can be used to identify a bad clone or culture (e.g., BS4-iPS5 P8), when the pluripotent stem cell is compared to similar pluripotent stem cells lines at the same time point. FIG. 7B shows that the differentiation assays, methods and systems as disclosed herein can also identify cell lines which have a predisposition to differentiate along a particular lineage, e.g., in FIG. 7B, the hNSDup cell line has increased ectoderm levels indicating the cell line has a predisposition to differentiate along an ectoderm lineage. Furthermore, the differentiation assays, methods and systems as disclosed herein are useful for identifying stem cell lines which are no longer pluripotent, as demonstrated in FIG. 7C shows BJ fibroblasts and HJF fetal cells have a significant decrease in pluripotent genes. Additionally, the assay can also detect the effect of contamination of MEF (see FIG. 7C).

Example 7

Until recently, only a few human pluripotent cell lines were widely available for biomedical research. For this reason, researchers have mostly relied on these readily accessible and well characterized cell lines (Cowan et al., 2004; Mitalipova et al., 2003; Thomson et al., 1998). Funding restrictions placed on human ES cell research in the United States further limited the selection of cell lines available. As a result, investigators simply used any lines they could for their application of interest with little need for a diagnostic that could predict how well a given cell line would behave in a given assay.

However, the continued derivation of human ES cell lines by many labs (Chen et al., 2009) and the lifting of funding restrictions in the US, has substantially increased the number of ES cell lines that investigators can choose from. Additionally, it has become clear that not all human ES cell lines are equally suited for every purpose (Osafune et al., 2008). This suggests that any new research project should perform a deliberate and informed selection of the cell lines that are most qualified for an application of interest.

The discovery of factors that reprogram somatic cells from patients into iPS cells has lead to a further inflection in the number of pluripotent cell lines available to, and needed by, the research community. As investigators gather together existing cell lines, or derive new ones for their application of interest, there is little information or guidance concerning how to select cell lines that are most appropriate. The inventors herein provide a clear path to guide investigators to proceed from patient samples, to fully reprogrammed iPS cells, to a selected and manageable set of lines that can be used at a reasonable scale for disease modeling.

Here, the inventors demonstrate methods to accurately predict the differentiation propensities of human pluripotent cell lines, thereby allowing investigators to select lines that would perform optimally in their given application. Importantly, the use of the "scorecard" as disclosed herein for pluripotent cell line quality and utility, can be readily scaled for the characterization of any number of pluripotent cell lines, e.g., as few as about 5 pluripotent stem cell lines to 10's and 100's and 1000's of pluripotent stem cell lines.

In aggregate, the scorecard as disclosed herein reports the differentiation characteristics and likely behavior of a given pluripotent cell line that an investigator would wish to understand before investing significant time and resources into its use in any particular application. For instance, the scorecard as disclosed herein incorporates developmental gene expression profiles for the pluripotent cell lines, allowing investigators to be confident that cell lines they select have the ability, or even increased efficiency to differentiate into their desirable cell lineage, and are not non-pluripotent stem cell lines.

For those interested in developing cell therapies, it can be critical to demonstrate that a pluripotent cell line being put forward for clinical development fits to "standard" criteria from preparation to preparation and can either differentiate into all three germ line lineages, and/or in certain criteria, the stem cell line selected has an increased efficiency of differentiating along a particular cell lineage. Accordingly, the inventors production and use of the "scorecard" as disclosed herein is useful for these important safety measures before administering a pluripotent stem cell or their progeny to a subject in therapeutic use.

The quantitative differentiation assay as disclosed herein provides information on a pluripotent cell line propensity to differentiate along a number and/or a particular cell lineage, as well as if the stem cell line is no longer pluripotent. As disclosed herein, this quantitative differentiation assay uses DNA expression profiles of early developmental genes expressed in specific lineages as a measure to quantitatively demonstrate the differentiation potential of the stem cell to differentiate along each lineage (e.g., mesoderm, ectoderm and endoderm) as well as specific lineages, e.g., neuronal lineages, pancreatic lineages etc.

Epigenetic and transcriptional differences can distinguish the average ES cell line from the average iPS cell line, but these differences are insufficient to draw conclusions about the characteristics of any single ES or iPS cell line under consideration. Herein, by using the differentiation assay, the inventors determined that some stem cell lines are more suited for a given application than others, and the same is true of iPS cells.

The inventors also determined that rather than trying to find the optimal ES cell line or the perfect reprogramming protocol for all needs and applications, what seems to be required is a rapid assay that can match suitable cell lines to a given application. Accordingly, the methods, systems and kits of the differentiation assay as disclosed herein are useful to determine and predict the propensities of human pluripotent cell lines, such that an appropriate pluripotent stem cell with desired propensities could be matched and selected for use in specific downstream applications.

In some embodiments, the differentiation assay can be adapted in different ways to assess the selective pressures of in vitro culture on the differentiation of the stem cell clone. Accordingly, based on this data, ES cell lines are also useful to provide a model system for investigating the ramifications of cellular competition and adaption to growth conditions.

Presently, without the current invention, after obtaining an existing pluripotent stem cell line, or generating a new one, an investigator would perform a number of time-consuming, laborious and expensive assays including immunostaining for specific antigens and teratoma generation. While these assays can provide some confidence that a given cell line is pluripotent, they are unable to predict whether a pluripotent cell line is well suited to a given application. In contrast, the present methods, kits, systems, differentiation assays and differentiation scorecards as disclosed herein are useful to predict the behavior of the pluripotent stem cell in a quick, efficient and effective manner, which is not time or labor intensive and relatively inexpensive.

Accordingly, using the methods, kits, systems, assays and scorecards as disclosed herein, a researcher interested in disease modeling of, for example, cells which differentiate along an ectoderm lineage, and then into neurons, which can be used in the treatment of neurodegenerative diseases, e.g., amyotrophic lateral sclerosis (ALS). In some embodiments, an investigator could analyze their pluripotent stem cells of interest and perform the quantitative differentiation assay and array as disclosed herein. The researcher can then select those pluripotent stem cell lines exhibiting normal to high differentiation propensity to differentiate into an ectoderm lineage (see FIG. 7B) and then into neural lineages for further studies. Accordingly, using the methods, assays, kits and systems and scorecards as disclosed herein, an investigator can inspect cell lines for variation in the parameters that would best predict the utility of the pluripotent stem cell line in their particular desired application (FIG. 7E).

The inventors methods, assays, scorecards and kits as disclosed herein enable an investigator to delay the most time-consuming and expensive assay, teratoma formation, to be started on a particular pluripotent stem cell line only at a time when the "scorecard" has predicted that the selected pluripotent cell line is likely to differentiate into motor neurons, or other cells of interest at a high efficiency. Over time, the use of the methods, assays, scorecards and kits as disclosed herein can enable one to eliminate the teratoma generation assay completely if the methods, assays, scorecards as disclosed herein are used to accurately predict pluripotent stem cell lines with the potential to form a teratoma.

In conclusion, the discovery of human pluripotent cells and the reprogramming methods to produce human iPS cells from selected patient populations has revolutionized how researchers think about studying and treating human disease. However, if use of human pluripotent stem cells and iPS cells are to efficiently and effectively used in research as well as cell therapy and therapeutic use to improve the lives of patients, it is imperative to establish a quality assessment and validation method such as the methods, assays, systems and "scorecard" as disclosed herein to streamline, standardize and optimize the selection of pluripotent cell lines for studying, for drug development and toxicity assays as well as for a particular therapeutic implication, or for treating a given indication or disease.

REFERENCES

The references are incorporated herein in their entirety by reference.

The invention claimed is:

1. A method to determine the differentiation potential of a pluripotent stem cell, the method comprising:
contacting a sample comprising mRNA obtained from at least one pluripotent stem cell with an array composition, the array composition comprising a solid support and at least 10 oligonucleotides or at least 10 pairs of oligonucleotides, wherein the at least 10 oligonucleotides or at least 10 pairs of oligonucleotides are each attached to the solid support and located on the solid support at an assigned position defined by x and y coordinates, wherein the oligonucleotides or pairs of oligonucleotides specifically bind the mRNA of group of selected early developmental genes consisting of:
at least 3 ectoderm genes selected from: SEQ ID NO: 11, 13, 14, 15, 19, 20, 21, 22;
at least 3 endoderm genes selected from: 23, 24, 25, 27, 28, 30, 32, 33, 34, 36, 37, 44, 45, 46, 48, 49;
at least 3 mesoderm genes selected from: 53, 59, 61, 62, 63, 65, 66, 68, 70, 76, 78, 81, 84, 86, 87 and 88,
and performing amplification of the mRNA and measuring the expression level of the amplified early developmental genes, and
performing a comparison of the measured expression level of the early developmental genes with a reference expression level of each of the early developmental genes to determine the differentiation potential of the pluripotent stem cell.

2. The method of claim 1, comprising at least 20 oligonucleotides, or at least 20 pairs of oligonucleotides, that amplify the mRNA of a set of at least 20 early developmental genes, wherein said oligonucleotides or pairs of oligonucleotides specifically bind the mRNA of group of at least 20 early developmental genes selected from the group consisting of: SEQ ID NO: 11, 13, 14, 15, 19, 20, 21, 22, 23, 24, 25, 27, 28, 30, 32, 33, 34, 36, 37, 44, 45, 46, 48, 49, 53, 59, 61, 62, 63, 65, 66, 68, 70, 76, 78, 81, 84, 86, 87 and 88.

3. The method of claim 1, wherein the composition comprises no more than 100 oligonucleotides or no more than 100 pairs of oligonucleotides.

4. The method of claim 3, wherein the composition array comprises at least 20 oligonucleotides or at least 20 pairs of oligonucleotides that bind to the group of early developmental genes consisting of:
at least 3 ectoderm genes selected from: SEQ ID NO: 11, 13, 14, 15, 19, 20, 21, 22;
at least 3 endoderm genes selected from: 23, 24, 25, 27, 28, 30, 32, 33, 34, 36, 37, 44, 45, 46, 48, 49;
at least 3 mesoderm genes selected from: 53, 59, 61, 62, 63, 65, 66, 68, 70, 76, 78, 81, 84, 86, 87 and 88.

5. The method of claim 3, wherein the composition array contains at least 30 oligonucleotides or at least 30 pairs of oligonucleotides that bind to the group of early developmental genes consisting of:
at least 3 ectoderm genes selected from: SEQ ID NO: 11, 13, 14, 15, 19, 20, 21, 22;
at least 3 endoderm genes selected from: 23, 24, 25, 27, 28, 30, 32, 33, 34, 36, 37, 44, 45, 46, 48, 49;
at least 3 mesoderm genes selected from: 53, 59, 61, 62, 63, 65, 66, 68, 70, 76, 78, 81, 84, 86, 87 and 88.

6. The method of claim 1, wherein the composition comprises no more than 100 pairs of PCR primers.

7. The method of claim 6, wherein the composition array comprises at least 20 oligonucleotides or at least 20 pairs of oligonucleotides that bind to the group of early developmental genes consisting of:
at least 3 ectoderm genes selected from: SEQ ID NO: 11, 13, 14, 15, 19, 20, 21, 22;
at least 3 endoderm genes selected from: 23, 24, 25, 27, 28, 30, 32, 33, 34, 36, 37, 44, 45, 46, 48, 49;
at least 3 mesoderm genes selected from: 53, 59, 61, 62, 63, 65, 66, 68, 70, 76, 78, 81, 84, 86, 87 and 88.

8. The method of claim 6, wherein the composition array contains at least 30 oligonucleotides or at least 30 pairs of oligonucleotides that bind to the group of early developmental genes consisting of:
at least 3 ectoderm genes selected from: SEQ ID NO: 11, 13, 14, 15, 19, 20, 21, 22;
at least 3 endoderm genes selected from: 23, 24, 25, 27, 28, 30, 32, 33, 34, 36, 37, 44, 45, 46, 48, 49;
at least 3 mesoderm genes selected from: 53, 59, 61, 62, 63, 65, 66, 68, 70, 76, 78, 81, 84, 86, 87 and 88.

* * * * *